United States Patent
Lee et al.

(10) Patent No.: US 8,368,062 B2
(45) Date of Patent: *Feb. 5, 2013

(54) NITROGEN-CONTAINING HETEROCYCLIC COMPOUND AND ORGANIC ELECTRONIC DEVICE USING THE SAME

(75) Inventors: Dong-Hoon Lee, Daejeon (KR); Tae-Yoon Park, Daejeon (KR); Jae-Soon Bae, Daejeon (KR); Hyun Nam, Daejeon (KR); Jun-Gi Jang, Daejeon (KR); Sung-Kil Hong, Daejeon (KR)

(73) Assignee: LG Chem, Ltd., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 13/054,047

(22) PCT Filed: Nov. 3, 2009

(86) PCT No.: PCT/KR2009/006437
§ 371 (c)(1),
(2), (4) Date: Jan. 13, 2011

(87) PCT Pub. No.: WO2010/062065
PCT Pub. Date: Jun. 3, 2010

(65) Prior Publication Data
US 2011/0127513 A1     Jun. 2, 2011

(30) Foreign Application Priority Data

Nov. 3, 2008    (KR) ........................ 10-2008-0108602

(51) Int. Cl.
*H01L 51/00* (2006.01)
*H01L 51/54* (2006.01)
*C07D 235/00* (2006.01)
*C07D 471/00* (2006.01)
*C07D 487/00* (2006.01)

(52) U.S. Cl. .................. 257/40; 257/E51.05; 313/504; 313/506; 428/690; 428/917; 136/263; 548/301.7; 546/41; 546/48; 544/342

(58) Field of Classification Search ................ 548/301.7
See application file for complete search history.

(56) References Cited

U.S. PATENT DOCUMENTS
2009/0140637 A1    6/2009   Hosokawa et al.

FOREIGN PATENT DOCUMENTS
| KR | 10-2007-0049080 A | 5/2007 |
| KR | 10-2008-0028425 A | 3/2008 |
| WO | WO 2007/052985 A1 | 5/2007 |
| WO | WO 2007-095118 A2 | 8/2007 |
| WO | WO 2008/156879 | 12/2008 |

OTHER PUBLICATIONS

Haruhiko Tomoda et al., "Substituent Effects on Fluorescent Properties of Imidazo [1, 2-a] pyridine-Based Compounds", Bulletin of the Chemical Society of Japan, 1999, vol. 72, pp. 1327-1334.
Alexis D.C. Parenty et al., "Discovery of an imidazo-phenanthridine synthon produced in a 'five-step one-pot reaction' leading to a new family of hetero cycles with novel physical properties", Chem. Comm., 2006, pp. 1194-1196.

*Primary Examiner* — Marie R. Yamnitzky
(74) *Attorney, Agent, or Firm* — McKenna Long & Aldridge LLP

(57) ABSTRACT

The present invention provides a nitrogen-containing heterocyclic derivative and an organic electronic device using the same. The nitrogen-containing heterocyclic derivative that is represented by the following Formula 2 or includes two or more structures of the following Formula 2:

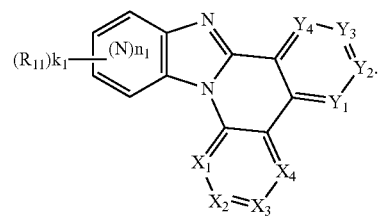

The organic electronic device according to the present invention has excellent properties in terms of efficiency, driving voltage, and a life span.

17 Claims, 30 Drawing Sheets

Figure 4 Mass spectrum of the compound 1-a-15

Mass spectrum of the compound 1-a-34

Mass spectrum of the compound 1-a-58

Figure 8  Mass spectrum of the compound 1-b-100

Figure 10  Mass spectrum of the compound 5-a-3.4

Figure 11 Mass spectrum of the compound 5-a-33

Mass spectrum of the compound 1-a-74

Mass spectrum of the compound 1-a-31

Figure 14 Mass spectrum of the compound 1-b-136

Figure 15 Mass spectrum of the compound 1-b-31

Figure 16  Mass spectrum of the compound 1-b-32

Mass spectrum of the compound 1-b-122

Figure 18  Mass spectrum of the compound 6-a-1

Figure 19 Mass spectrum of the compound 6-a-3

Mass spectrum of the compound 5-a-13

Figure 21 Mass spectrum of the compound 1-b-139

Figure 22 Mass spectrum of the compound 1-b-80

Figure 23  Mass spectrum of the compound 6-a-2

Mass spectrum of the compound 1-b-123

Figure 25 Mass spectrum of the compound 1-a-68

Figure 26  Mass spectrum of the compound 1-α-77

Figure 27  Mass spectrum of the compound 1-b-39

Figure 28  Mass spectrum of the compound 1-b-146

Figure 29 Mass spectrum of the compound 5-a-2

Compound 6-a-18
(phosphorescent PL that is measure in Methyl THF at 77K)

NITROGEN-CONTAINING HETEROCYCLIC COMPOUND AND ORGANIC ELECTRONIC DEVICE USING THE SAME

This application claims the benefit of PCT/KR2009/006437 filed on Nov. 3, 2009 and priority from Korean Patent Application No. 10-2008-0108602 filed on Nov. 3, 2008 both the disclosure of which are incorporated herein by reference in their entirety.

TECHNICAL FIELD

The present invention relates to a novel nitrogen-containing heterocyclic derivative and an organic electronic device using the same.

BACKGROUND ART

An organic electronic device means a device that requires exchanging of electric charges between electrodes using holes and/or electrons and organic materials. The organic electronic device may be largely divided into the following categories according to an operation principle. First, there is an electronic device in which an exiton is formed in an organic layer by a photon that flows from an external light source to the device, the exiton is separated into electrons and holes, and the electrons and the holes are transferred to the other electrodes and used as a current source (voltage source). Second, there is an electronic device in which holes and/or electrons are injected into an organic material semiconductor forming an interface in respects to the electrode by applying a voltage or a current to two or more electrodes, and the device is operated by the injected electrons and holes.

As examples of the organic electronic device, there are an organic light emitting device, an organic solar cell, an organic photoconductor (OPC), an organic transistor and the like, and all of them require a hole injection or transport material, an electron injection or transport material or a light emitting material in order to drive the device. Hereinafter, an organic light emitting device will be mainly described in detail. However, in the organic electronic devices, all of the hole injection or transport material, an electron injection or transport material or a light emitting material are operated on the basis of the similar principle.

In general, an organic light emitting phenomenon means a phenomenon that converts electric energy into light energy by using an organic material. The organic light emitting device using the organic light emitting phenomenon has a structure which generally includes an anode, a cathode, and an organic layer that is disposed between them. Herein, most organic layers have a multilayered structure that includes different materials in order to increase efficiency and stability of the organic light emitting device, and for example, it may include a hole injection layer, a hole transport layer, a light emitting layer, an electron transport layer, an electron injection layer and the like. In the organic light emitting device structure, if a voltage is applied between two electrodes, holes are injected from an anode and electrons are injected from a cathode to the organic layer, and when the injected holes and the electrons meet each other, an exciton is formed, and light is emitted when the exciton falls to a bottom state. It is known that this organic light emitting device has properties such as magnetic light emission, high brightness, high efficiency, low driving voltage, a wide viewing angle, high contrast, high speed response and the like.

In the organic light emitting device, the material that is used in the organic material layer may be classified into a light emitting material and an electric charge material, for example, a hole injection material, a hole transport material, an electron transport material, an electron injection material according to a function thereof. In addition, the light emitting material may be classified into blue, green, and red light emitting materials and yellow and orange light emitting materials in order to realize better natural colors according to the emission color. Meanwhile, in the case of when only one material is used as a light emitting material, by interaction between molecules, there are problems in that the maximum light emitting wavelength moves to the long wavelength, the color purity is lowered, or efficiency of the device is lowered because of reduced effect of light emission. Therefore, in order to increase color purity and increase emission efficiency through transferring of energy, a host/dopant system may be used as the light emitting material.

In order to sufficiently show excellent properties of the above organic light emitting device, a material constituting the organic material layer in the device, for example, the hole injection material, the hole transport material, the light emitting material, the electron transport material, the electron injection material and the like should be supported by stable and efficient materials. However, the development of a stable and efficient organic material layer material for organic light emitting devices has not yet been made. Therefore, there is a demand for developing a novel material, and the demand for developing the novel material is similarly applied to the other organic electronic device.

DISCLOSURE

Technical Problem

In consideration of the problems in the related art, it is an object of the present invention to provide a material that is capable of largely improving low voltage, light emitting efficiency, stability and a life span of a device, and an organic electronic device using the same.

It is another object of the present invention to provide a material that has thermal stability and a subliming ability required in a vacuum deposition process, and an organic electronic device using the same.

Technical Solution

In order to accomplish the above objects, the present invention provides a novel nitrogen-containing heterocyclic derivative that is represented by the following Formula 1 or includes two or more structures of the following Formula 1:

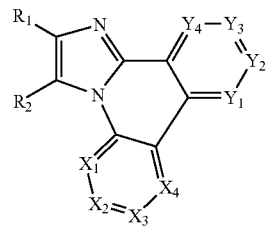

[Formula 1]

wherein $X_1$ is N or $CR_3$, $X_2$ is N or $CR_4$, $X_3$ is N or $CR_5$, $X_4$ is N or $CR_6$, $Y_1$ is N or $CR_7$, $Y_2$ is N or $CR_8$, $Y_3$ is N or $CR_9$, $Y_4$ is N or $CR_{10}$, $X_1$ to $X_4$ and $Y_1$ to $Y_4$ are not simultaneously N, $R_3$ to $R_{10}$ are each independently -(L)p-(Y)q, in which p is an integer in the range of 0 to 10, q is an integer in the range of 1 to 10, and two or more adjacent groups of $R_3$ to $R_{10}$ may form a monocyclic or polycyclic ring, L is oxygen; sulfur; substituted or unsubstituted nitrogen; substituted or unsubstituted phosphorus; substituted or unsubstituted arylene group; substituted or unsubstituted alkenylene group; substituted or unsubstituted fluorenylene group; substituted or unsubstituted carbazolylene group; or substituted or unsubstituted heteroarylene group that includes one or more of n, o, and s atoms, Y is hydrogen; heavy hydrogen; halogen group; nitrile group; nitro group; hydroxy group; substituted or unsubstituted cycloalkyl group; substituted or unsubstituted alkoxy group; substituted or unsubstituted aryloxy group; substituted or unsubstituted alkylthioxy group; substituted or unsubstituted arylthioxy group; substituted or unsubstituted alkylsulfoxy group; substituted or unsubstituted arylsulfoxy group; substituted or unsubstituted alkenyl group; substituted or unsubstituted silyl group; substituted or unsubstituted boron group; substituted or unsubstituted alkylamine group; substituted or unsubstituted aralkylamine group; substituted or unsubstituted arylamine group; substituted or unsubstituted heteroarylamine group; substituted or unsubstituted aryl group; substituted or unsubstituted fluorenyl group; substituted or unsubstituted carbazole group; or substituted or unsubstituted heterorng group that includes one or more of n, o, and s atoms;

$R_1$ and $R_2$ may be connected to each other to form or not to form substituted or unsubstituted aliphatic, aromatic, or heteroaromatic monocyclic or polycyclic ring, in the case of when $R_1$ and $R_2$ do not form a ring, $R_1$ and $R_2$ are the same as each other or different from each other, and each independently substituted or unsubstituted $C_3 \sim C_{40}$ cycloalkyl group; substituted or unsubstituted $C_6 \sim C_{60}$ aryl group; substituted or unsubstituted $C_2 \sim C_{40}$ alkenyl group; substituted or unsubstituted $C_2 \sim C_{60}$ heterorng group, an aromatic or heteroaromatic monocyclic or polycyclic ring that is formed by connecting $R_1$, $R_2$ and $R_1$ and $R_2$ to each other may be each independently substituted by -(L)p-(Y)q, in the case of when there are two or more L and Y in Formula 1, they are each independently the same as or different from each other, in the case of when $X_1$ to $X_4$ and $Y_1$ to $Y_4$ are simultaneously $CR_3$ to $CR_{10}$, at least one of $R_3$ to $R_{10}$ has a substituent group rather than hydrogen, or $R_1$ and $R_2$ are connected to each other to form the substituted monocyclic or polycyclic ring.

In addition, since the compound of Formula 1 has a high glass transition temperature (Tg), it has excellent thermal stability. Such increase in thermal stability is an important factor providing driving stability to the device.

In Formula 1, in the case of when $R_1$ and $R_2$ are connected to each other to form one ring, it may be represented by the following Formula 2:

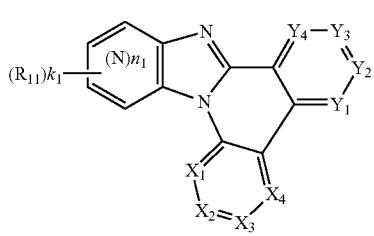

[Formula 2]

wherein $X_1$ to $X_4$ and $Y_1$ to $Y_4$ are the same as those defined in Formula 1, in (N)$n_1$, N means a nitrogen atom, and the nitrogen atom is used instead of a carbon atom in a benzene ring, in (N)$n_1$, $n_1$ is an integer in the range of 0 to 6, $R_{11}$ is the same as definitions of $R_3$ to $R_{10}$ in Formula 1, and $k_1$ is an integer in the range of 0 to 4, and in the case of when $k_1$ is an integer of 2 or more, $R_{11}$ may be different from each other.

In the case of when $R_1$ and $R_2$ are connected to each other to form two or more polycyclic rings, it may be represented by the following Formulas 3-1 and 3-2:

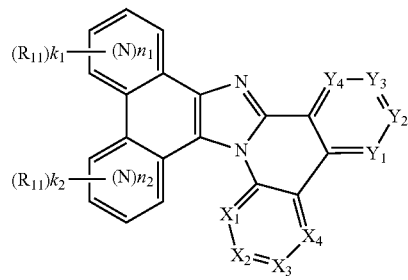

[Formula 3-1]

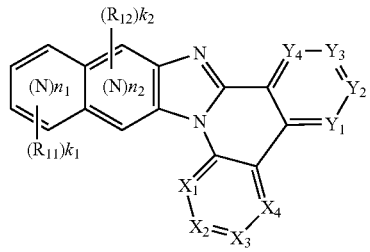

[Formula 3-2]

in Formulas 3-1 and 3-2, $X_1$ to $X_4$ and $Y_1$ to $Y_4$ are the same as those defined in Formula 1, in (N)$n_1$ and (N)$n_2$, N means a nitrogen atom, and the nitrogen atom is used instead of a carbon atom in a benzene ring, in (N)$n_1$, $n_1$ is an integer in the range of 0 to 2, in (N)$n_2$, $n_2$ is an integer in the range of 0 to 2, $R_{11}$ and $R_{12}$ are the same as definitions of $R_3$ to $R_{10}$ in Formula 1, in Formula 3-1, $k_1$ is an integer in the range of 0 to 4, $k_2$ is an integer in the range of 0 to 4, in Formula 3-2, $k_1$ is an integer in the range of 0 to 4, $k_2$ is an integer in the range of 0 to 2, in the case of when $k_1$ is an integer of 2 or more, $R_{11}$ may be different from each other, and in the case of when $k_2$ is an integer of 2 or more, $R_{12}$ may be different from each other.

In the case of when $R_1$ and $R_2$ do not form a ring, $R_1$ and $R_2$ may be a hexagonal heteroaromatic ring group that includes a phenyl group substituted or unsubstituted by $R_{11}$ and $R_{12}$ or substituted or unsubstituted nitrogen (N) atom. For example, Formula 1 may be represented by the following Formula 4-1.

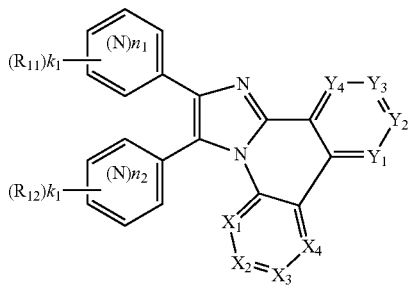

[Formula 4-1]

wherein $X_1$ to $X_4$ and $Y_1$ to $Y_4$ are the same as those defined in Formula 1, in $(N)n_1$ and $(N)n_2$, N means a nitrogen atom, and the nitrogen atom is used instead of a carbon atom in a benzene ring, in $(N)n_1$, $n_1$ is an integer in the range of 0 to 2, in $(N)n_2$, $n_2$ is an integer in the range of 0 to 2, $R_{11}$ and $R_{12}$ are the same as definitions of $R_3$ to $R_{10}$ in Formula 1, $k_1$ is an integer in the range of 0 to 4, $k_2$ is an integer in the range of 0 to 4, in the case of when $k_1$ is an integer of 2 or more, $R_{11}$ may be different from each other, and in the case of when $k_2$ is an integer of 2 or more, $R_{12}$ may be different from each other.

In addition, the present invention provides an organic electronic device which includes a first electrode, a second electrode, and one or more organic material layers that are disposed between the first electrode and the second electrode, wherein one or more layers of the organic material layers include the novel nitrogen-containing heterocyclic derivative.

Advantageous Effects

A novel nitrogen-containing heterocyclic derivative according to the present invention may be used as a material of an organic material layer of an organic light emitting device and an organic electronic device, and the organic light emitting device and organic electronic device using the same have excellent properties in views of an increase in efficiency, a reduction in driving voltage, lengthening of a life span, and an increase in stability. In particular, the novel nitrogen-containing heterocyclic derivative according to the present invention has excellent thermal stability, deep HOMO level, a wide band gap, a high triplet state and hole stability. It may be used alone or as a mixture with impurity in the organic light emitting device and the organic electronic device, improve light efficiency, and improve a life span property of the device by thermal stability of the compound.

DESCRIPTION OF REFERENCE NUMERALS AND SIGNS

Figure 1:
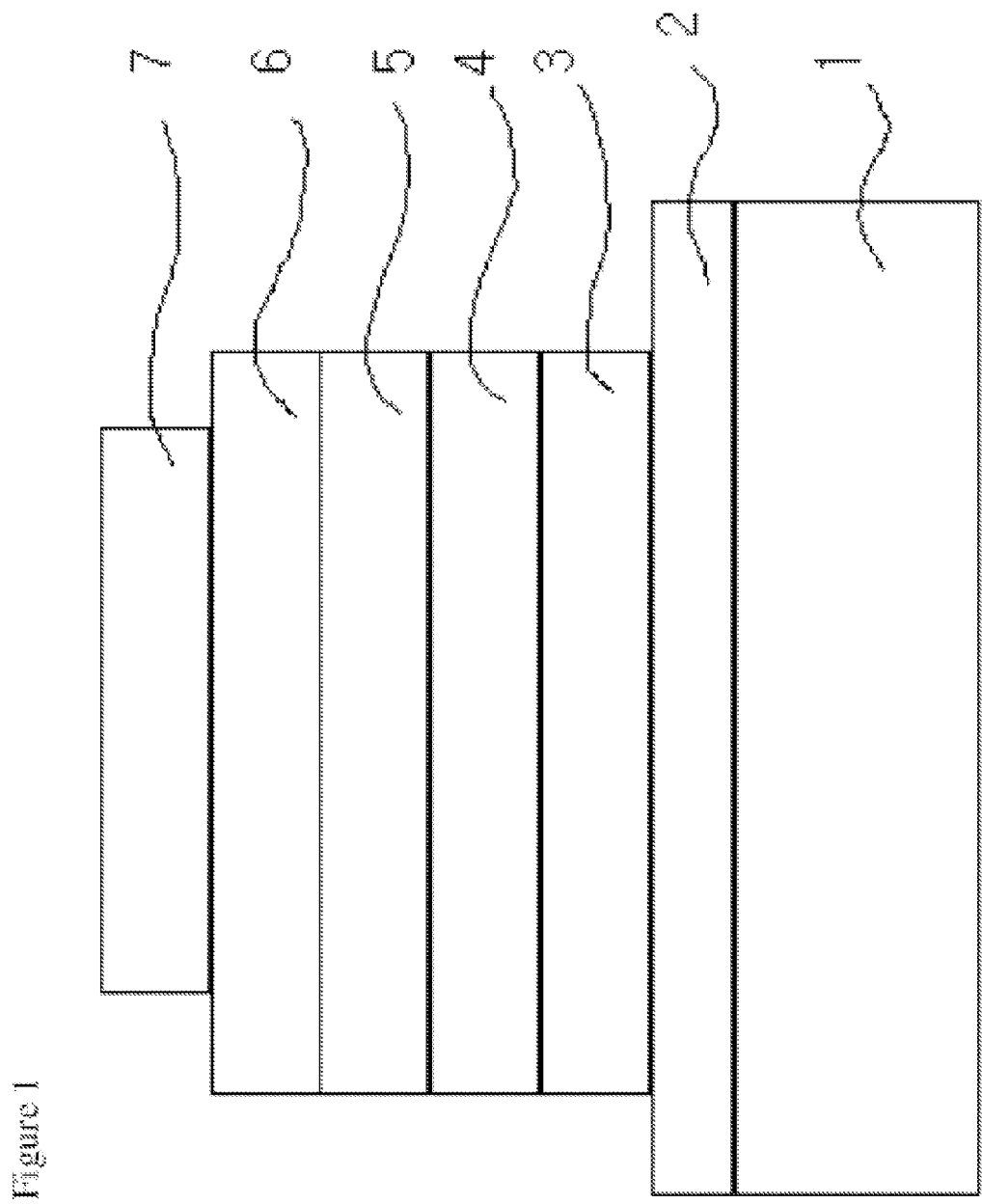
FIG. 1 illustrates an example of an organic light emitting device according to the present invention.
Figure 2:
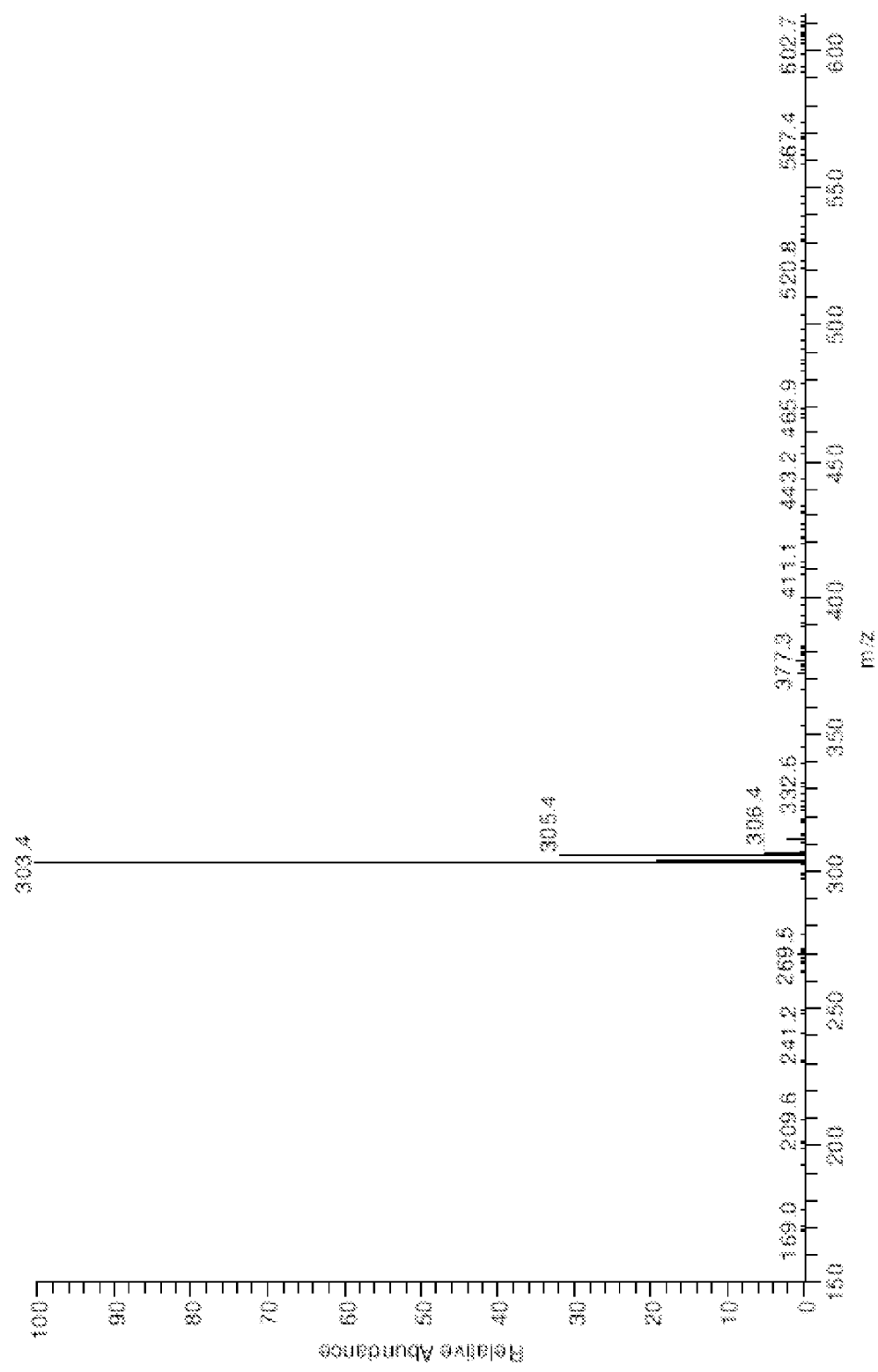
FIG. 2 is a mass spectrum of the compound A-13.
Figure 3:
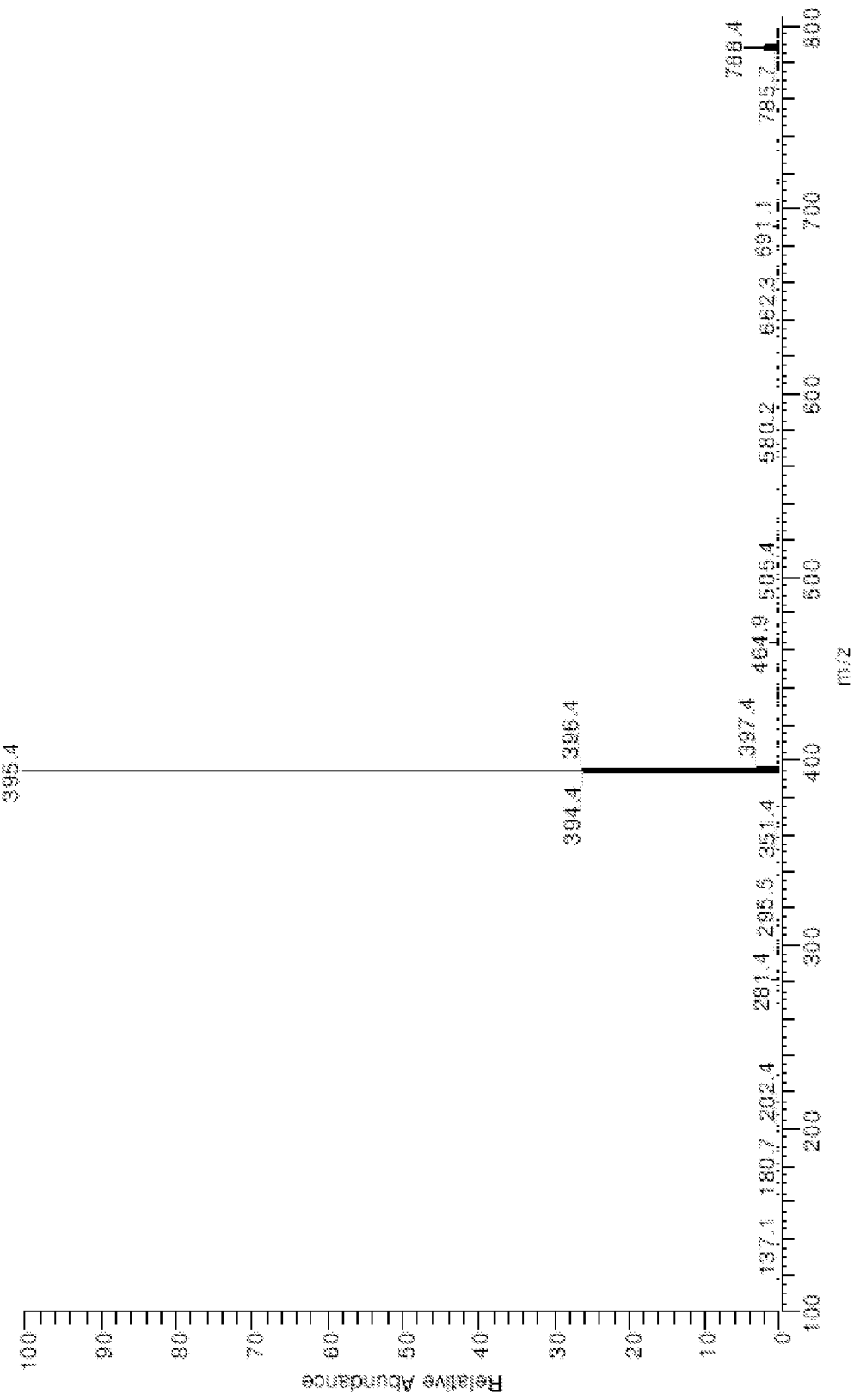
FIG. 3 is a mass spectrum of the compound A-14.
Figure 4:
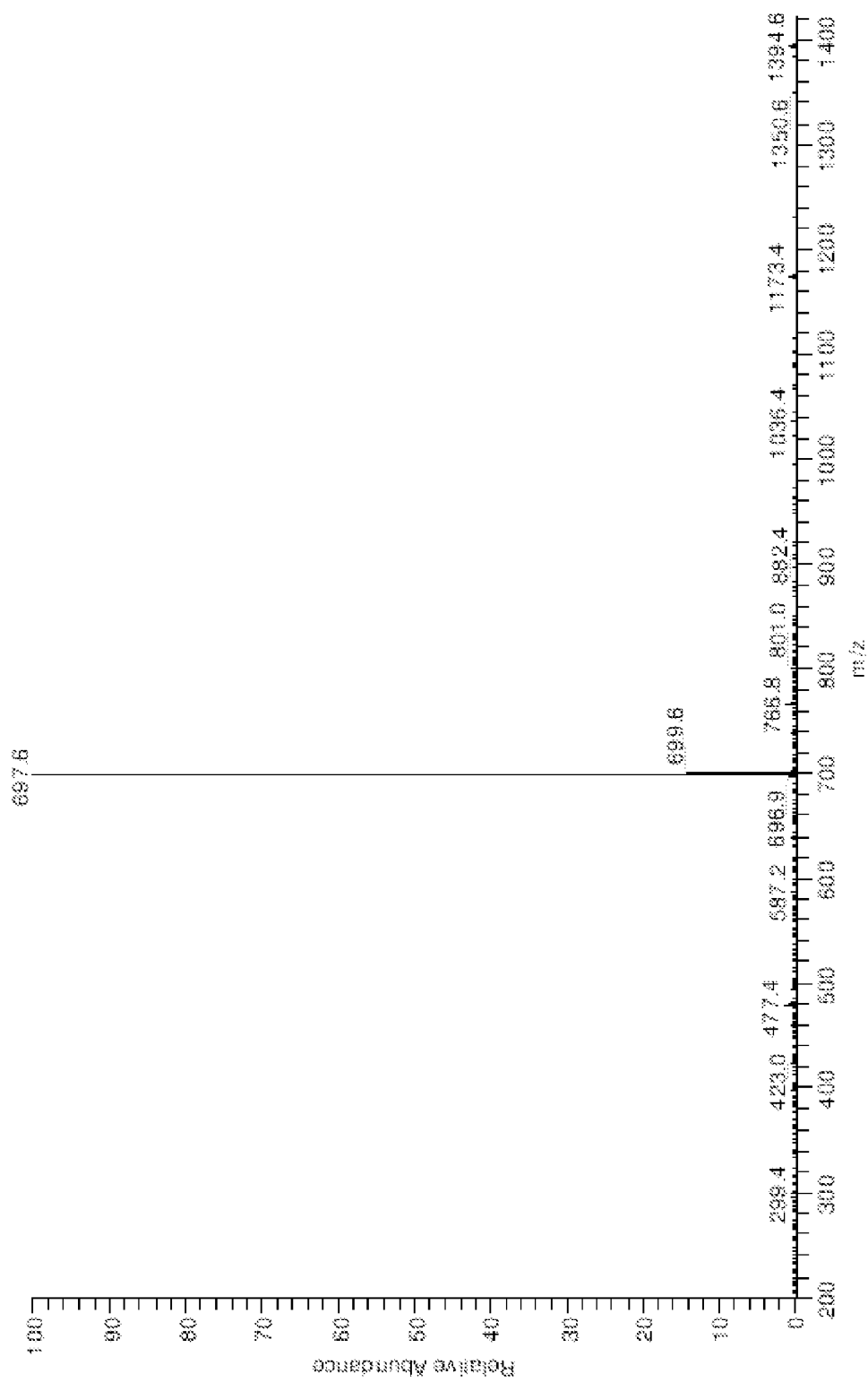
FIG. 4 is a mass spectrum of the compound 1-a-15.
Figure 5:
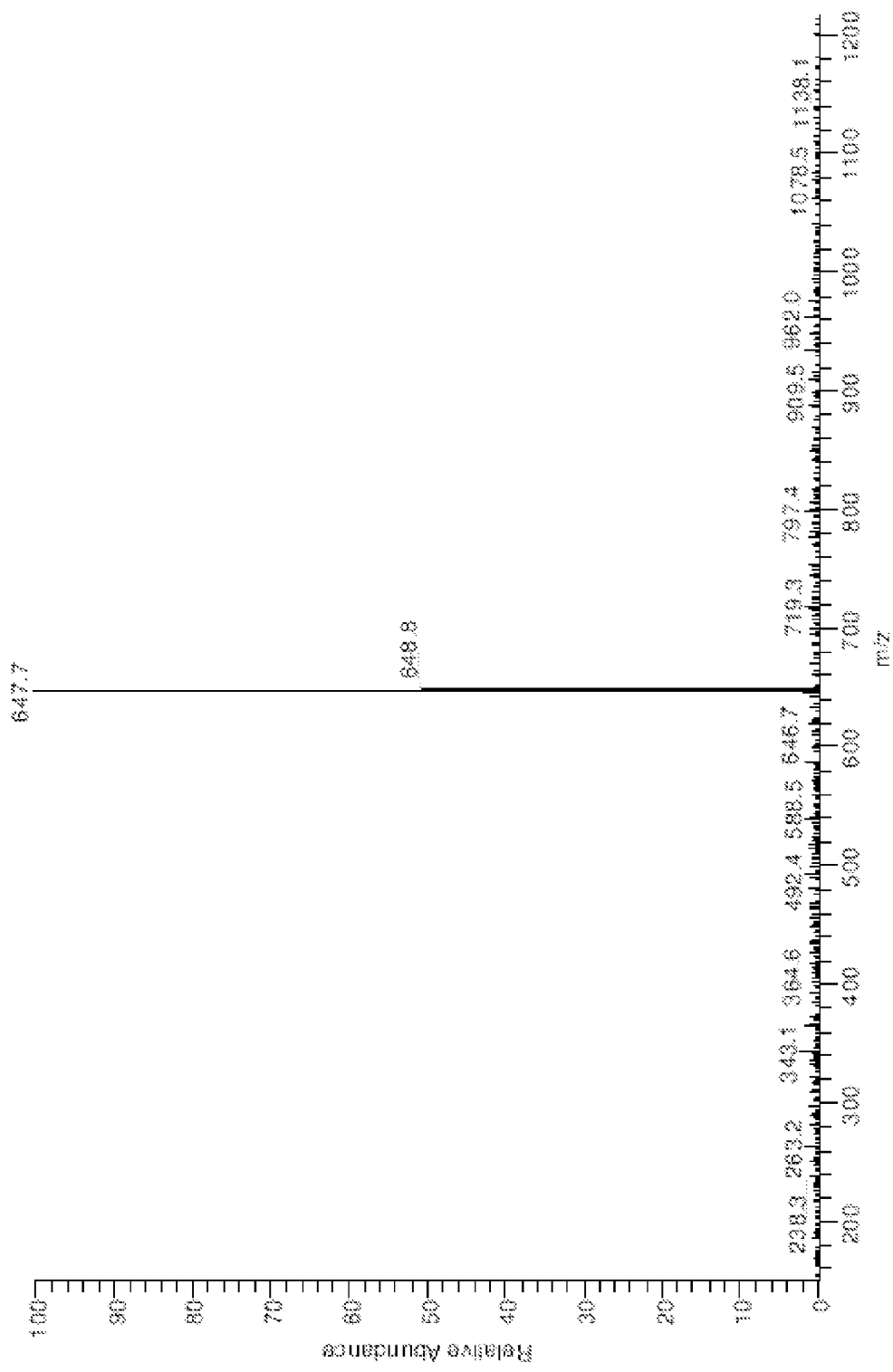
FIG. 5 is a mass spectrum of the compound 1-a-34.
Figure 6:
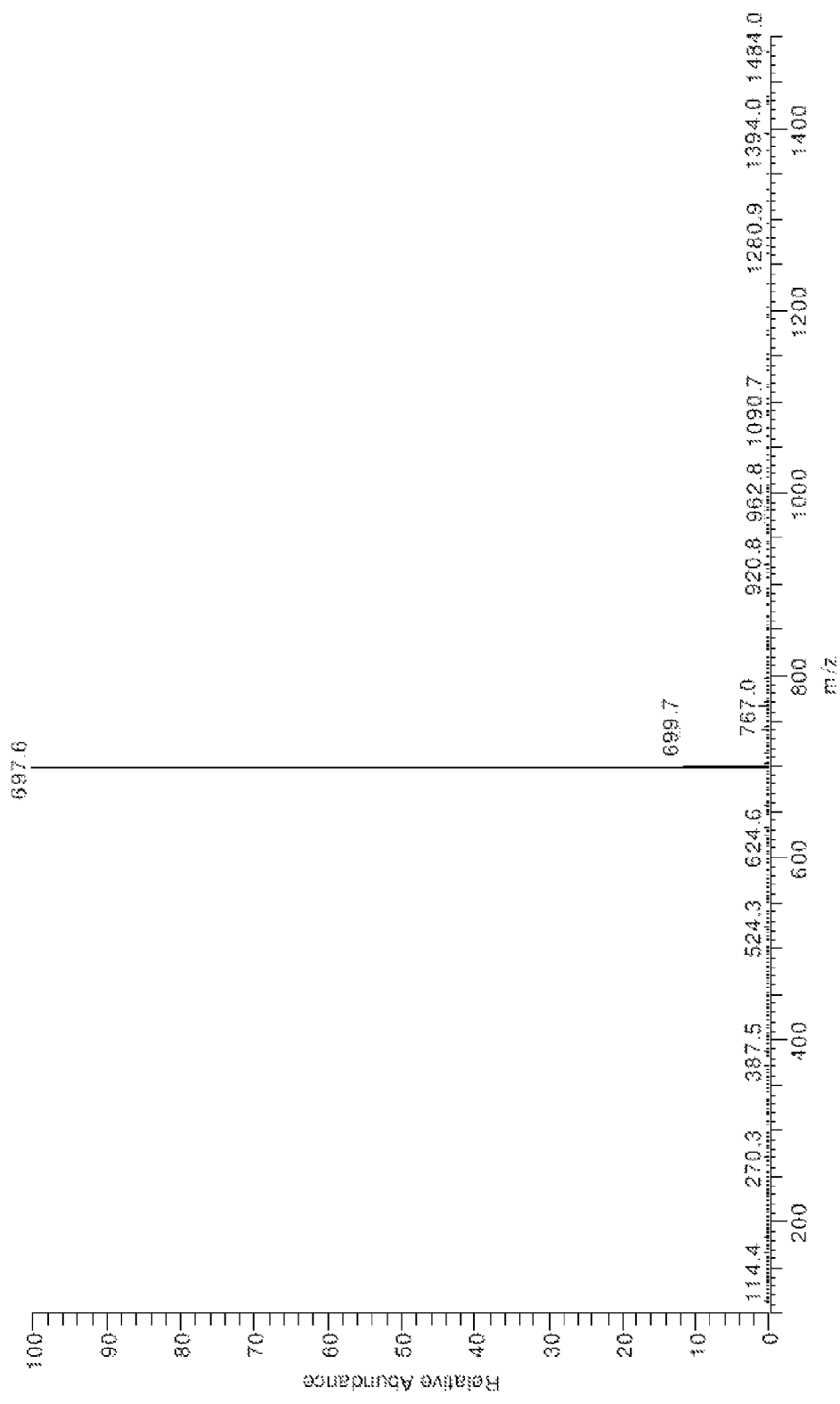
FIG. 6 is a mass spectrum of the compound 1-a-58.
Figure 7:
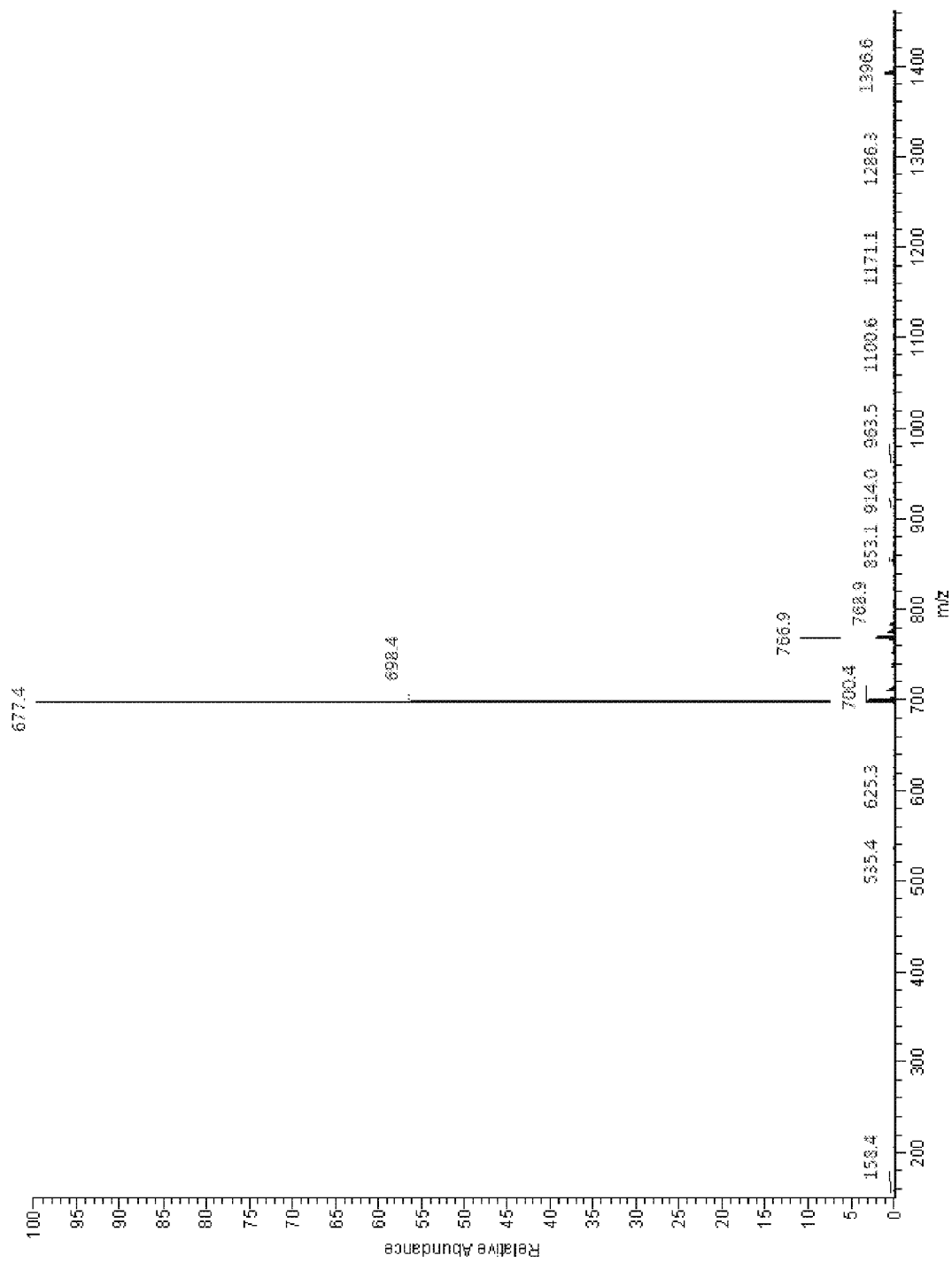
FIG. 7 is a mass spectrum of the compound 1-b-15.
Figure 8:
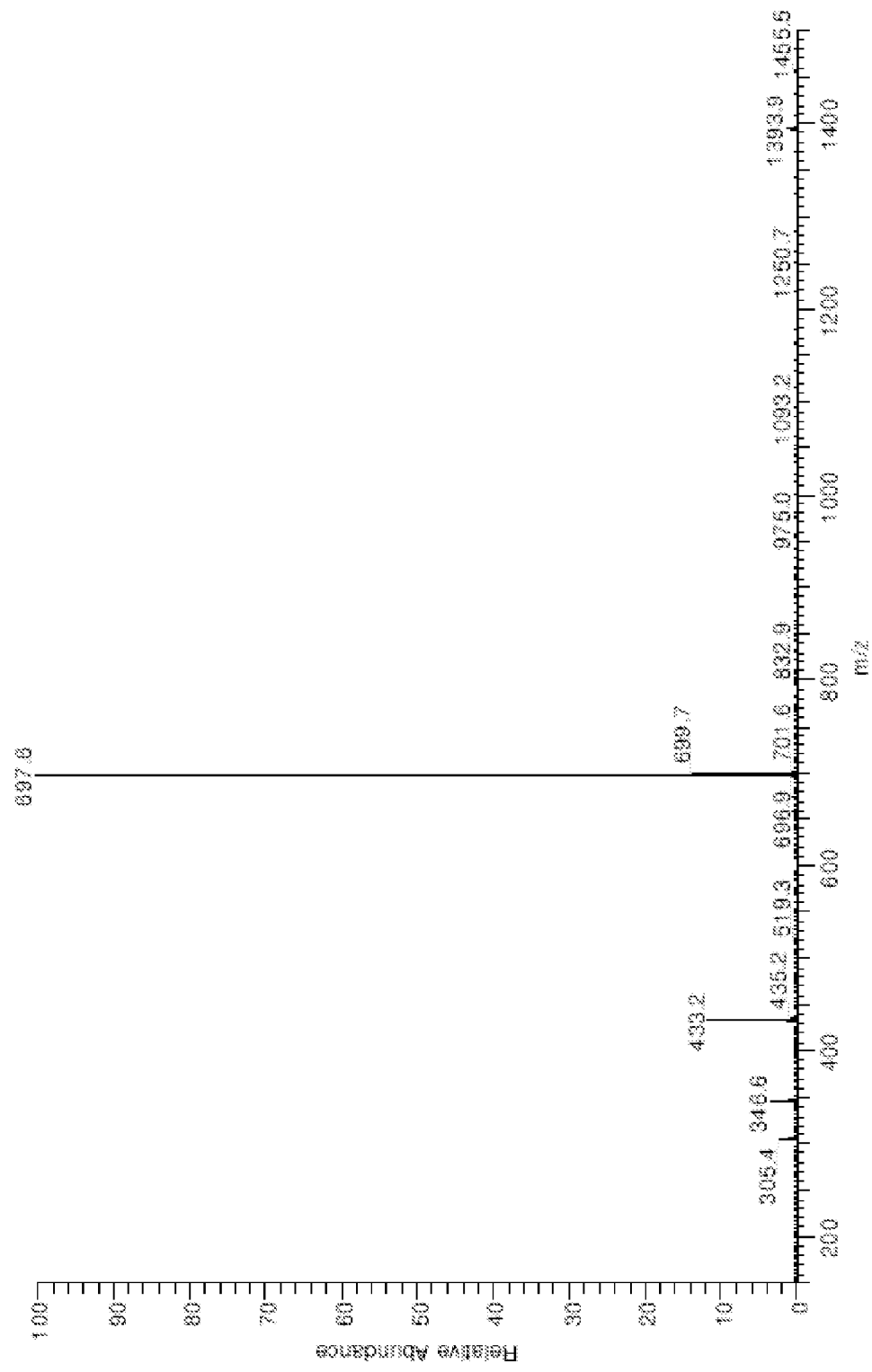
FIG. 8 is a mass spectrum of the compound 1-b-100.
Figure 9:
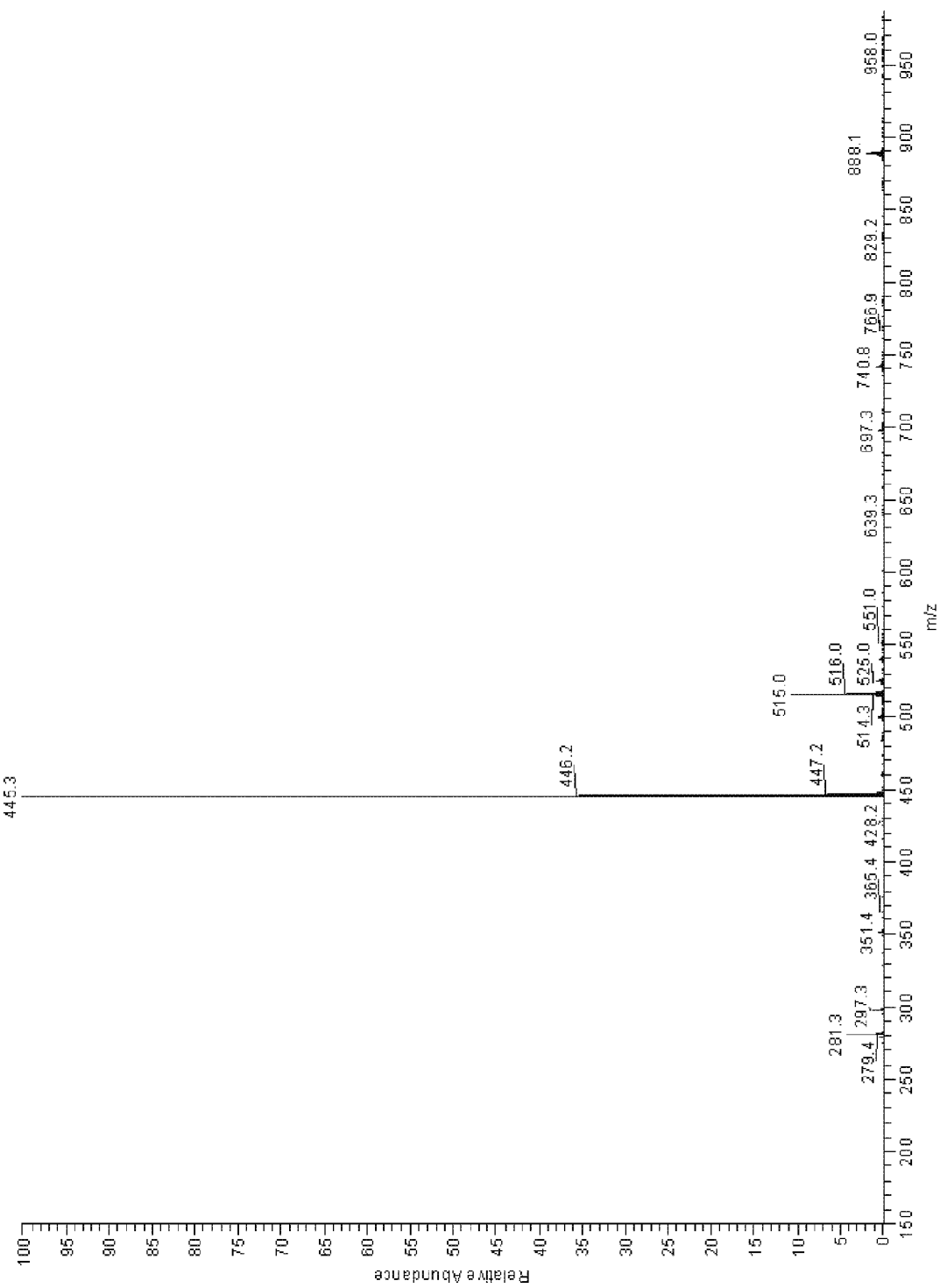
FIG. 9 is a mass spectrum of the compound 1-b-117.
Figure 10:
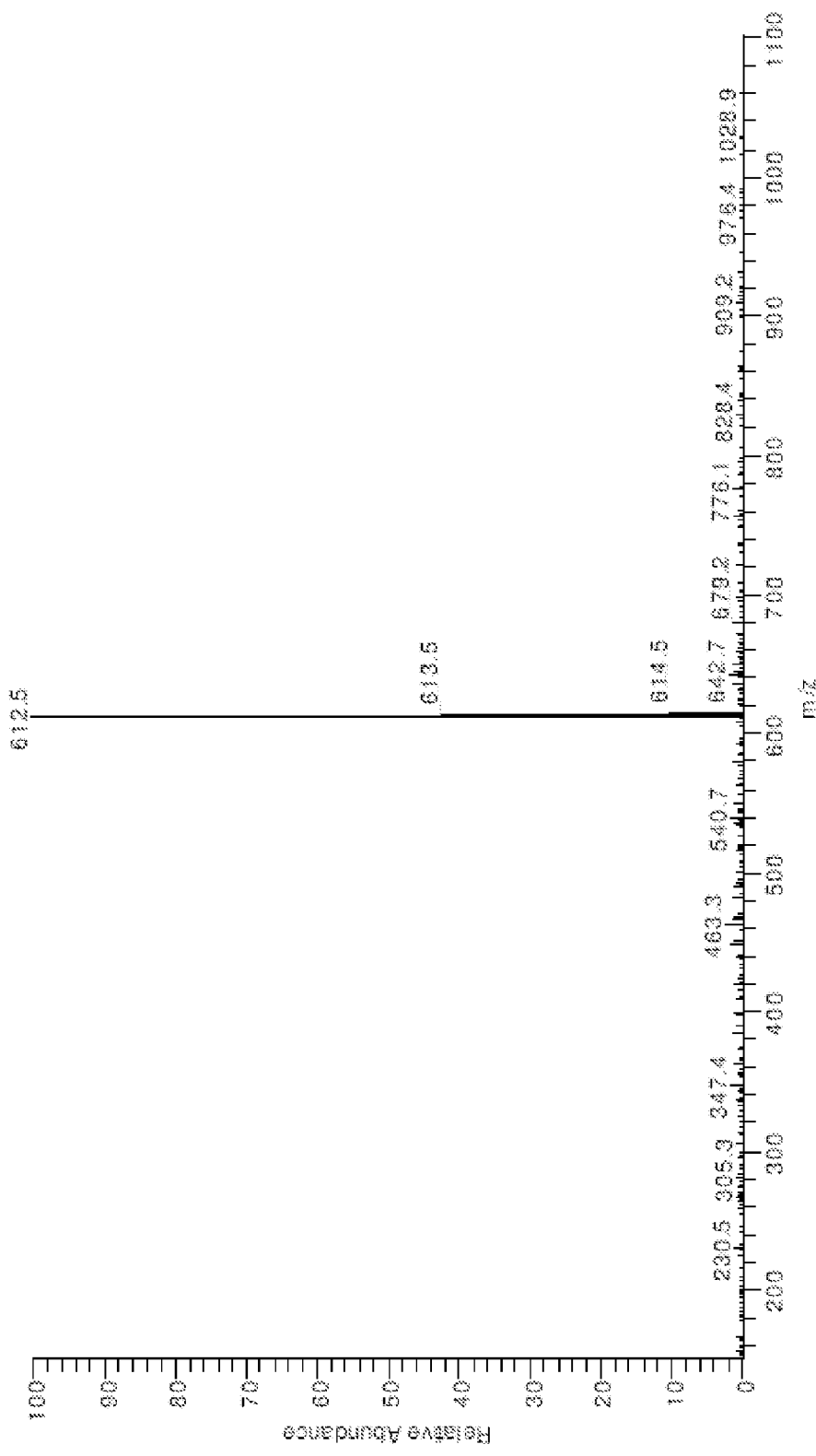
FIG. 10 is a mass spectrum of the compound 5-a-34.
Figure 11:
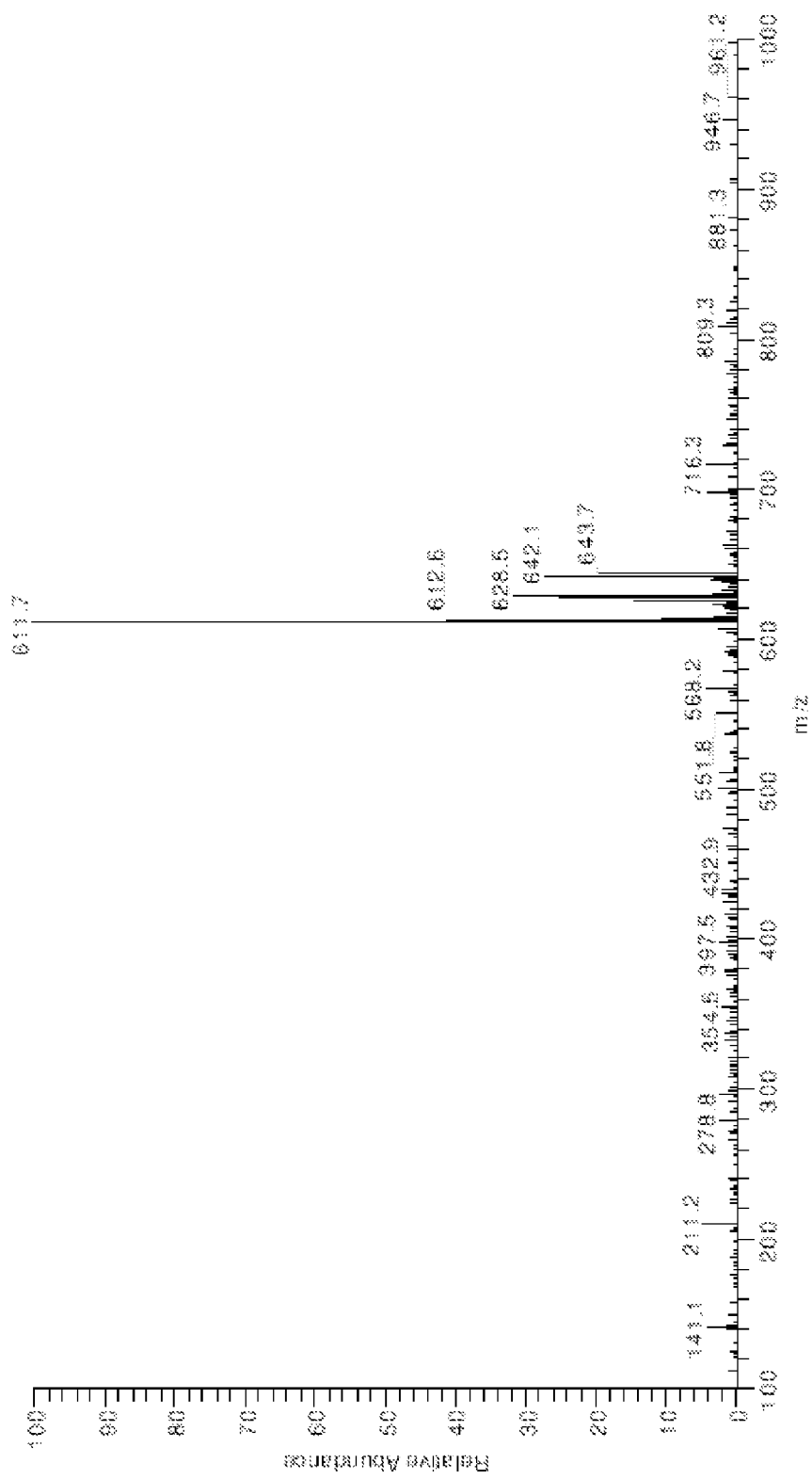
FIG. 11 is a mass spectrum of the compound 5-a-33.
Figure 12:
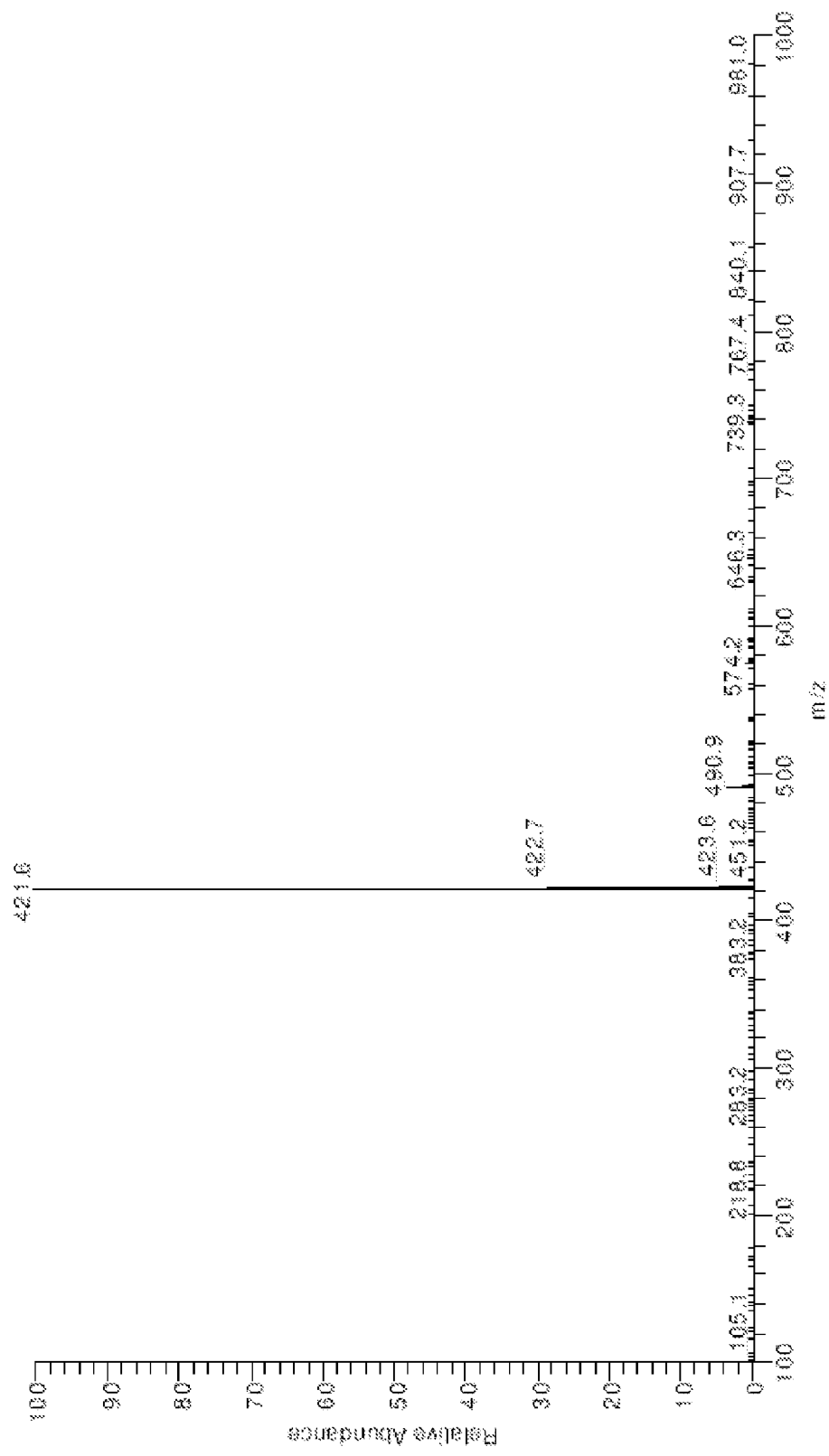
FIG. 12 is a mass spectrum of the compound 1-a-74.
Figure 13:
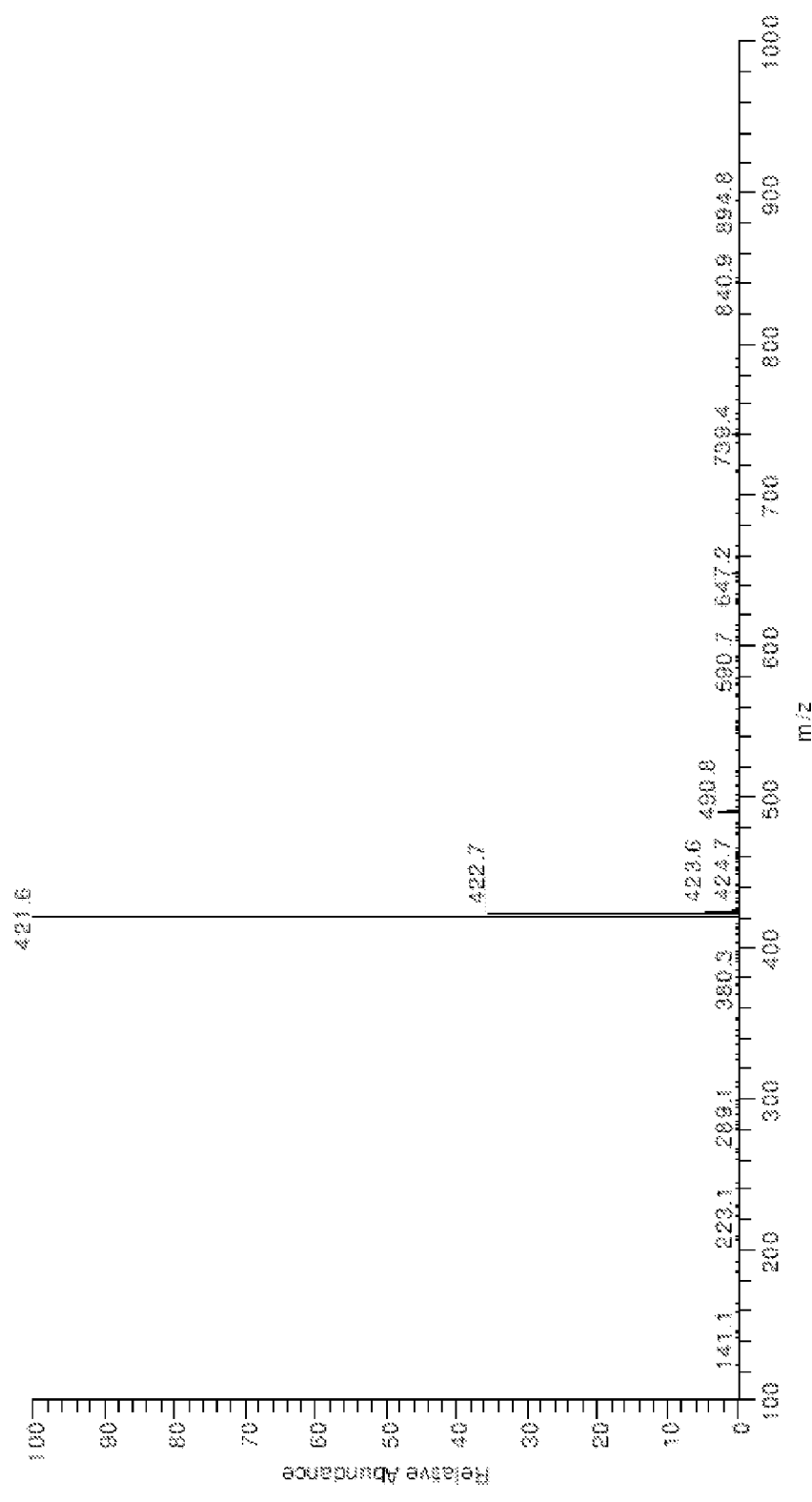
FIG. 13 is a mass spectrum of the compound 1-a-31.
Figure 14:
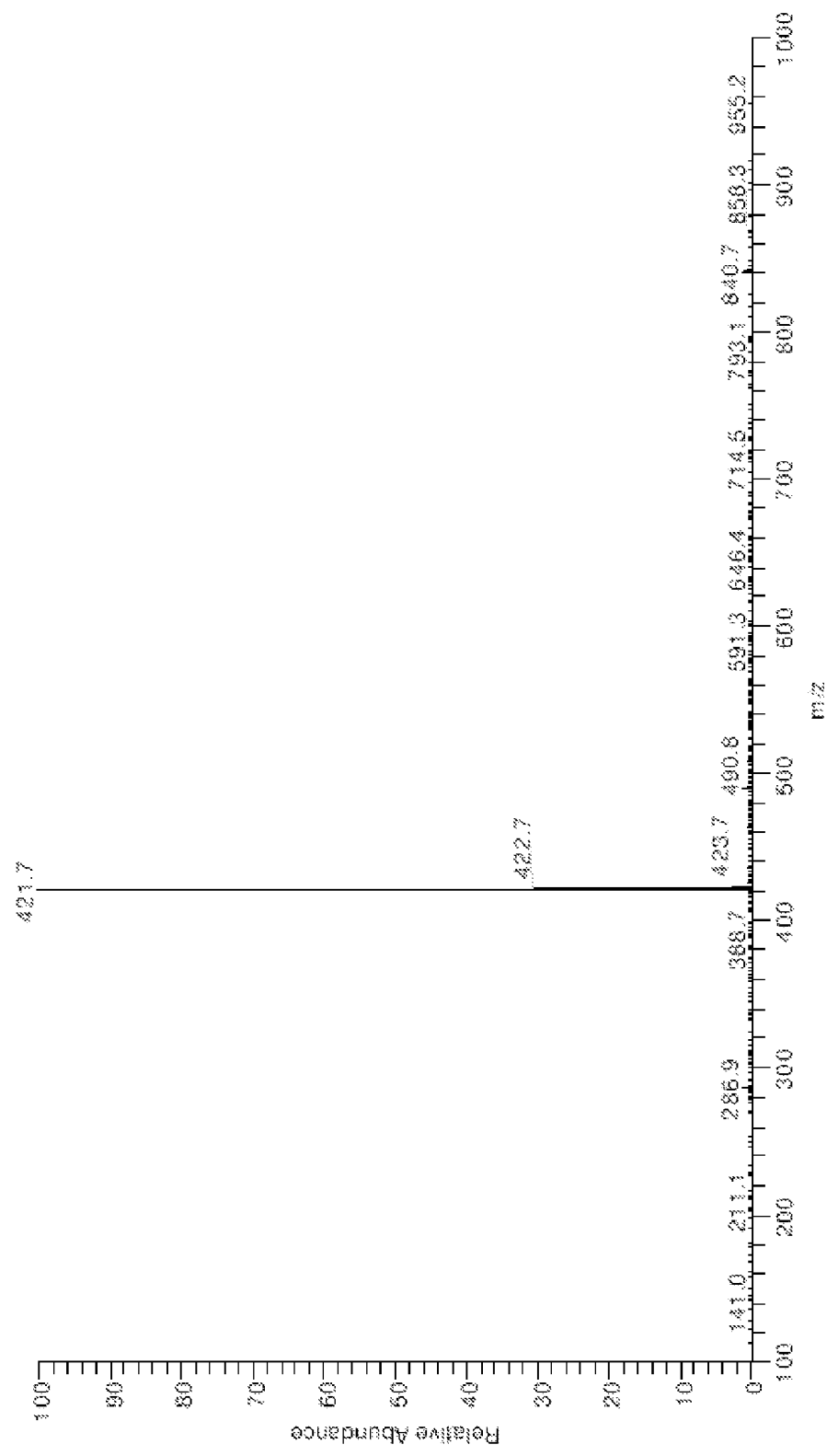
FIG. 14 is a mass spectrum of the compound 1-b-136.
Figure 15:
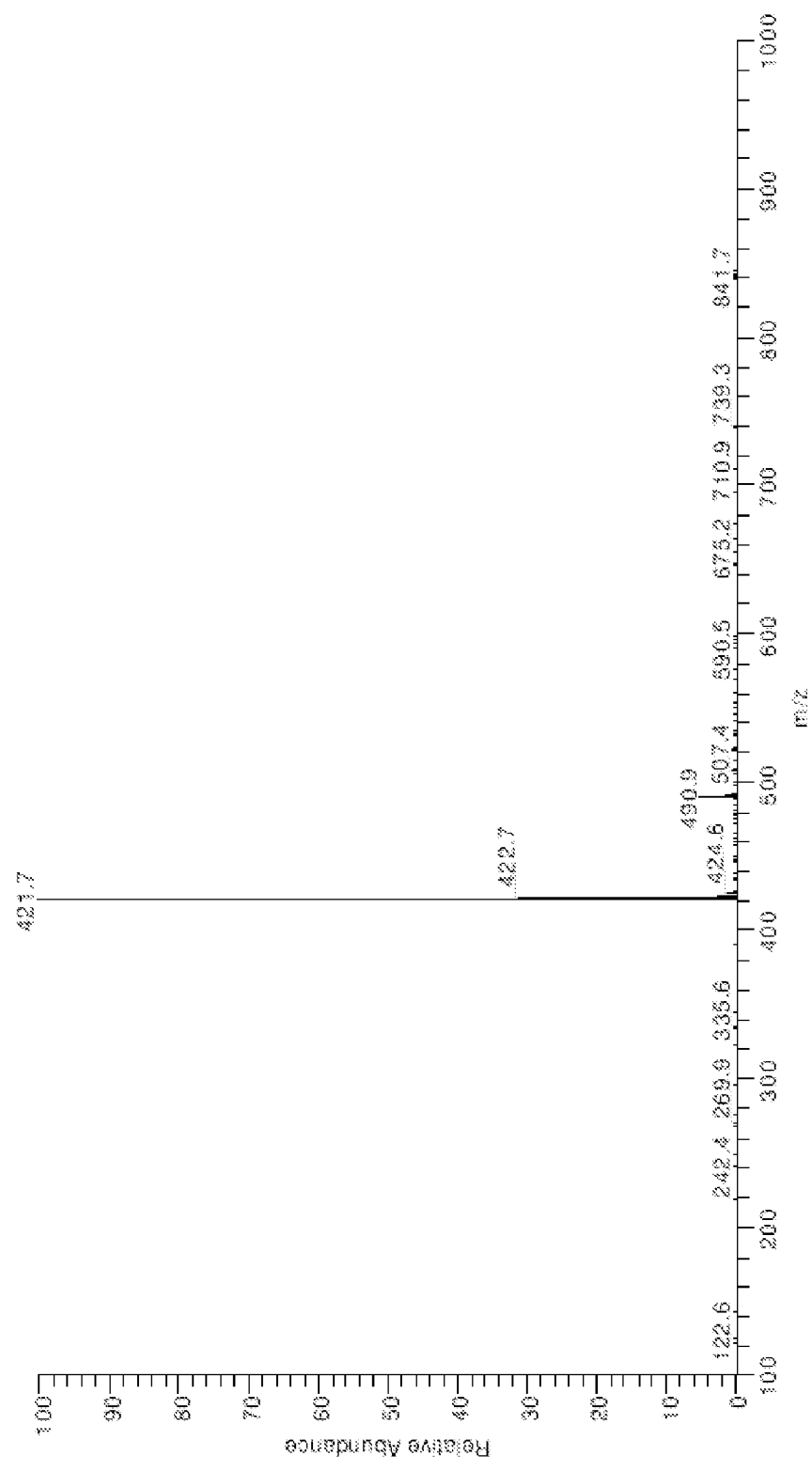
FIG. 15 is a mass spectrum of the compound 1-b-31.
Figure 16:
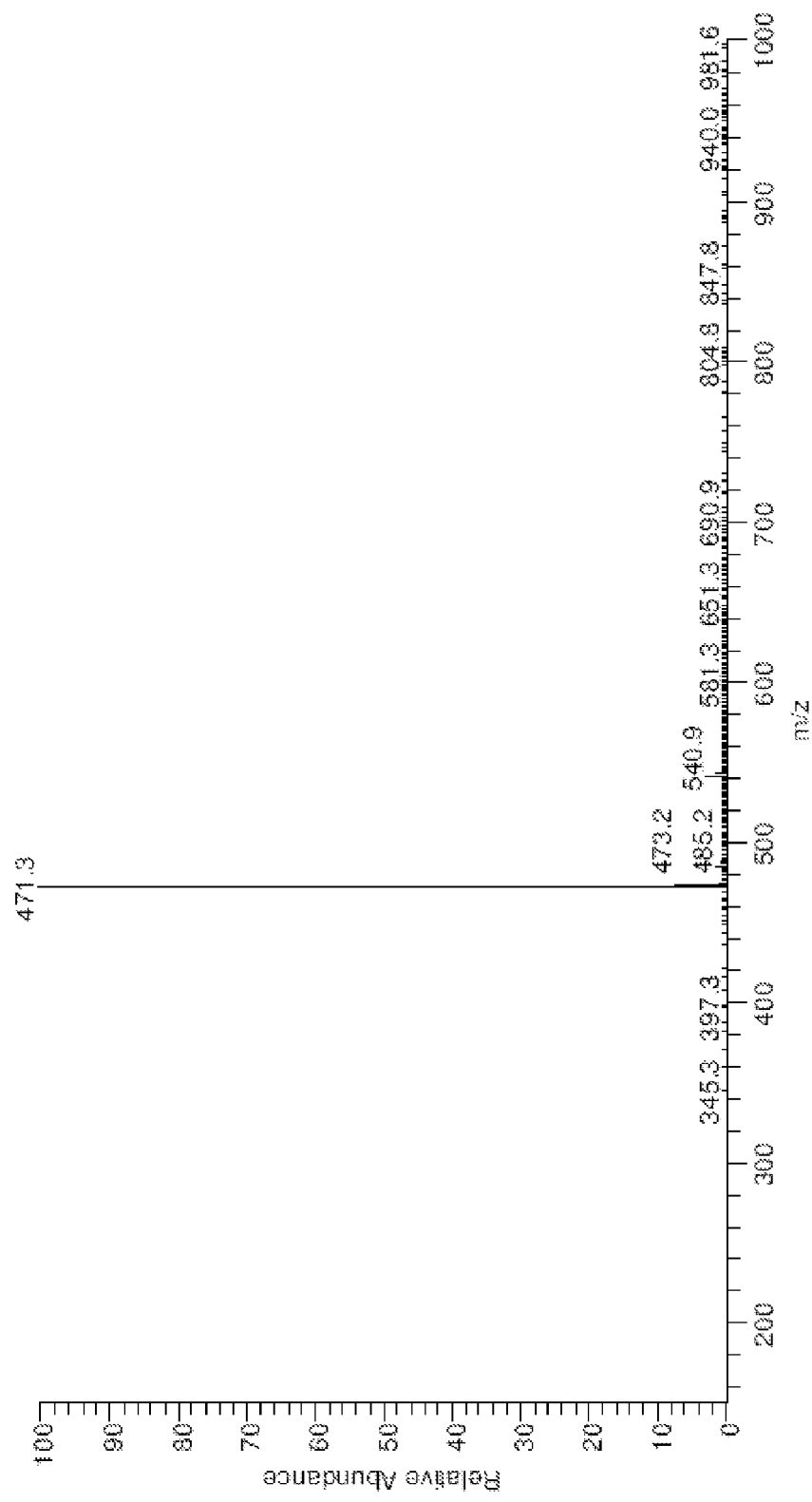
FIG. 16 is a mass spectrum of the compound 1-b-32.
Figure 17:
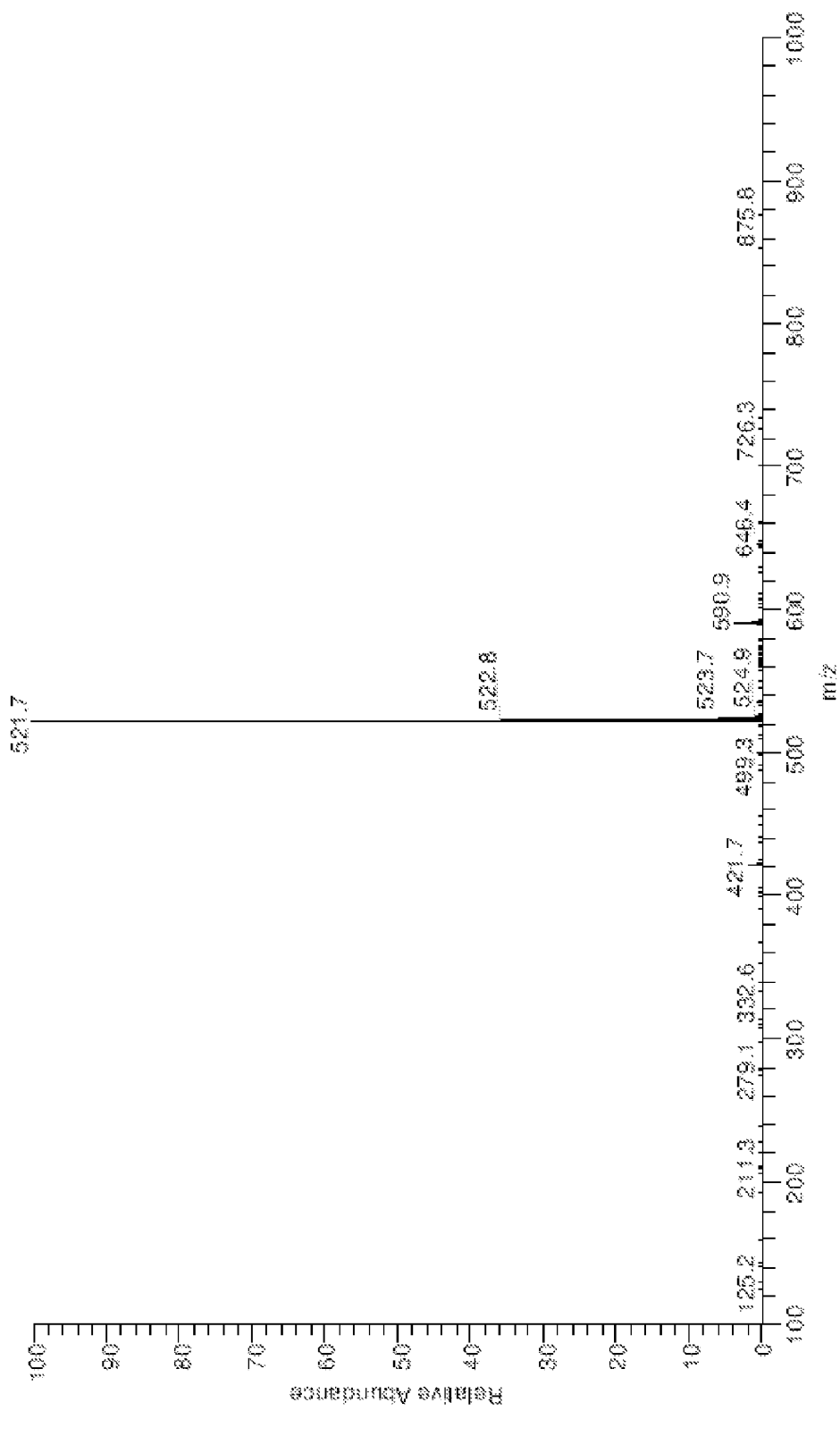
FIG. 17 is a mass spectrum of the compound 1-b-122.
Figure 18:
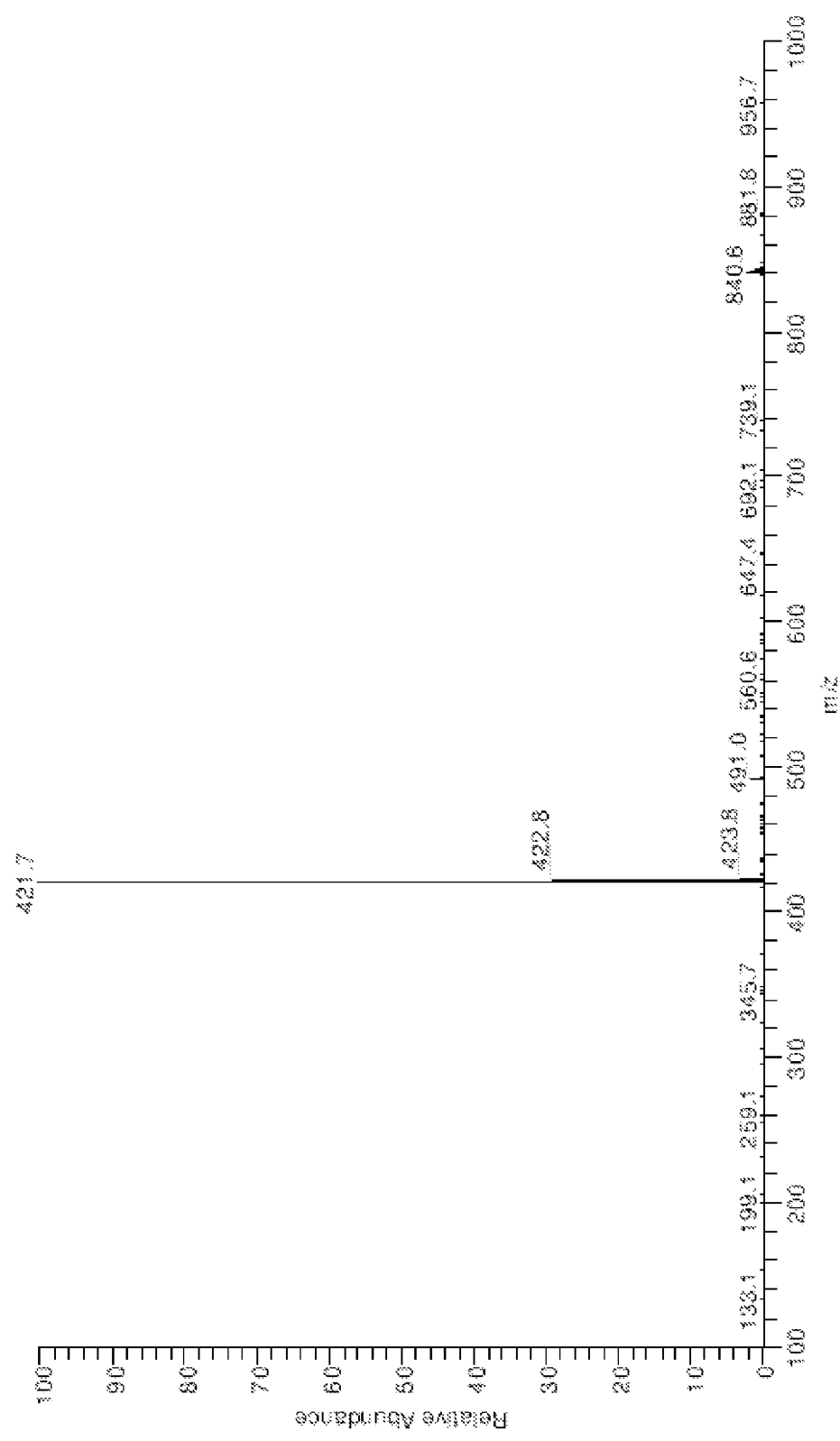
FIG. 18 is a mass spectrum of the compound 6-a-1.
Figure 19:
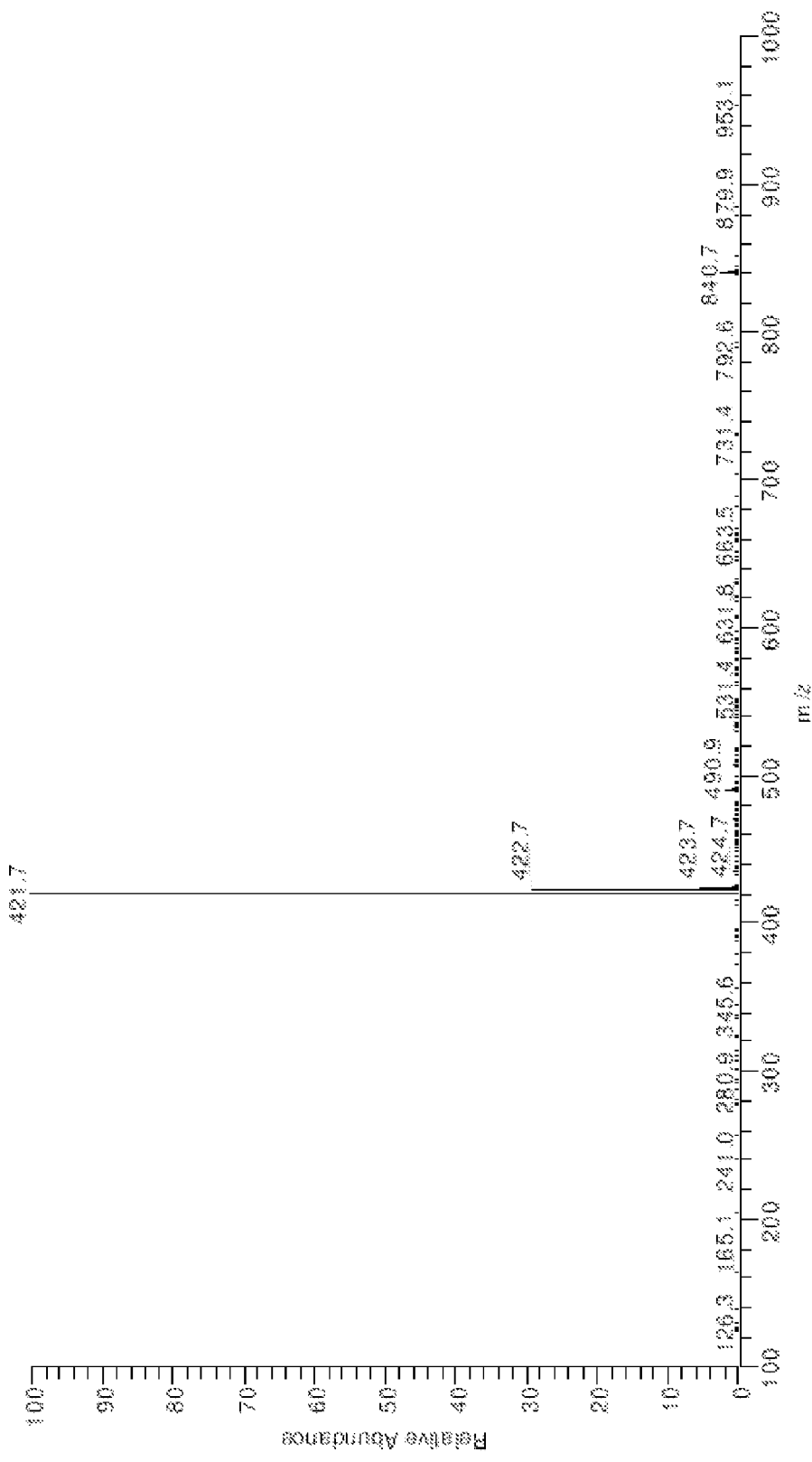
FIG. 19 is a mass spectrum of the compound 6-a-3.
Figure 20:
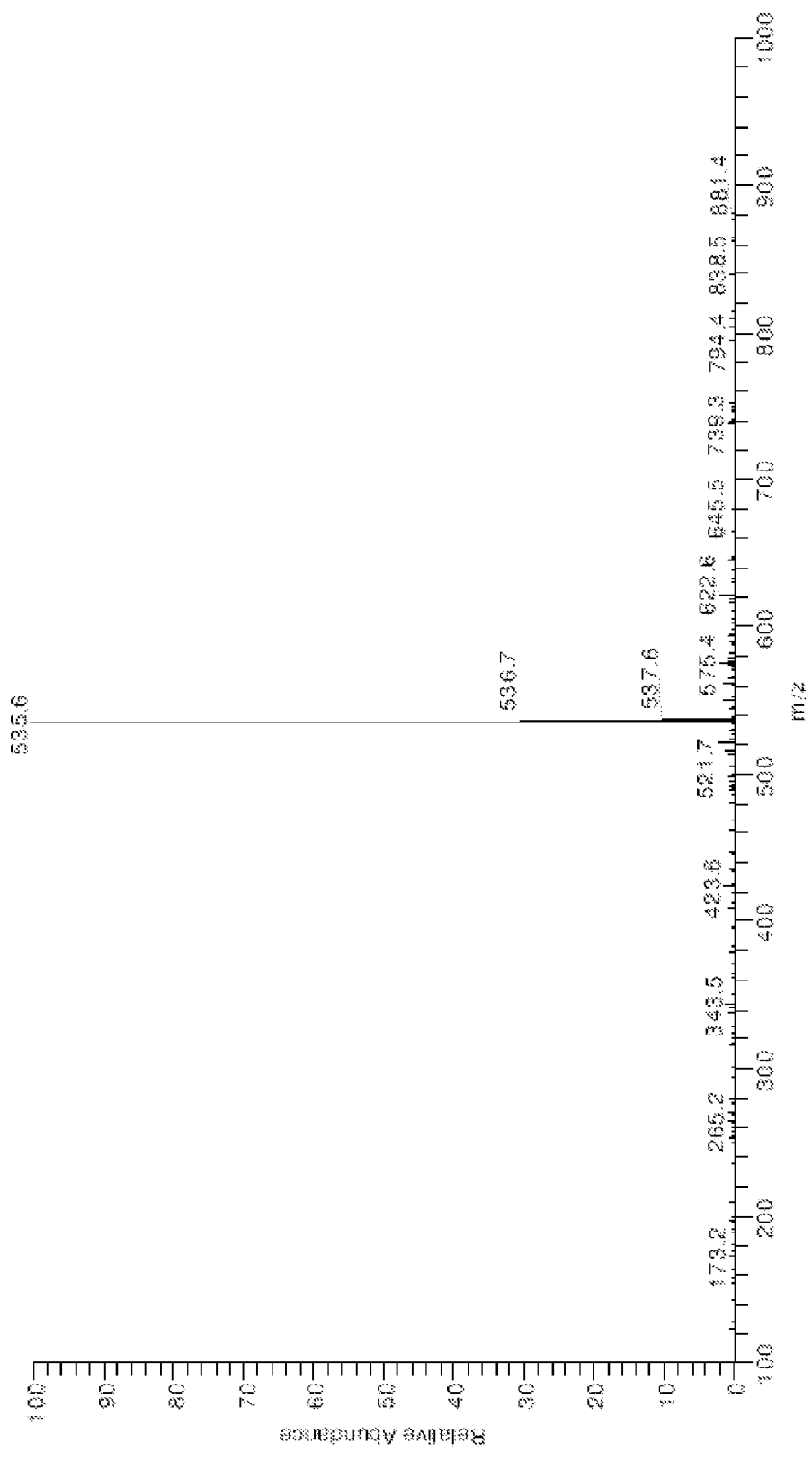
FIG. 20 is a mass spectrum of the compound 5-a-13.
Figure 21:
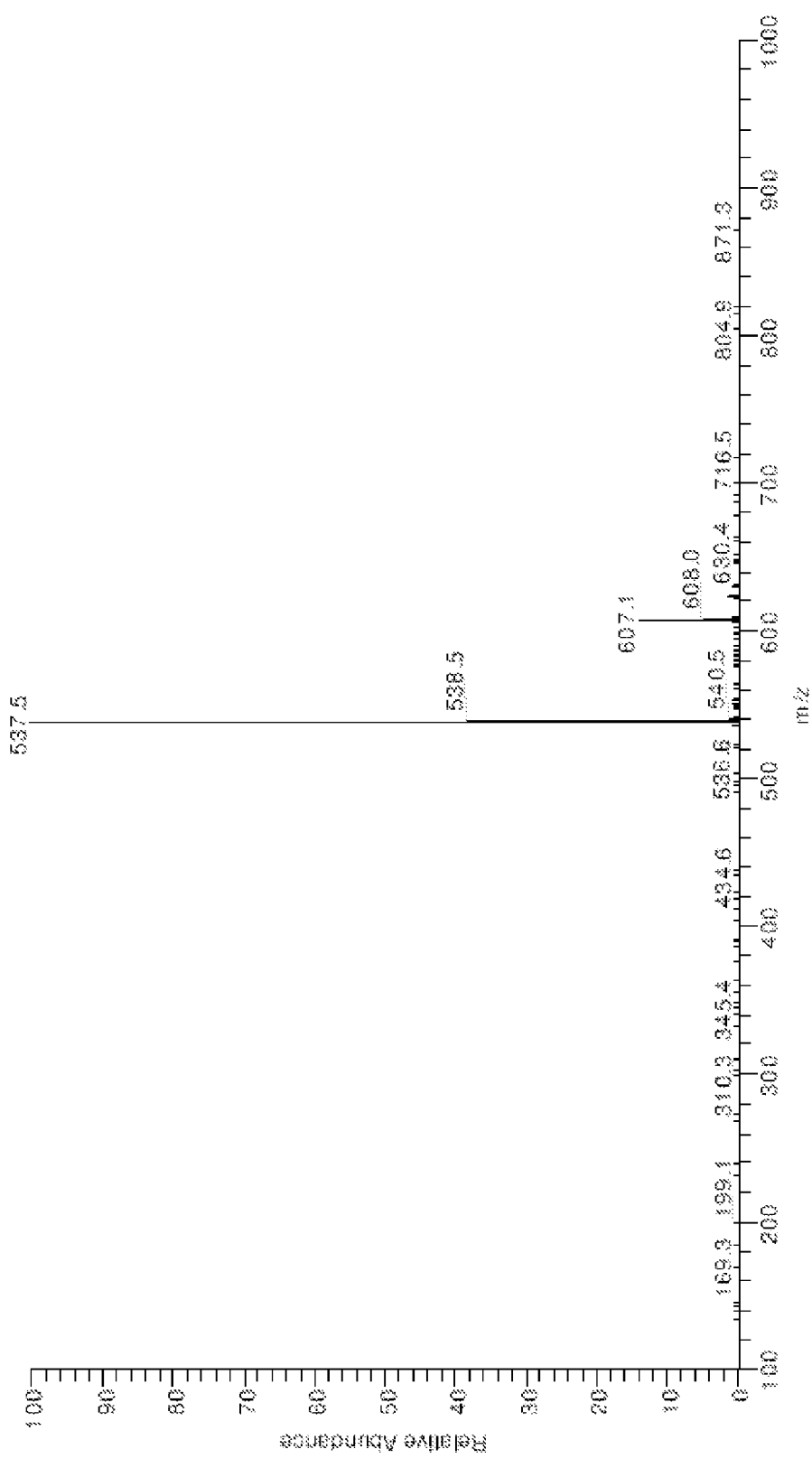
FIG. 21 is a mass spectrum of the compound 1-b-139.
Figure 22:
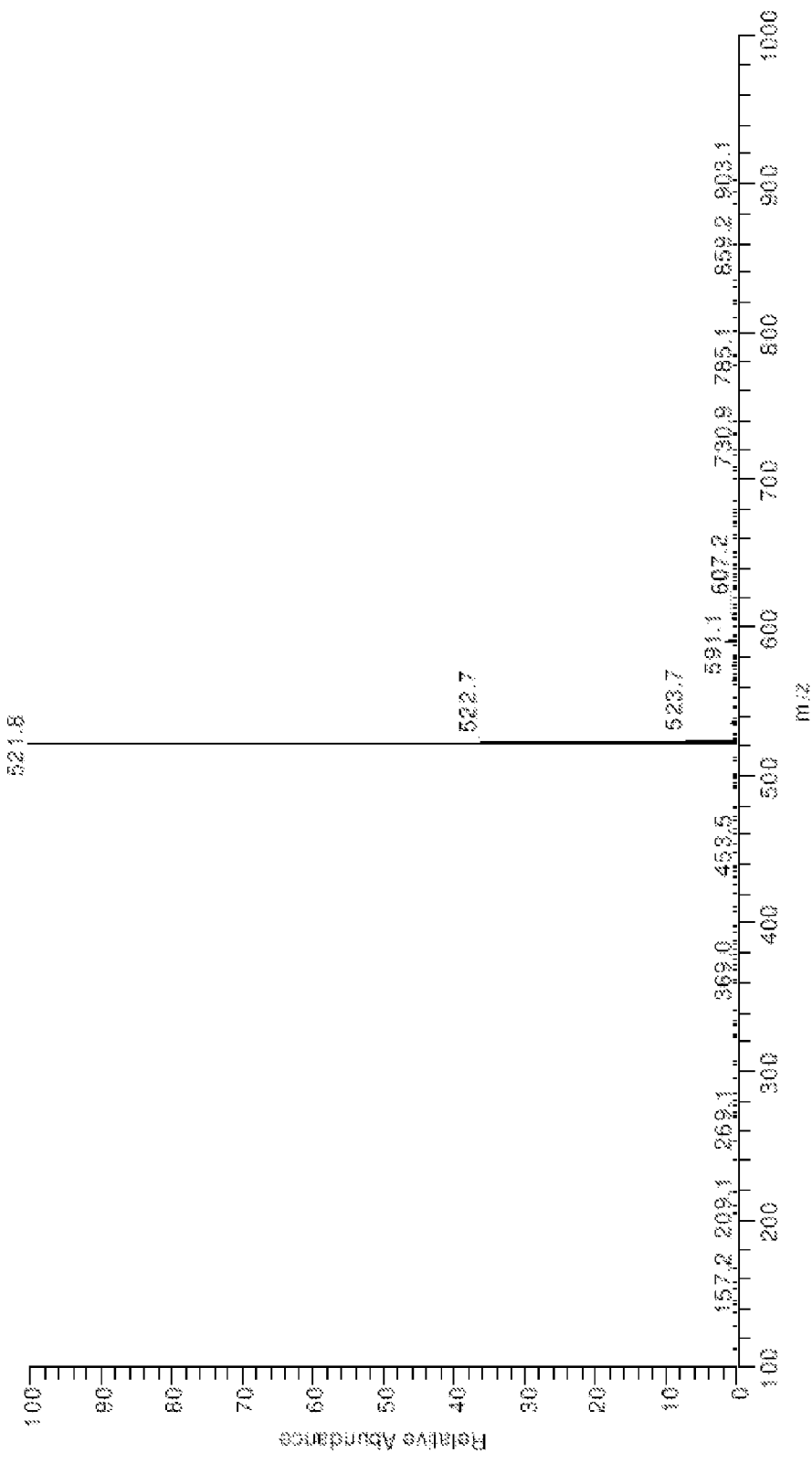
FIG. 22 is a mass spectrum of the compound 1-b-80.
Figure 23:
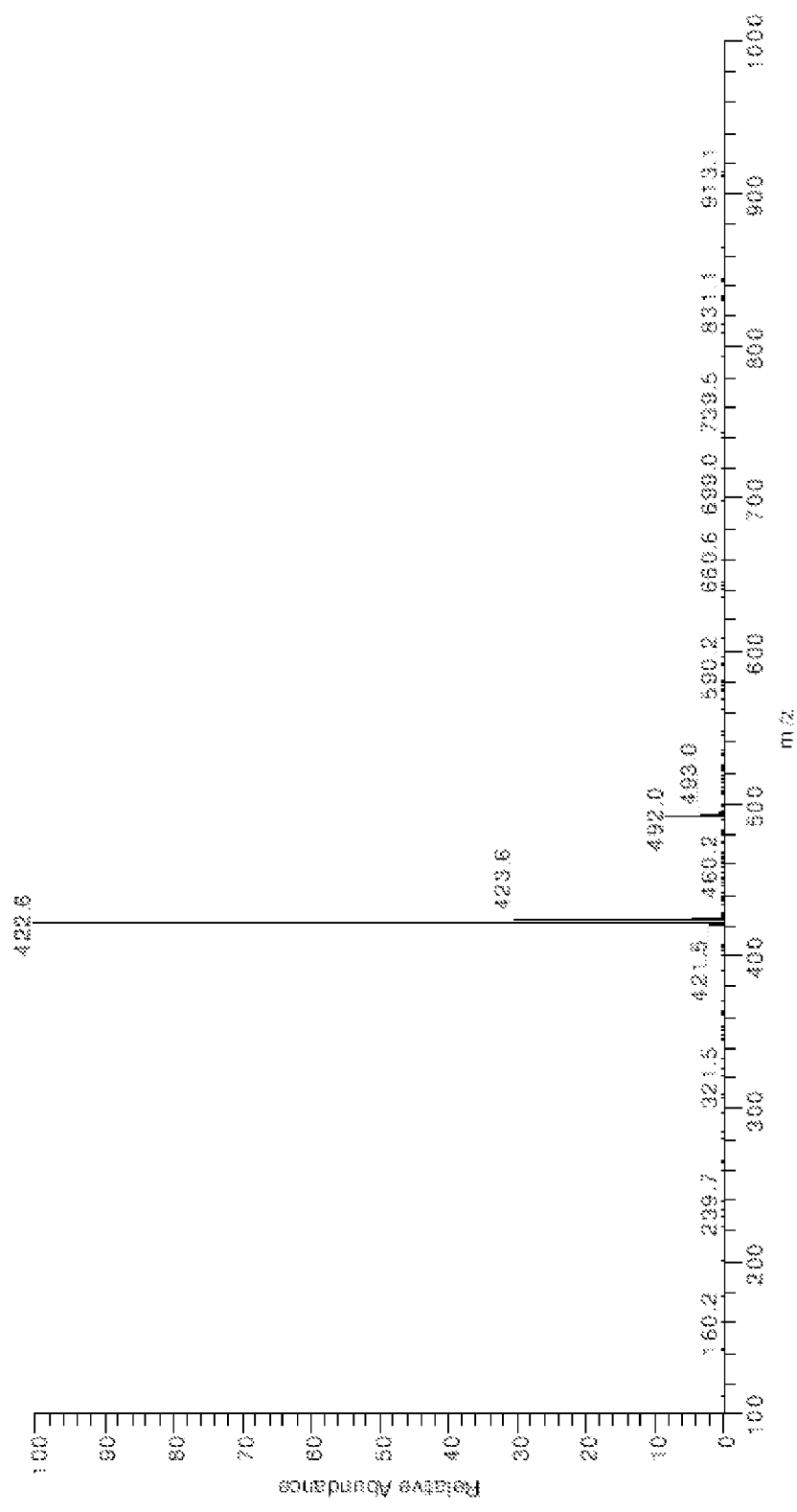
FIG. 23 is a mass spectrum of the compound 6-a-2.
Figure 24:
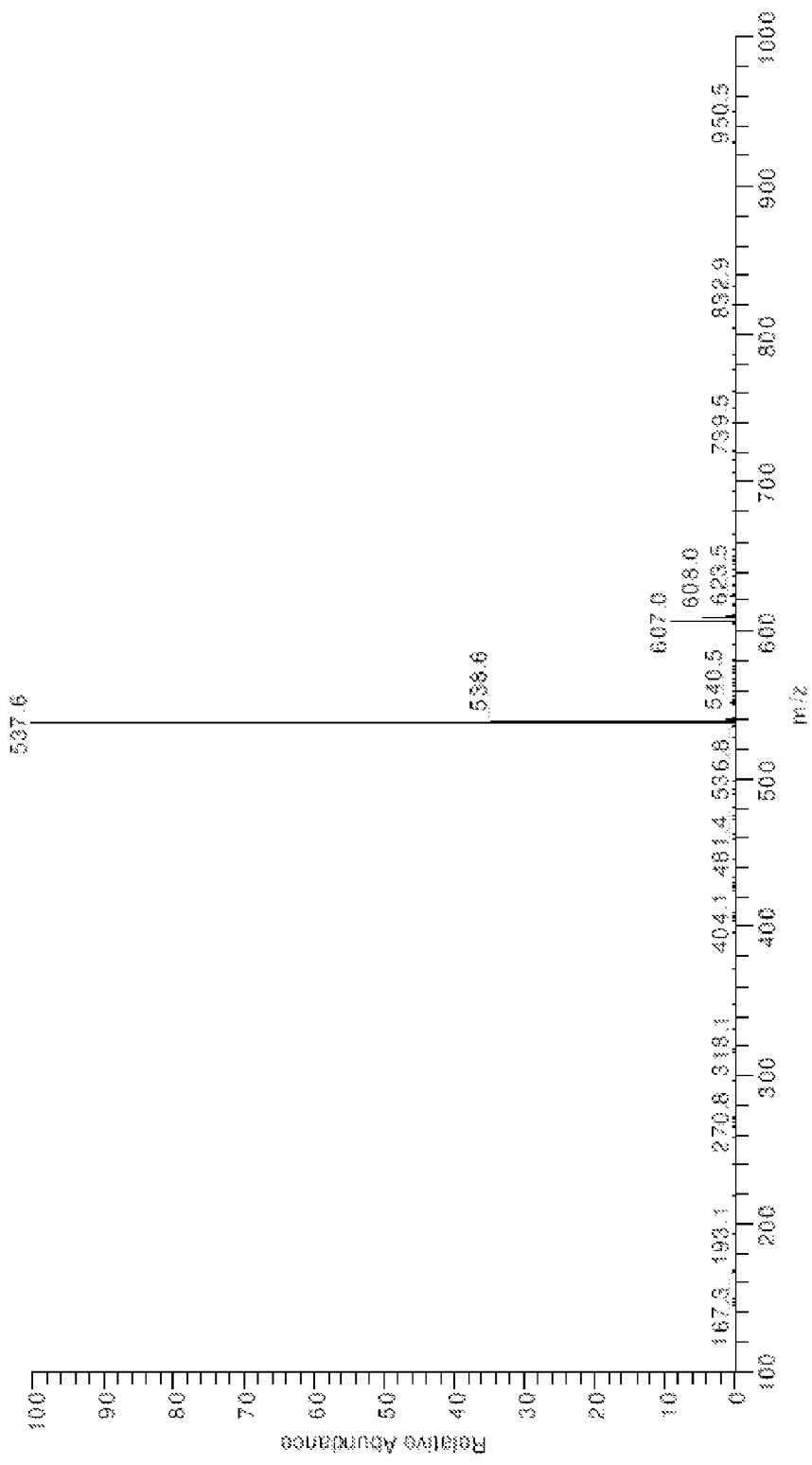
FIG. 24 is a mass spectrum of the compound 1-b-123.
Figure 25:
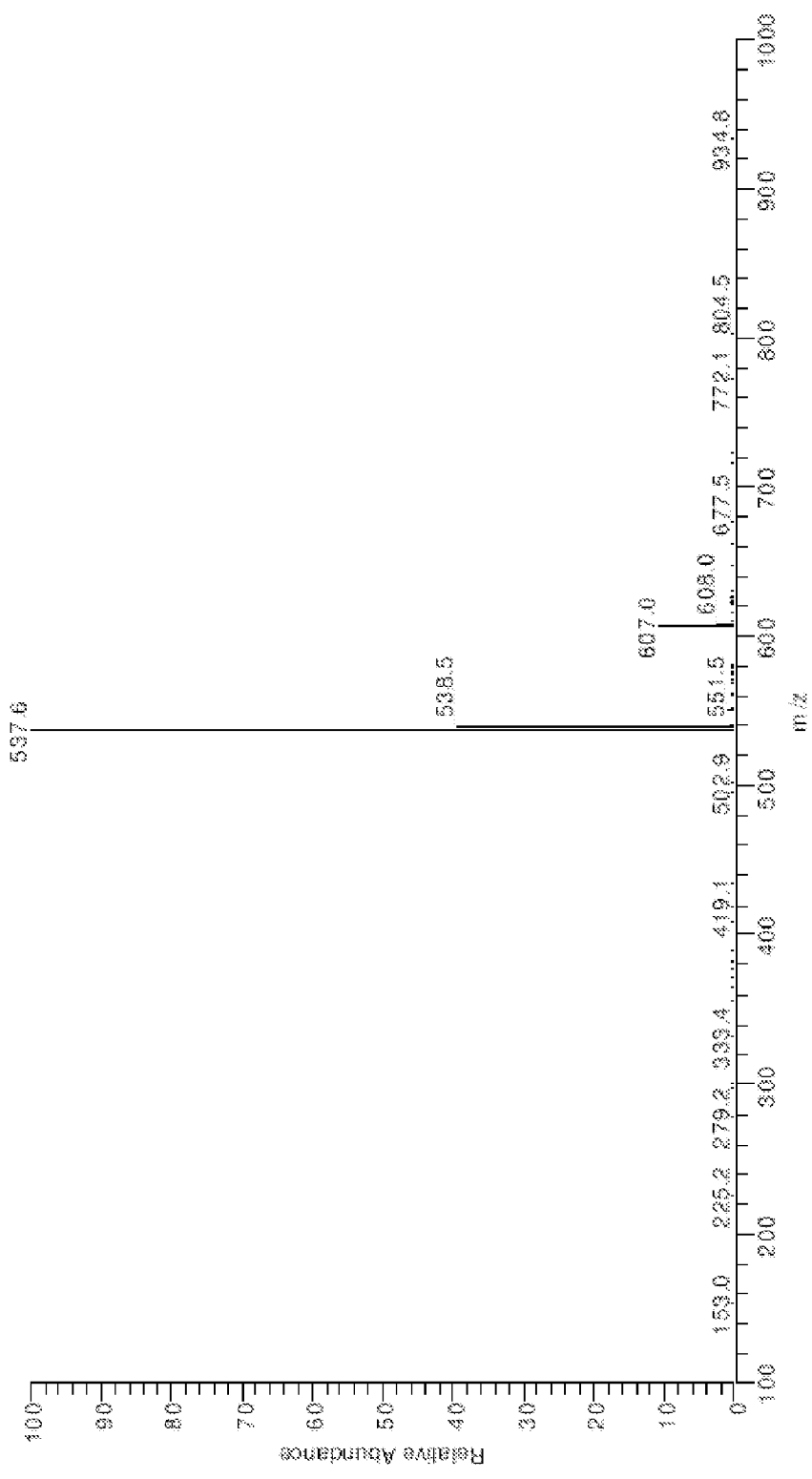
FIG. 25 is a mass spectrum of the compound 1-a-68.
Figure 26:
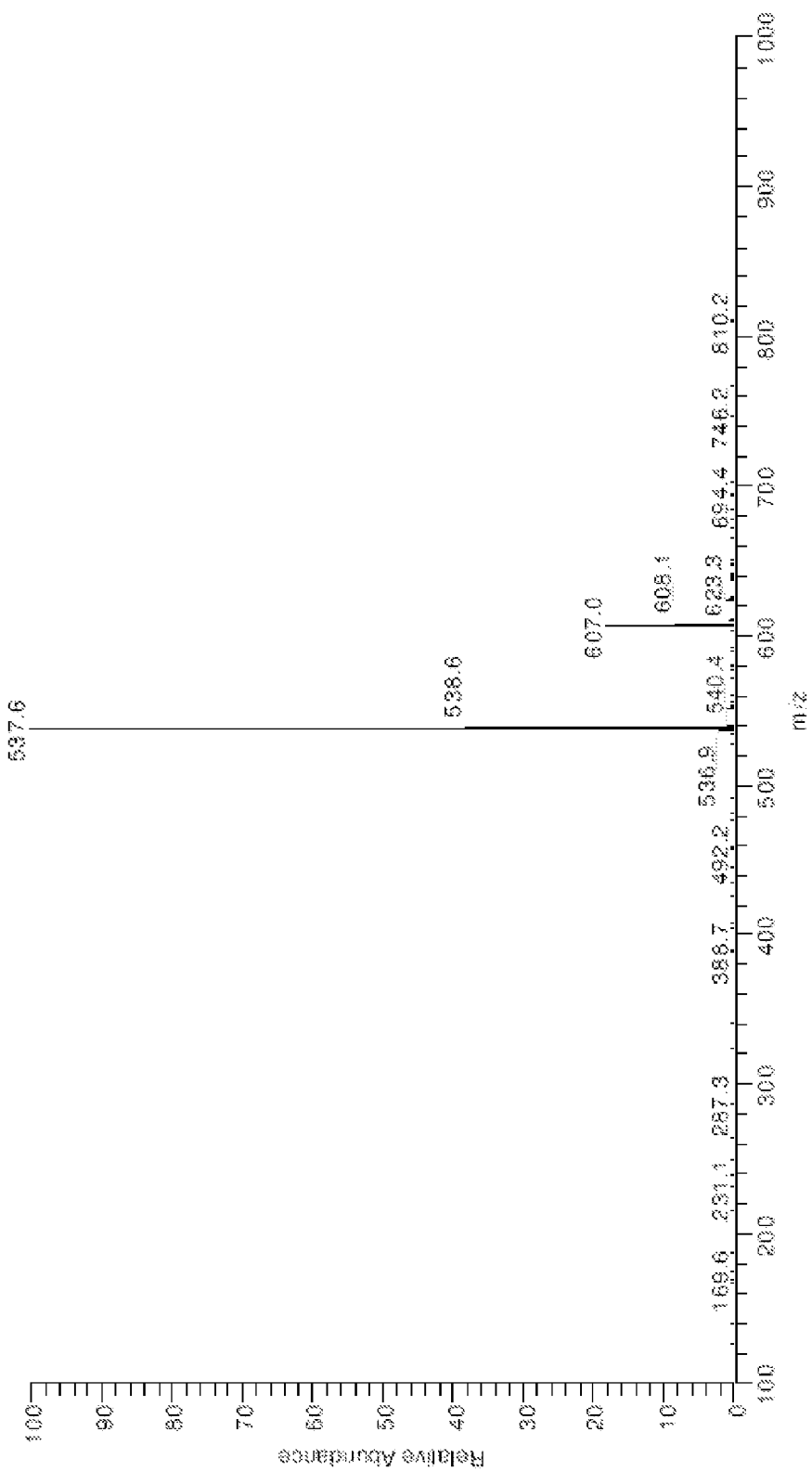
FIG. 26 is a mass spectrum of the compound 1-a-77.
Figure 27:
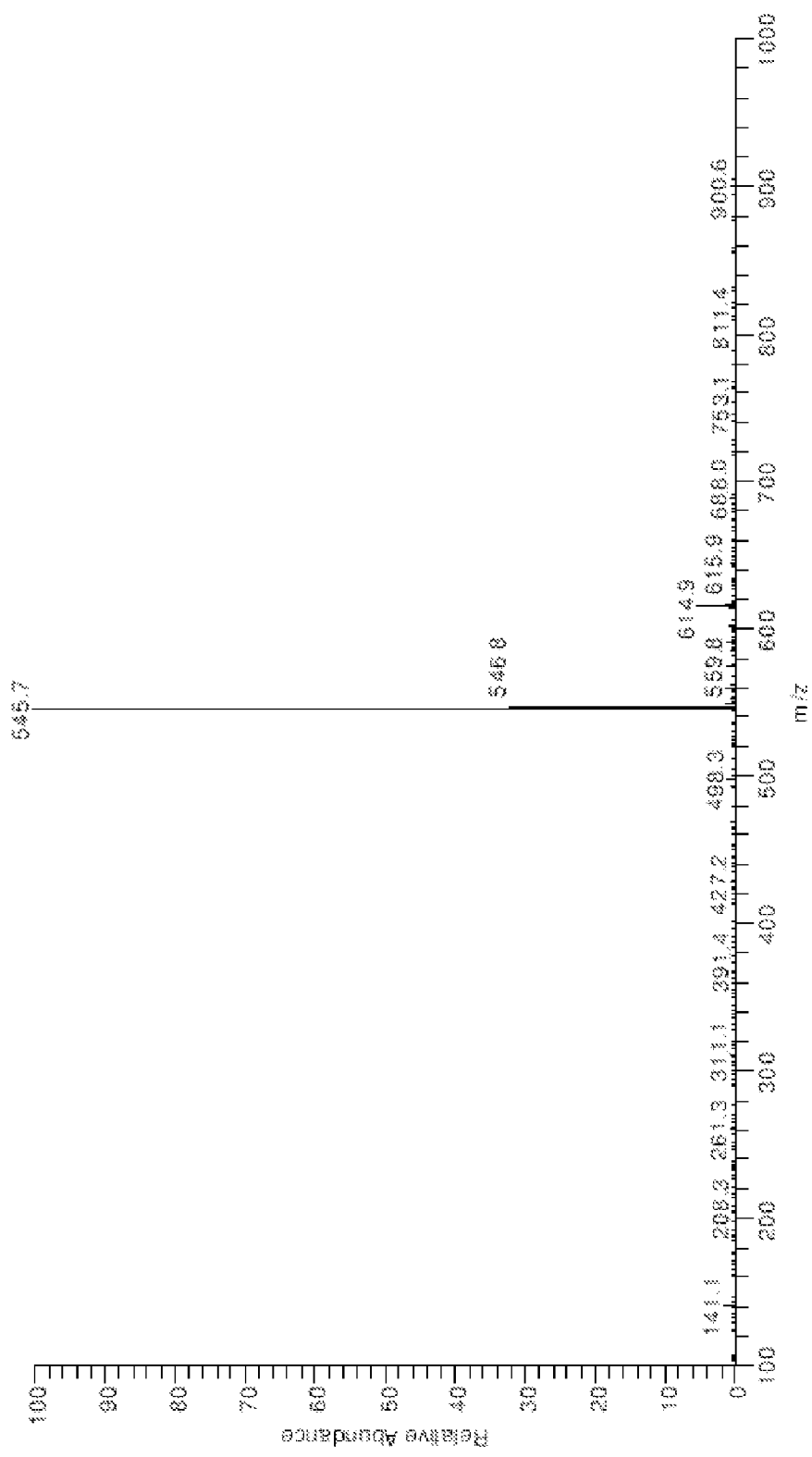
FIG. 27 is a mass spectrum of the compound 1-b-39.
Figure 28:
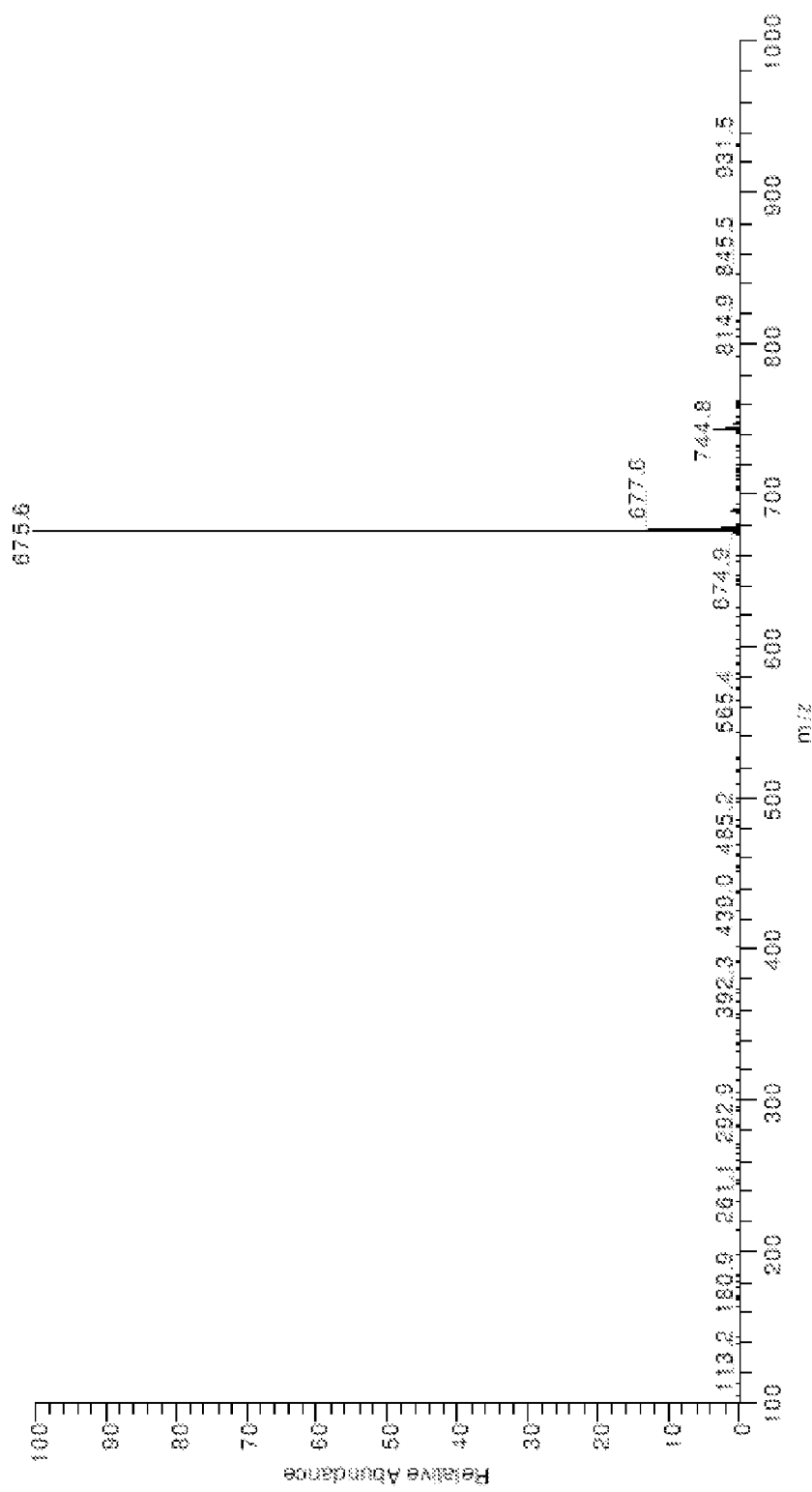
FIG. 28 is a mass spectrum of the compound 1-b-146.
Figure 29:
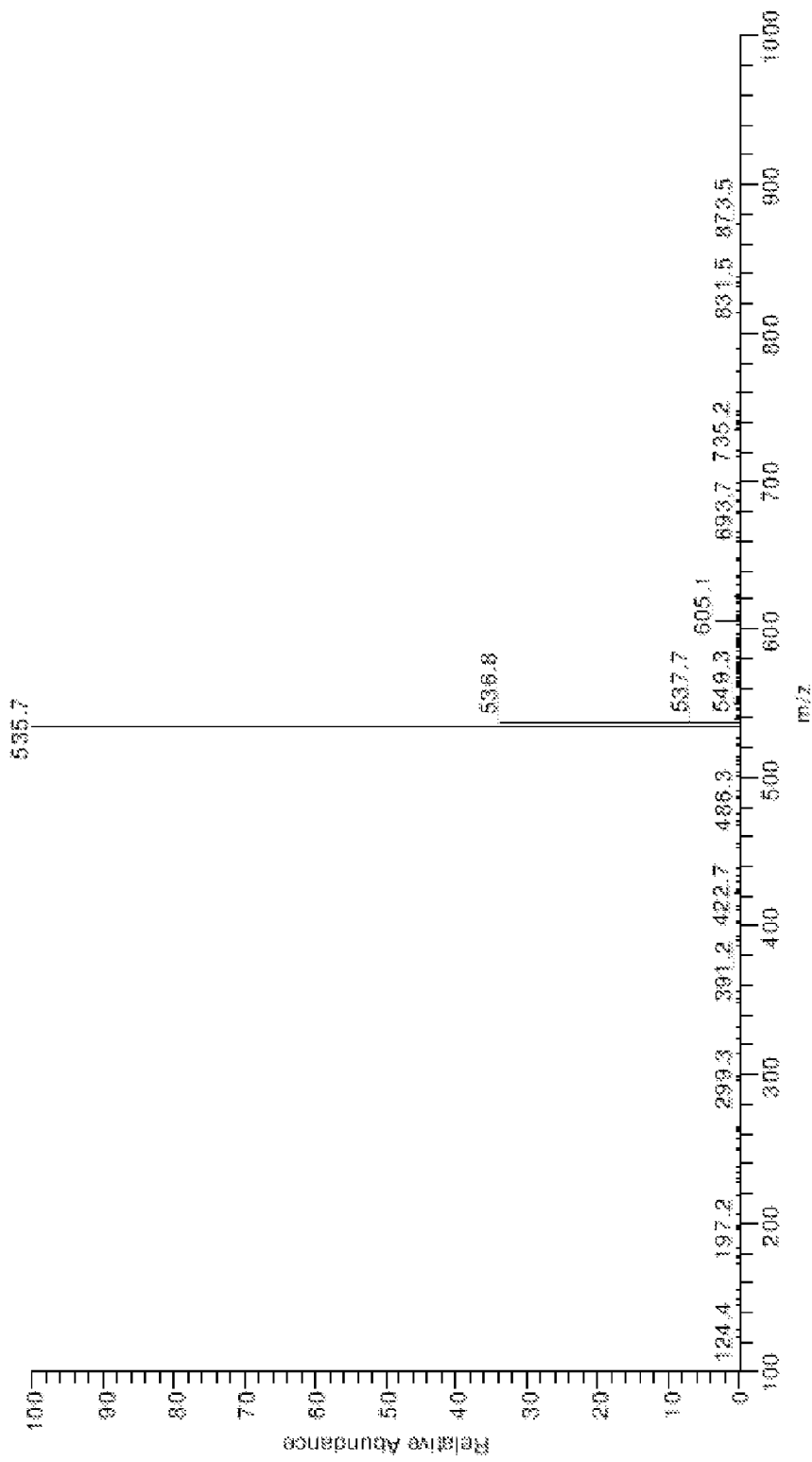
FIG. 29 is a mass spectrum of the compound 5-a-2.

| | |
|---|---|
| 1 | substrate |
| 2 | anode |
| 3 | hole injection layer |
| 4 | hole transport layer |
| 5 | organic light emitting layer |
| 6 | electron transport layer |
| 7 | cathode |

BEST MODE

Hereinafter, the present invention will be described in detail.

A nitrogen-containing heterocyclic derivative according to the present invention is represented by Formula 1 or includes two or more structures of Formula 1.

According to an embodiment of the present invention, the inclusion of two or more structures of Formula 1 means that the compounds having the structures of Formula 1 are directly connected to each other without a connecting group. In this case, among Formulas 1, 2, 3-1, 3-2, and 4-1, the same Formula or different Formulas are directly bonded to include two or more Formula structures.

According to the other embodiment of the present invention, the meaning of the inclusion of two or more structures of Formula 1 is that two or more structures of Formula 1 may be connected to alkane that has two or more divalent connection groups of Formula 1, cycloalkane having divalent or more connection group; an aryl compound that has divalent or more connection group; a pentagonal or hexagonal heteroaryl compound that includes at least one of nitrogen, sulfur, oxygen atoms and has divalent or more connection group; oxygen atom, sulfur atom, substituted or unsubstituted nitrogen atom, or substituted or unsubstituted phosphorus atom. In this case, among Formulas 1, 2, 3-1, 3-2, and 4-1, the same Formula or different Formulas are bonded to include two or more Formula structures.

In Formula 1, alkoxy group may be a straight- or branched-chained. The number of carbon atoms of the alkoxy group is not particularly limited, but it is preferable that it is in the range of 1 to −40, which is the range that does not provide sterical hindrance. For example, in Formula 1, in the case of when Y of -(L)p-(Y)q is an alkoxy group, the number of carbon atom of the alkoxy group does not affect the conjugation length of the compound but affect the application method of the compound to the organic electronic device, for example, the application of the vacuum deposition method or the solution coating method, such that the number of carbon atom of the alkoxy group is not particularly limited.

In the present invention, as the alkenyl group, the alkenyl group that may be a straight- or branched-chained and have 2 to 40 carbon atoms is preferable, and in detail, the alkenyl group that is substituted with the aryl group, such as the stylbenzyl group, the styrenyl group and the like is preferable, but it is not limited thereto.

In Formula 1, the aryl group may be a monocycle or a polycycle, and the number of carbon atoms is not particularly limited, but it is preferable that it is in the range of 6 to 60. As examples of the monocyclic aryl group, there are the phenyl group, the biphenyl group, the terphenyl group, stilbene and the like, and as examples of the polycyclic aryl group, there are the naphthyl group, the anthracenyl group, the phenanthryl group, the pyrenyl group, the perylenyl group, the crycenyl group and the like, but the scope of the present invention is not limited thereto.

In Formula 1, the hetero ring group is a heteroatom, and a heteroring group that includes O, N or S, and the number of carbon atoms is not particularly limited, but it is preferable that the number of carbon atoms is in the range of 2 to 60. As an example of the heteroring group, there are thiophene group, furane group, pyrole group, imidazole group, thiazole group, oxazole group, oxadiazole group, triazole group, pyridyl group, bipyridyl group, triazine group, acrydyl group, pyridazine group, quinolinyl group, isoquinoline group, indol group, carbazole group, benzoxazole group, benzimidazole group, benzthiazole group, benzcarbazole group, benzthiophene group, dibenzothiophene group, benzfuranyl group, dibenzofuranyl group, but it is not limited thereto.

In Formula 1, the cycloalkyl group is not particularly limited, but it has preferably the number of carbon atoms in the range of 3 to 60, and it is particularly preferable that it is the cyclopentyl group and the cyclohexyl group.

In the present invention, as examples of the halogen group, there are fluorine, chlorine, bromine, or iodine.

In the present invention, the fluorenyl group is a structure in which two ring organic compounds are connected to each other through one atom, and as examples thereof, there are

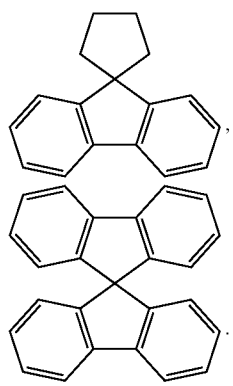

In the present invention, the fluorenyl group includes a structure of an open fluorenyl group, and the open fluorenyl group is a structure in which two ring organic compounds are connected to each other through one atom and the connection of one ring compound is broken, and as examples thereof, there are

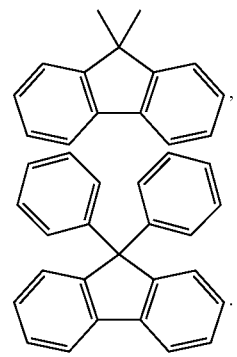

In the present invention, an example of the aryl amine group means substituted or unsubstituted monocyclic diarylamine group, substituted or unsubstituted polycyclic diarylamine group or substituted or unsubstituted monocyclic and polycyclic diarylamine group.

In the present invention, the term "substituted or unsubstituted" means that it is substituted or unsubstituted by at least one substituent group of heavy hydrogen; halogen group; nitrile group; nitro group; hydroxy group; cycloalkyl group; alkoxy group; aryloxy group; alkylthioxy group; arylthioxy group; alkylsulfoxy group; arylsulfoxy group; alkenyl group; silyl group; boron group; alkylamine group; aralkylamine group; arylamine group; aryl group; fluorenyl group; carbazole group; and the heteroring group that includes one or more of N, O, and S atoms.

In the compound according to the present invention, in the case of when $R_1$ and $R_2$ are substituted or unsubstituted aryl group or substituted or unsubstituted heteroring group, it is preferable that they are the same as each other.

In the compound according to the present invention, in the case of when p of -(L)p-(Y)q is 0, it is preferable that at least one of Y is heavy hydrogen, nitrile group, halogen group, substituted or unsubstituted boron group, substituted or unsubstituted aryl group, substituted or unsubstituted heteroring group.

In the compound according to the present invention, in the case of when p of -(L)p-(Y)q is 1 or more, it is preferable that L is substituted or unsubstituted arylene group, or substituted or unsubstituted heteroarylene group, and it is preferable that Y is substituted or unsubstituted boron group; substituted or unsubstituted alkylamine group; substituted or unsubstituted aralkylamine group; substituted or unsubstituted arylamine group; substituted or unsubstituted heteroarylamine group; substituted or unsubstituted aryl group; substituted or unsubstituted fluorenyl group; substituted or unsubstituted carbazole group; or substituted or unsubstituted heteroring group that includes one or more of n, o, and s atoms.

In Formula 1, in the case of when L is an arylene group or heteroallylene group, and Y is an aryl group or heteroaryl group, it is preferable that p+q is 2 or more.

In the case of when p of -(L)p-(Y)q is 2 or more, L is the same as or different from each other, and in the case of when q of -(L)p-(Y)q is 2 or more, Y is the same as or different from each other.

In the compound according to the present invention, it is preferable that at least one of $R_3$ to $R_{12}$ is heavy hydrogen, nitrile group, halogen group, aryl group, substituted arylene group, heteroring group, substituted heteroring group, fluorenyl group, carbazole group.

In the present invention, the substituted arylene group means that phenyl group, biphenyl group, naphthalene group, fluorenyl group, pyrenyl group, phenanthrenyl group, perylene group, tetracenyl group, anthracenyl group are substituted by the other substituent group.

In the present invention, the substituted heteroarylene group means a group in which pyridyl group, thiophenyl group, triazine group, quinoline group, phenanthroline group, imidazole group, thiazole group, oxazole group, carbazole group and condensate heteroring group thereof, for example, benzquinoline group, benzimidazole group, benzoxazole group, benzthiazole group, benzcarbazole group, dibenzothiophenyl group are substituted.

In Formulas 2, 3-1, 3-2, and 4-1, $(N)n_1$ and $(N)n_2$ means that the carbon atom in the ring is capable of being substituted by the nitrogen atom. Herein, it is preferable that $n_1$ and $n_2$ are each independently an integer in the range of 0 to 2.

In an embodiment of the present invention, in the case of when $R_1$ and $R_2$ are substituted or unsubstituted aryl group or substituted or unsubstituted heteroaryl group, it is preferable that they are the same as each other.

In addition, $R_1$ to $R_2$ may be each independently the same as or different from each other, it is preferable that they are substituted by phenyl, biphenyl, naphthyl group, pyridinyl, or phenyl that is substituted by nitrile.

The vacuum deposition process of the manufacturing method of the organic light emitting device performs deposition by subliming a material at the high vacuum, for example, about $10^{-6}$ to $10^{-7}$ torr and high temperature. Accordingly, it is important to maintain the property of the compound at a high temperature for a long time without deformation and easily sublime it.

Meanwhile, the imidazole group is a heteroring compound that includes two nitrogen atoms in the pentagonal ring, and has excellent electron injection and electron transport properties, such that it is used as the electron injection and electron transport layer or the light emitting layer in the organic light emitting device. The compound TPBi that is Formula X-1 and Formula X-2 has an ability for functionally transporting electrons and an ability for blocking holes flowing to the light emitting layer, such that it is capable of being used as a hole blocking layer. However, it has a problem in that stability is too low to apply it to a real device. Therefore, in the present invention, even though it has excellent characteristic performance, the problem thereof of physically or electrically low stability will be overcome.

In order to maintain the properties of the compound without a deformation in the organic light emitting device, the compound should be electrically stable, and high glass transition temperature (Tg) and high melting point (Tm) in physical view. However, Formula X-1 and Formula X-2 have very low Tg and Tm.

In addition, in the course of manufacturing the organic light emitting device, since the compounds are deposited under the vacuum for a long time at high temperature, the compounds that have low thermal stability are easily deformed, such that it cannot be deposited under the vacuum for a long time. In order to overcome this, the material that is capable of being sublimed at a low temperature and a high subliming ability is required. In order to have the high subliming ability at the low temperature, the molecular weight of the compound should be lowered or interaction between the molecules should be lowered. In addition, the crystallinity is increased by deforming the structure of the compound, such that the subliming ability is increased at Tg or Tm or less, and it is preferable that the structure of the compound is a plate structure, a symmetric structure, or a spherical structure.

In the present invention, it is deemed that the reduction in stability of the N-phenylbenzimidazole group may be caused by free rotation of N and the phenyl group like the following structure, and if 2-position and N-phenyl group obtain heat energy by the free rotation, it may be activated, such that the reduction in stability of the compound may be caused.

Formula X-1 [TPBi]

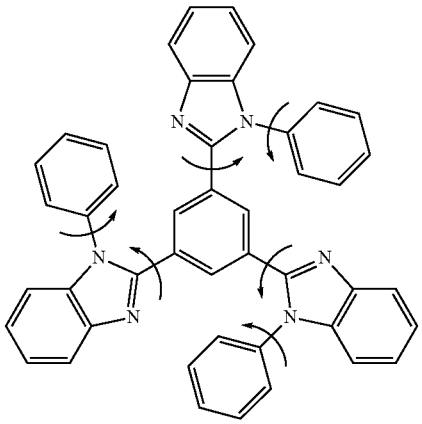

Formula X-2

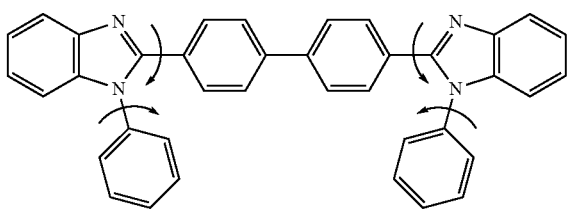

In order to overcome the problems, the present invention, as shown in Formula 1, connects the ortho position of the aryl group or heteroaryl group that includes $X_1$ to $X_4$ bonded to N of the imidazole group, and the ortho position of the aryl group or heteroaryl group that includes $Y_1$ to $Y_4$ bonded to the 2-position of the imidazole group to each other to increase the stability and the subliming ability of the compound.

[Formula 1]

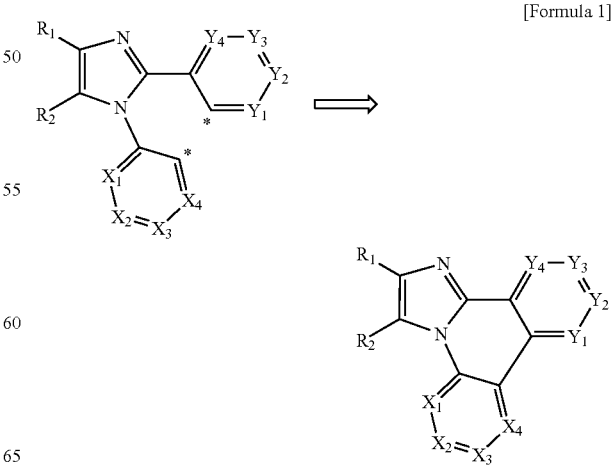

The structure of the compound of Formula 1 that is developed as described above approaches the plate structure, and in particular, in the case of when the monocyclic or polycyclic condensate ring in which $R_1$ and $R_2$ are that are the substituent groups of the imidazole group are connected to each other is formed, it forms the plate structure, such that the thermal stability and the subliming ability are more increased. The structure of Formula 1 makes the free rotation difficult and increases the thermal stability and the subliming ability, such that the stability can be maintained in the vacuum deposition process.

In the case of when the substituent group of Formula 1 is aryl group and heteroaryl group, it is most preferable in views of stability, and the substituent having the large rotation like the alkyl group is less preferable.

In addition, in the case of the compound in which the halogen, nitrile group, nitro group, or heteroring group is introduced to the above Formula, the HOMO value of the compound is made deep, such that the hole flowing from the light emitting layer can be blocked and the amount of hole remaining in the light emitting layer is increased, thereby increasing efficiency and stability.

In the present invention, the operation principle as described above is applied to the case of when it includes the monocyclic or polycyclic condensate imidazole group in which $R_1$ and $R_2$ are connected to each other and the case of when it includes the open arylimidazole group and the open heteroarylimidazole group, that is, the case of when $R_1$ and $R_2$ that are substituent groups of the imidazole group are not connected to the ring and are the aryl group or heteroaryl group. Accordingly, these structures are all included in the scope of the present invention.

In addition, the compound according to the present invention may be used for various purposes in the organic light emitting electronic device according to the kind and the property of the substituent group. For example, in the case of when the substituted or unsubstituted aryl group or heteroaryl group is substituted, or two or more structures of Formula 1 are connected to each other, since the properties thereof have a deep HOMO value and an appropriate LUMO value that is capable of injecting electrons well because of an increase in electron affinity and electronegativity, it is advantageous that it is used as the electron injection, electron transport or hole blocking layer. Meanwhile, since the substituted or unsubstituted arylamino group, alkylamino group, heteroarylamino group, arylkylamino group and aryl group or heteroaryl group that is substituted by them relatively well form the holes, it is useful to hole injection and transport layer. Basically, since the structure of Formula 1 has very large band gap, if the substituent that is suitable to the structure of Formula 1 is introduced, for example, if the substituent such as carbazole group is introduced, the energy bandgap and stability in a triplet state can be ensured. From these results, various phosphorescence dopants from red color to blue color can be used and applied to light emitting layers of fluorescent and phosphorescent devices. In particular, the compound according to the present invention may be used as the host of the light emitting layer. In the case of when the compound according to the present invention is used as the host of any one organic material layer of the organic light emitting device, for example, the light emitting layer or the electron transport layer, the other organic compounds, metal or metal compounds may be used as the dopant.

As preferable detailed examples of the compound that is represented by Formula 1, there are the following compounds, but they are not limited thereto.

TABLE 1

1-a-1

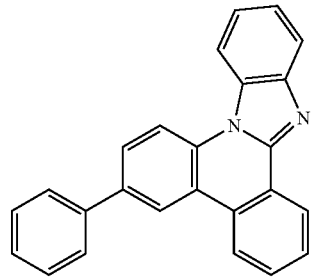 [SMILES: c1ccc(-c2ccc3c(c2)c2ccccc2c2nc4ccccc4n32)cc1]

1-a-2

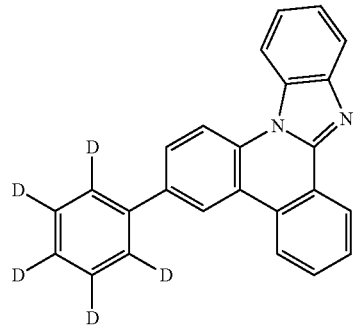 [SMILES: [2H]c1c([2H])c([2H])c(-c2ccc3c(c2)c2ccccc2c2nc4ccccc4n32)c([2H])c1[2H]]

TABLE 1-continued
1-a-3
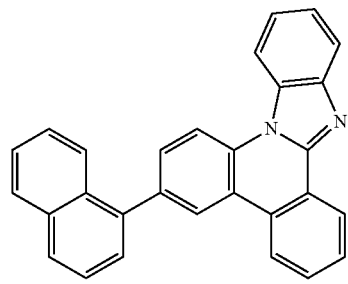 [SMILES: c1ccc2c(-c3ccc4c(c3)c3ccccc3c3nc5ccccc5n43)cccc2c1]
1-a-4
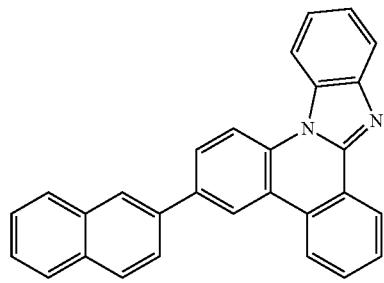
1-a-5
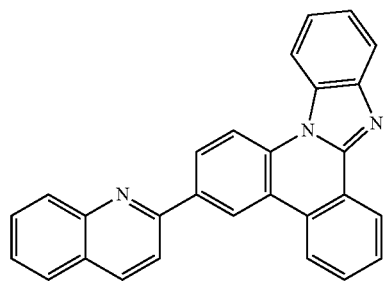 [SMILES: c1ccc2nc(-c3ccc4c(c3)c3ccccc3c3nc5ccccc5n43)ccc2c1]
1-a-6
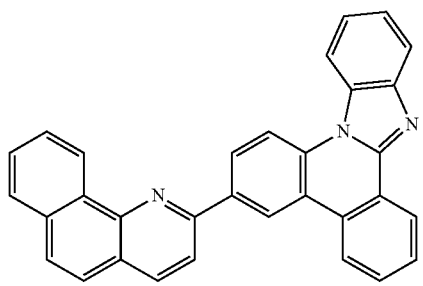 [SMILES: c1ccc2c(c1)ccc1ccc(-c3ccc4c(c3)c3ccccc3c3nc5ccccc5n43)nc12]
1-a-7
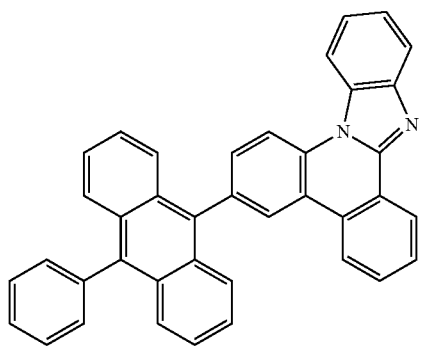 [SMILES: c1ccc(-c2c3ccccc3c(-c3ccc4c(c3)c3ccccc3c3nc5ccccc5n43)c3ccccc23)cc1]

TABLE 1-continued
1-a-8
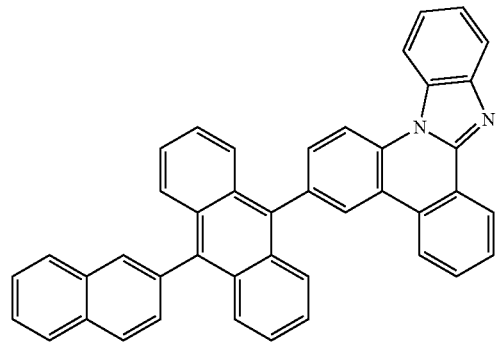 [SMILES: c1ccc2cc(-c3c4ccccc4c(-c4ccc5c(c4)c4ccccc4c4nc6ccccc6n54)c4ccccc34)ccc2c1]
1-a-9
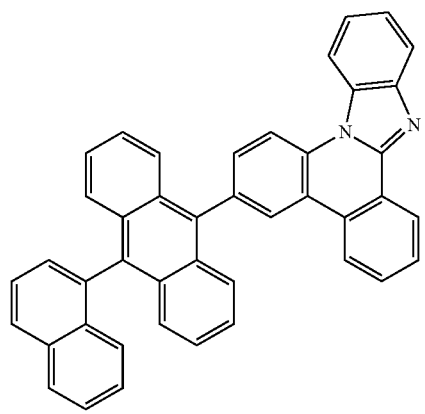 [SMILES: c1ccc2c(-c3c4ccccc4c(-c4ccc5c(c4)c4ccccc4c4nc6ccccc6n54)c4ccccc34)cccc2c1]
1-a-10
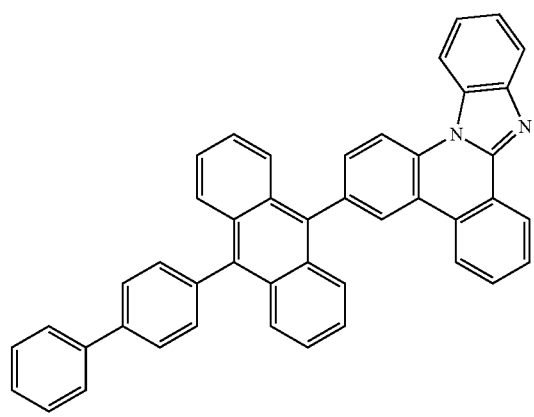 [SMILES: c1ccc(-c2ccc(-c3c4ccccc4c(-c4ccc5c(c4)c4ccccc4c4nc6ccccc6n54)c4ccccc34)cc2)cc1]
1-a-11
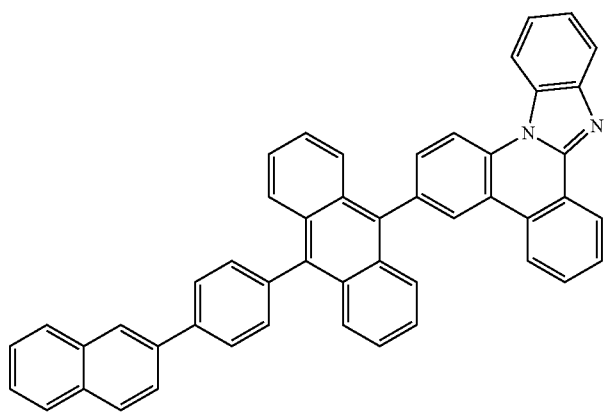 [SMILES: c1ccc2cc(-c3ccc(-c4c5ccccc5c(-c5ccc6c(c5)c5ccccc5c5nc7ccccc7n65)c5ccccc45)cc3)ccc2c1]

TABLE 1-continued
1-a-12
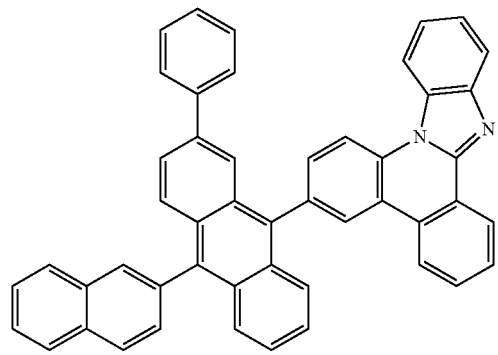 [SMILES: c1ccc(-c2ccc3c(-c4ccc5ccccc5c4)c4ccccc4c(-c4ccc5c(c4)c4ccccc4c4nc6ccccc6n54)c3c2)cc1]
1-a-13
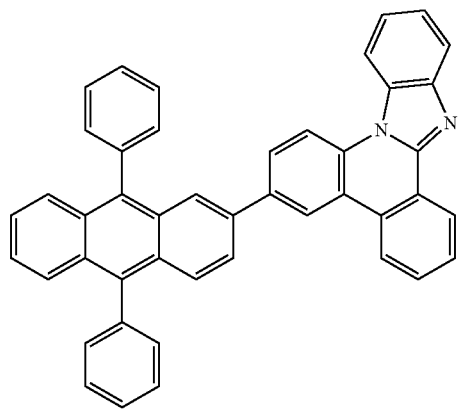 [SMILES: c1ccc(-c2c3ccccc3c(-c3ccccc3)c3cc(-c4ccc5c(c4)c4ccccc4c4nc6ccccc6n54)ccc23)cc1]
1-a-14
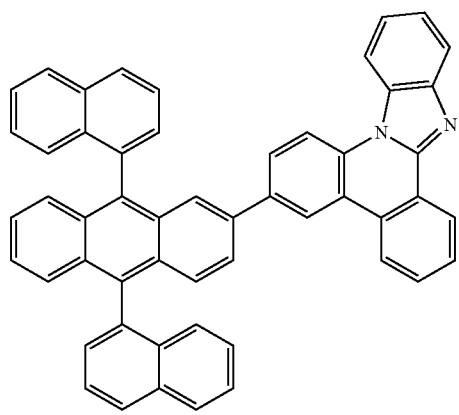 [SMILES: c1ccc2c(-c3c4ccccc4c(-c4cccc5ccccc45)c4cc(-c5ccc6c(c5)c5ccccc5c5nc7ccccc7n65)ccc34)cccc2c1]
1-a-15
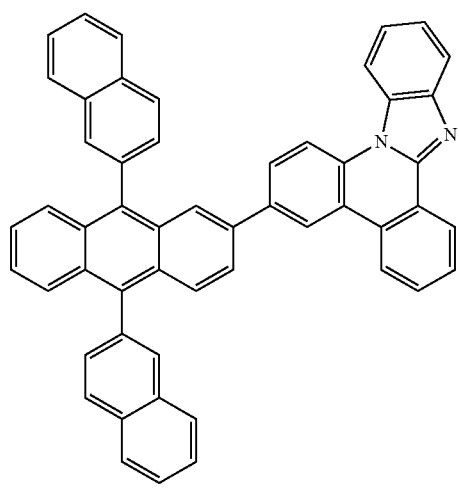 [SMILES: c1ccc2cc(-c3c4ccccc4c(-c4ccc5ccccc5c4)c4cc(-c5ccc6c(c5)c5ccccc5c5nc7ccccc7n65)ccc34)ccc2c1]

TABLE 1-continued
1-a-16
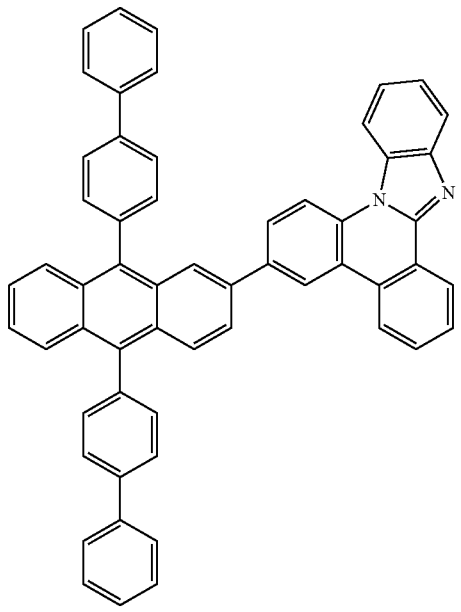 [SMILES: c1ccc(-c2ccc(-c3c4ccccc4c(-c4ccc(-c5ccccc5)cc4)c4cc(-c5ccc6c(c5)c5ccccc5c5nc7ccccc7n65)ccc34)cc2)cc1]
1-a-17
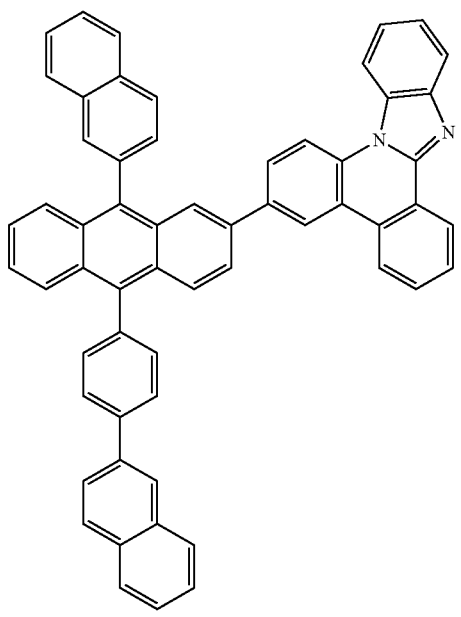 [SMILES: c1ccc2cc(-c3ccc(-c4c5ccccc5c(-c5ccc6ccccc6c5)c5cc(-c6ccc7c(c6)c6ccccc6c6nc8ccccc8n76)ccc45)cc3)ccc2c1]
1-a-18
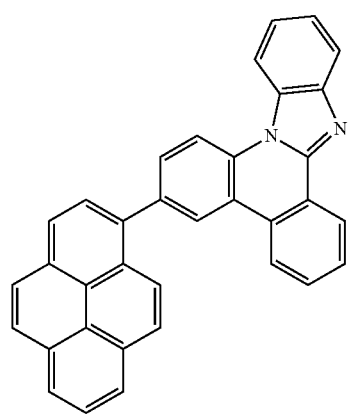 [SMILES: c1cc2ccc3ccc(-c4ccc5c(c4)c4ccccc4c4nc6ccccc6n54)c4ccc(c1)c2c34]

TABLE 1-continued
1-a-19
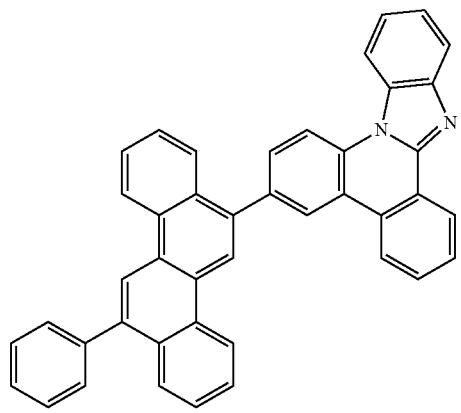 [SMILES: c1ccc(-c2cc3c4ccccc4c(-c4ccc5c(c4)c4ccccc4c4nc6ccccc6n54)cc3c3ccccc23)cc1]
1-a-20
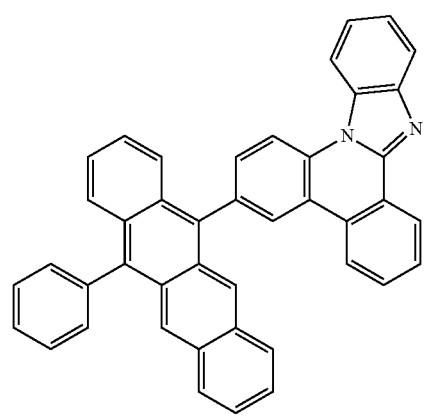 [SMILES: c1ccc(-c2c3ccccc3c(-c3ccc4c(c3)c3ccccc3c3nc5ccccc5n43)c3cc4ccccc4cc23)cc1]
1-a-21
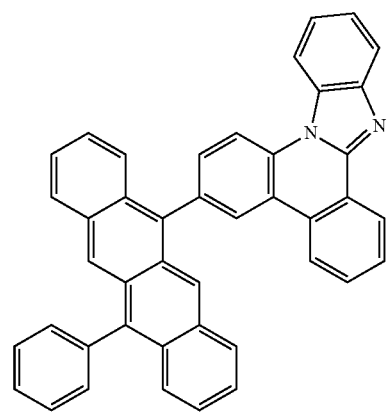 [SMILES: c1ccc(-c2c3ccccc3cc3c(-c4ccc5c(c4)c4ccccc4c4nc6ccccc6n54)c4ccccc4cc23)cc1]
1-a-22
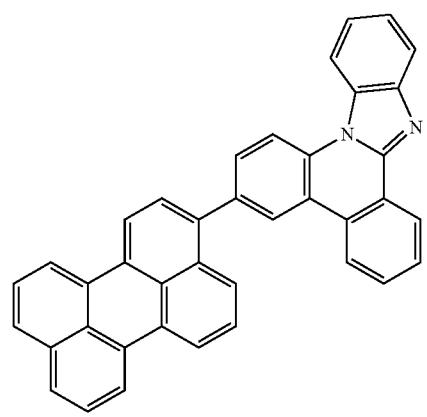 [SMILES: c1ccc2c(c1)nc1c3ccccc3c3cc(-c4ccc5c6cccc7cccc(c8cccc4c85)c76)ccc3n21]

TABLE 1-continued
1-a-23
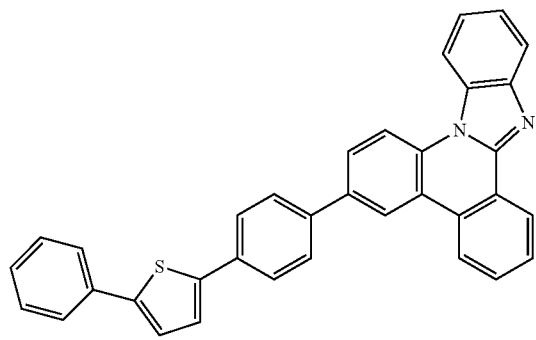 [SMILES: c1ccc(-c2ccc(-c3ccc(-c4ccc5c(c4)c4ccccc4c4nc6ccccc6n54)cc3)s2)cc1]
1-a-24
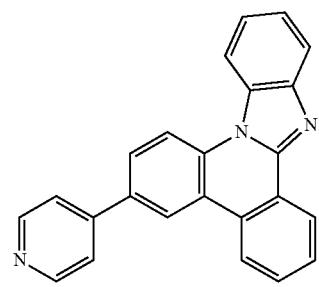 [SMILES: c1ccc2c(c1)nc1c3ccccc3c3cc(-c4ccncc4)ccc3n21]
1-a-25
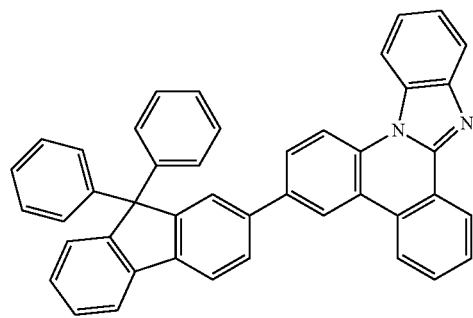 [SMILES: c1ccc(C2(c3ccccc3)c3ccccc3-c3ccc(-c4ccc5c(c4)c4ccccc4c4nc6ccccc6n54)cc32)cc1]
1-a-26
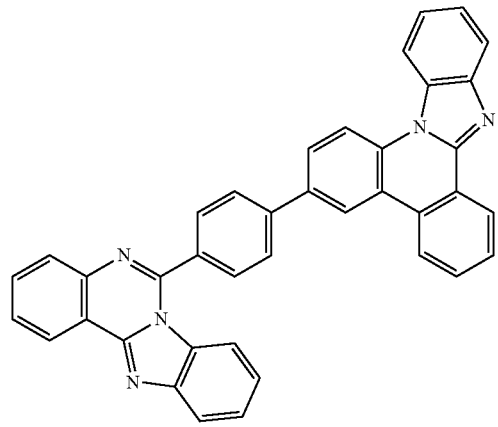 [SMILES: c1ccc2c(c1)nc(-c1ccc(-c3ccc4c(c3)c3ccccc3c3nc5ccccc5n43)cc1)n1c3ccccc3nc21]

TABLE 1-continued
1-a-27 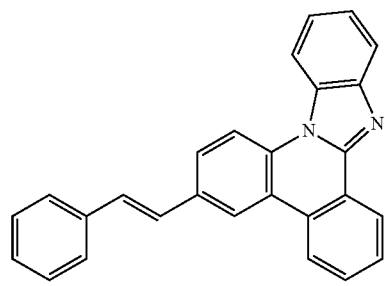 [SMILES: C(=C\c1ccc2c(c1)c1ccccc1c1nc3ccccc3n21)/c1ccccc1]
1-a-28 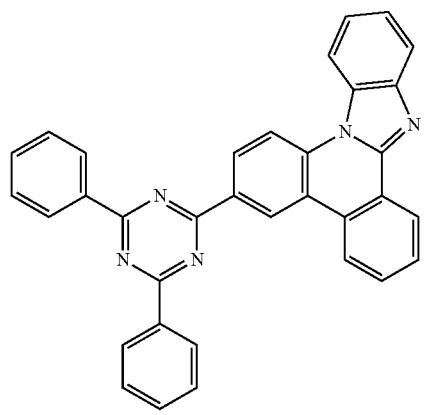 [SMILES: c1ccc(-c2nc(-c3ccccc3)nc(-c3ccc4c(c3)c3ccccc3c3nc5ccccc5n43)n2)cc1]
1-a-29 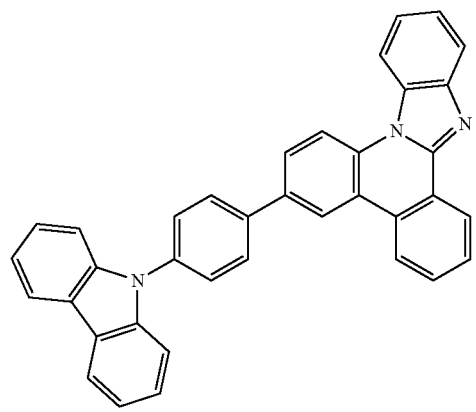 [SMILES: c1ccc2c(c1)nc1c3ccccc3c3cc(-c4ccc(-n5c6ccccc6c6ccccc65)cc4)ccc3n21]
1-a-30 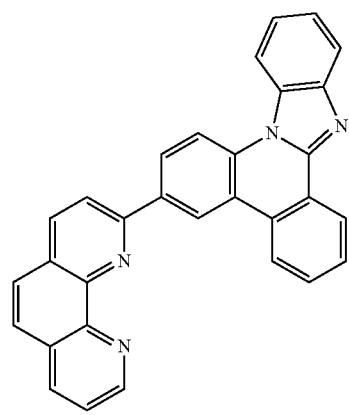 [SMILES: c1cnc2c(c1)ccc1ccc(-c3ccc4c(c3)c3ccccc3c3nc5ccccc5n43)nc12]

TABLE 1-continued
1-a-31
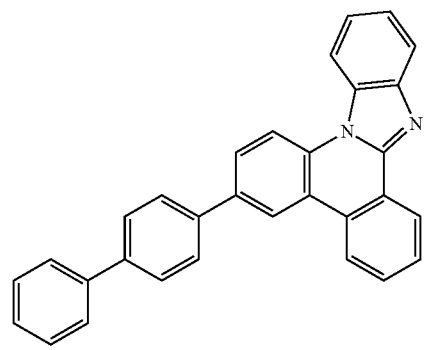 [SMILES: c1ccc(-c2ccc(-c3ccc4c(c3)c3ccccc3c3nc5ccccc5n43)cc2)cc1]
1-a-32
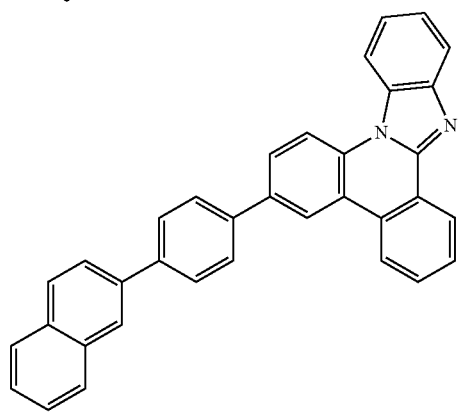
1-a-33
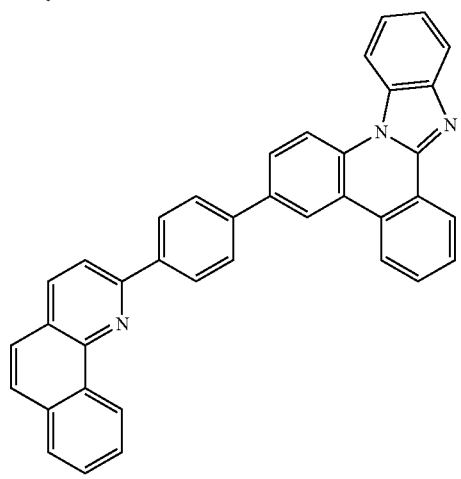
1-a-34
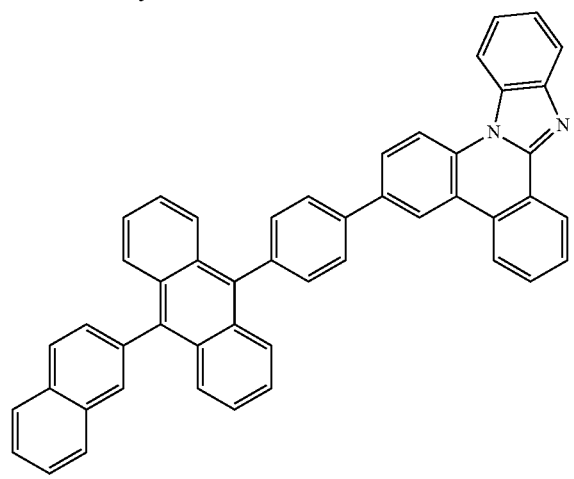

TABLE 1-continued
1-a-35
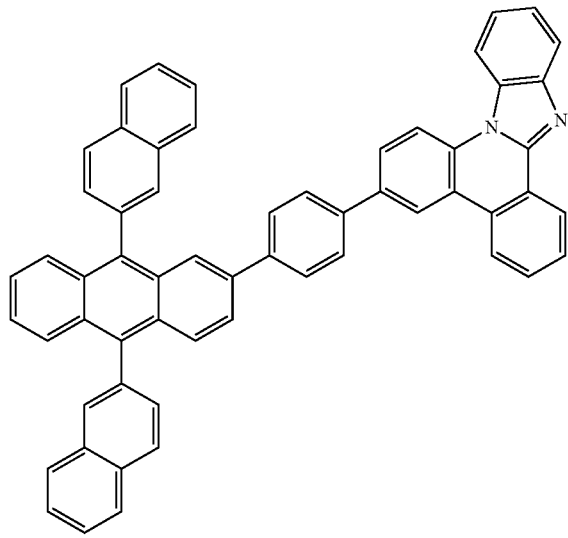 [SMILES: c1ccc2cc(-c3c4ccccc4c(-c4ccc5ccccc5c4)c4cc(-c5ccc(-c6ccc7c(c6)c6ccccc6c6nc8ccccc8n76)cc5)ccc34)ccc2c1]
1-a-36
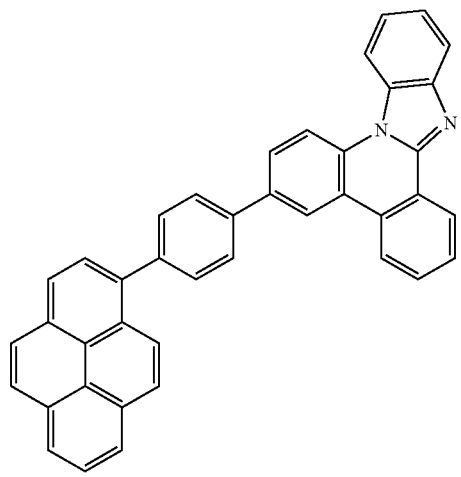 [SMILES: c1cc2ccc3ccc(-c4ccc(-c5ccc6c(c5)c5ccccc5c5nc7ccccc7n65)cc4)c4ccc(c1)c2c34]
1-a-37
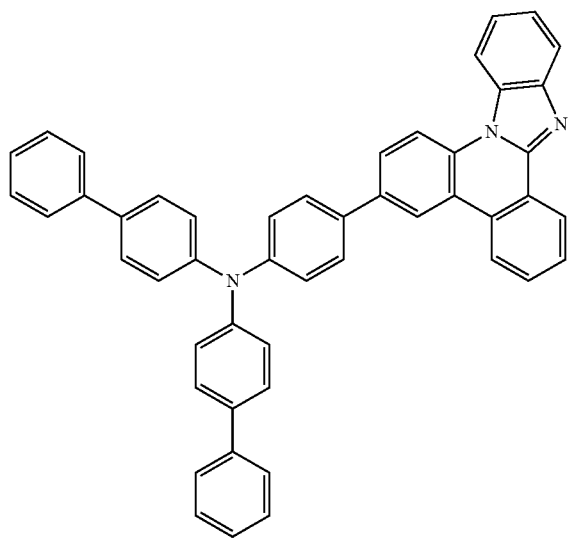 [SMILES: c1ccc(-c2ccc(N(c3ccc(-c4ccccc4)cc3)c3ccc(-c4ccc5c(c4)c4ccccc4c4nc6ccccc6n54)cc3)cc2)cc1]

TABLE 1-continued
1-a-38
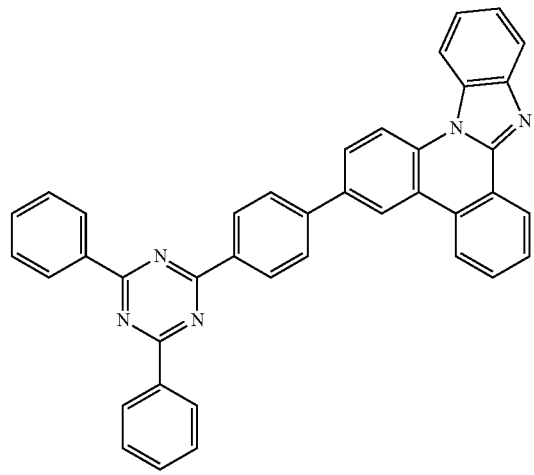 [SMILES: c1ccc(-c2nc(-c3ccccc3)nc(-c3ccc(-c4ccc5c(c4)c4ccccc4c4nc6ccccc6n54)cc3)n2)cc1]
1-a-39
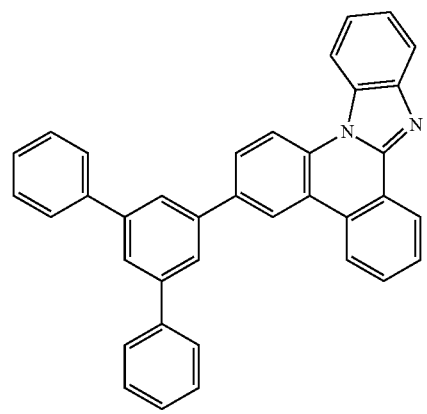 [SMILES: c1ccc(-c2cc(-c3ccccc3)cc(-c3ccc4c(c3)c3ccccc3c3nc5ccccc5n43)c2)cc1]
1-a-40
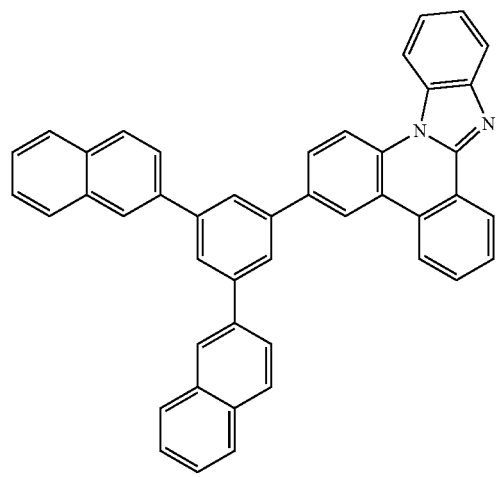 [SMILES: c1ccc2cc(-c3cc(-c4ccc5ccccc5c4)cc(-c4ccc5c(c4)c4ccccc4c4nc6ccccc6n54)c3)ccc2c1]

TABLE 1-continued
1-a-41
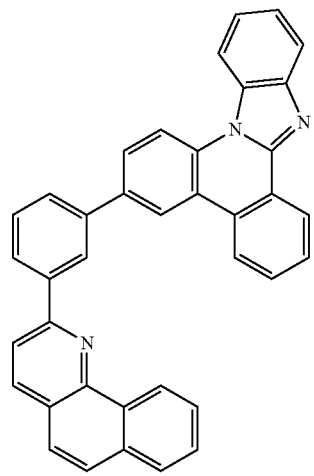 [SMILES: c1cc(-c2ccc3c(c2)c2ccccc2c2nc4ccccc4n32)cc(-c2ccc3ccc4ccccc4c3n2)c1]
1-a-42
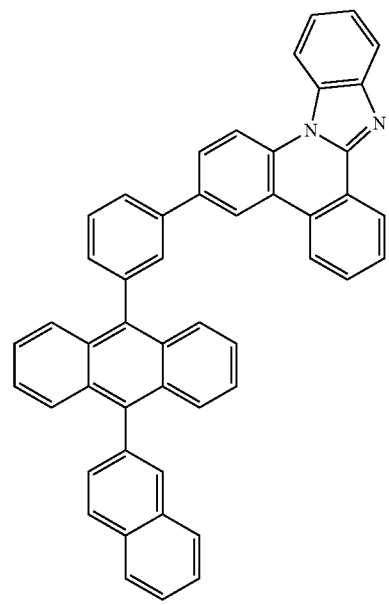 [SMILES: c1cc(-c2ccc3c(c2)c2ccccc2c2nc4ccccc4n32)cc(-c2c3ccccc3c(-c3ccc4ccccc4c3)c3ccccc23)c1]
1-a-43
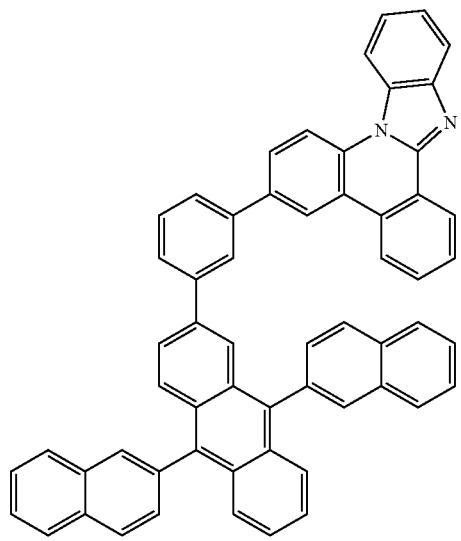 [SMILES: c1cc(-c2ccc3c(-c4ccc5ccccc5c4)c4ccccc4c(-c4ccc5ccccc5c4)c3c2)cc(-c2ccc3c(c2)c2ccccc2c2nc4ccccc4n32)c1]

TABLE 1-continued
1-a-44
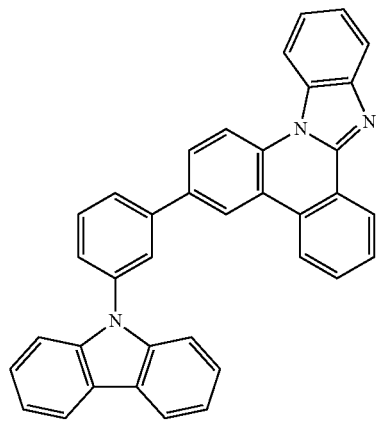 [SMILES: c1cc(-c2ccc3c(c2)c2ccccc2c2nc4ccccc4n32)cc(-n2c3ccccc3c3ccccc32)c1]
1-a-45
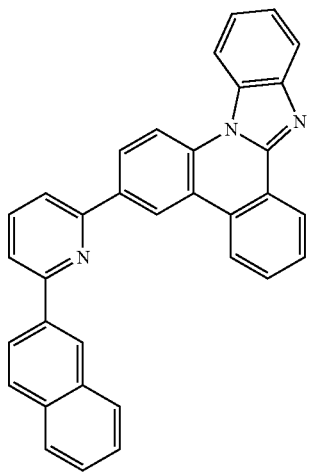 [SMILES: c1cc(-c2ccc3ccccc3c2)nc(-c2ccc3c(c2)c2ccccc2c2nc4ccccc4n32)c1]
1-a-46
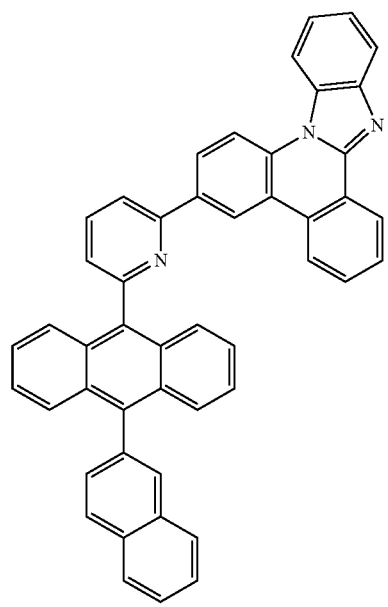 [SMILES: c1cc(-c2ccc3c(c2)c2ccccc2c2nc4ccccc4n32)nc(-c2c3ccccc3c(-c3ccc4ccccc4c3)c3ccccc23)c1]

TABLE 1-continued
1-a-47 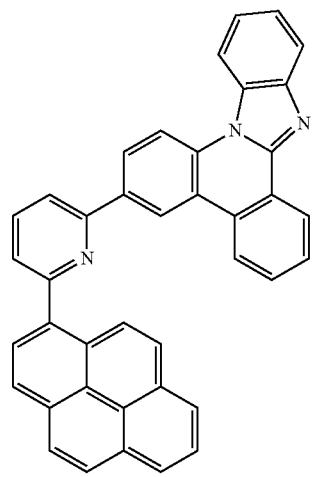 [SMILES: c1cc(-c2ccc3c(c2)c2ccccc2c2nc4ccccc4n32)nc(-c2ccc3ccc4cccc5ccc2c3c45)c1]
1-a-48 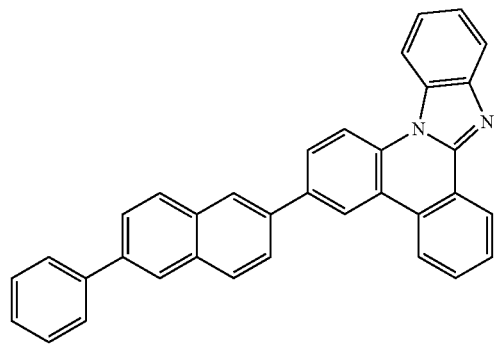 [SMILES: c1ccc(-c2ccc3cc(-c4ccc5c(c4)c4ccccc4c4nc6ccccc6n54)ccc3c2)cc1]
1-a-49 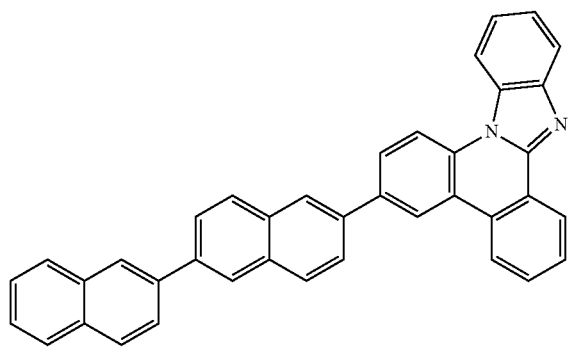 [SMILES: c1ccc2cc(-c3ccc4cc(-c5ccc6c(c5)c5ccccc5c5nc7ccccc7n65)ccc4c3)ccc2c1]
1-a-50 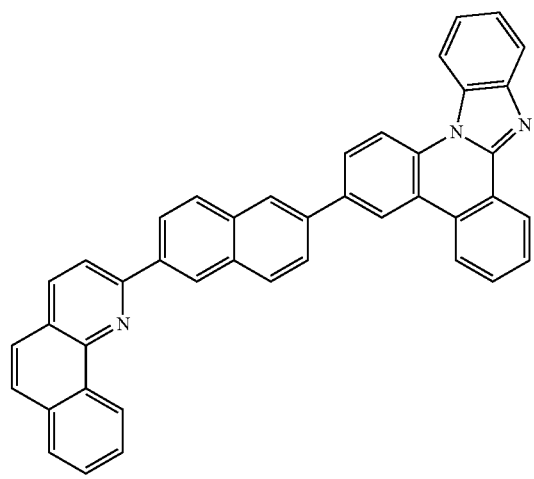 [SMILES: c1ccc2c(c1)ccc1ccc(-c3ccc4cc(-c5ccc6c(c5)c5ccccc5c5nc7ccccc7n65)ccc4c3)nc12]

TABLE 1-continued
1-a-51
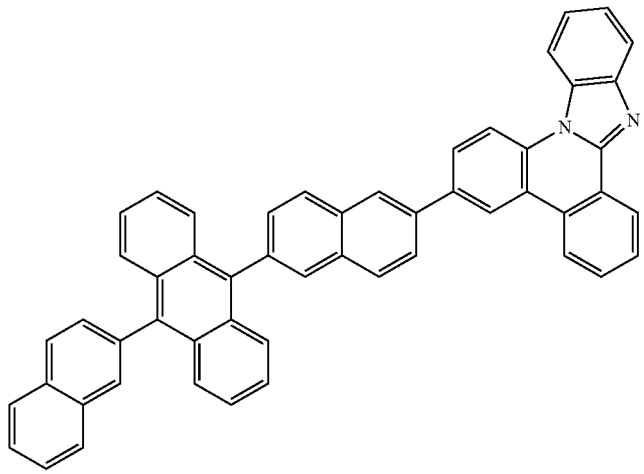 [SMILES: c1ccc2cc(-c3c4ccccc4c(-c4ccc5cc(-c6ccc7c(c6)c6ccccc6c6nc8ccccc8n76)ccc5c4)c4ccccc34)ccc2c1]
1-a-52
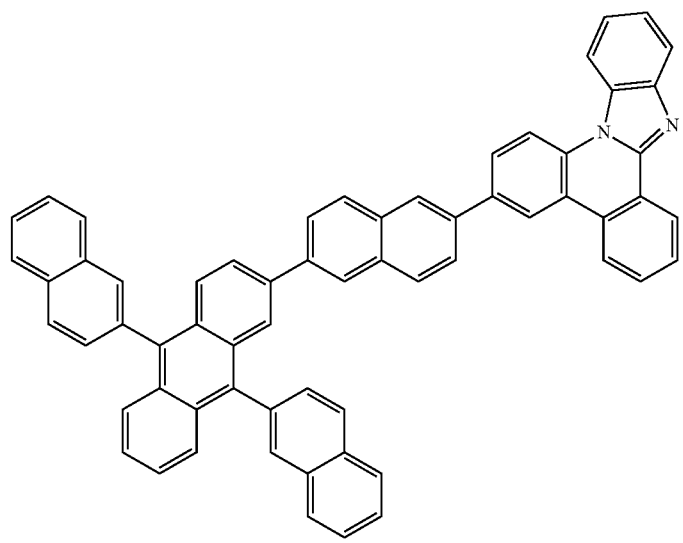 [SMILES: c1ccc2cc(-c3c4ccccc4c(-c4ccc5ccccc5c4)c4cc(-c5ccc6cc(-c7ccc8c(c7)c7ccccc7c7nc9ccccc9n87)ccc6c5)ccc34)ccc2c1]
1-a-53
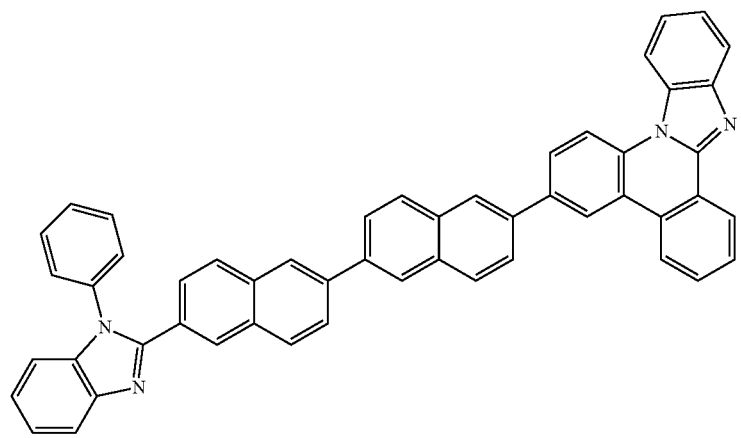 [SMILES: c1ccc(-n2c(-c3ccc4cc(-c5ccc6cc(-c7ccc8c(c7)c7ccccc7c7nc9ccccc9n87)ccc6c5)ccc4c3)nc3ccccc32)cc1]

TABLE 1-continued
1-a-54
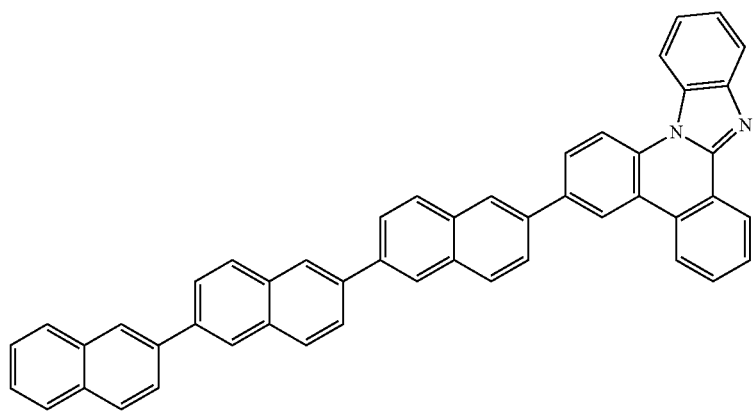 [SMILES: c1ccc2cc(-c3ccc4cc(-c5ccc6cc(-c7ccc8c(c7)c7ccccc7c7nc9ccccc9n87)ccc6c5)ccc4c3)ccc2c1]
1-a-55
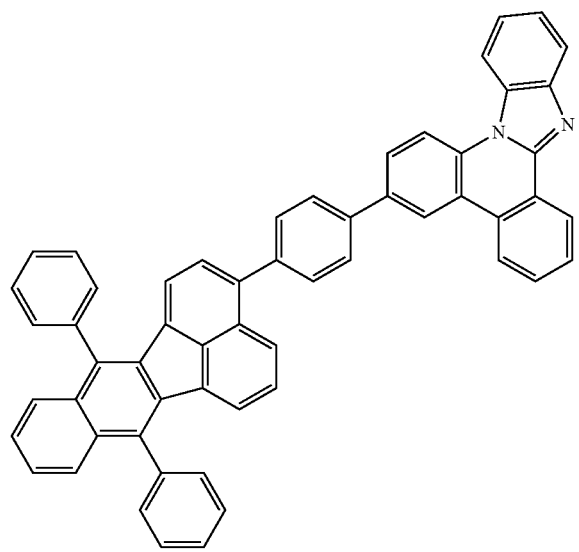 [SMILES: c1ccc(-c2c3c(c(-c4ccccc4)c4ccccc24)-c2ccc(-c4ccc(-c5ccc6c(c5)c5ccccc5c5nc7ccccc7n65)cc4)c4cccc-3c24)cc1]
1-a-56
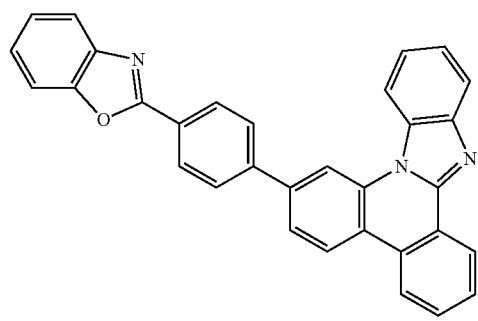 [SMILES: c1ccc2oc(-c3ccc(-c4ccc5c6ccccc6c6nc7ccccc7n6c5c4)cc3)nc2c1]
1-a-57
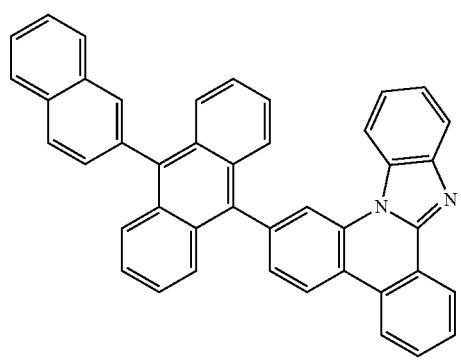 [SMILES: c1ccc2cc(-c3c4ccccc4c(-c4ccc5c6ccccc6c6nc7ccccc7n6c5c4)c4ccccc34)ccc2c1]

TABLE 1-continued
1-a-58
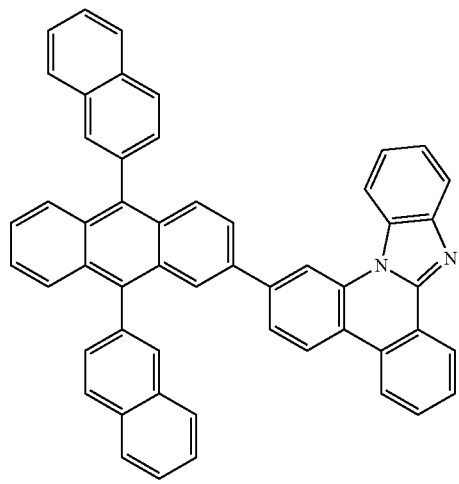 [SMILES: c1ccc2cc(-c3c4ccccc4c(-c4ccc5ccccc5c4)c4cc(-c5ccc6c7ccccc7c7nc8ccccc8n7c6c5)ccc34)ccc2c1]
1-a-59
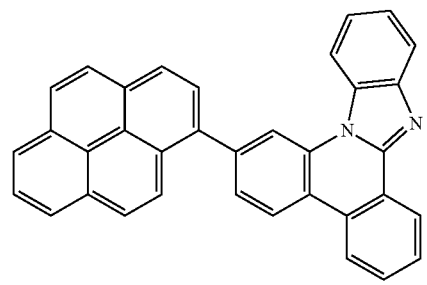 [SMILES: c1cc2ccc3ccc(-c4ccc5c6ccccc6c6nc7ccccc7n6c5c4)c4ccc(c1)c2c34]
1-a-60
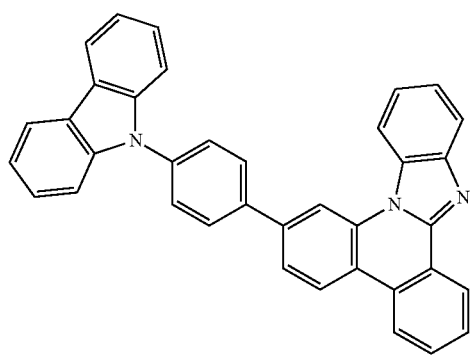 [SMILES: c1ccc2c(c1)nc1c3ccccc3c3ccc(-c4ccc(-n5c6ccccc6c6ccccc65)cc4)cc3n21]
1-a-61
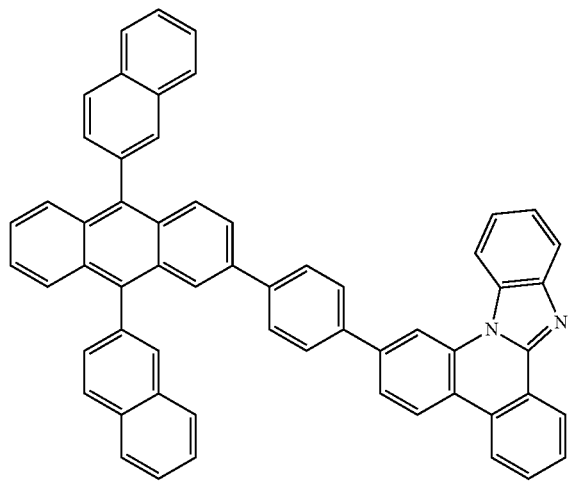 [SMILES: c1ccc2cc(-c3c4ccccc4c(-c4ccc5ccccc5c4)c4cc(-c5ccc(-c6ccc7c8ccccc8c8nc9ccccc9n8c7c6)cc5)ccc34)ccc2c1]

TABLE 1-continued
1-a-62
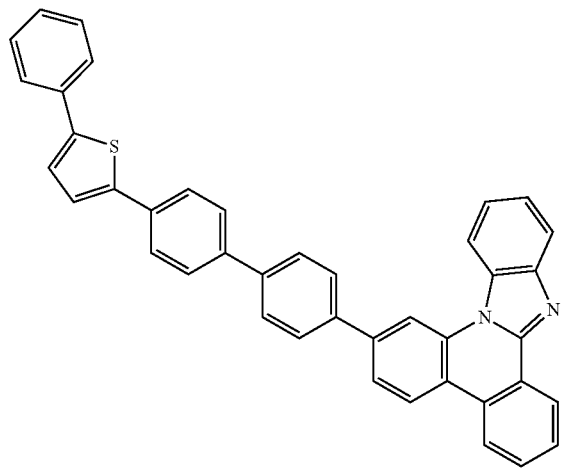 [SMILES: c1ccc(-c2ccc(-c3ccc(-c4ccc(-c5ccc6c7ccccc7c7nc8ccccc8n7c6c5)cc4)cc3)s2)cc1]
1-a-63
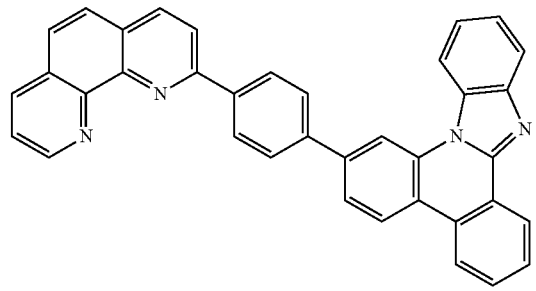 [SMILES: c1cnc2c(c1)ccc1ccc(-c3ccc(-c4ccc5c6ccccc6c6nc7ccccc7n6c5c4)cc3)nc12]
1-a-64
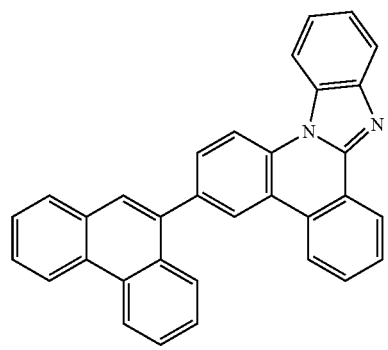 [SMILES: c1ccc2c(c1)cc(-c1ccc3c(c1)c1ccccc1c1nc4ccccc4n31)c1ccccc12]
1-a-65
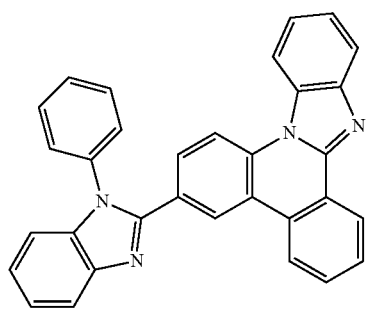 [SMILES: c1ccc(-n2c(-c3ccc4c(c3)c3ccccc3c3nc5ccccc5n43)nc3ccccc32)cc1]

TABLE 1-continued
1-a-66
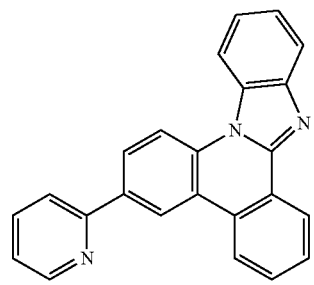 [SMILES: c1ccc(-c2ccc3c(c2)c2ccccc2c2nc4ccccc4n32)nc1]
1-a-67
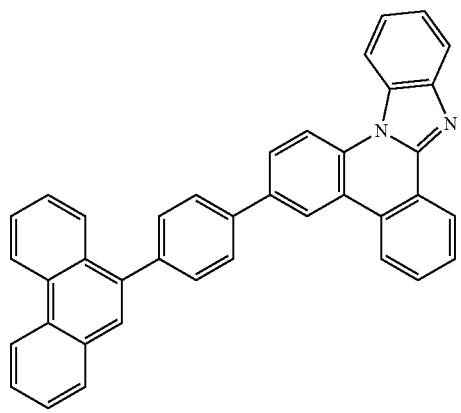 [SMILES: c1ccc2c(c1)cc(-c1ccc(-c3ccc4c(c3)c3ccccc3c3nc5ccccc5n43)cc1)c1ccccc12]
1-a-68
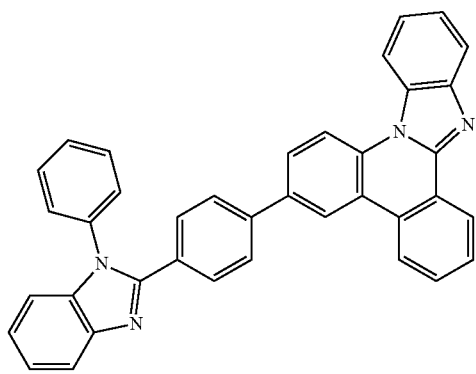 [SMILES: c1ccc(-n2c(-c3ccc(-c4ccc5c(c4)c4ccccc4c4nc6ccccc6n54)cc3)nc3ccccc32)cc1]
1-a-69
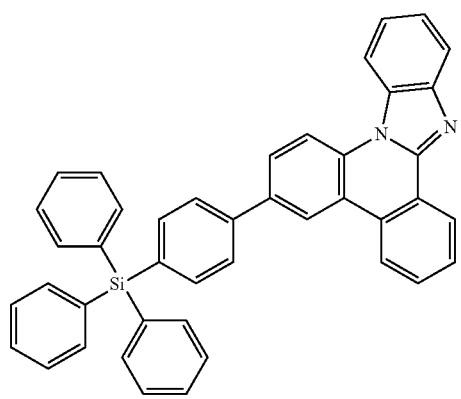 [SMILES: c1ccc([Si](c2ccccc2)(c2ccccc2)c2ccc(-c3ccc4c(c3)c3ccccc3c3nc5ccccc5n43)cc2)cc1]

TABLE 1-continued
1-a-70
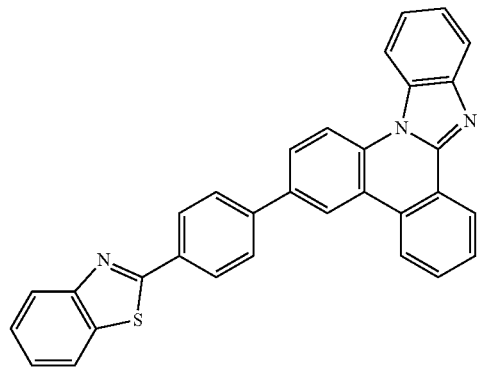 [SMILES: c1ccc2sc(-c3ccc(-c4ccc5c(c4)c4ccccc4c4nc6ccccc6n54)cc3)nc2c1]
1-a-71
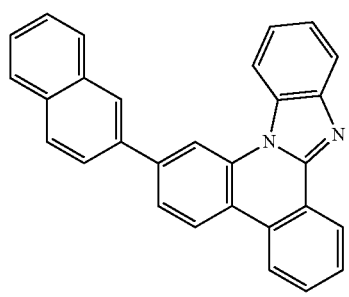 [SMILES: c1ccc2cc(-c3ccc4c5ccccc5c5nc6ccccc6n5c4c3)ccc2c1]
1-a-72
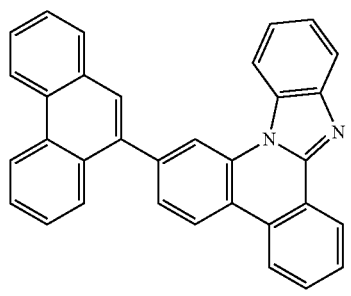 [SMILES: c1ccc2c(c1)cc(-c1ccc3c4ccccc4c4nc5ccccc5n4c3c1)c1ccccc12]
1-a-73
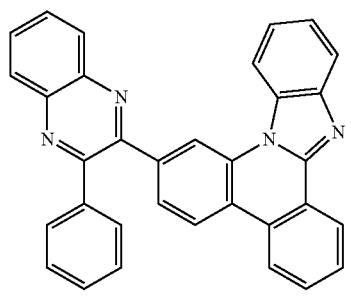 [SMILES: c1ccc(-c2nc3ccccc3nc2-c2ccc3c4ccccc4c4nc5ccccc5n4c3c2)cc1]
1-a-74
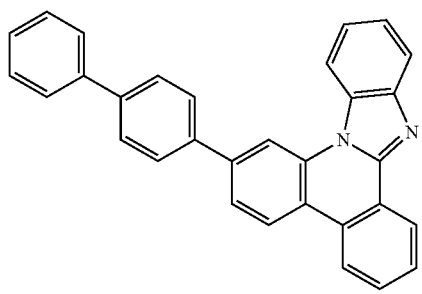 [SMILES: c1ccc(-c2ccc(-c3ccc4c5ccccc5c5nc6ccccc6n5c4c3)cc2)cc1]

TABLE 1-continued
1-a-75
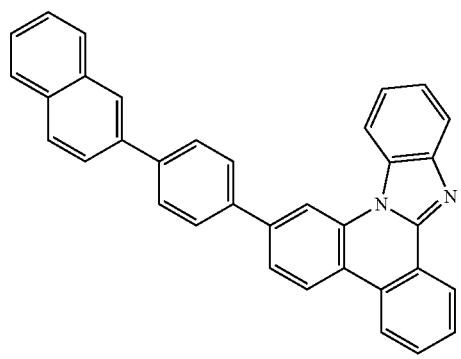 [SMILES: c1ccc2cc(-c3ccc(-c4ccc5c6ccccc6c6nc7ccccc7n6c5c4)cc3)ccc2c1]
1-a-76
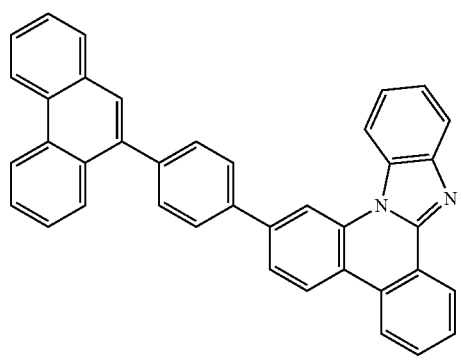 [SMILES: c1ccc2c(c1)cc(-c1ccc(-c3ccc4c5ccccc5c5nc6ccccc6n5c4c3)cc1)c1ccccc12]
1-a-77
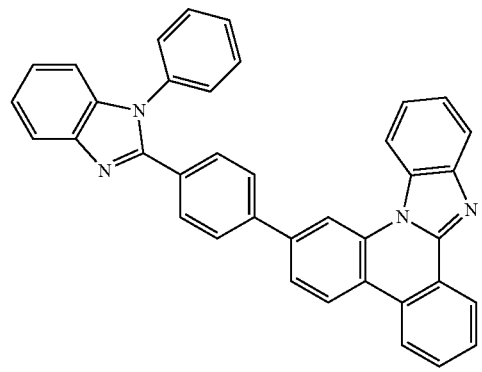 [SMILES: c1ccc(-n2c(-c3ccc(-c4ccc5c6ccccc6c6nc7ccccc7n6c5c4)cc3)nc3ccccc32)cc1]
1-a-78
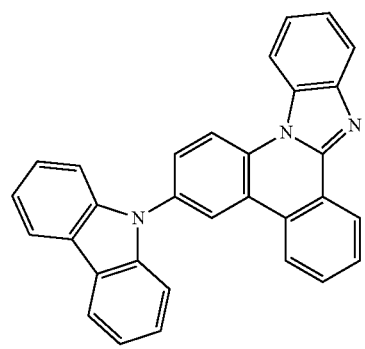 [SMILES: c1ccc2c(c1)nc1c3ccccc3c3cc(-n4c5ccccc5c5ccccc54)ccc3n21]

TABLE 1-continued
1-a-79 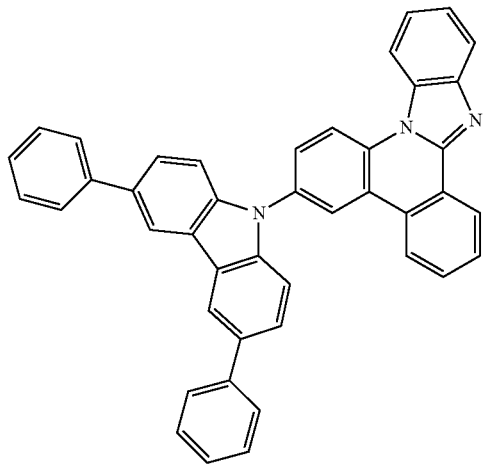 [SMILES: c1ccc(-c2ccc3c(c2)c2cc(-c4ccccc4)ccc2n3-c2ccc3c(c2)c2ccccc2c2nc4ccccc4n32)cc1]
1-a-80 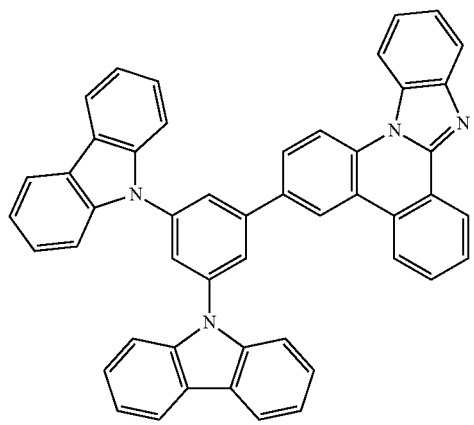 [SMILES: c1ccc2c(c1)nc1c3ccccc3c3cc(-c4cc(-n5c6ccccc6c6ccccc65)cc(-n5c6ccccc6c6ccccc65)c4)ccc3n21]
1-a-81 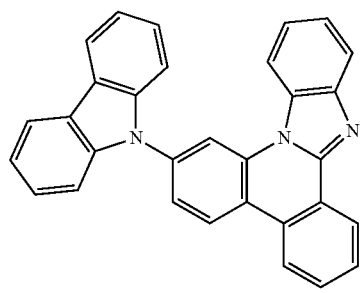 [SMILES: c1ccc2c(c1)nc1c3ccccc3c3ccc(-n4c5ccccc5c5ccccc54)cc3n21]
1-a-82 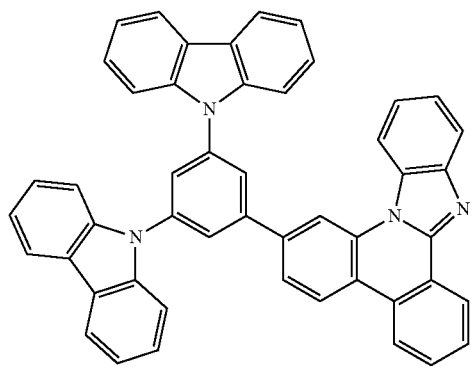 [SMILES: c1ccc2c(c1)nc1c3ccccc3c3ccc(-c4cc(-n5c6ccccc6c6ccccc65)cc(-n5c6ccccc6c6ccccc65)c4)cc3n21]

TABLE 1-continued
1-a-83 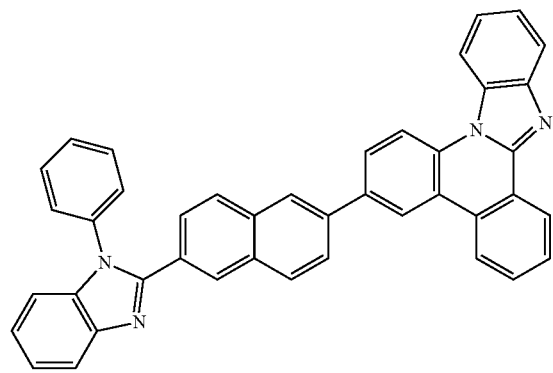 [SMILES: c1ccc(-n2c(-c3ccc4cc(-c5ccc6c(c5)c5ccccc5c5nc7ccccc7n65)ccc4c3)nc3ccccc32)cc1]
1-a-84 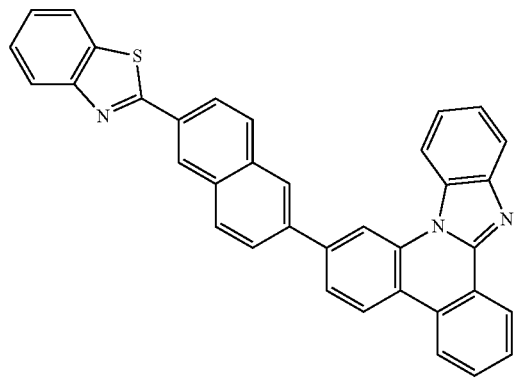 [SMILES: c1ccc2sc(-c3ccc4cc(-c5ccc6c7ccccc7c7nc8ccccc8n7c6c5)ccc4c3)nc2c1]
1-a-85 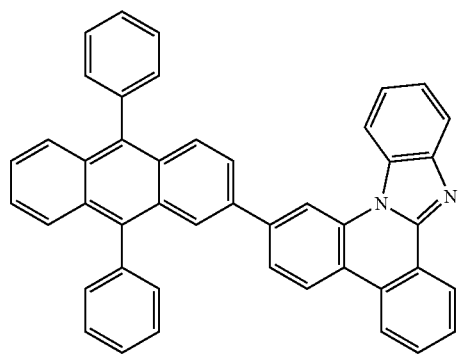 [SMILES: c1ccc(-c2c3ccccc3c(-c3ccccc3)c3cc(-c4ccc5c6ccccc6c6nc7ccccc7n6c5c4)ccc23)cc1]
1-a-86 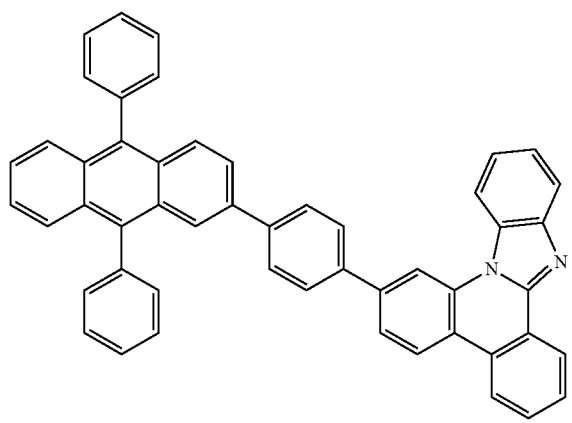 [SMILES: c1ccc(-c2c3ccccc3c(-c3ccccc3)c3cc(-c4ccc(-c5ccc6c7ccccc7c7nc8ccccc8n7c6c5)cc4)ccc23)cc1]

TABLE 1-continued
1-a-87
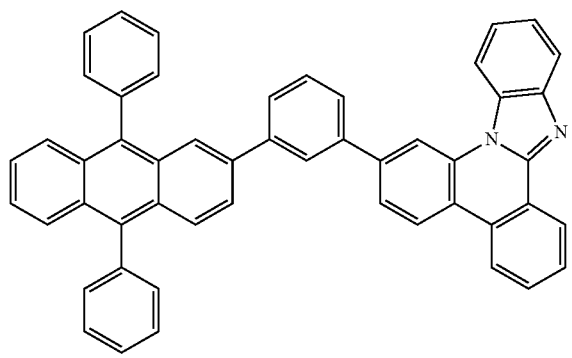 [SMILES: c1ccc(-c2c3ccccc3c(-c3ccccc3)c3cc(-c4cccc(-c5ccc6c7ccccc7c7nc8ccccc8n7c6c5)c4)ccc23)cc1]
1-a-88
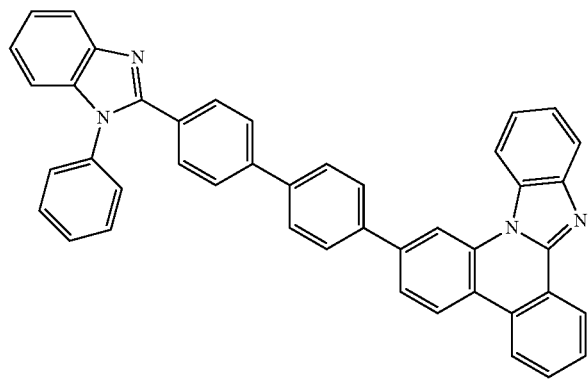 [SMILES: c1ccc(-n2c(-c3ccc(-c4ccc(-c5ccc6c7ccccc7c7nc8ccccc8n7c6c5)cc4)cc3)nc3ccccc32)cc1]
1-a-89
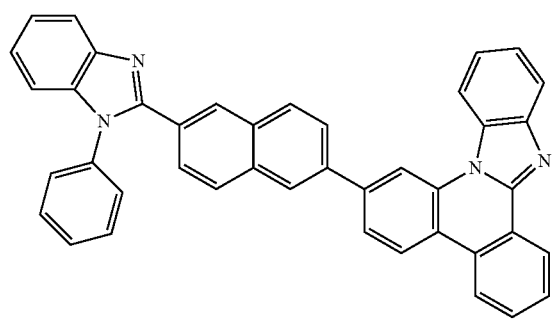 [SMILES: c1ccc(-n2c(-c3ccc4cc(-c5ccc6c7ccccc7c7nc8ccccc8n7c6c5)ccc4c3)nc3ccccc32)cc1]
1-a-90
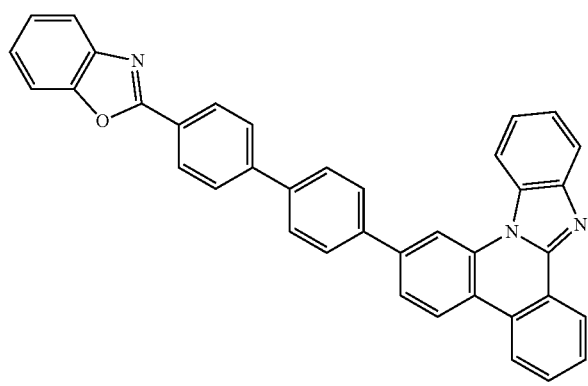 [SMILES: c1ccc2oc(-c3ccc(-c4ccc(-c5ccc6c7ccccc7c7nc8ccccc8n7c6c5)cc4)cc3)nc2c1]

TABLE 1-continued
1-a-91
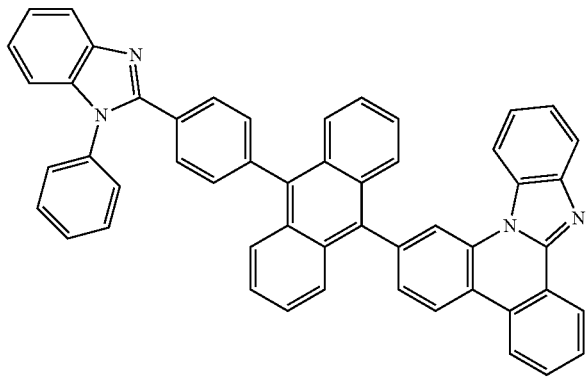 [SMILES: c1ccc(-n2c(-c3ccc(-c4c5ccccc5c(-c5ccc6c7ccccc7c7nc8ccccc8n7c6c5)c5ccccc45)cc3)nc3ccccc32)cc1]
1-a-92
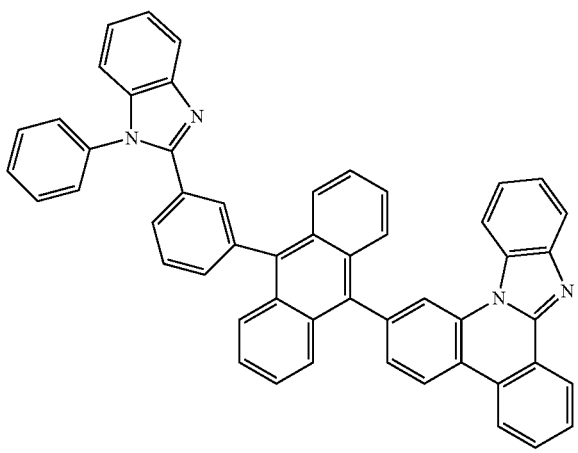 [SMILES: c1ccc(-n2c(-c3cccc(-c4c5ccccc5c(-c5ccc6c7ccccc7c7nc8ccccc8n7c6c5)c5ccccc45)c3)nc3ccccc32)cc1]
1-a-93
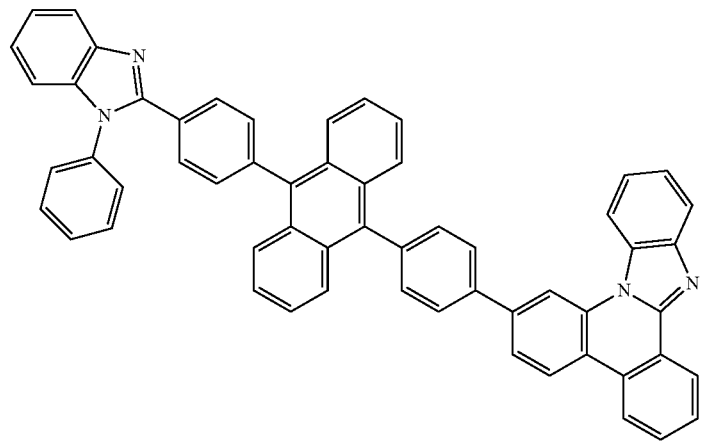 [SMILES: c1ccc(-n2c(-c3ccc(-c4c5ccccc5c(-c5ccc(-c6ccc7c8ccccc8c8nc9ccccc9n8c7c6)cc5)c5ccccc45)cc3)nc3ccccc32)cc1]
1-a-94
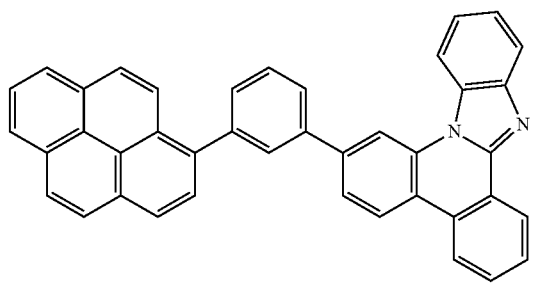 [SMILES: c1cc(-c2ccc3c4ccccc4c4nc5ccccc5n4c3c2)cc(-c2ccc3ccc4cccc5ccc2c3c45)c1]

TABLE 1-continued
1-a-95 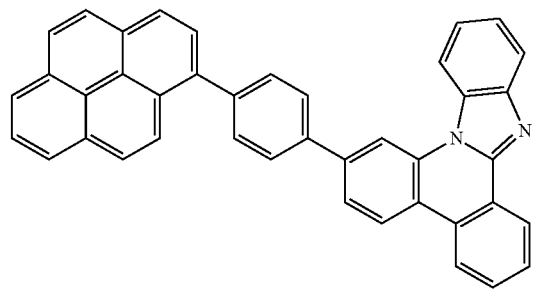 [SMILES: c1cc2ccc3ccc(-c4ccc(-c5ccc6c7ccccc7c7nc8ccccc8n7c6c5)cc4)c4ccc(c1)c2c34]
1-a-96 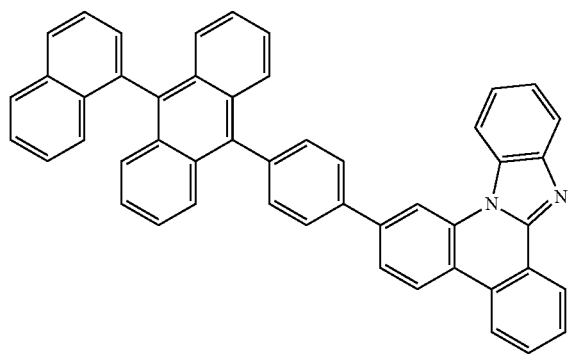 [SMILES: c1ccc2c(-c3c4ccccc4c(-c4ccc(-c5ccc6c7ccccc7c7nc8ccccc8n7c6c5)cc4)c4ccccc34)cccc2c1]
1-a-97 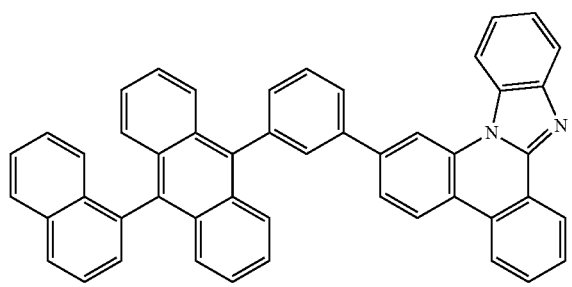 [SMILES: c1cc(-c2ccc3c4ccccc4c4nc5ccccc5n4c3c2)cc(-c2c3ccccc3c(-c3cccc4ccccc34)c3ccccc23)c1]
1-a-98 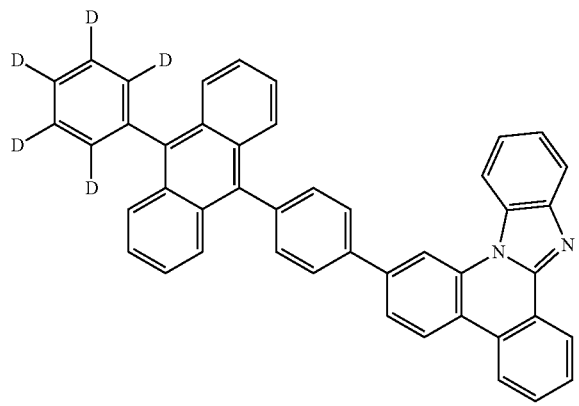 [SMILES: [2H]c1c([2H])c([2H])c(-c2c3ccccc3c(-c3ccc(-c4ccc5c6ccccc6c6nc7ccccc7n6c5c4)cc3)c3ccccc23)c([2H])c1[2H]]

TABLE 1-continued
1-a-99 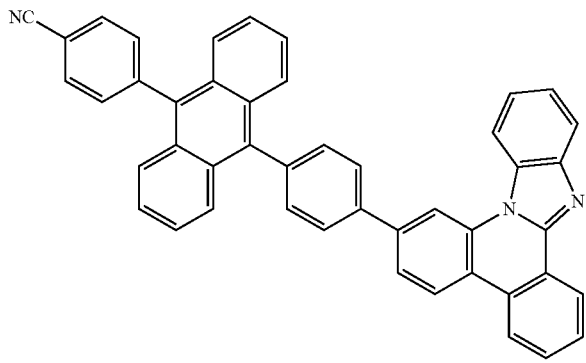 [SMILES: N#Cc1ccc(-c2c3ccccc3c(-c3ccc(-c4ccc5c6ccccc6c6nc7ccccc7n6c5c4)cc3)c3ccccc23)cc1]
1-a-100 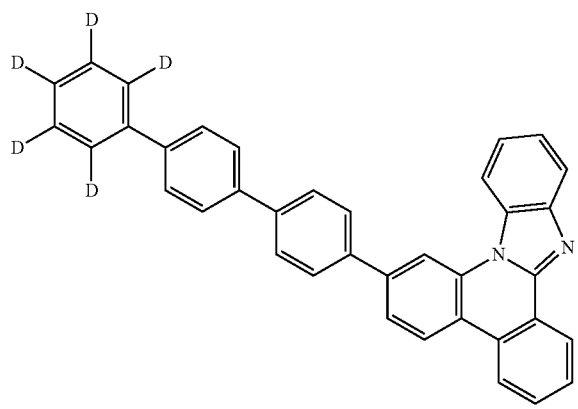 [SMILES: [2H]c1c([2H])c([2H])c(-c2ccc(-c3ccc(-c4ccc5c6ccccc6c6nc7ccccc7n6c5c4)cc3)cc2)c([2H])c1[2H]]
1-a-101 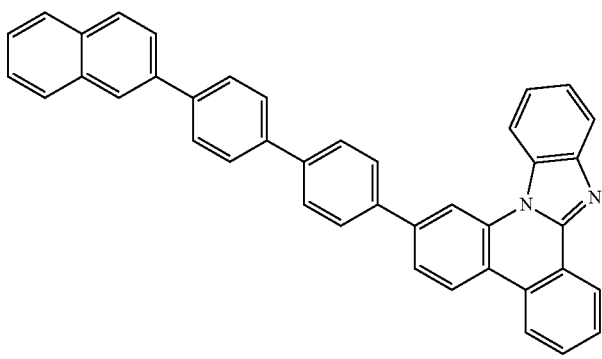 [SMILES: c1ccc2cc(-c3ccc(-c4ccc(-c5ccc6c7ccccc7c7nc8ccccc8n7c6c5)cc4)cc3)ccc2c1]
1-a-102 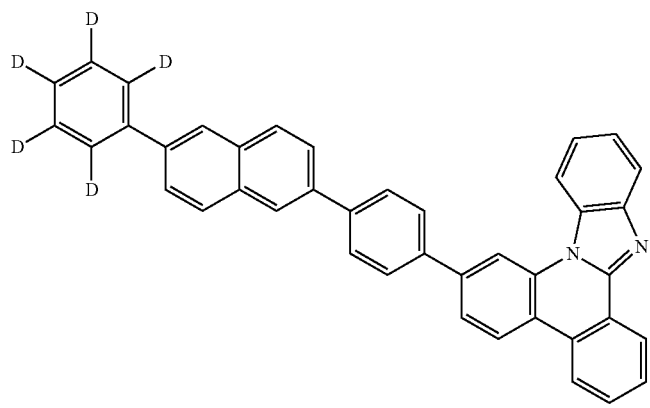 [SMILES: [2H]c1c([2H])c([2H])c(-c2ccc3cc(-c4ccc(-c5ccc6c7ccccc7c7nc8ccccc8n7c6c5)cc4)ccc3c2)c([2H])c1[2H]]

In addition, as preferable detailed examples of the compound that is represented by Formula 1, there are the following compounds, but they are not limited thereto.
TABLE 2
1-b-1
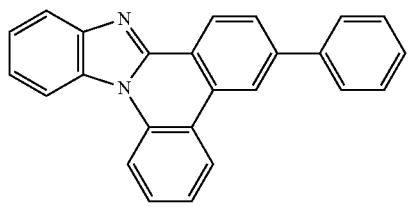 [SMILES: c1ccc(-c2ccc3c(c2)c2ccccc2n2c4ccccc4nc32)cc1]
1-b-2
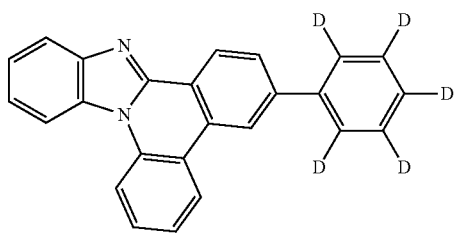 [SMILES: [2H]c1c([2H])c([2H])c(-c2ccc3c(c2)c2ccccc2n2c4ccccc4nc32)c([2H])c1[2H]]
1-b-3
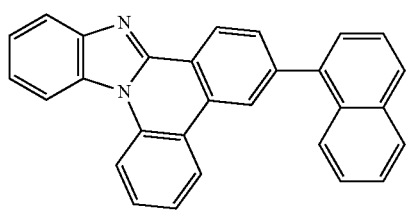 [SMILES: c1ccc2c(-c3ccc4c(c3)c3ccccc3n3c5ccccc5nc43)cccc2c1]
1-b-4
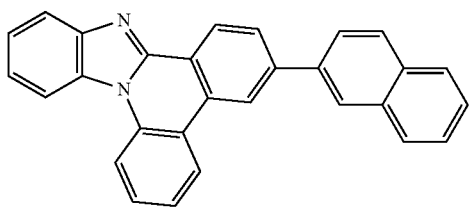 [SMILES: c1ccc2cc(-c3ccc4c(c3)c3ccccc3n3c5ccccc5nc43)ccc2c1]
1-b-5
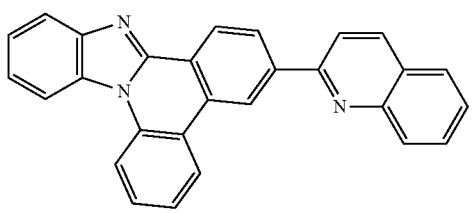
1-b-6
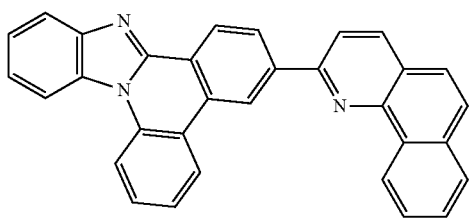 [SMILES: c1ccc2c(c1)ccc1ccc(-c3ccc4c(c3)c3ccccc3n3c5ccccc5nc43)nc12]

TABLE 2-continued
1-b-7
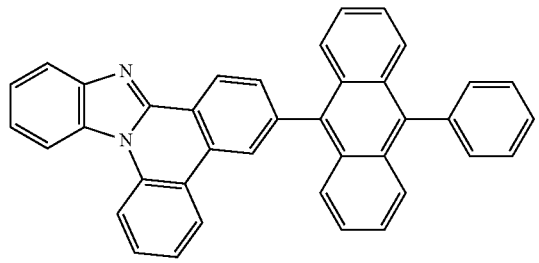 [SMILES: c1ccc(-c2c3ccccc3c(-c3ccc4c(c3)c3ccccc3n3c5ccccc5nc43)c3ccccc23)cc1]
1-b-8
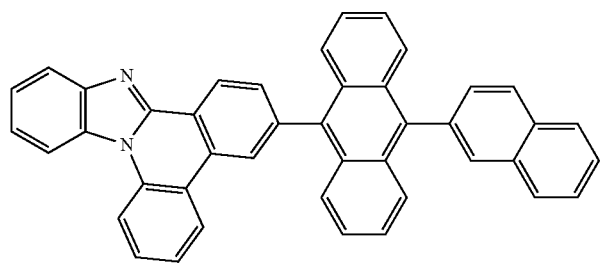 [SMILES: c1ccc2cc(-c3c4ccccc4c(-c4ccc5c(c4)c4ccccc4n4c6ccccc6nc54)c4ccccc34)ccc2c1]
1-b-9
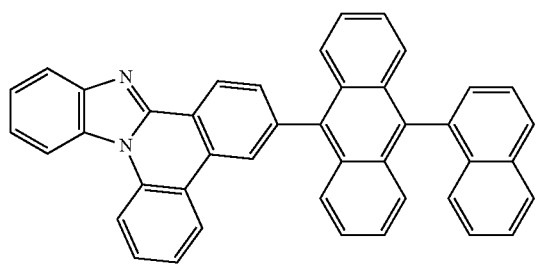 [SMILES: c1ccc2c(-c3c4ccccc4c(-c4ccc5c(c4)c4ccccc4n4c6ccccc6nc54)c4ccccc34)cccc2c1]
1-b-10
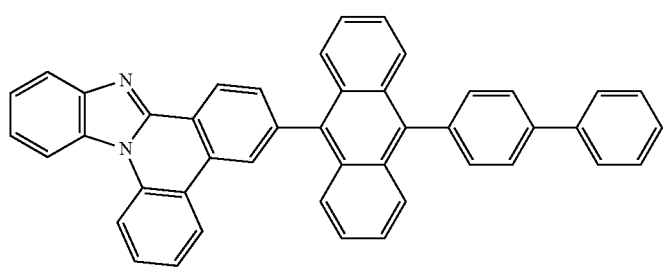 [SMILES: c1ccc(-c2ccc(-c3c4ccccc4c(-c4ccc5c(c4)c4ccccc4n4c6ccccc6nc54)c4ccccc34)cc2)cc1]
1-b-11
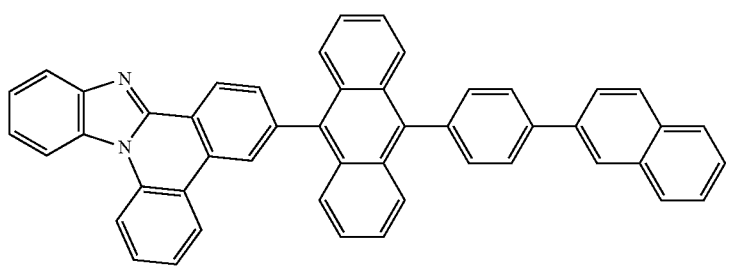 [SMILES: c1ccc2cc(-c3ccc(-c4c5ccccc5c(-c5ccc6c(c5)c5ccccc5n5c7ccccc7nc65)c5ccccc45)cc3)ccc2c1]

TABLE 2-continued
1-b-12
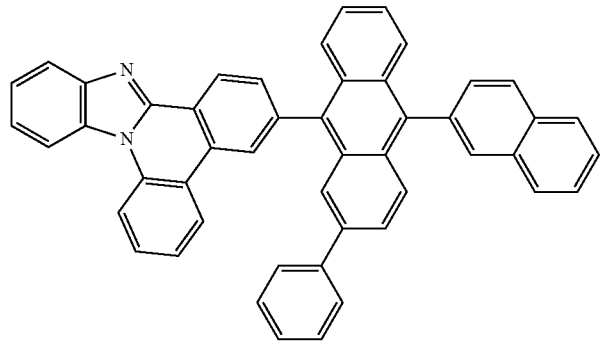 [SMILES: c1ccc(-c2ccc3c(-c4ccc5ccccc5c4)c4ccccc4c(-c4ccc5c(c4)c4ccccc4n4c6ccccc6nc54)c3c2)cc1]
1-b-13
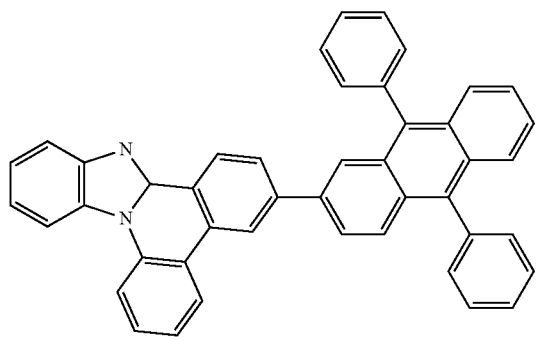 [SMILES: c1ccc(-c2c3ccccc3c(-c3ccccc3)c3cc(-c4ccc5c(c4)-c4ccccc4N4c6ccccc6NC54)ccc23)cc1]
1-b-14
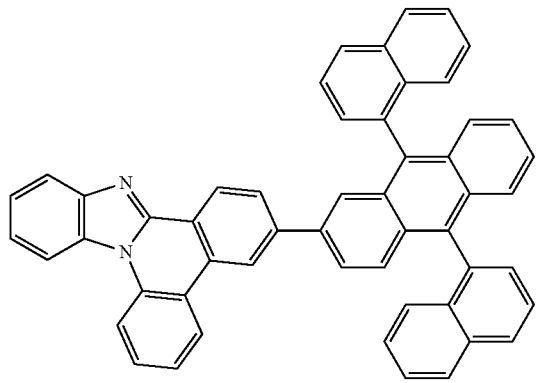 [SMILES: c1ccc2c(-c3c4ccccc4c(-c4cccc5ccccc45)c4cc(-c5ccc6c(c5)c5ccccc5n5c7ccccc7nc65)ccc34)cccc2c1]
1-b-15
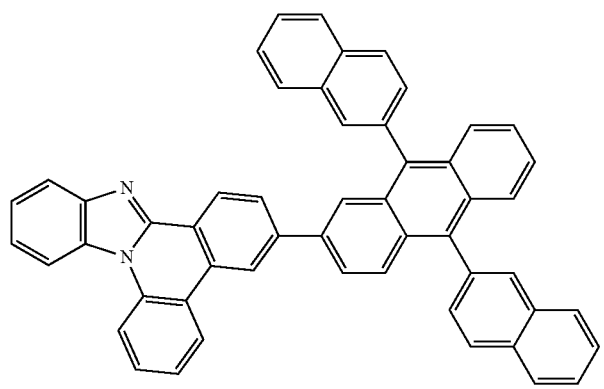 [SMILES: c1ccc2cc(-c3c4ccccc4c(-c4ccc5ccccc5c4)c4cc(-c5ccc6c(c5)c5ccccc5n5c7ccccc7nc65)ccc34)ccc2c1]

TABLE 2-continued
1-b-16
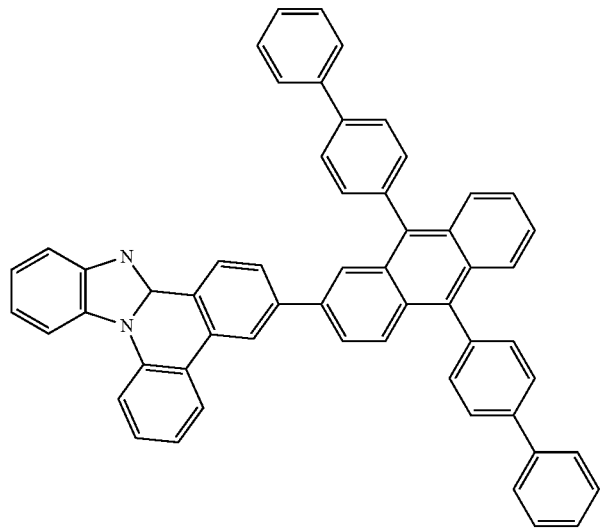 [SMILES: c1ccc(-c2ccc(-c3c4ccccc4c(-c4ccc(-c5ccccc5)cc4)c4cc(-c5ccc6c(c5)-c5ccccc5N5c7ccccc7NC65)ccc34)cc2)cc1]
1-b-17
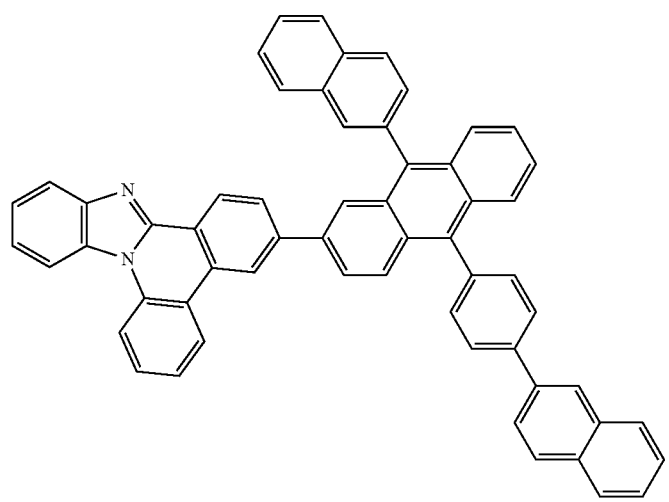 [SMILES: c1ccc2cc(-c3ccc(-c4c5ccccc5c(-c5ccc6ccccc6c5)c5cc(-c6ccc7c(c6)c6ccccc6n6c8ccccc8nc76)ccc45)cc3)ccc2c1]
1-b-18
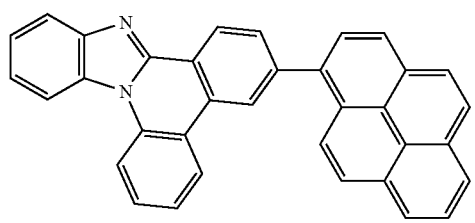 [SMILES: c1cc2ccc3ccc(-c4ccc5c(c4)c4ccccc4n4c6ccccc6nc54)c4ccc(c1)c2c34]
1-b-19
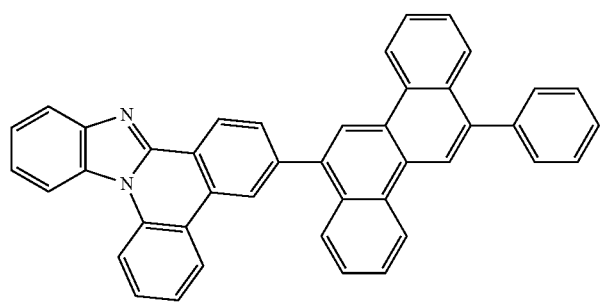 [SMILES: c1ccc(-c2cc3c4ccccc4c(-c4ccc5c(c4)c4ccccc4n4c6ccccc6nc54)cc3c3ccccc23)cc1]

TABLE 2-continued
1-b-20
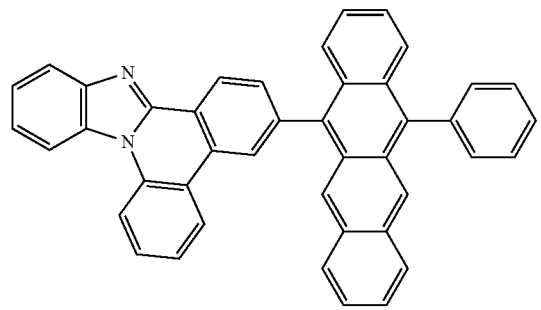 [SMILES: c1ccc(-c2c3ccccc3c(-c3ccc4c(c3)c3ccccc3n3c5ccccc5nc43)c3cc4ccccc4cc23)cc1]
1-b-21
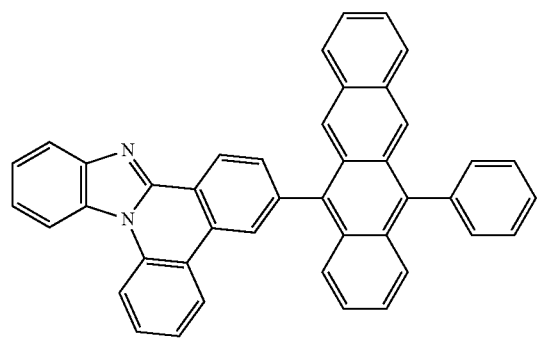 [SMILES: c1ccc(-c2c3ccccc3c(-c3ccc4c(c3)c3ccccc3n3c5ccccc5nc43)c3cc4ccccc4cc23)cc1]
1-b-22
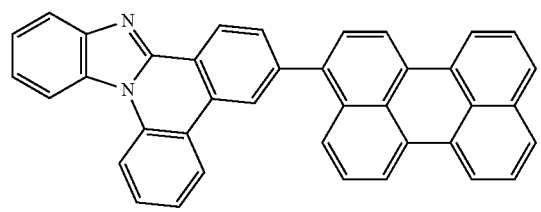 [SMILES: c1ccc2c(c1)nc1c3ccc(-c4ccc5c6cccc7cccc(c8cccc4c85)c76)cc3c3ccccc3n21]
1-b-23
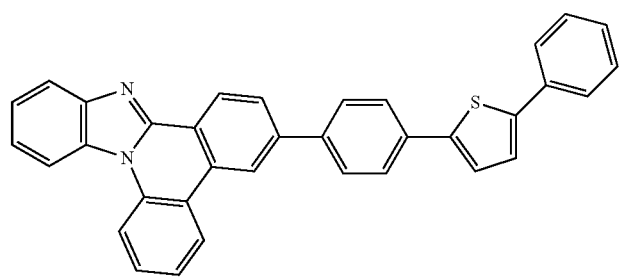 [SMILES: c1ccc(-c2ccc(-c3ccc(-c4ccc5c(c4)c4ccccc4n4c6ccccc6nc54)cc3)s2)cc1]
1-b-24
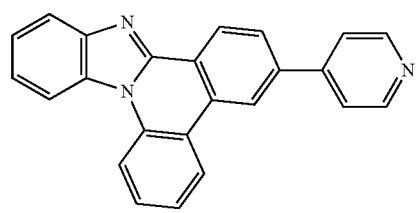 [SMILES: c1ccc2c(c1)nc1c3ccc(-c4ccncc4)cc3c3ccccc3n21]

TABLE 2-continued
1-b-25
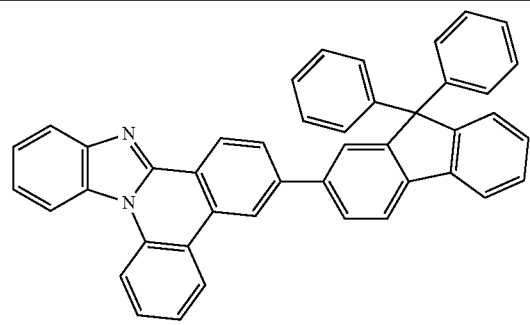
1-b-26
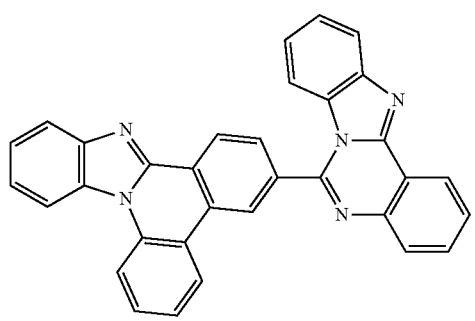 [SMILES: c1ccc2c(c1)nc(-c1ccc3c(c1)c1ccccc1n1c4ccccc4nc31)n1c3ccccc3nc21]
1-b-27
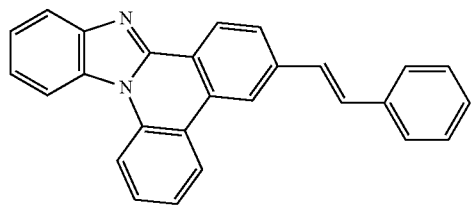 [SMILES: C(=C\c1ccc2c(c1)c1ccccc1n1c3ccccc3nc21)/c1ccccc1]
1-b-28
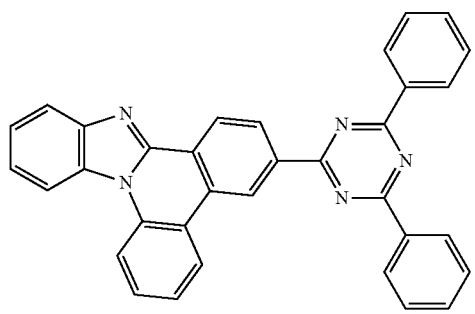 [SMILES: c1ccc(-c2nc(-c3ccccc3)nc(-c3ccc4c(c3)c3ccccc3n3c5ccccc5nc43)n2)cc1]
1-b-29
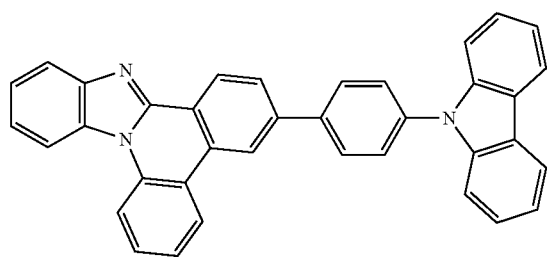 [SMILES: c1ccc2c(c1)nc1c3ccc(-c4ccc(-n5c6ccccc6c6ccccc65)cc4)cc3c3ccccc3n21]

TABLE 2-continued
1-b-30 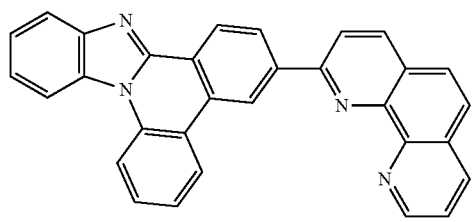
1-b-31 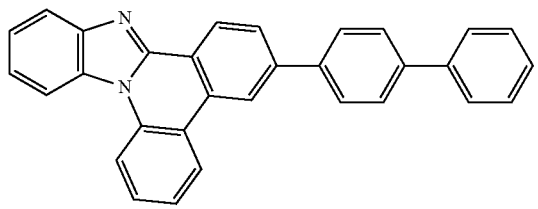
1-b-32 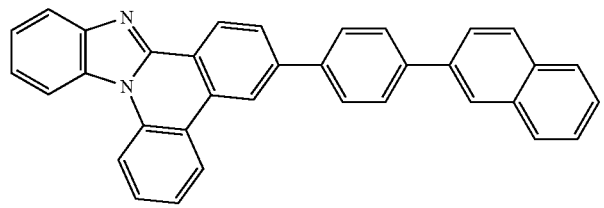 [SMILES: c1ccc2cc(-c3ccc(-c4ccc5c(c4)c4ccccc4n4c6ccccc6nc54)cc3)ccc2c1]
1-b-33 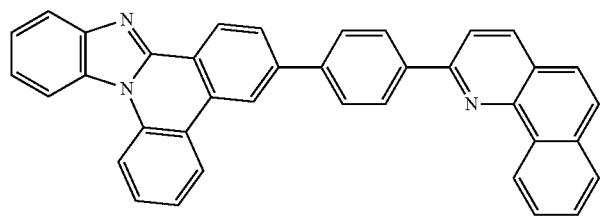 [SMILES: c1ccc2c(c1)ccc1ccc(-c3ccc(-c4ccc5c(c4)c4ccccc4n4c6ccccc6nc54)cc3)nc12]
1-b-34 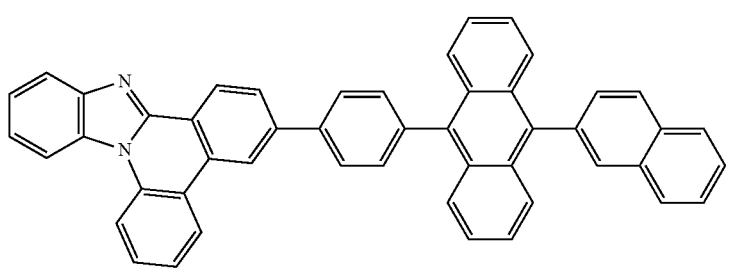 [SMILES: c1ccc2cc(-c3c4ccccc4c(-c4ccc(-c5ccc6c(c5)c5ccccc5n5c7ccccc7nc65)cc4)c4ccccc34)ccc2c1]
1-b-35 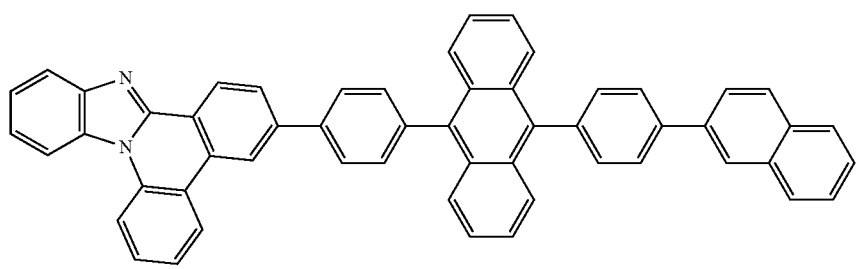 [SMILES: c1ccc2cc(-c3ccc(-c4c5ccccc5c(-c5ccc(-c6ccc7c(c6)c6ccccc6n6c8ccccc8nc76)cc5)c5ccccc45)cc3)ccc2c1]

TABLE 2-continued
1-b-36
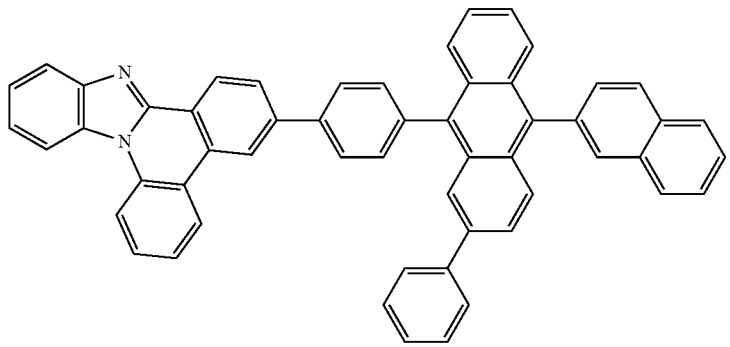 [SMILES: c1ccc(-c2ccc3c(-c4ccc5ccccc5c4)c4ccccc4c(-c4ccc(-c5ccc6c(c5)c5ccccc5n5c7ccccc7nc65)cc4)c3c2)cc1]
1-b-37
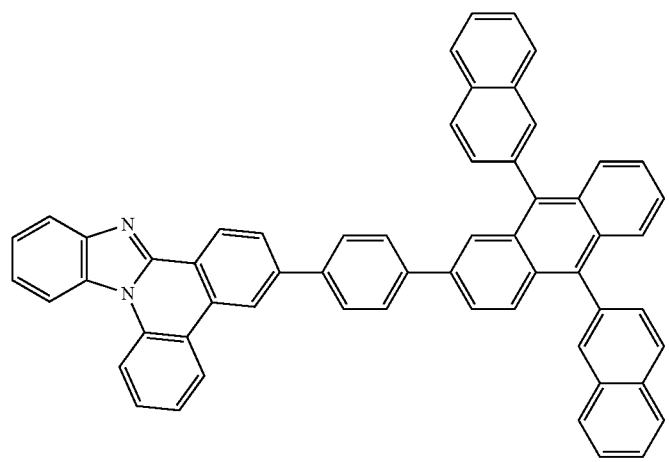 [SMILES: c1ccc2cc(-c3c4ccccc4c(-c4ccc5ccccc5c4)c4cc(-c5ccc(-c6ccc7c(c6)c6ccccc6n6c8ccccc8nc76)cc5)ccc34)ccc2c1]
1-b-38
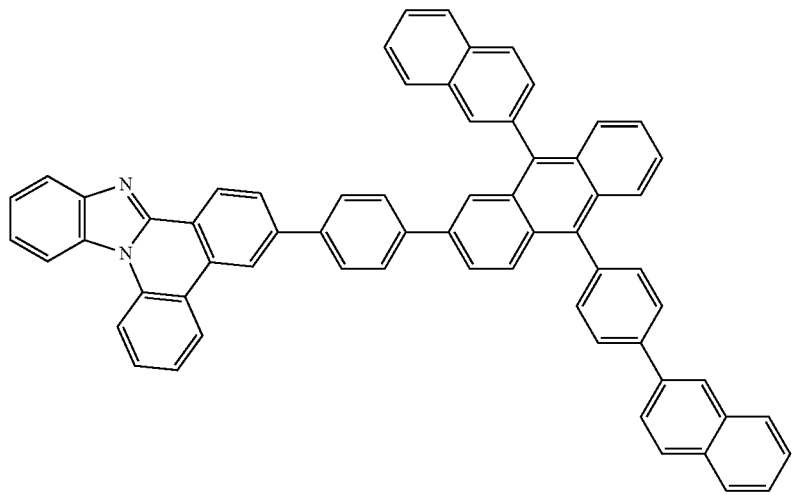 [SMILES: c1ccc2cc(-c3ccc(-c4c5ccccc5c(-c5ccc6ccccc6c5)c5cc(-c6ccc(-c7ccc8c(c7)c7ccccc7n7c9ccccc9nc87)cc6)ccc45)cc3)ccc2c1]
1-b-39
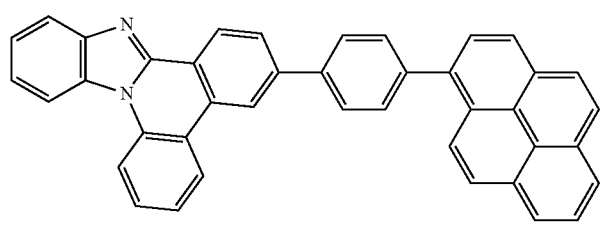 [SMILES: c1cc2ccc3ccc(-c4ccc(-c5ccc6c(c5)c5ccccc5n5c7ccccc7nc65)cc4)c4ccc(c1)c2c34]

TABLE 2-continued
1-b-40
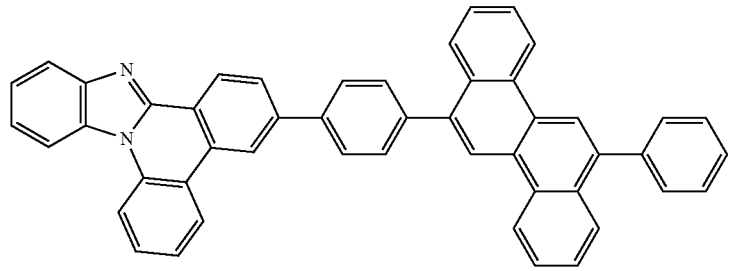 [SMILES: c1ccc(-c2cc3c4ccccc4c(-c4ccc(-c5ccc6c(c5)c5ccccc5n5c7ccccc7nc65)cc4)cc3c3ccccc23)cc1]
1-b-41
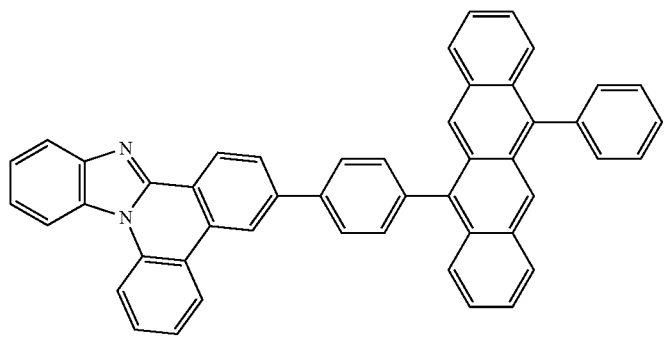 [SMILES: c1ccc(-c2c3ccccc3cc3c(-c4ccc(-c5ccc6c(c5)c5ccccc5n5c7ccccc7nc65)cc4)c4ccccc4cc23)cc1]
1-b-42
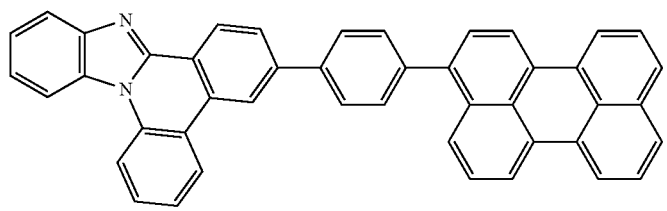 [SMILES: c1ccc2c(c1)nc1c3ccc(-c4ccc(-c5ccc6c7cccc8cccc(c9cccc5c96)c87)cc4)cc3c3ccccc3n21]
1-b-43
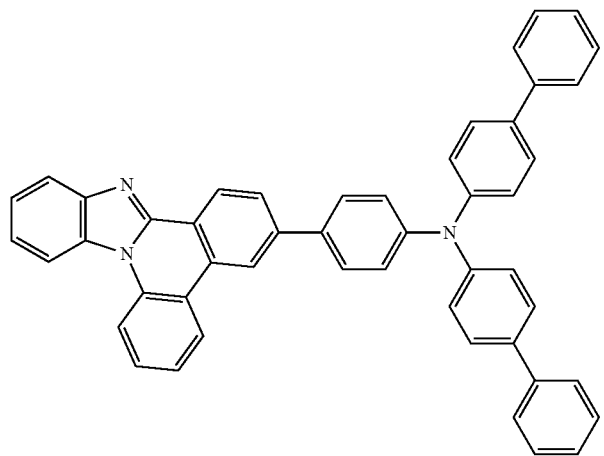 [SMILES: c1ccc(-c2ccc(N(c3ccc(-c4ccccc4)cc3)c3ccc(-c4ccc5c(c4)c4ccccc4n4c6ccccc6nc54)cc3)cc2)cc1]
1-b-44
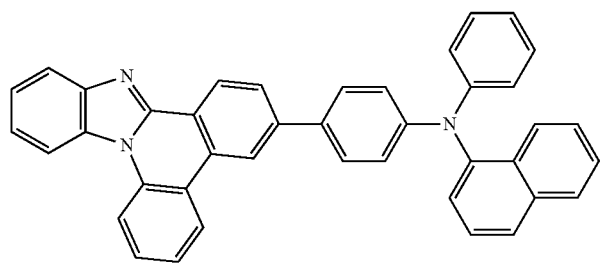 [SMILES: c1ccc(N(c2ccc(-c3ccc4c(c3)c3ccccc3n3c5ccccc5nc43)cc2)c2cccc3ccccc23)cc1]

TABLE 2-continued
1-b-45
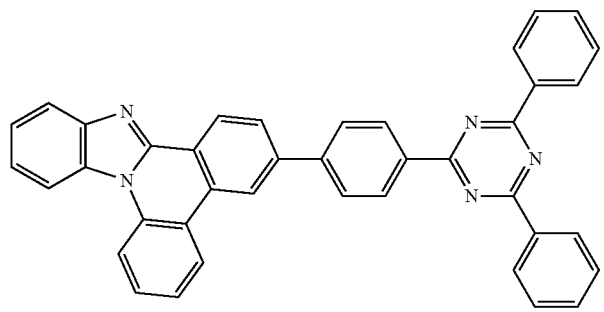 [SMILES: c1ccc(-c2nc(-c3ccccc3)nc(-c3ccc(-c4ccc5c(c4)c4ccccc4n4c6ccccc6nc54)cc3)n2)cc1]
1-b-46
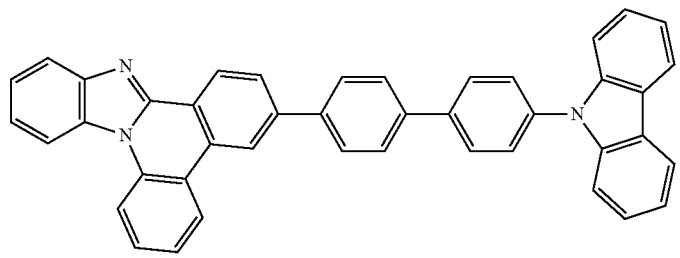 [SMILES: c1ccc2c(c1)nc1c3ccc(-c4ccc(-c5ccc(-n6c7ccccc7c7ccccc76)cc5)cc4)cc3c3ccccc3n21]
1-b-47
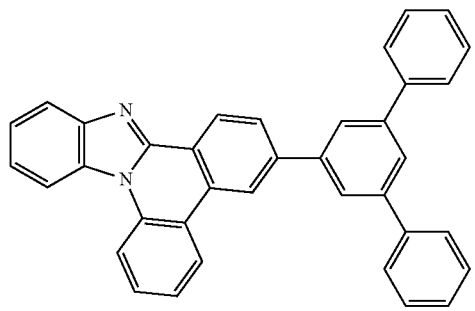 [SMILES: c1ccc(-c2cc(-c3ccccc3)cc(-c3ccc4c(c3)c3ccccc3n3c5ccccc5nc43)c2)cc1]
1-b-48
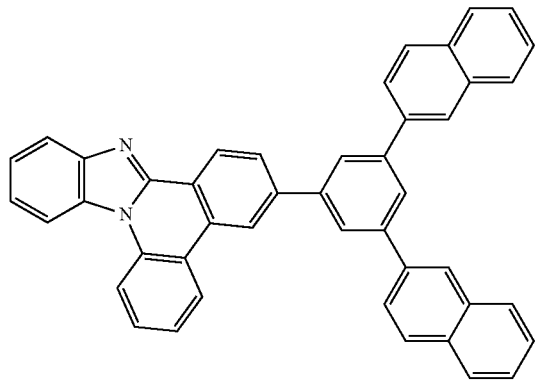 [SMILES: c1ccc2cc(-c3cc(-c4ccc5ccccc5c4)cc(-c4ccc5c(c4)c4ccccc4n4c6ccccc6nc54)c3)ccc2c1]
1-b-49
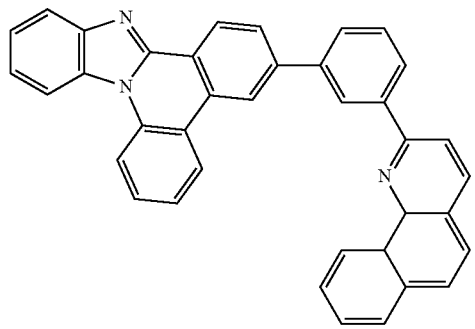 [SMILES: C1=CC2=CC=C3C=CC(c4cccc(-c5ccc6c(c5)c5ccccc5n5c7ccccc7nc65)c4)=NC3C2C=C1]

TABLE 2-continued
1-b-50
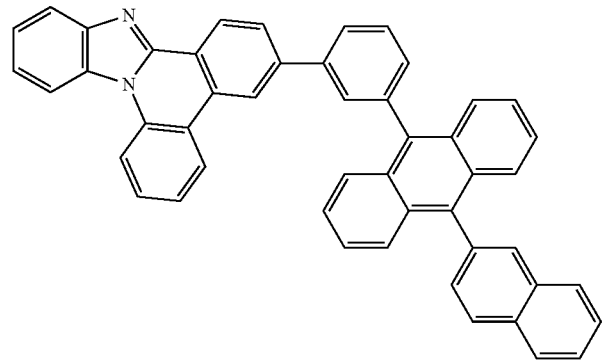
1-b-51
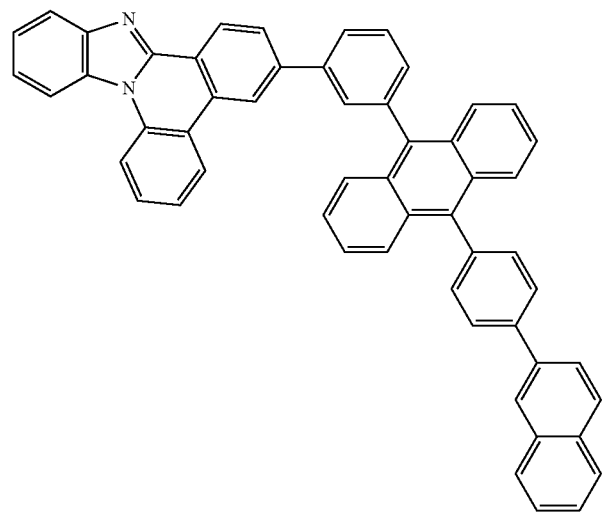 [SMILES: c1cc(-c2ccc3c(c2)c2ccccc2n2c4ccccc4nc32)cc(-c2c3ccccc3c(-c3ccc(-c4ccc5ccccc5c4)cc3)c3ccccc23)c1]
1-b-52
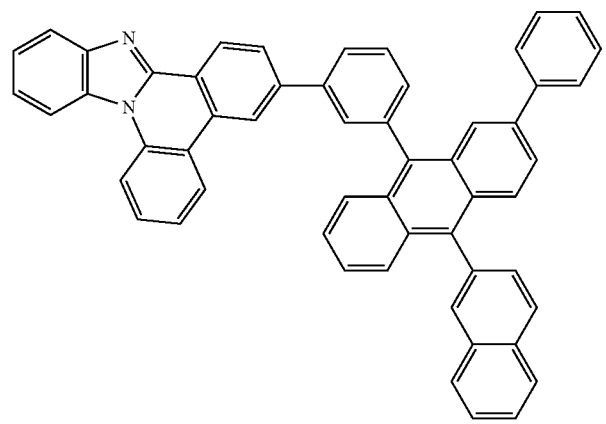 [SMILES: c1ccc(-c2ccc3c(-c4ccc5ccccc5c4)c4ccccc4c(-c4cccc(-c5ccc6c(c5)c5ccccc5n5c7ccccc7nc65)c4)c3c2)cc1]

TABLE 2-continued
1-b-53 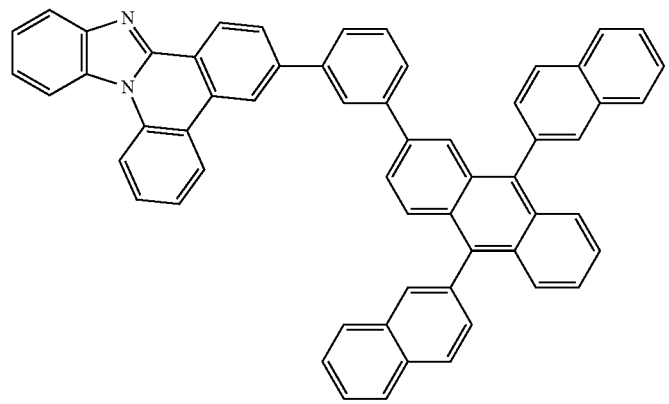 [SMILES: c1cc(-c2ccc3c(-c4ccc5ccccc5c4)c4ccccc4c(-c4ccc5ccccc5c4)c3c2)cc(-c2ccc3c(c2)c2ccccc2n2c4ccccc4nc32)c1]
1-b-54 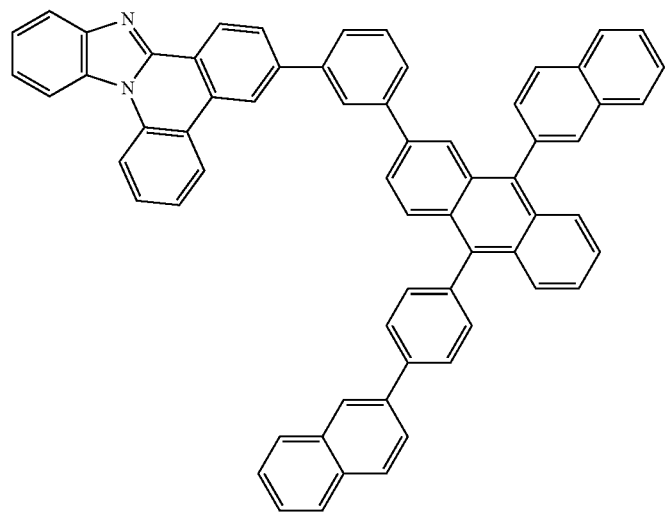 [SMILES: c1cc(-c2ccc3c(-c4ccc(-c5ccc6ccccc6c5)cc4)c4ccccc4c(-c4ccc5ccccc5c4)c3c2)cc(-c2ccc3c(c2)c2ccccc2n2c4ccccc4nc32)c1]
1-b-55 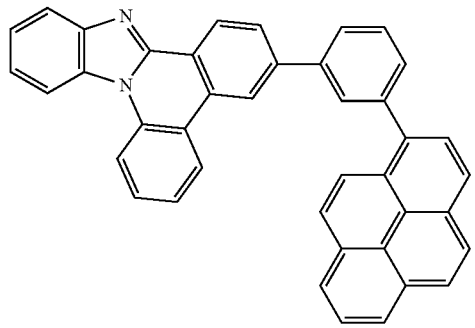 [SMILES: c1cc(-c2ccc3c(c2)c2ccccc2n2c4ccccc4nc32)cc(-c2ccc3ccc4cccc5ccc2c3c45)c1]
1-b-56 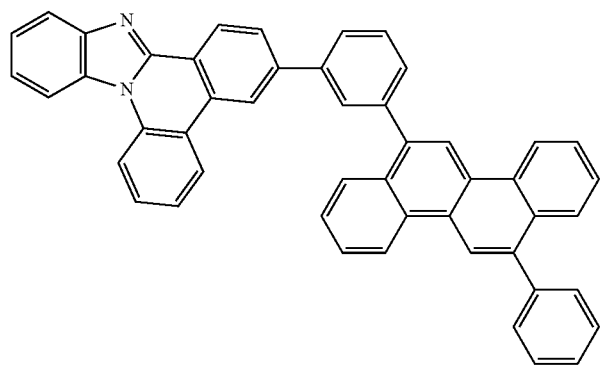

TABLE 2-continued
1-b-57
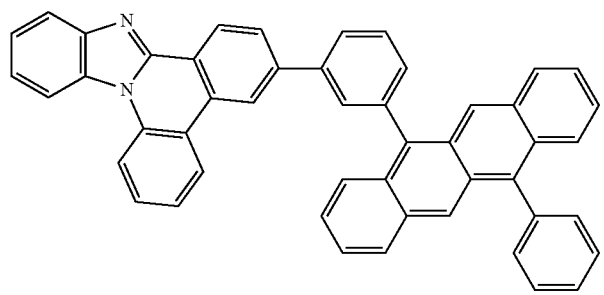 [SMILES: c1ccc(-c2c3ccccc3cc3c(-c4cccc(-c5ccc6c(c5)c5ccccc5n5c7ccccc7nc65)c4)c4ccccc4cc23)cc1]
1-b-58
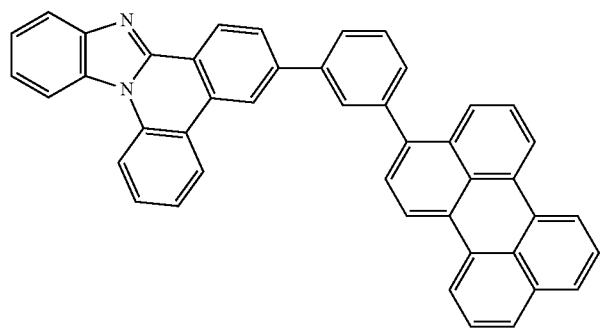 [SMILES: c1cc(-c2ccc3c(c2)c2ccccc2n2c4ccccc4nc32)cc(-c2ccc3c4cccc5cccc(c6cccc2c63)c54)c1]
1-b-59
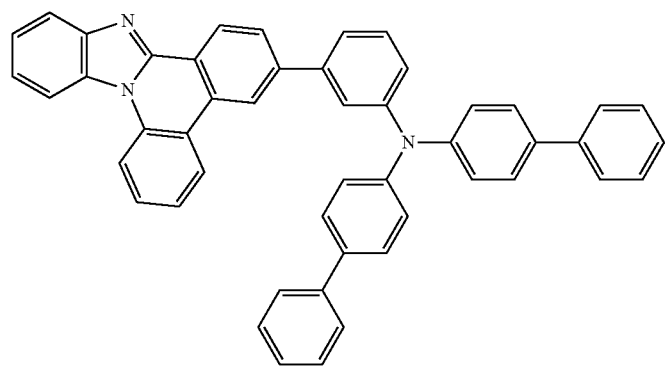 [SMILES: c1ccc(-c2ccc(N(c3ccc(-c4ccccc4)cc3)c3cccc(-c4ccc5c(c4)c4ccccc4n4c6ccccc6nc54)c3)cc2)cc1]
1-b-60
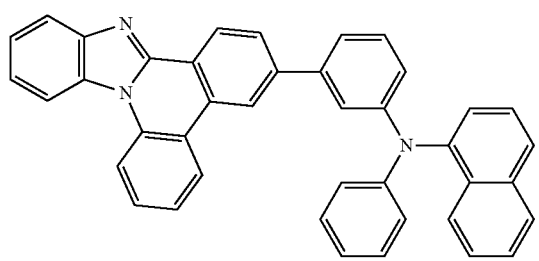 [SMILES: c1ccc(N(c2cccc(-c3ccc4c(c3)c3ccccc3n3c5ccccc5nc43)c2)c2cccc3ccccc23)cc1]
1-b-61
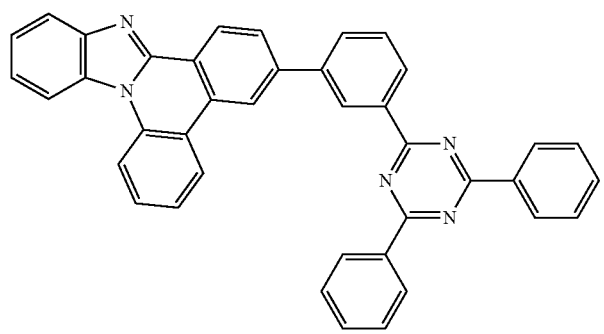 [SMILES: c1ccc(-c2nc(-c3ccccc3)nc(-c3cccc(-c4ccc5c(c4)c4ccccc4n4c6ccccc6nc54)c3)n2)cc1]

TABLE 2-continued
1-b-62
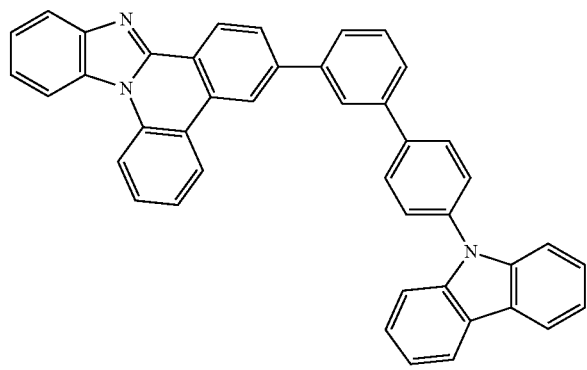 [SMILES: c1cc(-c2ccc(-n3c4ccccc4c4ccccc43)cc2)cc(-c2ccc3c(c2)c2ccccc2n2c4ccccc4nc32)c1]
1-b-63
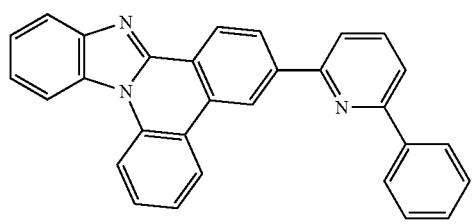 [SMILES: c1ccc(-c2cccc(-c3ccc4c(c3)c3ccccc3n3c5ccccc5nc43)n2)cc1]
1-b-64
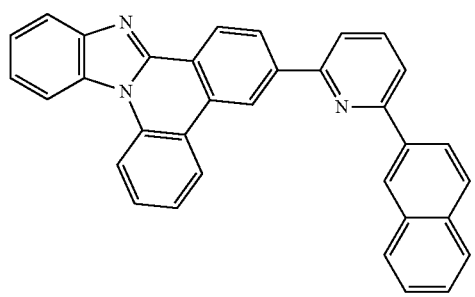 [SMILES: c1cc(-c2ccc3ccccc3c2)nc(-c2ccc3c(c2)c2ccccc2n2c4ccccc4nc32)c1]
1-b-65
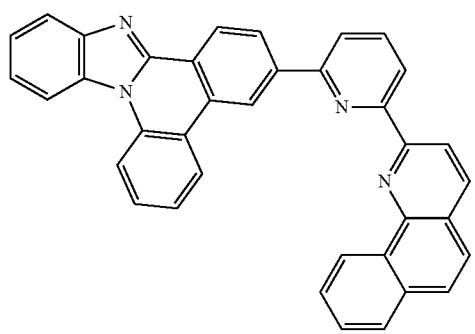 [SMILES: c1cc(-c2ccc3c(c2)c2ccccc2n2c4ccccc4nc32)nc(-c2ccc3ccc4ccccc4c3n2)c1]
1-b-66
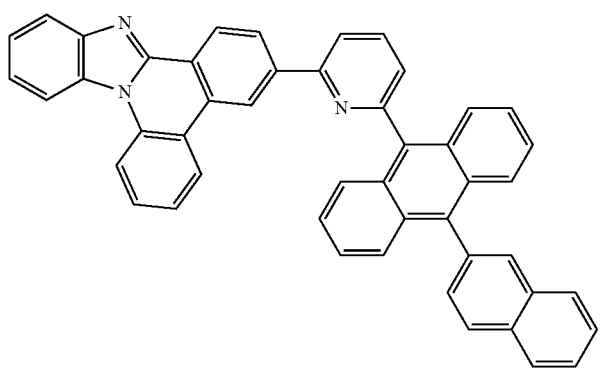 [SMILES: c1cc(-c2ccc3c(c2)c2ccccc2n2c4ccccc4nc32)nc(-c2c3ccccc3c(-c3ccc4ccccc4c3)c3ccccc23)c1]

TABLE 2-continued
1-b-67 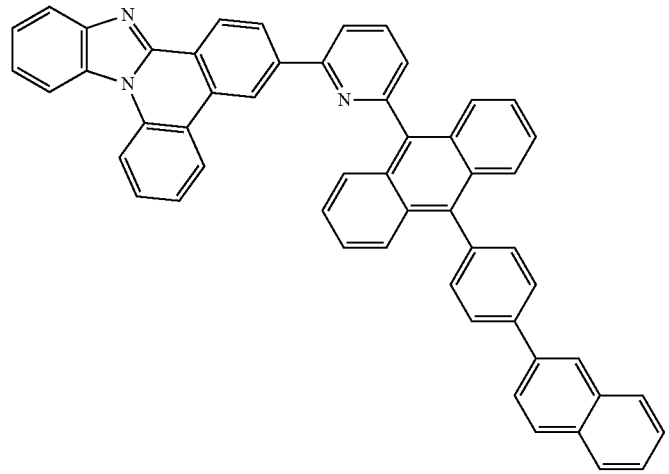 [SMILES: c1cc(-c2ccc3c(c2)c2ccccc2n2c4ccccc4nc32)nc(-c2c3ccccc3c(-c3ccc(-c4ccc5ccccc5c4)cc3)c3ccccc23)c1]
1-b-68 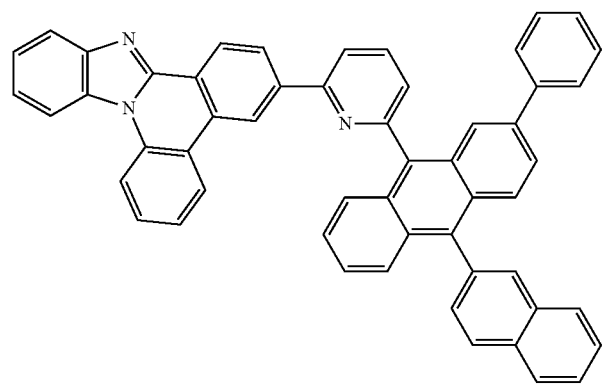 [SMILES: c1ccc(-c2ccc3c(-c4ccc5ccccc5c4)c4ccccc4c(-c4cccc(-c5ccc6c(c5)c5ccccc5n5c7ccccc7nc65)n4)c3c2)cc1]
1-b-69 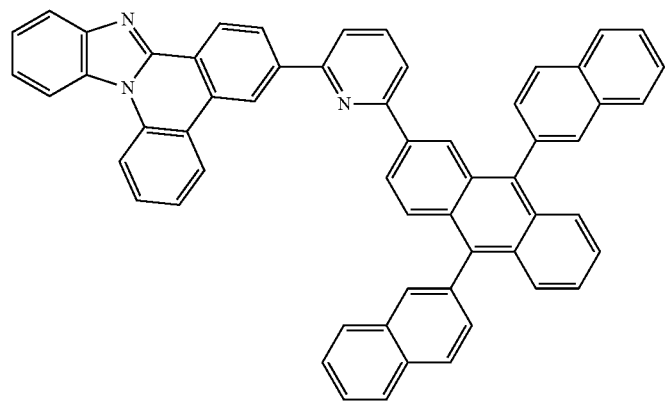 [SMILES: c1cc(-c2ccc3c(-c4ccc5ccccc5c4)c4ccccc4c(-c4ccc5ccccc5c4)c3c2)nc(-c2ccc3c(c2)c2ccccc2n2c4ccccc4nc32)c1]

TABLE 2-continued
1-b-70 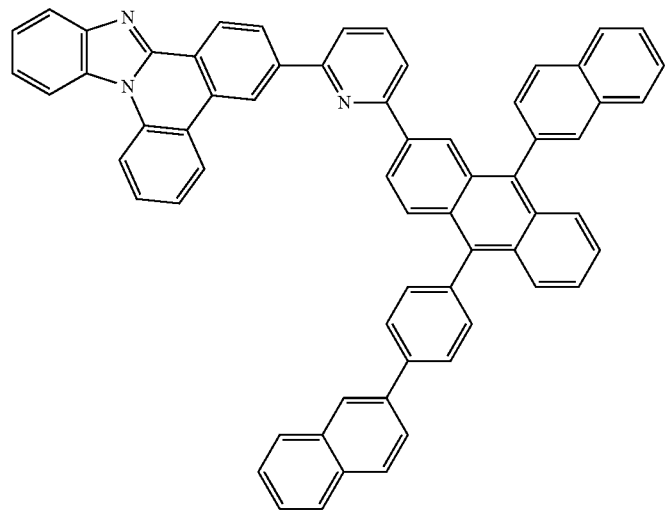 [SMILES: c1cc(-c2ccc3c(-c4ccc(-c5ccc6ccccc6c5)cc4)c4ccccc4c(-c4ccc5ccccc5c4)c3c2)nc(-c2ccc3c(c2)c2ccccc2n2c4ccccc4nc32)c1]
1-b-71 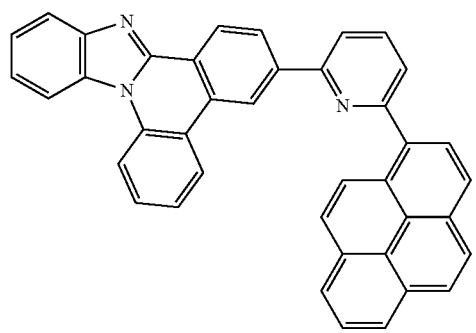 [SMILES: c1cc(-c2ccc3c(c2)c2ccccc2n2c4ccccc4nc32)nc(-c2ccc3ccc4cccc5ccc2c3c45)c1]
1-b-72 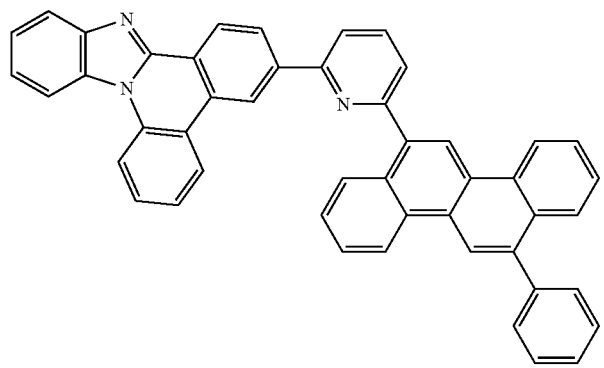 [SMILES: c1ccc(-c2cc3c4ccccc4c(-c4cccc(-c5ccc6c(c5)c5ccccc5n5c7ccccc7nc65)n4)cc3c3ccccc23)cc1]
1-b-73 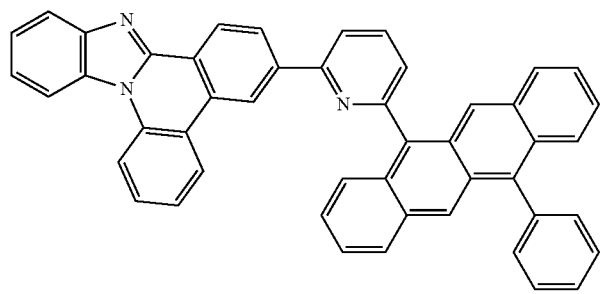

TABLE 2-continued
1-b-74 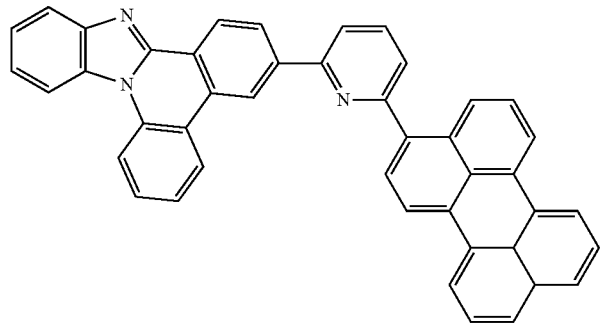 [SMILES: C1=CC2C=CC=C3c4ccc(-c5cccc(-c6ccc7c(c6)c6ccccc6n6c8ccccc8nc76)n5)c5cccc(c45)C(=C1)C32]
1-b-75 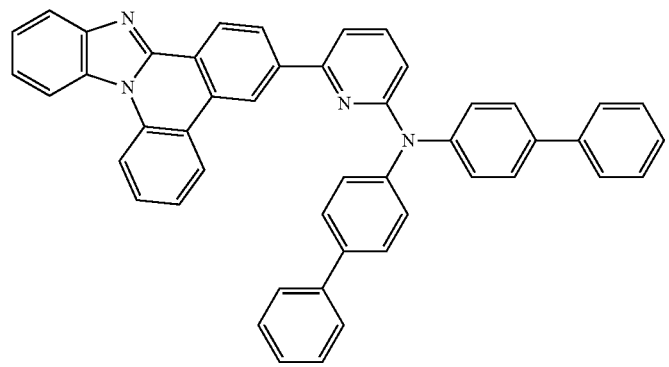 [SMILES: c1ccc(-c2ccc(N(c3ccc(-c4ccccc4)cc3)c3cccc(-c4ccc5c(c4)c4ccccc4n4c6ccccc6nc54)n3)cc2)cc1]
1-b-76 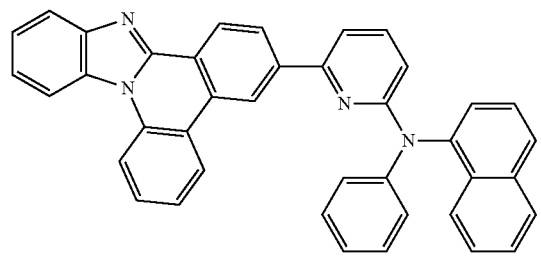
1-b-77 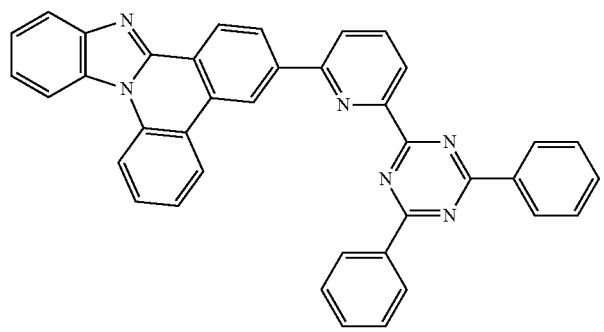 [SMILES: c1ccc(-c2nc(-c3ccccc3)nc(-c3cccc(-c4ccc5c(c4)c4ccccc4n4c6ccccc6nc54)n3)n2)cc1]

TABLE 2-continued
1-b-78 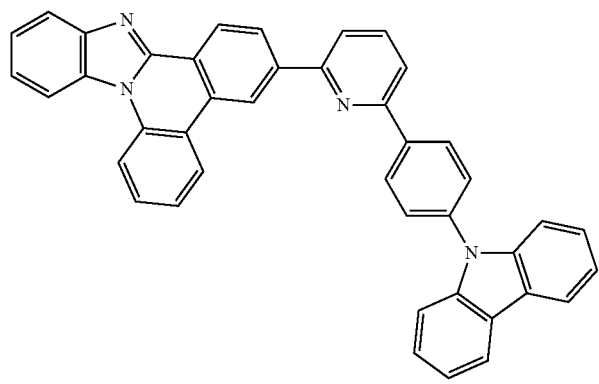 [SMILES: c1cc(-c2ccc(-n3c4ccccc4c4ccccc43)cc2)nc(-c2ccc3c(c2)c2ccccc2n2c4ccccc4nc32)c1]
1-b-79 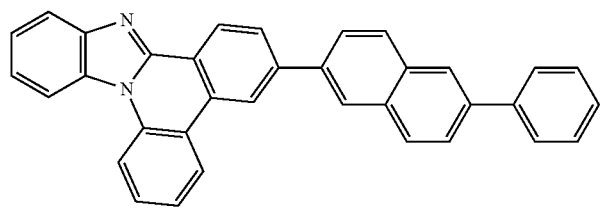 [SMILES: c1ccc(-c2ccc3cc(-c4ccc5c(c4)c4ccccc4n4c6ccccc6nc54)ccc3c2)cc1]
1-b-80 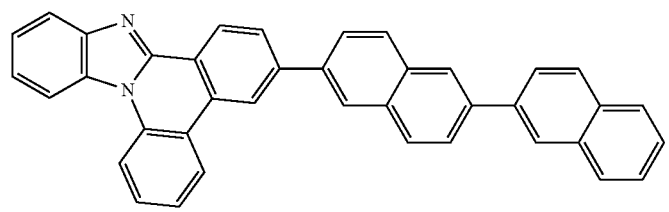 [SMILES: c1ccc2cc(-c3ccc4cc(-c5ccc6c(c5)c5ccccc5n5c7ccccc7nc65)ccc4c3)ccc2c1]
1-b-81 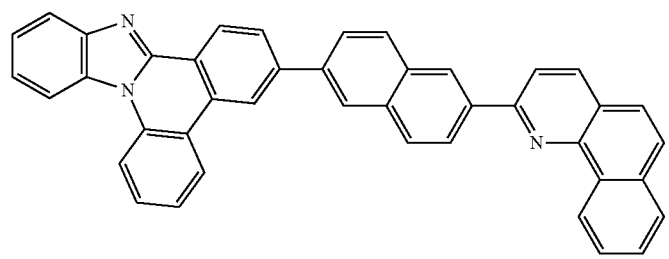 [SMILES: c1ccc2c(c1)ccc1ccc(-c3ccc4cc(-c5ccc6c(c5)c5ccccc5n5c7ccccc7nc65)ccc4c3)nc12]
1-b-82 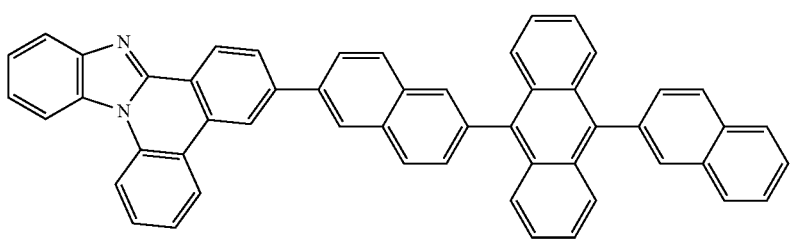 [SMILES: c1ccc2cc(-c3c4ccccc4c(-c4ccc5cc(-c6ccc7c(c6)c6ccccc6n6c8ccccc8nc76)ccc5c4)c4ccccc34)ccc2c1]
1-b-83 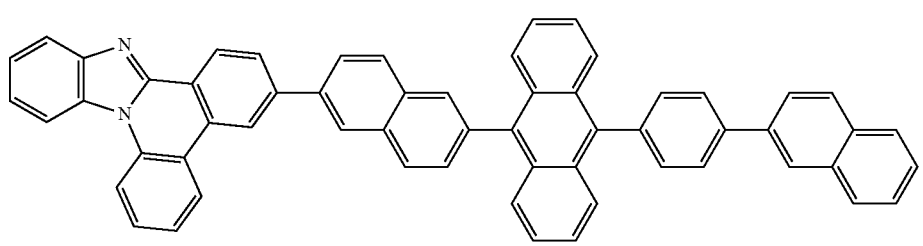 [SMILES: c1ccc2cc(-c3ccc(-c4c5ccccc5c(-c5ccc6cc(-c7ccc8c(c7)c7ccccc7n7c9ccccc9nc87)ccc6c5)c5ccccc45)cc3)ccc2c1]

TABLE 2-continued
1-b-84
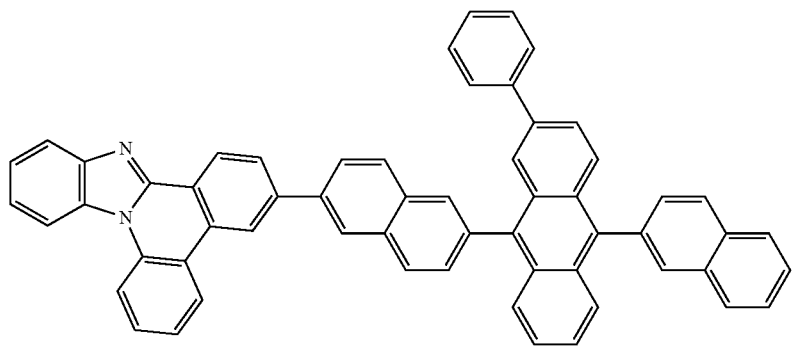 [SMILES: c1ccc(-c2ccc3c(-c4ccc5ccccc5c4)c4ccccc4c(-c4ccc5cc(-c6ccc7c(c6)c6ccccc6n6c8ccccc8nc76)ccc5c4)c3c2)cc1]
1-b-85
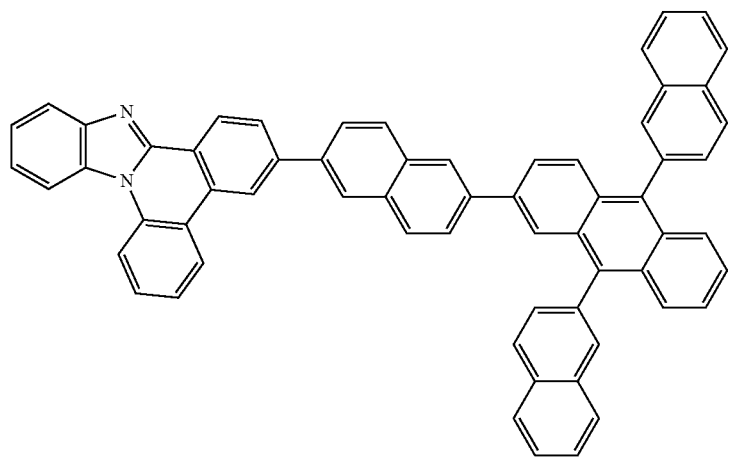 [SMILES: c1ccc2cc(-c3c4ccccc4c(-c4ccc5ccccc5c4)c4cc(-c5ccc6cc(-c7ccc8c(c7)c7ccccc7n7c9ccccc9nc87)ccc6c5)ccc34)ccc2c1]
1-b-86
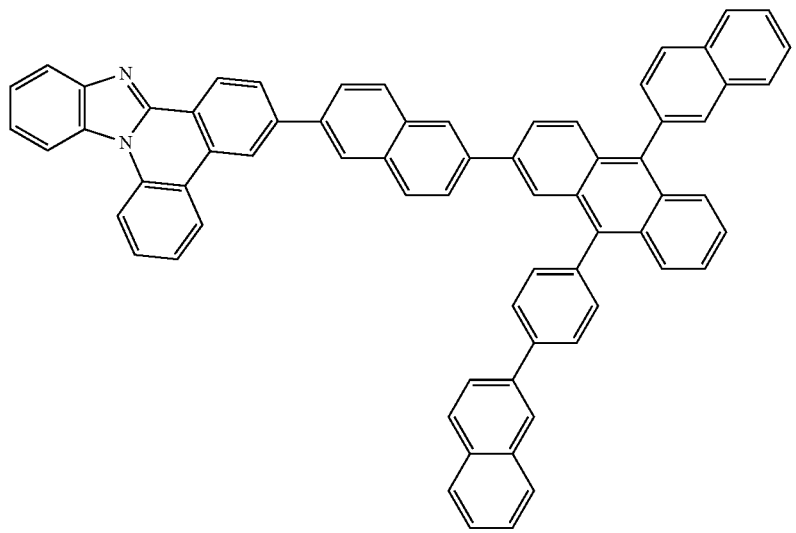 [SMILES: c1ccc2cc(-c3ccc(-c4c5ccccc5c(-c5ccc6ccccc6c5)c5ccc(-c6ccc7cc(-c8ccc9c(c8)c8ccccc8n8c%10ccccc%10nc98)ccc7c6)cc45)cc3)ccc2c1]
1-b-87
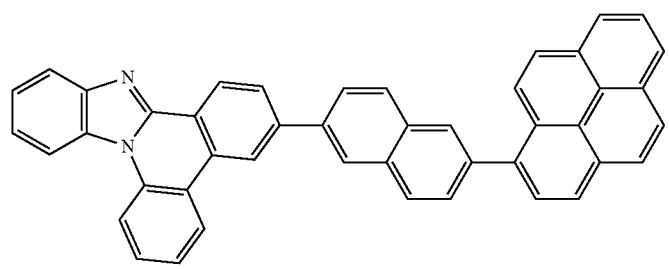 [SMILES: c1cc2ccc3ccc(-c4ccc5cc(-c6ccc7c(c6)c6ccccc6n6c8ccccc8nc76)ccc5c4)c4ccc(c1)c2c34]

TABLE 2-continued
1-b-88
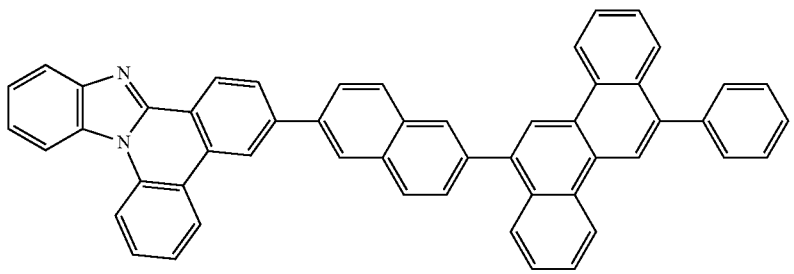 [SMILES: c1ccc(-c2cc3c4ccccc4c(-c4ccc5cc(-c6ccc7c(c6)c6ccccc6n6c8ccccc8nc76)ccc5c4)cc3c3ccccc23)cc1]
1-b-89
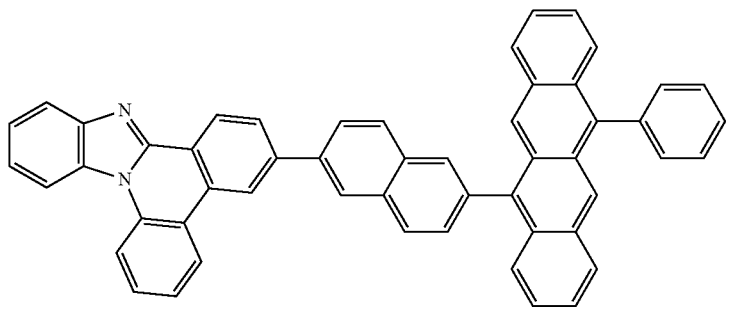 [SMILES: c1ccc(-c2c3ccccc3cc3c(-c4ccc5cc(-c6ccc7c(c6)c6ccccc6n6c8ccccc8nc76)ccc5c4)c4ccccc4cc23)cc1]
1-b-90
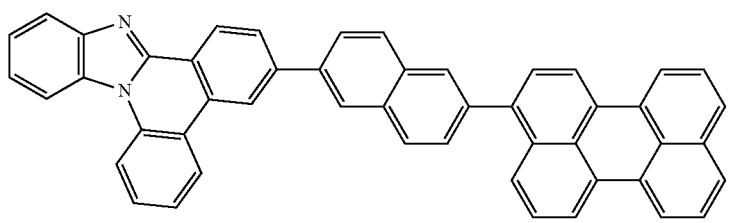 [SMILES: c1ccc2c(c1)nc1c3ccc(-c4ccc5cc(-c6ccc7c8cccc9cccc(c%10cccc6c%107)c98)ccc5c4)cc3c3ccccc3n21]
1-b-91
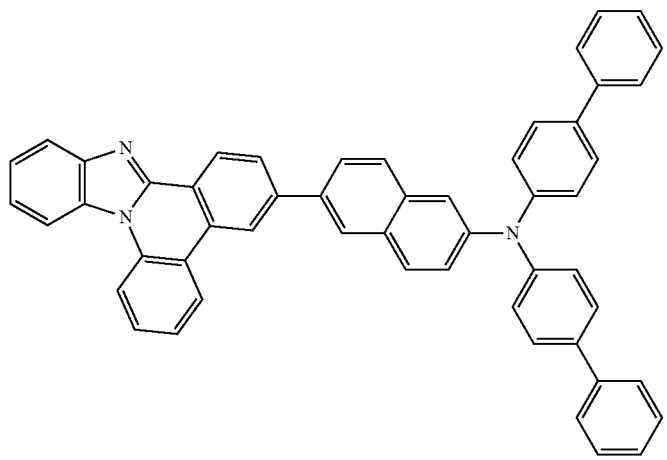 [SMILES: c1ccc(-c2ccc(N(c3ccc(-c4ccccc4)cc3)c3ccc4cc(-c5ccc6c(c5)c5ccccc5n5c7ccccc7nc65)ccc4c3)cc2)cc1]
1-b-92
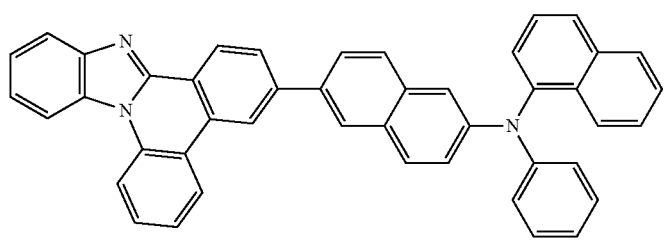 [SMILES: c1ccc(N(c2ccc3cc(-c4ccc5c(c4)c4ccccc4n4c6ccccc6nc54)ccc3c2)c2cccc3ccccc23)cc1]

TABLE 2-continued
1-b-93
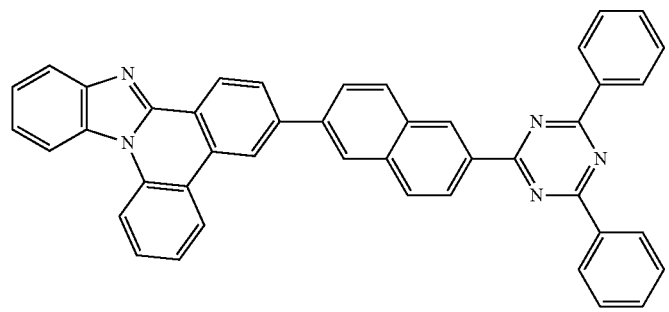 [SMILES: c1ccc(-c2nc(-c3ccccc3)nc(-c3ccc4cc(-c5ccc6c(c5)c5ccccc5n5c7ccccc7nc65)ccc4c3)n2)cc1]
1-b-94
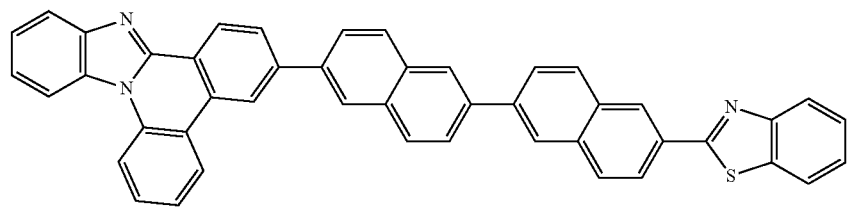 [SMILES: c1ccc2sc(-c3ccc4cc(-c5ccc6cc(-c7ccc8c(c7)c7ccccc7n7c9ccccc9nc87)ccc6c5)ccc4c3)nc2c1]
1-b-95
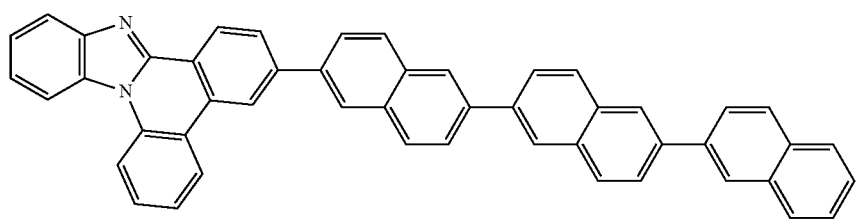 [SMILES: c1ccc2cc(-c3ccc4cc(-c5ccc6cc(-c7ccc8c(c7)c7ccccc7n7c9ccccc9nc87)ccc6c5)ccc4c3)ccc2c1]
1-b-96
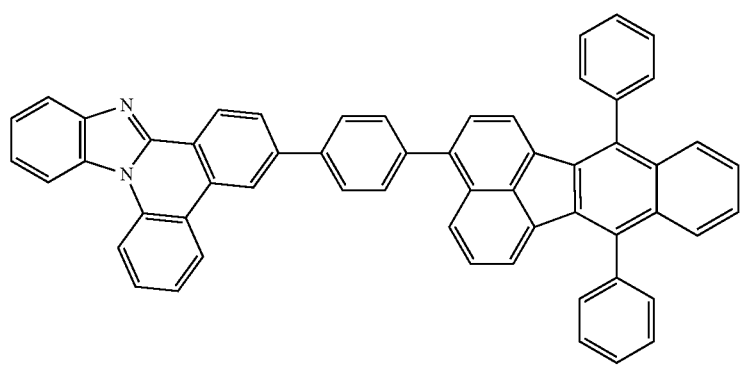 [SMILES: c1ccc(-c2c3c(c(-c4ccccc4)c4ccccc24)-c2ccc(-c4ccc(-c5ccc6c(c5)c5ccccc5n5c7ccccc7nc65)cc4)c4cccc-3c24)cc1]
1-b-97
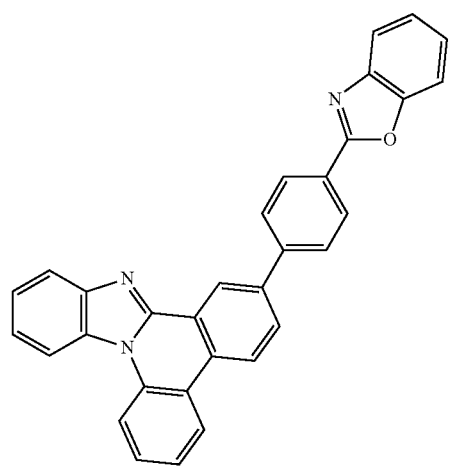 [SMILES: c1ccc2oc(-c3ccc(-c4ccc5c6ccccc6n6c7ccccc7nc6c5c4)cc3)nc2c1]

TABLE 2-continued
1-b-98
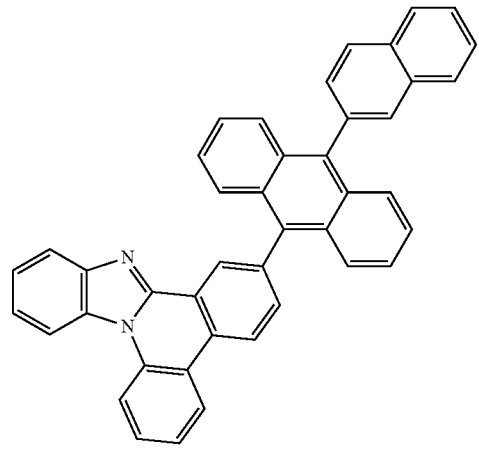 [SMILES: c1ccc2cc(-c3c4ccccc4c(-c4ccc5c6ccccc6n6c7ccccc7nc6c5c4)c4ccccc34)ccc2c1]
1-b-99
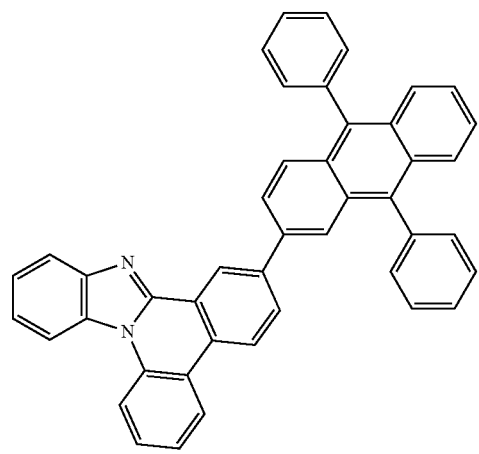 [SMILES: c1ccc(-c2c3ccccc3c(-c3ccccc3)c3cc(-c4ccc5c6ccccc6n6c7ccccc7nc6c5c4)ccc23)cc1]
1-b-100
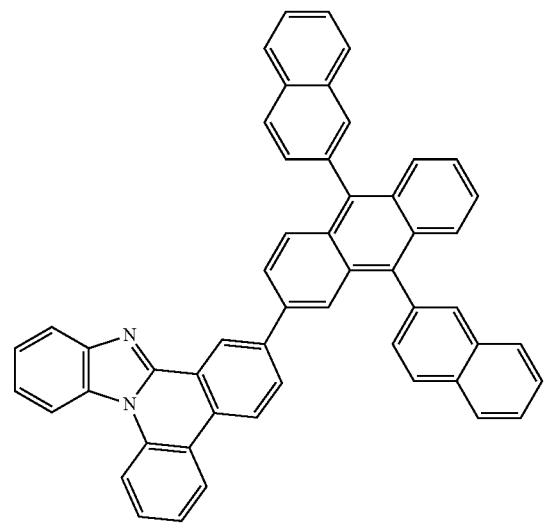 [SMILES: c1ccc2cc(-c3c4ccccc4c(-c4ccc5ccccc5c4)c4cc(-c5ccc6c7ccccc7n7c8ccccc8nc7c6c5)ccc34)ccc2c1]

TABLE 2-continued
1-b-101
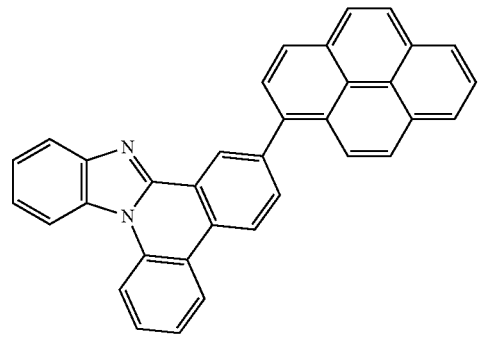 [SMILES: c1cc2ccc3ccc(-c4ccc5c6ccccc6n6c7ccccc7nc6c5c4)c4ccc(c1)c2c34]
1-b-102
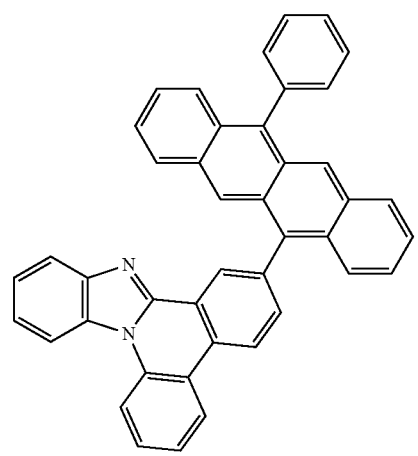 [SMILES: c1ccc(-c2c3ccccc3cc3c(-c4ccc5c6ccccc6n6c7ccccc7nc6c5c4)c4ccccc4cc23)cc1]
1-b-103
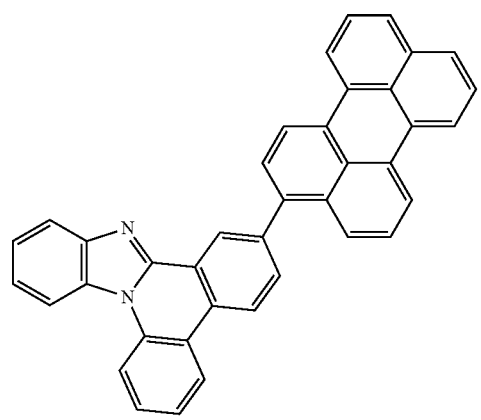 [SMILES: c1ccc2c(c1)nc1c3cc(-c4ccc5c6cccc7cccc(c8cccc4c85)c76)ccc3c3ccccc3n21]

TABLE 2-continued
1-b-104
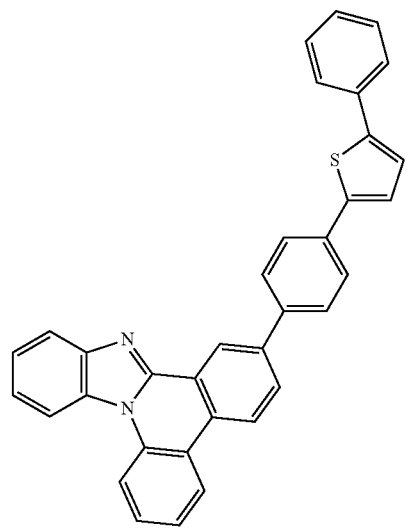 [SMILES: c1ccc(-c2ccc(-c3ccc(-c4ccc5c6ccccc6n6c7ccccc7nc6c5c4)cc3)s2)cc1]
1-b-105
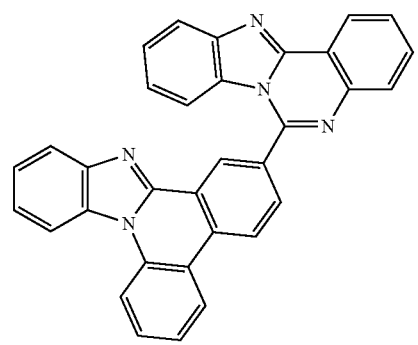 [SMILES: c1ccc2c(c1)nc(-c1ccc3c4ccccc4n4c5ccccc5nc4c3c1)n1c3ccccc3nc21]
1-b-106
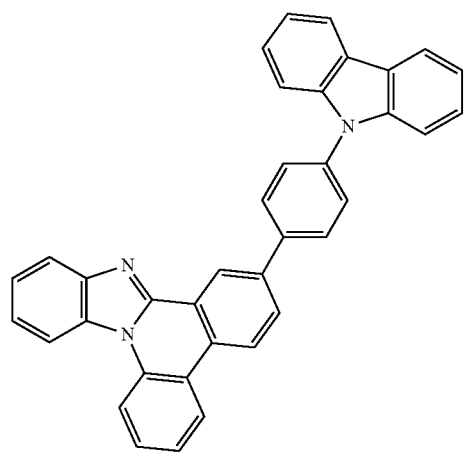 [SMILES: c1ccc2c(c1)nc1c3cc(-c4ccc(-n5c6ccccc6c6ccccc65)cc4)ccc3c3ccccc3n21]

TABLE 2-continued
1-b-107
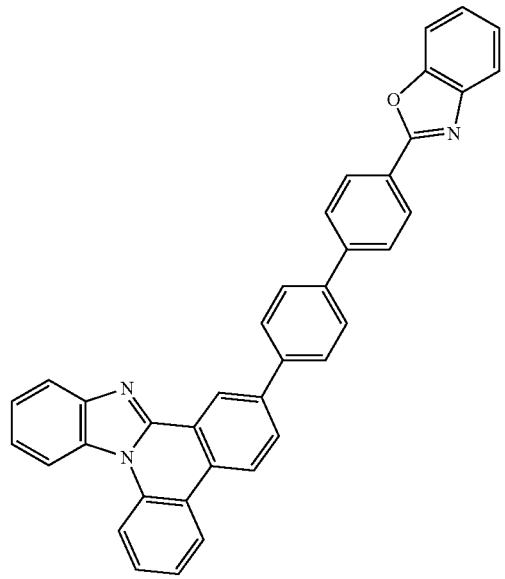 [SMILES: c1ccc2oc(-c3ccc(-c4ccc(-c5ccc6c7ccccc7n7c8ccccc8nc7c6c5)cc4)cc3)nc2c1]
1-b-108
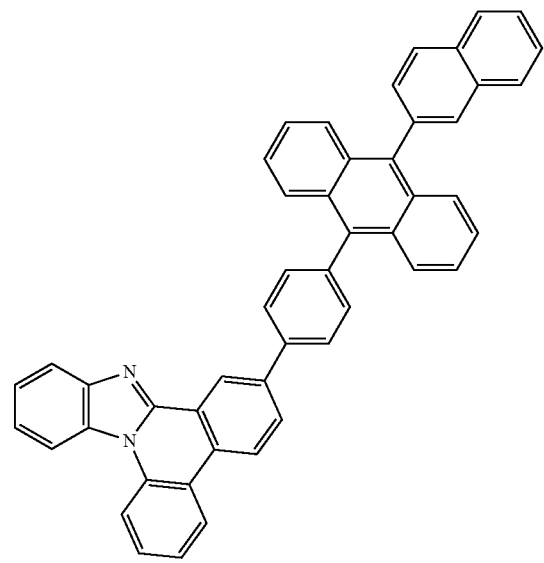 [SMILES: c1ccc2cc(-c3c4ccccc4c(-c4ccc(-c5ccc6c7ccccc7n7c8ccccc8nc7c6c5)cc4)c4ccccc34)ccc2c1]

TABLE 2-continued
1-b-109
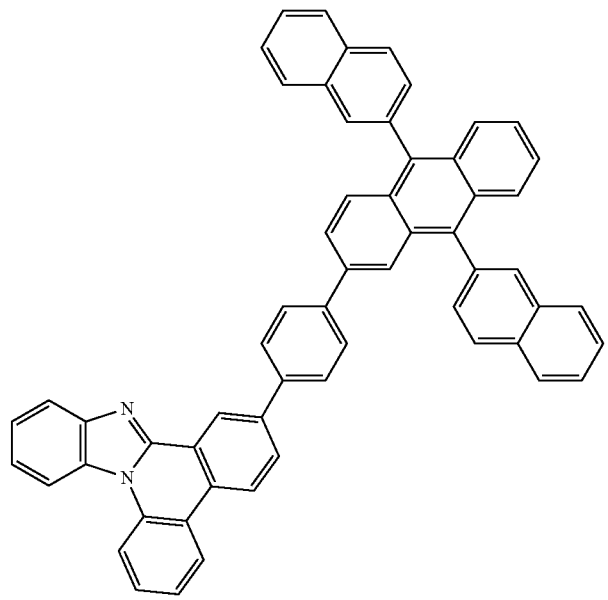 [SMILES: c1ccc2cc(-c3c4ccccc4c(-c4ccc5ccccc5c4)c4cc(-c5ccc(-c6ccc7c8ccccc8n8c9ccccc9nc8c7c6)cc5)ccc34)ccc2c1]
1-b-110
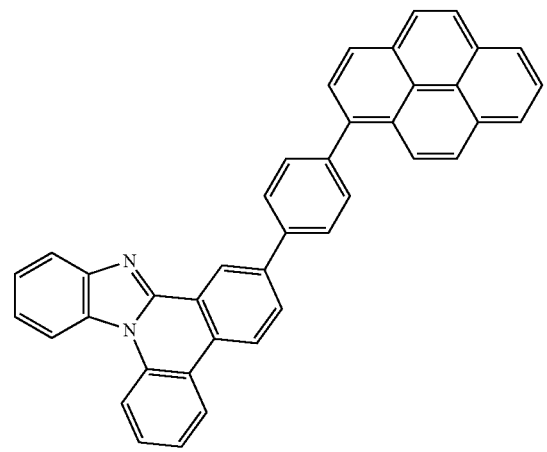 [SMILES: c1cc2ccc3ccc(-c4ccc(-c5ccc6c7ccccc7n7c8ccccc8nc7c6c5)cc4)c4ccc(c1)c2c34]
1-b-111
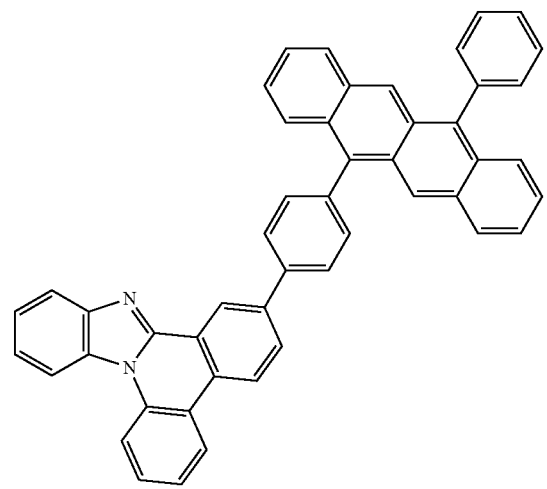 [SMILES: c1ccc(-c2c3ccccc3cc3c(-c4ccc(-c5ccc6c7ccccc7n7c8ccccc8nc7c6c5)cc4)c4ccccc4cc23)cc1]

TABLE 2-continued
1-b-112
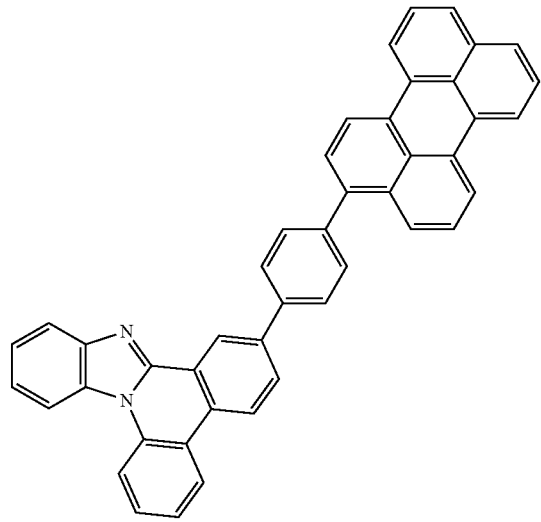 [SMILES: c1ccc2c(c1)nc1c3cc(-c4ccc(-c5ccc6c7cccc8cccc(c9cccc5c96)c87)cc4)ccc3c3ccccc3n21]
1-b-113
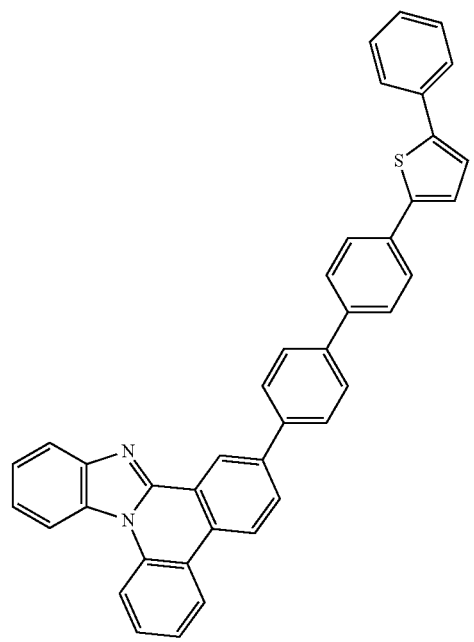 [SMILES: c1ccc(-c2ccc(-c3ccc(-c4ccc(-c5ccc6c7ccccc7n7c8ccccc8nc7c6c5)cc4)cc3)s2)cc1]

TABLE 2-continued
1-b-114
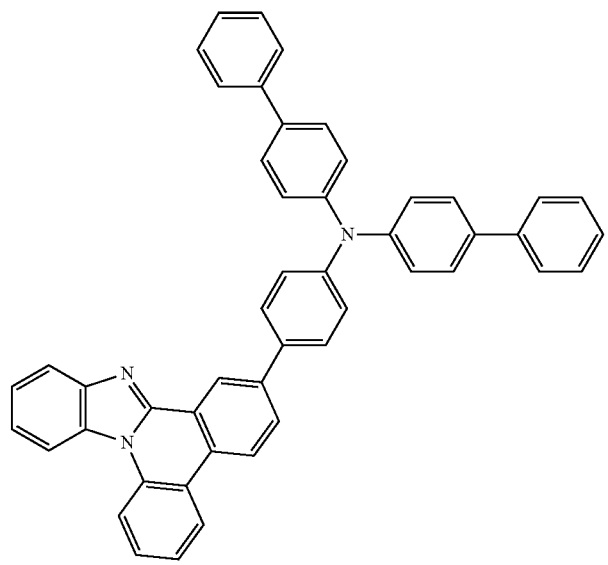 [SMILES: c1ccc(-c2ccc(N(c3ccc(-c4ccccc4)cc3)c3ccc(-c4ccc5c6ccccc6n6c7ccccc7nc6c5c4)cc3)cc2)cc1]
1-b-115
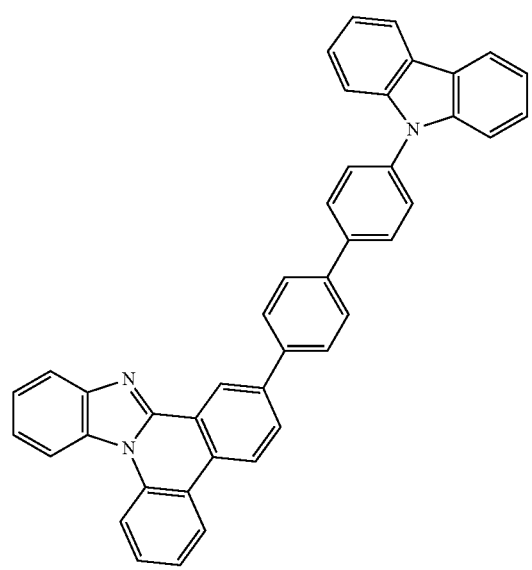 [SMILES: c1ccc2c(c1)nc1c3cc(-c4ccc(-c5ccc(-n6c7ccccc7c7ccccc76)cc5)cc4)ccc3c3ccccc3n21]
1-b-116
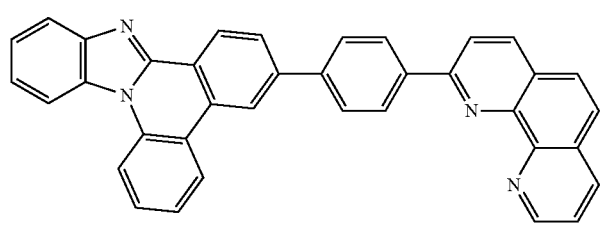 [SMILES: c1cnc2c(c1)ccc1ccc(-c3ccc(-c4ccc5c(c4)c4ccccc4n4c6ccccc6nc54)cc3)nc12]
1-b-117
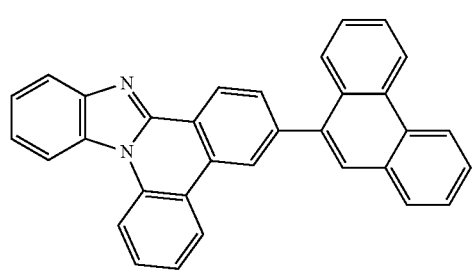 [SMILES: c1ccc2c(c1)cc(-c1ccc3c(c1)c1ccccc1n1c4ccccc4nc31)c1ccccc12]

TABLE 2-continued
1-b-118
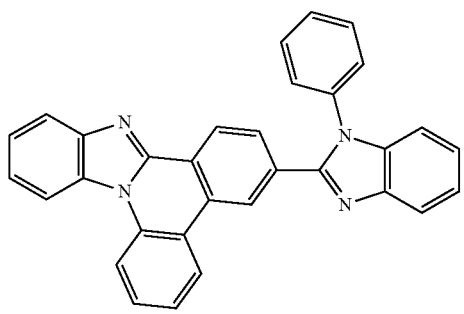 [SMILES: c1ccc(-n2c(-c3ccc4c(c3)c3ccccc3n3c5ccccc5nc43)nc3ccccc32)cc1]
1-b-119
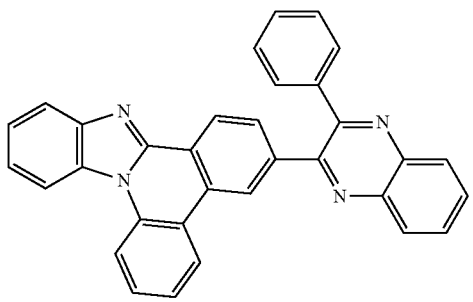 [SMILES: c1ccc(-c2nc3ccccc3nc2-c2ccc3c(c2)c2ccccc2n2c4ccccc4nc32)cc1]
1-b-120
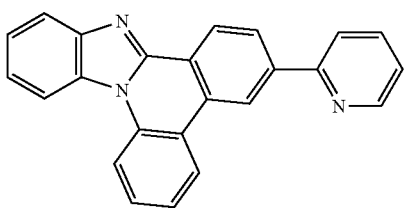 [SMILES: c1ccc(-c2ccc3c(c2)c2ccccc2n2c4ccccc4nc32)nc1]
1-b-121
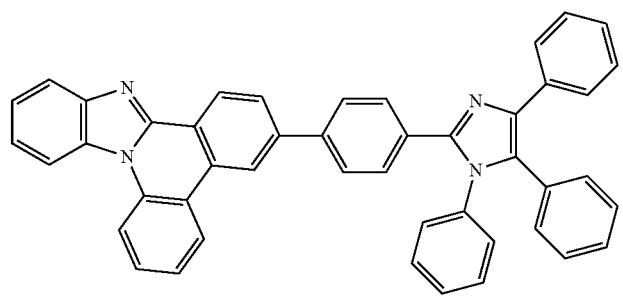 [SMILES: c1ccc(-c2nc(-c3ccc(-c4ccc5c(c4)c4ccccc4n4c6ccccc6nc54)cc3)n(-c3ccccc3)c2-c2ccccc2)cc1]
1-b-122
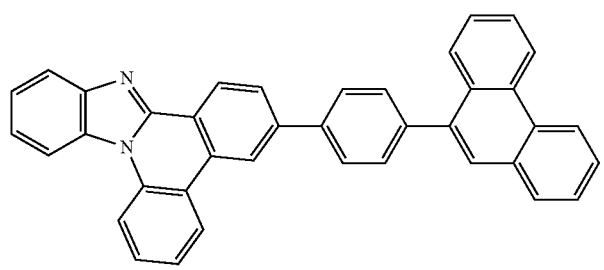 [SMILES: c1ccc2c(c1)cc(-c1ccc(-c3ccc4c(c3)c3ccccc3n3c5ccccc5nc43)cc1)c1ccccc12]
1-b-123
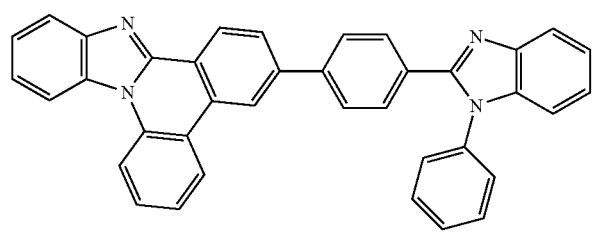 [SMILES: c1ccc(-n2c(-c3ccc(-c4ccc5c(c4)c4ccccc4n4c6ccccc6nc54)cc3)nc3ccccc32)cc1]

TABLE 2-continued
1-b-124
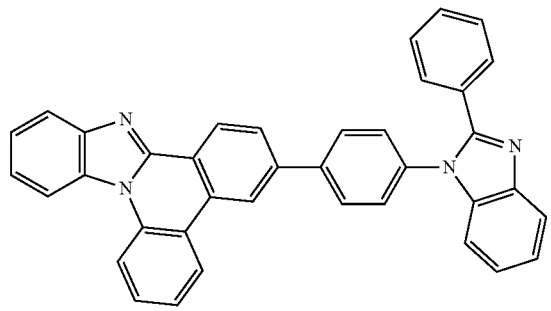 [SMILES: c1ccc(-c2nc3ccccc3n2-c2ccc(-c3ccc4c(c3)c3ccccc3n3c5ccccc5nc43)cc2)cc1]
1-b-125
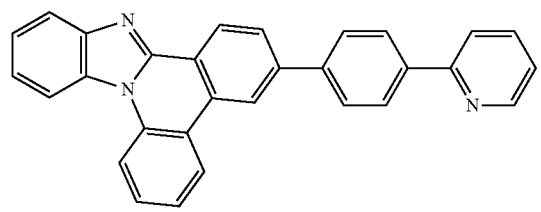 [SMILES: c1ccc(-c2ccc(-c3ccc4c(c3)c3ccccc3n3c5ccccc5nc43)cc2)nc1]
1-b-126
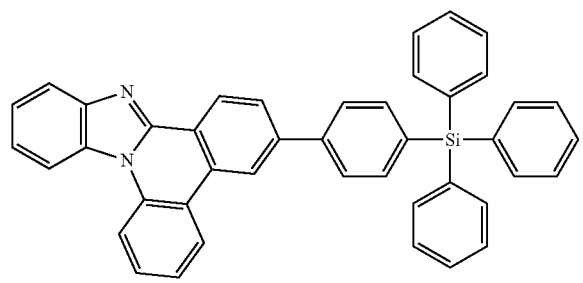 [SMILES: c1ccc([Si](c2ccccc2)(c2ccccc2)c2ccc(-c3ccc4c(c3)c3ccccc3n3c5ccccc5nc43)cc2)cc1]
1-b-127
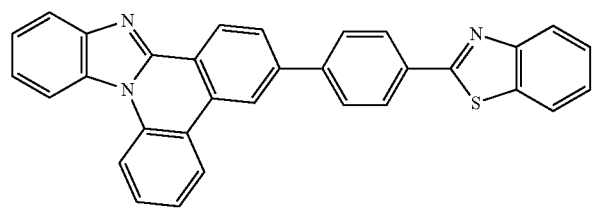 [SMILES: c1ccc2sc(-c3ccc(-c4ccc5c(c4)c4ccccc4n4c6ccccc6nc54)cc3)nc2c1]
1-b-128
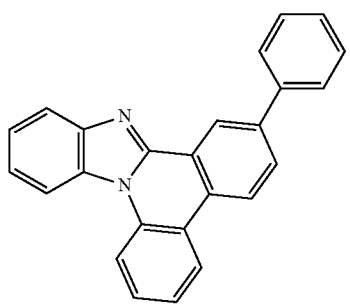 [SMILES: c1ccc(-c2ccc3c4ccccc4n4c5ccccc5nc4c3c2)cc1]

TABLE 2-continued
1-b-129
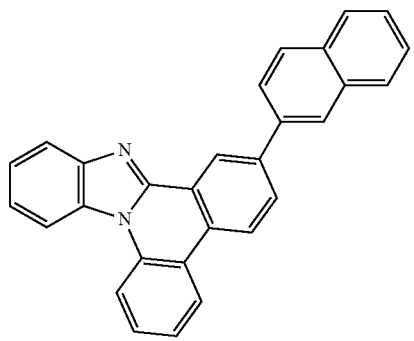 [SMILES: c1ccc2cc(-c3ccc4c5ccccc5n5c6ccccc6nc5c4c3)ccc2c1]
1-b-130
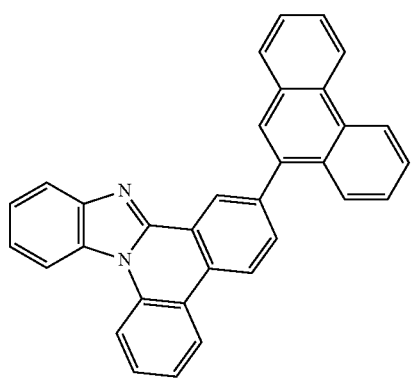 [SMILES: c1ccc2c(c1)cc(-c1ccc3c4ccccc4n4c5ccccc5nc4c3c1)c1ccccc12]
1-b-131
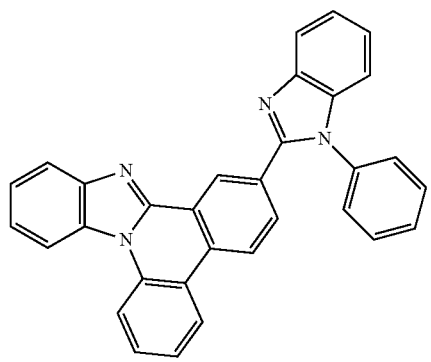 [SMILES: c1ccc(-n2c(-c3ccc4c5ccccc5n5c6ccccc6nc5c4c3)nc3ccccc32)cc1]
1-b-132
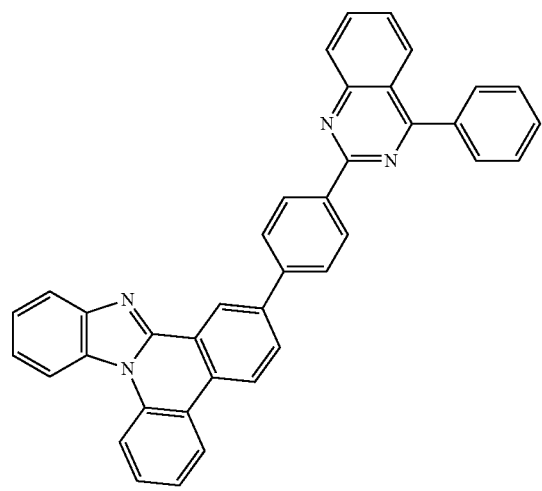 [SMILES: c1ccc(-c2nc(-c3ccc(-c4ccc5c6ccccc6n6c7ccccc7nc6c5c4)cc3)nc3ccccc23)cc1]

TABLE 2-continued
1-b-133
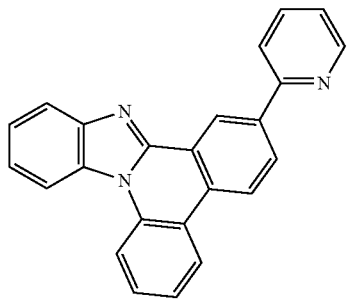 [SMILES: c1ccc(-c2ccc3c4ccccc4n4c5ccccc5nc4c3c2)nc1]
1-b-134
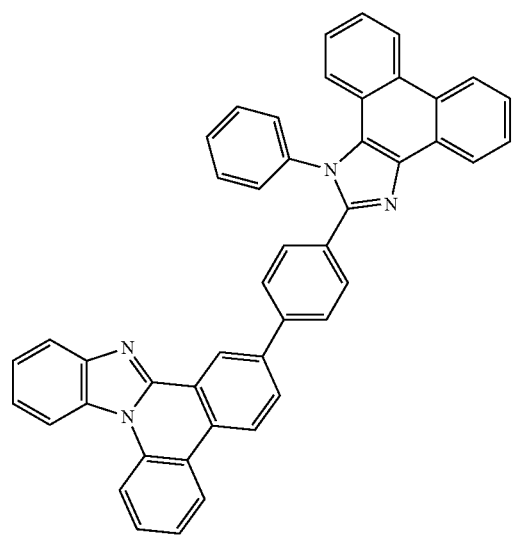 [SMILES: c1ccc(-n2c(-c3ccc(-c4ccc5c6ccccc6n6c7ccccc7nc6c5c4)cc3)nc3c4ccccc4c4ccccc4c32)cc1]
1-b-135
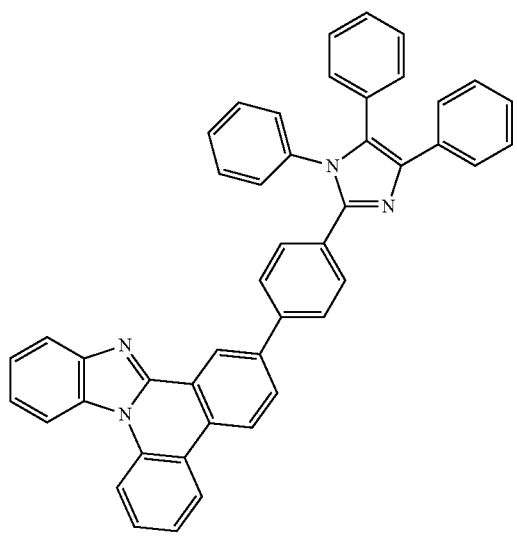 [SMILES: c1ccc(-c2nc(-c3ccc(-c4ccc5c6ccccc6n6c7ccccc7nc6c5c4)cc3)n(-c3ccccc3)c2-c2ccccc2)cc1]

TABLE 2-continued
1-b-136
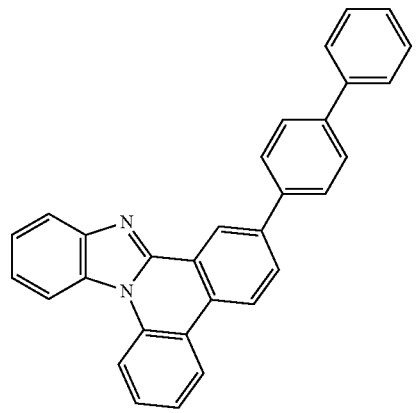 [SMILES: c1ccc(-c2ccc(-c3ccc4c5ccccc5n5c6ccccc6nc5c4c3)cc2)cc1]
1-b-137
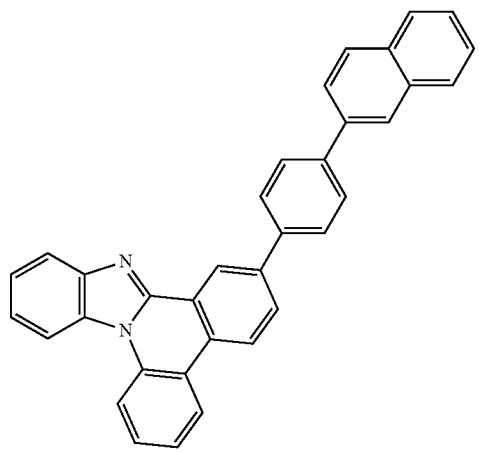 [SMILES: c1ccc2cc(-c3ccc(-c4ccc5c6ccccc6n6c7ccccc7nc6c5c4)cc3)ccc2c1]
1-b-138
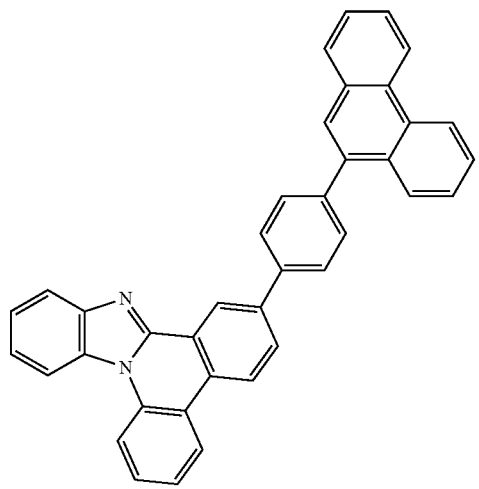 [SMILES: c1ccc2c(c1)cc(-c1ccc(-c3ccc4c5ccccc5n5c6ccccc6nc5c4c3)cc1)c1ccccc12]

TABLE 2-continued
1-b-139
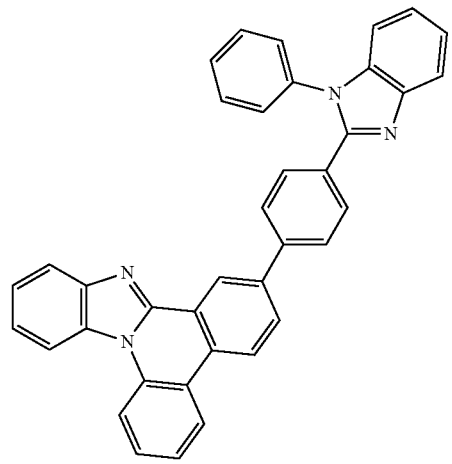 [SMILES: c1ccc(-n2c(-c3ccc(-c4ccc5c6ccccc6n6c7ccccc7nc6c5c4)cc3)nc3ccccc32)cc1]
1-b-140
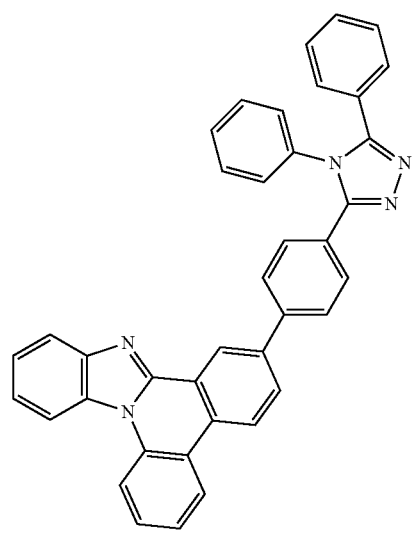 [SMILES: c1ccc(-c2nnc(-c3ccc(-c4ccc5c6ccccc6n6c7ccccc7nc6c5c4)cc3)n2-c2ccccc2)cc1]
1-b-141
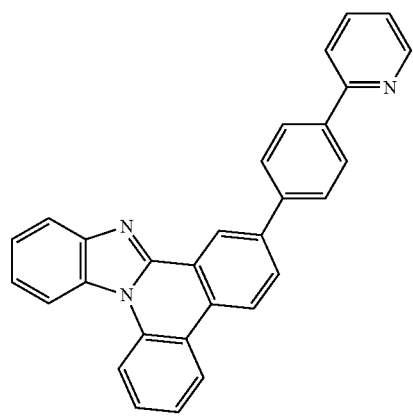 [SMILES: c1ccc(-c2ccc(-c3ccc4c5ccccc5n5c6ccccc6nc5c4c3)cc2)nc1]

TABLE 2-continued
1-b-142
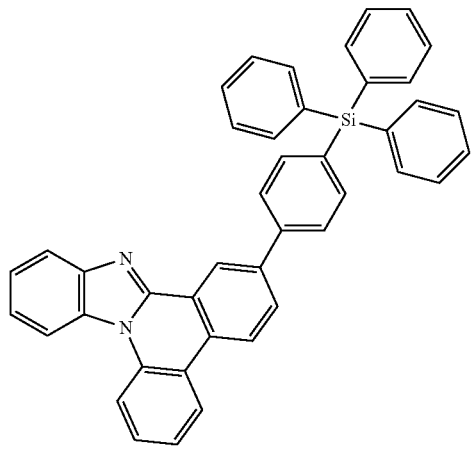 [SMILES: c1ccc([Si](c2ccccc2)(c2ccccc2)c2ccc(-c3ccc4c5ccccc5n5c6ccccc6nc5c4c3)cc2)cc1]
1-b-143
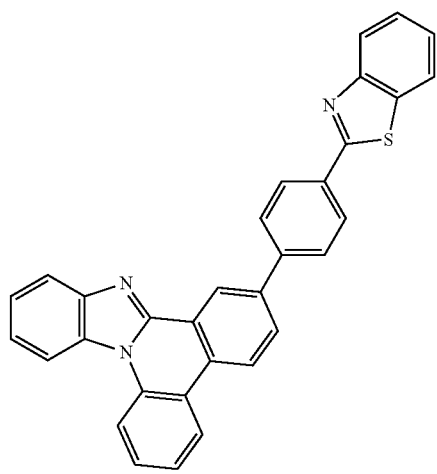 [SMILES: c1ccc2sc(-c3ccc(-c4ccc5c6ccccc6n6c7ccccc7nc6c5c4)cc3)nc2c1]
1-b-144
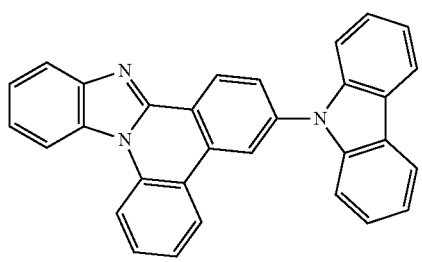 [SMILES: c1ccc2c(c1)nc1c3ccc(-n4c5ccccc5c5ccccc54)cc3c3ccccc3n21]
1-b-145
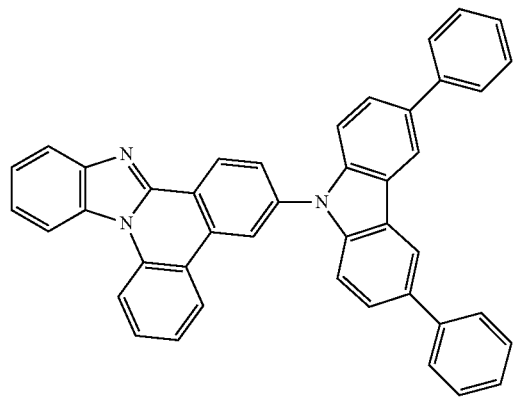 [SMILES: c1ccc(-c2ccc3c(c2)c2cc(-c4ccccc4)ccc2n3-c2ccc3c(c2)c2ccccc2n2c4ccccc4nc32)cc1]

TABLE 2-continued
1-b-146
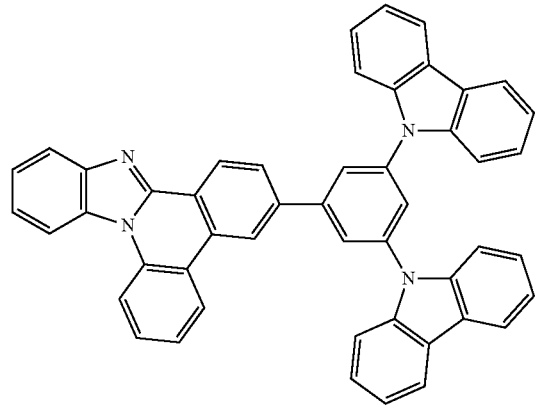 [SMILES: c1ccc2c(c1)nc1c3ccc(-c4cc(-n5c6ccccc6c6ccccc65)cc(-n5c6ccccc6c6ccccc65)c4)cc3c3ccccc3n21]
1-b-147
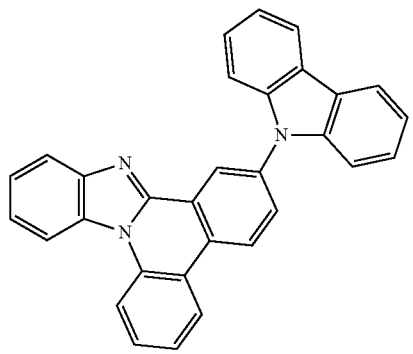 [SMILES: c1ccc2c(c1)nc1c3cc(-n4c5ccccc5c5ccccc54)ccc3c3ccccc3n21]
1-b-148
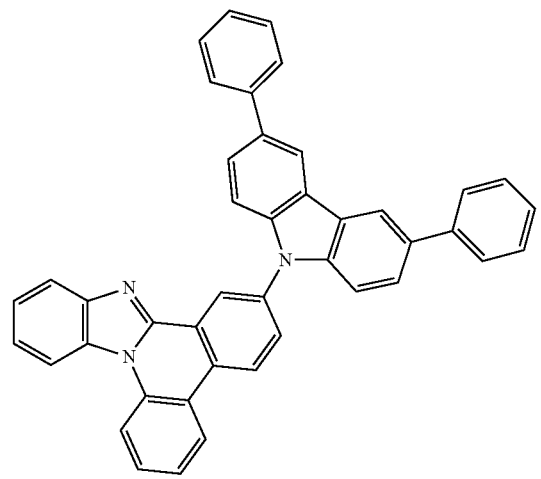 [SMILES: c1ccc(-c2ccc3c(c2)c2cc(-c4ccccc4)ccc2n3-c2ccc3c4ccccc4n4c5ccccc5nc4c3c2)cc1]

TABLE 2-continued
1-b-149
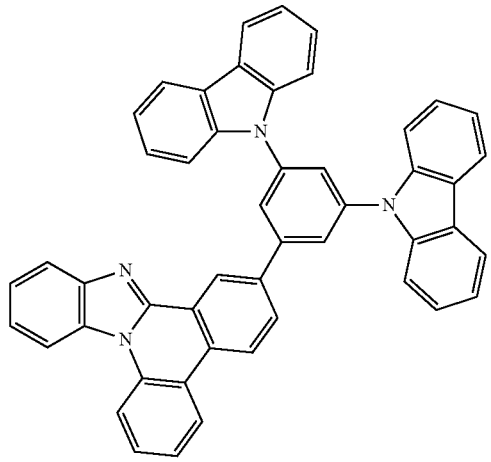 [SMILES: c1ccc2c(c1)nc1c3cc(-c4cc(-n5c6ccccc6c6ccccc65)cc(-n5c6ccccc6c6ccccc65)c4)ccc3c3ccccc3n21]
1-b-150
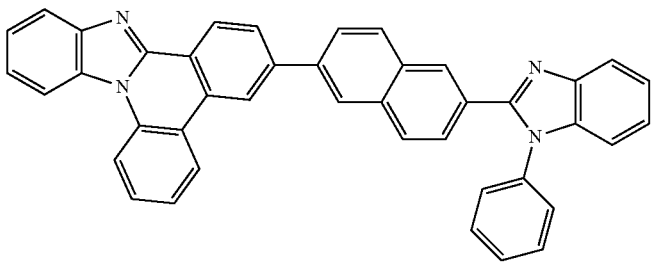 [SMILES: c1ccc(-n2c(-c3ccc4cc(-c5ccc6c(c5)c5ccccc5n5c7ccccc7nc65)ccc4c3)nc3ccccc32)cc1]
1-b-151
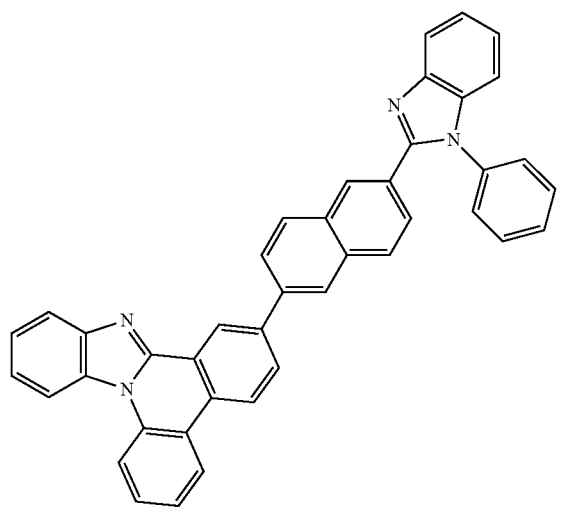 [SMILES: c1ccc(-n2c(-c3ccc4cc(-c5ccc6c7ccccc7n7c8ccccc8nc7c6c5)ccc4c3)nc3ccccc32)cc1]
1-b-152
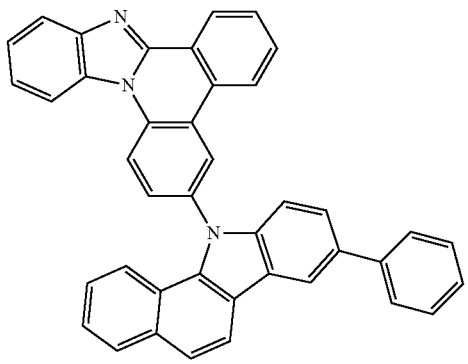 [SMILES: c1ccc(-c2ccc3c(c2)c2ccc4ccccc4c2n3-c2ccc3c(c2)c2ccccc2c2nc4ccccc4n32)cc1]

TABLE 2-continued
1-b-153 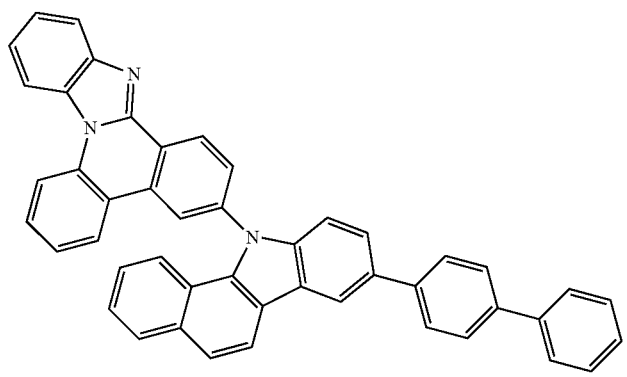 [SMILES: c1ccc(-c2ccc(-c3ccc4c(c3)c3ccc5ccccc5c3n4-c3ccc4c(c3)c3ccccc3n3c5ccccc5nc43)cc2)cc1]
1-b-154 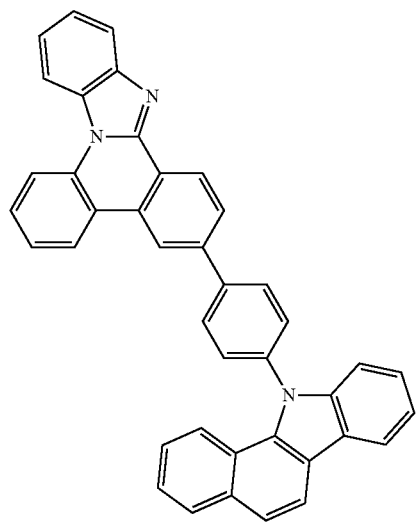 [SMILES: c1ccc2c(c1)ccc1c3ccccc3n(-c3ccc(-c4ccc5c(c4)c4ccccc4n4c6ccccc6nc54)cc3)c21]
1-b-155 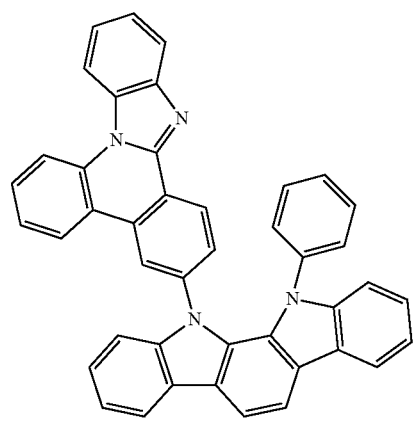 [SMILES: c1ccc(-n2c3ccccc3c3ccc4c5ccccc5n(-c5ccc6c(c5)c5ccccc5n5c7ccccc7nc65)c4c32)cc1]
1-b-156 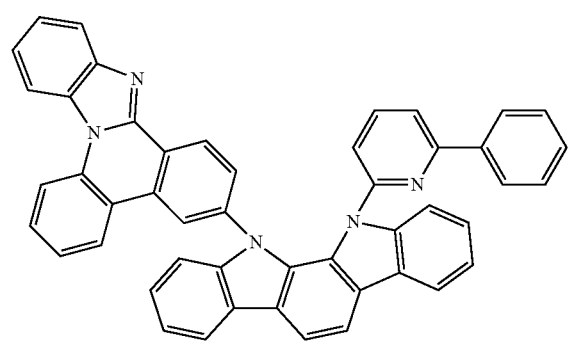 [SMILES: c1ccc(-c2cccc(-n3c4ccccc4c4ccc5c6ccccc6n(-c6ccc7c(c6)c6ccccc6n6c8ccccc8nc76)c5c43)n2)cc1]

As preferable detailed examples of the compound that is represented by Formula 1, there are the following compounds, but they are not limited thereto.
TABLE 3
1-c-1
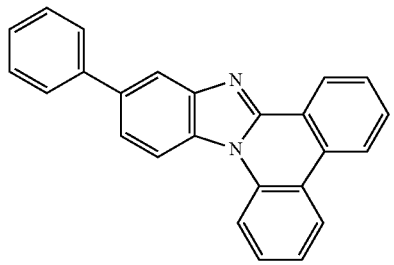 [SMILES: c1ccc(-c2ccc3c(c2)nc2c4ccccc4c4ccccc4n32)cc1]
1-c-2
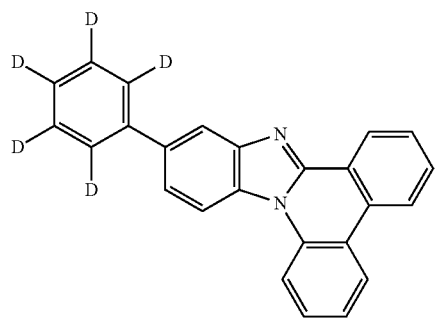 [SMILES: [2H]c1c([2H])c([2H])c(-c2ccc3c(c2)nc2c4ccccc4c4ccccc4n32)c([2H])c1[2H]]
1-c-3
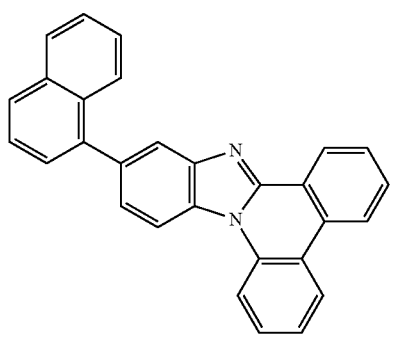 [SMILES: c1ccc2c(-c3ccc4c(c3)nc3c5ccccc5c5ccccc5n43)cccc2c1]
1-c-4
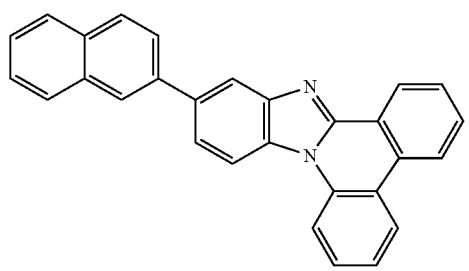 [SMILES: c1ccc2cc(-c3ccc4c(c3)nc3c5ccccc5c5ccccc5n43)ccc2c1]
1-c-5
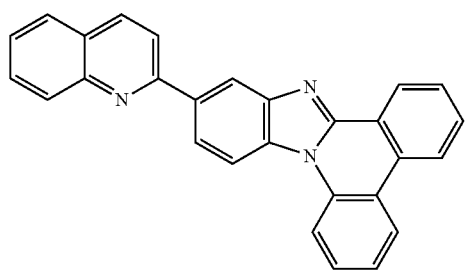 [SMILES: c1ccc2nc(-c3ccc4c(c3)nc3c5ccccc5c5ccccc5n43)ccc2c1]

TABLE 3-continued
1-c-6
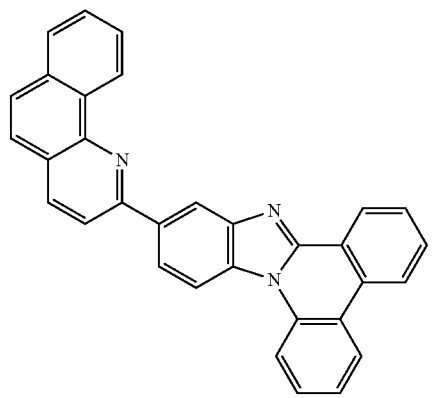 [SMILES: c1ccc2c(c1)ccc1ccc(-c3ccc4c(c3)nc3c5ccccc5c5ccccc5n43)nc12]
1-c-7
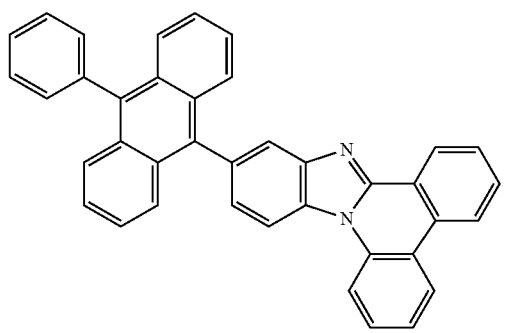 [SMILES: c1ccc(-c2c3ccccc3c(-c3ccc4c(c3)nc3c5ccccc5c5ccccc5n43)c3ccccc23)cc1]
1-c-8
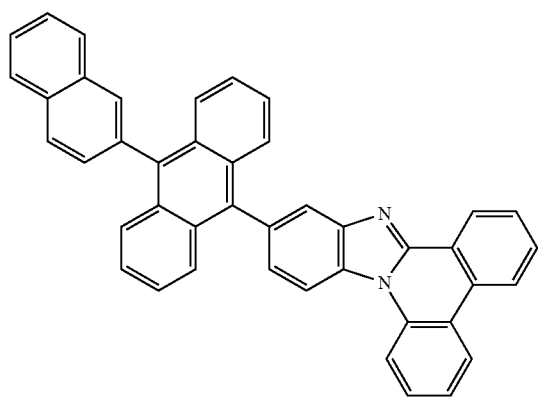 [SMILES: c1ccc2cc(-c3c4ccccc4c(-c4ccc5c(c4)nc4c6ccccc6c6ccccc6n54)c4ccccc34)ccc2c1]
1-c-9
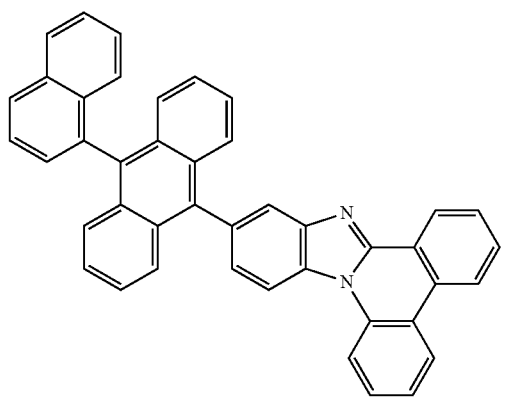 [SMILES: c1ccc2c(-c3c4ccccc4c(-c4ccc5c(c4)nc4c6ccccc6c6ccccc6n54)c4ccccc34)cccc2c1]

TABLE 3-continued
1-c-10
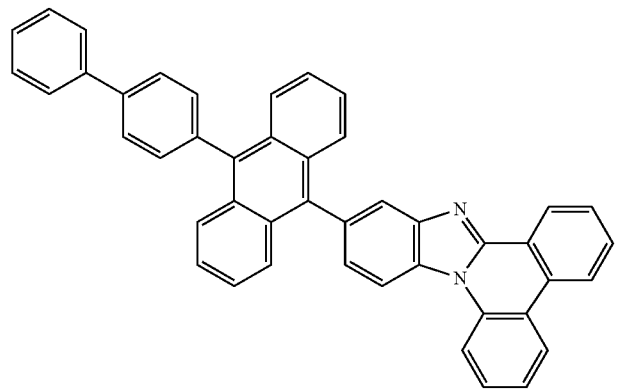 [SMILES: c1ccc(-c2ccc(-c3c4ccccc4c(-c4ccc5c(c4)nc4c6ccccc6c6ccccc6n54)c4ccccc34)cc2)cc1]
1-c-11
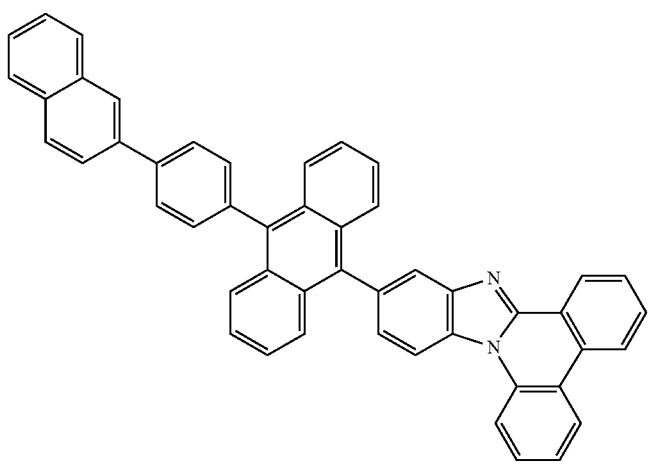 [SMILES: c1ccc2cc(-c3ccc(-c4c5ccccc5c(-c5ccc6c(c5)nc5c7ccccc7c7ccccc7n65)c5ccccc45)cc3)ccc2c1]
1-c-12
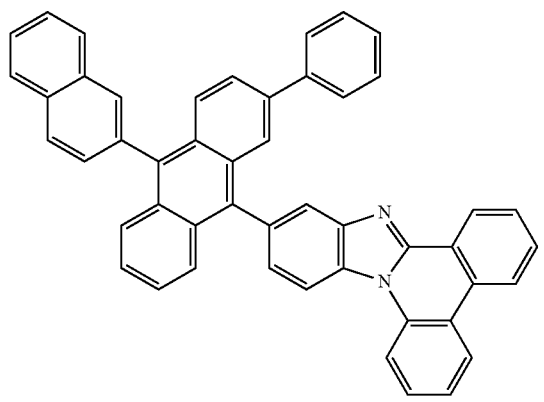 [SMILES: c1ccc(-c2ccc3c(-c4ccc5ccccc5c4)c4ccccc4c(-c4ccc5c(c4)nc4c6ccccc6c6ccccc6n54)c3c2)cc1]
1-c-13
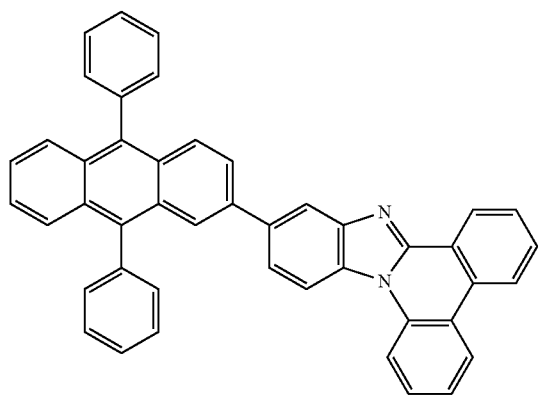 [SMILES: c1ccc(-c2c3ccccc3c(-c3ccccc3)c3cc(-c4ccc5c(c4)nc4c6ccccc6c6ccccc6n54)ccc23)cc1]

TABLE 3-continued
1-c-14
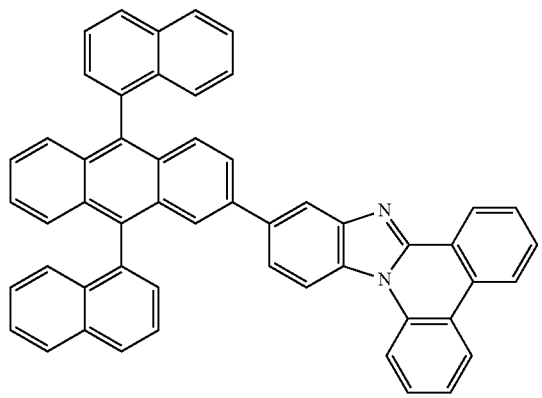 [SMILES: c1ccc2c(-c3c4ccccc4c(-c4cccc5ccccc45)c4cc(-c5ccc6c(c5)nc5c7ccccc7c7ccccc7n65)ccc34)cccc2c1]
1-c-15
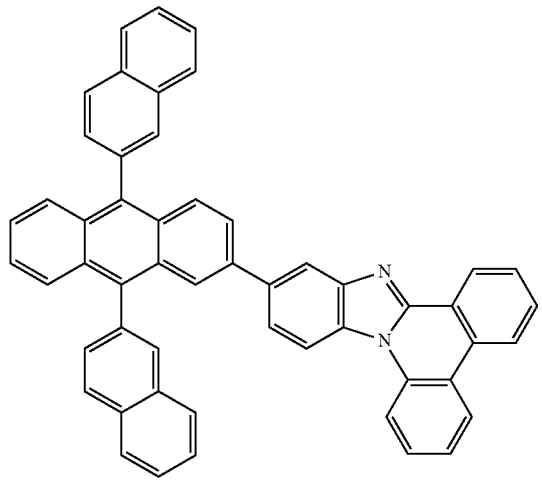 [SMILES: c1ccc2cc(-c3c4ccccc4c(-c4ccc5ccccc5c4)c4cc(-c5ccc6c(c5)nc5c7ccccc7c7ccccc7n65)ccc34)ccc2c1]
1-c-16
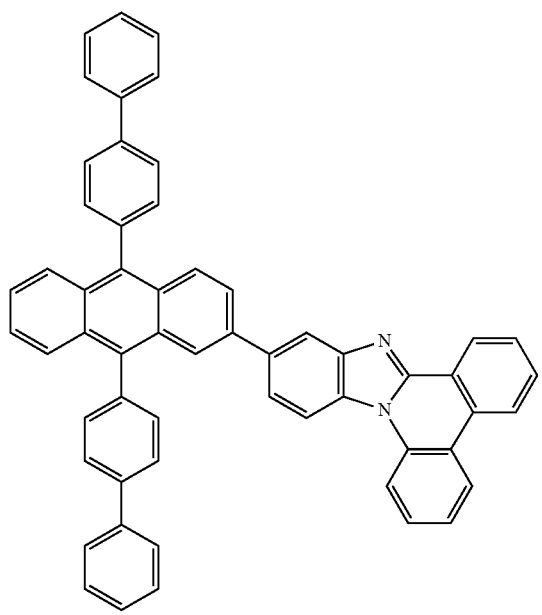 [SMILES: c1ccc(-c2ccc(-c3c4ccccc4c(-c4ccc(-c5ccccc5)cc4)c4cc(-c5ccc6c(c5)nc5c7ccccc7c7ccccc7n65)ccc34)cc2)cc1]

TABLE 3-continued
1-c-17
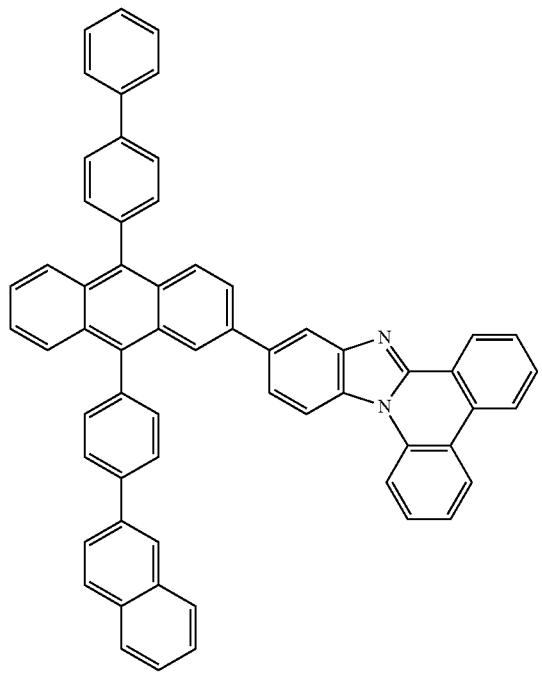 [SMILES: c1ccc(-c2ccc(-c3c4ccccc4c(-c4ccc(-c5ccc6ccccc6c5)cc4)c4cc(-c5ccc6c(c5)nc5c7ccccc7c7ccccc7n65)ccc34)cc2)cc1]
1-c-18
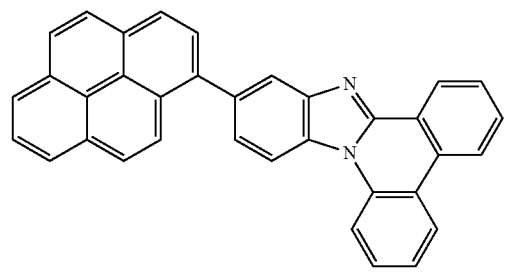 [SMILES: c1cc2ccc3ccc(-c4ccc5c(c4)nc4c6ccccc6c6ccccc6n54)c4ccc(c1)c2c34]
1-c-19
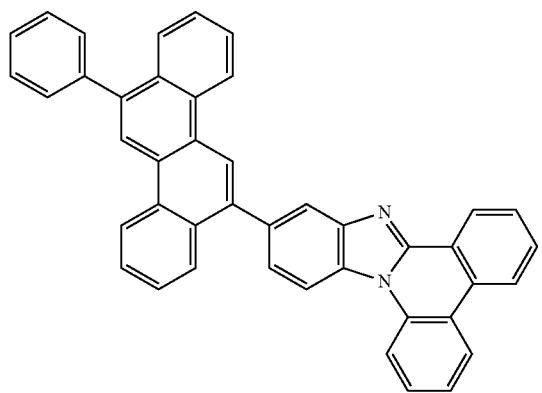 [SMILES: c1ccc(-c2cc3c4ccccc4c(-c4ccc5c(c4)nc4c6ccccc6c6ccccc6n54)cc3c3ccccc23)cc1]

TABLE 3-continued
1-c-20
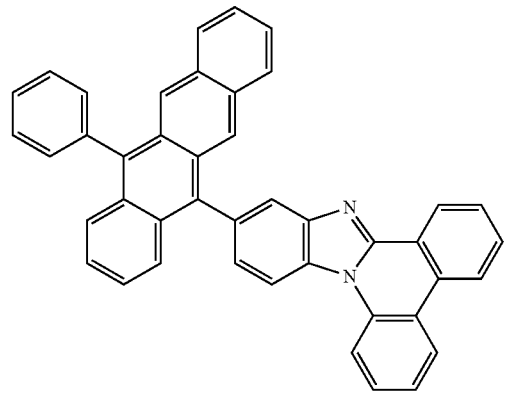 [SMILES: c1ccc(-c2c3ccccc3c(-c3ccc4c(c3)nc3c5ccccc5c5ccccc5n43)c3cc4ccccc4cc23)cc1]
1-c-21
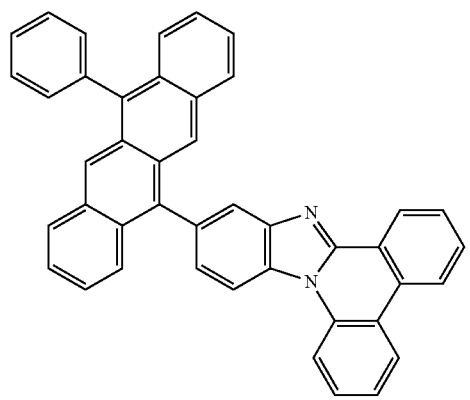 [SMILES: c1ccc(-c2c3ccccc3cc3c(-c4ccc5c(c4)nc4c6ccccc6c6ccccc6n54)c4ccccc4cc23)cc1]
1-c-22
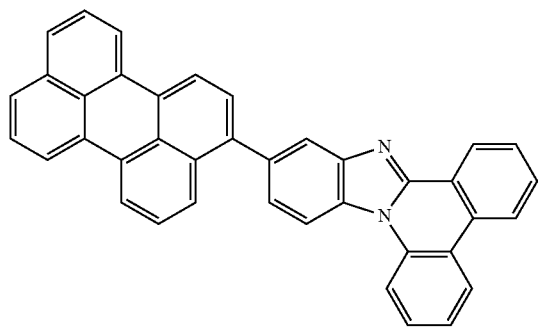 [SMILES: c1ccc2c(c1)c1ccccc1n1c3ccc(-c4ccc5c6cccc7cccc(c8cccc4c85)c76)cc3nc21]
1-c-23
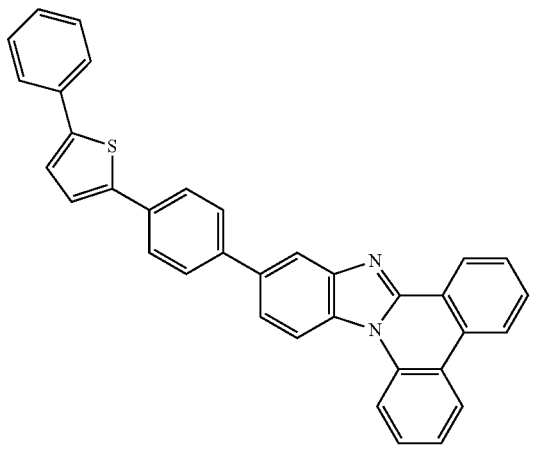 [SMILES: c1ccc(-c2ccc(-c3ccc(-c4ccc5c(c4)nc4c6ccccc6c6ccccc6n54)cc3)s2)cc1]

TABLE 3-continued
1-c-24
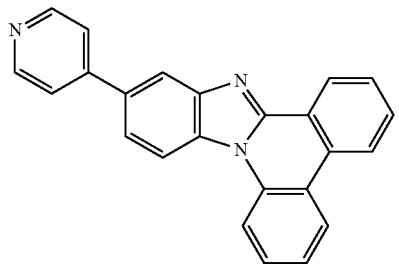 [SMILES: c1ccc2c(c1)c1ccccc1n1c3ccc(-c4ccncc4)cc3nc21]
1-c-25
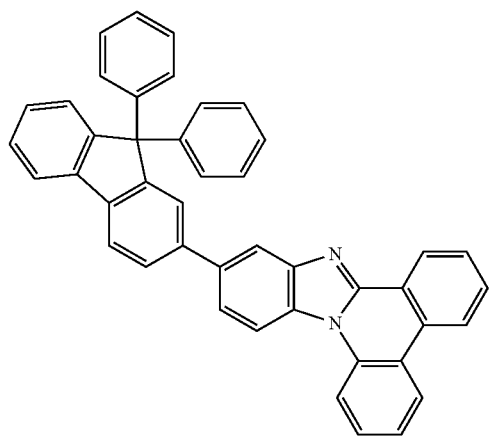 [SMILES: c1ccc(C2(c3ccccc3)c3ccccc3-c3ccc(-c4ccc5c(c4)nc4c6ccccc6c6ccccc6n54)cc32)cc1]
1-c-26
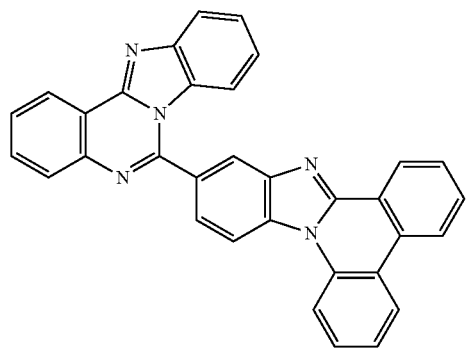 [SMILES: c1ccc2c(c1)nc(-c1ccc3c(c1)nc1c4ccccc4c4ccccc4n31)n1c3ccccc3nc21]
1-c-27
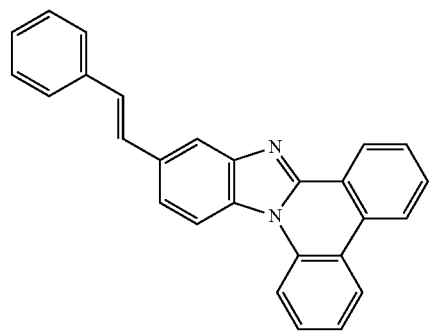 [SMILES: C(=C\c1ccc2c(c1)nc1c3ccccc3c3ccccc3n21)/c1ccccc1]

TABLE 3-continued
1-c-28
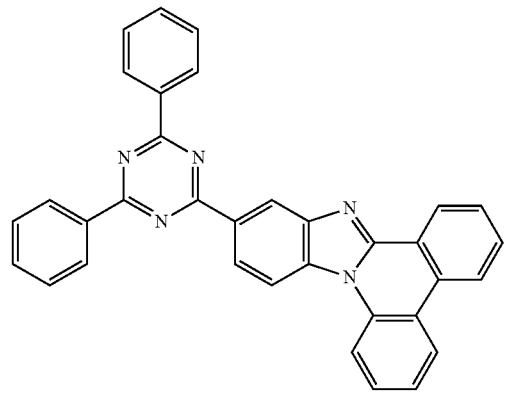 [SMILES: c1ccc(-c2nc(-c3ccccc3)nc(-c3ccc4c(c3)nc3c5ccccc5c5ccccc5n43)n2)cc1]
1-c-29
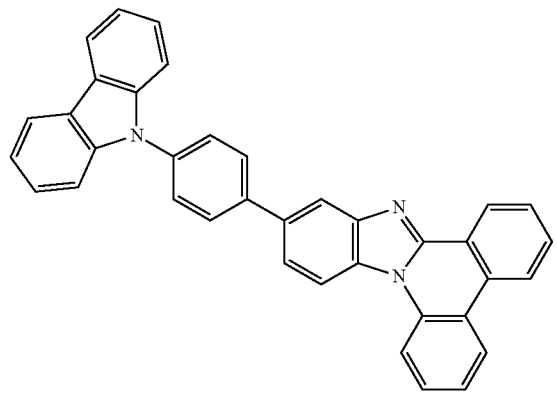 [SMILES: c1ccc2c(c1)c1ccccc1n1c3ccc(-c4ccc(-n5c6ccccc6c6ccccc65)cc4)cc3nc21]
1-c-30
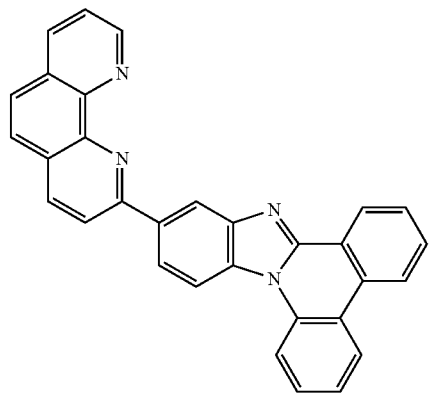 [SMILES: c1cnc2c(c1)ccc1ccc(-c3ccc4c(c3)nc3c5ccccc5c5ccccc5n43)nc12]
1-c-31
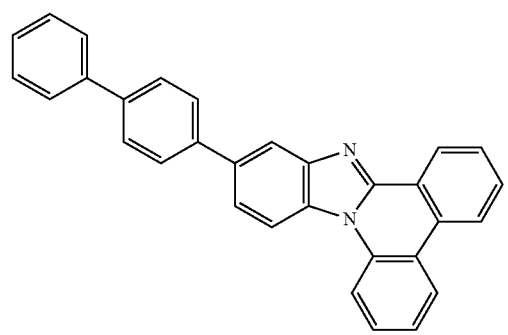 [SMILES: c1ccc(-c2ccc(-c3ccc4c(c3)nc3c5ccccc5c5ccccc5n43)cc2)cc1]

TABLE 3-continued
1-c-32
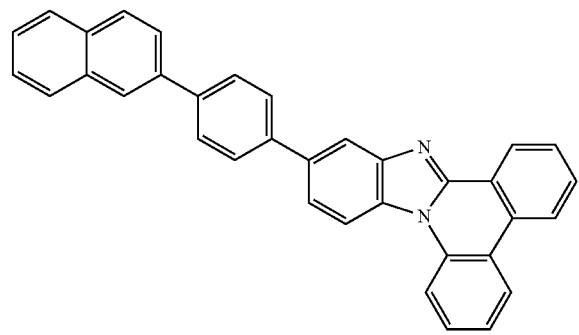 [SMILES: c1ccc2cc(-c3ccc(-c4ccc5c(c4)nc4c6ccccc6c6ccccc6n54)cc3)ccc2c1]
1-c-33
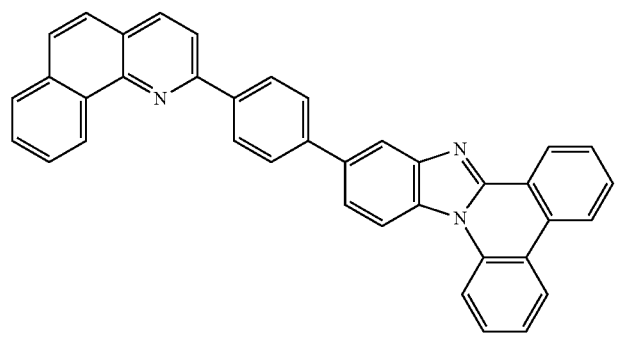 [SMILES: c1ccc2c(c1)ccc1ccc(-c3ccc(-c4ccc5c(c4)nc4c6ccccc6c6ccccc6n54)cc3)nc12]
1-c-34
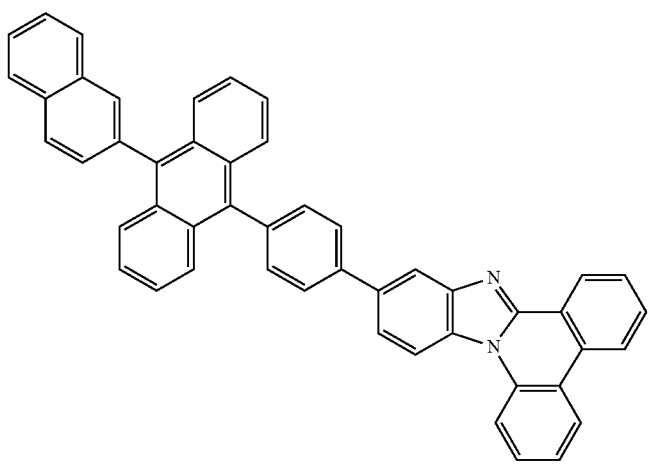 [SMILES: c1ccc2cc(-c3c4ccccc4c(-c4ccc(-c5ccc6c(c5)nc5c7ccccc7c7ccccc7n65)cc4)c4ccccc34)ccc2c1]
1-c-35
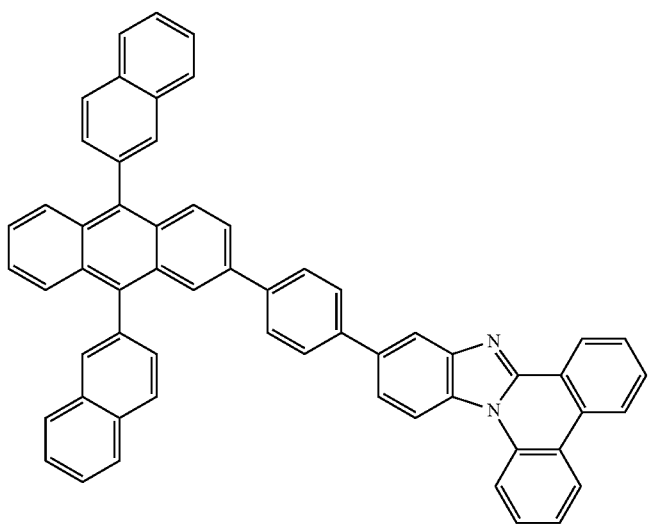 [SMILES: c1ccc2cc(-c3c4ccccc4c(-c4ccc5ccccc5c4)c4cc(-c5ccc(-c6ccc7c(c6)nc6c8ccccc8c8ccccc8n76)cc5)ccc34)ccc2c1]

TABLE 3-continued
1-c-36
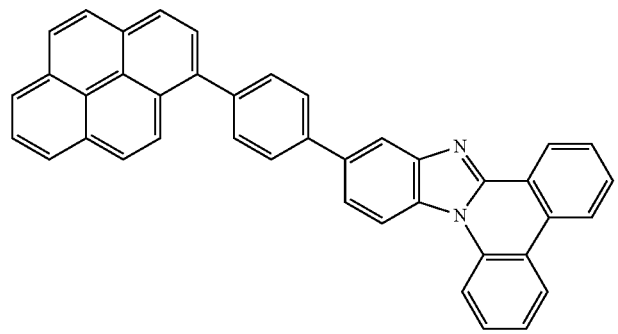 [SMILES: c1cc2ccc3ccc(-c4ccc(-c5ccc6c(c5)nc5c7ccccc7c7ccccc7n65)cc4)c4ccc(c1)c2c34]
1-c-37
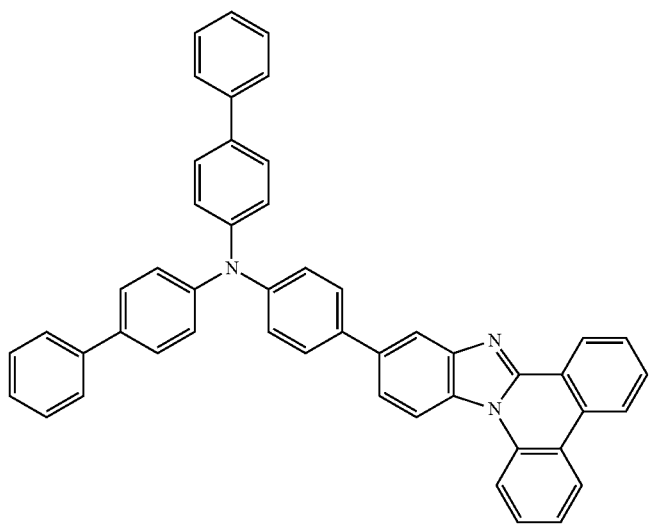 [SMILES: c1ccc(-c2ccc(N(c3ccc(-c4ccccc4)cc3)c3ccc(-c4ccc5c(c4)nc4c6ccccc6c6ccccc6n54)cc3)cc2)cc1]
1-c-38
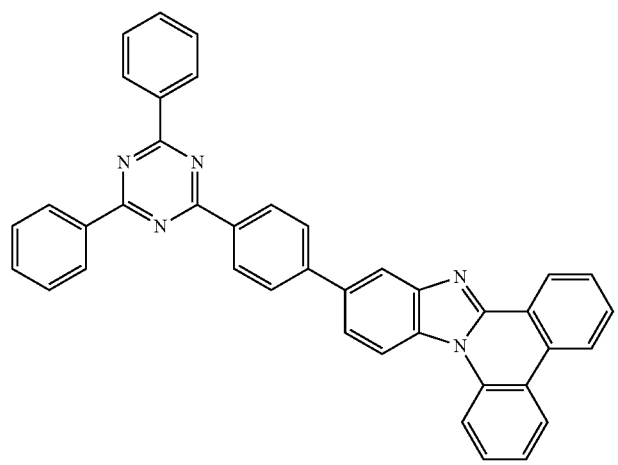 [SMILES: c1ccc(-c2nc(-c3ccccc3)nc(-c3ccc(-c4ccc5c(c4)nc4c6ccccc6c6ccccc6n54)cc3)n2)cc1]

TABLE 3-continued
1-c-39
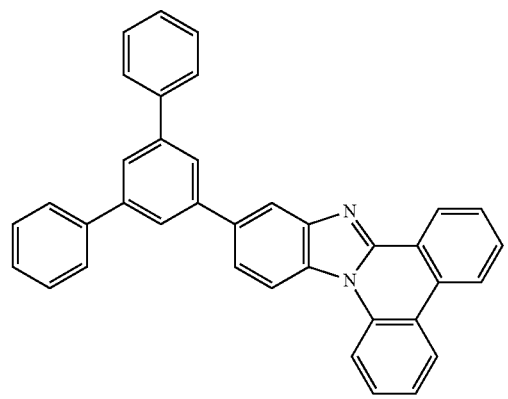 [SMILES: c1ccc(-c2cc(-c3ccccc3)cc(-c3ccc4c(c3)nc3c5ccccc5c5ccccc5n43)c2)cc1]
1-c-40
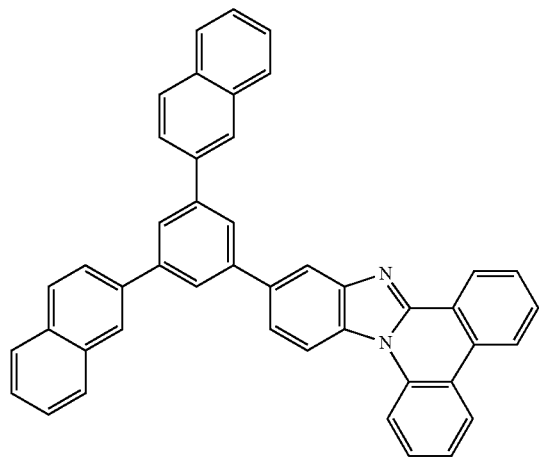 [SMILES: c1ccc2cc(-c3cc(-c4ccc5ccccc5c4)cc(-c4ccc5c(c4)nc4c6ccccc6c6ccccc6n54)c3)ccc2c1]
1-c-41
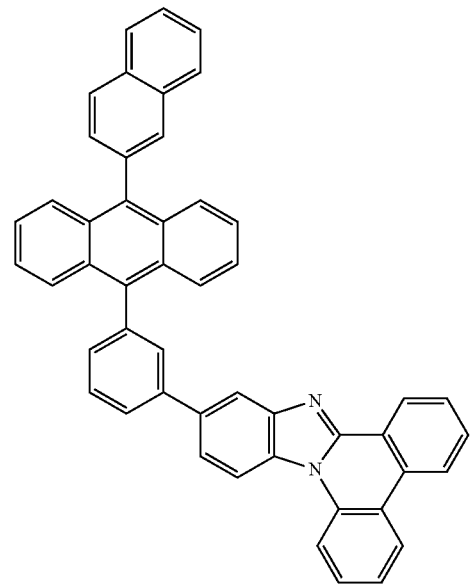 [SMILES: c1cc(-c2ccc3c(c2)nc2c4ccccc4c4ccccc4n32)cc(-c2c3ccccc3c(-c3ccc4ccccc4c3)c3ccccc23)c1]

TABLE 3-continued
1-c-42
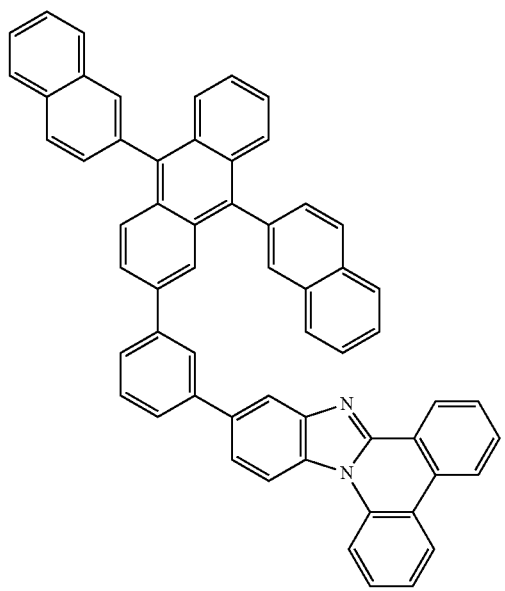 [SMILES: c1cc(-c2ccc3c(c2)nc2c4ccccc4c4ccccc4n32)cc(-c2ccc3c(-c4ccc5ccccc5c4)c4ccccc4c(-c4ccc5ccccc5c4)c3c2)c1]
1-c-43
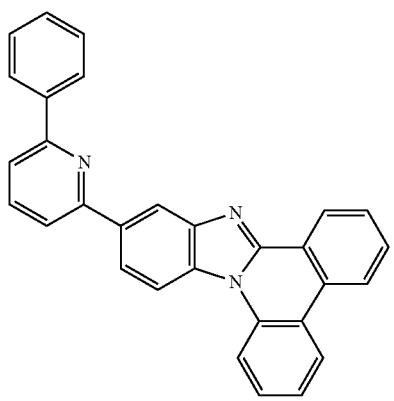 [SMILES: c1ccc(-c2cccc(-c3ccc4c(c3)nc3c5ccccc5c5ccccc5n43)n2)cc1]
1-c-44
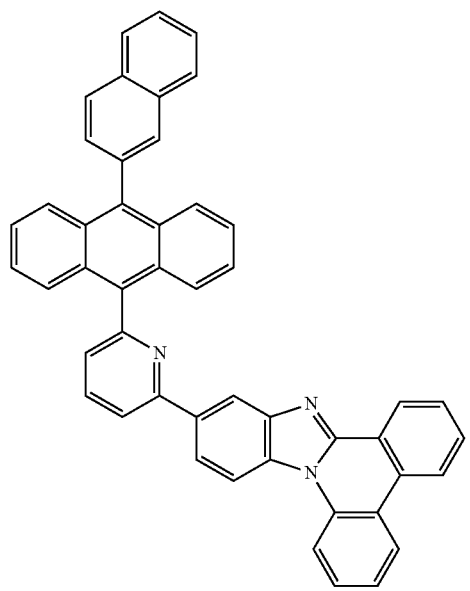 [SMILES: c1cc(-c2ccc3c(c2)nc2c4ccccc4c4ccccc4n32)nc(-c2c3ccccc3c(-c3ccc4ccccc4c3)c3ccccc23)c1]

TABLE 3-continued
1-c-45
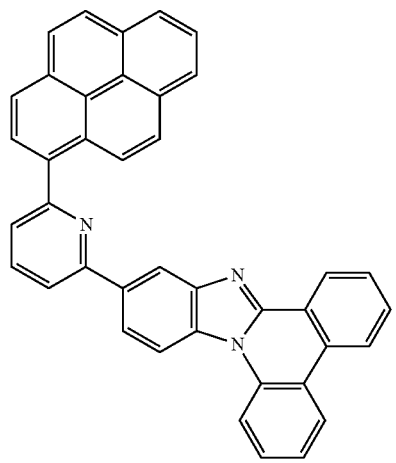 [SMILES: c1cc(-c2ccc3c(c2)nc2c4ccccc4c4ccccc4n32)nc(-c2ccc3ccc4cccc5ccc2c3c45)c1]
1-c-46
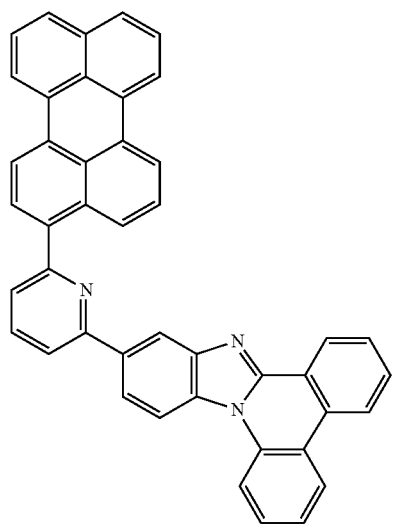 [SMILES: c1cc(-c2ccc3c(c2)nc2c4ccccc4c4ccccc4n32)nc(-c2ccc3c4cccc5cccc(c6cccc2c63)c54)c1]
1-c-47
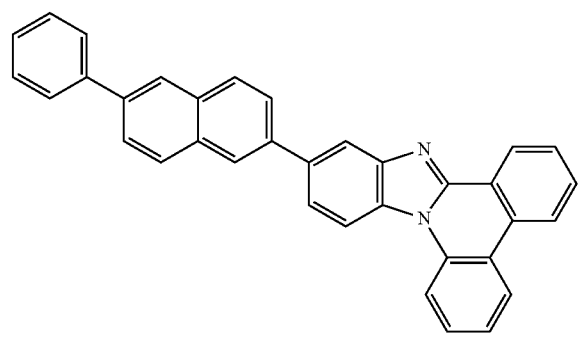 [SMILES: c1ccc(-c2ccc3cc(-c4ccc5c(c4)nc4c6ccccc6c6ccccc6n54)ccc3c2)cc1]

TABLE 3-continued
1-c-48
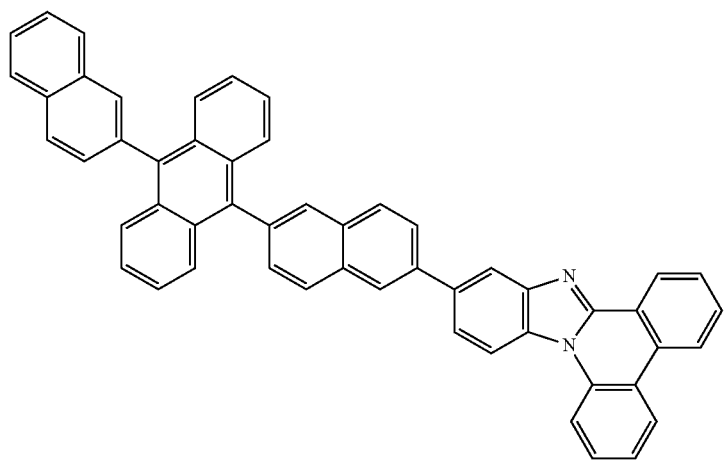 [SMILES: c1ccc2cc(-c3c4ccccc4c(-c4ccc5cc(-c6ccc7c(c6)nc6c8ccccc8c8ccccc8n76)ccc5c4)c4ccccc34)ccc2c1]
1-c-49
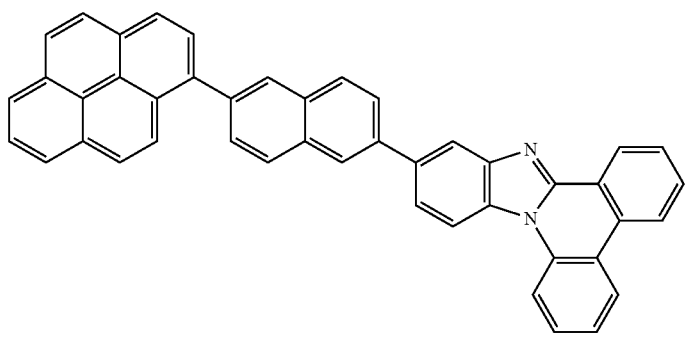 [SMILES: c1cc2ccc3ccc(-c4ccc5cc(-c6ccc7c(c6)nc6c8ccccc8c8ccccc8n76)ccc5c4)c4ccc(c1)c2c34]
1-c-50
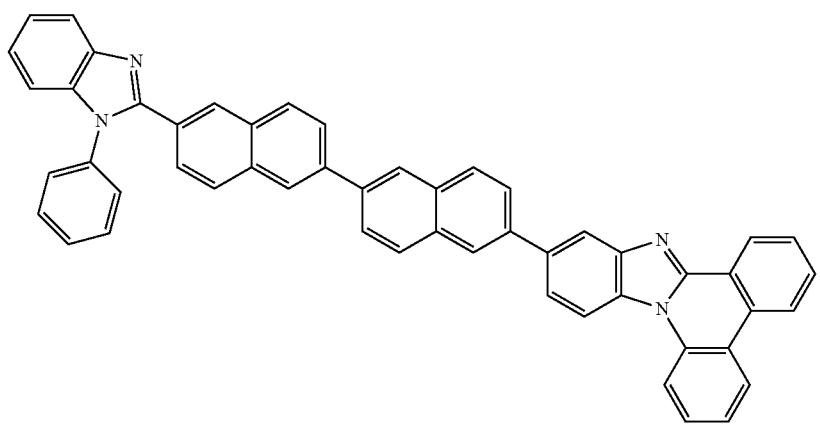 [SMILES: c1ccc(-n2c(-c3ccc4cc(-c5ccc6cc(-c7ccc8c(c7)nc7c9ccccc9c9ccccc9n87)ccc6c5)ccc4c3)nc3ccccc32)cc1]
1-c-51
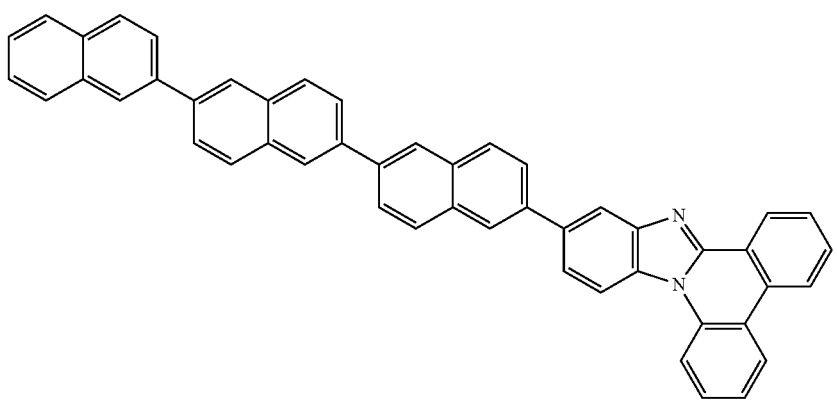 [SMILES: c1ccc2cc(-c3ccc4cc(-c5ccc6cc(-c7ccc8c(c7)nc7c9ccccc9c9ccccc9n87)ccc6c5)ccc4c3)ccc2c1]

TABLE 3-continued
1-c-52
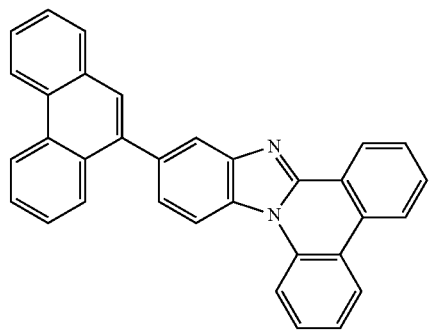 [SMILES: c1ccc2c(c1)cc(-c1ccc3c(c1)nc1c4ccccc4c4ccccc4n31)c1ccccc12]
1-c-53
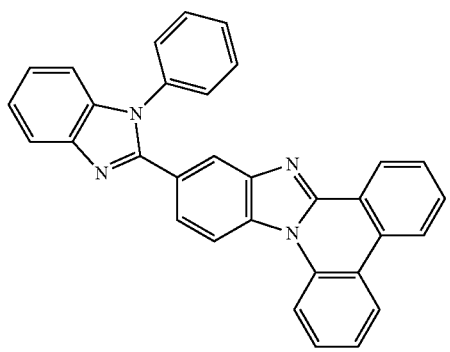 [SMILES: c1ccc(-n2c(-c3ccc4c(c3)nc3c5ccccc5c5ccccc5n43)nc3ccccc32)cc1]
1-c-54
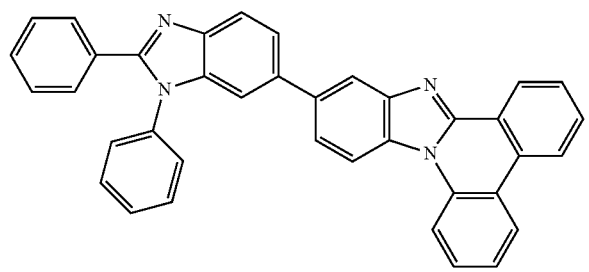 [SMILES: c1ccc(-c2nc3ccc(-c4ccc5c(c4)nc4c6ccccc6c6ccccc6n54)cc3n2-c2ccccc2)cc1]
1-c-55
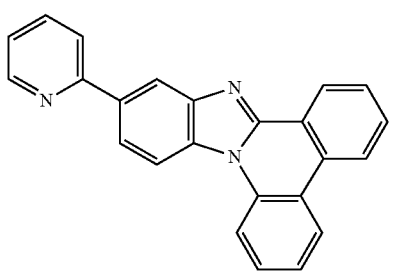
1-c-56
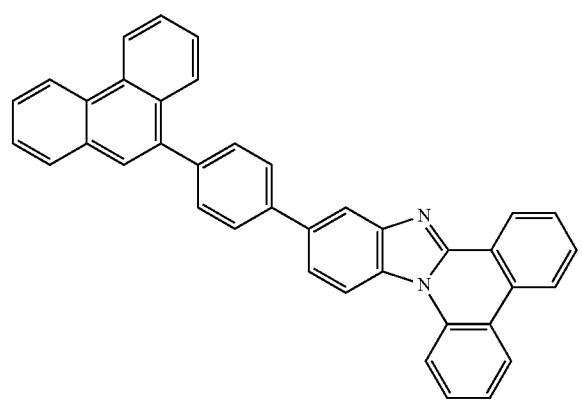 [SMILES: c1ccc2c(c1)cc(-c1ccc(-c3ccc4c(c3)nc3c5ccccc5c5ccccc5n43)cc1)c1ccccc12]

TABLE 3-continued
1-c-57
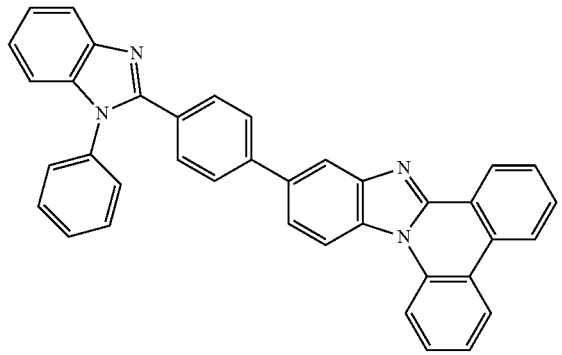 [SMILES: c1ccc(-n2c(-c3ccc(-c4ccc5c(c4)nc4c6ccccc6c6ccccc6n54)cc3)nc3ccccc32)cc1]
1-c-58
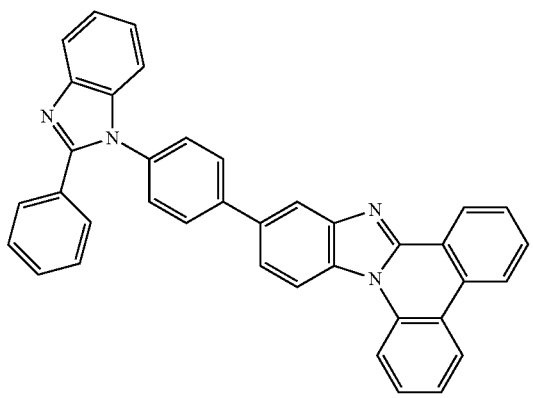 [SMILES: c1ccc(-c2nc3ccccc3n2-c2ccc(-c3ccc4c(c3)nc3c5ccccc5c5ccccc5n43)cc2)cc1]
1-c-59
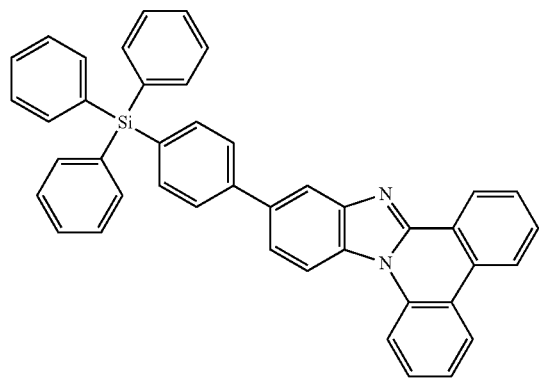 [SMILES: c1ccc([Si](c2ccccc2)(c2ccccc2)c2ccc(-c3ccc4c(c3)nc3c5ccccc5c5ccccc5n43)cc2)cc1]
1-c-60
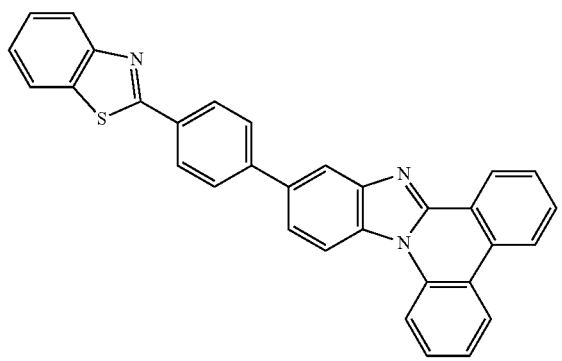 [SMILES: c1ccc2sc(-c3ccc(-c4ccc5c(c4)nc4c6ccccc6c6ccccc6n54)cc3)nc2c1]

TABLE 3-continued
1-c-61
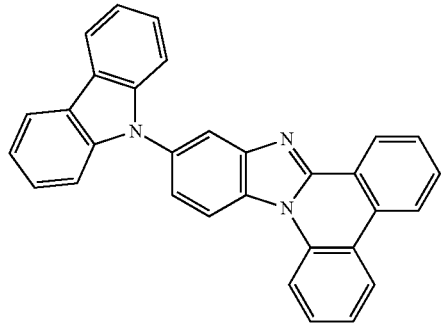 [SMILES: c1ccc2c(c1)c1ccccc1n1c3ccc(-n4c5ccccc5c5ccccc54)cc3nc21]
1-c-62
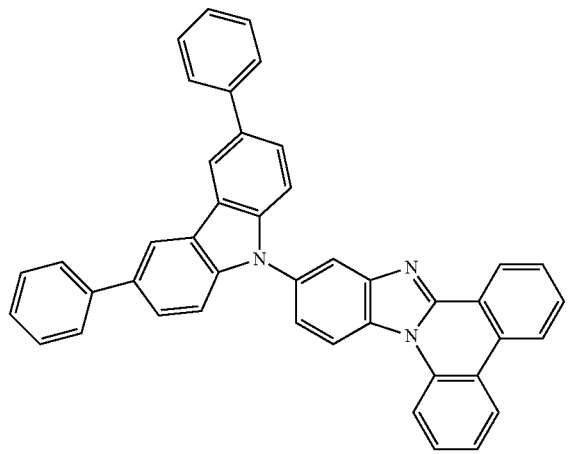 [SMILES: c1ccc(-c2ccc3c(c2)c2cc(-c4ccccc4)ccc2n3-c2ccc3c(c2)nc2c4ccccc4c4ccccc4n32)cc1]
1-c-63
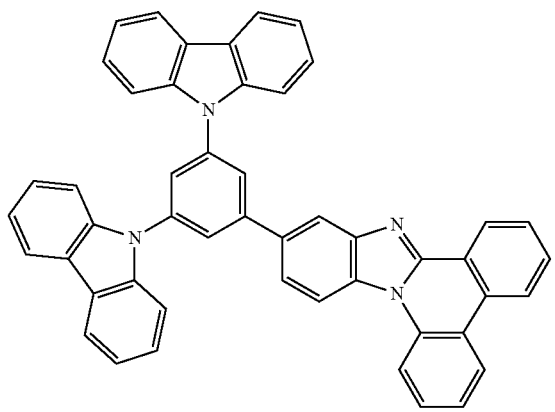 [SMILES: c1ccc2c(c1)c1ccccc1n1c3ccc(-c4cc(-n5c6ccccc6c6ccccc65)cc(-n5c6ccccc6c6ccccc65)c4)cc3nc21]
1-c-64
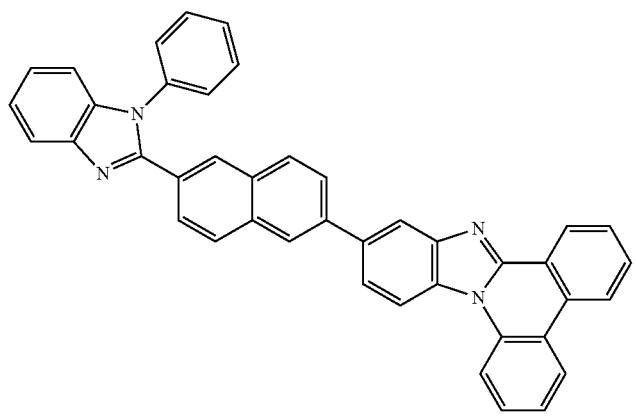 [SMILES: c1ccc(-n2c(-c3ccc4cc(-c5ccc6c(c5)nc5c7ccccc7c7ccccc7n65)ccc4c3)nc3ccccc32)cc1]

As preferable detailed examples of the compound that is represented by Formula 1, there are the following compounds, but they are not limited thereto.
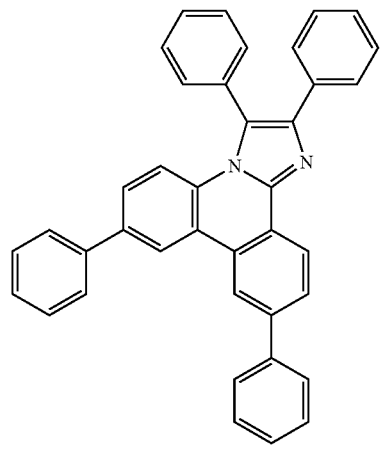
[2-a-1]
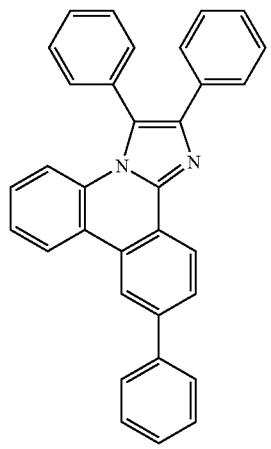
[2-a-2]
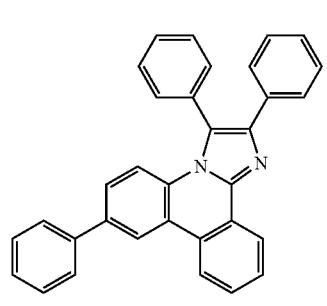
[2-a-3]
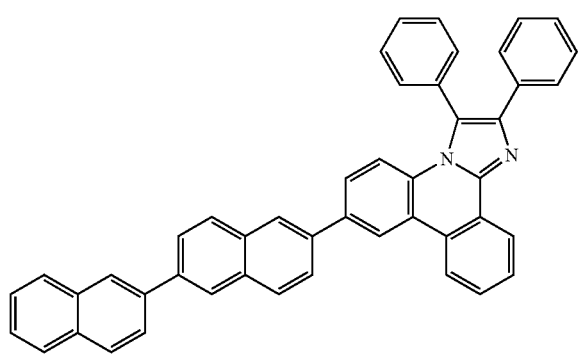
[2-a-4]
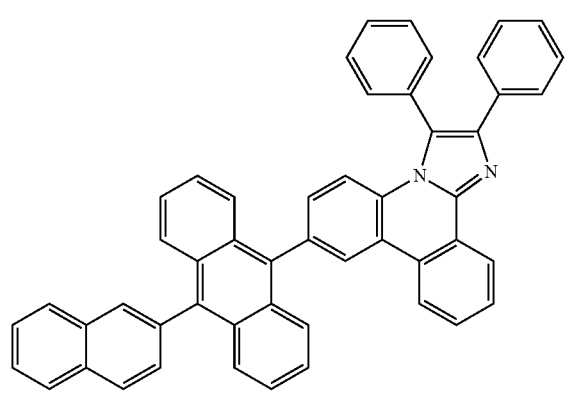
[2-a-5]
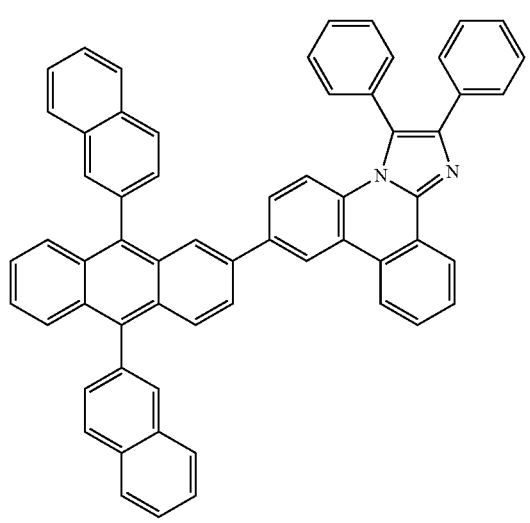
[2-a-6]

-continued
[2-a-7]
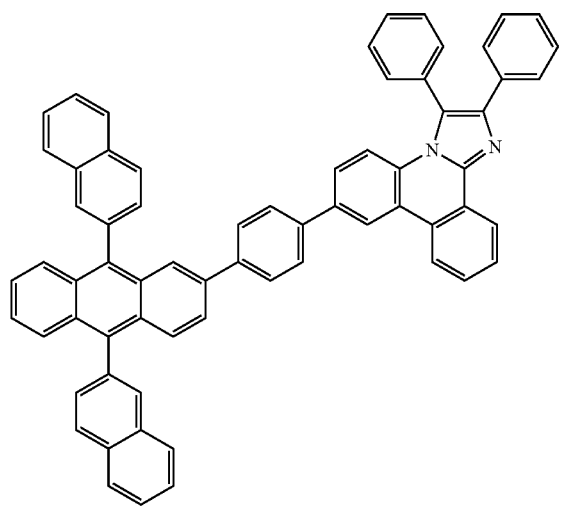
[2-a-8]
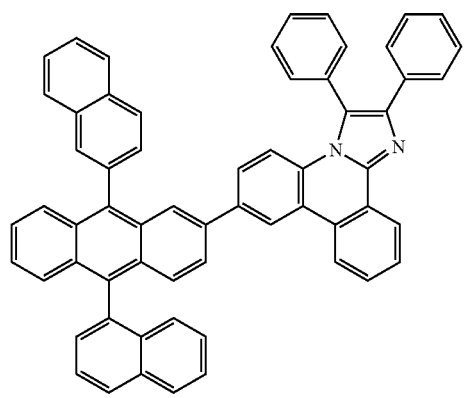
[2-a-9]
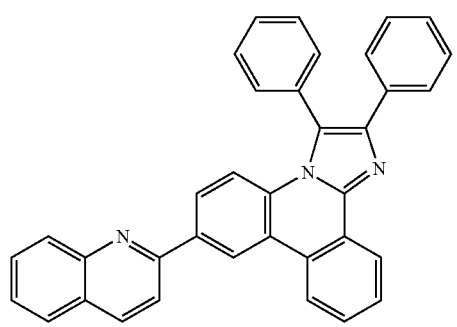
[2-a-10]
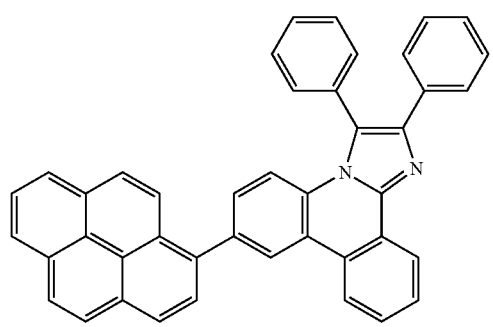
[2-a-11]
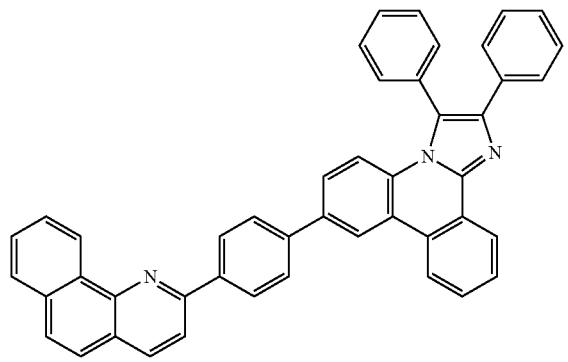
[2-a-12]
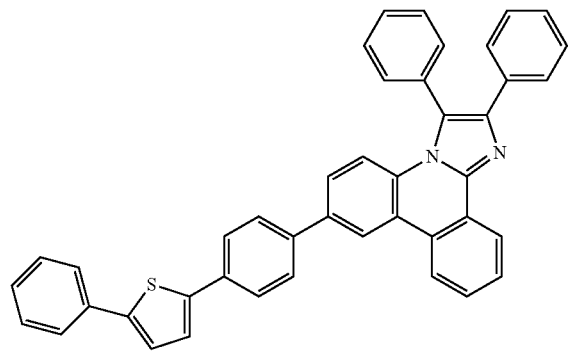
[2-a-13]
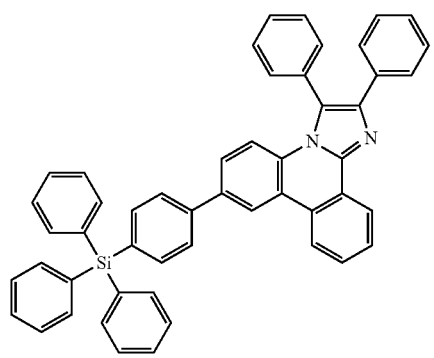
[2-a-14]
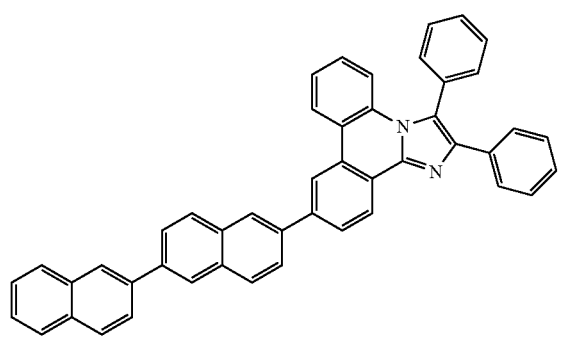

-continued
[2-a-15]
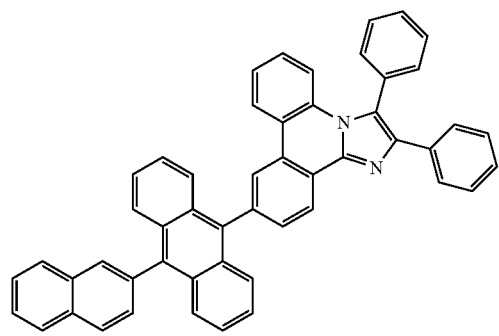
[2-a-16]
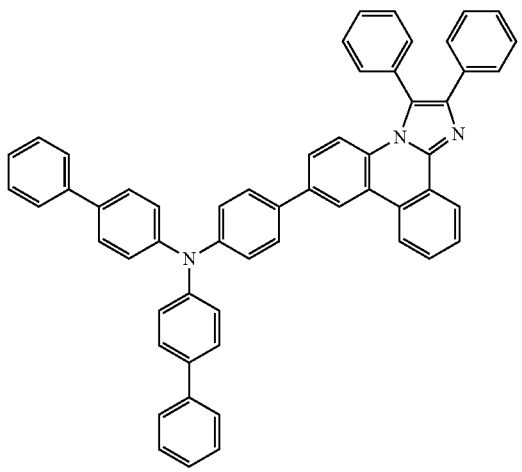
[2-a-17]
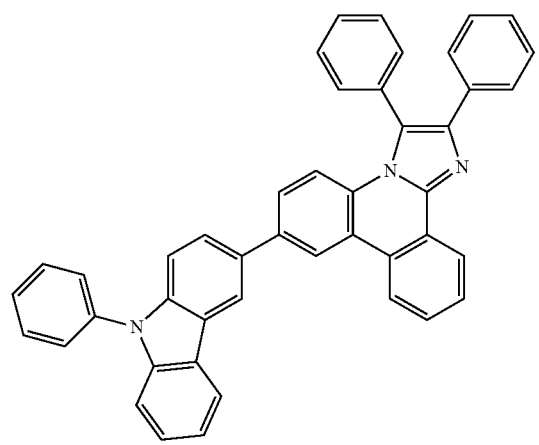
[2-a-18]
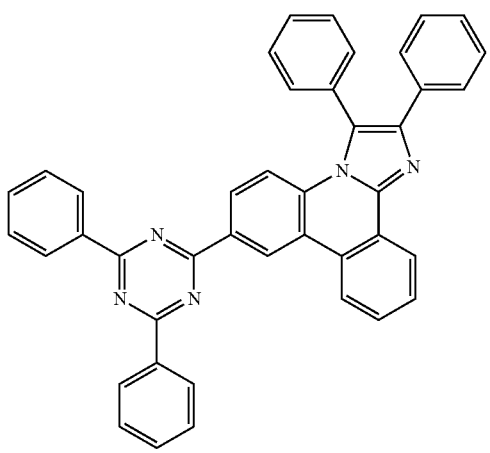
[2-a-19]
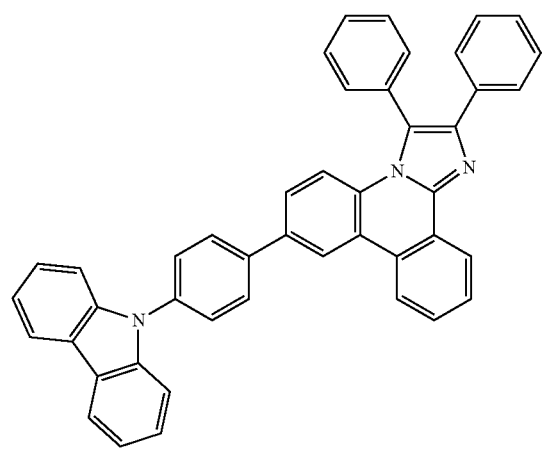
[2-a-20]
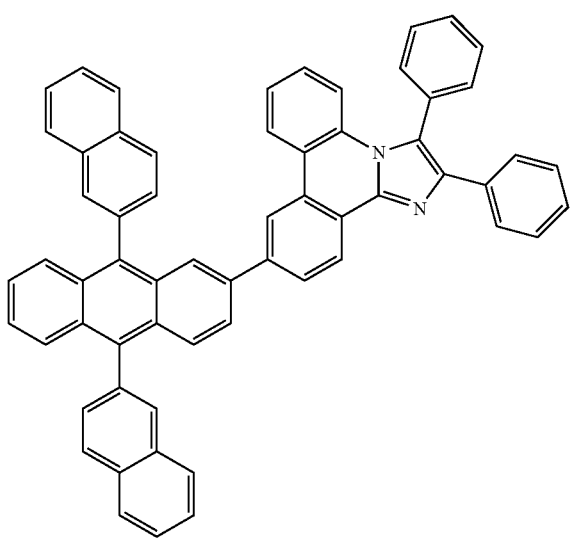

[2-a-21]
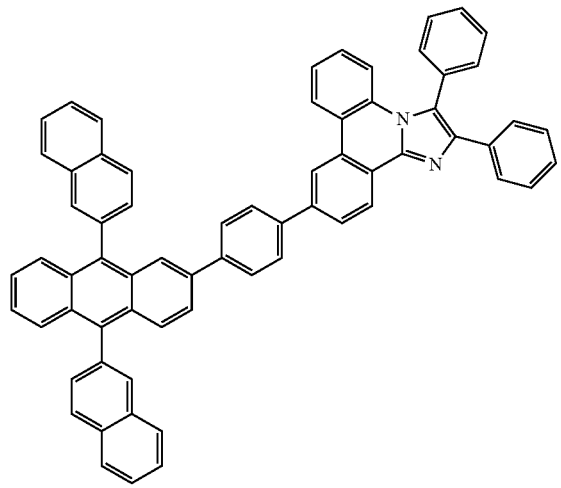
[2-a-22]
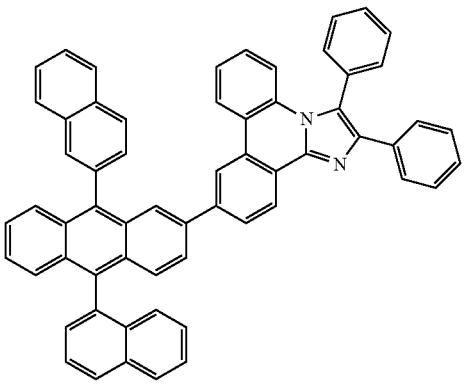
[2-a-23]
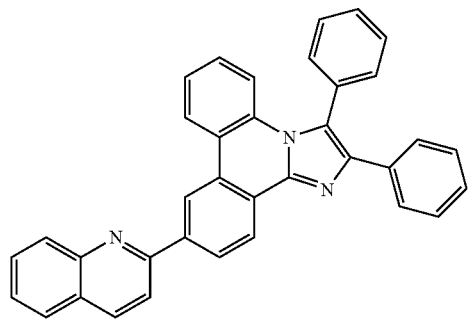
[2-a-24]
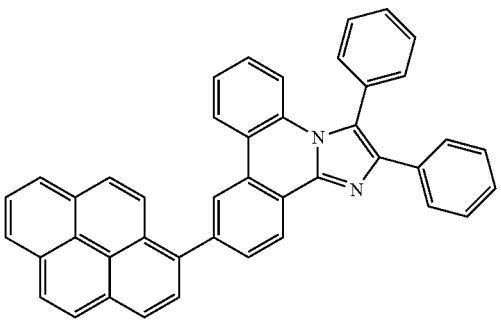
[2-a-25]
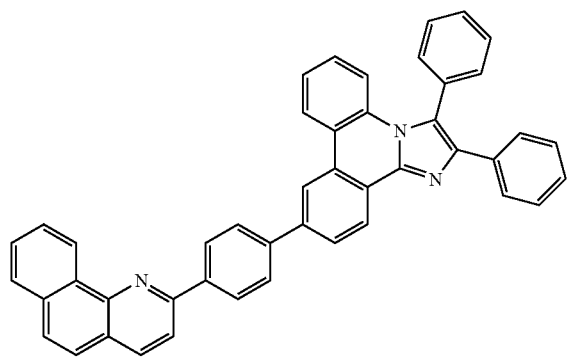
[2-a-26]
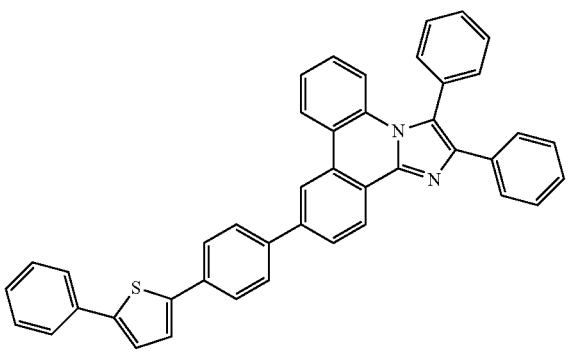

[2-a-27]
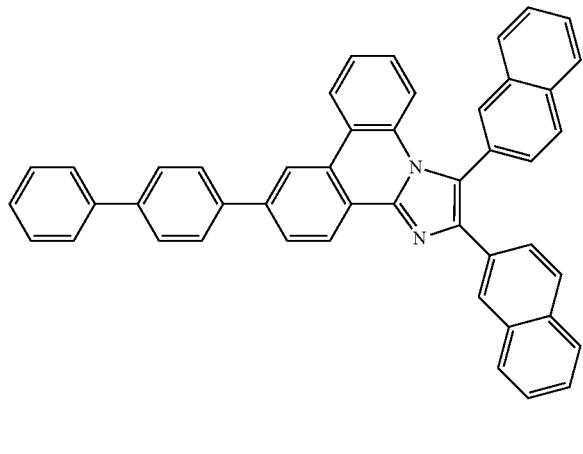
[2-a-28]
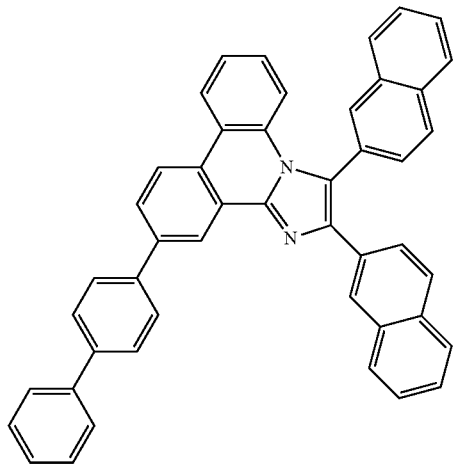
[2-a-29]
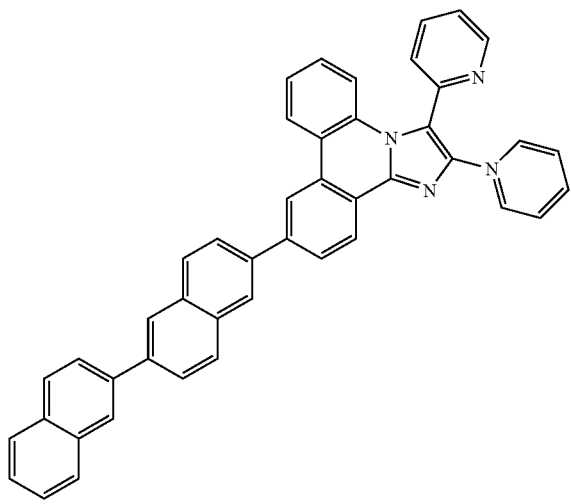
[2-a-30]
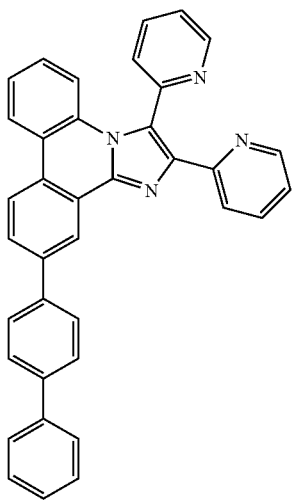
[2-a-31]
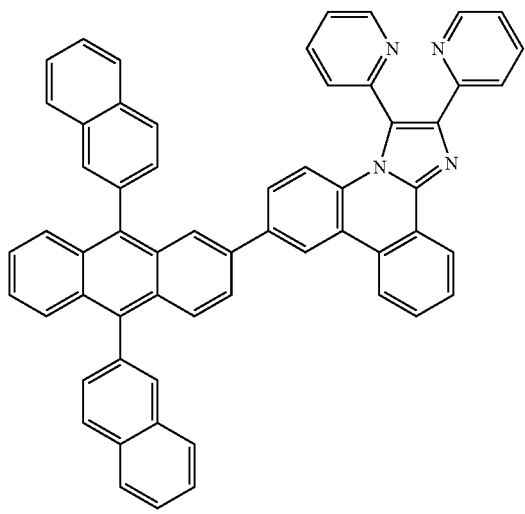
[2-a-32]
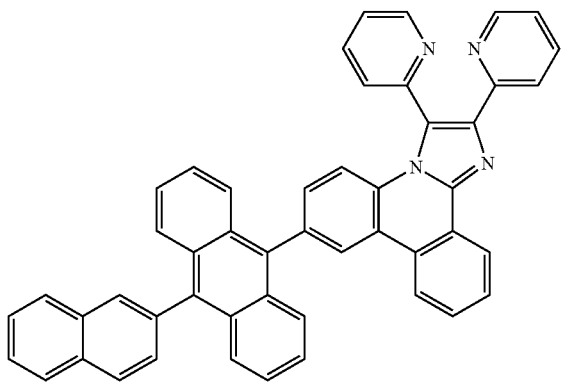

-continued
[2-a-33]
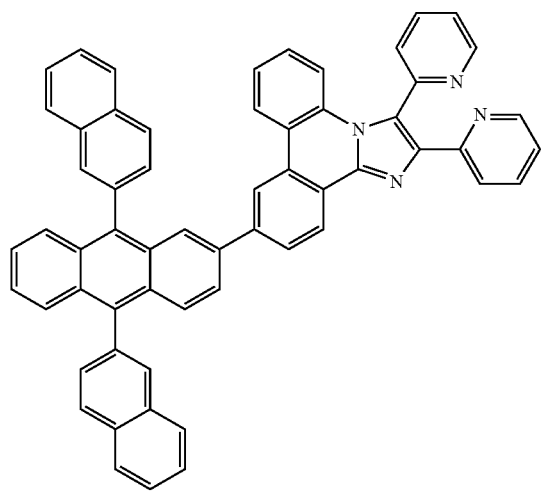
[2-a-34]
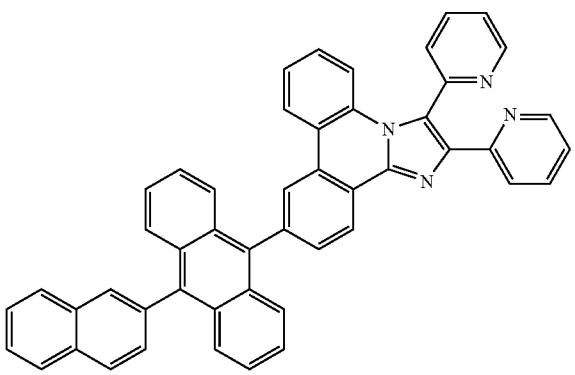
[2-a-35]
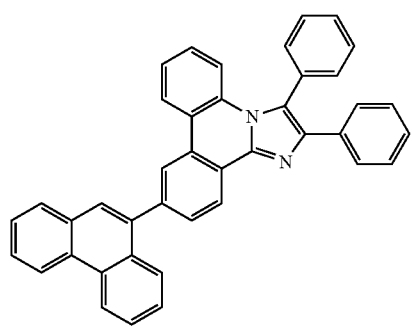
[2-a-36]
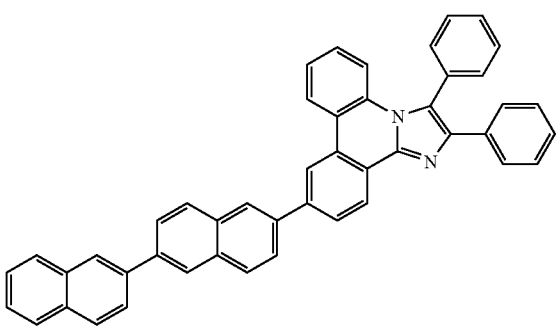
[2-a-37]
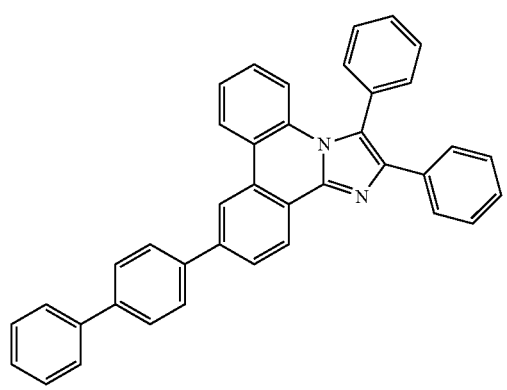
[2-a-38]
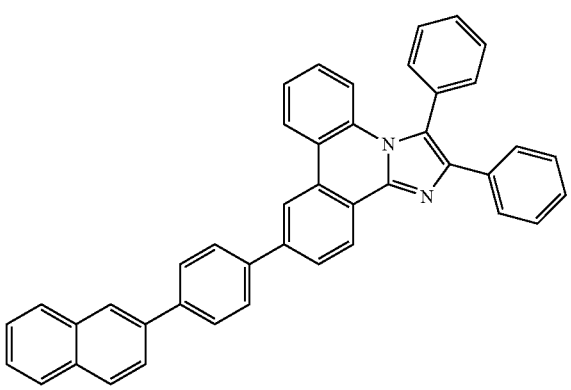

-continued
[2-a-39]
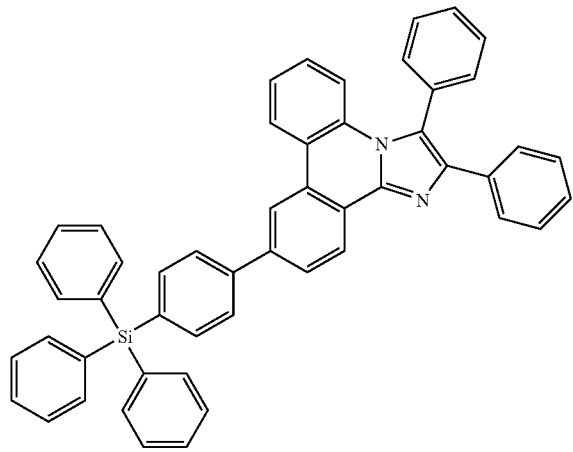
[2-a-40]
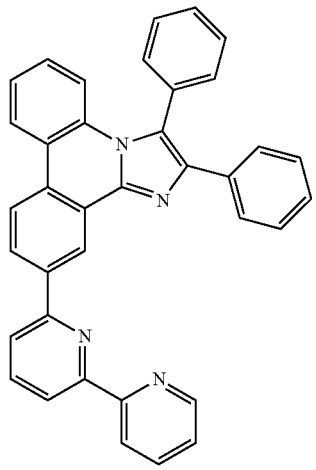
[2-a-41]
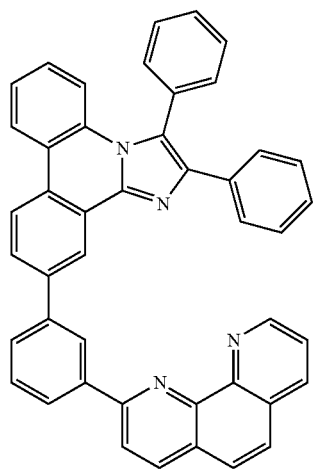
[2-a-42]
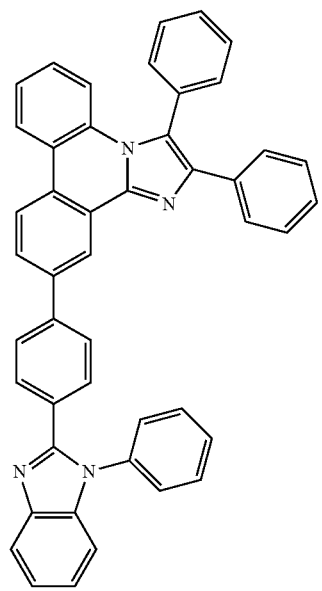
[2-a-43]
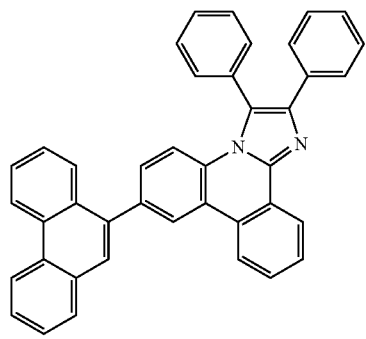
[2-a-44]
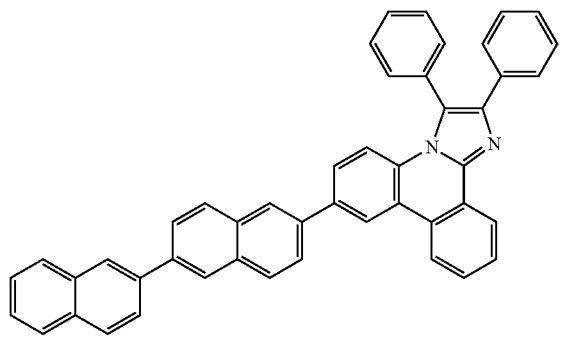

[2-a-45]
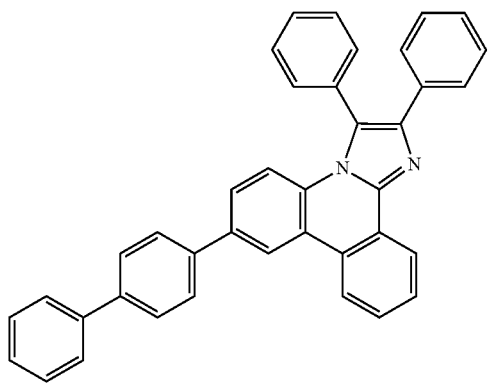
[2-a-46]
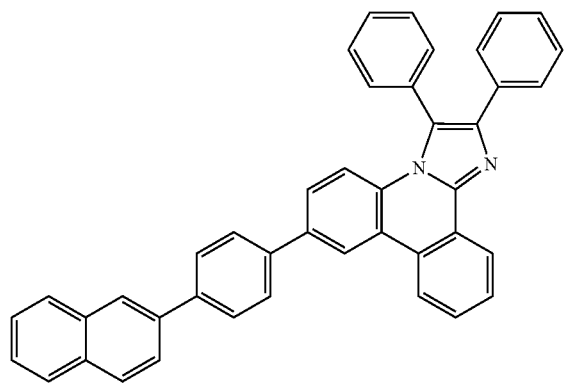
[2-a-47]
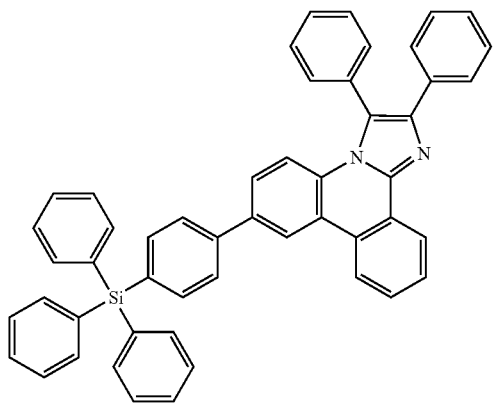
[2-a-48]
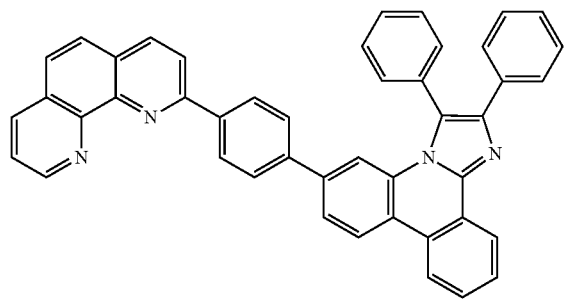
[2-a-49]
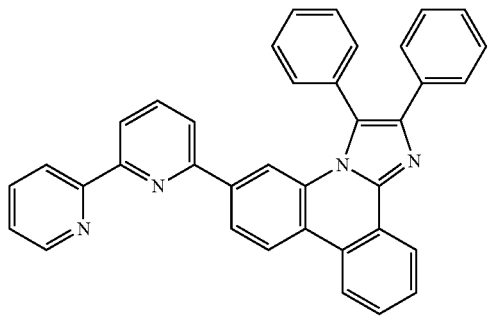
[2-a-50]
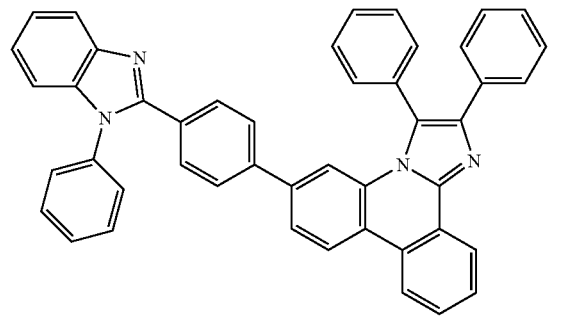
[2-a-51]
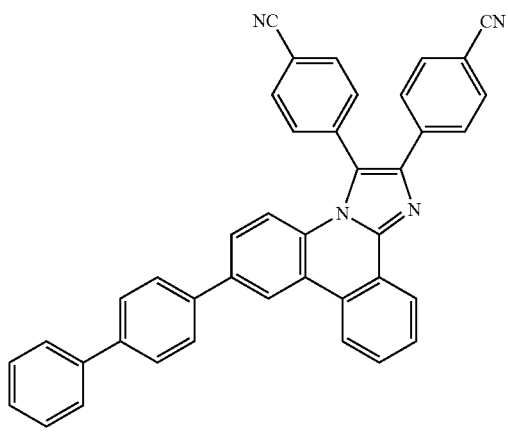
[2-a-52]
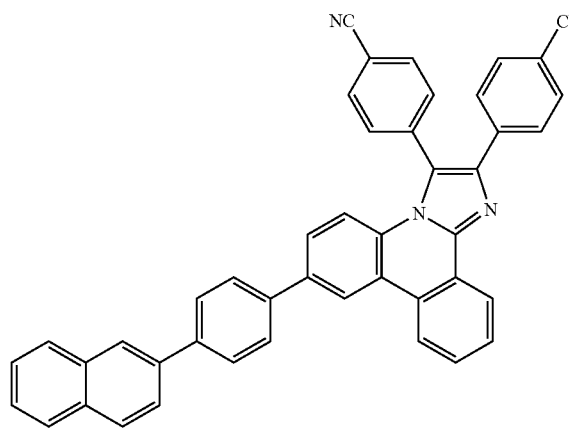

[2-a-53]
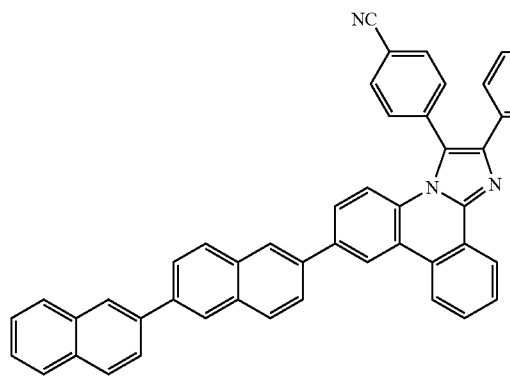
[2-a-54]
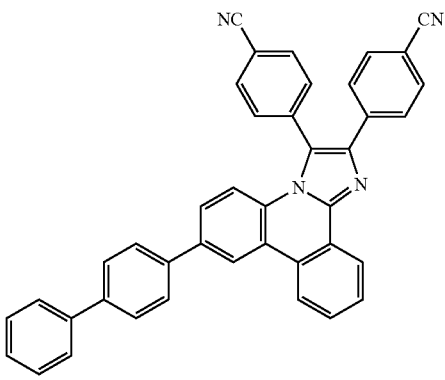
[2-a-55]
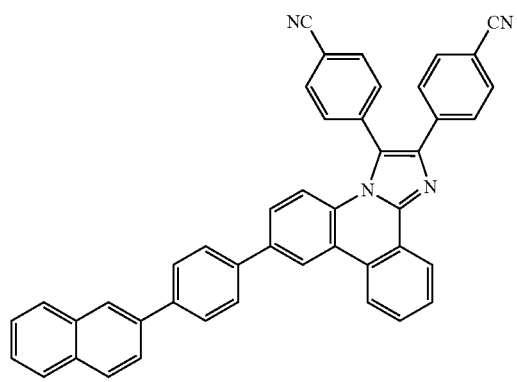
[2-a-56]
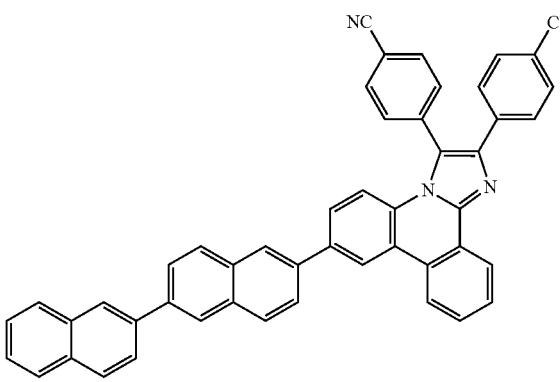
[2-a-57]
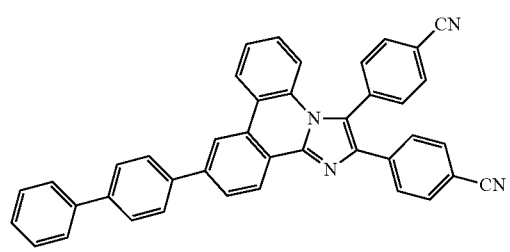
[2-a-58]
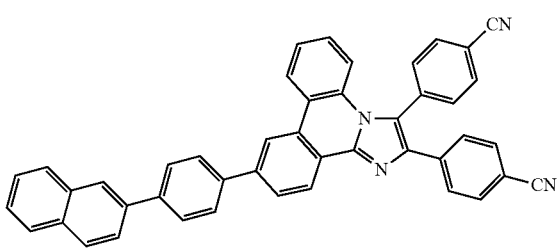
[2-a-59]
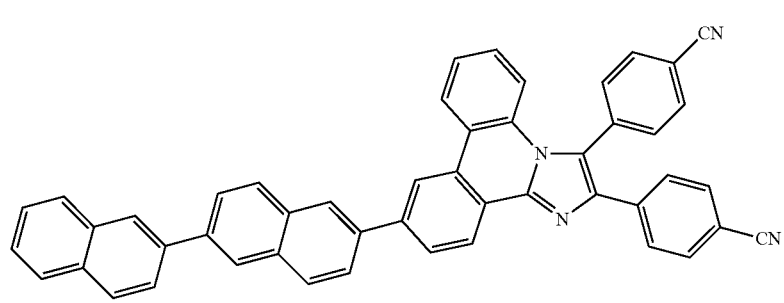

[2-a-60]
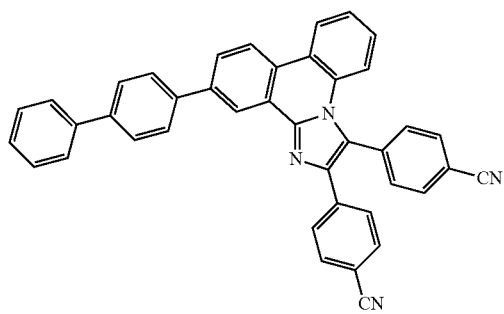
[2-a-61]
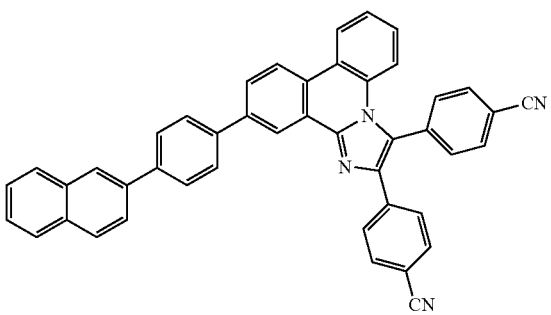
[2-a-62]
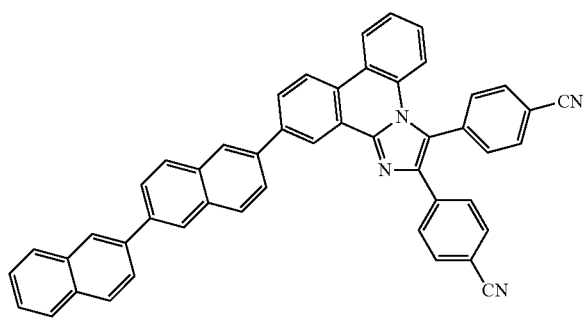
[2-a-63]
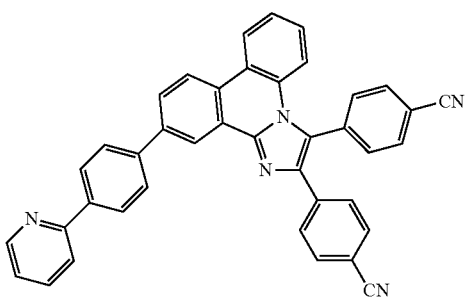
[2-a-64]
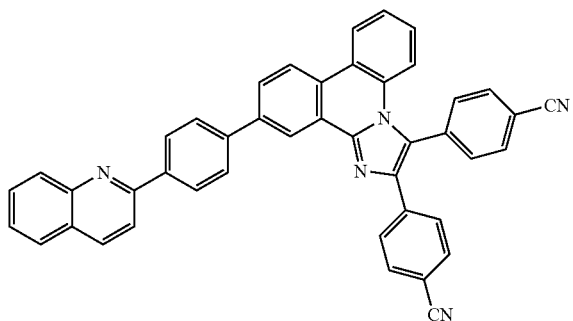
[2-a-65]
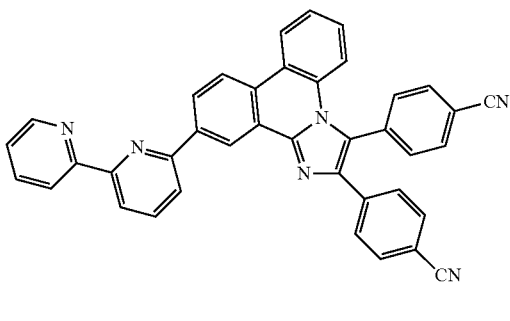
As preferable detailed examples of the compound that is represented by Formula 1, there are the following compounds, but they are not limited thereto.
[2-b-1]
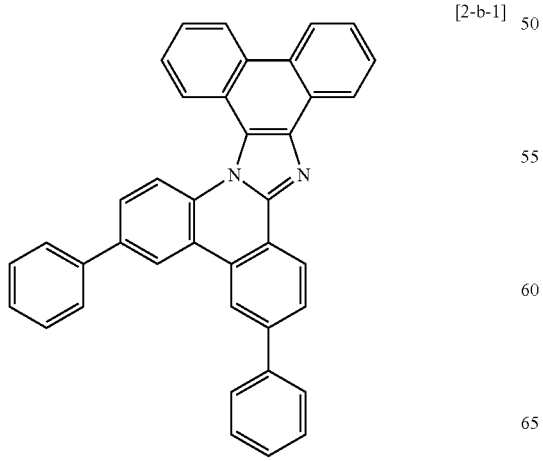
[2-b-2]
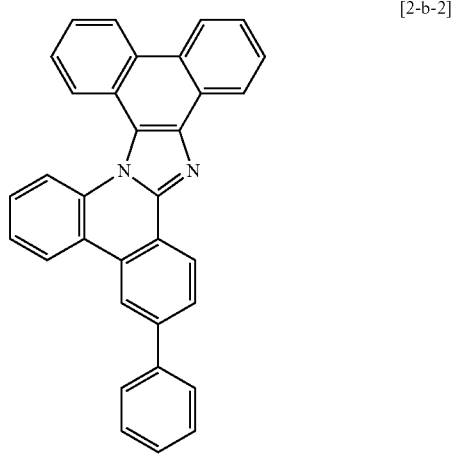

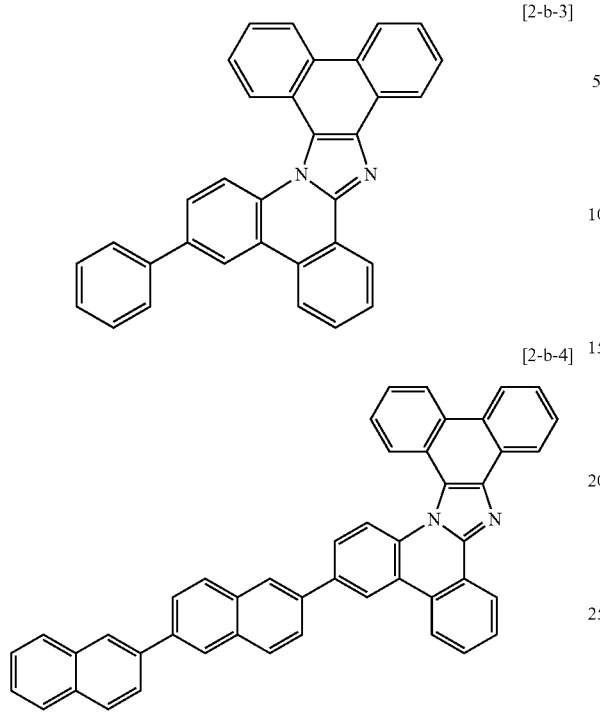
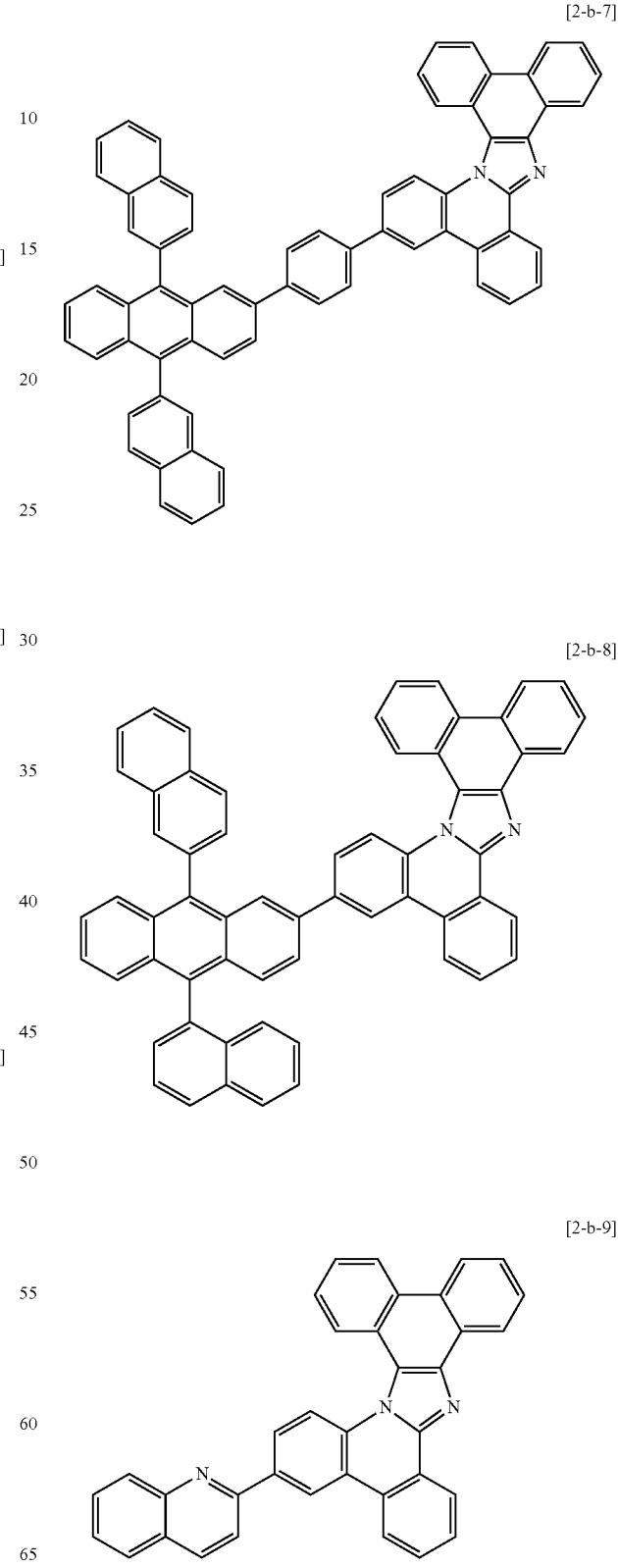

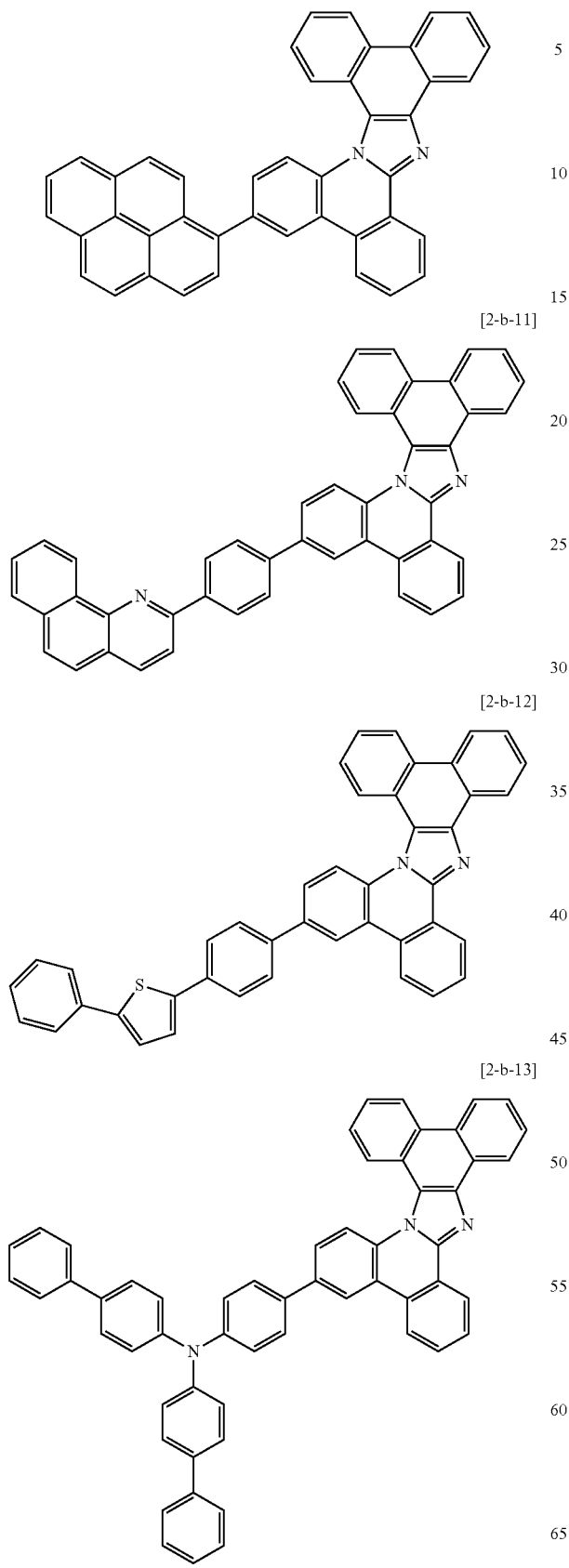

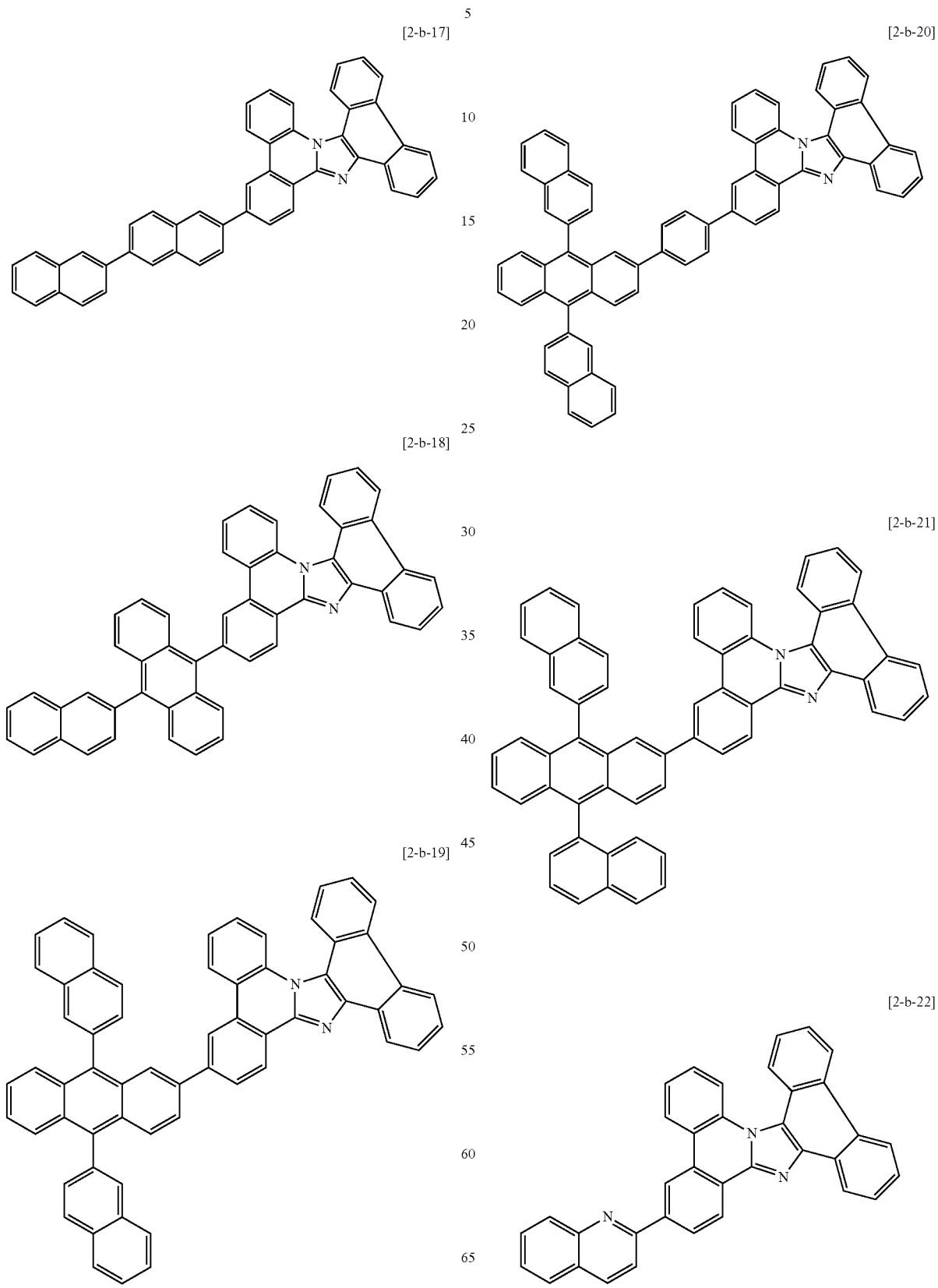

[2-b-23]
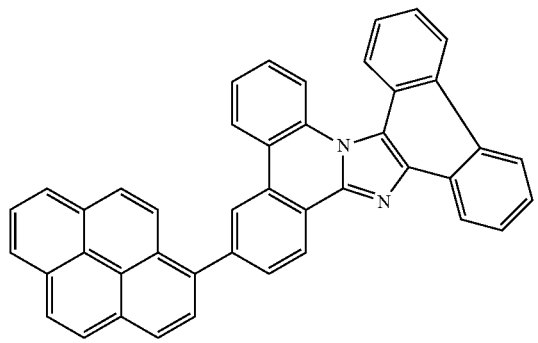
[2-b-24]
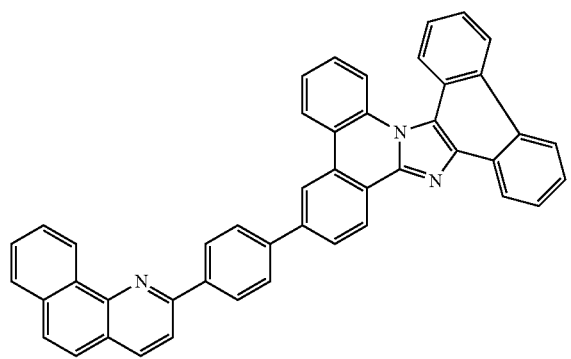
[2-b-25]
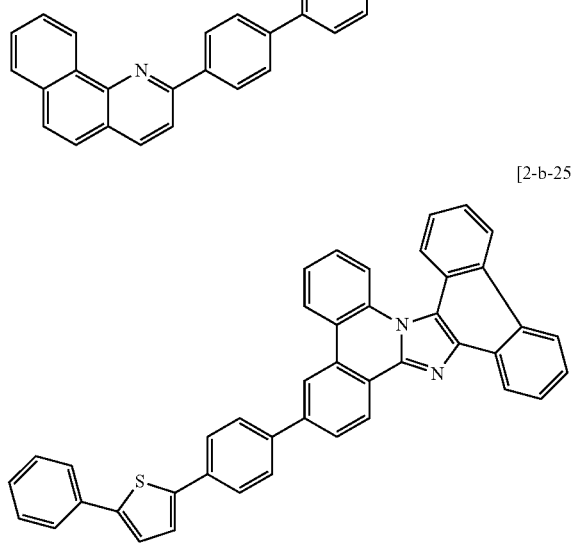
[2-b-26]
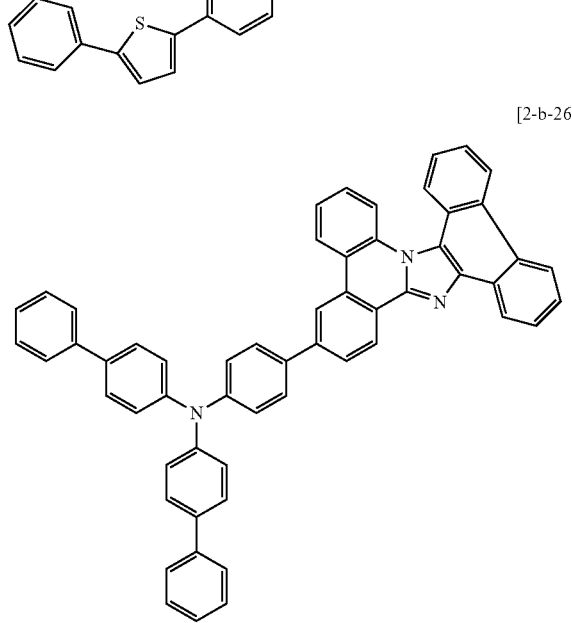
[2-b-27]
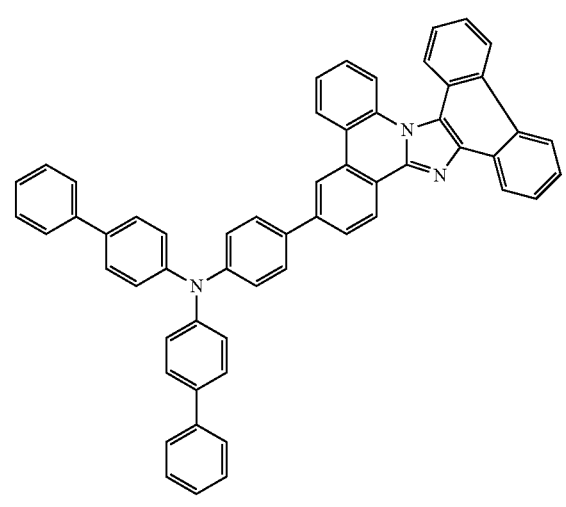
[2-b-28]
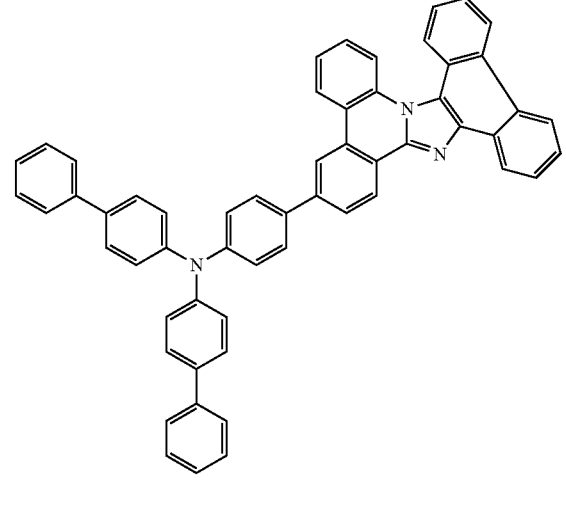
[2-b-29]

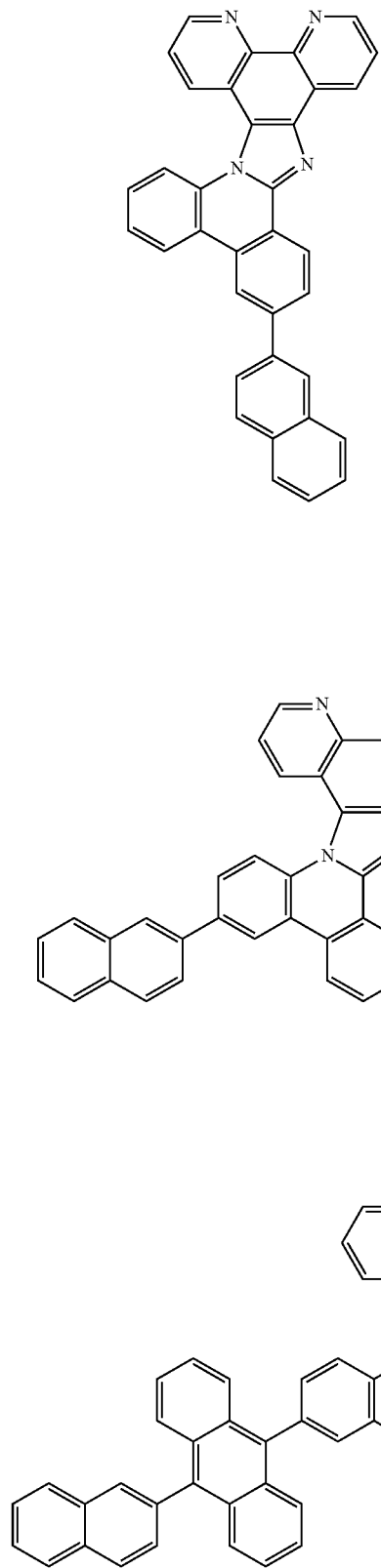
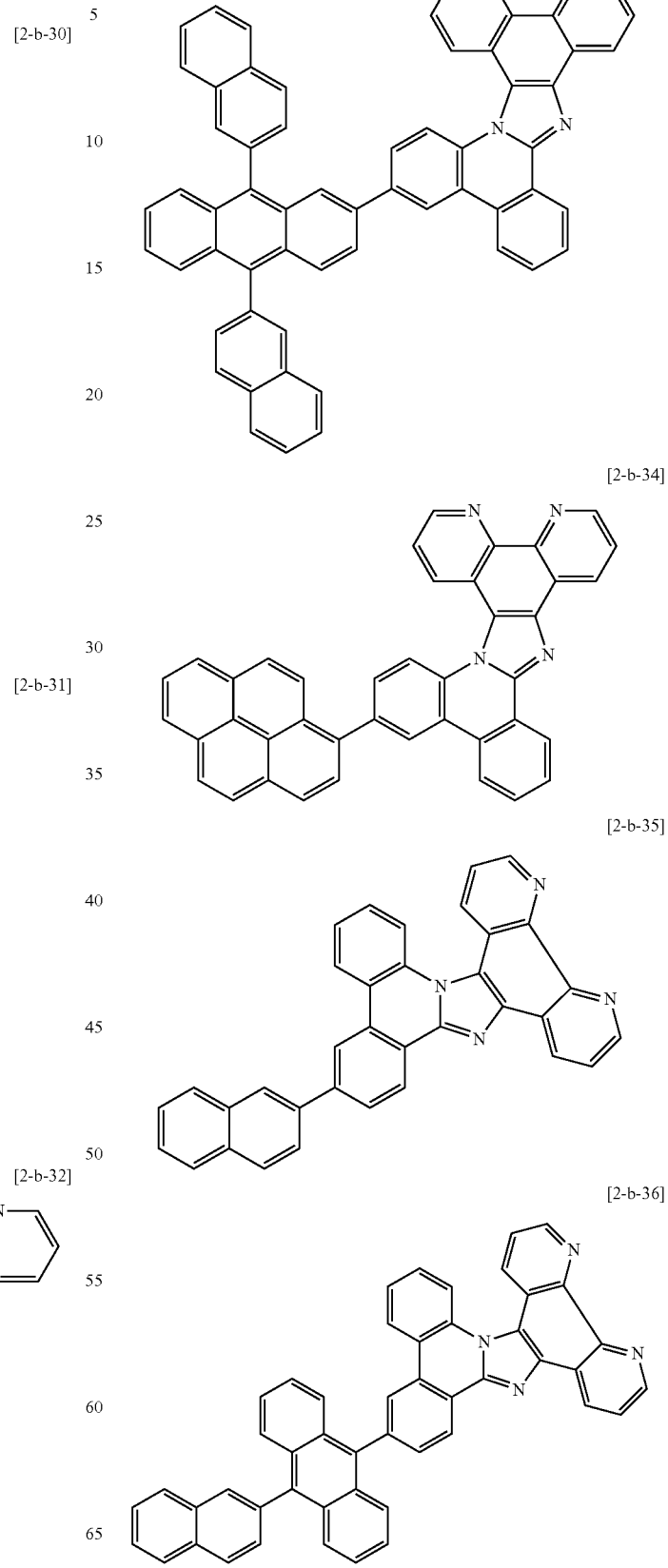

[2-b-37]
[2-b-38]
[2-b-39]
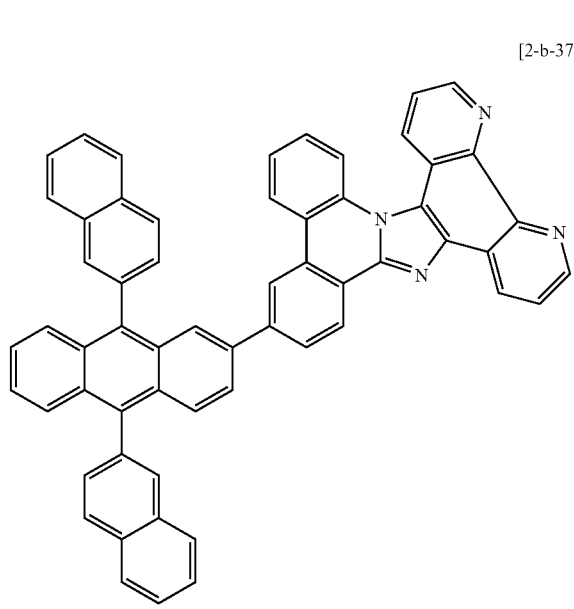
[2-b-40]
[2-b-41]
[2-b-42]
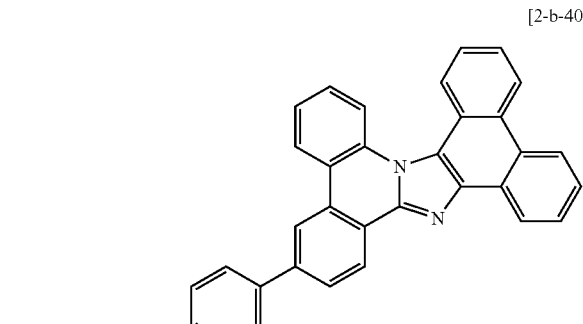
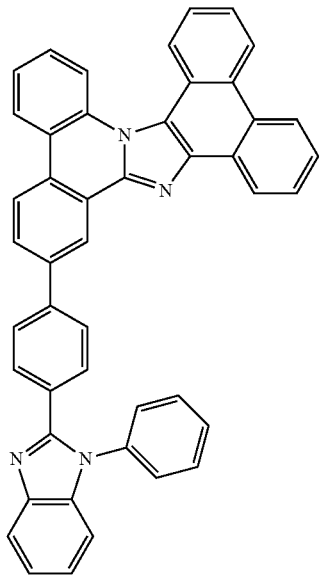

[2-b-43]
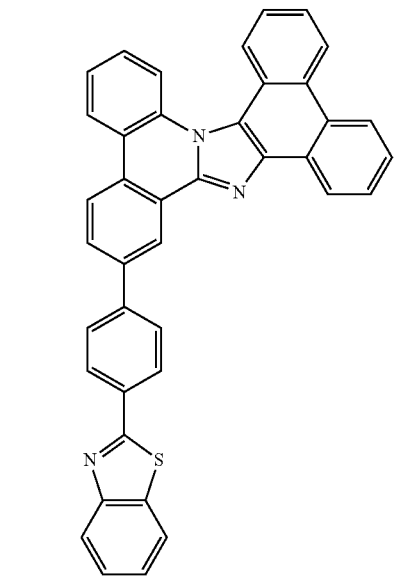
[2-b-44]
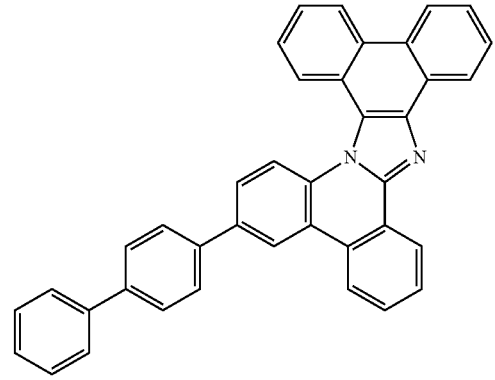
[2-b-45]
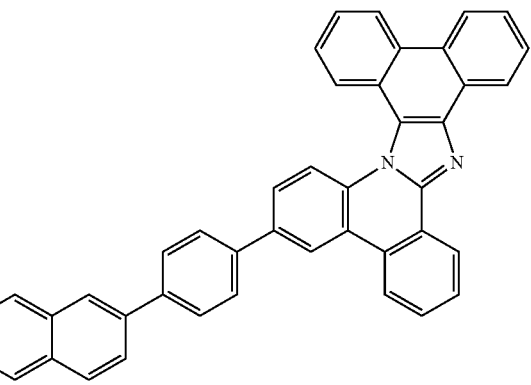
[2-b-46]
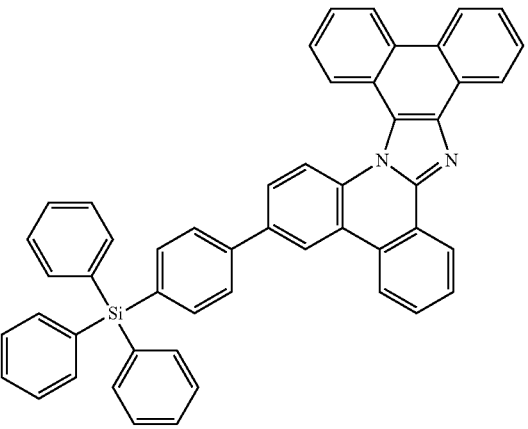
[2-b-47]
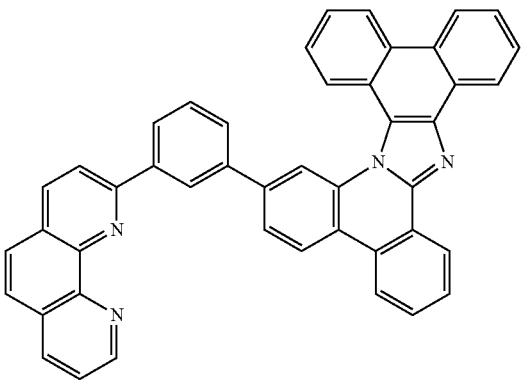
[2-b-48]
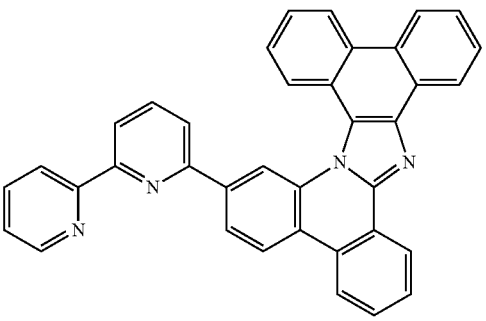
[2-b-49]
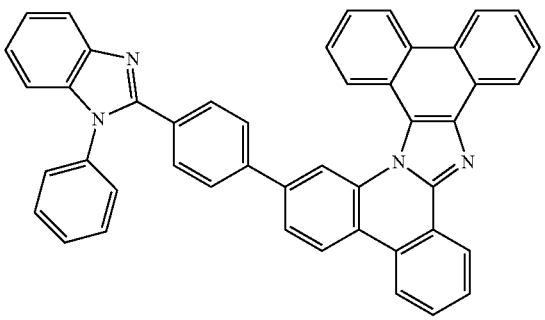

[2-b-50]
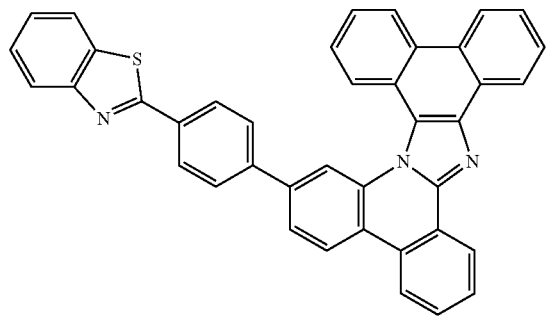
[3-a-4]
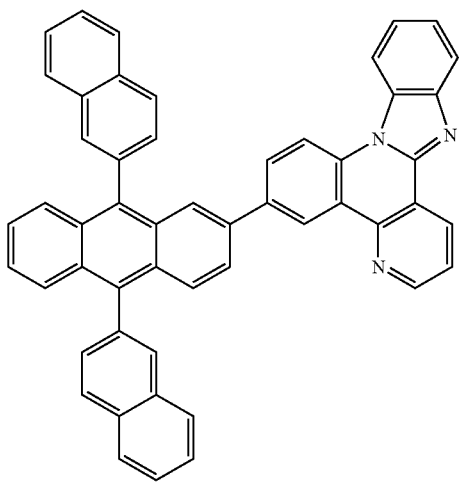
As preferable detailed examples of the compound that is represented by Formula 1, there are the following compounds, but they are not limited thereto.
[3-a-1]
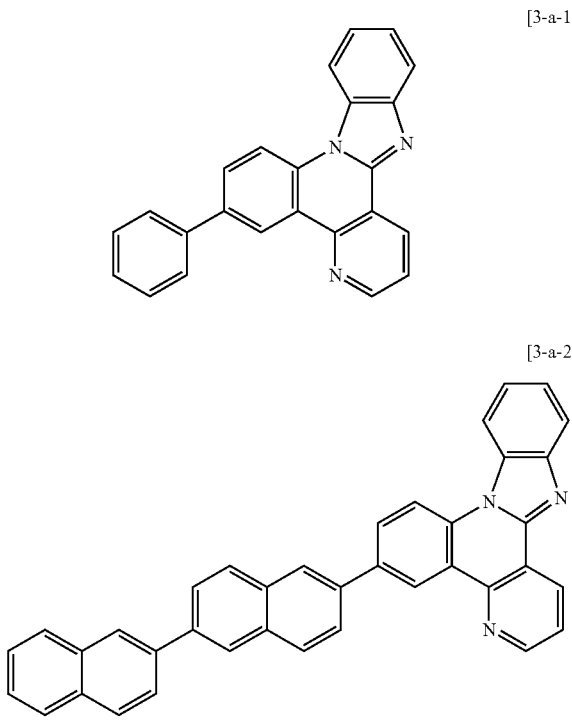
[3-a-5]
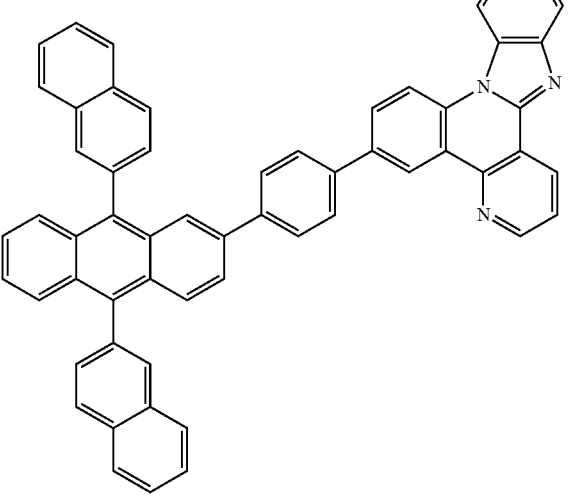
[3-a-2]
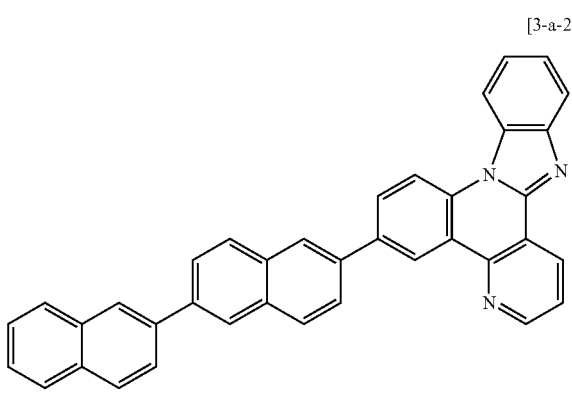
[3-a-3]
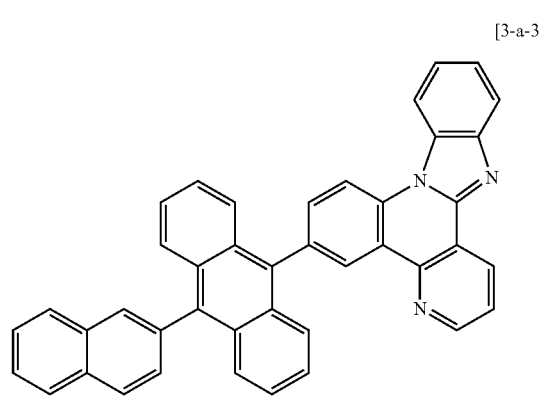
[3-a-6]
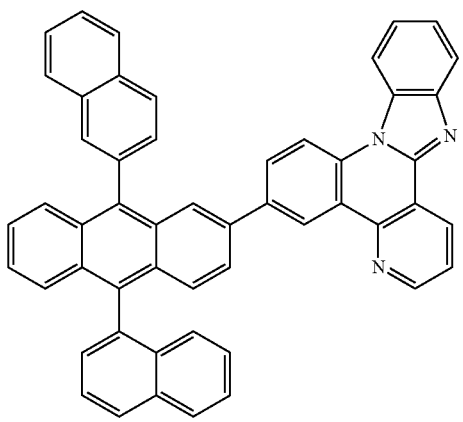

-continued
[3-a-7]
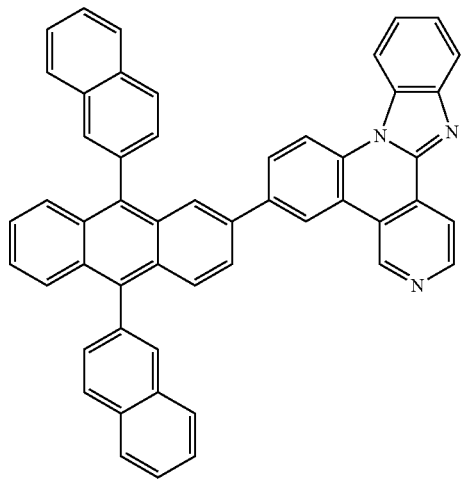
[3-a-8]
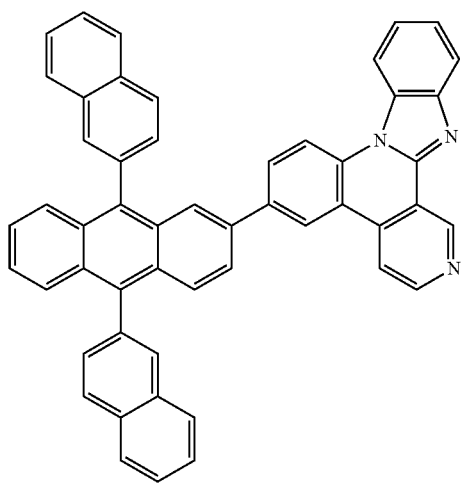
[3-a-9]
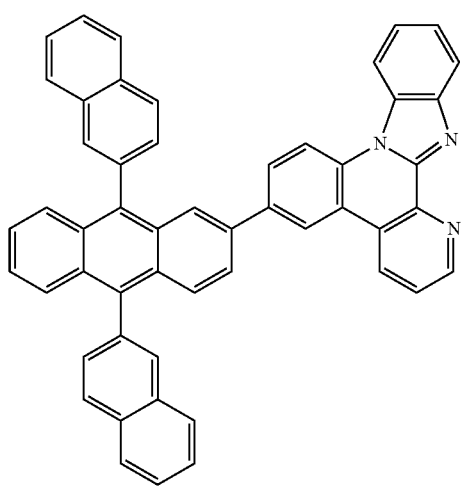
-continued
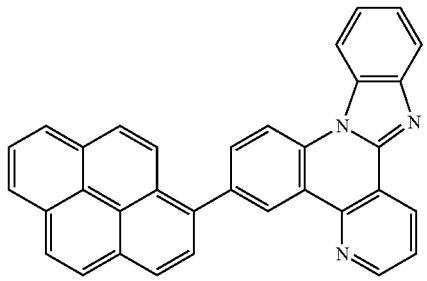
[3-a-10]
[3-a-11]
[3-a-12]
[3-a-13]

[3-a-14]
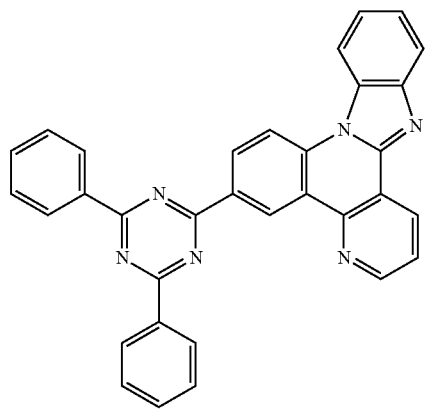
[3-a-15]
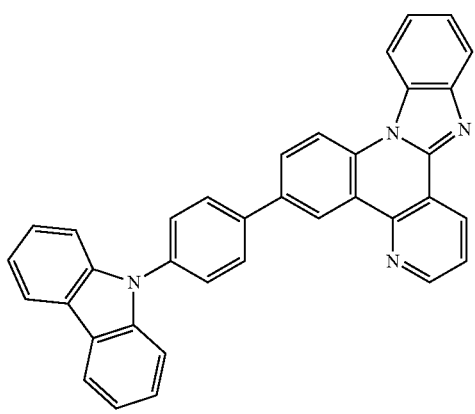
[3-a-16]
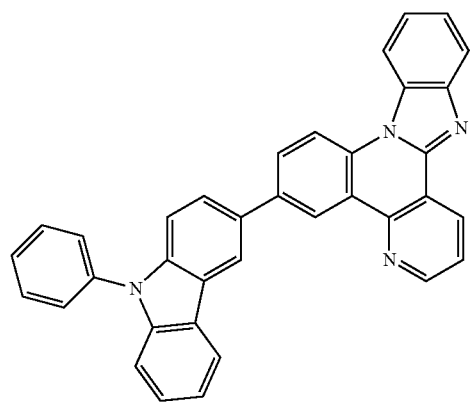
[3-b-1]
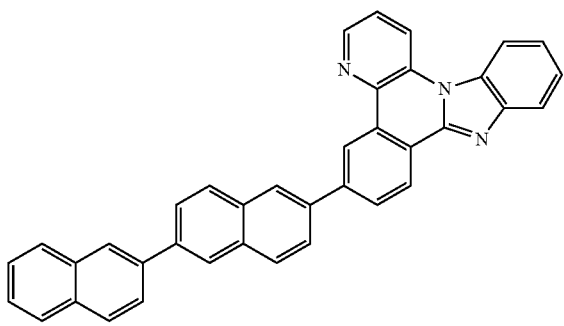
[3-b-2]
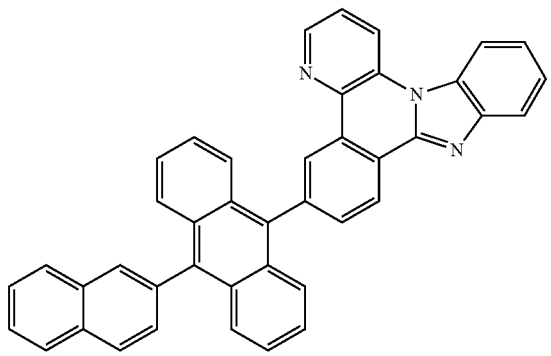
[3-b-3]
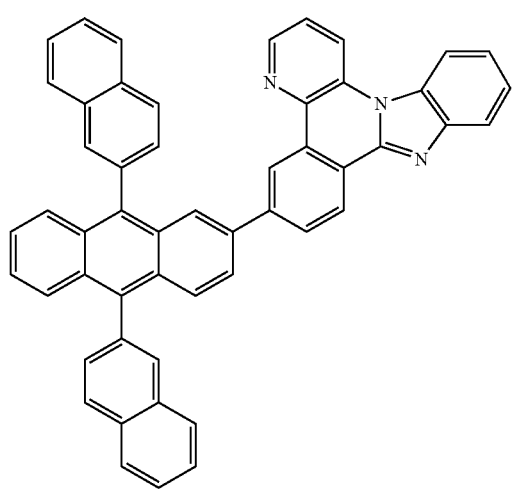
[3-b-4]
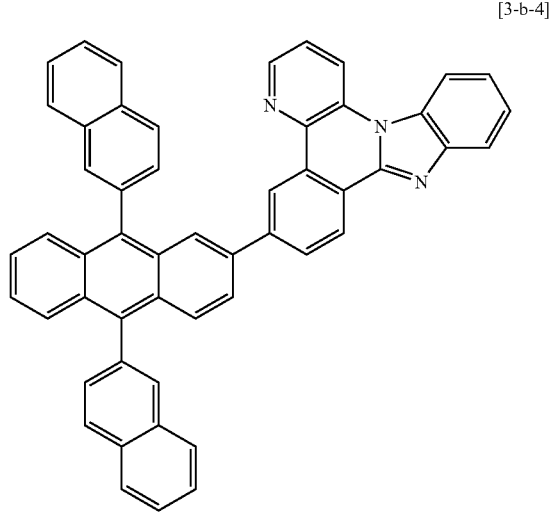

215
-continued
[3-b-5]
[3-b-6]
[3-b-7]
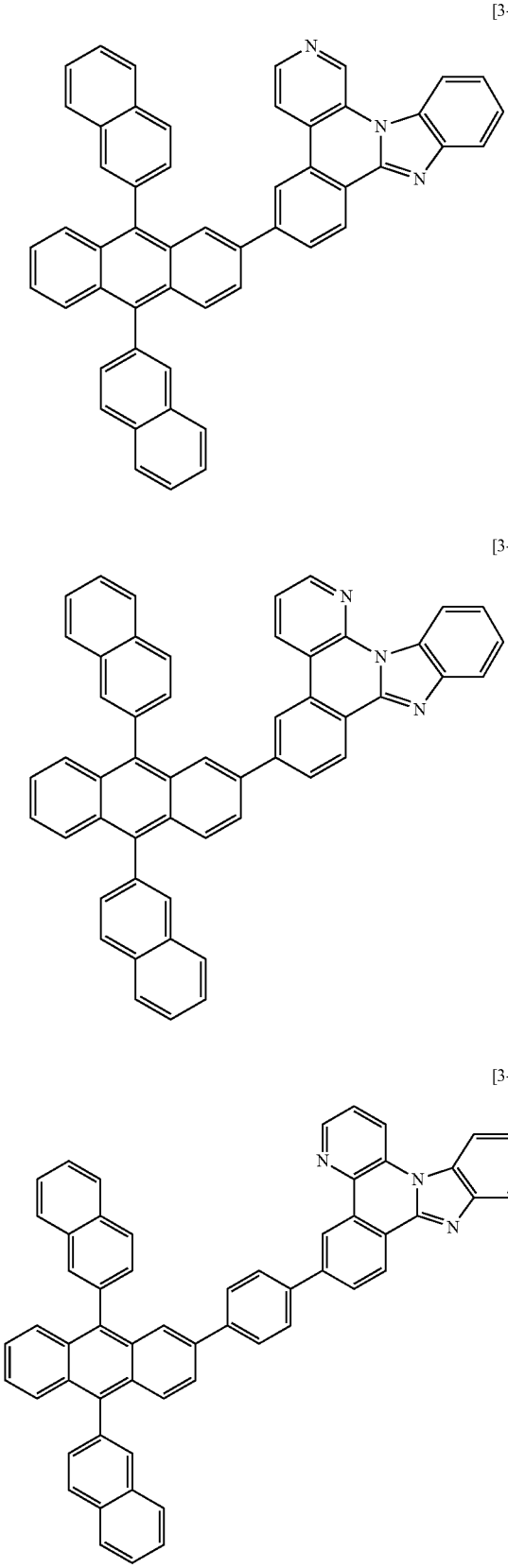
216
-continued
[3-b-8]
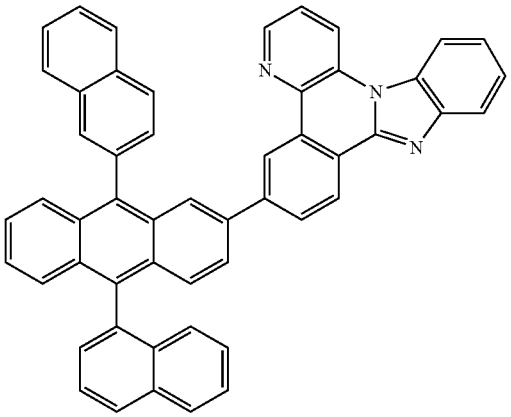
[3-b-9]
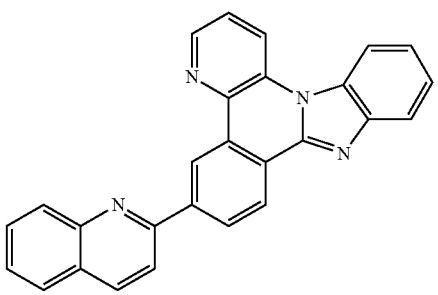
[3-b-10]
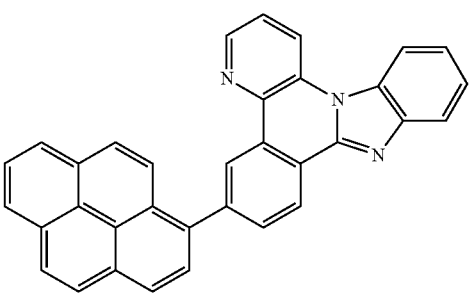
[3-b-11]
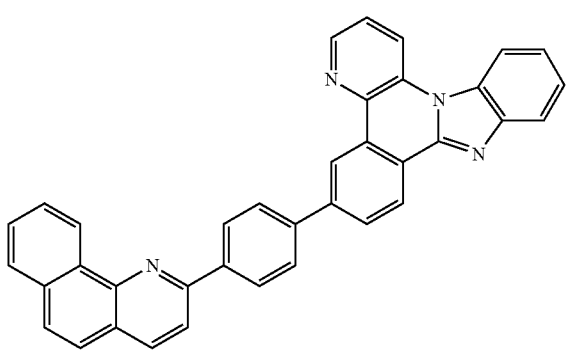

[3-b-12]
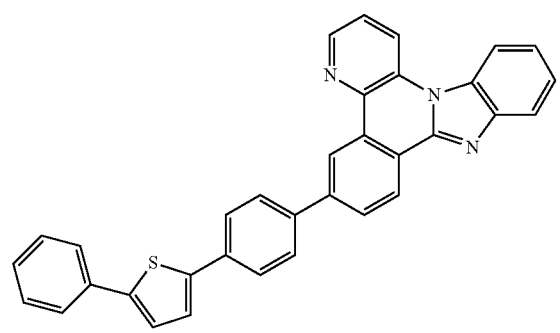
[3-b-13]
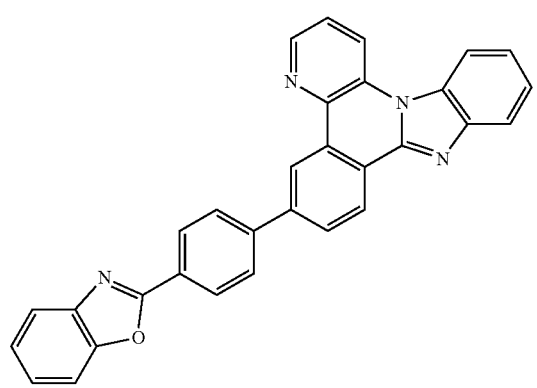
[3-c-1]
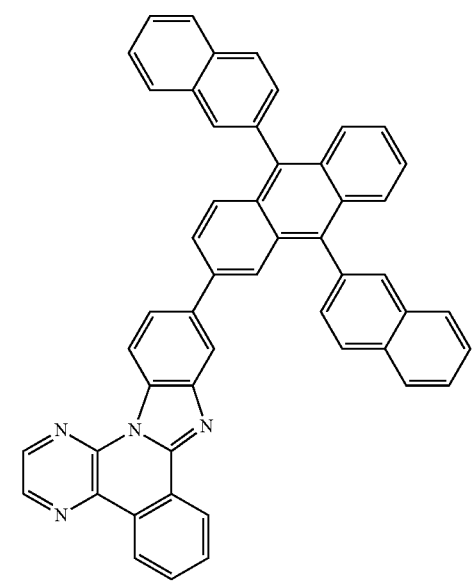
[3-c-2]
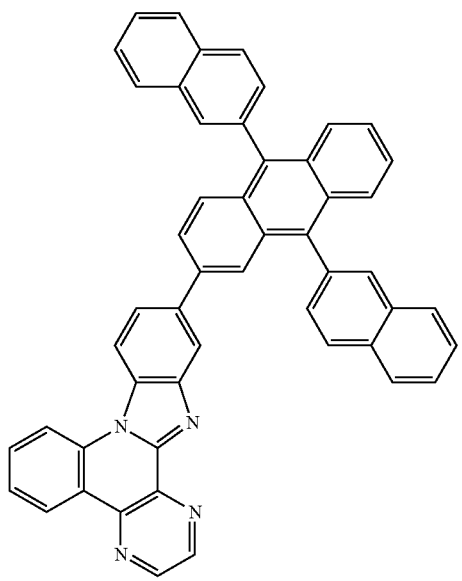
[3-c-3]
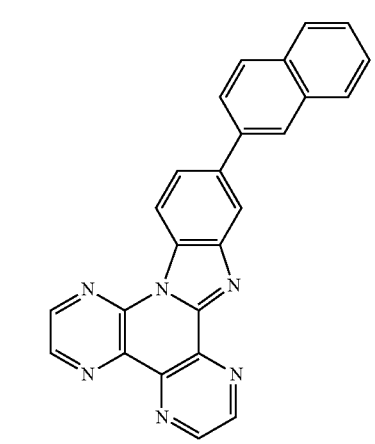
[3-c-4]
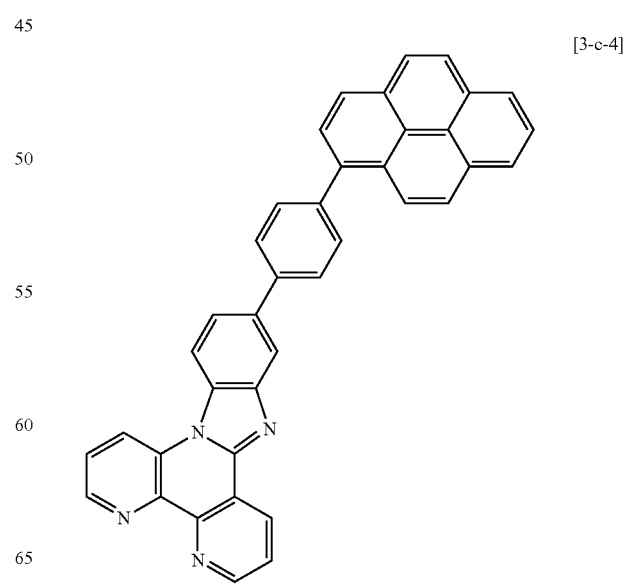

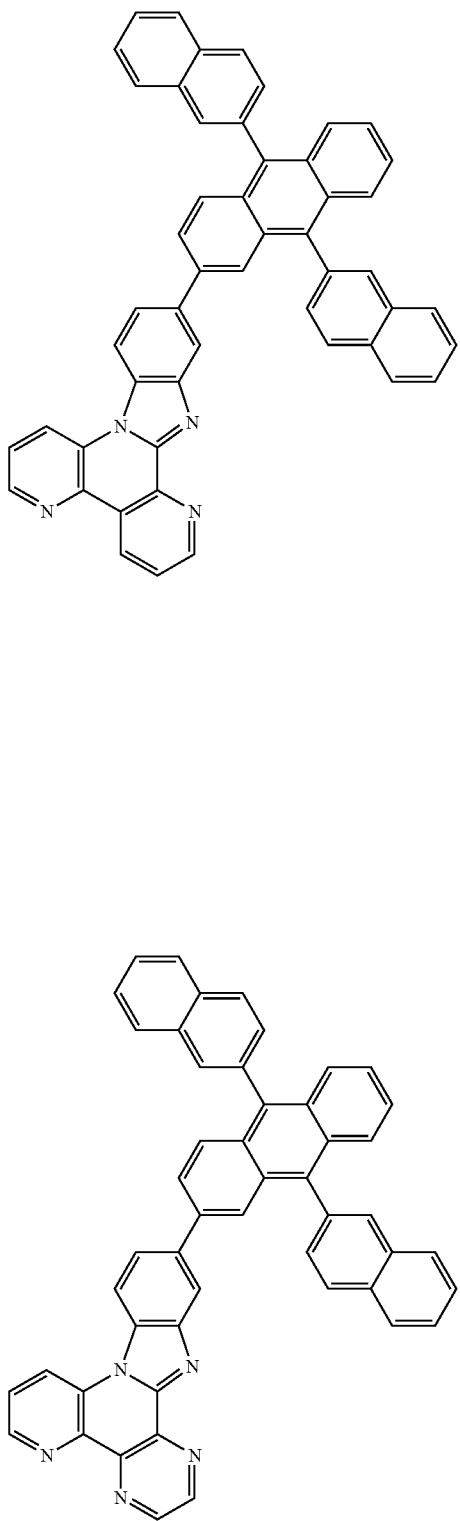
[3-c-5]
[3-c-6]
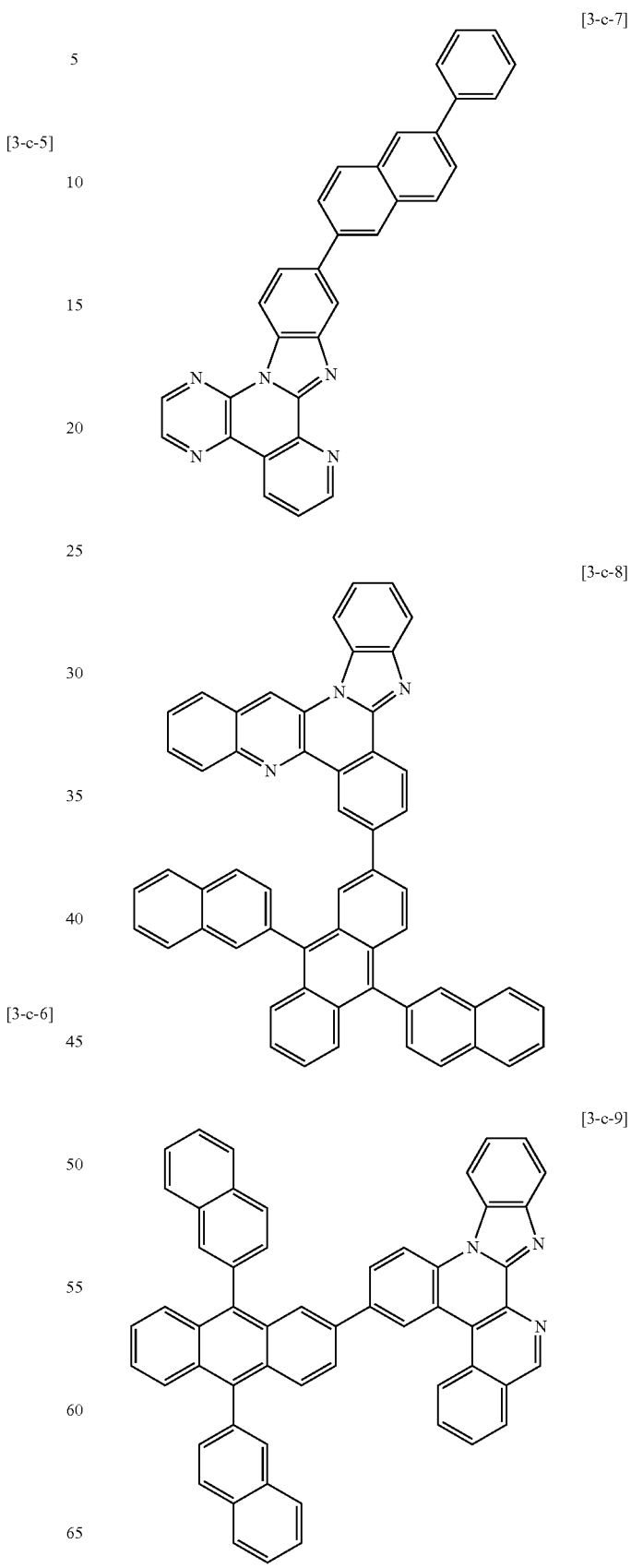
[3-c-7]
[3-c-8]
[3-c-9]

[3-c-10]
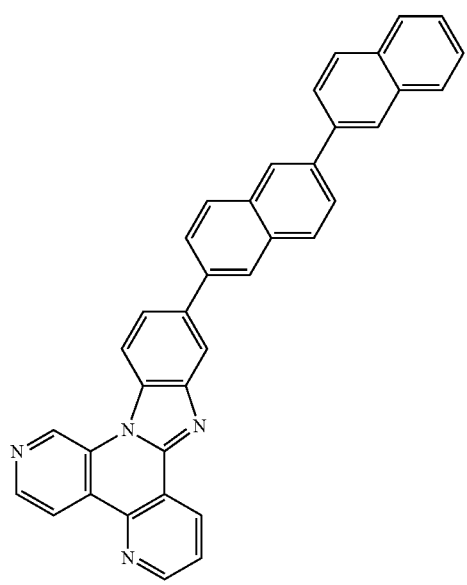
[3-c-11]
[3-c-12]
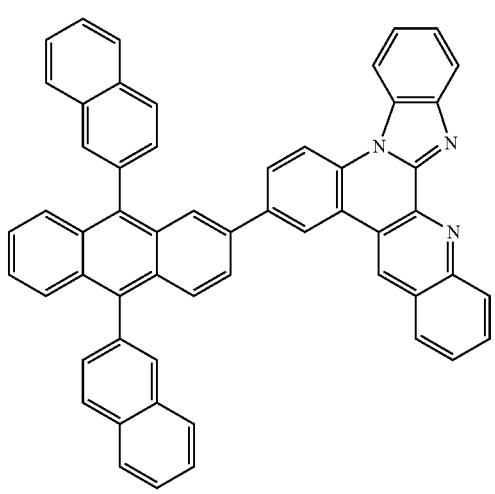
[3-c-13]
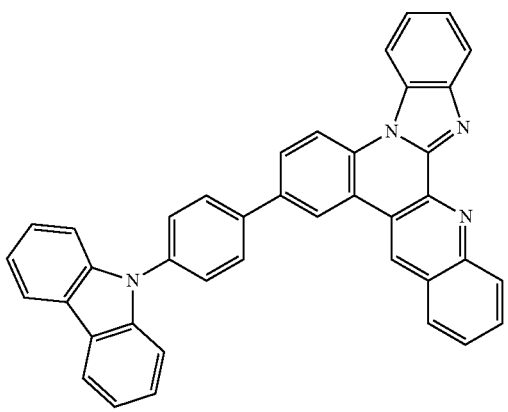
[3-c-14]
[3-c-15]
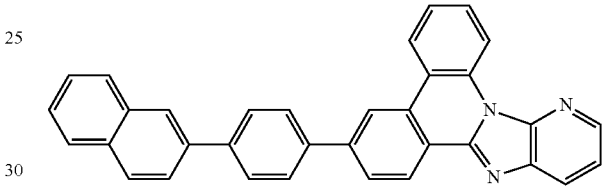
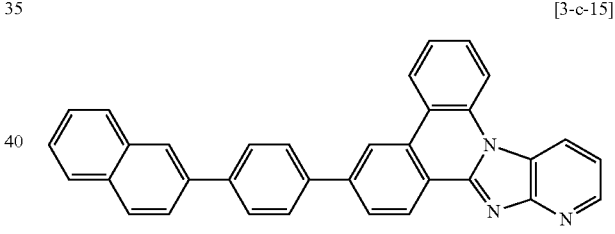
[3-c-16]

-continued
[3-c-17]
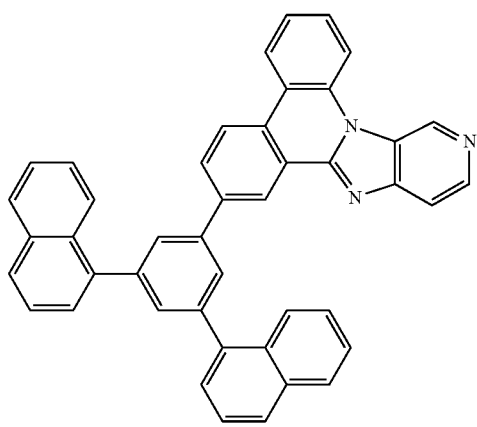
[3-c-18]
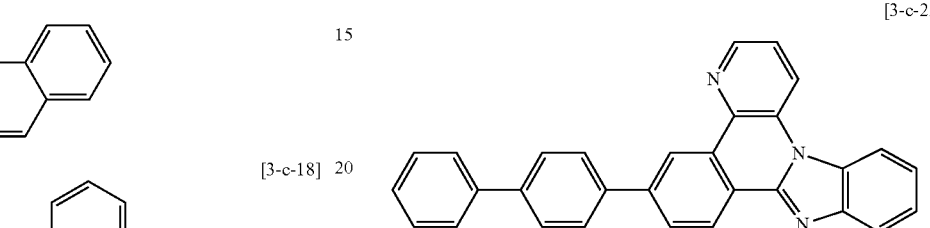
[3-c-19]
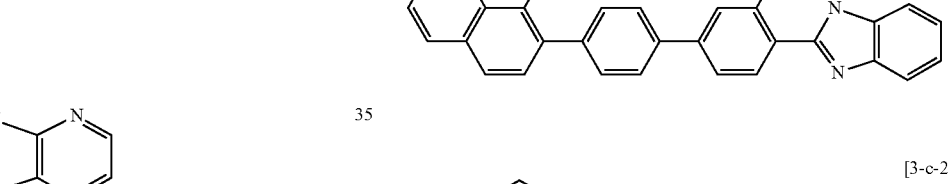
[3-c-20]
-continued
[3-c-21]
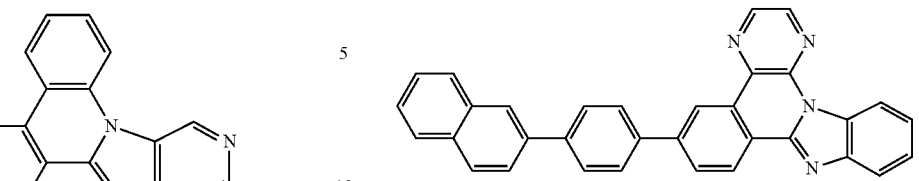
[3-c-22]

[3-c-23]
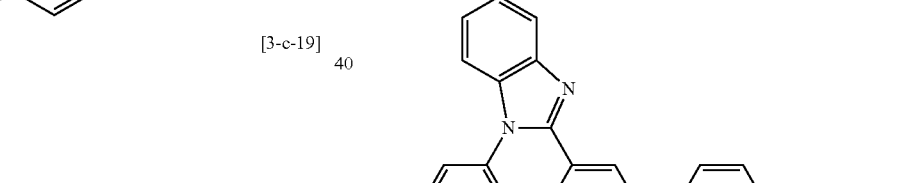
[3-c-24]
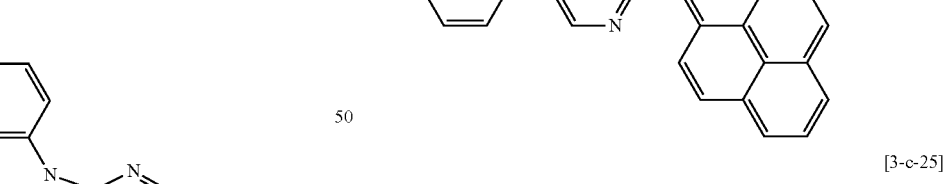
[3-c-25]
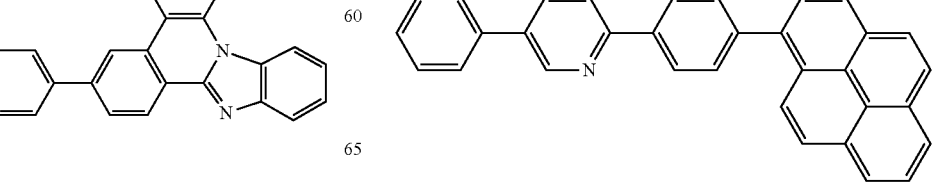

-continued
[3-c-26]
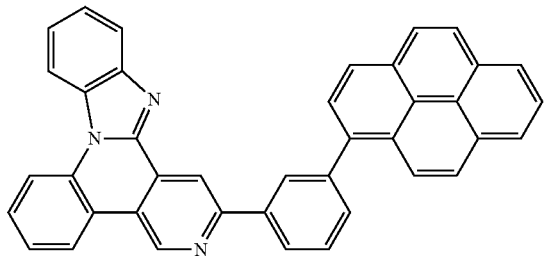
[3-c-27]
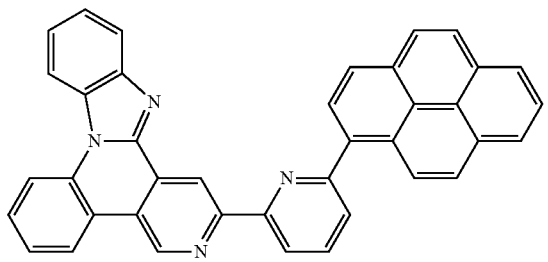
[3-c-28]
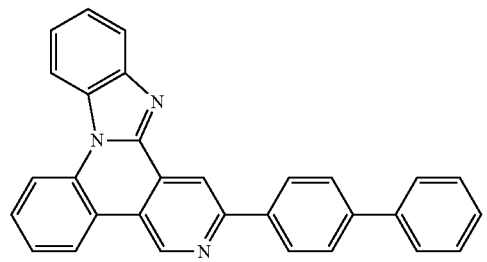
[3-c-29]
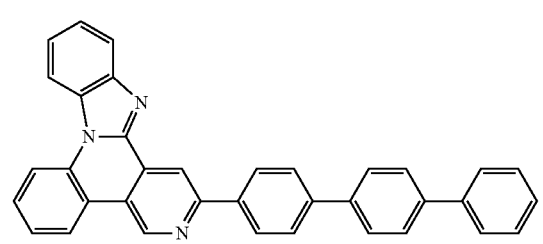
[3-c-30]
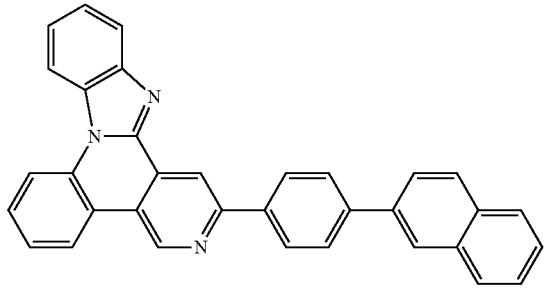
-continued
[3-c-31]
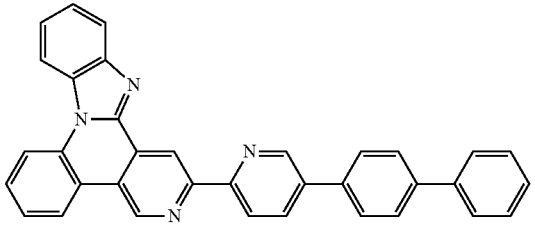
[3-c-32]
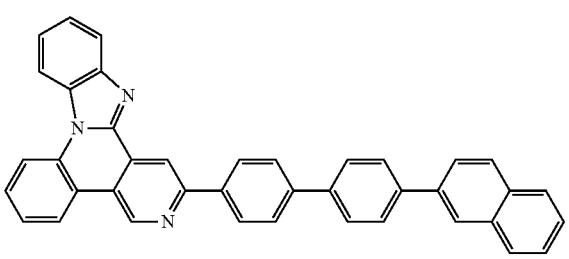
[3-c-33]
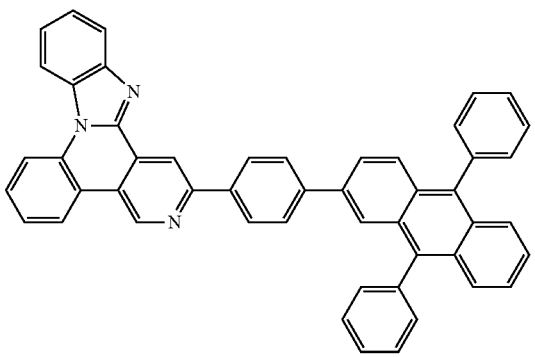
[3-c-34]
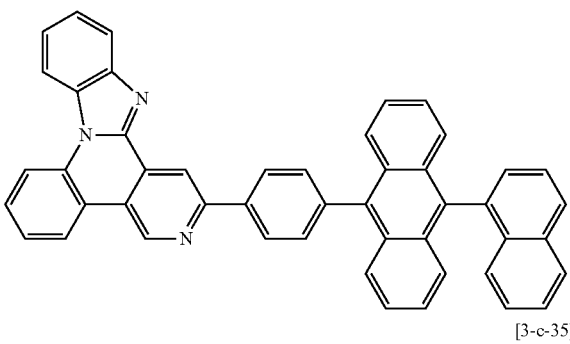
[3-c-35]
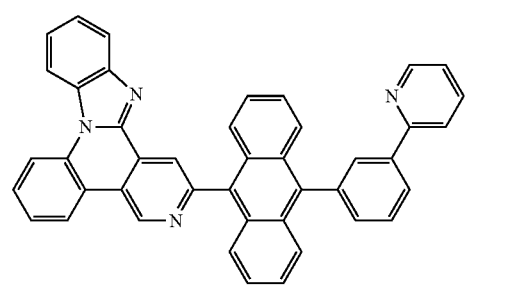

As preferable detailed examples of the compound that is represented by Formula 1, there are the following compounds, but they are not limited thereto.
[3-c-36]
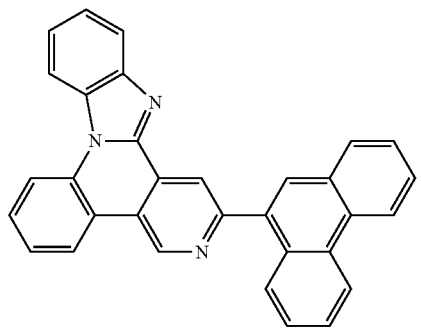
[3-c-37]
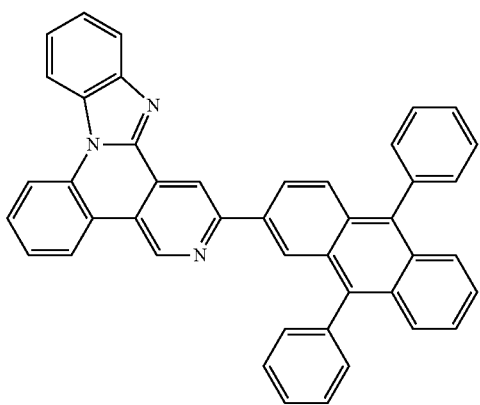
[3-c-38]
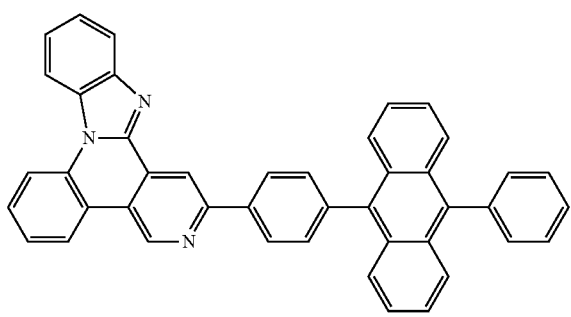
[3-c-39]
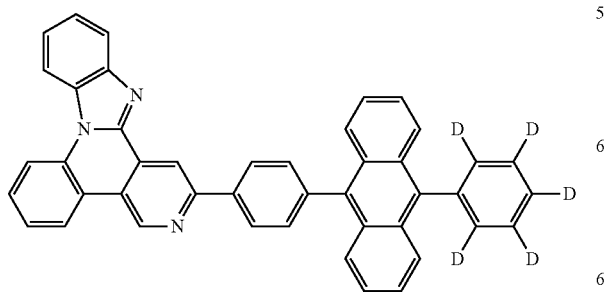
[4-a-1]
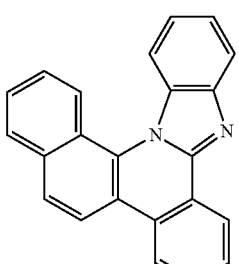
[4-a-2]
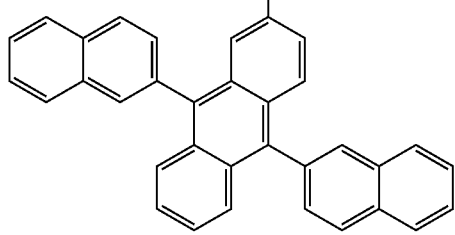
[4-a-3]
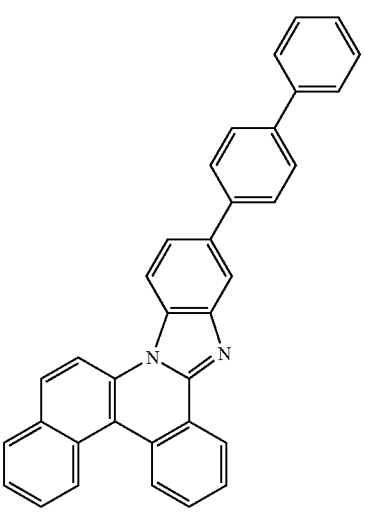

[4-a-4]
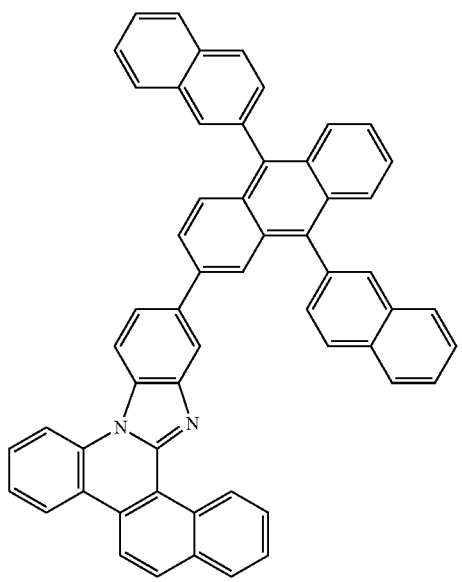
[4-a-5]
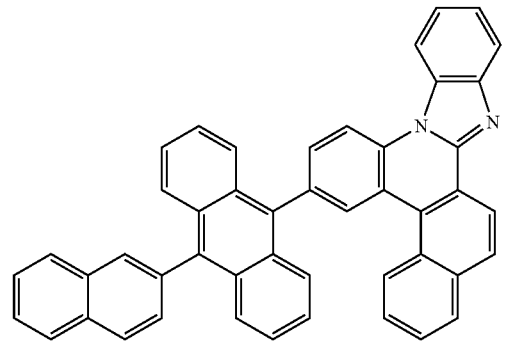
[4-a-6]
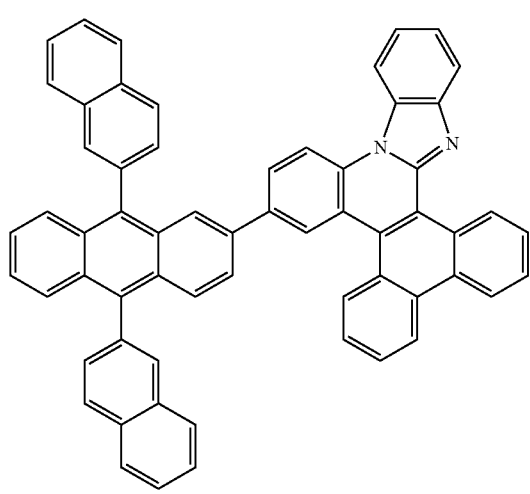
[4-a-7]
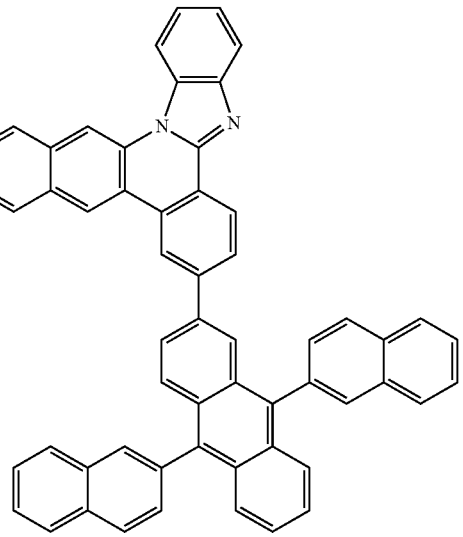
[4-a-8]
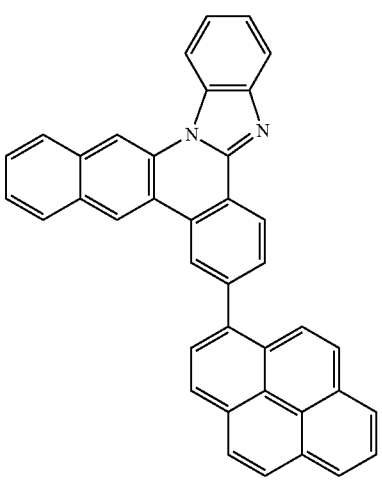
[4-a-9]
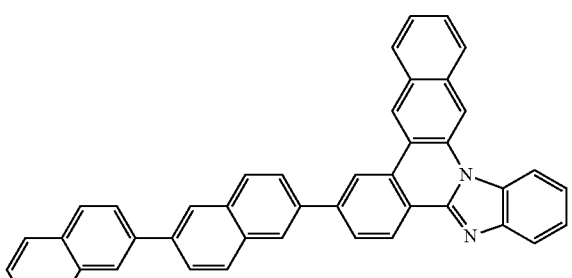
As preferable detailed examples of the compound that is represented by Formula 1, there are the following compounds, but they are not limited thereto.

231  232
[5-a-1]
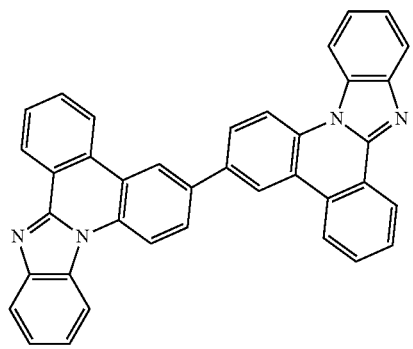
[5-a-2]
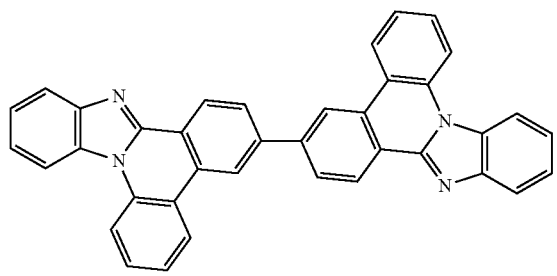
[5-a-3]
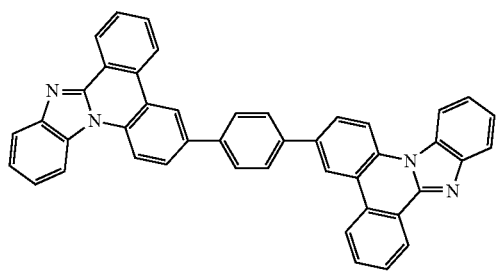
[5-a-4]
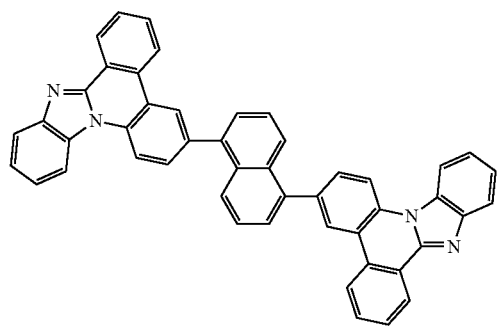
[5-a-5]
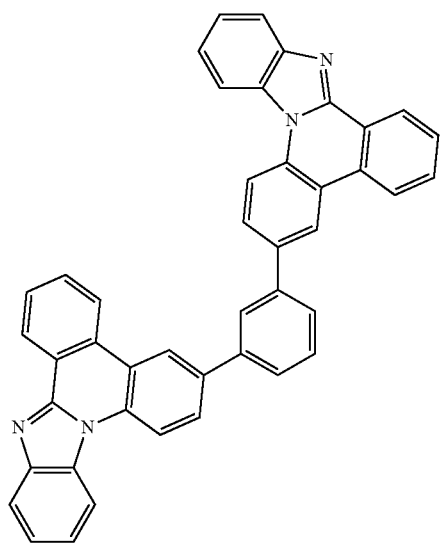
[5-a-6]
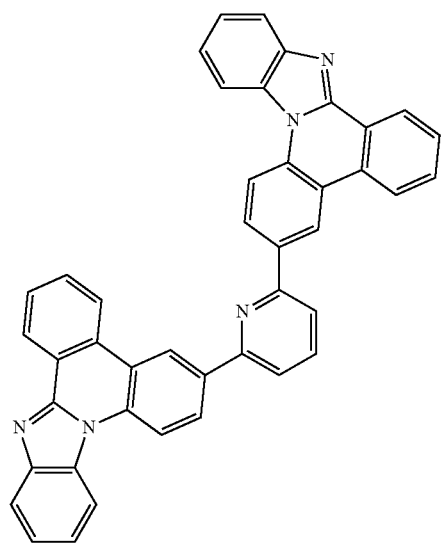
[5-a-7]
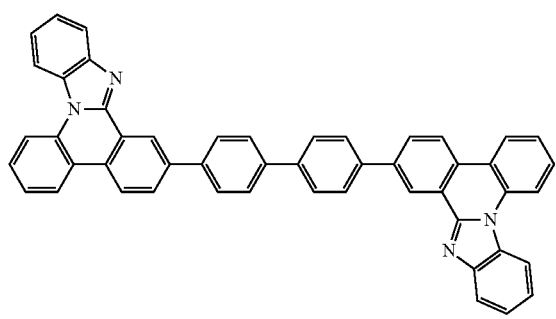
[5-a-8]
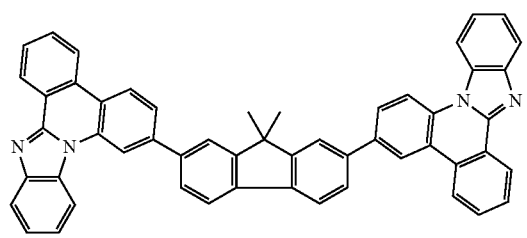

-continued
[5-a-9]
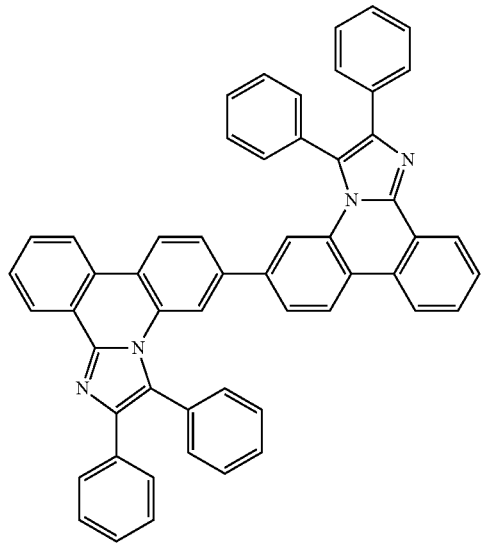
[5-a-10]
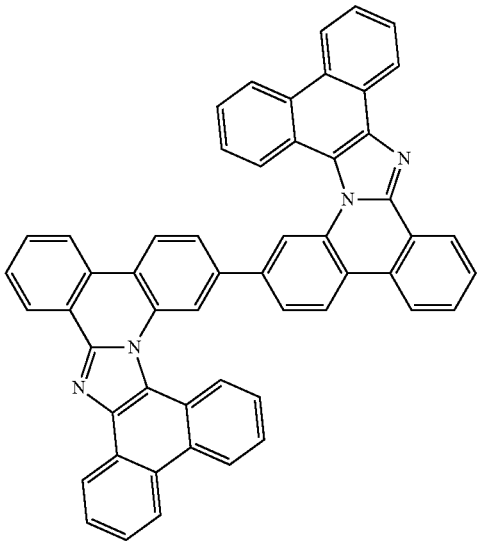
[5-a-11]
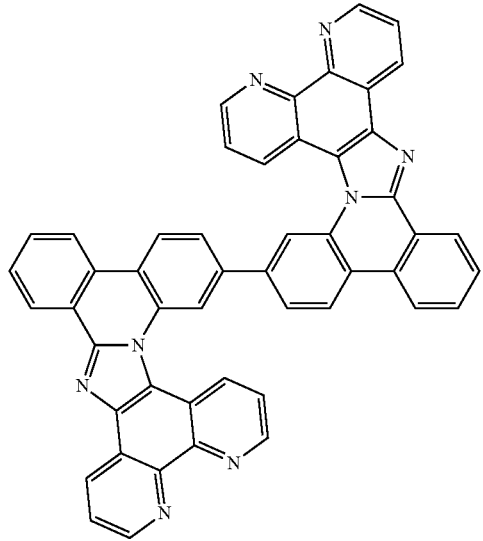
[5-a-12]
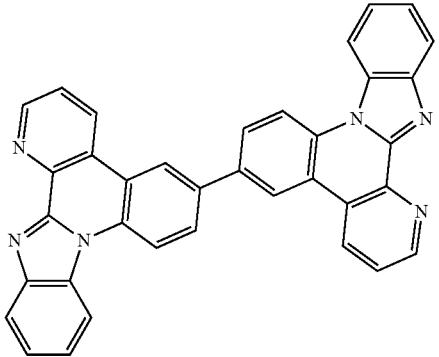
[5-a-13]
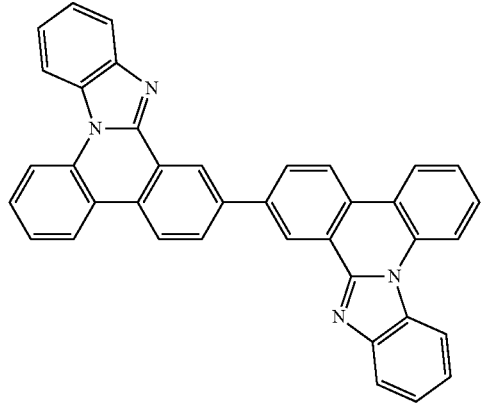
[5-a-14]
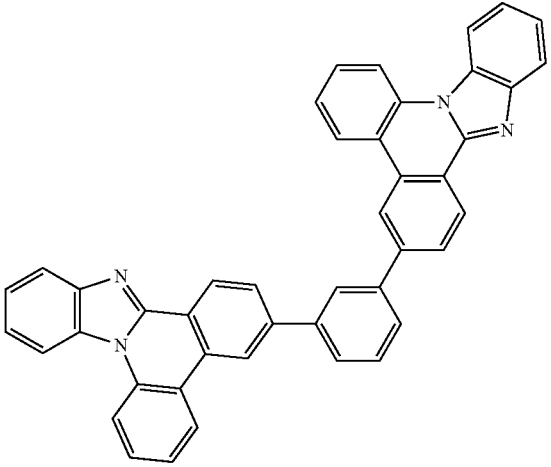

[5-a-15]
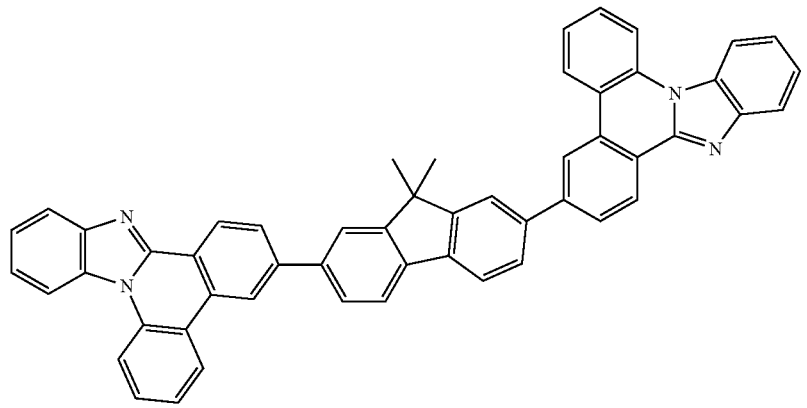
[5-a-16]
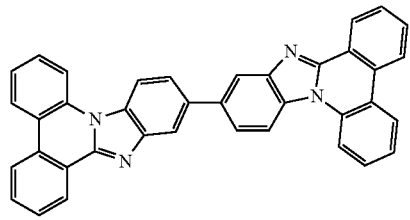
[5-a-17]
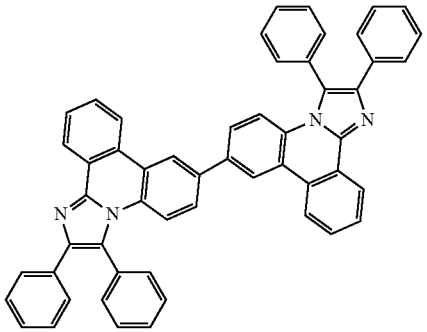
[5-a-18]
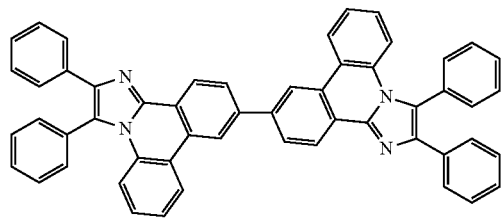
[5-a-19]
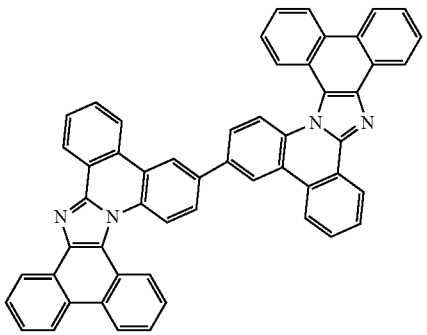
[5-a-20]
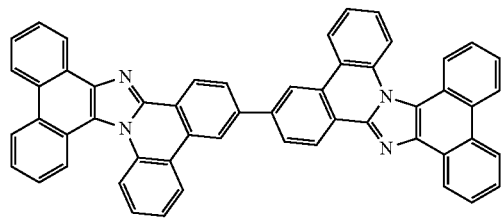
[5-a-21]
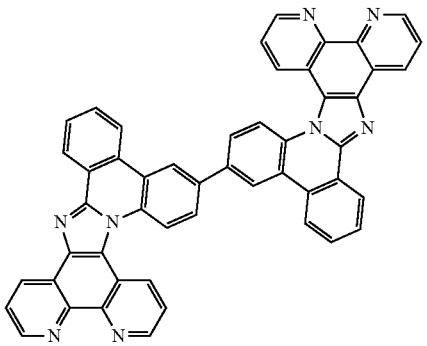

-continued
[5-a-22]
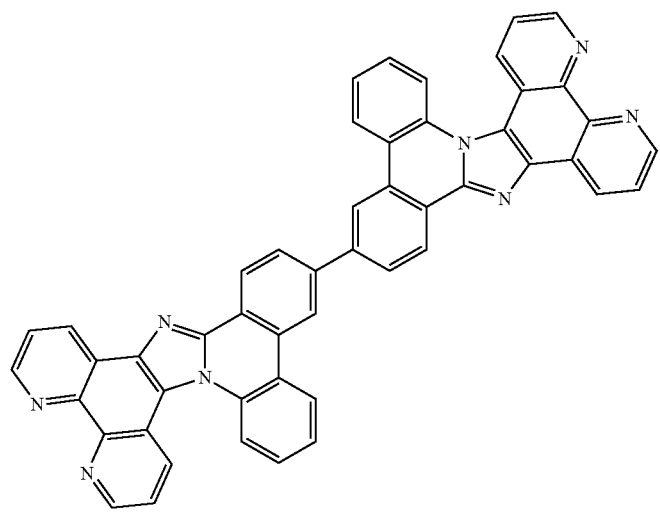
[5-a-23]
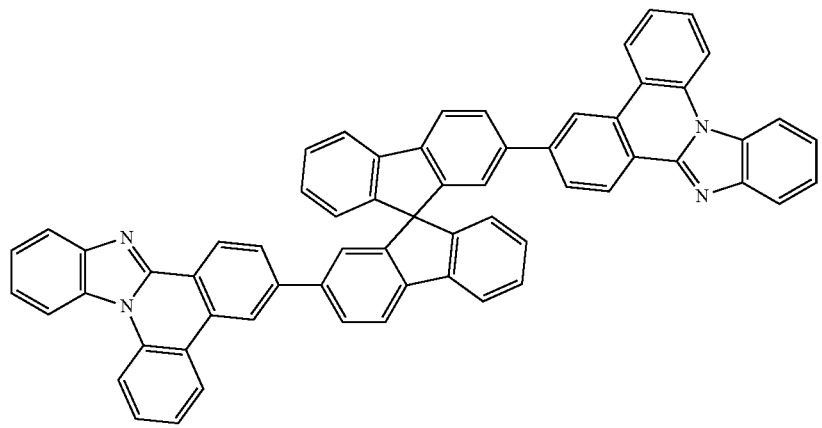
[5-a-24]
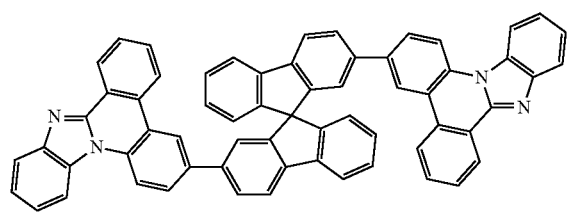
[5-a-25]
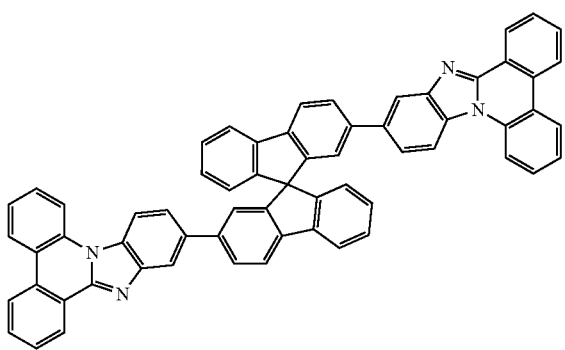
[5-a-26]
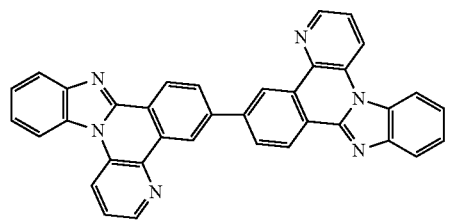
[5-a-27]
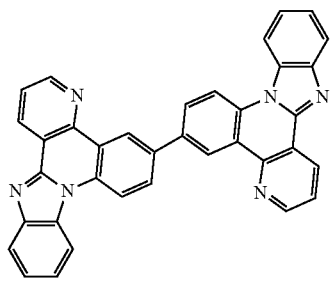

-continued
[5-a-28]
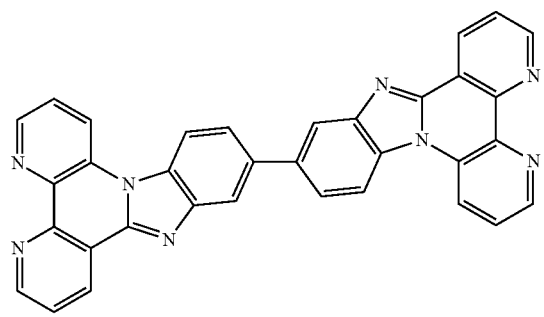
[5-a-29]
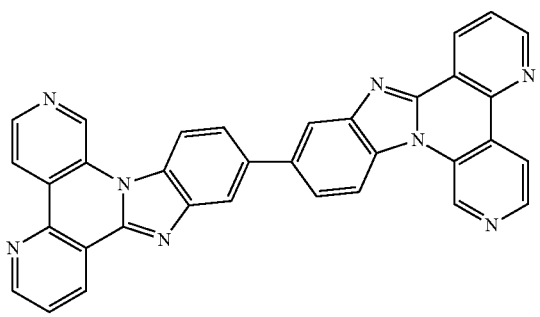
[5-a-30]
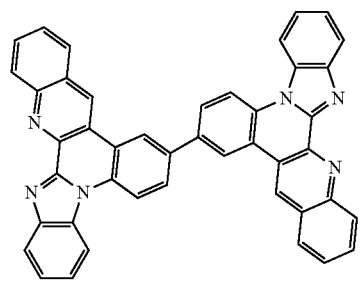
[5-a-31]
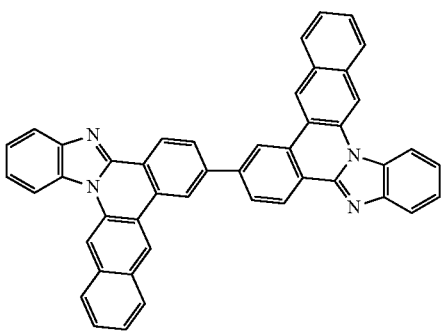
[5-a-32]
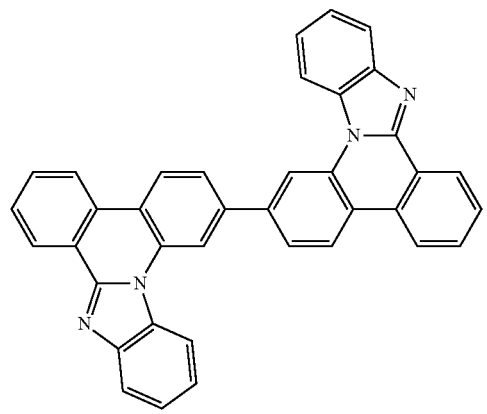
[5-a-33]
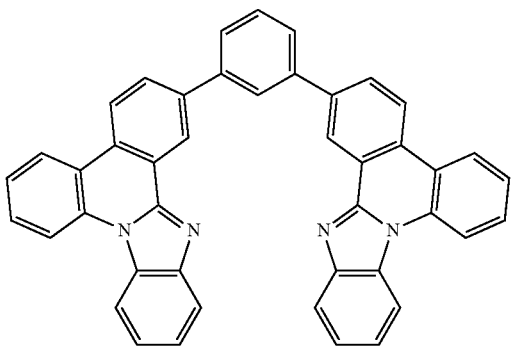
[5-a-34]
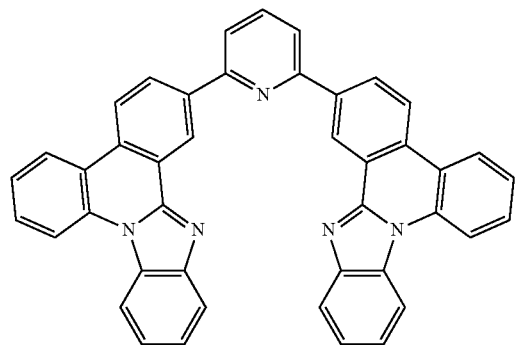
[5-a-35]
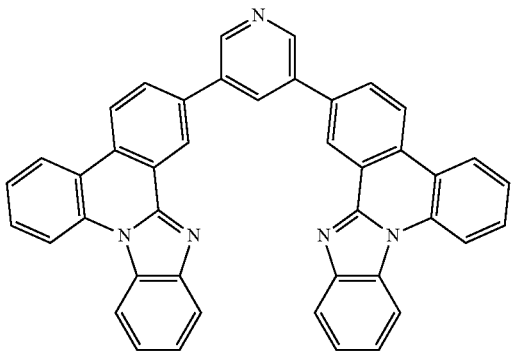

-continued
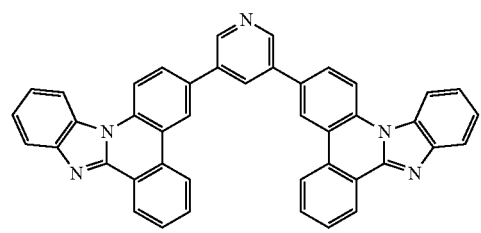
[5-a-36]
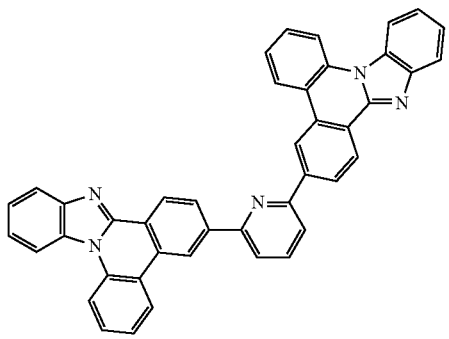
[5-a-37]
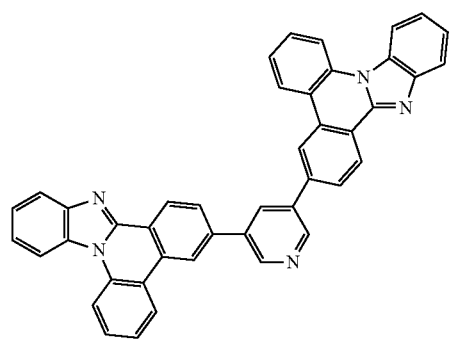
[5-a-38]
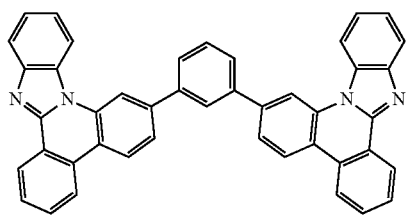
[5-a-39]
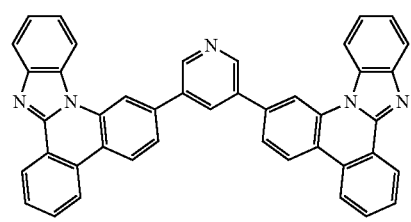
[5-a-40]
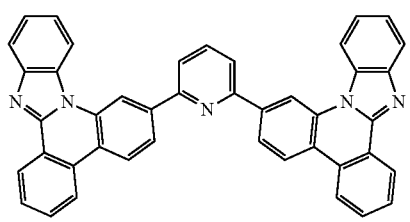
[5-a-41]
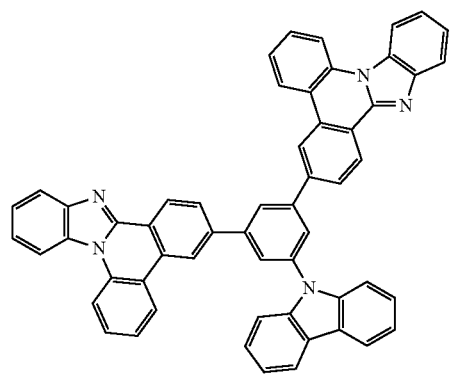
[5-a-42]
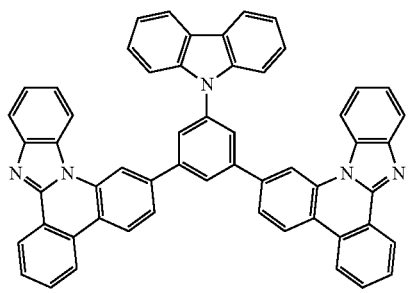
[5-a-43]

-continued
[5-a-44]
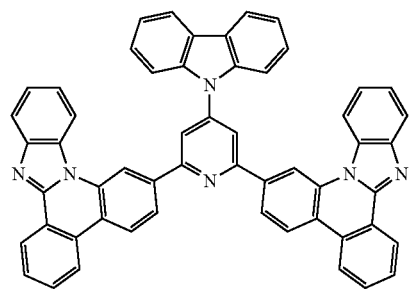
[5-a-45]
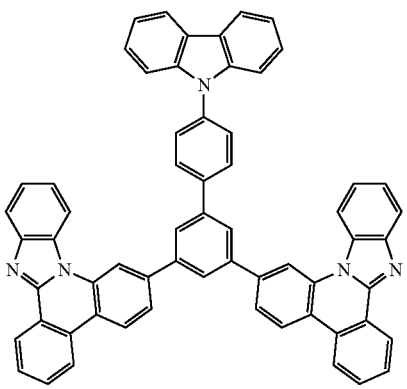
[5-a-46]
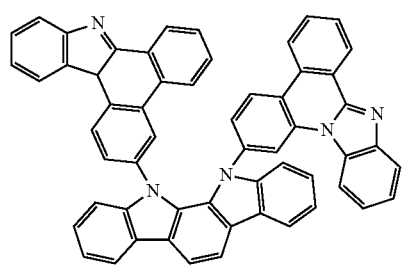
[5-a-47]
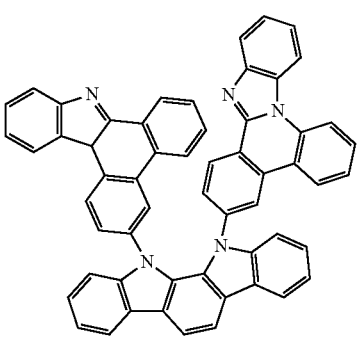
[5-a-48]
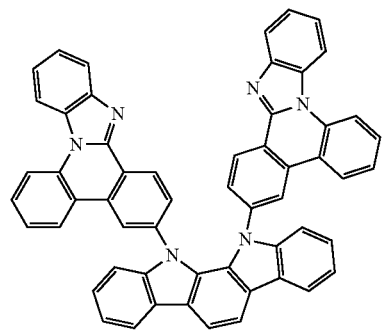
[5-a-49]
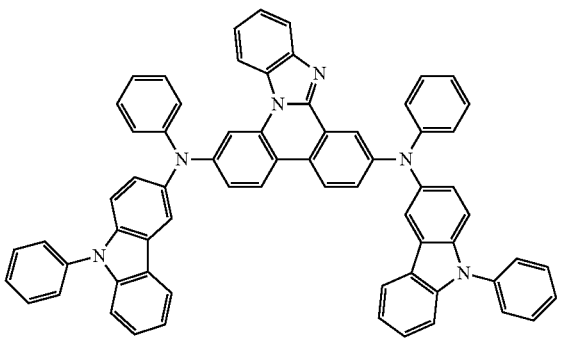
[5-a-50]
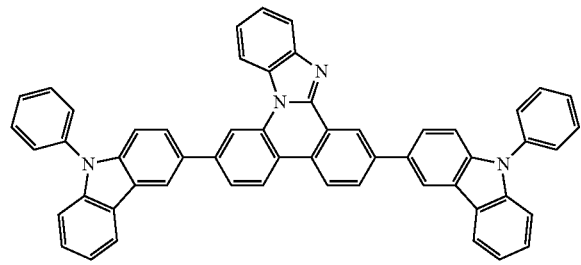
[5-a-51]
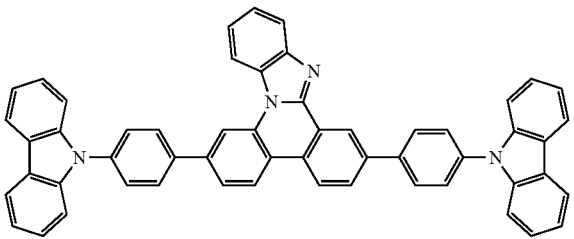

-continued
[5-a-52]
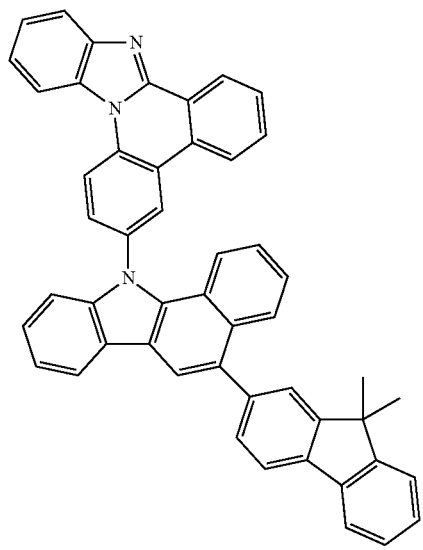
[5-a-53]
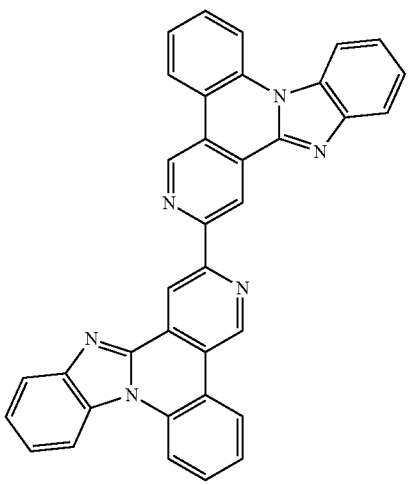
[5-a-54]
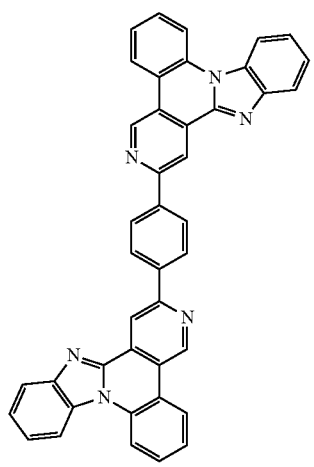
[5-a-55]
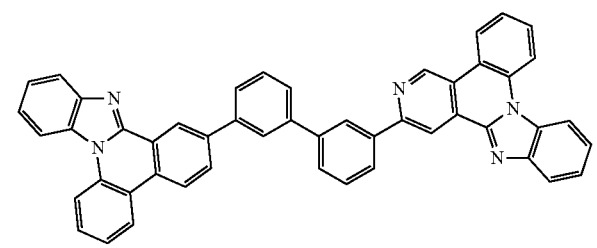
[5-a-56]
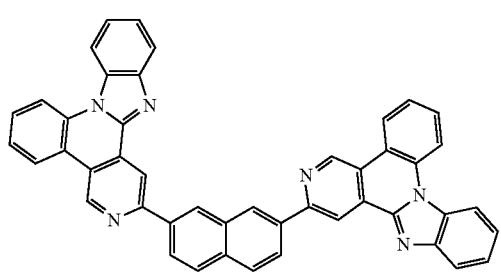
[5-a-57]
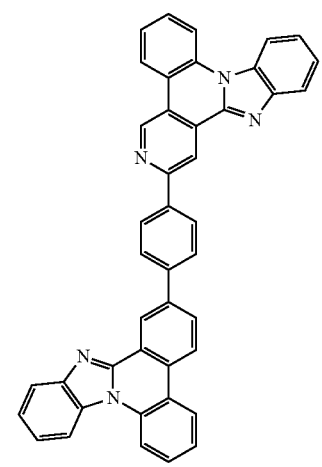

-continued
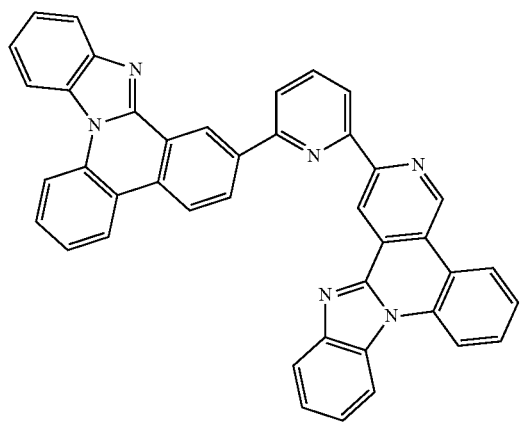
[5-a-58]
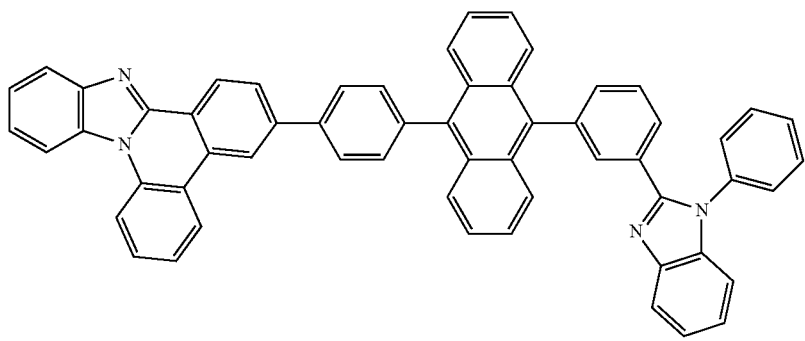
[5-a-59]
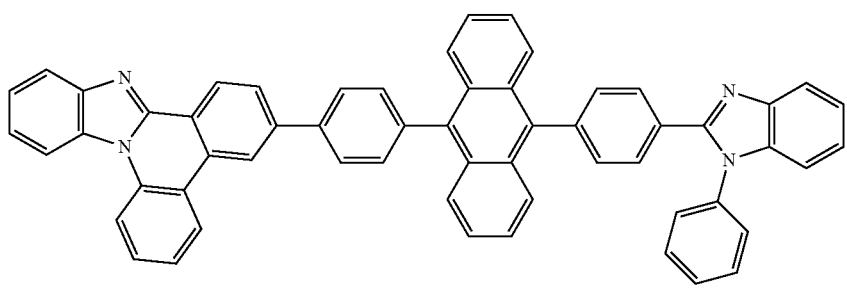
[5-a-60]
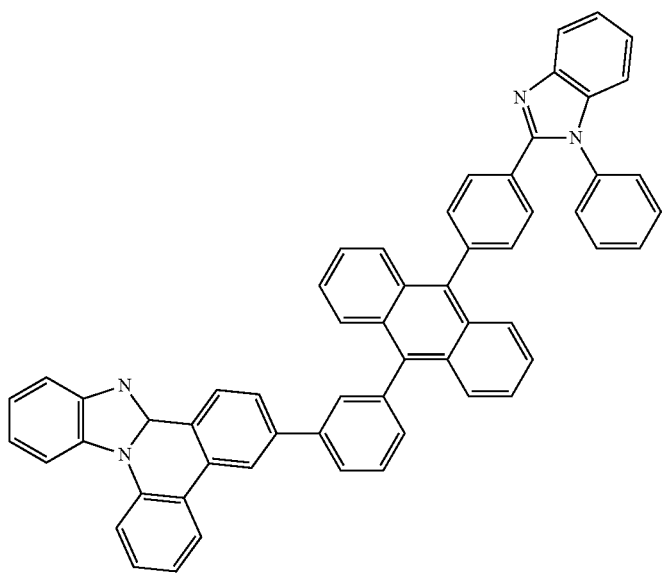
[5-a-61]

-continued
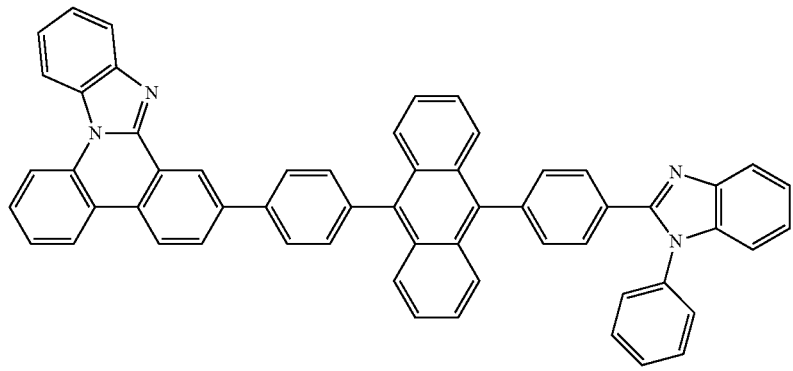
[5-a-62]
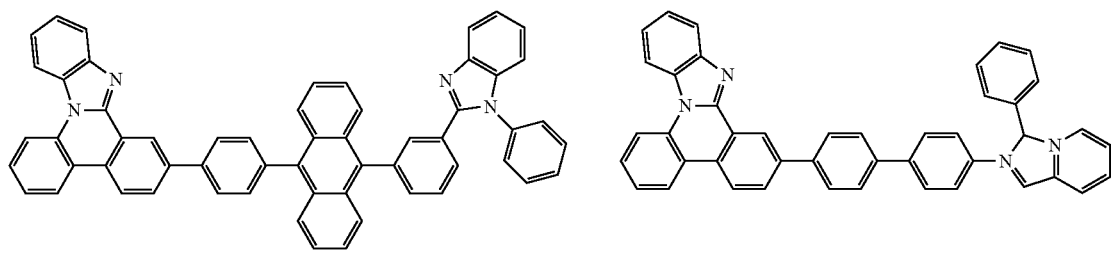
[5-a-63]  [5-a-64]
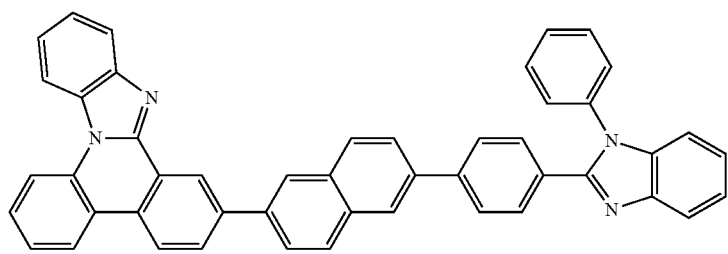
[5-a-65]
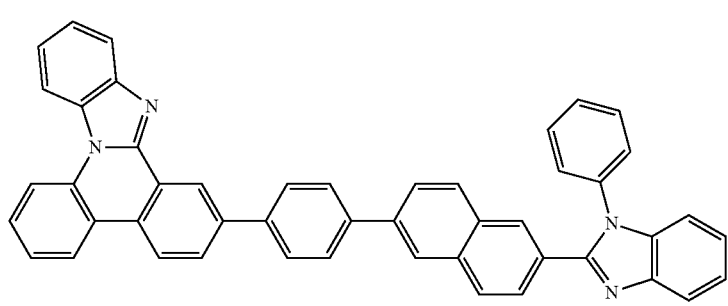
[5-a-66]
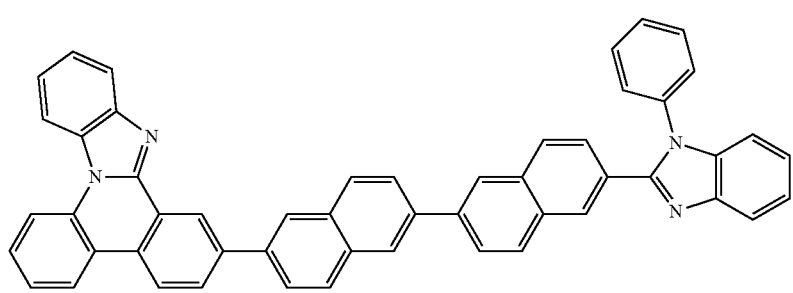
[5-a-67]

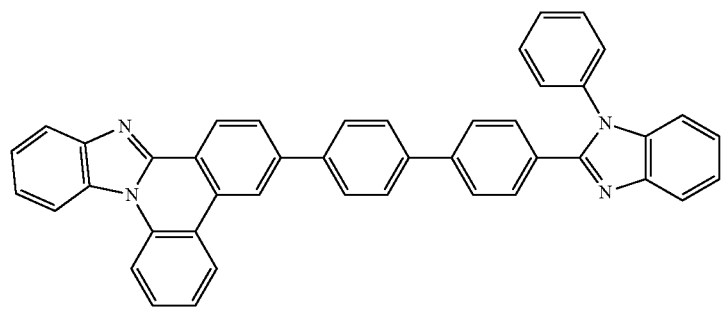
[5-a-68]
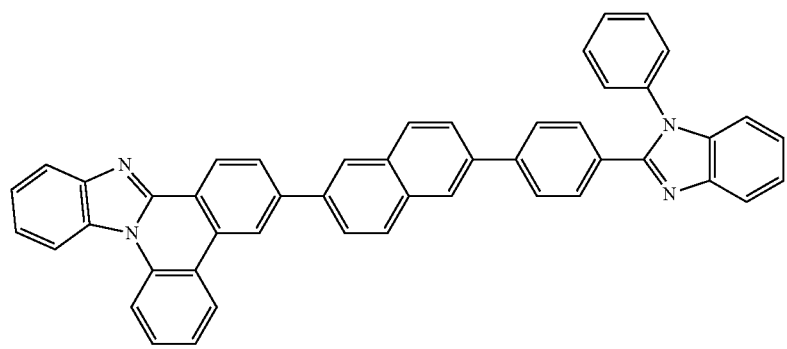
[5-a-69]
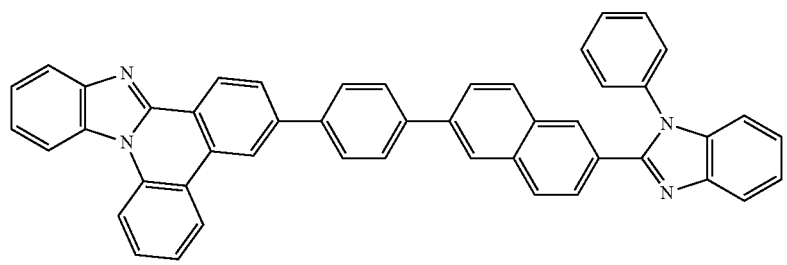
[5-a-70]
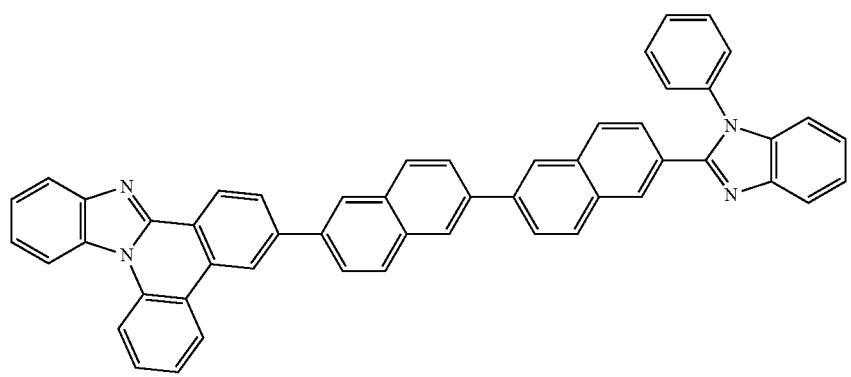
[5-a-71]

As preferable detailed examples of the compound that is represented by Formula 1, there are the following compounds, but they are not limited thereto.
[6-a-1]
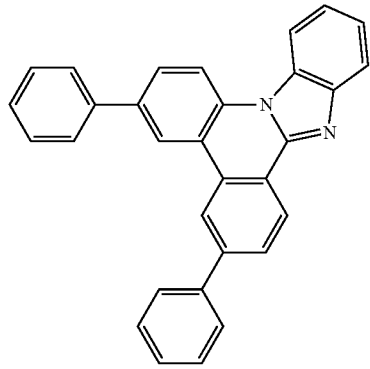
[6-a-2]
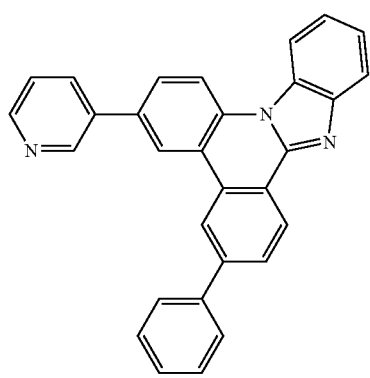
[6-a-3]
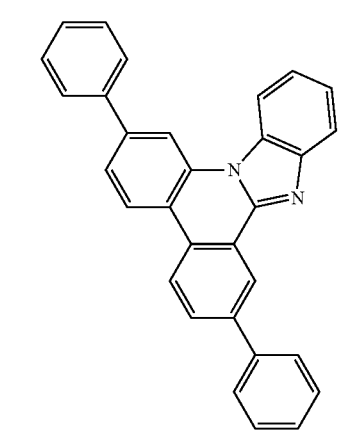
[6-a-4]
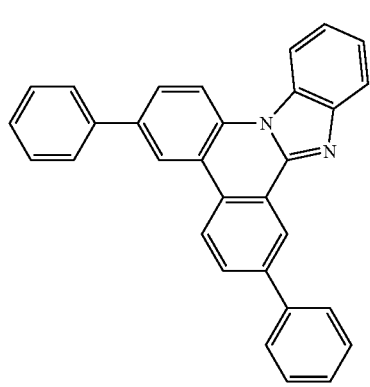
-continued
[6-a-5]
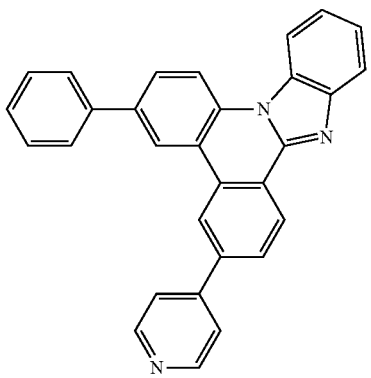
[6-a-6]
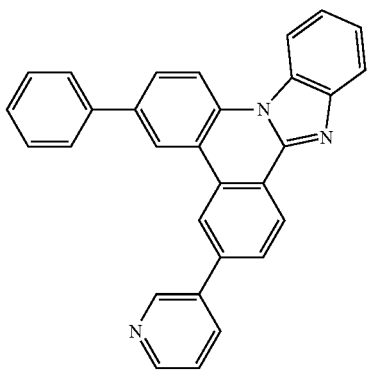
[6-a-7]
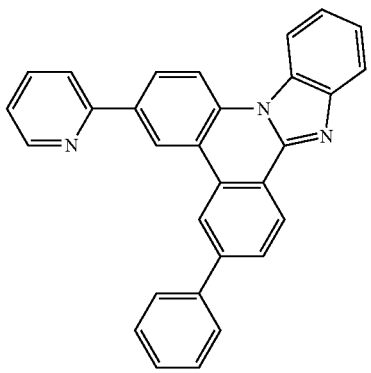
[6-a-8]
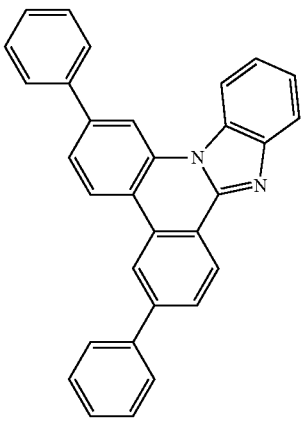

[6-a-9]
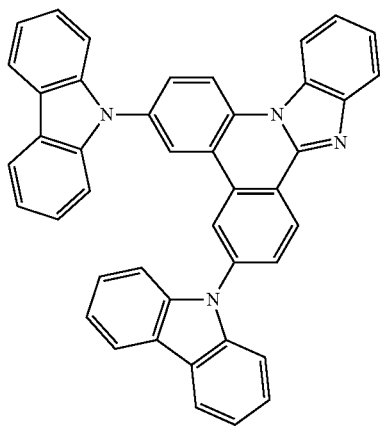
[6-a-10]
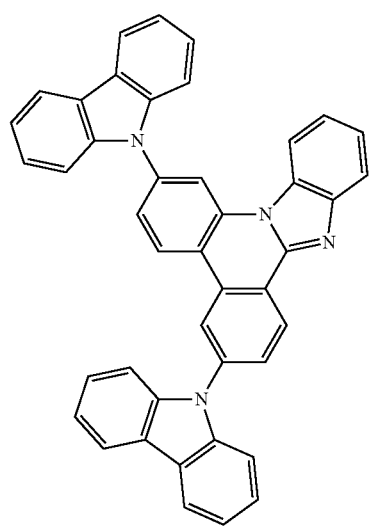
[6-a-11]
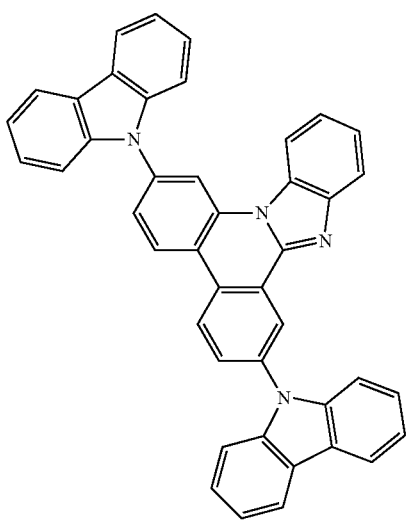
[6-a-12]
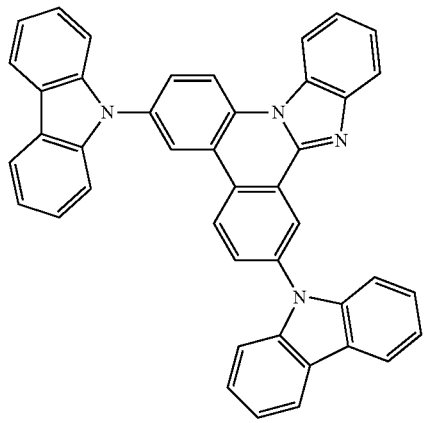
[6-a-13]
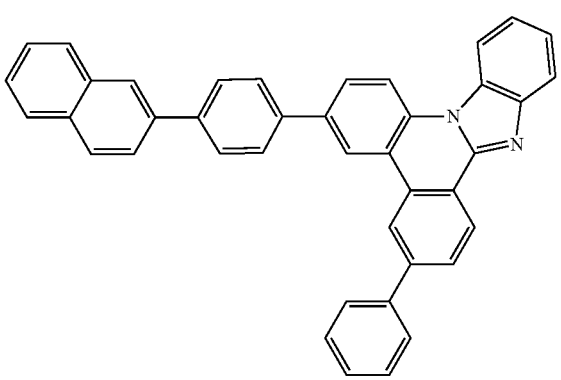
[6-a-14]
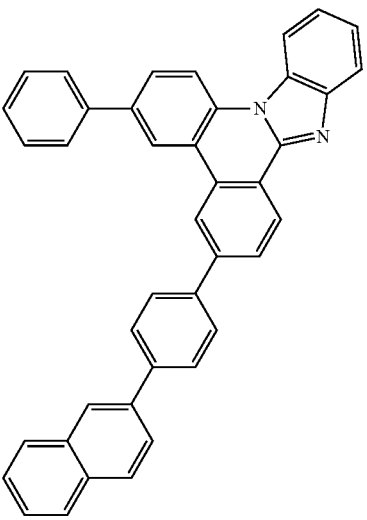

[6-a-15]
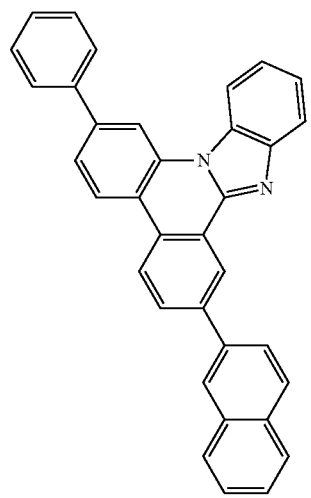
[6-a-16]
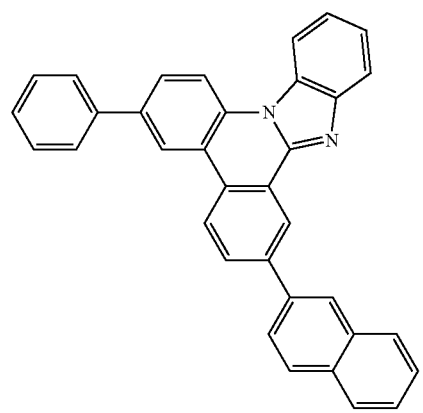
[6-a-17]
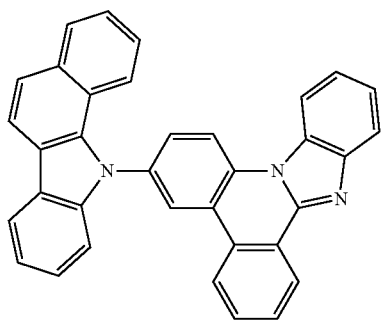
[6-a-18]
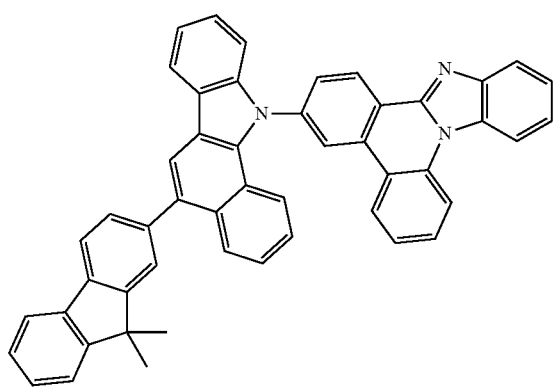
[6-a-19]
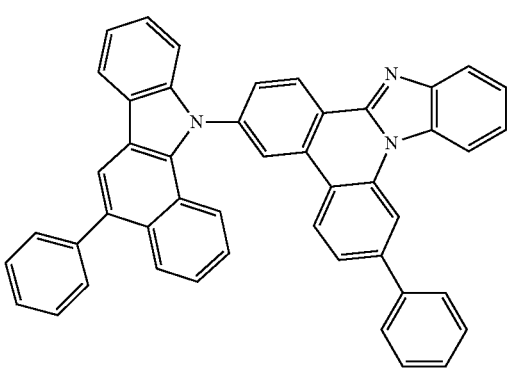
[6-a-20]
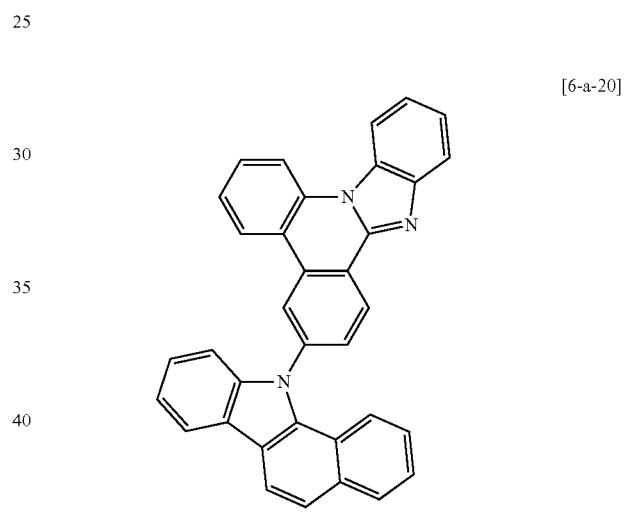
[6-a-21]
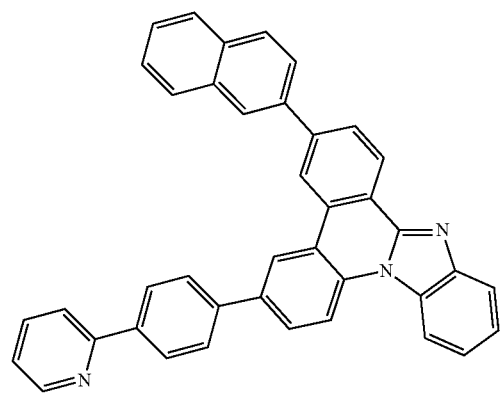

[6-a-22]
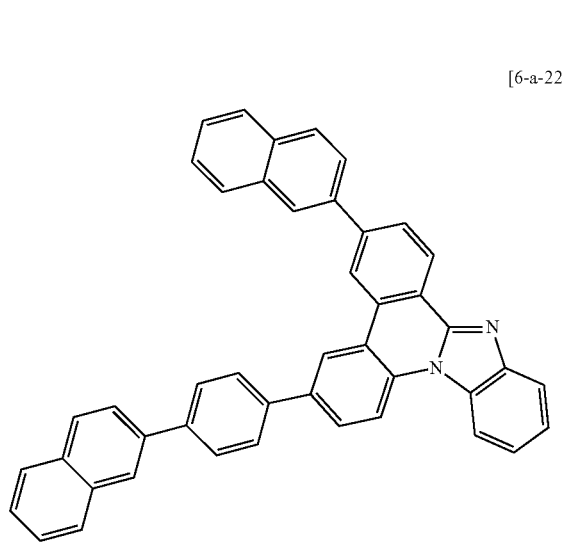
[6-a-23]
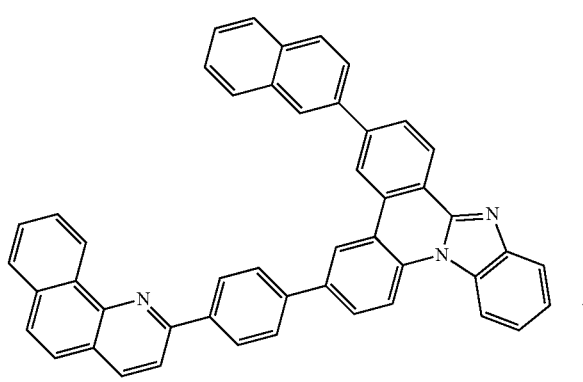
[6-a-24]
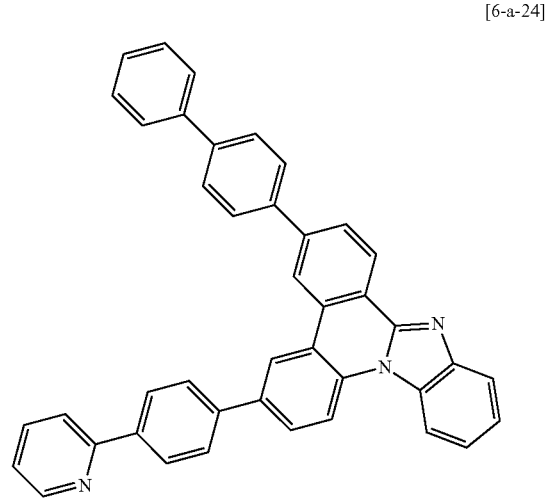
[6-a-25]
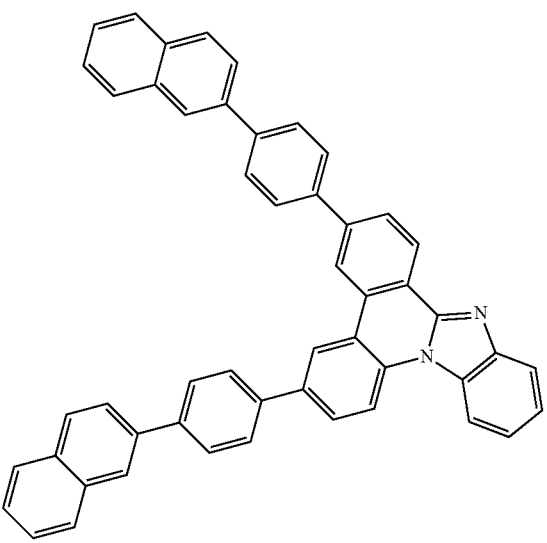
[6-a-26]
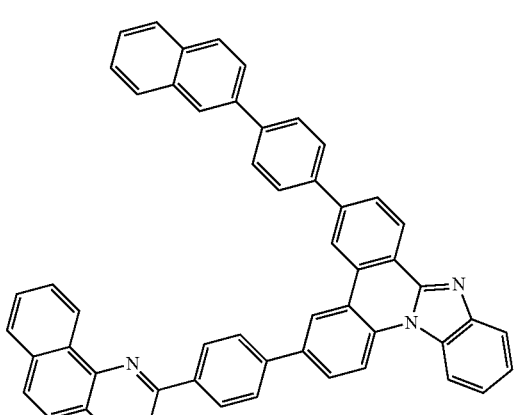
[6-a-27]
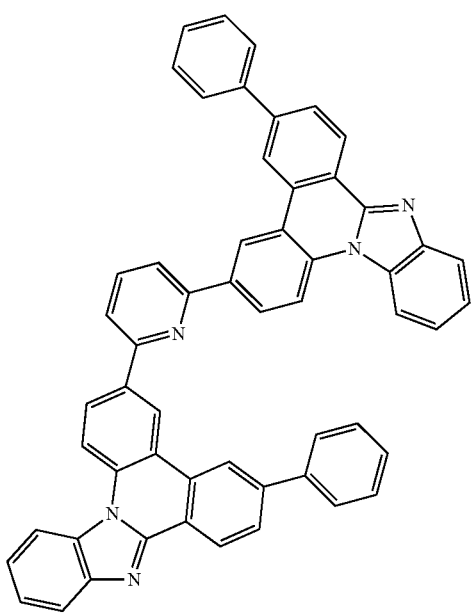

-continued
[6-a-28]
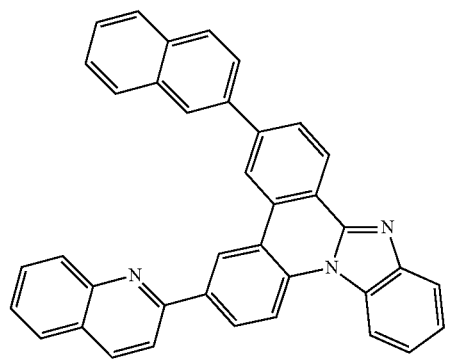
[6-a-29]
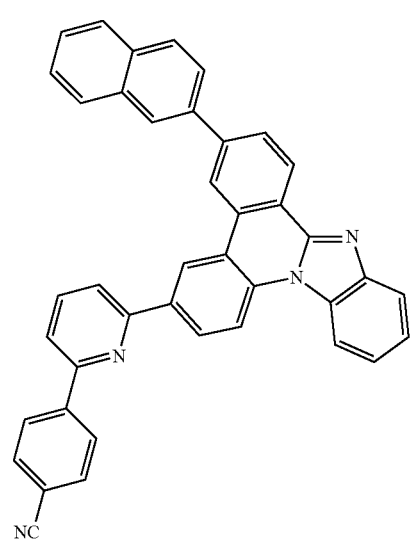
[6-a-30]
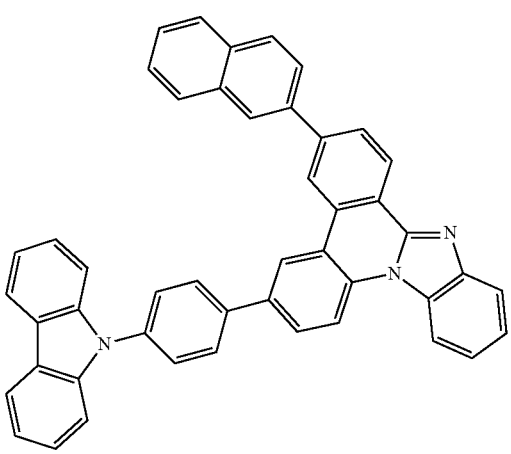
-continued
[6-a-31]
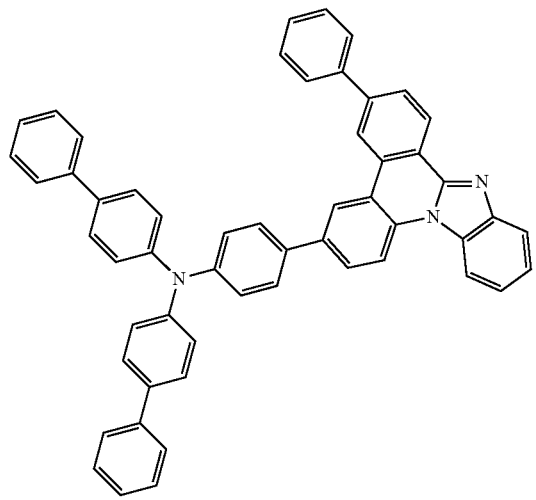
[6-a-32]
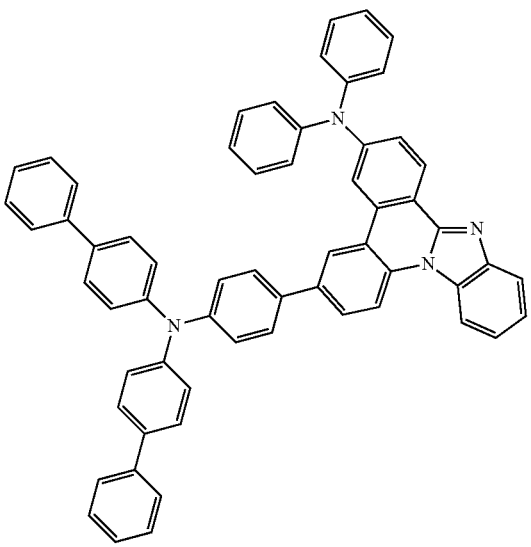
[6-a-33]
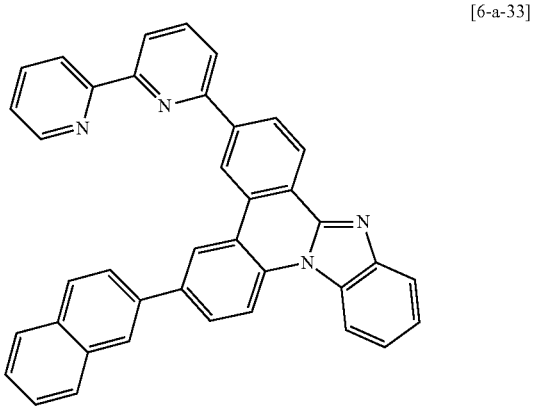

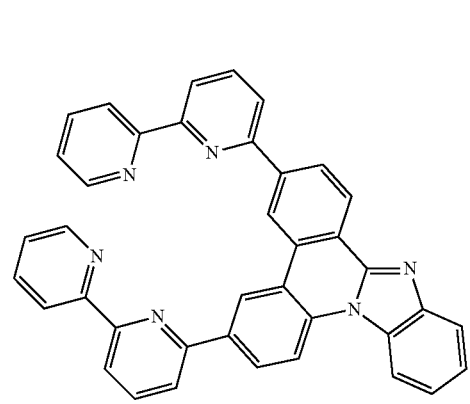 [6-a-34]
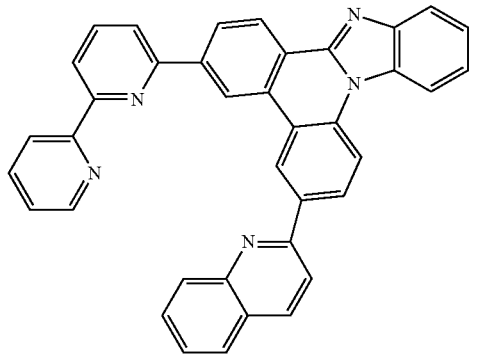 [6-a-37]
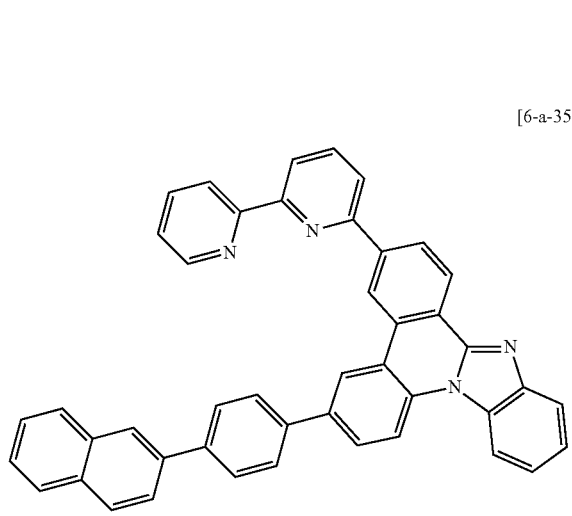 [6-a-35]
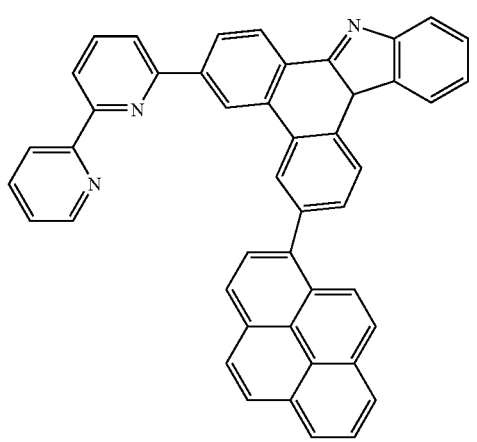 [6-a-38]
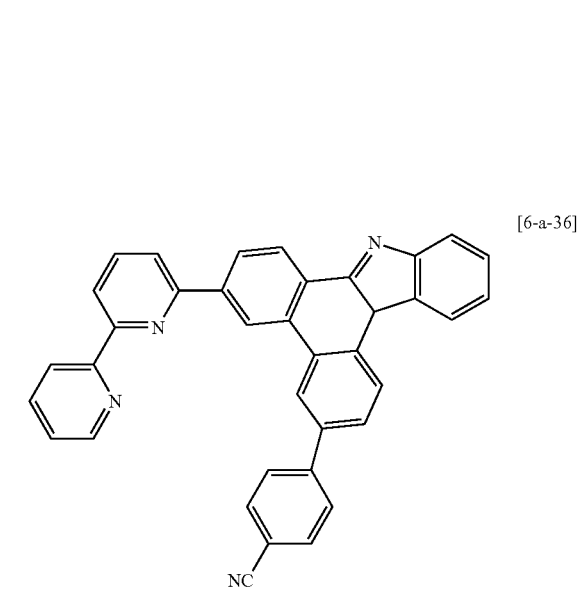 [6-a-36]
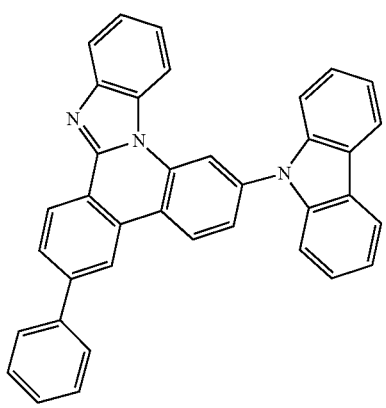 [6-a-39]

[6-a-40]
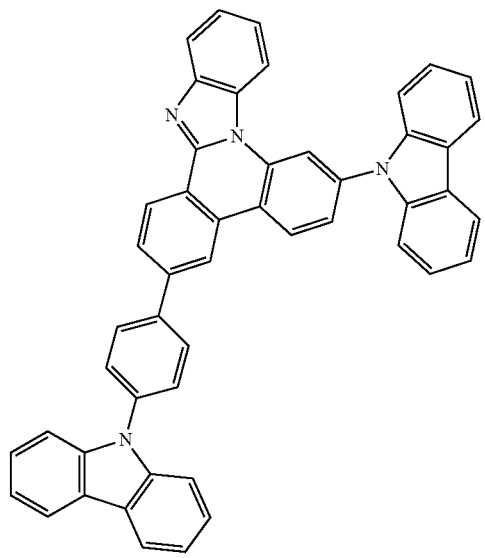
[6-a-41]
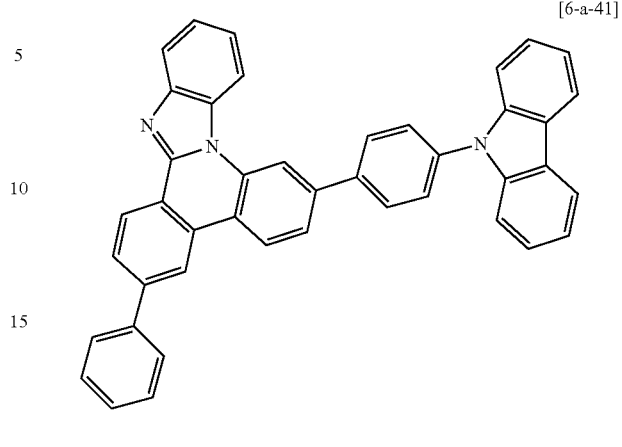
As preferable detailed examples of the compound that is represented by Formula 1, there are the following compounds, but they are not limited thereto.
[7-a-1]
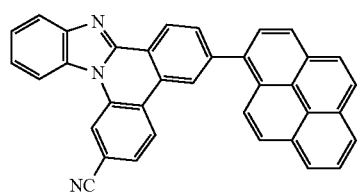
[7-a-2]
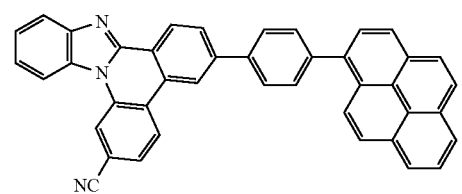
[7-a-3]
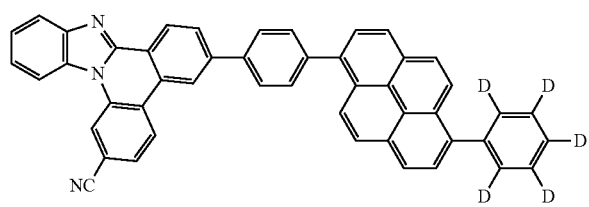
[7-a-4]
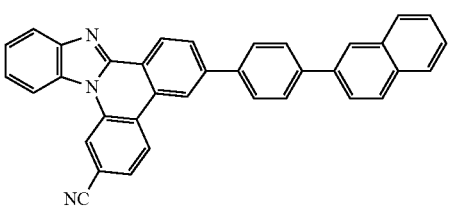
[7-a-5]
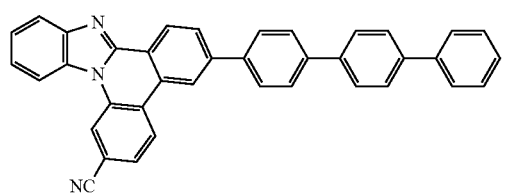
[7-a-6]
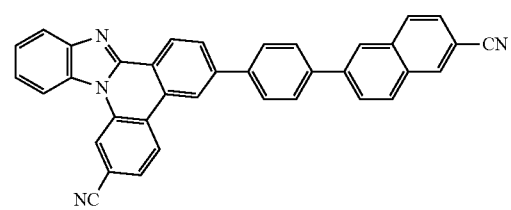
[7-a-7]
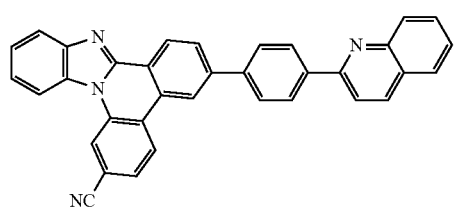
[7-a-8]
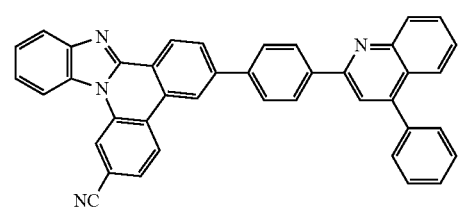
[7-a-9]
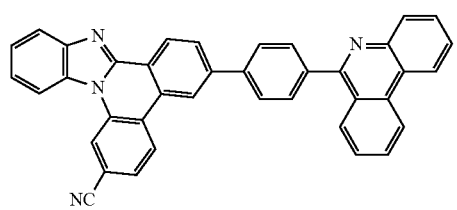
[7-a-10]
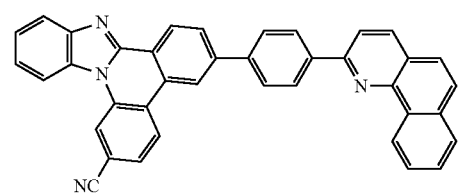

-continued
[7-a-11] 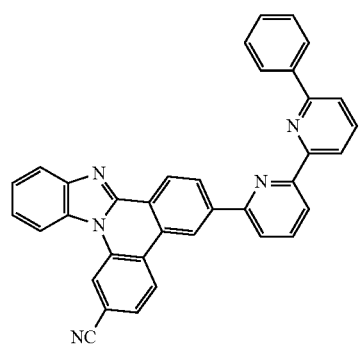
[7-a-12] 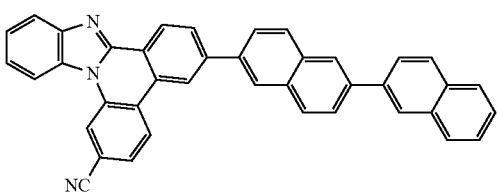
[7-a-13] 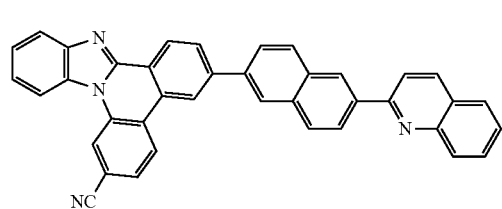
[7-a-14]
[7-a-15] 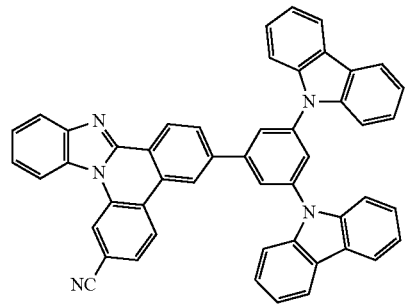
[7-a-16]
[7-a-17] 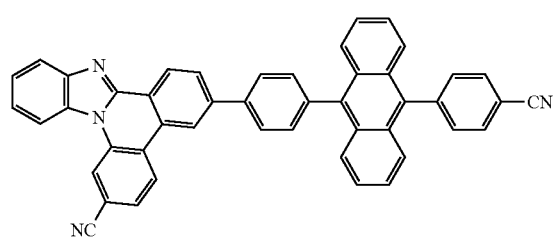
[7-a-18]
[7-a-19] 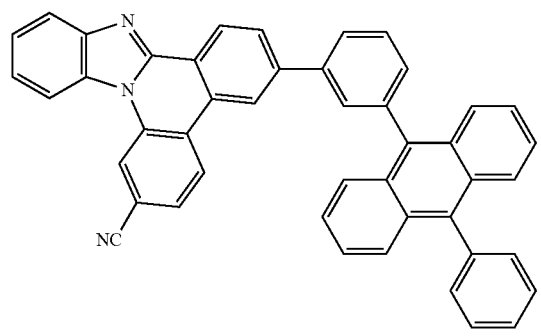
[7-a-20] 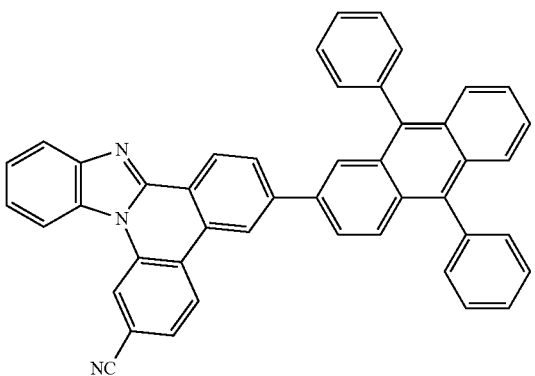

-continued
[7-a-21]
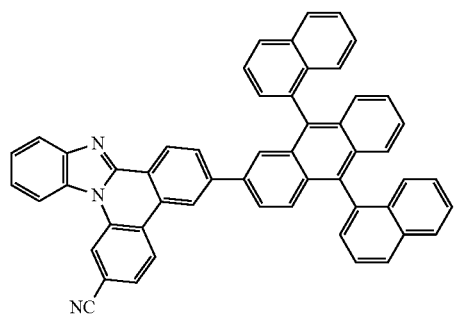
[7-a-21]
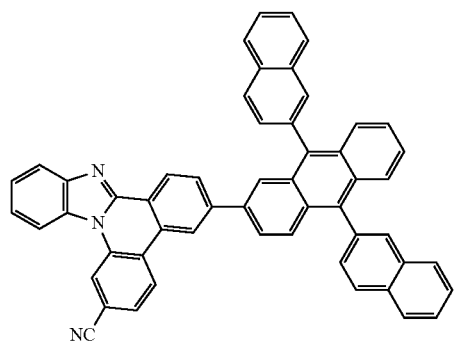
[7-a-22]
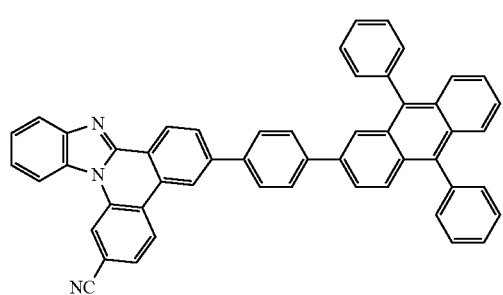
[7-a-23]
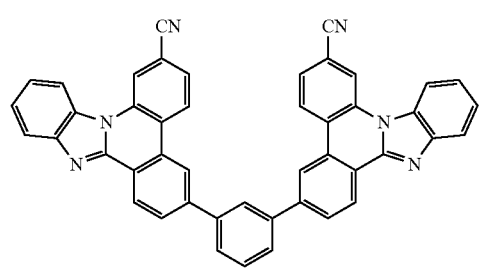
[7-a-24]
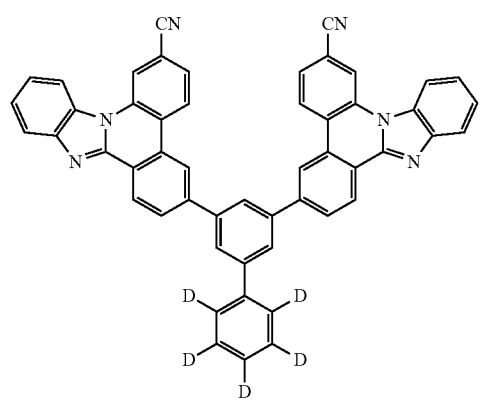
[7-a-25]
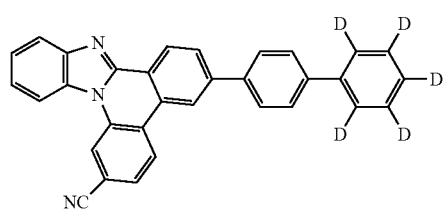
[7-a-26]
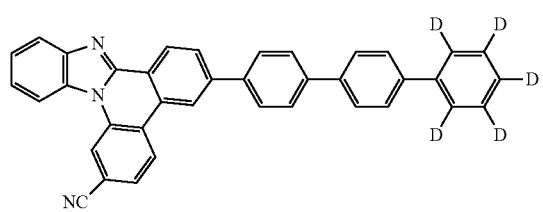
[7-a-27]
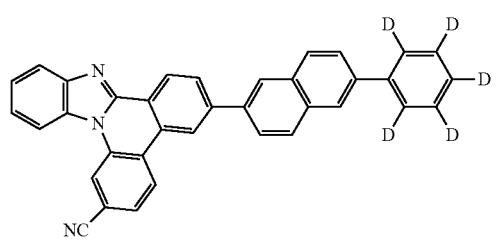
[7-a-28]
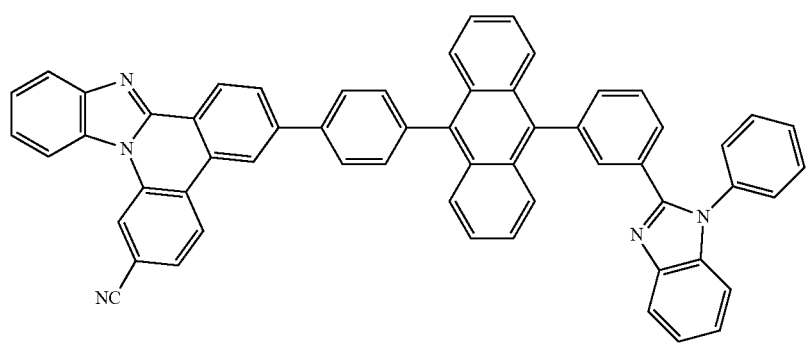

In addition, the present invention provides a method for manufacturing the derivative that is represented by Formula 1.

The compound (Cpd C) that is represented by Formula 1 may be prepared by using the following method. First, under the Pd catalyst, after the compound Cpd A is prepared through a Suzuki bonding reaction, the imidazole derivative Cpd B may be prepared by reacting the compound to which 1,2-diaminobenzene and the formyl group are introduced. Next, the structure of Formula 1 may be manufactured through the cyclization reaction of the —NH of the imidazole group and the aryl group or heteroaryl group that includes the chloro (Cl) group in the molecule under the Pd catalyst. As described above, Formula 1 in which the ortho position of the aryl group or heteroaryl group that includes $X_1$ to $X_4$ and the ortho position of the aryl group or heteroaryl group that includes $Y_1$ to $Y_4$ are connected to each other may be prepared.

In detail, the compound that is represented by Cpd B may be prepared through 1) the Suzuki bonding reaction of the compound Cpd 1 in which halogens are substituted, boronic acid Cpd 2 in which the formyl group is substituted, or boron ester Cpd 3 under the Pd catalyst. Also, it may be prepared through the Suzuki bonding reaction of boronic acid Cpd 4 in which halogens are substituted, boron ester Cpd 5, or the compound Cpd 6 in which the formyl group is substituted under the Pd catalyst.

The manufacturing method may be represented by the following Reaction Equation 1.

[Reaction Equation 1]

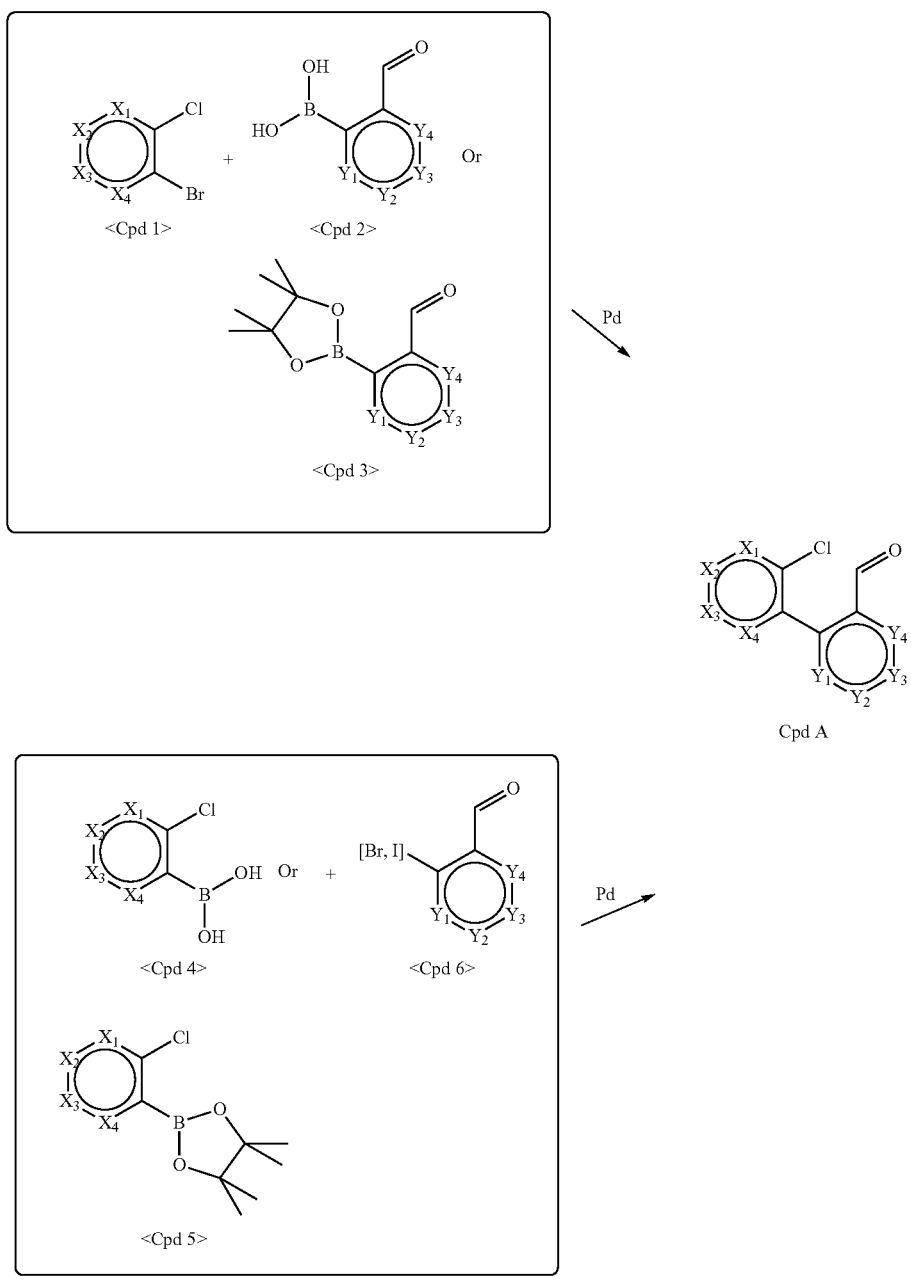

In detail, the compound that is represented by Cpd A may prepare 2) the imidazole group through the acid catalyst by mixing Cpd A in which the halogen group and the formyl group are substituted, the diketo derivative (Cpd 7) that has the R1 and R2 substituents, and, ammonium acetate. Also, it may prepare the imidazole group through the acid catalyst by mixing Cpd A in which the halogen group and the formyl group are substituted, the diamine derivative (Cpd 8) that has the R1 and R2 substituents.

The manufacturing method may be represented by the following Reaction Equation 2.

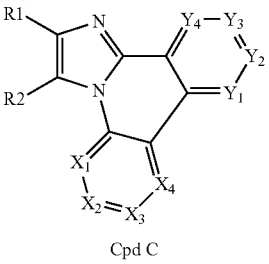

Cpd C

[Reaction Equation 2]

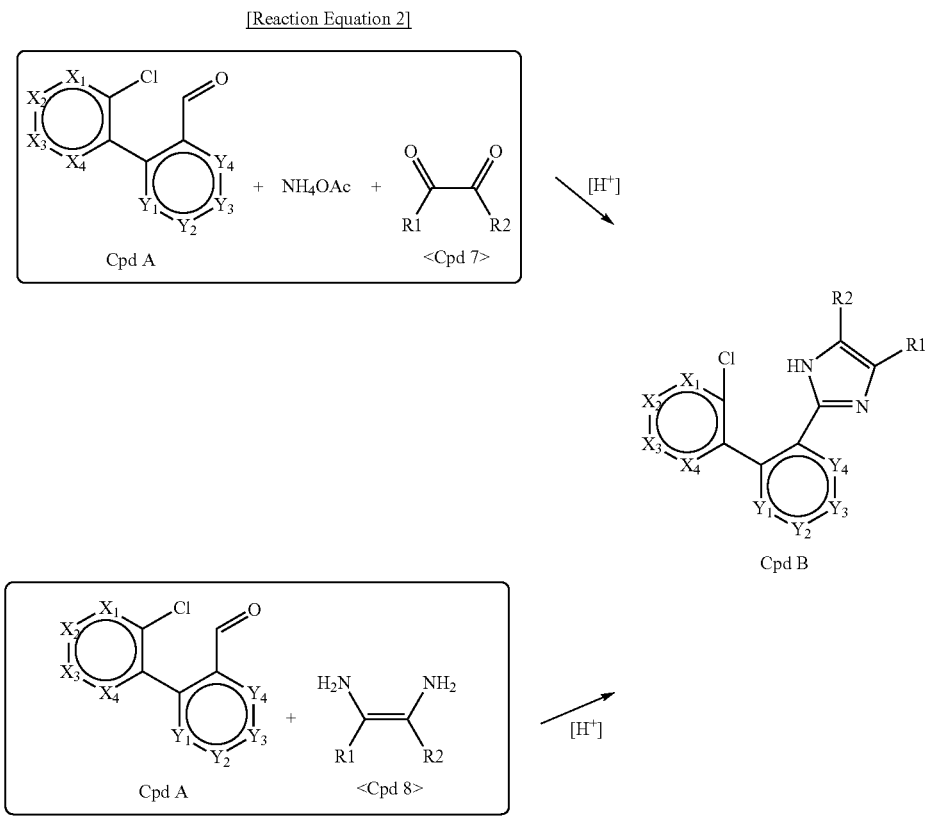

In detail, the compound that is represented by Cpd C may prepared Cpd C (Formula 1) through 3) the cyclization reaction of the halogen group and Cpd B in which the imidazole group is substituted by using the Pd catalyst in the molecule.

The manufacturing method may be represented by the following Reaction Equation 3.

[Reaction Equation 3]

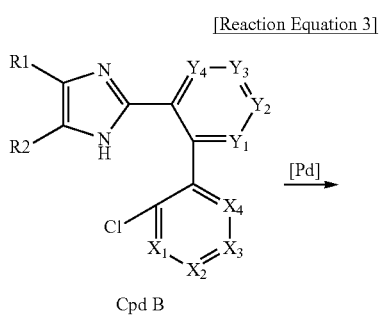

Cpd B

Additionally, by introducing various substituent groups into the core structure, compounds having intrinsic characteristics of the substituent groups may be obtained. For example, substituent groups, which are frequently applied to hole injection layer material, hole transport layer material, light emitting layer material, and electron transport layer materials during the production of the organic light emitting device and the organic electronic device, are introduced into the core structure so as to produce substances capable of satisfying the requirements of each organic material layer.

In Formula 1, in the case of when Y is the aryl group, the aryl group has stability in respects to both electrons and holes, and in particular, in the case of when L has a predetermined length, it is possible to control the bandgap. In addition, it is possible to ensure thermal stability, the subliming ability, and electric stability, and in the real device, it is possible to improve performance.

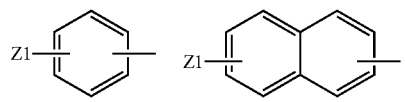

-continued

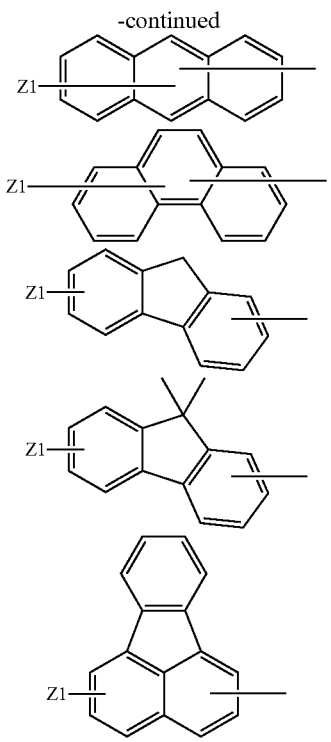

In Formula 1, in the case of when p of -(L)p- is 0 and the core structure is directly connected to Y, stability is shown in respects to the electrons and the holes in terms of the properties of the substituent group, and an appropriate Tg (glass transition temperature) is ensured, thereby improving thermal stability.

In the compound in which

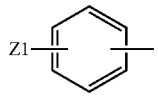

is directly bonded, in the case of when Z1 is the aryl group, it is preferable that it is substituted by the aryl group having 6 or more carbon atoms. The reason is that since it has an appropriate length of substituent, properties of the organic electronic light emitting device are improved.

Figure 30:
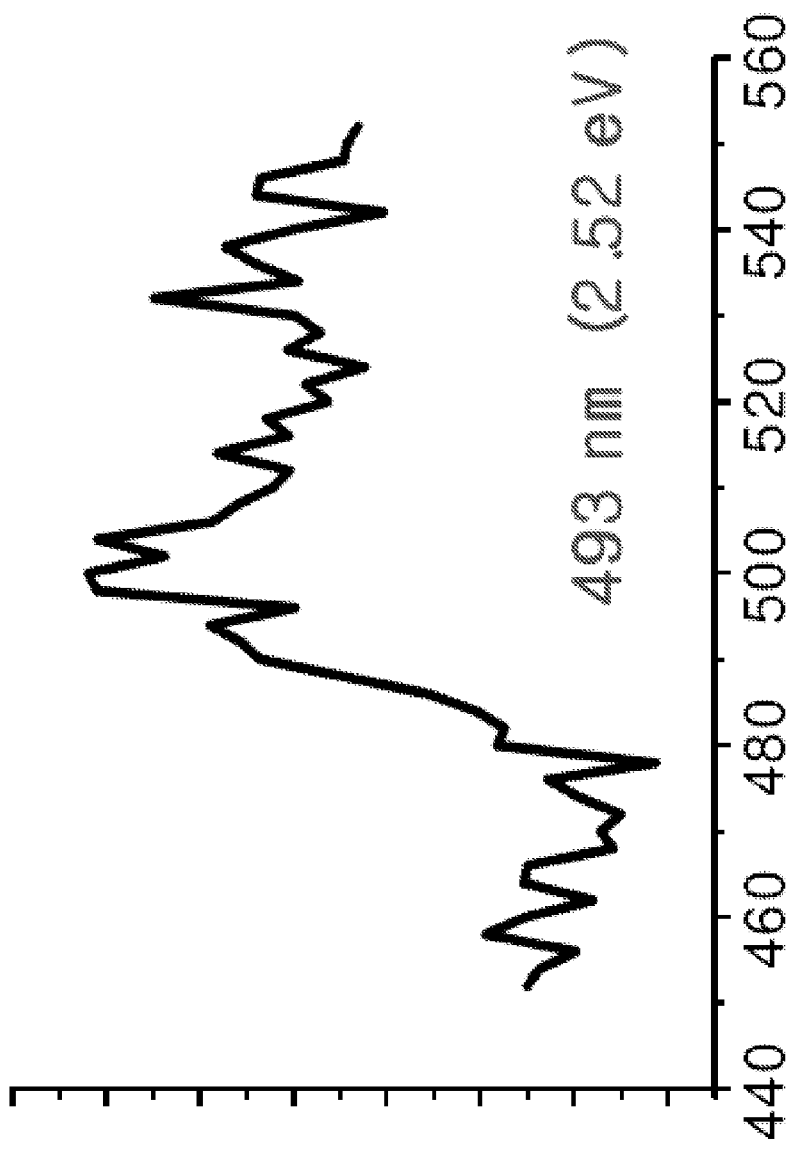
FIG. 30 illustrates phosphorescent PL that is measured in Methyl THF at 77K in the case of when the compound 6-a-18 is used.

In addition, if an appropriate substituent, for example, carbazole or benz carbazole, is introduced to the structure of Formula 1, energy band gap (e.g. FIG. 30) and stability can be ensured at a triplet state. From these results, various phosphorescence dopants from red color to blue color can be used and applied to the host of the light emitting layers of fluorescent and phosphorescent devices.

As a result, since the structure of Formula 1 including the appropriate substituent has a high glass transition temperature (Tg), it has excellent thermal stability. Such increase in thermal stability is an important factor providing driving stability to the device. According to the length and the kind of the substituent group, it is possible to finely control HOMO and LUMO energy level and energy band gap, improve interfacial characteristics with organic materials, and make the purpose of material various.

Since the compound according to the present invention is freely controlled by the core and the substituent, it may act as various layers in addition to the host of the phosphorescent or fluorescent light emitting layer.

In addition, the present invention provides an organic electronic device which includes a first electrode, a second electrode, and one or more organic material layers that are disposed between the first electrode and the second electrode, wherein one or more layers of the organic material layers include the compound that is represented by Formula 1.

The organic electronic device is selected from the group consisting of an organic light emitting device, an organic solar cell, an organic photoconductor (OPC) drum and an organic transistor.

In addition, the organic electronic device may be an organic light emitting device.

In addition, the organic light emitting device may be an organic light emitting device that has a positive direction structure, in which an anode, one or more organic material layers and a cathode are sequentially layered on a substrate.

In addition, the organic light emitting device may be an organic light emitting device that has a negative direction structure, in which a cathode, one or more organic material layers and an anode are sequentially layered on a substrate.

In addition, the organic material layer of the organic light emitting device may include a hole injection layer, a hole transport layer, a light emitting layer, and an electron injection and/or transport layer.

In addition, the organic material layer of the organic light emitting device includes a light emitting layer, and the light emitting layer includes the nitrogen-containing heterocyclic derivative. At this time, the nitrogen-containing heterocyclic derivative may act as a host of the light emitting layer.

In addition, the organic material layer of the organic light emitting device includes an electron transport and/or injection layer, and the layer includes the nitrogen-containing heterocyclic derivative.

In addition, the organic material layer of the organic light emitting device includes a layer that simultaneously transport holes and emit light, and the layer includes the nitrogen-containing heterocyclic derivative.

In addition, the organic material layer of the organic light emitting device includes a layer that simultaneously transport electrons and emit light, and the layer includes the nitrogen-containing heterocyclic derivative.

The organic material layer that includes the nitrogen-containing heterocyclic derivative according to the present invention includes the nitrogen-containing heterocyclic derivative as the host, and other organic compounds, metal or metal compounds as a dopant.

It is preferable that the organic electronic device according to the present invention includes the organic material layer including the nitrogen-containing heterocyclic derivative, and a hole injection layer or a hole transport layer that includes the compound including arylamino group, carbazole group or benzcarbazole group.

The organic electronic device according to the present invention may be manufactured by using a manufacturing method and a material of a general organic electronic device, except that one or more organic material layers are formed by using the above compounds.

Hereinafter, the organic light emitting device will be described.

In an embodiment of the present invention, the organic light emitting device may be comprised of a first electrode, a second electrode and an organic material layer that is disposed between them. The organic material layer of the organic light emitting device according to the present invention may have a single layer structure including one layer and a multilayered structure that includes two or more layers including a light emitting layer. In the case of when the organic material layer of the organic light emitting device according to the present invention has the multilayered structure, for example, this may be a structure in which hole injection layer, hole transport layer, light emitting layer, electron transport layer and the like are layered. However, the structure of the organic light emitting device is not limited to this, but may comprise a smaller number of organic material layers. For example, the organic light emitting device according to the present invention may have the same structure as the structure shown in FIG. 1. In FIG. 1, reference numeral 1 means a substrate, reference numeral 2 means an anode, reference numeral 3 means a hole injection layer, reference numeral 4 means a hole transport layer, reference numeral 5 means an organic light emitting layer, reference numeral 6 means an electronic transport layer, reference numeral 7 means a cathode. The organic light emitting device that has the same structure as FIG. 1 is an organic light emitting device having a positive direction structure, but the present invention is not limited thereto but includes an organic light emitting device having a negative direction structure. That is, the organic light emitting device according to the present invention may have a structure in which a substrate, a cathode, an electronic transport layer, an organic light emitting layer, a hole transport layer, a hole injection layer, and an anode are sequentially layered.

In the case of when the organic light emitting device according to the present invention has the organic material layer having a multilayered structure, the compound of Formula 1 may be included in a light emitting layer, a hole transport layer, a layer that performs simultaneously hole transport and light emission, a layer that performs simultaneously electron transport and light emission, an electronic transport layer, and an electron transport and/or injection layer. In the present invention, it is preferable that the compound of Formula 1 is included in the electron injection and/or transport or light emitting layer.

The organic light emitting device according to the present invention may be manufactured by using the general manufacturing method and the material of the organic light emitting device, except that the compound of Formula 1 is used in one or more of the organic material layers of the organic light emitting device. For example, the organic light emitting device according to the present invention may be manufactured by forming an anode by depositing metal or metal oxides having the conductivity or an alloy thereof on a substrate by using a PVD (physical vapor deposition) method such as sputtering or e-beam evaporation, forming the organic material layer that includes hole injection layer, hole transport layer, light emitting layer and electron transport layer thereon, and depositing the material that is capable of being used as a cathode thereon. In addition to this method, in order to manufacture the organic light emitting device having the negative direction structure, an organic light emitting device may be manufactured by sequentially depositing a cathode, an organic material layer, and an anode material on a substrate.

The organic material layer may be manufactured in a smaller number of layer by using various polymer materials and by using not a deposition method but a solvent process, for example, spin coating, dip coating, doctor blading, screen printing, inkjet printing, heat transferring method and the like.

As the anode material, in general, it is preferable to use the material having the large work function so as to smoothly perform hole injection into the organic material layer. As examples of the anode material that is capable of being used in the present invention, there are metal or alloy thereof such as vanadium, chrome, copper, zinc, gold and the like; metal oxides such as zinc oxides, indium oxides, indium tin oxides (ITO), indium zinc oxides (IZO) and the like; a combination of metal and oxides such as ZnO:Al or $SnO_2$:Sb; conductive polymers such as poly(3-methyl compound), poly[3,4-(ethylene-1,2-dioxy) compound] (PEDT), polypyrole and polyaniline, but it is not limited thereto.

As the cathode material, in general, it is preferable to use the material having the small work function so as to smoothly perform electron injection into the organic material layer. As detailed examples of the cathode material, there are metal such as magnesium, calcium, sodium, potassium, titanium, indium, yttrium, lithium, gadolinium, aluminum, silver, tin, and lead or an alloy thereof; a multilayered structure material such as LiF/Al or $LiO_2$/Al, but it is not limited thereto.

The hole injection material is a material that is capable of well receiving holes from the anode at a low voltage, and it is preferable that the HOMO (highest occupied molecular orbital) of the hole injection material is a value between the work function of the anode material and the HOMO of the organic material layer around them. As detailed examples of the hole injection material, there are metal porphyrine, oligo thiophene, arylamine-based organic material, hexanitrile-hexaazatriphenylene-based organic material, quinacridone-based organic material, perylene-based organic material, anthraquinone and polyaniline and poly thiophene-based conductive polymers, but it is not limited thereto.

The hole transport material is a material that receives the holes from the anode or the hole injection layer and transfer them to the light emitting layer, and it is preferable to use the material having the large mobility to the holes. As detailed examples thereof, there are arylamine-based compound, carbazole-based compound, anthracene-based compound, pyrene-based compound, a conductive polymer, and a block copolymer in which a conjugate portion and a conjugate portion are simultaneously included, but it is not limited thereto.

The light emitting material is a material that receives the holes and the electrons from the hole transport layer and the electron transport layer, combines them, such that light at a range of visible rays is emitted, and it is preferable to use the material having excellent photon efficiency to fluorescence or phosphorescence. As detailed examples thereof, there are a 8-hydroxy-quinoline aluminium complex ($Alq_3$); a carbazole-based compound; a dimerized styryl compound; bis-methyl-8-hydroxyquinoline paraphenylphenol aluminum complex (Balq); 10-hydroxybenzoquinoline-metal compound; a benzoxazole, benzthiazole and benzimidazole-based compound; an anthracene-based compound; a pyrene-based compound; a poly(p-phenylenevinylene) (PPV)-based polymer; a spiro compound; polyfluorene, lubrene, and the like, but it is not limited thereto.

The electron transport material is a material that receives the electrons from the cathode and transfer them to the light emitting layer, and it is preferable to use the material having the large mobility to the electrons. As detailed examples thereof, there are Al complex of 8-hydroxyquinoline; complex including $Alq_a$; organic radical compounds; hydroxyflavone-metal complexes; anthracene-based compounds; pyrene-based compounds; benzoxazole, benzthiazole and benzimidazole-based compounds; pyridyl-based compounds; penanthroline-based compounds; quinoline-based compounds; quinazoline-based compounds and the like, and these compounds may be doped with metal or metal compounds to form the electron transport layer, but they are not limited thereto.

The organic light emitting device according to the present invention may be a front side light emitting type, a rear side light emitting type, or a both sides light emitting type according to the used material.

The compound according to the present invention may be operated in a principle that is similar to a principle applied to the organic light emitting device in organic solar cell, organic photoconductor, organic transistor, and organic electronic device. Hereinafter, preferable Examples will be described in order to help understanding of the present invention. The following Examples are set forth to illustrate but are not to be construed to limit the present invention.

PREPARATION EXAMPLE (1) Preparation of the Following Compounds A-1, A-2, A-3, A-4

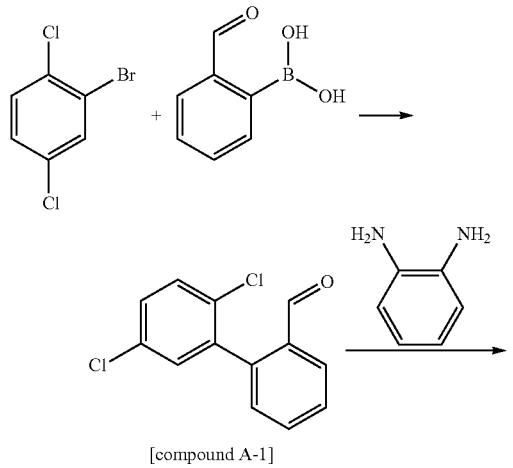

[compound A-1]

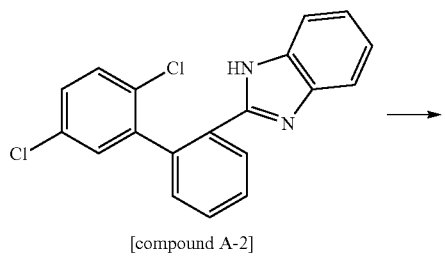

[compound A-2]

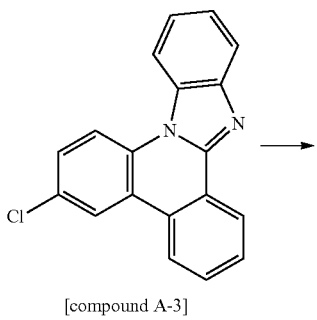

[compound A-3]

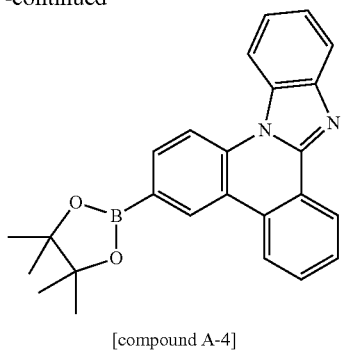

[compound A-4]

Preparation Example 1

Preparation of the Compound A-1

After 1-bromo-2,5-dichlorobenzene (15.6 g, 69.1 mmol) and 2-formylphenylboronic acid (11.4 g, 76 mmol) were dissolved in tetrahydrofuran (THF) (200 mL), 2M potassium carbonate aqueous solution (70 mL) was added thereto, and tetrakistriphenylphosphino palladium ($Pd(PPh_3)_4$) (1.6 g, 2 mol %) was put thereinto, agitated and refluxed for 5 hours. The temperature was lowered to normal temperature, the water layer was removed, and the organic layer was dried with anhydrous magnesium sulfate ($MgSO_4$) and filtered. The filtered solution was concentrated under the reduced pressure, and columned with tetrahydrofuran:hexane=1:10 to prepare the compound A-1 (13.9 g, 80%). MS: $[M+H]^+$=251

Preparation Example 2

Preparation of the Compound A-2

The compound A-1 (17.3 g, 69.1 mmol) that was prepared in Preparation Example 1 and diaminobenzene (7.47 g, 69.1 mmol) were suspended in dioxane (1,4-dioxane) (200 mL) and the acetic acid (AcOH) (20 mL). The mixture was agitated and refluxed for about 6 hours, and cooled to normal temperature. After the mixture was diluted with water (100 mL), the generated solid was filtered, washed with water and ethyl ether to prepare the compound A-2 (12.9 g, 55%). MS: $[M+H]^+$=339

Preparation Example 3

Preparation of the Compound A-3

The compound A-2 (1.7 g, 5.1 mmol) that was prepared in Preparation Example 2 and sodium-tertiary-butoxide (NaOt-Bu) (0.58 g, 6.01 mmol) and $Pd[P(t-Bu)_3]_2$ (51 mg, 2 mol %) were suspended in toluene (50 mL). The mixture was agitated and refluxed for about 6 hours, and cooled to normal temperature. Distilled water was put into the reaction solution, the termination of the reaction was carried out, and the organic material layer was extracted and dried with anhydrous magnesium sulfate ($MgSO_4$) and filtered. The filtered solution was concentrated under the reduced pressure, and columned with tetrahydrofuran:hexane=1:5 to prepare the compound A-3 (0.618 g, 40%). MS: $[M+H]^+$=303

Preparation Example 4

Preparation of the Compound A-4

The compound A-3 (5.1 g, 16.8 mmol) that was prepared in Preparation Example 3, bis(pinacolato)diboron (4.7 g, 18.5 mmol) and potassium acetate (4.96 g, 50.5 mmol) were suspended in dioxane (100 mL). To the suspension solution, Pd(dba)$_2$ (0.29 g, 3 mol %) and PCy$_3$ (0.28 g, 6 mol %) were added. The mixture was agitated and refluxed for about 8 hours, and cooled to normal temperature. The mixture was diluted with water (100 mL), and extracted with dichloromethane (3×50 mL). The organic extract material was dried over magnesium sulfate and filtered. The filtered solution was concentrated under the reduced pressure, recrystallized with ethyl ether and hexane to prepare the compound A-4 (5.62 g, 85%). MS: [M+H]$^+$=395

(2) Preparation of the Following Compounds A-5, A-6, A-7

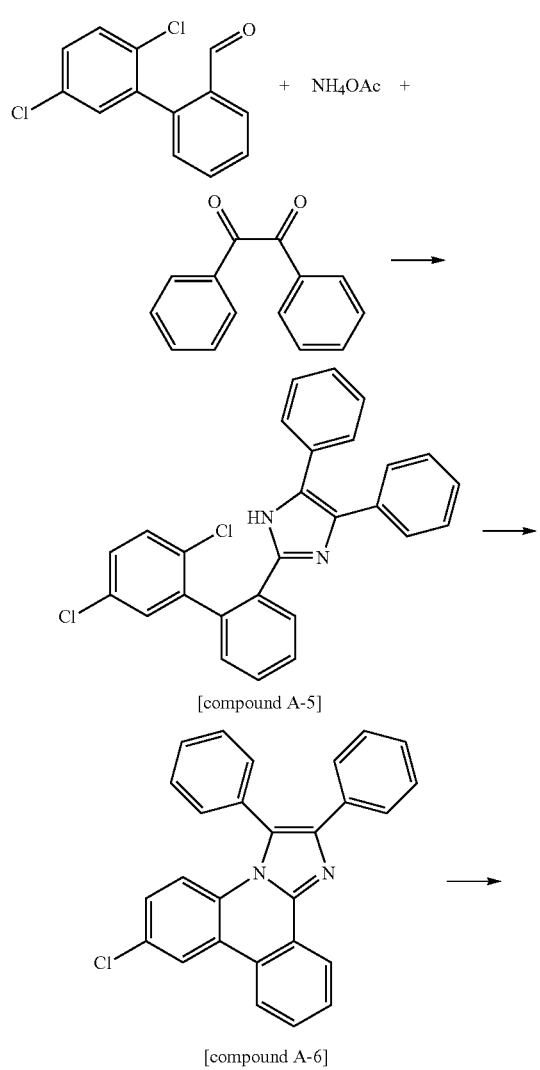

[compound A-5]

[compound A-6]

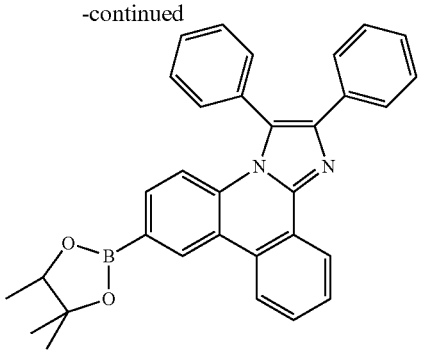

[compound A-7]

Preparation Example 5

Preparation of the Compound A-5

The compound A-2 (2.51 g, 10 mmol) that was prepared in Preparation Example 2, Benzil (2.1 g, 10 mmol), and ammonium acetate (2.32 g, 30 mmol) were suspended in the acetic acid (20 mL). The mixture was agitated and refluxed for about 6 hours, and cooled to normal temperature. After the mixture was diluted with water (50 mL), the generated solid was filtered, washed with water and ethyl ether to prepare the compound (2.73 g, 62%). MS: [M+H]$^+$=441

Preparation Example 6

Preparation of the Compound A-6

The compound A-6 (0.929 g, 45%) was prepared by using the same method as Preparation Example 3, except that the compound A-5 that was prepared in Preparation Example 5 was used instead of the compound A-2 in Preparation Example 3. MS: [M+H]$^+$=405

Preparation Example 1

Preparation of the Compound A-7

The compound A-7 (6.85 g, 82%) was prepared by using the same method as Preparation Example 4, except that the compound A-6 that was prepared in Preparation Example 6 was used instead of the compound A-3 in Preparation Example 4. MS: [M+H]$^+$=497

(3) Preparation of the Following Compounds A-8, A-9, A-10

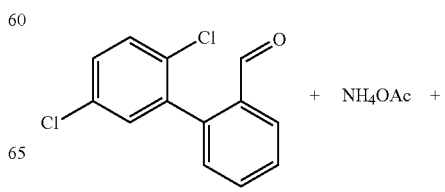 + NH$_4$OAc +

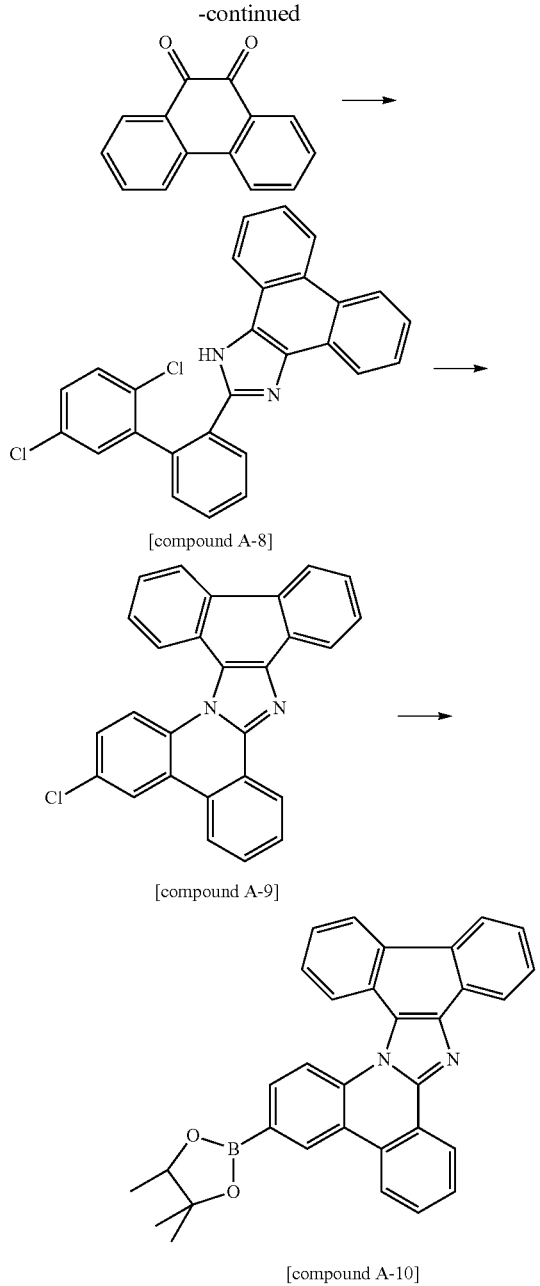

[compound A-8]

[compound A-9]

[compound A-10]

Preparation Example 8

Preparation of the Compound A-8

The compound A-2 (2.51 g, 10 mmol) that was prepared in Preparation Example 2,9,10-Phenanthrenequinone (2.08 g, 10 mmol) and ammonium acetate (2.32 g, 30 mmol) were suspended in the acetic acid (20 mL). The mixture was agitated and refluxed for about 6 hours, and cooled to normal temperature. After the mixture was diluted with water (50 mL), the generated solid was filtered, washed with water and ethyl ether to prepare the compound A-8 (3.07 g, 70%). MS: $[M+H]^+$=439

Preparation Example 9

Preparation of the Compound A-9

The compound A-9 (0.863 g, 42%) was prepared by using the same method as Preparation Example 3, except that the compound A-8 that was prepared in Preparation Example 8 was used instead of the compound A-2 in Preparation Example 3. MS: $[M+H]^+$=403

Preparation Example 10

Preparation of the Compound A-10

The compound A-10 (6.24 g, 75%) was prepared by using the same method as Preparation Example 4, except that the compound A-9 that was prepared in Preparation Example 9 was used instead of the compound A-3 in Preparation Example 4. MS: $[M+H]^+$=495

(4) Preparation of the Following Compounds A-11, A-12, A-13, A-14

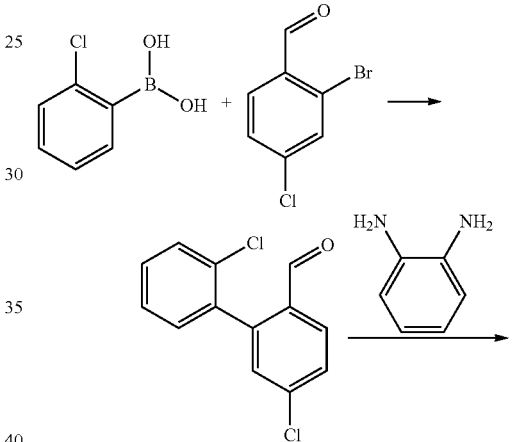

[compound A-11]

[compound A-12]

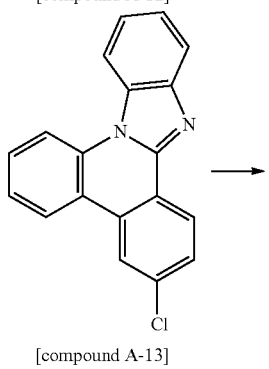

[compound A-13]

-continued

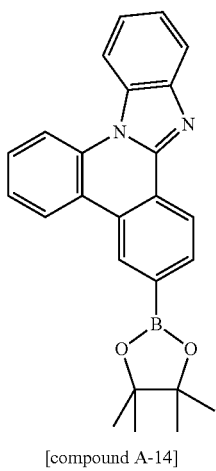
[compound A-14]

Preparation Example 11

Preparation of the Compound A-11

After 2-bromo-4-chlorobenzaldehyde (15.1 g, 69.1 mmol) and 2-chlorophenylboronic acid (11.9 g, 76 mmol) were dissolved in tetrahydrofuran (THF) (200 mL), 2M potassium carbonate aqueous solution (70 mL) was added thereto, and tetrakistriphenylphosphino palladium (Pd(PPh$_3$)$_4$ (1.6 g, 2 mol %) was put thereinto, agitated and refluxed for 5 hours. The temperature was lowered to normal temperature, the water layer was removed, and the organic layer was dried with anhydrous magnesium sulfate and filtered. The filtered solution was concentrated under the reduced pressure, and columned with tetrahydrofuran:hexane=1:10 to prepare the compound A-11 (13.0 g, 80%). MS: [M+H]$^+$=251

Preparation Example 12

Preparation of the Compound A-12

The compound A-11 (17.3 g, 69.1 mmol) that was prepared in Preparation Example 11 and diaminobenzene (7.47 g, 69.1 mmol) were suspended in dioxane (1,4-dioxane) (200 mL) and the acetic acid (AcOH) (20 mL). The mixture was agitated and refluxed for about 6 hours, and cooled to normal temperature. After the mixture was diluted with water (100 mL), the generated solid was filtered, washed with water and ethyl ether to prepare the compound A-12 (13.4 g, 57%). MS: [M+H]$^+$=339

Preparation Example 13

Preparation of the Compound A-13

The compound A-12 (1.7 g, 5.1 mmol) that was prepared in Preparation Example 12 and sodium-tertiary-butoxide (NaOt-Bu) (0.58 g, 6.01 mmol) and Pd[P(t-Bu)$_3$]$_{12}$ (51 mg, 2 mol %) were suspended in toluene (50 mL). The mixture was agitated and refluxed for about 6 hours, and cooled to normal temperature. Distilled water was put into the reaction solution, the termination of the reaction was carried out, and the organic material layer was extracted and dried with anhydrous magnesium sulfate (MgSO$_4$) and filtered. The filtered solution was concentrated under the reduced pressure, and columned with tetrahydrofuran:hexane=1:5 to prepare the compound A-13 (0.664 g, 43%). MS: [M+H]$^+$=303

Preparation Example 14

Preparation of the Compound A-14

The compound A-13 (5.1 g, 16.8 mmol) that was prepared in Preparation Example 13, bis(pinacolato)diboron (4.7 g, 18.5 mmol) and potassium acetate (4.96 g, 50.5 mmol) were suspended in dioxane (100 mL). To the suspension solution, Pd(dba)$_2$ (0.29 g, 3 mol %) and PCy$_3$ (0.28 g, 6 mol %) were added. The mixture was agitated and refluxed for about 8 hours, and cooled to normal temperature. The mixture was diluted with water (100 mL), and extracted with dichloromethane (3×50 mL). The organic extract material was dried over magnesium sulfate and filtered. The filtered solution was concentrated under the reduced pressure, recrystallized with ethyl ether and hexane to prepare the compound A-14 (5.95 g, 90%). MS: [M+H]$^+$=395

(5) Preparation of the Following Compounds A-15, A-16, A-17

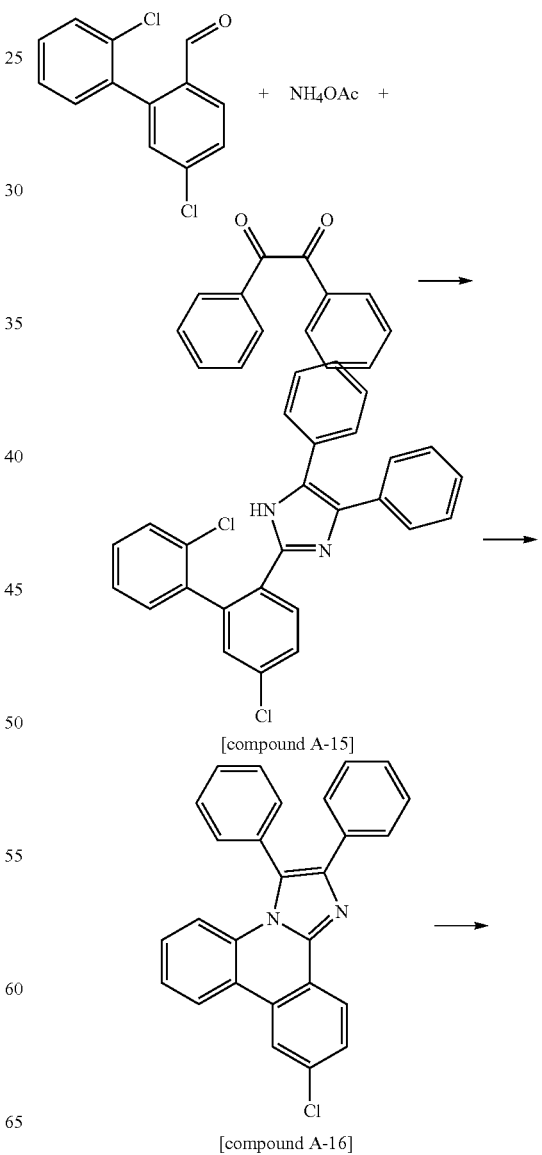
[compound A-15]

[compound A-16]

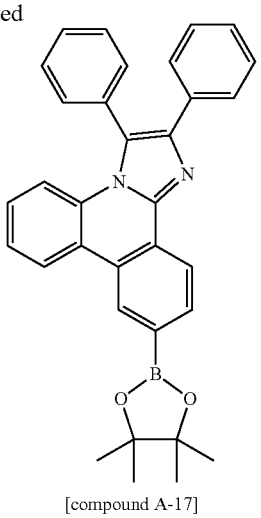

[compound A-17]

Preparation Example 15

Preparation of the Compound A-15

The compound A-12 (2.51 g, 10 mmol) that was prepared in Preparation Example 12, benzil (2.1 g, 10 mmol) and ammonium acetate (2.32 g, 30 mmol) were suspended in the acetic acid (20 mL). The mixture was agitated and refluxed for about 6 hours, and cooled to normal temperature. After the mixture was diluted with water (50 mL), the generated solid was filtered, washed with water and ethyl ether to prepare the compound A-15 (3.09 g, 70%). MS: $[M+H]^+=441$ Preparation Example 16

Preparation of the Compound A-16

The compound A-16 (0.847 g, 41%) was prepared by using the same method as Preparation Example 13, except that the compound A-15 that was prepared in Preparation Example 15 was used instead of the compound A-12 in Preparation Example 13. MS: $[M+H]^+=405$ Preparation Example 17

Preparation of the Compound A-17

The compound A-17 (7.09 g, 85%) was prepared by using the same method as Preparation Example 14, except that the compound A-16 that was prepared in Preparation Example 16 was used instead of the compound A-13 in Preparation Example 14. MS: $[M+H]^+=497$ (6) Preparation of the Following Compounds A-18, A-19, A-20

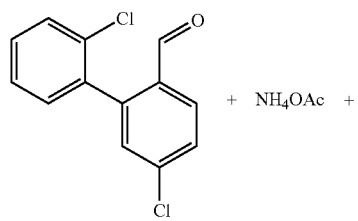 + NH₄OAc +

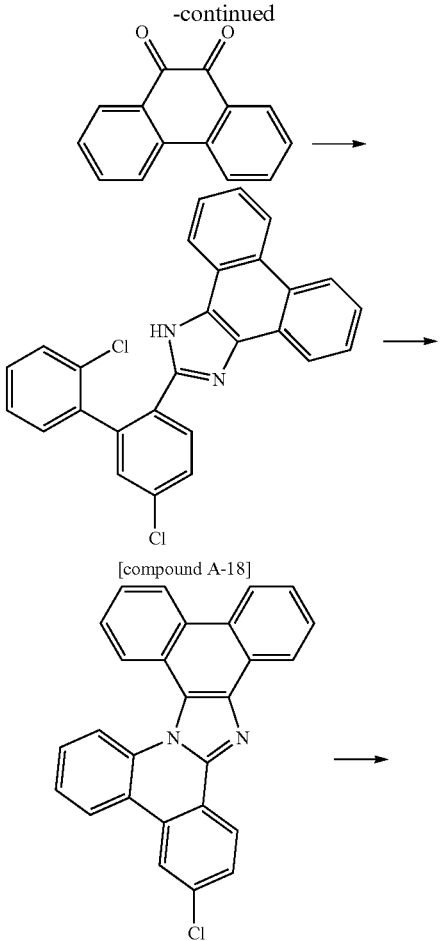

[compound A-18]

[compound A-19]

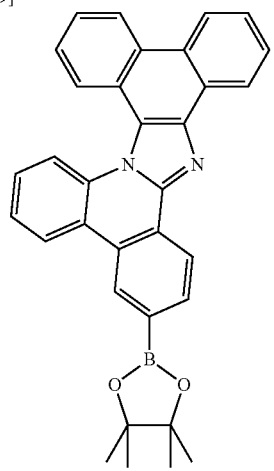

[compound A-20]

Preparation Example 18

Preparation of the Compound A-18

The compound A-12 (2.51 g, 10 mmol) that was prepared in Preparation Example 12, 9,10-Phenanthrenequinone (2.08 g, 10 mmol) and ammonium acetate (2.32 g, 30 mmol) were suspended in the acetic acid (20 mL). The mixture was agitated and refluxed for about 6 hours, and cooled to normal temperature. After the mixture was diluted with water (50 mL), the generated solid was filtered, washed with water and ethyl ether to prepare the compound A-18 (3.51 g, 80%). MS: [M+H]$^+$=439

Preparation Example 19

Preparation of the Compound A-19

The compound A-19 (0.822 g, 40%) was prepared by using the same method as Preparation Example 13, except that the compound A-18 that was prepared in Preparation Example 18 was used instead of the compound A-12 in Preparation Example 13. MS: [M+H]$^+$=403

Preparation Example 20

Preparation of the Compound A-20

The compound A-20 (6.82 g, 82%) was prepared by using the same method as Preparation Example 14, except that the compound A-19 that was prepared in Preparation Example 19 was used instead of the compound A-13 in Preparation Example 14. MS: [M+H]$^+$=495

(7) Preparation of the Following Compounds A-21, A-22, A-23, A-24

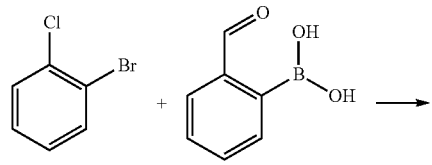

[compound A-21]

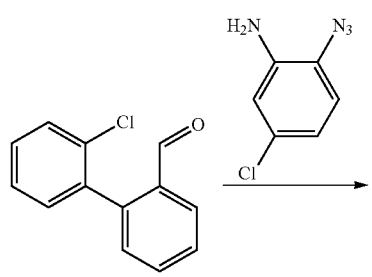

[compound A-22]

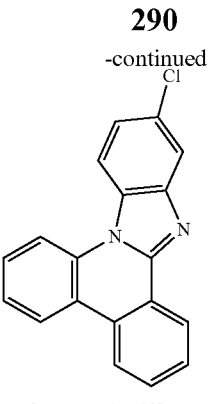

[compound A-23]

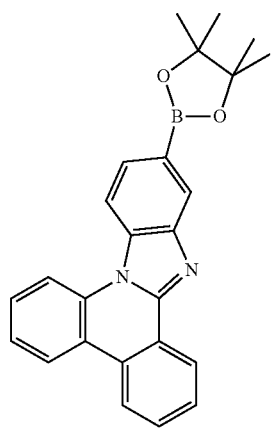

[compound A-24]

Preparation Example 21

Preparation of the Compound A-21

After 2-chloro-bromobenzene (13.2 g, 69.1 mmol) and 2-formylphenylboronic acid (11.4 g, 76 mmol) were dissolved in tetrahydrofuran (THF) (200 mL), 2M potassium carbonate aqueous solution (70 mL) was added thereto, and tetrakistriphenylphosphino palladium (Pd(PPh$_3$)$_4$ (1.6 g, 2 mol %) was put thereinto, agitated and refluxed for 5 hours. The temperature was lowered to normal temperature, the water layer was removed, and the organic layer was dried with anhydrous magnesium sulfate and filtered. The filtered solution was concentrated under the reduced pressure, and columned with tetrahydrofuran:hexane=1:10 to prepare the compound A-21 (11.2 g, 75%). MS: [M+H]$^+$=217

Preparation Example 22

Preparation of the Compound A-22

The compound A-21 (14.9 g, 69.1 mmol) that was prepared in Preparation Example 21 and 2-azido-5-chlorobenzeneamine (11.6 g, 69.1 mmol) were suspended in ethanol (200 mL) and the acetic acid (10 mL). The mixture was agitated and refluxed for about 21 hours. The temperature was lowered to normal temperature, concentrated under the reduced pressure, and recrystallized with hexane to prepare the compound A-22 (5.85 g, 25%). MS: [M+H]$^+$=339

Preparation Example 23

Preparation of the Compound A-23

The compound A-22 (1.73 g, 5.1 mmol) that was prepared in Preparation Example 22 and sodium-tertiary-butoxide (NaOt-Bu) (0.58 g, 6.01 mmol) and Pd[P(t-Bu)$_3$]$_{22}$ (51 mg, 2 mol %) were suspended in toluene (50 mL). The mixture was agitated and refluxed for about 6 hours, and cooled to normal temperature. Distilled water was put into the reaction solution, the termination of the reaction was carried out, and the organic material layer was extracted and dried with anhydrous magnesium sulfate and filtered. The filtered solution was concentrated under the reduced pressure, and columned with tetrahydrofuran:hexane=1:5 to prepare the compound A-23 (0.618 g, 40%). MS: [M+H]$^+$=303

Preparation Example 24

Preparation of the Compound A-24

The compound A-23 (5.09 g, 16.8 mmol) that was prepared in Preparation Example 23, bis(pinacolato)diboron (4.7 g, 18.5 mmol) and potassium acetate (4.96 g, 50.5 mmol) were suspended in dioxane (100 mL). To the suspension solution, Pd(dba)$_2$ (0.29 g, 3 mol %) and PCy$_3$ (0.28 g, 6 mol %) were added. The mixture was agitated and refluxed for about 8 hours, and cooled to normal temperature. The mixture was diluted with water (100 mL), and extracted with dichloromethane (3×50 mL). The organic extract material was dried over magnesium sulfate and filtered. The filtered solution was concentrated under the reduced pressure, recrystallized with ethyl ether and hexane to prepare the compound A-24 (5.3 g, 80%). MS: [M+H]$^+$=395

(8) Preparation of the Following Compounds A-25, A-26-1, A-26-2

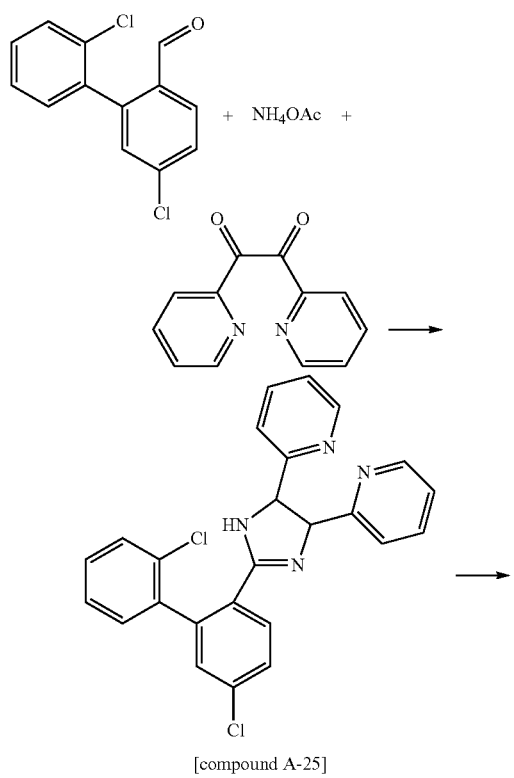

[compound A-25]

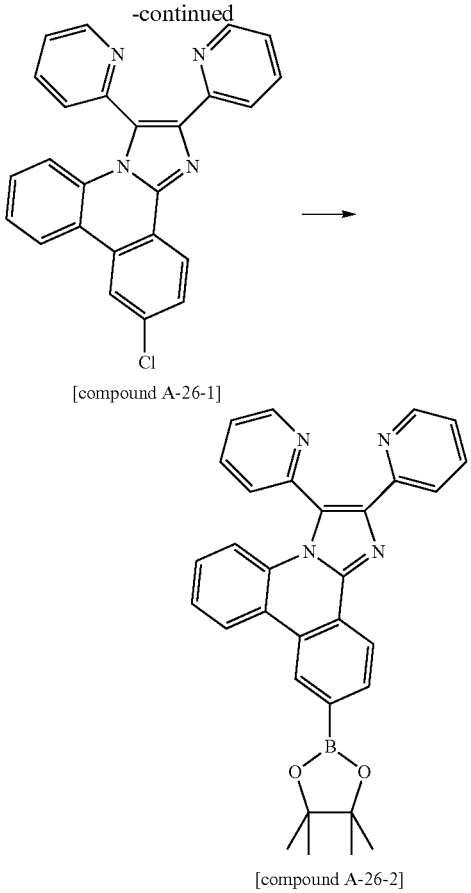

[compound A-26-1]

[compound A-26-2]

Preparation Example 25

Preparation of the Compound A-25

The compound A-11 (2.51 g, 10 mmol) that was prepared in Preparation Example 11, 2,2'-Pyridil (2.12 g, 10 mmol) and ammonium acetate (2.32 g, 30 mmol) were suspended in the acetic acid (20 mL). The mixture was agitated and refluxed for about 6 hours, and cooled to normal temperature. After the mixture was diluted with water (50 mL), the generated solid was filtered, washed with water and ethyl ether to prepare the compound A-25 (2.66 g, 60%).
MS: [M+H]$^+$=443

Preparation Example 26-1

Preparation of the Compound A-26-1

The compound A-26-1 (0.726 g, 35%) was prepared by using the same method as Preparation Example 13, except that the compound A-25 that was prepared in Preparation Example 25 was used instead of the compound A-12 in Preparation Example 13. MS: [M+H]$^+$=407

Preparation Example 26-2

Preparation of the Compound A-26-2

The compound A-26-2 (3.35 g, 40%) was prepared by using the same method as Preparation Example 14, except that the compound A-26-1 that was prepared as described above was used instead of the compound A-13 in Preparation Example 14. MS: [M+H]⁺=499

(9) Preparation of the Following Compounds A-27, A-28, A-29, A-30

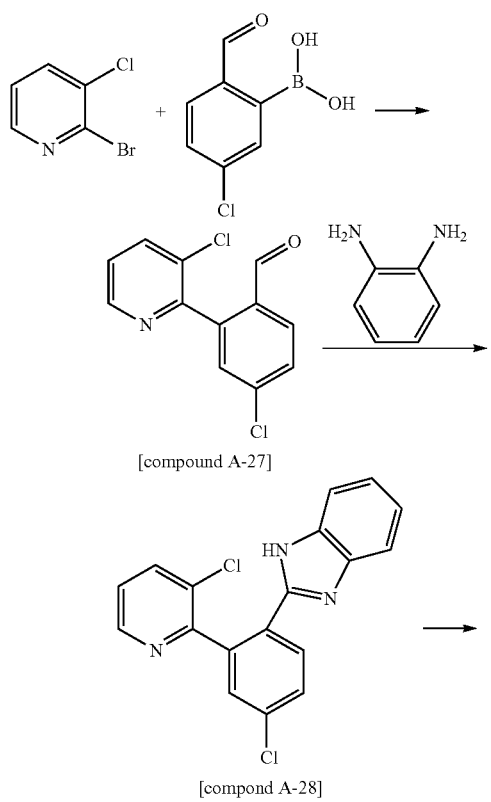

[compound A-27]

[compond A-28]

[compound A-29]   [compound A-30]

Preparation Example 27

Preparation of the Compound A-27

After 2-bromo-3-chloro-pyridine (13.26 g, 69.1 mmol) and 5-chloro-2-formyl-benzeneboronic acid (13.98 g, 76 mmol) were dissolved in tetrahydrofuran (THF) (200 mL), 2M potassium carbonate aqueous solution (70 mL) was added thereto, and tetrakistriphenylphosphino palladium (Pd(PPh₃)₄ (1.6 g, 2 mol %) was put thereinto, agitated and refluxed for 5 hours. The temperature was lowered to normal temperature, the water layer was removed, and the organic layer was dried with anhydrous magnesium sulfate and filtered. The filtered solution was concentrated under the reduced pressure, recrystallized with hexane to prepare the compound A-27 (7 g, 40%). MS: [M+H]⁺=252

Preparation Example 28

Preparation of the Compound A-28

The compound A-28 (9.4 g, 40%) was prepared by using the same method as Preparation Example 12, except that the compound A-27 that was prepared in Preparation Example 27 was used instead of the compound A-11 in Preparation Example 12. MS: [M+H]⁺=340

Preparation Example 29

Preparation of the Compound A-29

The compound A-29 (0.620 g, 40%) was prepared by using the same method as Preparation Example 13, except that the compound A-28 that was prepared in Preparation Example 28 was used instead of the compound A-12 in Preparation Example 13. MS: [M+H]⁺=304

Preparation Example 30

Preparation of the Compound A-30

The compound A-30 (4.32 g, 65%) was prepared by using the same method as Preparation Example 14, except that the compound A-29 that was prepared in Preparation Example 29 was used instead of the compound A-13 in Preparation Example 14. MS: [M+H]⁺=396

(10) Preparation of the Following Compounds A-31, A-32, A-33, A-34

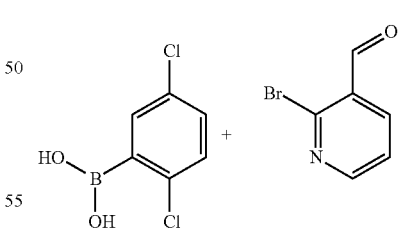

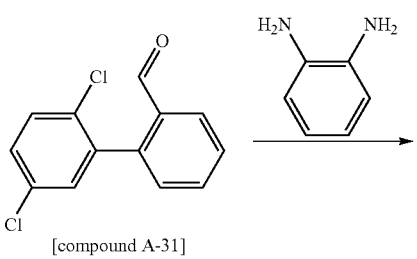

[compound A-31]

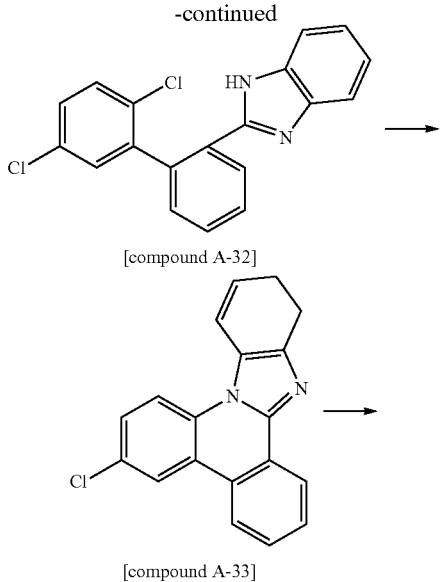

[compound A-32]

[compound A-33]

[compound A-34]

Preparation Example 31

Preparation of the Compound A-31

After 2-bromo-3-formyl-pyridine (12.85 g, 69.1 mmol) and 2,5-dichloro-benzeneboronic acid (14.4 g, 76 mmol) were completely dissolved in tetrahydrofuran (THF) (200 mL), 2M potassium carbonate aqueous solution (70 mL) was added thereto, and tetrakistriphenylphosphino palladium (Pd (PPh$_3$)$_4$ (1.6 g, 2 mol %) was put thereinto, agitated and refluxed for 5 hours. The temperature was lowered to normal temperature, the water layer was removed, and the organic layer was dried with anhydrous magnesium sulfate and filtered. The filtered solution was concentrated under the reduced pressure, recrystallized with hexane to prepare the compound A-31 (7.83 g, 45%).

MS: $[M+H]^+=252$

Preparation Example 32

Preparation of the Compound A-32

The compound A-32 (10.6 g, 45%) was prepared by using the same method as Preparation Example 2, except that the compound A-31 that was prepared in Preparation Example 31 was used instead of the compound A-1 in Preparation Example 2. MS: $[M+H]^+=340$

Preparation Example 33

Preparation of the Compound A-33

The compound A-33 (0.542 g, 35%) was prepared by using the same method as Preparation Example 3, except that the compound A-32 that was prepared in Preparation Example 32 was used instead of the compound A-2 in Preparation Example 3. MS: $[M+H]^+=304$

Preparation Example 34

Preparation of the Compound A-34

The compound A-34 (3.66 g, 55%) was prepared by using the same method as Preparation Example 4, except that the compound A-33 that was prepared in Preparation Example 33 was used instead of the compound A-3 in Preparation Example 4. MS: $[M+H]^+=396$

(11) Preparation of the Following Compounds A-35, A-36, A-37, A-38

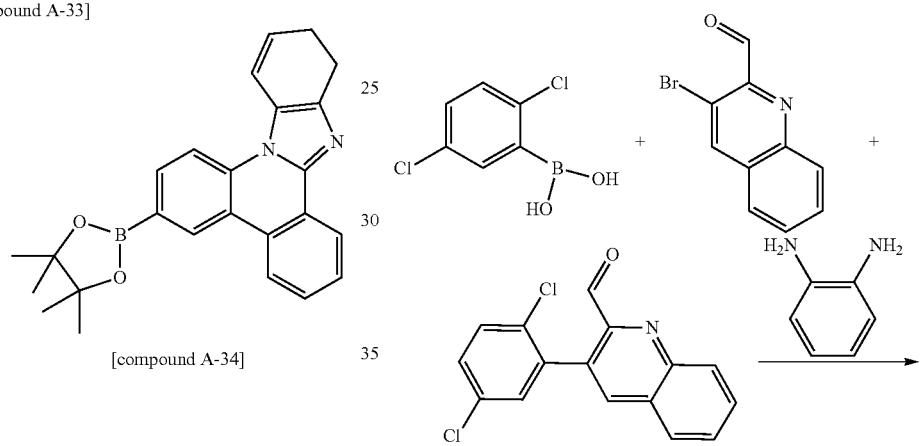

[compound A-35]

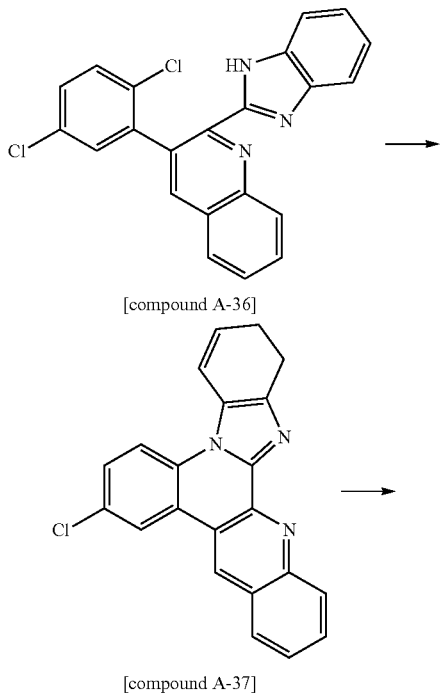

[compound A-36]

[compound A-37]

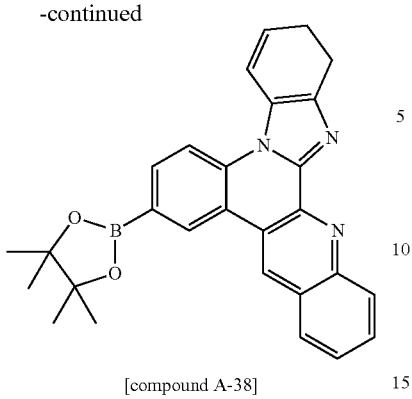

[compound A-38]

Preparation Example 35

Preparation of the Compound A-35

After 3-bromo-2-formyl-pyridine (16.3 g, 69.1 mmol) and 2,5-dichloro-benzeneboronic acid (14.4 g, 76 mmol) were completely dissolved in tetrahydrofuran (THF) (200 mL), 2M potassium carbonate aqueous solution (70 mL) was added thereto, and tetrakistriphenylphosphino palladium (Pd (PPh$_3$)$_4$ (1.6 g, 2 mol %) was put thereinto, agitated and refluxed for 5 hours. The temperature was lowered to normal temperature, the water layer was removed, and the organic layer was dried with anhydrous magnesium sulfate and filtered. The filtered solution was concentrated under the reduced pressure, recrystallized with ethylether to prepare the compound A-35 (14.6 g, 70%). MS: [M+H]$^+$=302

Preparation Example 36

Preparation of the Compound A-36

The compound A-36 (16.2 g, 60%) was prepared by using the same method as Preparation Example 2, except that the compound A-35 that was prepared in Preparation Example 35 was used instead of the compound A-1 in Preparation Example 2. MS: [M+H]$^+$=390

Preparation Example 37

Preparation of the Compound A-37

The compound A-37 (0.722 g, 40%) was prepared by using the same method as Preparation Example 3, except that the compound A-32 that was prepared in Preparation Example 32 was used instead of the compound A-2 in Preparation Example 3. MS: [M+H]$^+$=354

Preparation Example 38

Preparation of the Compound A-38

The compound A-38 (5.24 g, 70%) was prepared by using the same method as Preparation Example 4, except that the compound A-33 that was prepared in Preparation Example 33 was used instead of the compound A-3 in Preparation Example 4. MS: [M+H]$^+$=446

(12) Preparation of the Following Compounds A-39, A-40, A-41, A-42

[compound A-39] [compound A-40] [compound A-41] [compound A-42]

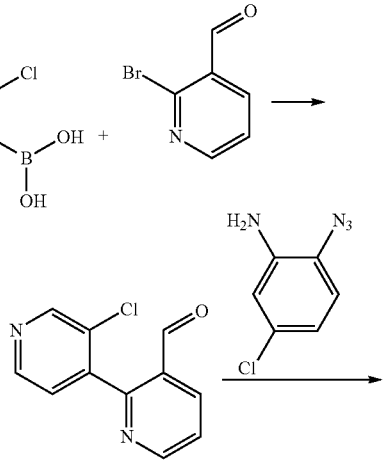

[compound A-39]

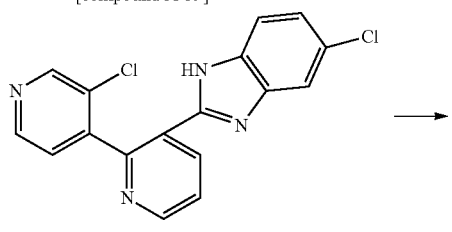

[compound A-40]

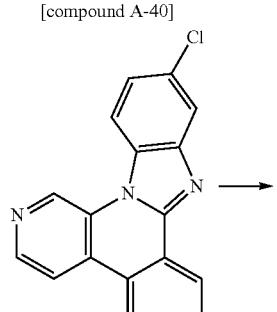

[compound A-41]

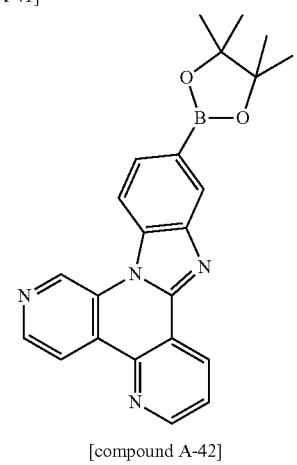

[compound A-42]

Preparation Example 39

Preparation of the Compound A-39

After 2-bromo-3-formyl-pyridine (1.86 g, 10 mmol) and 3-chloro-4-pyridylboronic acid (1.57 g, 10 mmol) were dissolved in tetrahydrofuran (THF) (30 mL), 2M potassium carbonate aqueous solution (20 mL) was added thereto, and tetrakistriphenylphosphino palladium (Pd(PPh$_3$)$_4$ (231 mg, 2 mol %) was put thereinto, agitated and refluxed for 5 hours. The temperature was lowered to normal temperature, the water layer was removed, and the organic layer was dried with anhydrous magnesium sulfate and filtered. The filtered solution was concentrated under the reduced pressure to prepare the compound A-39 (1.31 g, 60%). MS: [M+H]$^+$=219

Preparation Example 40

Preparation of the Compound A-40

The compound A-40 (5.9 g, 25%) was prepared by using the same method as Preparation Example 22, except that the compound A-39 that was prepared in Preparation Example 39 was used instead of the compound A-21 in Preparation Example 22. MS: [M+H]$^+$=341

Preparation Example 41

Preparation of the Compound A-41

The compound A-41 (0.622 g, 40%) was prepared by using the same method as Preparation Example 23, except that the compound A-40 that was prepared in Preparation Example 40 was used instead of the compound A-22 in Preparation Example 23. MS: [M+H]$^+$=305

Preparation Example 42

Preparation of the Compound A-42

The compound A-42 (4.67 g, 70%) was prepared by using the same method as Preparation Example 24, except that the compound A-41 that was prepared in Preparation Example 41 was used instead of the compound A-23 in Preparation Example 24. MS: [M+H]$^+$=397

(13) Preparation of the Following Compounds A-43, A-44, A-45, A-46

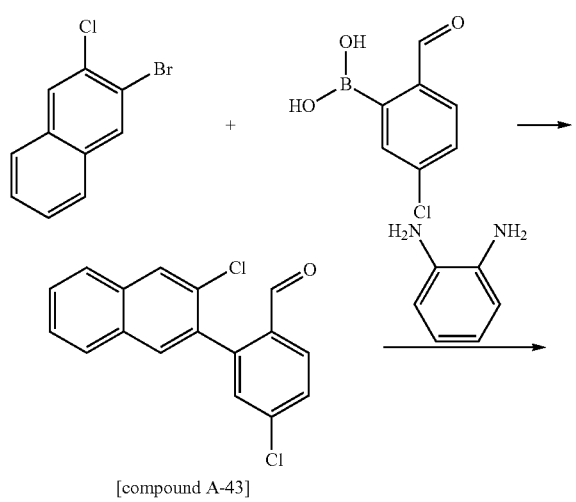

[compound A-43]

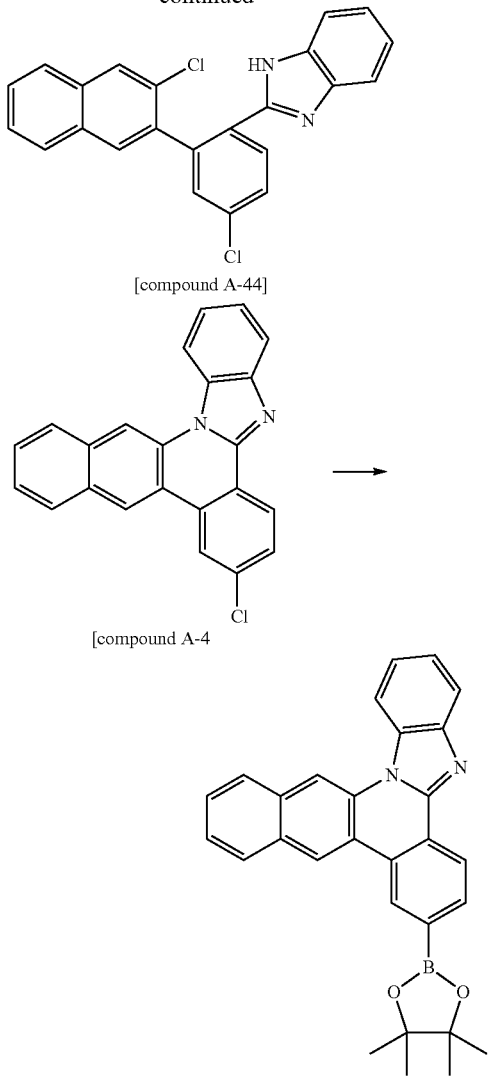

[compound A-44]

[compound A-4]

[compound A-46]

Preparation Example 43

Preparation of the Compound A-44

After 2-bromo-3-chloronaphthalene (2.41 g, 10 mmol) and 5-chloro-2-formyl-phenylboronic acid (1.84 g, 10 mmol) were completely dissolved in tetrahydrofuran (50 mL), 2M potassium carbonate aqueous solution (30 mL) was added thereto, and tetrakistriphenylphosphino palladium (Pd (PPh$_3$)$_4$ (231 mg, 2 mol %) was put thereinto, agitated and refluxed for 5 hours. The temperature was lowered to normal temperature, the water layer was removed, and the organic layer was dried with anhydrous magnesium sulfate and filtered. The filtered solution was concentrated under the reduced pressure, recrystallized with ethylether to prepare the compound A-43 (2.41 g, 80%). MS: [M+H]$^+$=301

Preparation Example 44

Preparation of the Compound A-44

The compound A-44 (18.82 g, 70%) was prepared by using the same method as Preparation Example 12, except that the compound A-43 that was prepared in Preparation Example 43 was used instead of the compound A-11 in Preparation Example 12. MS: [M+H]⁺=389

Preparation Example 45

Preparation of the Compound A-45

The compound A-45 (0.81 g, 45%) was prepared by using the same method as Preparation Example 13, except that the compound A-44 that was prepared in Preparation Example 44 was used instead of the compound A-12 in Preparation Example 13. MS: [M+H]⁺=353

Preparation Example 46

Preparation of the Compound A-46

The compound A-46 (5.98 g, 80%) was prepared by using the same method as Preparation Example 14, except that the compound A-45 that was prepared in Preparation Example 45 was used instead of the compound A-13 in Preparation Example 14. MS: [M+H]⁺=445

(14) Preparation of the Following Compounds A-47, A-48, A-49, A-50

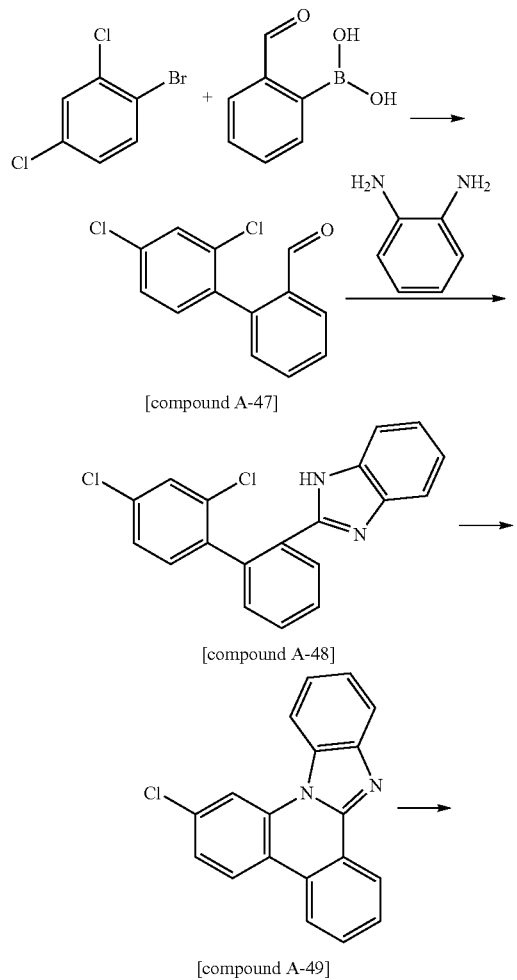

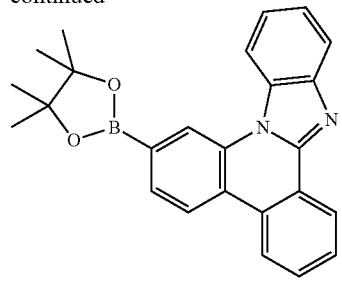

[compound A-50]

Preparation Example 47

Preparation of the Compound A-47

The compound A-47 (13.9 g, 25%) was prepared by using the same method as Preparation Example 1, except that 1-bromo-2,4-dichlorobenzene was used instead of the 1-bromo-2,5-dichlorobenzene compound in Preparation Example 1. MS: [M+H]⁺=251

Preparation Example 48

Preparation of the Compound A-48

The compound A-48 (12.9 g, 55%) was prepared by using the same method as Preparation Example 2, except that the compound A-47 that was prepared in Preparation Example 47 was used instead of the compound A-1 in Preparation Example 2. MS: [M+H]⁺=339

Preparation Example 49

Preparation of the Compound A-49

The compound A-49 (0.695 g, 45%) was prepared by using the same method as Preparation Example 3, except that the compound A-48 that was prepared in Preparation Example 48 was used instead of the compound A-2 in Preparation Example 3. MS: [M+H]⁺=303

Preparation Example 50

Preparation of the Compound A-50

The compound A-50 (5.62 g, 85%) was prepared by using the same method as Preparation Example 4, except that the compound A-49 that was prepared in Preparation Example 49 was used instead of the compound A-3 in Preparation Example 4. MS: [M+H]⁺=395

(15) Preparation of the Following Compounds A-51, A-52, A-53, A-54

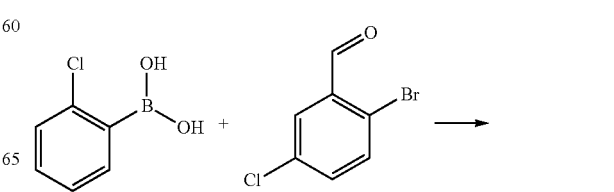

-continued

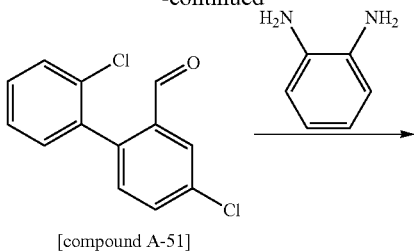

[compound A-51]

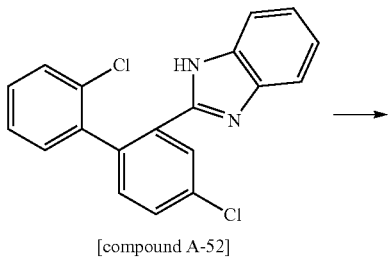

[compound A-52]

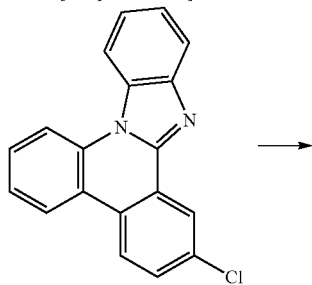

[compound A-53]

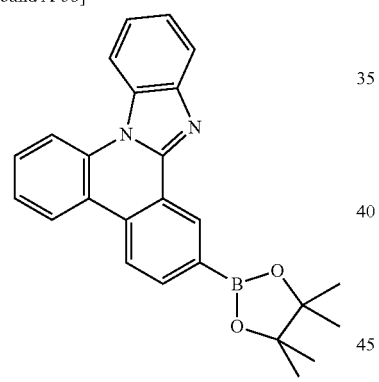

[compound A-54]

Preparation Example 51

Preparation of the Compound A-51

The compound A-51 was prepared by using the same method as Preparation Example 11, except that 2-bromo-5-dichlorobenzaldehyde was used instead of the 2-bromo-4-chlorobenzaldehyde compound in Preparation Example 11. MS: $[M+H]^+=251$ Preparation Example 52

Preparation of the Compound A-52

The compound A-52 (13.0 g, 80%) was prepared by using the same method as Preparation Example 12, except that the compound A-51 that was prepared in Preparation Example 51 was used instead of the compound A-11 in Preparation Example 12. MS: $[M+H]^+=339$ Preparation Example 53

Preparation of the Compound A-53

The compound A-53 (0.773 g, 50%) was prepared by using the same method as Preparation Example 13, except that the compound A-52 that was prepared in Preparation Example 52 was used instead of the compound A-12 in Preparation Example 13. MS: $[M+H]^+=303$ Preparation Example 54

Preparation of the Compound A-54

The compound A-54 (5.31 g, 80%) was prepared by using the same method as Preparation Example 14, except that the compound A-53 that was prepared in Preparation Example 53 was used instead of the compound A-11 in Preparation Example 14. MS: $[M+H]^+=395$ The following Preparation Examples are examples of intermediates progressed in order to prepare the compound of Formula 1.

Preparation Example 10

Preparation of the Compounds B-1, B-2, B-3

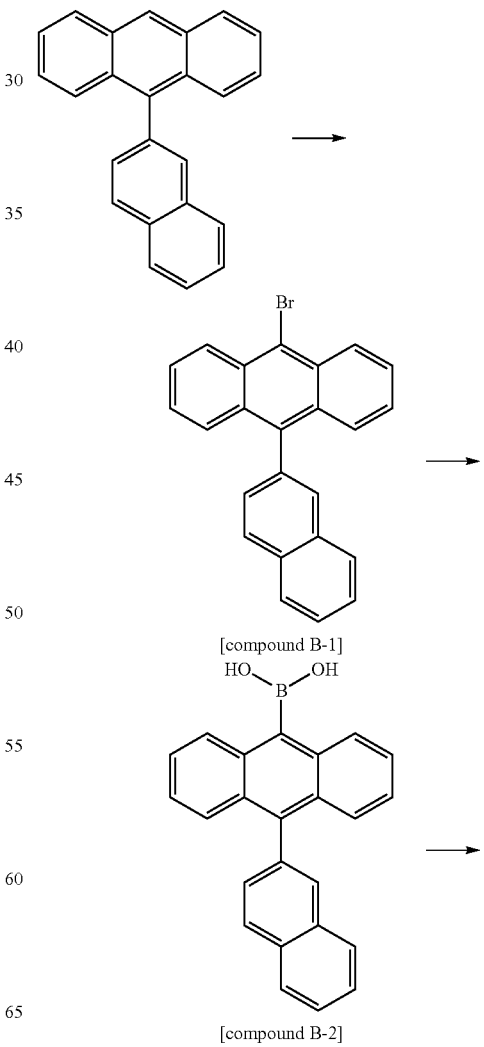

Preparation Example 102

Preparation of the Compounds B-4

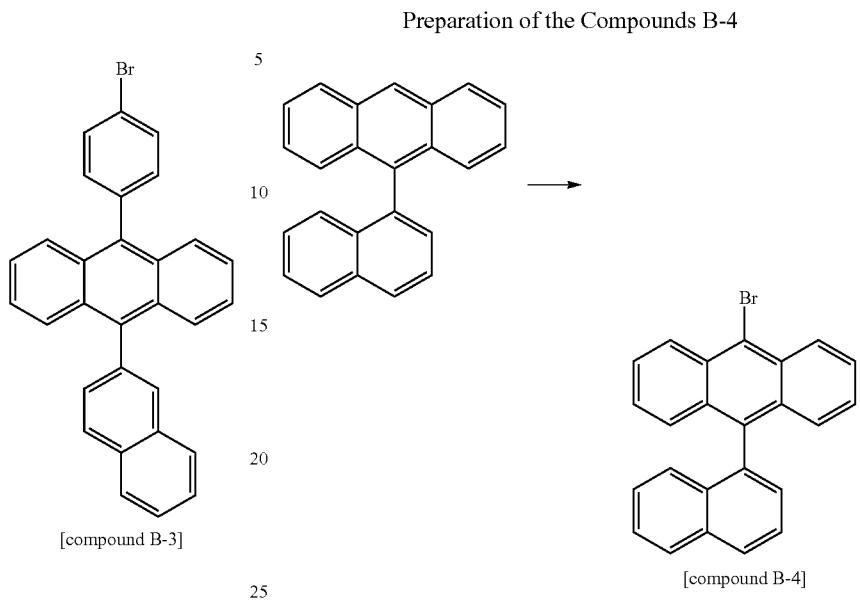

[compound B-3]

[compound B-4]

In the Preparation of the compound B-1 of Preparation Example 101, the compound B-4 (6.49 g, 70%)) was prepared by using the same method as the preparation method of the compound B-1, except that 9-(1-naphthyl)-anthracene was used instead of 9-(2-naphthyl)-anthracene. MS: $[M]^+=383$

Preparation Example 103

Preparation of the Compounds B-5, B-6

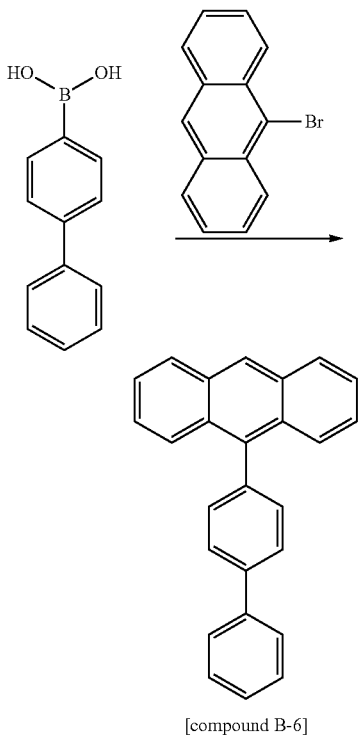

[compound B-6]

[Compound B-1]

9-(2-naphthyl)-anthracene (7.36 g, 24.2 mmol) was dissolved in chloroform (150 mL), acetic acid (150 mL) was added thereto, and $Br_2$ (1.3 mL, 25.4 mmol) was dropped at 0° C. The mixture was agitated at room temperature for 5 hour. After the reaction was finished, the reaction solution was recrystallized with ethanol to prepare the compound B-1 (6.49 g, 70%). MS: $[M]^+=383$

[Compound B-2]

The compound B-1 (6.86 g, 17.9 mmol) was dissolved in tetrahydrofuran (150 mL), the temperature was lowered to −78° C., and 1.7M tert-butyllithium (t-BuLi) (10.5 ml, 17.9 mmol) was slowly added thereto. After it was agitated for 1 hour at the same temperature, trimethyl borate ($B(OCH_3)_3$) (3.72 g, 35.8 mmol) was added thereto, and it was agitated for 3 hours while the temperature was slowly increased to normal temperature. 2N hydrochloric acid aqueous solution (30 ml) was added to the reaction mixture and agitated for 1.5 hours at normal temperature. The generated precipitate was filtered and sequentially washed with water and ethylether, and dried under the vacuum. It was dispersed in ethylether, agitated for 2 hours, filtered, and dried to prepare the compound B-2 (4.44 g, 71%). MS: $[M+H]^+=349$

[Compound B-3]

After the compound B-2 (3.48 g, 10.0 mmol) and 1-bromo-4-iodobenzene (3.4 g, 12.0 mmol) were dissolved in tetrahydrofuran (100 mL), 2M potassium carbonate aqueous solution (20 mL) was added thereto, and tetrakistriphenylphosphino palladium ($Pd(PPh_3)_4$) (0.231 g, 2 mol %) was put thereinto, agitated and refluxed for 5 hours. The temperature was cooled to normal temperature, and the produced solid was filtered. The filtered solid was dissolved in chloroform, and dried with anhydrous magnesium sulfate, and filtered. The reaction solution was concentrated under the reduced pressure and recrystallized with tetrahydrofuran and ethanol to prepare the compound B-3 (3.30 g, 72%). MS: $[M+H]^+=460$

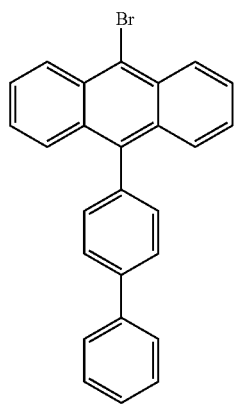

[compound B-6]

[Compound B-5]

9-bromoanthracene (8.2 g, 31.9 mmol), biphenyl boronic acid (7.6 g, 38.4 mmol) and Pd(PPh$_3$)$_4$ (0.737 g, 2 mol %) were put into 2M K$_2$CO$_3$ aqueous solution (300 mL) and tetrahydrofuran (300 mL), and refluxed and agitated for about 24 hours. It was cooled to normal temperature, the organic layer was separated from the reaction mixture solution, and the organic layer was dried with anhydrous magnesium sulfate, and filtered. The filtered solution was concentrated under the reduced pressure and recrystallized with tetrahydrofuran and ethanol to prepare the compound B-5 (8.5 g, 81%). MS: [M]$^+$=330

[Compound B-6]

In the Preparation of the compound B-1 of Preparation Example 101, the compound B-6 (7.03 g, 71%)) was prepared by using the same method as the preparation method of the compound B-1, except that the compound B-5 was used instead of 9-(2-naphthyl)-anthracene. MS: [M]$^+$=409

Preparation Example 104

Preparation of the Compounds B-7, B-8

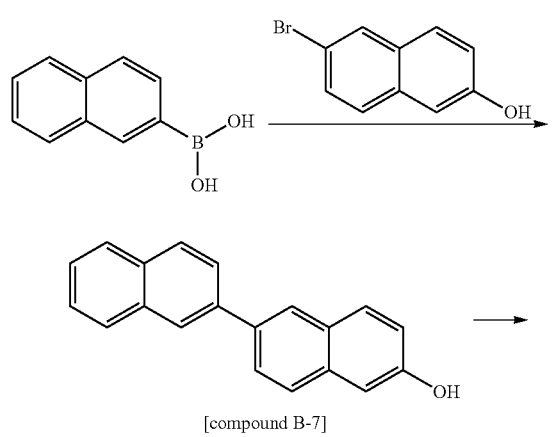

[compound B-7]

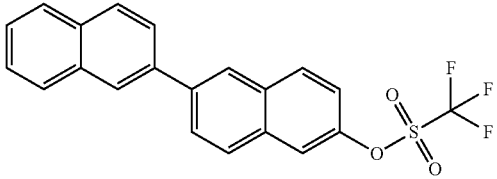

[compound B-8]

[Compound B-7]

After 2-naphthalene boronic acid (10 g 58.1 mmol) and 2-bromo-6-naphthol (10.8 g, 48.4 mmol) were completely dissolved in tetrahydrofuran (100 mL), 2M potassium carbonate aqueous solution (100 mL) was added thereto, and tetrakistriphenylphosphino palladium (Pd(PPh$_3$)$_4$ (1.12 g, 2 mol %) was put thereinto, agitated and refluxed for 5 hours. The temperature was lowered to normal temperature, the water layer was removed, and it was dried with anhydrous magnesium sulfate and filtered. The filtered solution was concentrated under the reduced pressure and recrystallized with hexane and ethanol to prepare the compound B-7 (8.5 g, 65%). MS: [M+H]$^+$=271

[Compound B-8]

After the compound B-7 (7.2 g, 26.7 mmol) was dissolved in dichloromethane, triethylamine (7.47 mL, 53.6 mmol) was added thereto, and agitated for 10 min. After the temperature was lowered to 0° C., trifluoromethanesulfonic acid ((CF$_3$SO$_2$)$_2$O) (6.76 mL, 40.2 mmol) was slowly added thereto, the temperature was increased to normal temperature, and it was agitated for 1 hour. After the sodium hydrogen carbonate aqueous solution was added, the water layer was removed, and water was removed with anhydrous magnesium sulfate. The filtered solution was concentrated under the reduced pressure and recrystallized with hexane and ethanol to prepare the compound B-8 (8.69 g, 81%). MS: [M+H]$^+$=403

Preparation Example 105

Preparation of the Compounds B-9, B-10

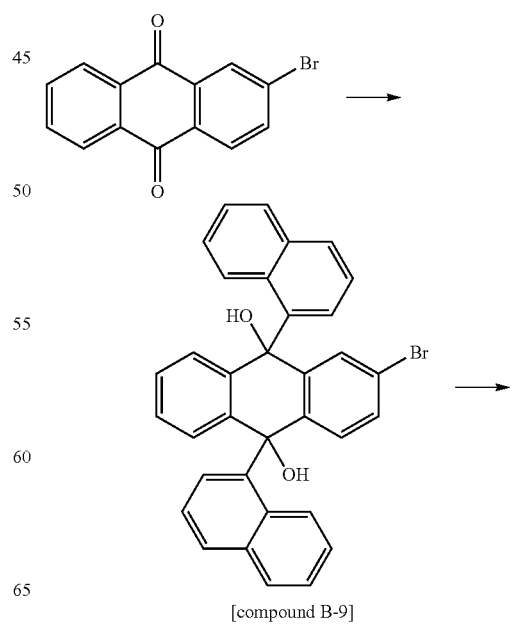

[compound B-9]

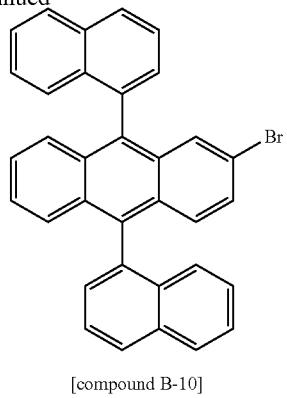

[compound B-10]

[Compound B-9]

1-bromonaphthalene (34.8 g, 168 mmol) was dissolved in tetrahydrofuran (170 ml), and cooled to −78° C., 2.5 M n-butyl lithium (67.3 ml, 168 mmol) was slowly added thereto, and it was agitated for 1 hour. 2-bromoanthraquinone (21 g, 73.1 mmol) was added, the temperature was increased to normal temperature, and it was agitated for 3 hours. The saturated ammonium chloride aqueous solution was added, the water layer was removed, dried with anhydrous magnesium sulfate, filtered, and dried under reduced pressure. It was recrystallized with ethylether to prepare the compound B-9 (32.5 g, 82%). MS: $[M+H]^+=544$

[Compound B-10]

The compound B-9 (32.3 g, 59.5 mmol), potassium iodide (29.6 g, 178.4 mmol) and sodium hyphophosphite (38 g, 256.8 mmol) were put into acetic acid (100 mL), and agitated and refluxed for 3 hours. The temperature was lowered to normal temperature, the generated precipitate was filtered, and washed with water and ethanol to prepare the compound B-10 (25.4 g, 84%). MS: $[M]^+=509$ Preparation Example 106

Preparation of the Compounds B-11, B-12, B-13

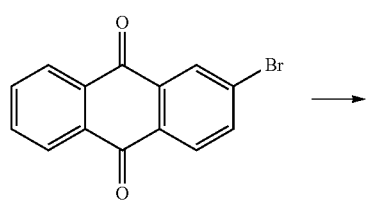

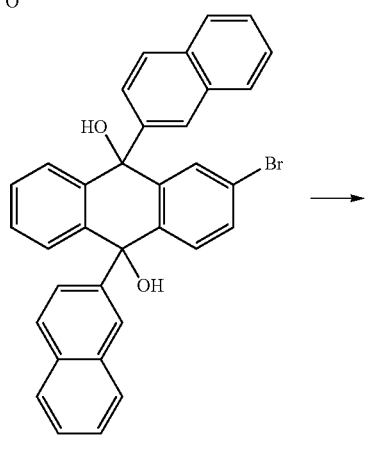

[compound B-11]

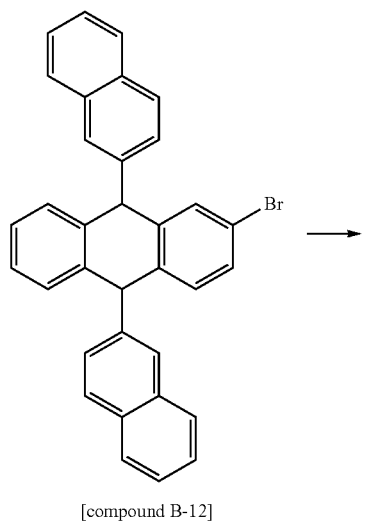

[compound B-12]

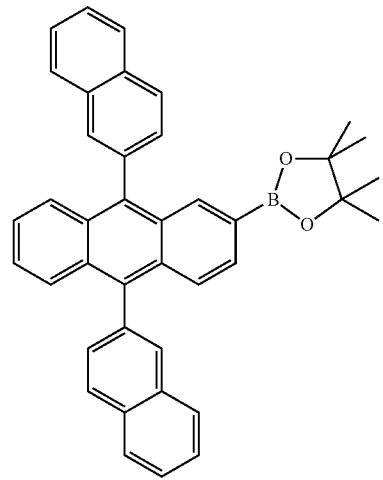

[compound B-13]

[Compound B-11]

In the Preparation of the compound B-9 of Preparation Example 105, the compound B-11 (31.8 g, 80%) was prepared by using the same method as the preparation method of the compound B-9, except that 2-bromonaphthalene was used instead of 1-bromonaphthalene. MS: $[M+H]^+=544$

[Compound B-12]

In the Preparation of the compound B-10 of Preparation Example 105, the compound B-12 (25.4 g, 84%) was prepared by using the same method as the preparation method of the compound B-10, except that the compound B-11 was used instead of the compound B-9. MS: $[M]^+=509$

[Compound B-13]

The compound B-13 (8.6 g, 92%) was prepared by using the same method as Preparation Example 4, except that the compound B-12 was used instead of the compound A-4 in Preparation Example 4. MS: $[M+H]^+=557$

Preparation Example 107

Preparation of the Compounds B-14

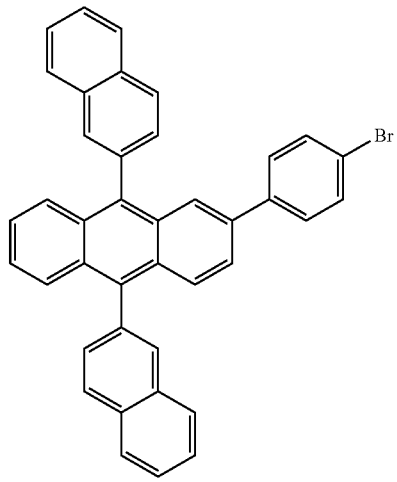

[compound B-14]

In the Preparation of the compound B-3 of Preparation Example 101, the compound B-14 (4.45 g, 76%) was prepared by using the same method as the preparation method of the compound B-3, except that the compound B-13 was used instead of the compound B-2. MS: $[M+H]^+=586$

Preparation Example 108

Preparation of the Compounds B-15

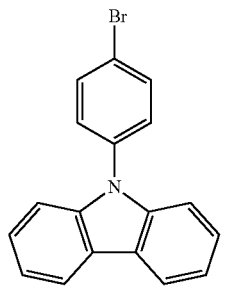

[compound B-15]

Carbazole (3.34 g, 20 mmol), 1-bromo-4-iodobenzene (6.79 g, 24 mmol), potassium carbonate ($K_2CO_3$) (5.52 g, 40 mmol), copper iodide (CuI) (0.381 g, 2 mmol) and 1,10-phenanthroline (0.360 g, 2 mmol) were suspended in xylene (50 mL) and agitated and refluxed for 24 hours. After it was cooled to normal temperature, the mixture was diluted with water (100 mL), and extracted with ethylacetate. The organic extract material was dried over anhydrous magnesium sulfate and filtered. The filtered solution was concentrated under the reduced pressure and recrystallized with ethylether and hexane to prepare the compound B-15 (4.83 g, 75%). MS: $[M+H]^+=322$

Preparation Example 109

Preparation of the Compounds B-16

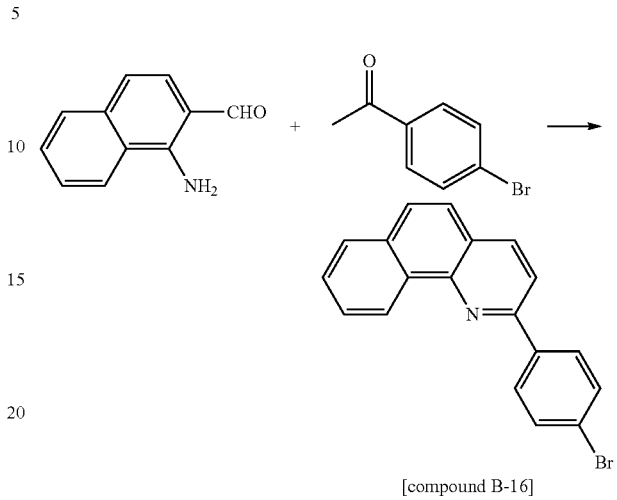

[compound B-16]

1-amino-2-naphthalenecarbaldehyde (0.25 g, 1.45 mmol) and 4-bromoacetophenone (2.88 g, 1.45 mmol) were dispersed in ethanol (15 mL), and 0.5 mL of the solution in which KOH was saturated and dissolved in ethanol was slowly added thereto. The mixture was agitated and refluxed for 15 hours. After it was cooled to normal temperature, the generated solid was filtered, washed with ethanol, and dried under the vacuum to prepare the compound B-16 (0.290 g, 60%). MS: $[M]^+=334$

Preparation Example 110

Preparation of the Compounds B-17

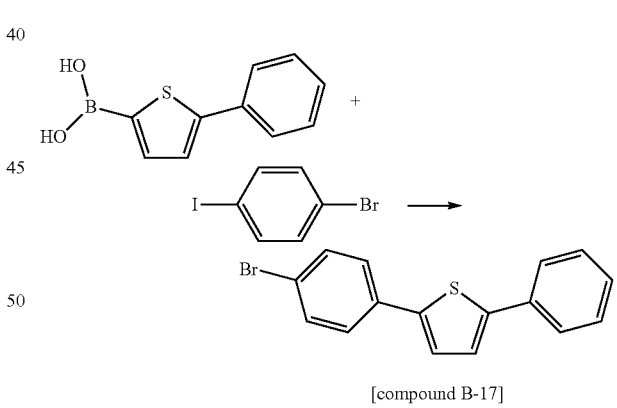

[compound B-17]

After 1-bromo-4-iodobenzene (2.82 g, 10 mmol) and 2-phenyl-cyophenboronic acid (2.04 g, 10 mmol) were dissolved in tetrahydrofuran (30 mL), 2M potassium carbonate aqueous solution (20 mL) was added thereto, and tetrakistriphenylphosphino palladium ($Pd(PPh_3)_4$) (231 mg, 2 mol %) was put thereinto, agitated and refluxed for 5 hours. The temperature was lowered to normal temperature, the water layer was removed, and the organic layer was dried with anhydrous magnesium sulfate and filtered. The filtered solution was concentrated under the reduced pressure and recrystallized with ethylether to prepare the compound B-17 (2.2 g, 70%). MS: $[M]^+=315$

Preparation Example 111

Preparation of the Compounds B-18

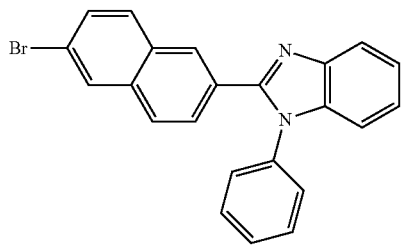
[compound B-18]

Thionyl chloride (SOCl$_2$) (20 mL) and dimethylformamide (DMF) (1 mL) were put into 6-bromo-2-naphthoic acid (5.0 g, 20 mmol), and agitated and refluxed for 4 hours. After an excessive amount of thionyl chloride (SOCl$_2$) was removed by the vacuum distillation, N-methylpyrolidyne (NMP) (20 mL), and N-phenyl-1,2-diaminobenzene (3.7 g, 20 mmol) were put into the reaction mixture and agitated at 160° C. for 12 hours. The temperature was lowered to normal temperature, and an excessive amount of water was added thereto to form a solid. It was filtered, washed with water and ethanol, and dried to prepare the compound B-18 (6.2 g, 78%). MS: [M]$^+$=399

Preparation Example 112

Preparation of the Compounds B-19

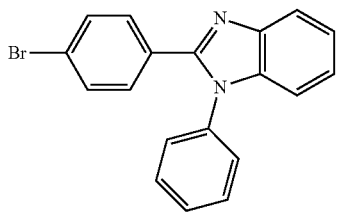
[compound B-19]

The compound B-19 (4.54 g, 65%) was prepared by using the same method as Preparation Example 111, except that 4-bromobenzoic acid was used instead of 6-bromo-2-naphthoic acid in Preparation Example 111. MS: [M]$^+$=349

Preparation Example 113

Preparation of the Compounds B-20

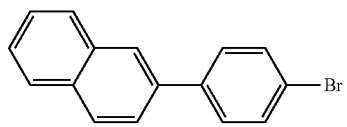
[compound B-20]

The compound B-20 (2.12 g, 75%) was prepared by using the same method as Preparation Example 110, except that 2-naphthalene boronic acid was used instead of 2-phenyl-5-cyophenboronic acid in Preparation Example 110. MS: [M]$^+$=283

Preparation Example 114

Preparation of the Compounds B-21

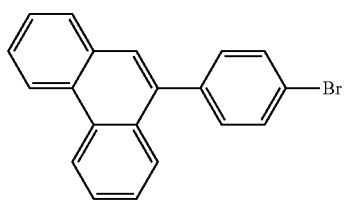
[compound B-21]

The compound B-21 (2.33 g, 70%) was prepared by using the same method as Preparation Example 110, except that 9-phenanthrene boronic acid was used instead of 2-phenyl-5-cyophenboronic acid in Preparation Example 110. MS: [M]$^+$=333

Preparation Example 115

Preparation of the Compounds B-22

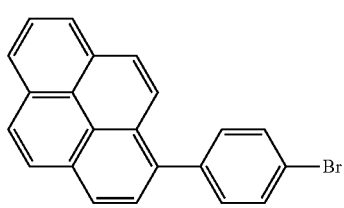
[compound B-22]

The compound B-22 (2.14 g, 60%) was prepared by using the same method as Preparation Example 110, except that 1-pyrene boronic acid was used instead of 2-phenyl-5-cyophenboronic acid in Preparation Example 110. MS: [M]$^+$=357

Preparation Example 116

Preparation of the Compounds B-23

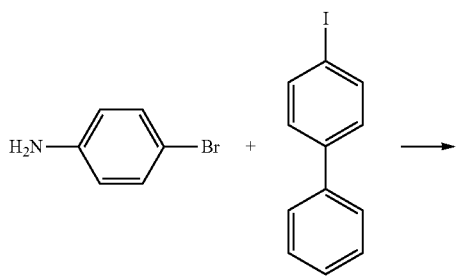

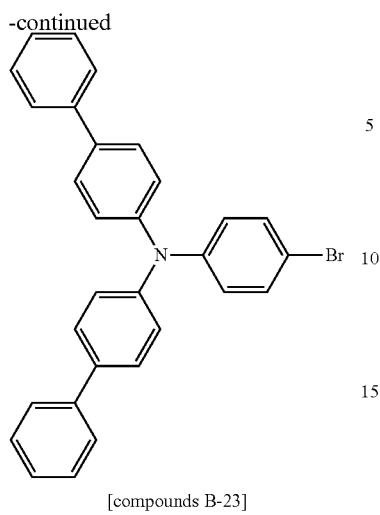

[compounds B-23]

4-bromo-aniline (1.72 g, 10 mmol), 4-iodobiphenyl) (6.72 g, 24 mmol), potassium carbonate (K$_2$CO$_3$) (5.52 g, 40 mmol), copper iodide (CuI) (0.381 g, 2 mmol) and 1,10-phenanthroline (0.360 g, 2 mmol) were suspended in xylene (50 mL) and agitated and refluxed for 24 hours. After it was cooled to normal temperature, the mixture was diluted with water (100 mL), and extracted with ethylacetate. The organic extract material was dried over anhydrous magnesium sulfate and filtered. The filtered solution was concentrated under the reduced pressure and recrystallized with hexane to prepare the compound B-23 (1.43 g, 30%). MS: [M]$^+$=476

Preparation Example 117

Preparation of the Compounds B-24

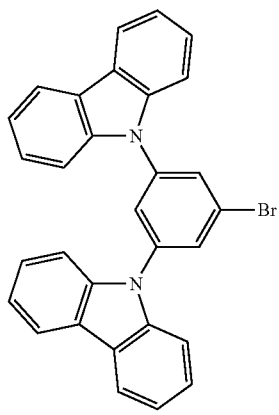

[compound B-24]

The compound B-24 (1.75 g, 40%) was prepared by using the same method as Preparation Example 108, except that 1-bromo-3,5-diiodobenzene) (3.68 g, 9.0 mmol) was used instead of 1-bromo-4-iodobenzene in Preparation Example 108. MS: [M]$^+$=487

EXAMPLE

Example 1

Preparation of the Compound of Formula 1-a-8

[compound 1-a-8]

After the compound B-1 (3.83 g, 10.0 mmol) and the compound A-4 (3.94 g, 10.0 mmol) were dissolved in tetrahydrofuran (100 mL), 2M potassium carbonate aqueous solution (20 mL) was added thereto, and tetrakistriphenylphosphino palladium (Pd(PPh$_3$)$_4$ (231 mg, 2 mol %) was put thereinto, agitated and refluxed for 5 hours. The temperature was cooled to normal temperature, and the produced solid was filtered. The filtered solid was recrystallized with chloroform and ethanol, filtered, and dried to manufacture the compound of Formula 1-a-8 (3.88 g, 68%). MS: [M+H]⁺= 571

Example 2

Preparation of the Compound of Formula 1-a-10

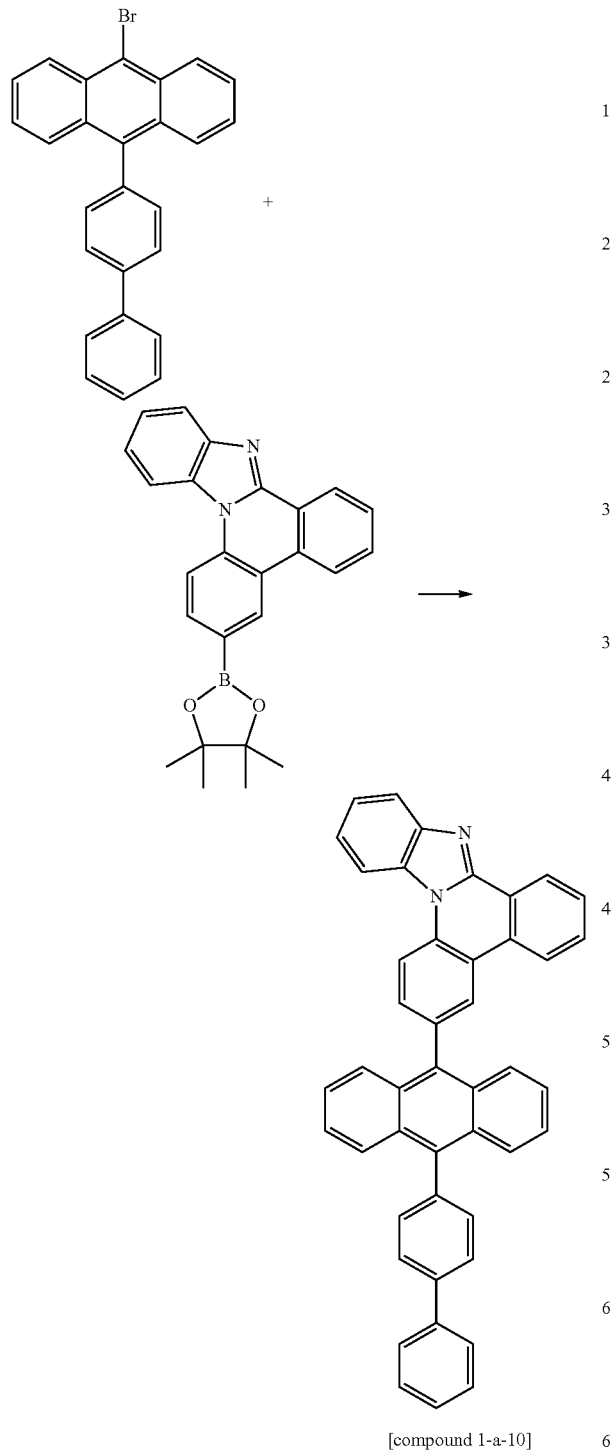

[compound 1-a-10]

The compound 1-a-10 (3.4 g, 57%) was prepared by using the same method as Example 1, except that the compound B-6 (4.09 g, 10.0 mmol) was used instead of the compound B-1 in Example 1. MS: [M+H]⁺=597

Example 3

Preparation of the Compound of Formula 1-a-14

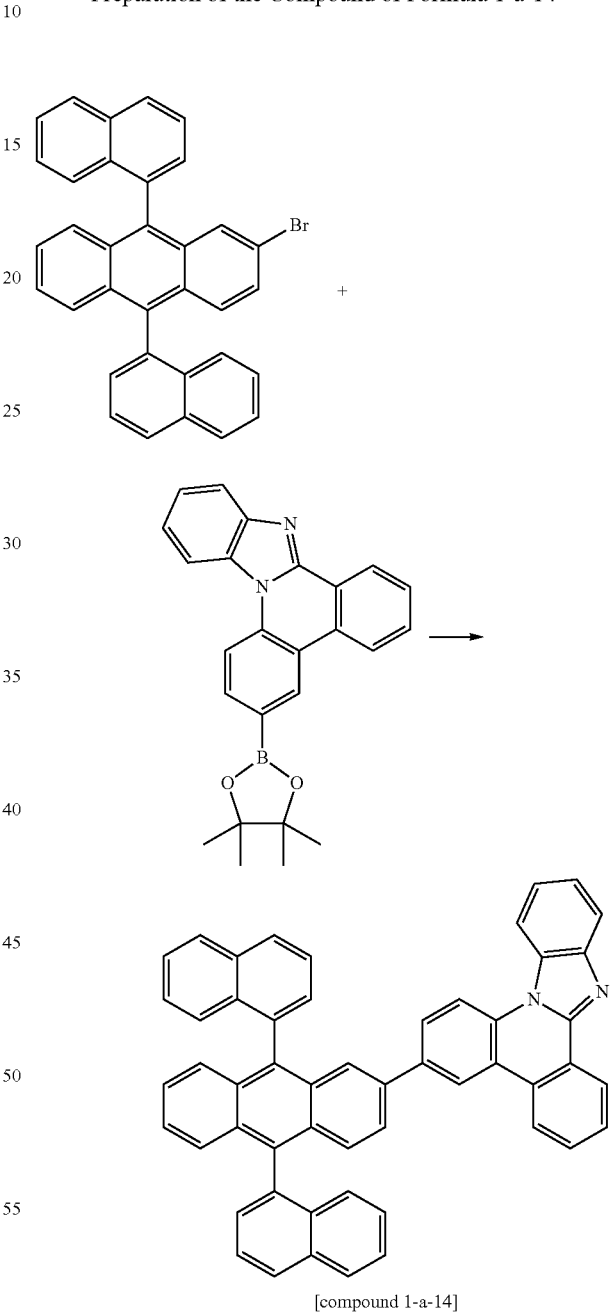

[compound 1-a-14]

The compound 1-a-14 (4.54 g, 65%) was prepared by using the same method as Example 1, except that the compound B-10 (5.09 g, 10.0 mmol) was used instead of the compound B-1 in Example 1. MS: [M+H]⁺=697

Example 4

Preparation of the Compound of Formula 1-a-15

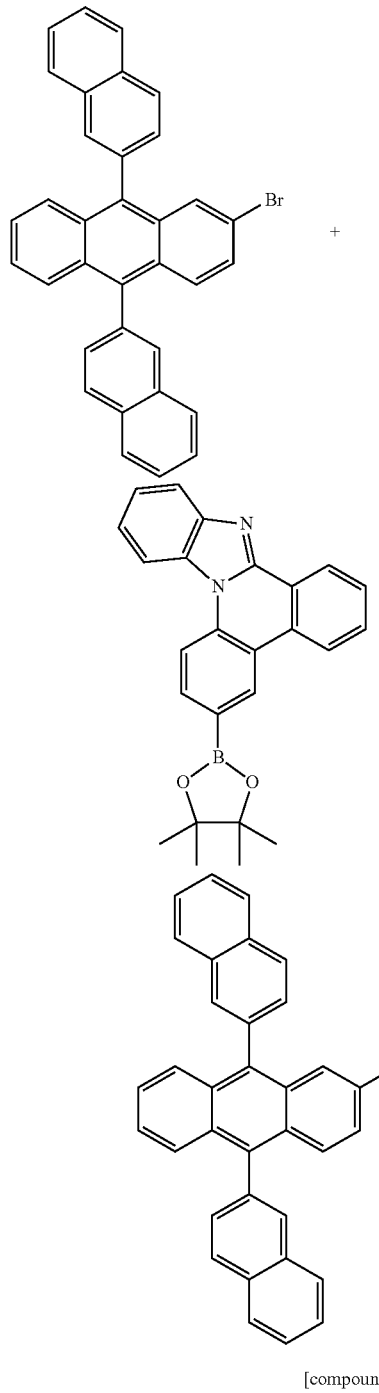

[compound 1-a-15]

The compound 1-a-15 (4.94 g, 71%) was prepared by using the same method as Example 1, except that the compound B-12 (5.09 g, 10.0 mmol) was used instead of the compound B-1 in Example 1. MS: [M+H]$^+$=697

Example 5

Preparation of the Compound of Formula 1-a-18

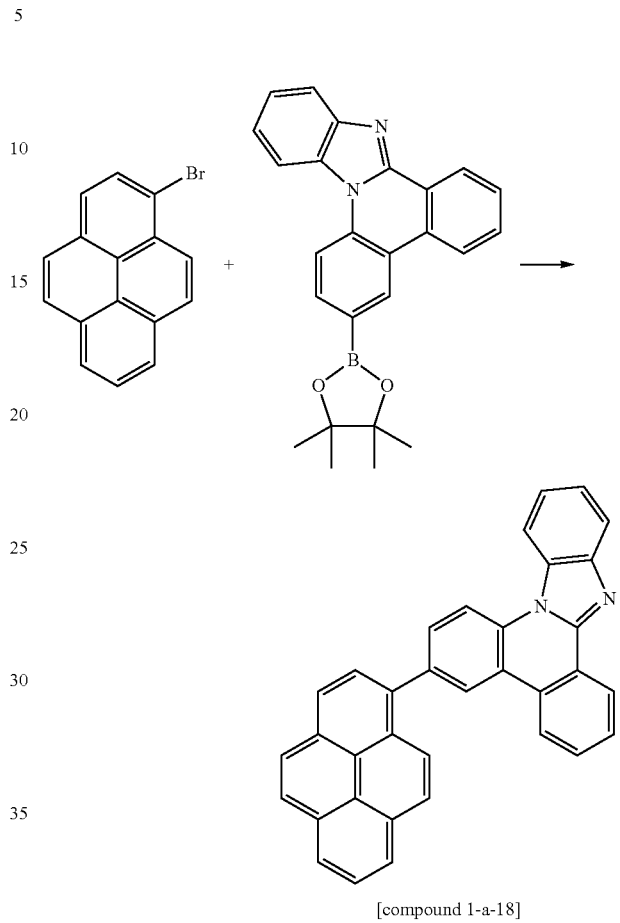

[compound 1-a-18]

The compound 1-a-18 (2.57 g, 55%) was prepared by using the same method as Example 1, except that 1-bromo pyrene (2.81 g, 10.0 mmol) was used instead of the compound B-1 in Example 1. MS: [M+H]$^+$=469

Example 6

Preparation of the Compound of Formula 1-a-29

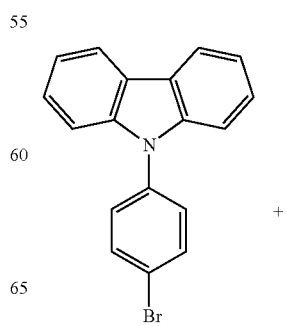

-continued

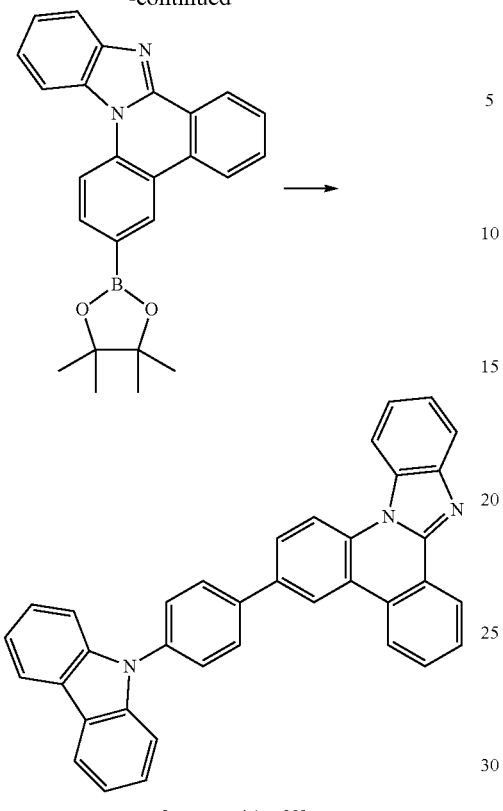

[compound 1-a-29]

The compound 1-a-29 (3.82 g, 75%) was prepared by using the same method as Example 1, except that the compound B-15 (3.22 g, 10.0 mmol) was used instead of the compound B-1 in Example 1. MS: [M+H]$^+$=510

Example 7

Preparation of the Compound of Formula 1-a-31

-continued

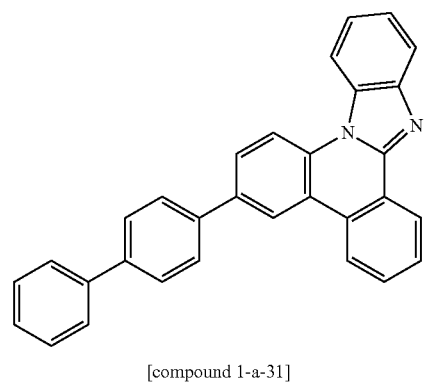

[compound 1-a-31]

The compound 1-a-18 (2.95 g, 70%) was prepared by using the same method as Example 1, except that 4-bromobiphenyl (2.33 g, 10.0 mmol) was used instead of the compound B-1 in Example -31. MS: [M+H]$^+$=421

Example 8

Preparation of the Compound of Formula 1-a-34

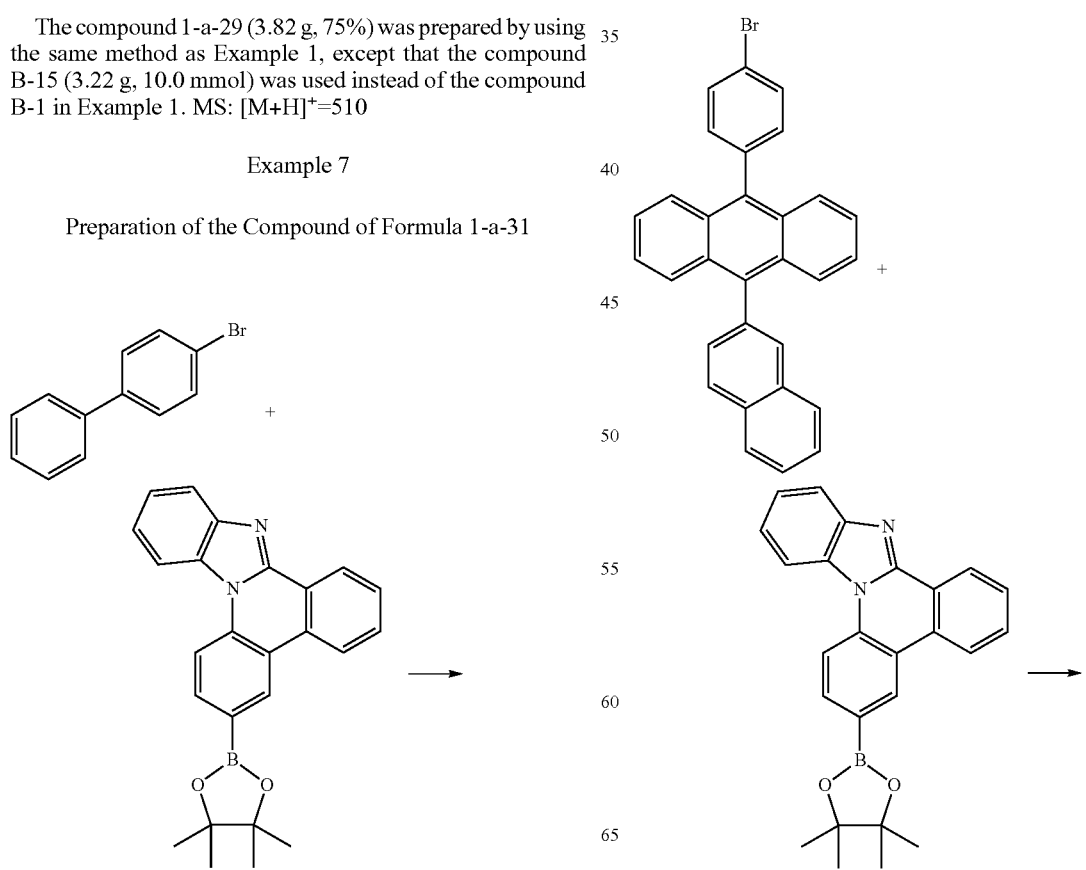

-continued

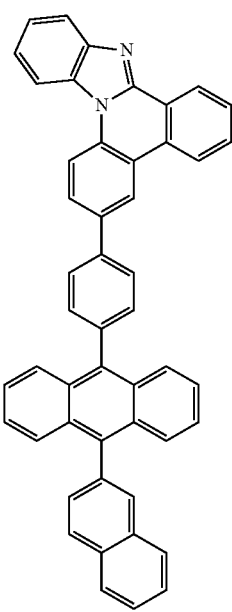

[compound 1-a-34]

The compound 1-a-34 (4.85 g, 75%) was prepared by using the same method as Example 1, except that the compound B-3 (4.59 g, 10.0 mmol) was used instead of the compound B-1 in Example 1. MS: [M+H]⁺=647

Example 9

Preparation of the Compound of Formula 1-a-35

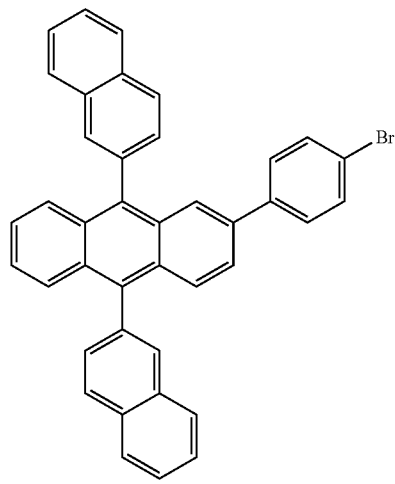

+

-continued

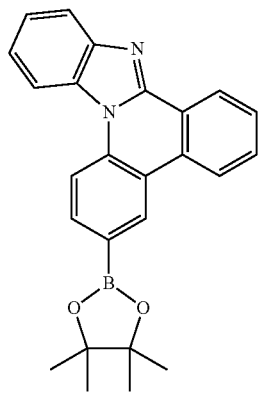 

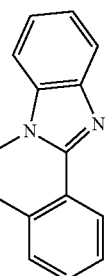

[compound 1-a-35]

The compound 1-a-35 (5.41 g, 70%) was prepared by using the same method as Example 1, except that the compound B-14 (5.85 g, 10.0 mmol) was used instead of the compound B-1 in Example 1. MS: [M+H]⁺=773

Example 10

Preparation of the Compound of Formula 1-a-37

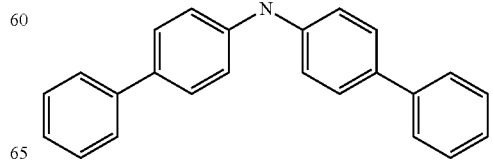

+

-continued

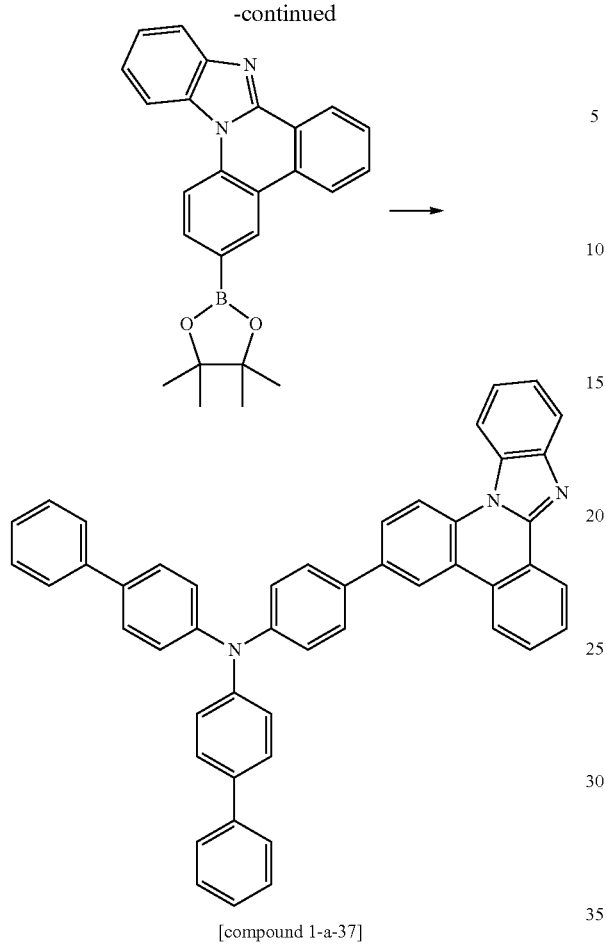

[compound 1-a-37]

The compound 1-a-37 (3.72 g, 56%) was prepared by using the same method as Example 1, except that the compound B-23 (4.76 g, 10.0 mmol) was used instead of the compound B-1 in Example 1. MS: [M+H]$^+$=664

Example 11

Preparation of the Compound of Formula 1-a-58

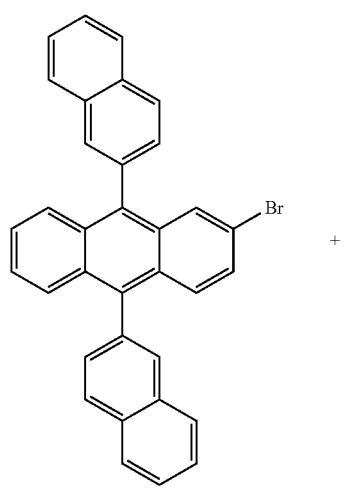

-continued

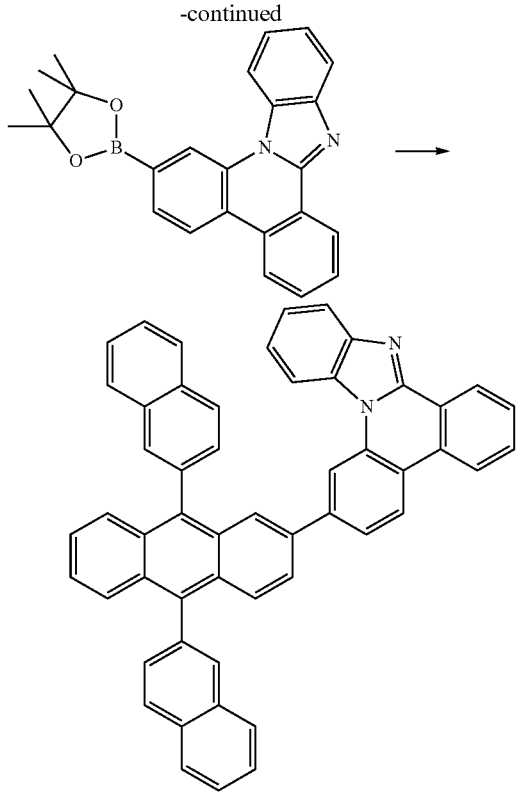

[compound 1-a-58]

After the compound B-12 (5.09 g, 10.0 mmol) and the compound A-50 (3.94 g, 10.0 mmol) were dissolved in tetrahydrofuran (100 mL), 2M potassium carbonate aqueous solution (20 mL) was added thereto, and tetrakistriphenylphosphino palladium (231 mg, 2 mol %) was put thereinto, agitated and refluxed for 5 hours. The temperature was cooled to normal temperature, and the produced solid was filtered. The filtered solid was recrystallized with chloroform and ethanol, filtered, and dried to manufacture the compound of Formula 1-a-58 (4.59 g, 66%). MS: [M+H]$^+$=697

Example 12

Preparation of the Compound of Formula 1-a-64

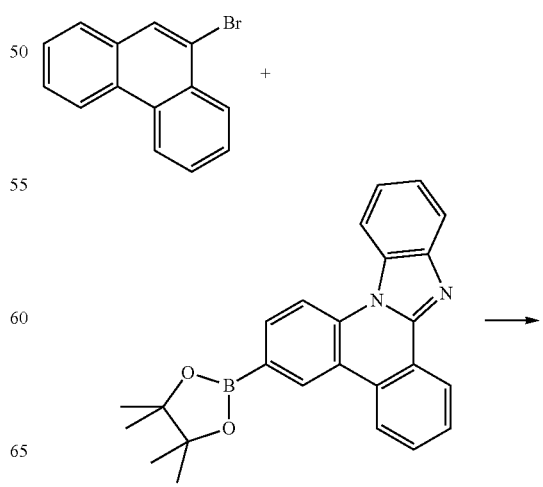

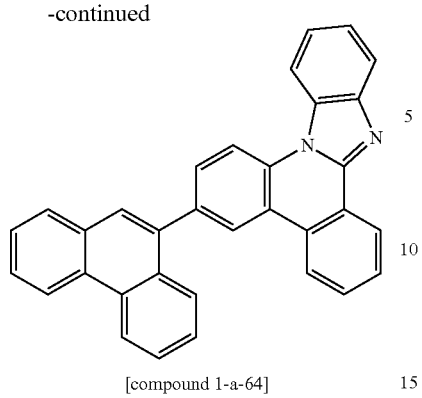

[compound 1-a-64]

The compound 1-a-64 (3.12 g, 70%) was prepared by using the same method as Example 1, except that 9-bromophenanthrene (2.57 g, 10.0 mmol) was used instead of the compound B-1 in Example 1. MS: $[M+H]^+=445$ Example 13

Preparation of the Compound of Formula 1-a-68

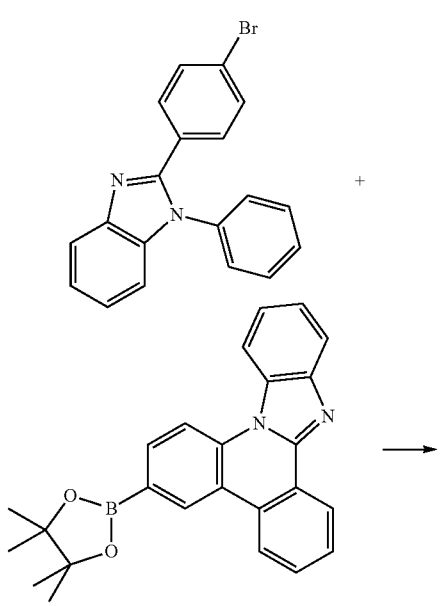

[compound 1-a-68]

The compound 1-a-68 (3.49 g, 65%) was prepared by using the same method as Example 1, except that the compound B-19 (3.49 g, 10.0 mmol) was used instead of the compound B-1 in Example 1. MS: $[M+H]^+=537$ Example 14

Preparation of the Compound of Formula 1-a-72

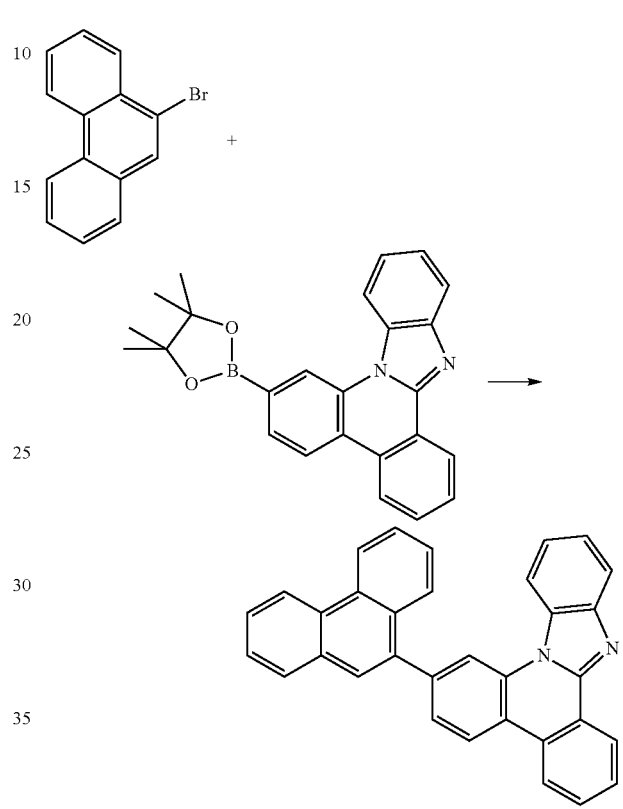

[compound 1-a-72]

The compound 11-a-72 (3.25 g, 73%) was prepared by using the same method as Example 11, except that 9-bromophenanthrene (2.57 g, 10.0 mmol) was used instead of the compound B-12 in Example 11. MS: $[M+H]^+=445$ Example 15

Preparation of the Compound of Formula 1-a-74

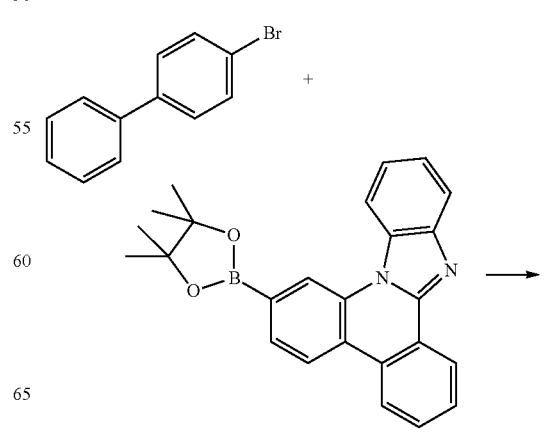

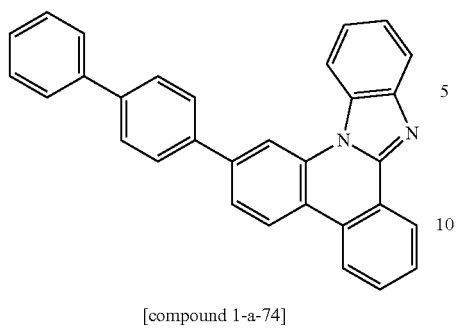

[compound 1-a-74]

The compound 1-a-74 (2.82 g, 67%) was prepared by using the same method as Example 11, except that 4-bromobiphenyl (2.33 g, 10.0 mmol) was used instead of the compound B-12 in Example 11. MS: [M+H]⁺=421

Example 16

Preparation of the Compound of Formula 1-a-77

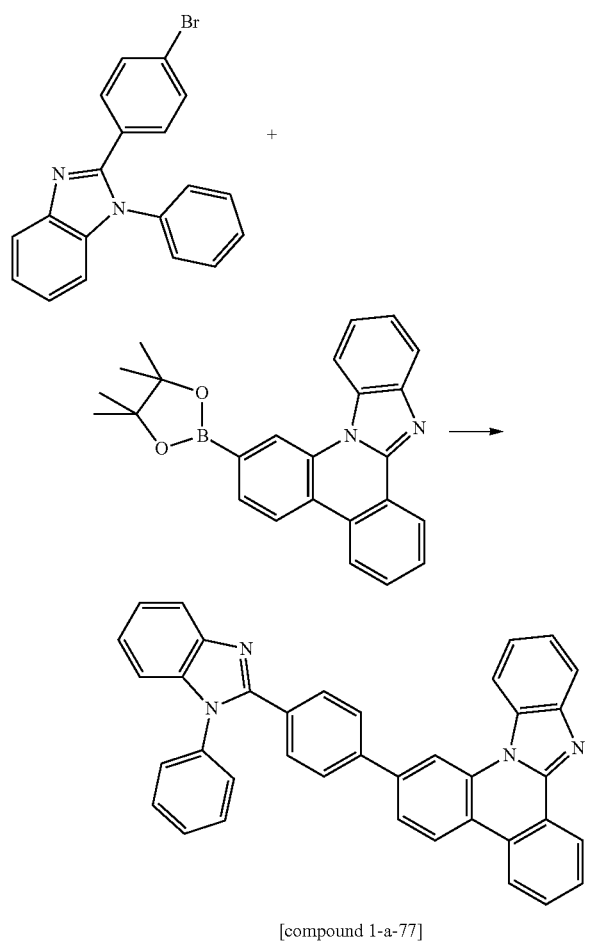

[compound 1-a-77]

The compound 1-a-77 (3.76 g, 70%) was prepared by using the same method as Example 11, except that the compound B-19 (3.49 g, 10.0 mmol) was used instead of the compound B-12 in Example 11. MS: [M±H]⁺=537

Example 17

Preparation of the Compound of Formula 1-b-8

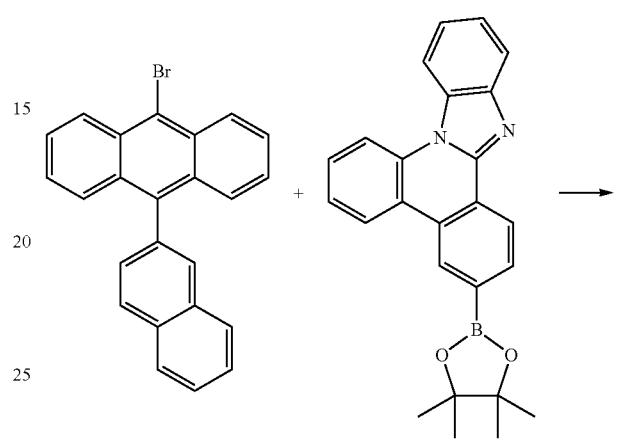

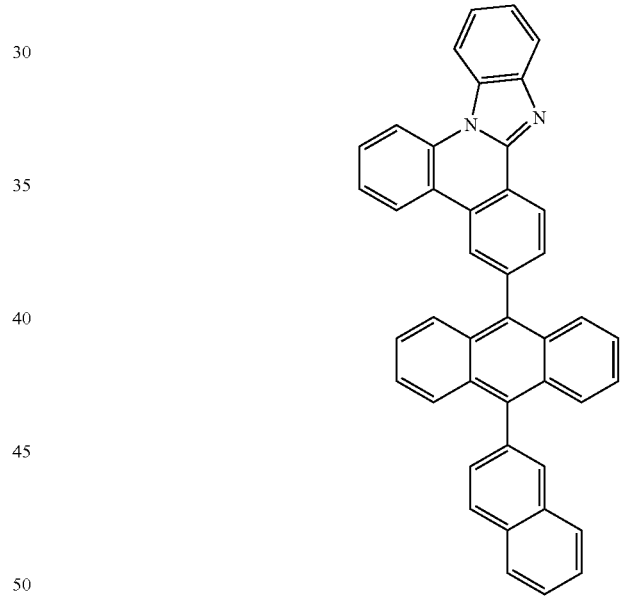

[compound 1-b-8]

After the compound B-1 (3.83 g, 10.0 mmol) the compound A-14 (3.94 g, 10.0 mmol) were dissolved in tetrahydrofuran (100 mL), 2M potassium carbonate aqueous solution (20 mL) was added thereto, and tetrakistriphenylphosphino palladium (231 mg, 2 mol %) was put thereinto, agitated and refluxed for 5 hours. The temperature was cooled to normal temperature, and the produced solid was filtered. The filtered solid was recrystallized with chloroform and ethanol, filtered, and dried to manufacture the compound of Formula 1-b-8 (3.88 g, 68%). MS: [M+H]⁺=571

Example 18
Preparation of the Compound of Formula 1-b-9

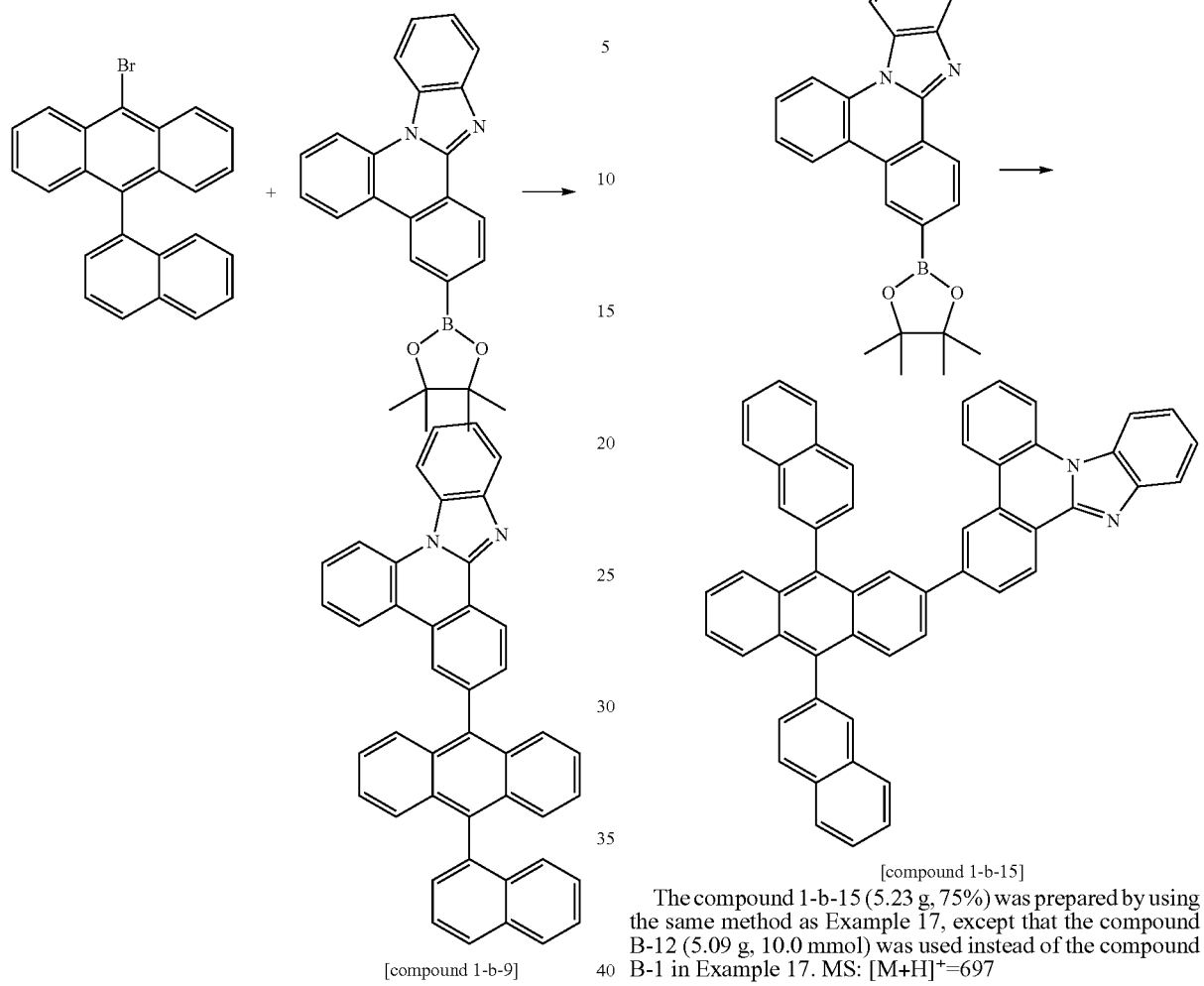

[compound 1-b-9]

The compound 1-b-9 (3.99 g, 70%) was prepared by using the same method as Example 17, except that the compound B-4 (3.83 g, 10.0 mmol) was used instead of the compound B-1 in Example 17. MS: [M+H]$^+$=571

Example 19
Preparation of the Compound of Formula 1-b-15

[compound 1-b-15]

The compound 1-b-15 (5.23 g, 75%) was prepared by using the same method as Example 17, except that the compound B-12 (5.09 g, 10.0 mmol) was used instead of the compound B-1 in Example 17. MS: [M+H]$^+$=697

Example 20
Preparation of the Compound of Formula 1-b-31

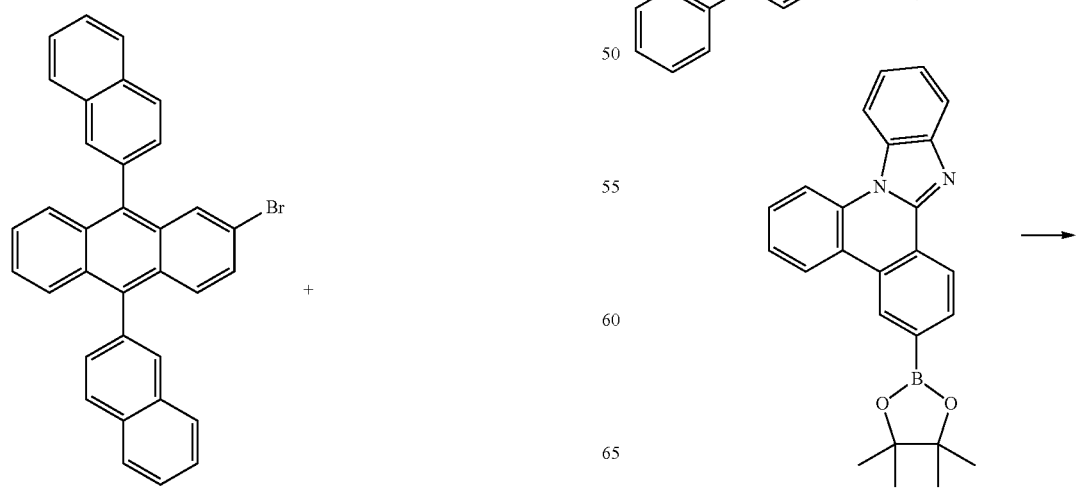

-continued

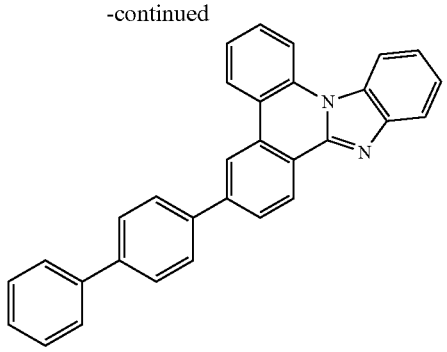

[compound 1-b-31]

The compound 1-b-31 (3.15 g, 75%) was prepared by using the same method as Example 17, except that 4-bromobiphenyl (2.33 g, 10.0 mmol) was used instead of the compound B-1 in Example 17. MS: [M+H]⁺=421

Example 21

Preparation of the Compound of Formula 1-b-32

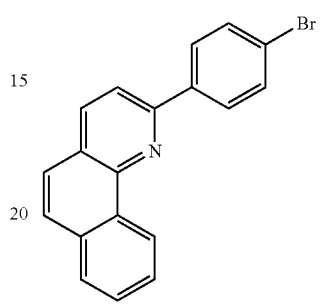

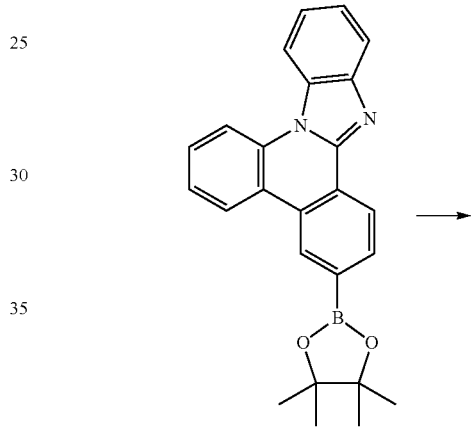

[compound 1-b-32]

The compound 1-b-32 (3.53 g, 75%) was prepared by using the same method as Example 17, except that the compound B-20 (2.83 g, 10.0 mmol) was used instead of the compound B-1 in Example 17. MS: [M+H]⁺=471

Example 22

Preparation of the Compound of Formula 1-b-33

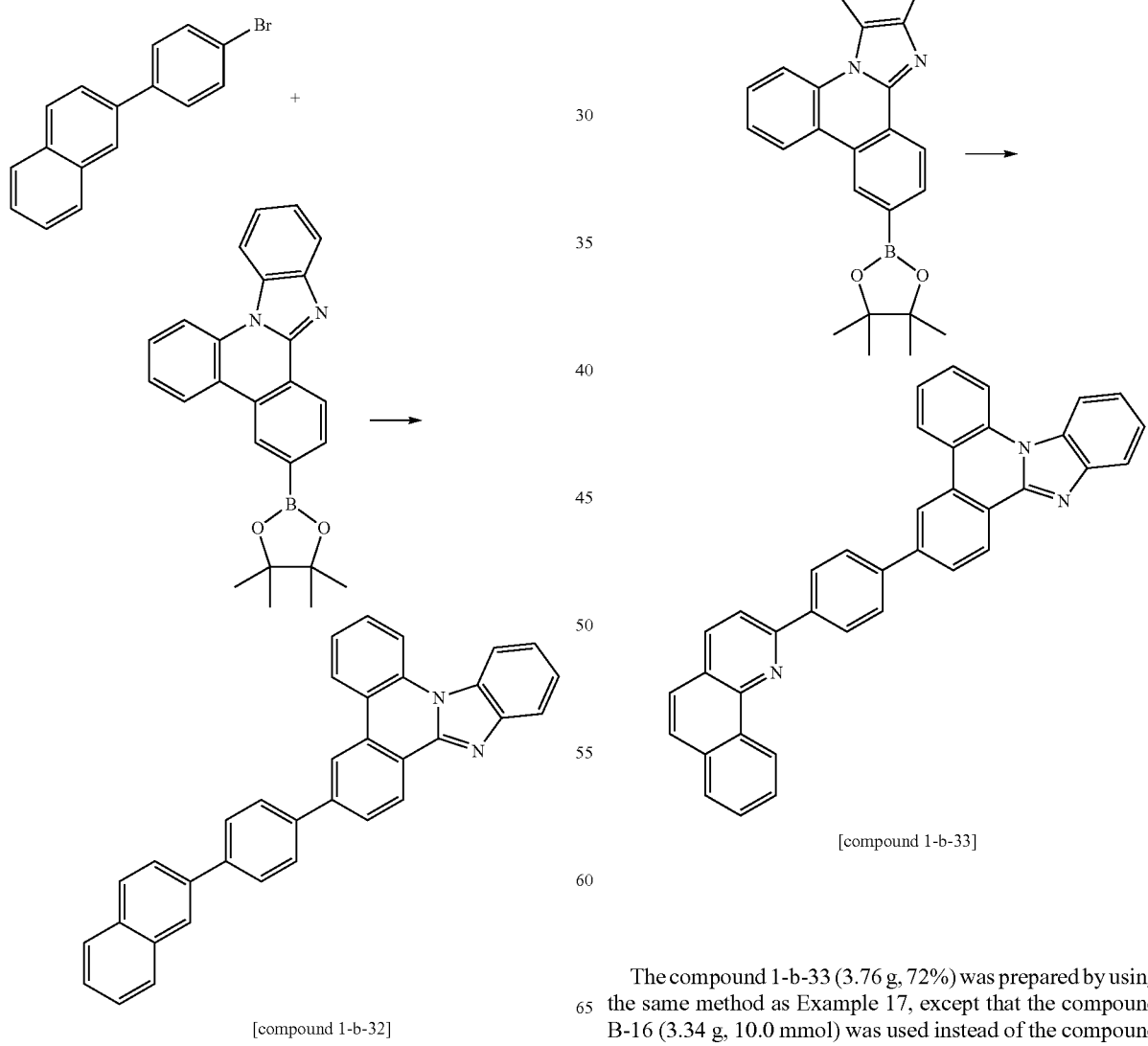

[compound 1-b-33]

The compound 1-b-33 (3.76 g, 72%) was prepared by using the same method as Example 17, except that the compound B-16 (3.34 g, 10.0 mmol) was used instead of the compound B-1 in Example 17. MS: [M+H]⁺=522

Example 23

Preparation of the Compound of Formula 1-b-37

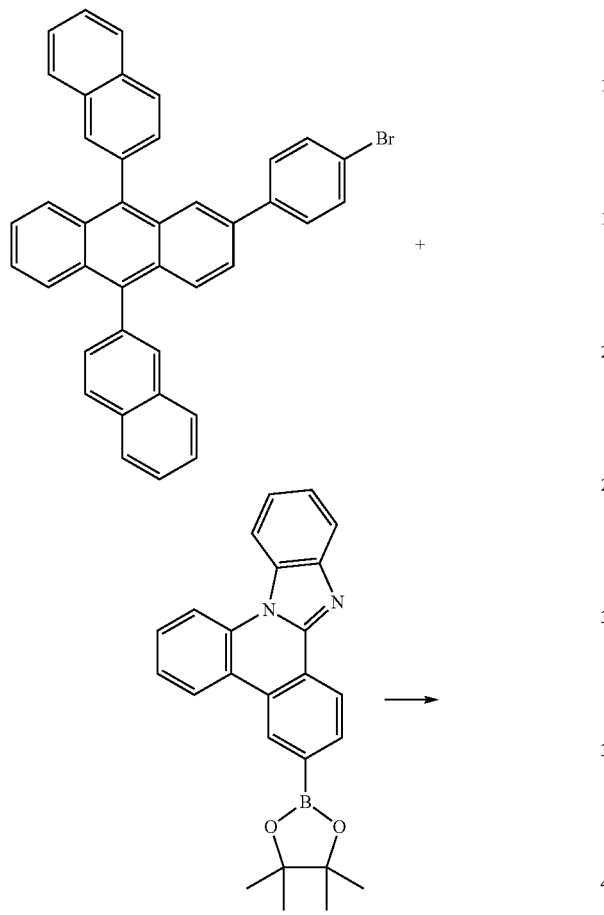

[compound 1-b-37]

The compound 1-b-37 (5.41 g, 70%) was prepared by using the same method as Example 17, except that the compound B-14 (5.85 g, 10.0 mmol) was used instead of the compound B-1 in Example 17. MS: [M+H]=773

Example 24

Preparation of the Compound of Formula 1-b-39

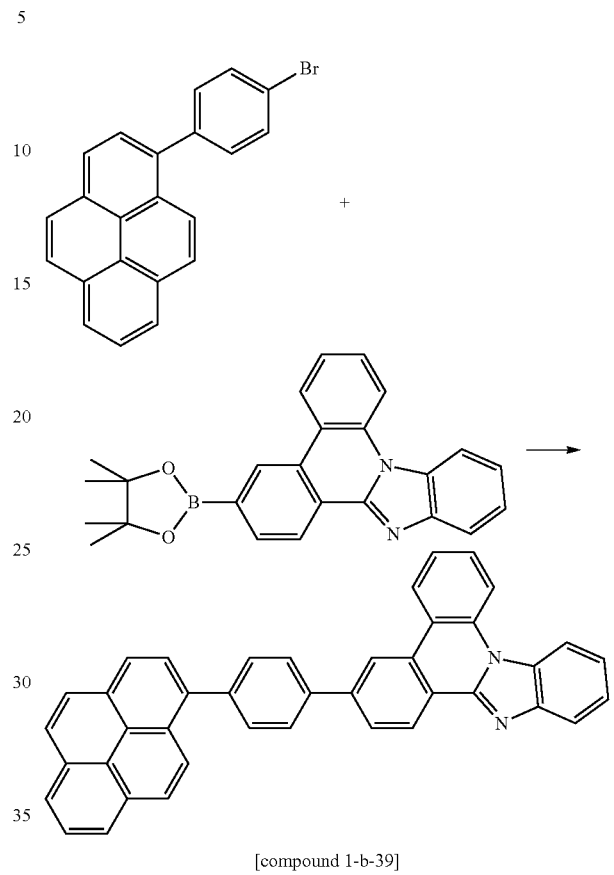

[compound 1-b-39]

The compound 1-b-39 (3.81 g, 70%) was prepared by using the same method as Example 17, except that the compound B-22 (3.57 g, 10.0 mmol) was used instead of the compound B-1 in Example 17. MS: [M+H]=545

Example 25

Preparation of the Compound of Formula 1-b-80

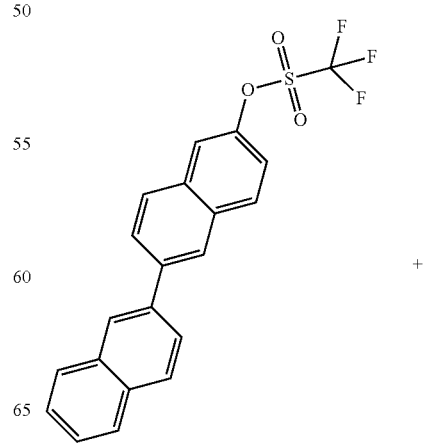

-continued

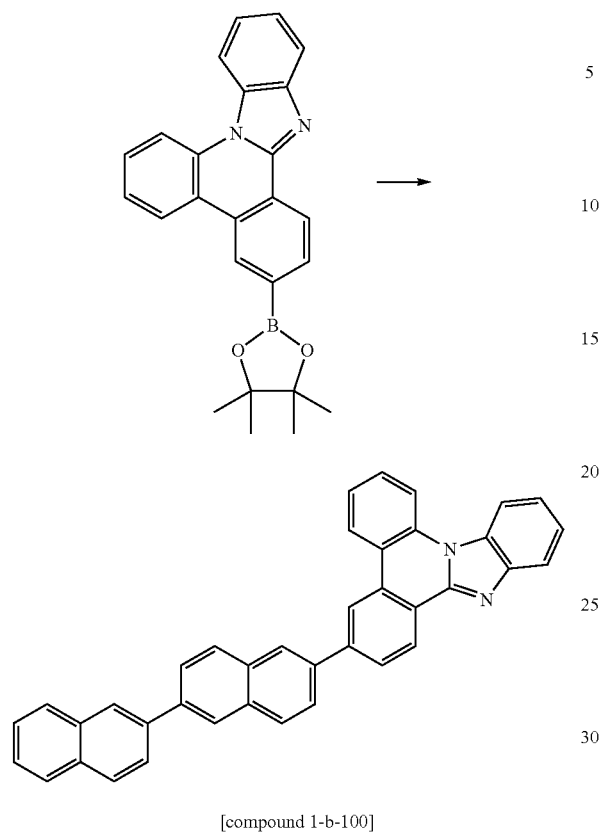

[compound 1-b-100]

The compound 1-b-80 (3.74 g, 72%) was prepared by using the same method as Example 17, except that the compound B-8 (4.02 g, 10.0 mmol) was used instead of the compound B-1 in Example 17. MS: [M+H]=521

Example 26

Preparation of the Compound of Formula 1-b-100

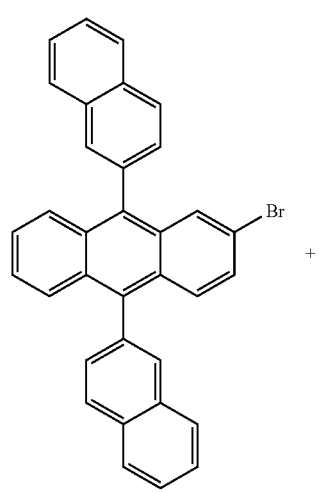

-continued

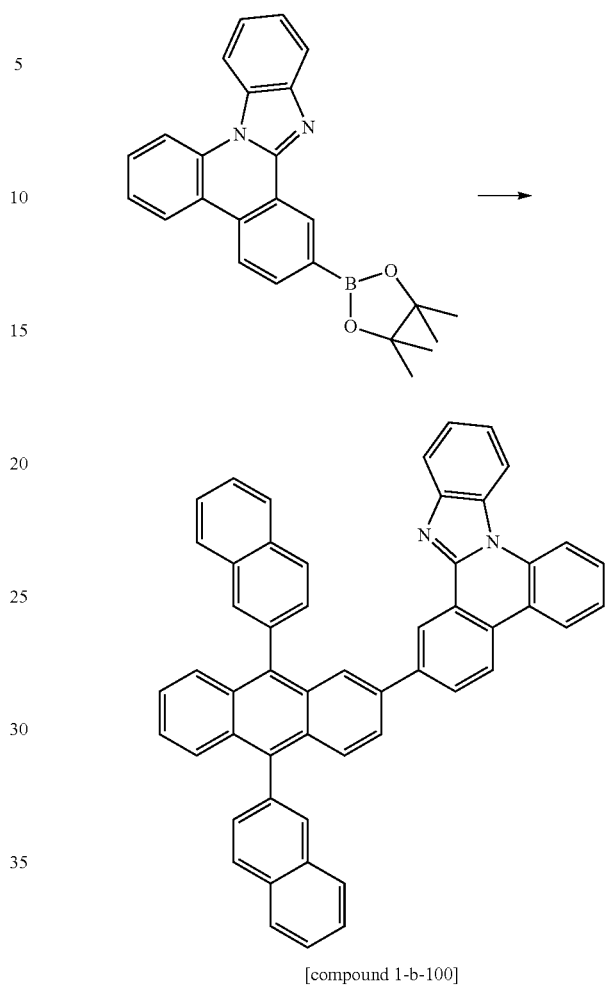

[compound 1-b-100]

After the compound B-12 (5.09 g, 10.0 mmol) and the compound A-54 (3.94 g, 10.0 mmol) were dissolved in tetrahydrofuran (100 mL), 2M potassium carbonate aqueous solution (20 mL) was added thereto, and tetrakistriphenylphosphino palladium (231 mg, 2 mol %) was put thereinto, agitated and refluxed for 5 hours. The temperature was cooled to normal temperature, and the produced solid was filtered. The filtered solid was recrystallized with chloroform and ethanol, filtered, and dried to manufacture the compound of Formula 1-b-100 (4.94 g, 71%). MS: [M+H]$^+$=697

Example 27

Preparation of the Compound of Formula 1-b-117

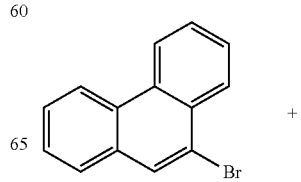

-continued

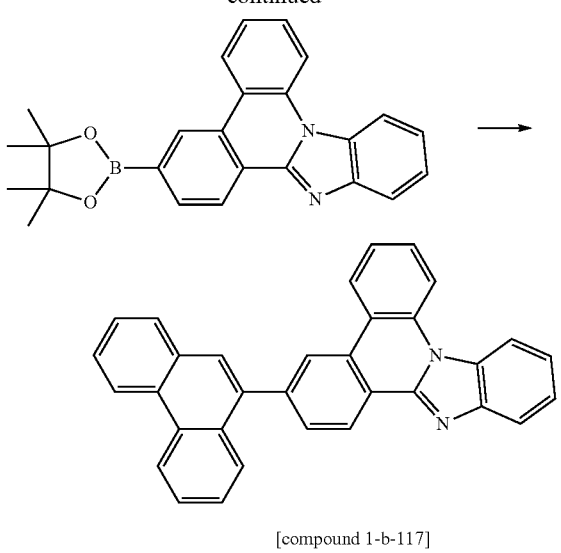

[compound 1-b-117]

The compound 1-b-117 (3.20 g, 72%) was prepared by using the same method as Example 17, except that 9-bromophenanthrene (2.57 g, 10.0 mmol) was used instead of the compound B-1 in Example 11. MS: [M+H]$^+$=445

Example 28

Preparation of the Compound of Formula 1-b-122

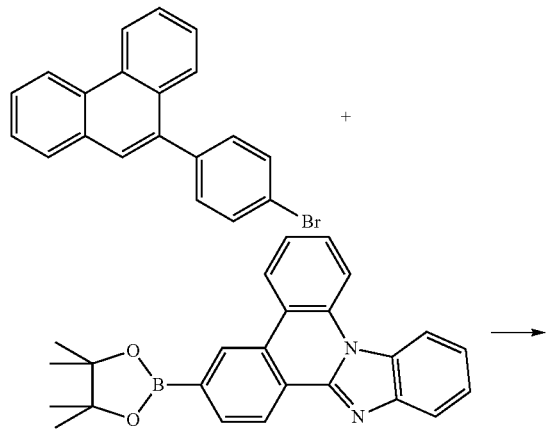

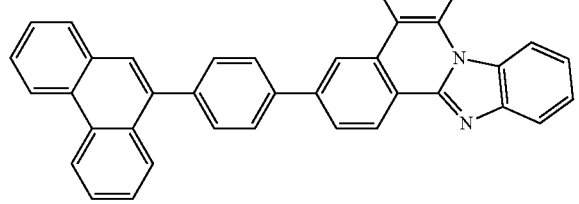

[compound 1-b-122]

The compound 1-b-122 (3.64 g, 70%) was prepared by using the same method as Example 17, except that the compound B-21 (3.33 g, 10.0 mmol) was used instead of the compound B-1 in Example 17. MS: [M+H]$^+$=521

Example 29

Preparation of the Compound of Formula 1-b-123

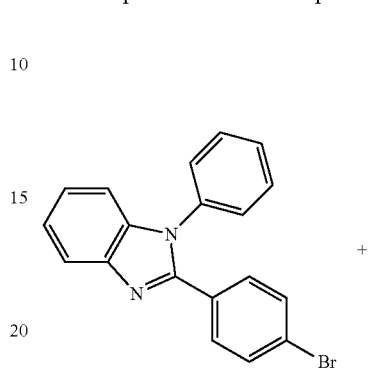

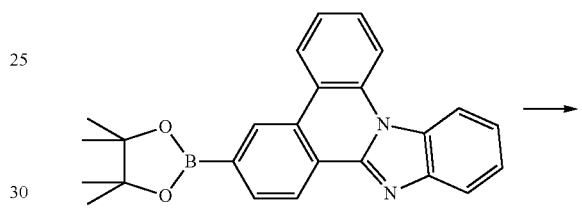

[compound 1-b-123]

The compound 1-b-123 (4.29 g, 80%) was prepared by using the same method as Example 17, except that the compound B-19 (3.49 g, 10.0 mmol) was used instead of the compound B-1 in Example 17. MS: [M+H]$^+$=537

Example 30

Preparation of the Compound of Formula 1-b-130

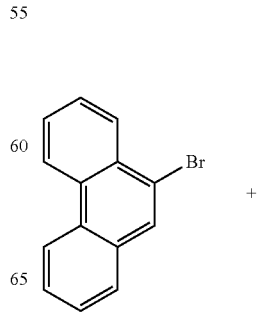

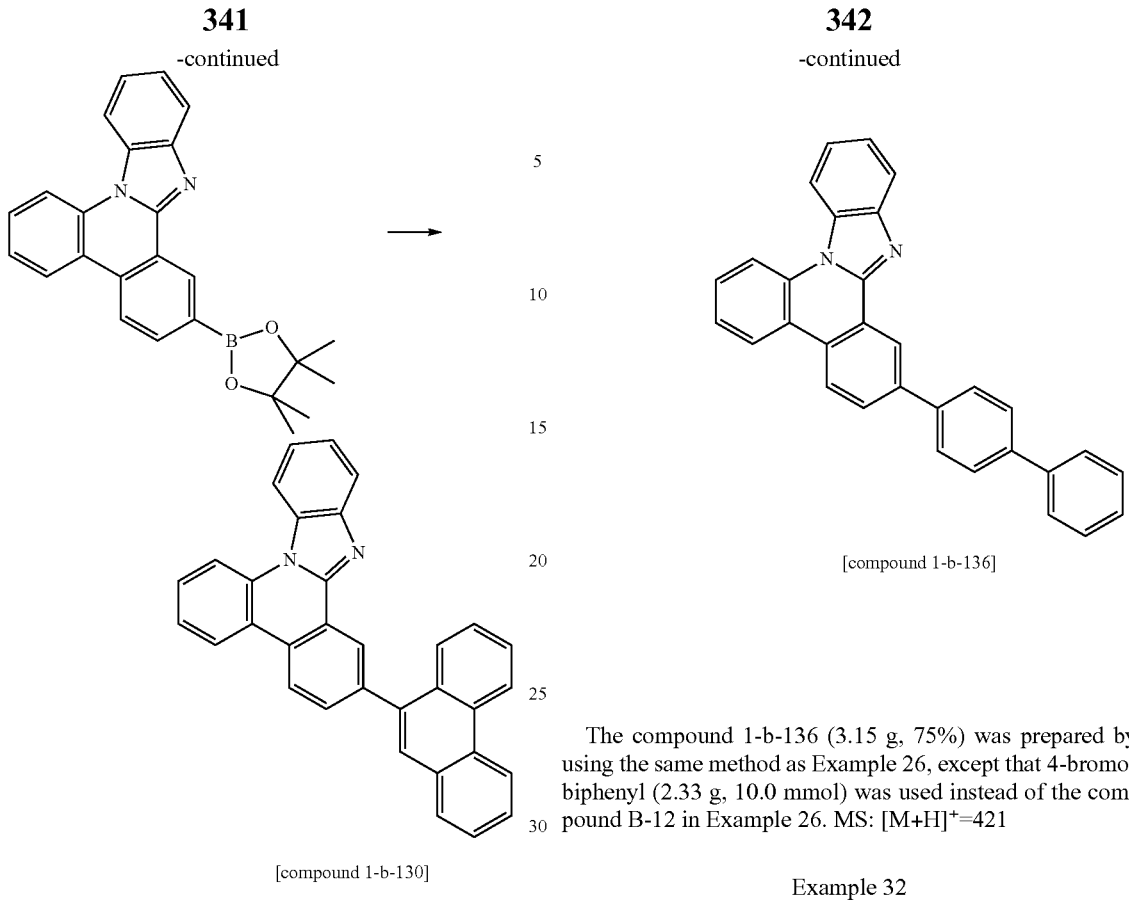

[compound 1-b-130]

The compound 1-b-130 (3.20 g, 72%) was prepared by using the same method as Example 26, except that 9-bromophenanthrene (2.57 g, 10.0 mmol) was used instead of the compound B-12 in Example 26. MS: $[M+H]^+=445$ Example 31

Preparation of the Compound of Formula 1-b-136

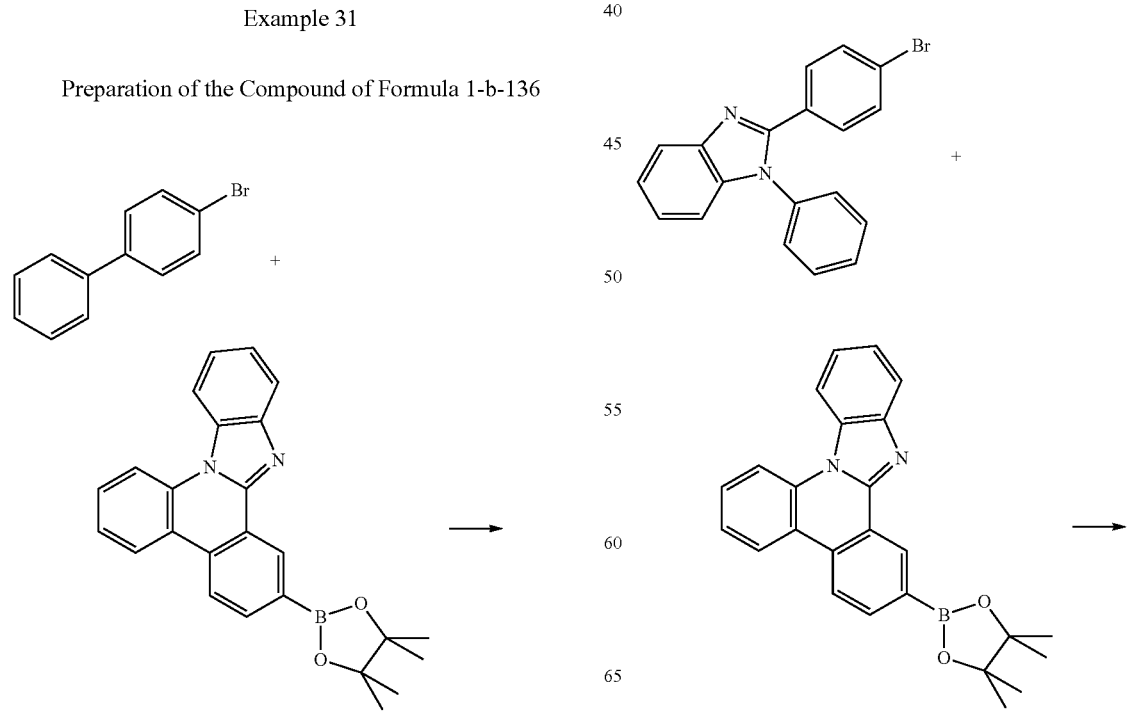

[compound 1-b-136]

The compound 1-b-136 (3.15 g, 75%) was prepared by using the same method as Example 26, except that 4-bromobiphenyl (2.33 g, 10.0 mmol) was used instead of the compound B-12 in Example 26. MS: $[M+H]^+=421$ Example 32

Preparation of the Compound of Formula 1-b-139

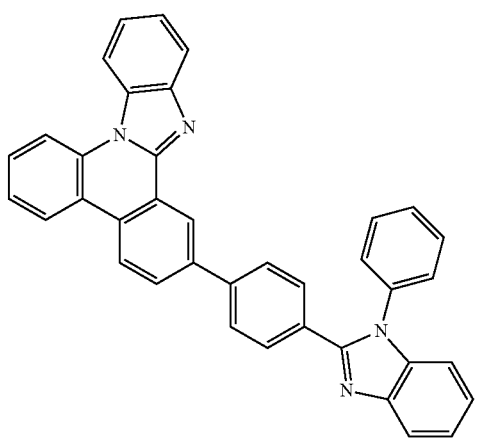

[compound 1-b-139]

The compound 1-b-139 (4.03 g, 75%) was prepared by using the same method as Example 26, except that the compound B-19 (3.49 g, 10.0 mmol) was used instead of the compound B-12 in Example 26. MS: [M+H]⁺=537

Example 33

Preparation of the Compound of Formula 1-b-151

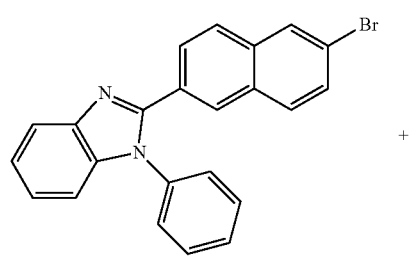

+

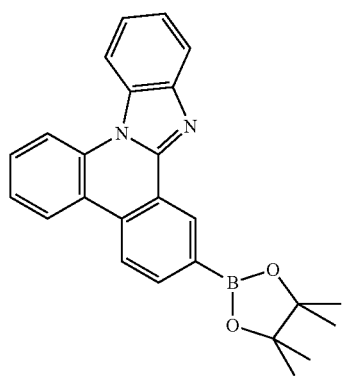

→

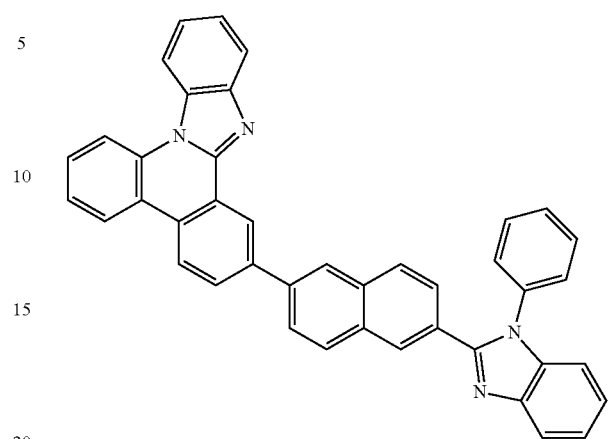

[compound 1-b-151]

The compound 1-b-151 (4.40 g, 75%) was prepared by using the same method as Example 26, except that the compound B-18 (3.99 g, 10.0 mmol) was used instead of the compound B-12 in Example 26. MS: [M+H]⁺=587

Example 34

Preparation of the Compound of Formula 1-c-8

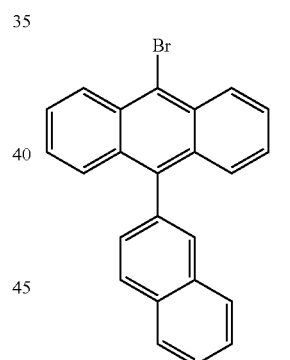

+

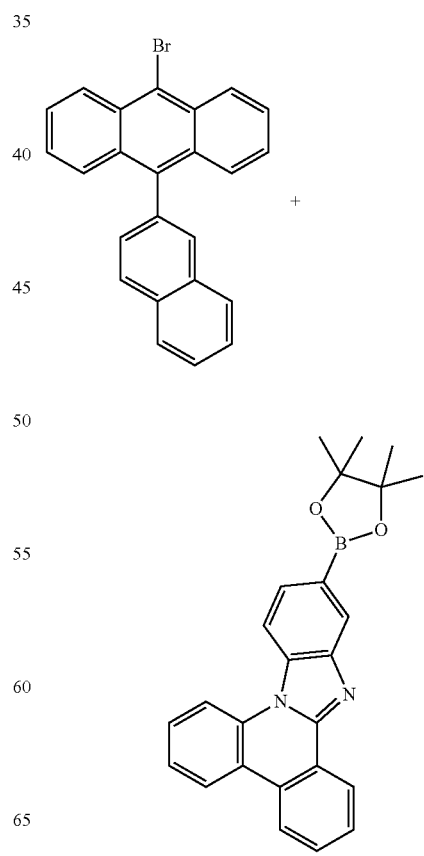

→

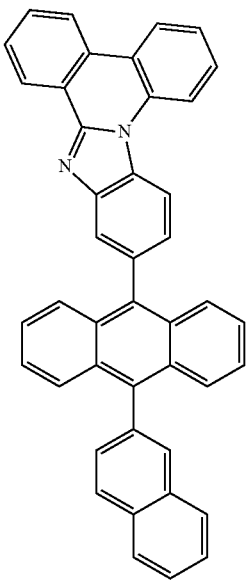

[compound 1-c-8]

After the compound B-1 (3.83 g, 10.0 mmol) and the compound A-24 (3.94 g, 10.0 mmol) were dissolved in tetrahydrofuran (100 mL), 2M potassium carbonate aqueous solution (20 mL) was added thereto, and tetrakistriphenylphosphino palladium (231 mg, 2 mol %) was put thereinto, agitated and refluxed for 5 hours. The temperature was cooled to normal temperature, and the produced solid was filtered. The filtered solid was recrystallized with chloroform and ethanol, filtered, and dried to manufacture the compound of Formula 1-c-8 (3.71 g, 65%). MS: [M+1]$^+$=571

Example 35

Preparation of the Compound of Formula 1-c-15

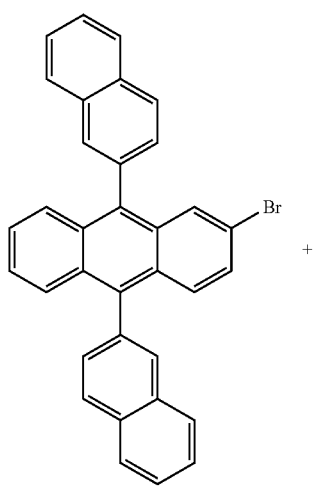

+

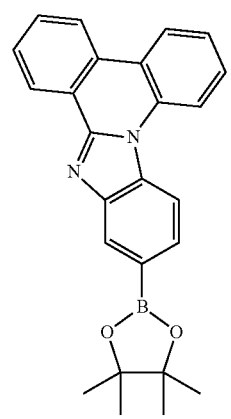 

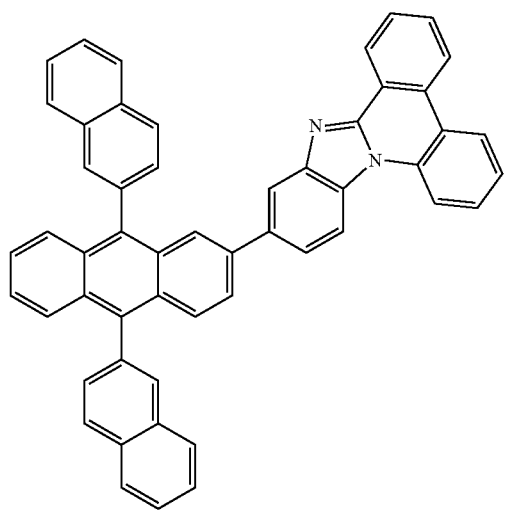

[compound 1-c-15]

The compound 1-c-15 (4.88 g, 70%) was prepared by using the same method as Example 34, except that the compound B-12 (5.09 g, 10.0 mmol) was used instead of the compound B-1 in Example 34. MS: [M+H]$^+$=697

Example 36

Preparation of the Compound of Formula 1-c-23

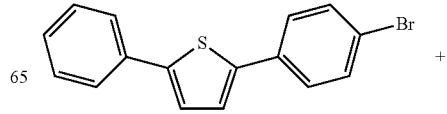

+

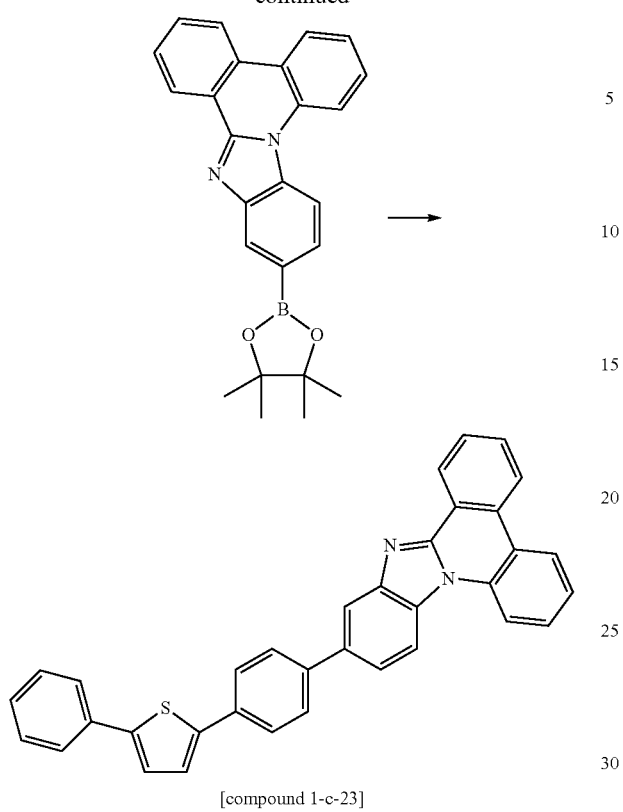

[compound 1-c-23]

The compound 1-c-23 (2.62 g, 52%) was prepared by using the same method as Example 34, except that the compound B-17 (3.15 g, 10.0 mmol) was used instead of the compound B-1 in Example 34. MS: [M+H]⁺=503

Example 37

Preparation of the Compound of Formula 2-a-6

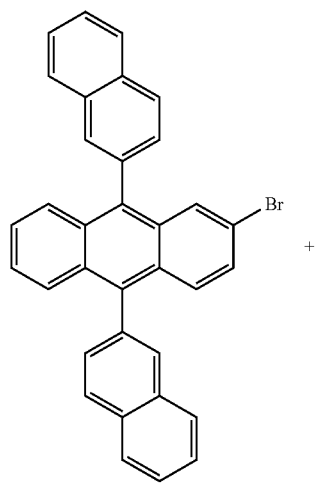

+

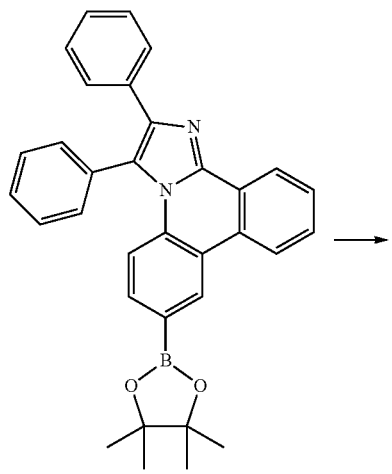

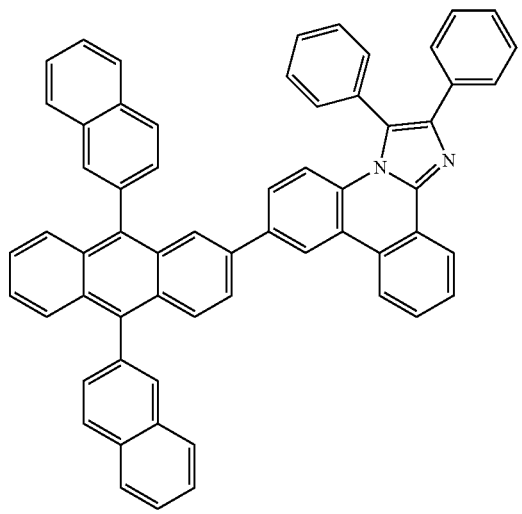

[compound 2-a-6]

After the compound B-12 (5.09 g, 10.0 mmol) and the compound A-7 (4.96 g, 10.0 mmol) were dissolved in tetrahydrofuran (100 mL), 2M potassium carbonate aqueous solution (20 mL) was added thereto, and tetrakistriphenylphosphino palladium (231 mg, 2 mol %) was put thereinto, agitated and refluxed for 5 hours. The temperature was cooled to normal temperature, and the produced solid was filtered. The filtered solid was recrystallized with chloroform and ethanol, filtered, and dried to manufacture the compound of Formula 2-a-6 (5.19 g, 65%). MS: [M+H]⁺=799

Example 38

Preparation of the Compound of Formula 2-a-20

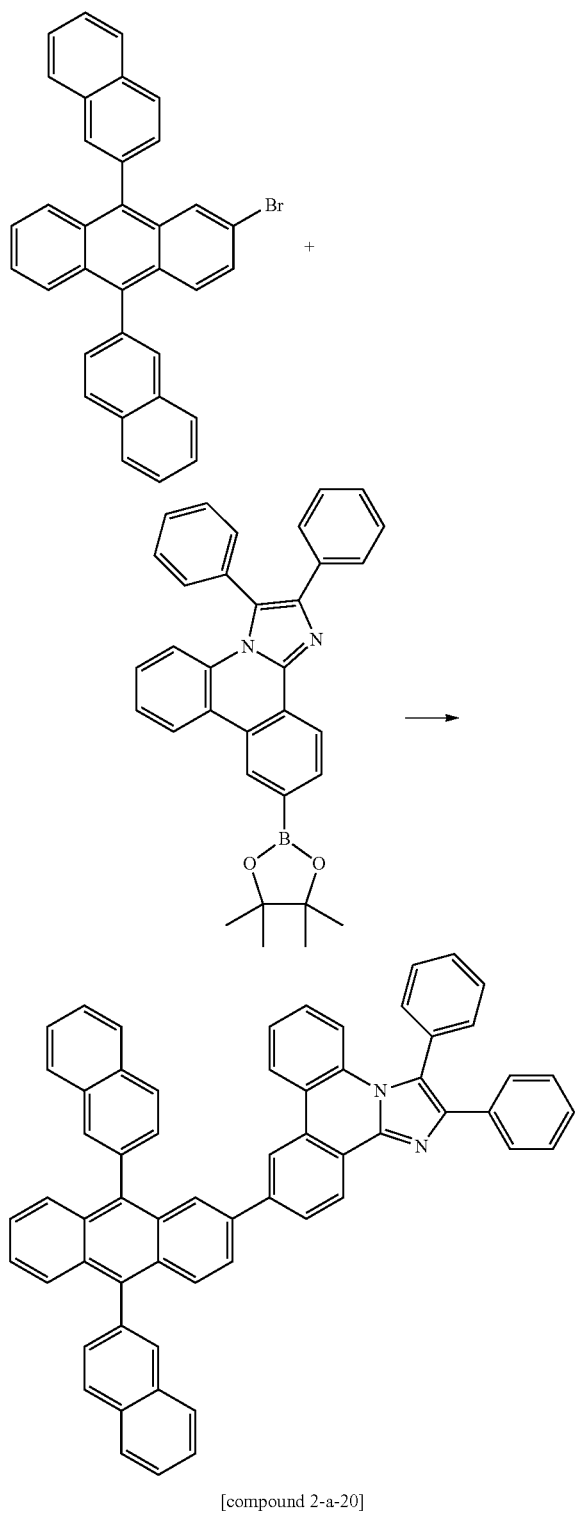

[compound 2-a-20]

The compound 2-a-20 (4.79 g, 60%) was prepared by using the same method as Example 37, except that the compound A-17 (4.96 g, 10.0 mmol) was used instead of the compound A-7 in Example 37. MS: [M+H]$^+$=799

Example 39

Preparation of the Compound of Formula 2-a-29

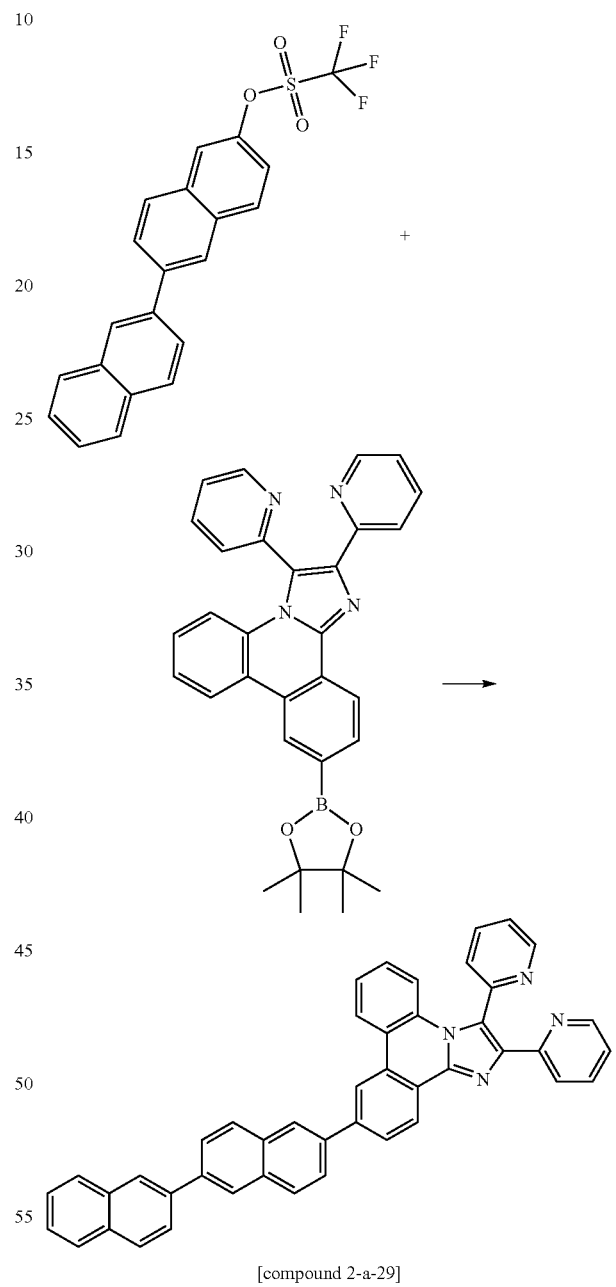

[compound 2-a-29]

After the compound B-8 (4.02 g, 10.0 mmol) and the compound A-26-2 (4.89 g, 10.0 mmol) were dissolved in tetrahydrofuran (100 mL), 2M potassium carbonate aqueous solution (20 mL) was added thereto, and tetrakistriphenylphosphino palladium (231 mg, 2 mol %) was put thereinto, agitated and refluxed for 5 hours. The temperature was cooled to normal temperature, and the produced solid was filtered. The filtered solid was recrystallized with chloroform and ethanol, filtered, and dried to manufacture the compound of Formula 2-a-29 (4.37 g, 70%). MS: [M+H]⁺=625

Example 40

Preparation of the Compound of Formula 2-a-38

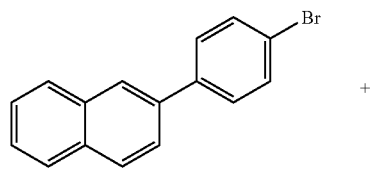

+

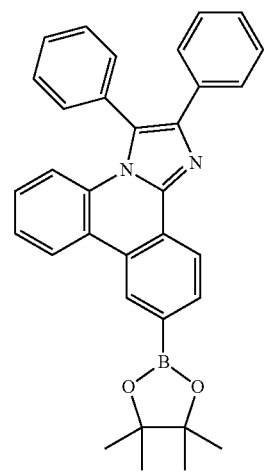

[compound 2-a-38]

The compound 2-a-38 (3.43 g, 60%) was prepared by using the same method as Example 1, except that the compound B-20 (2.83 g, 10.0 mmol) was used instead of the compound B-1 and the compound A-17 (4.96 g, 10.0 mmol) was used instead of the compound A-4 in Example 1. MS: [M+H]⁺=573

Example 41

Preparation of the Compound of Formula 2-b-6

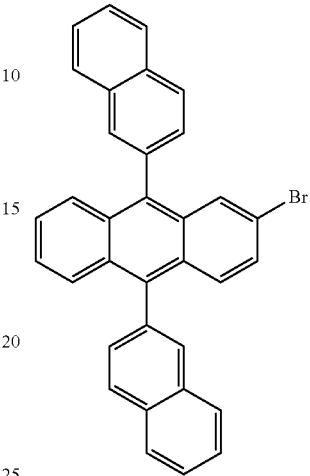

+

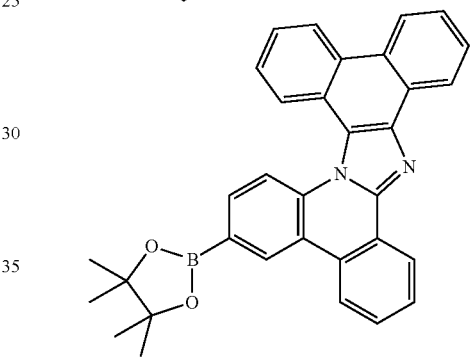

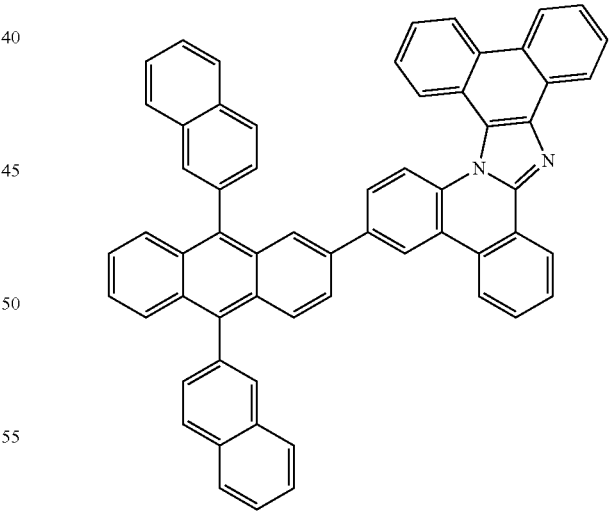

[compound 2-b-6]

The compound 2-b-6 (5.57 g, 70%) was prepared by using the same method as Example 1, except that the compound B-12 (5.09 g, 10.0 mmol) was used instead of the compound B-1 and the compound A-10 (4.94 g, 10.0 mmol) was used instead of the compound A-4 in Example 1. MS: [M+H]⁺=797

Example 42

Preparation of the Compound of Formula 2-b-16

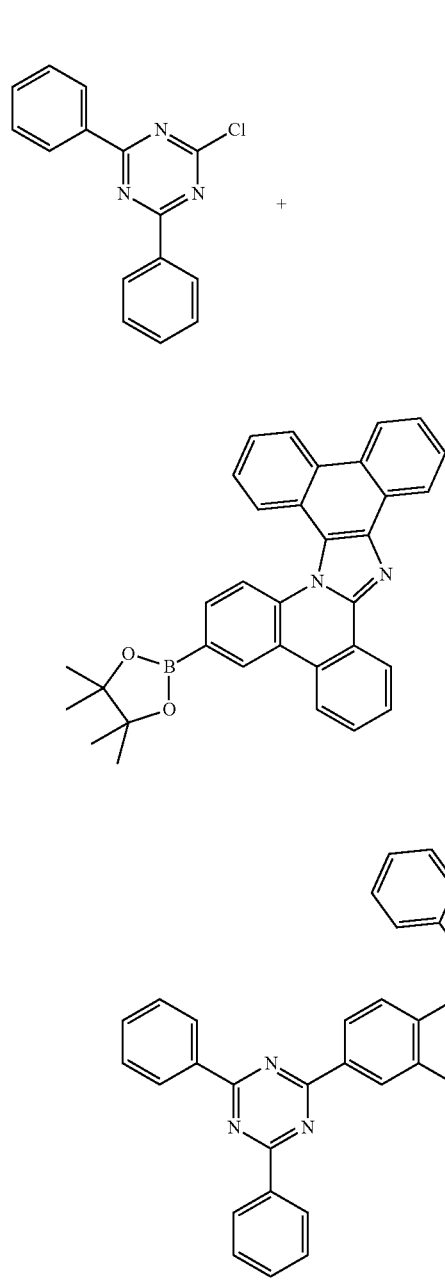

[compound 2-b-16]

The compound 2-b-16 (3.29 g, 55%) was prepared by using the same method as Example 1, except that 2-chloro-4,6-diphenyltriazine (2.67 g, 10.0 mmol) was used instead of the compound B-1 and the compound A-10 (4.94 g, 10.0 mmol) was used instead of the compound A-4 in Example 1. MS: [M+H]$^+$=600

Example 43

Preparation of the Compound of Formula 2-b-19

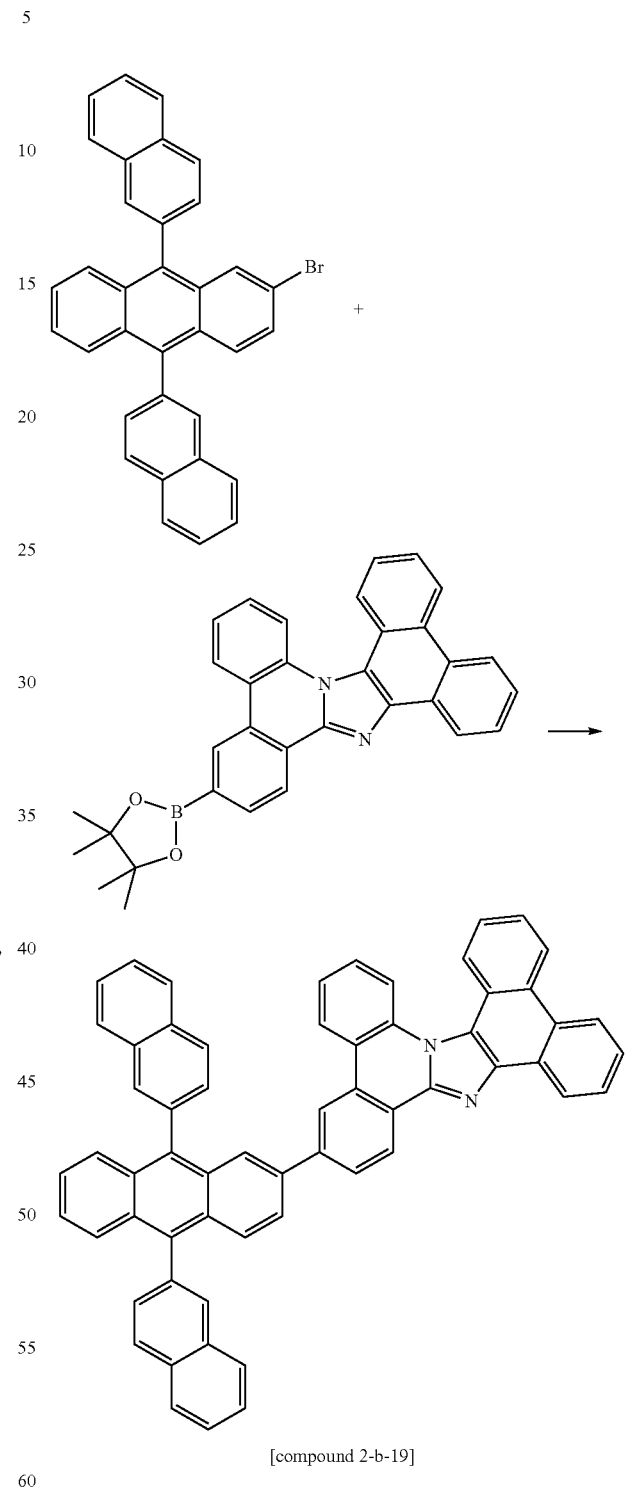

[compound 2-b-19]

The compound 2-b-19 (5.57 g, 70%) was prepared by using the same method as Example 1, except that the compound B-12 (5.09 g, 10.0 mmol) was used instead of the compound B-1 and the compound A-20 (4.94 g, 10.0 mmol) was used instead of the compound A-4 in Example 1. MS: [M+H]$^+$=797

Example 44

Preparation of the Compound of Formula 2-b-28

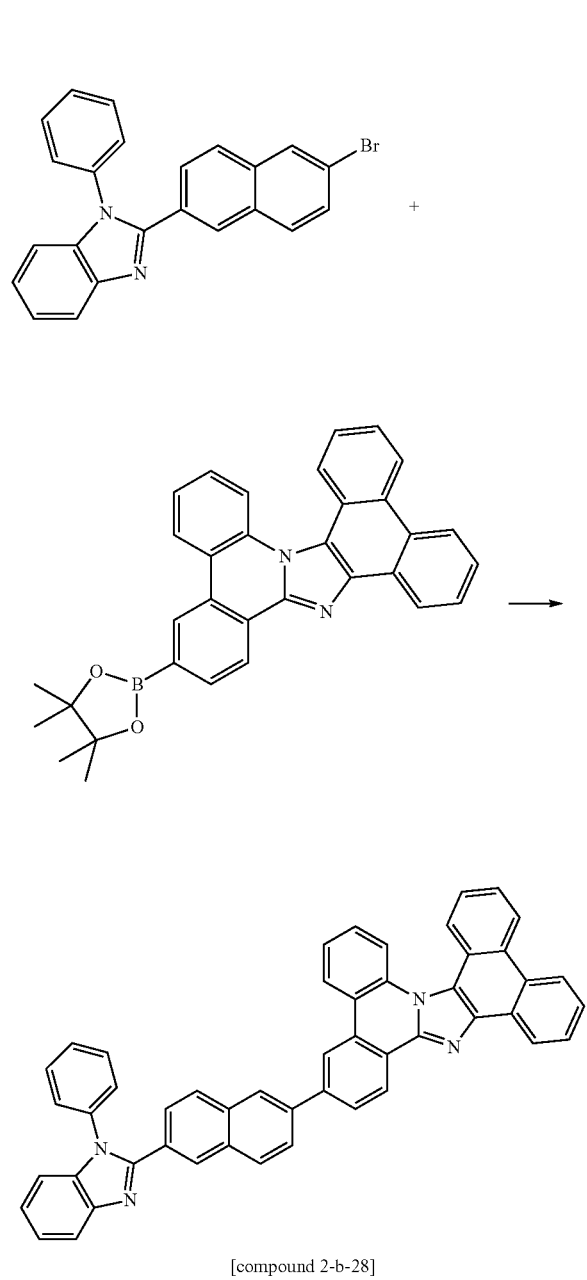

[compound 2-b-28]

Example 45

Preparation of the Compound of Formula 3-a-4

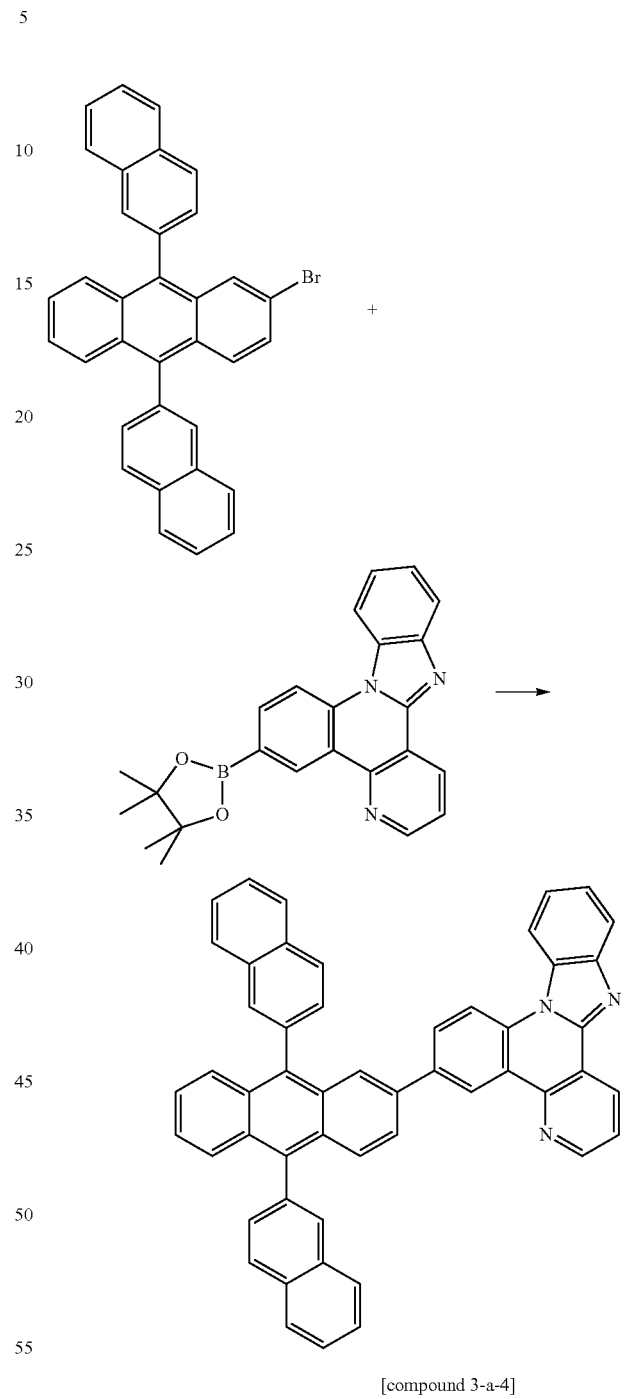

[compound 3-a-4]

The compound 2-b-28 (4.25 g, 62%) was prepared by using the same method as Example 1, except that the compound B-18 (3.99 g, 10.0 mmol) was used instead of the compound B-1 and the compound A-20 (4.94 g, 10.0 mmol) was used instead of the compound A-4 in Example 1. MS: $[M+H]^+$= 687

The compound 3-a-4 (3.84 g, 55%) was prepared by using the same method as Example 1, except that the compound B-12 (5.09 g, 10.0 mmol) was used instead of the compound B-1 and the compound A-34 (3.95 g, 10.0 mmol) was used instead of the compound A-4 in Example 1. MS: $[M+H]^+$= 698

Example 46

Preparation of the Compound of Formula 3-a-16

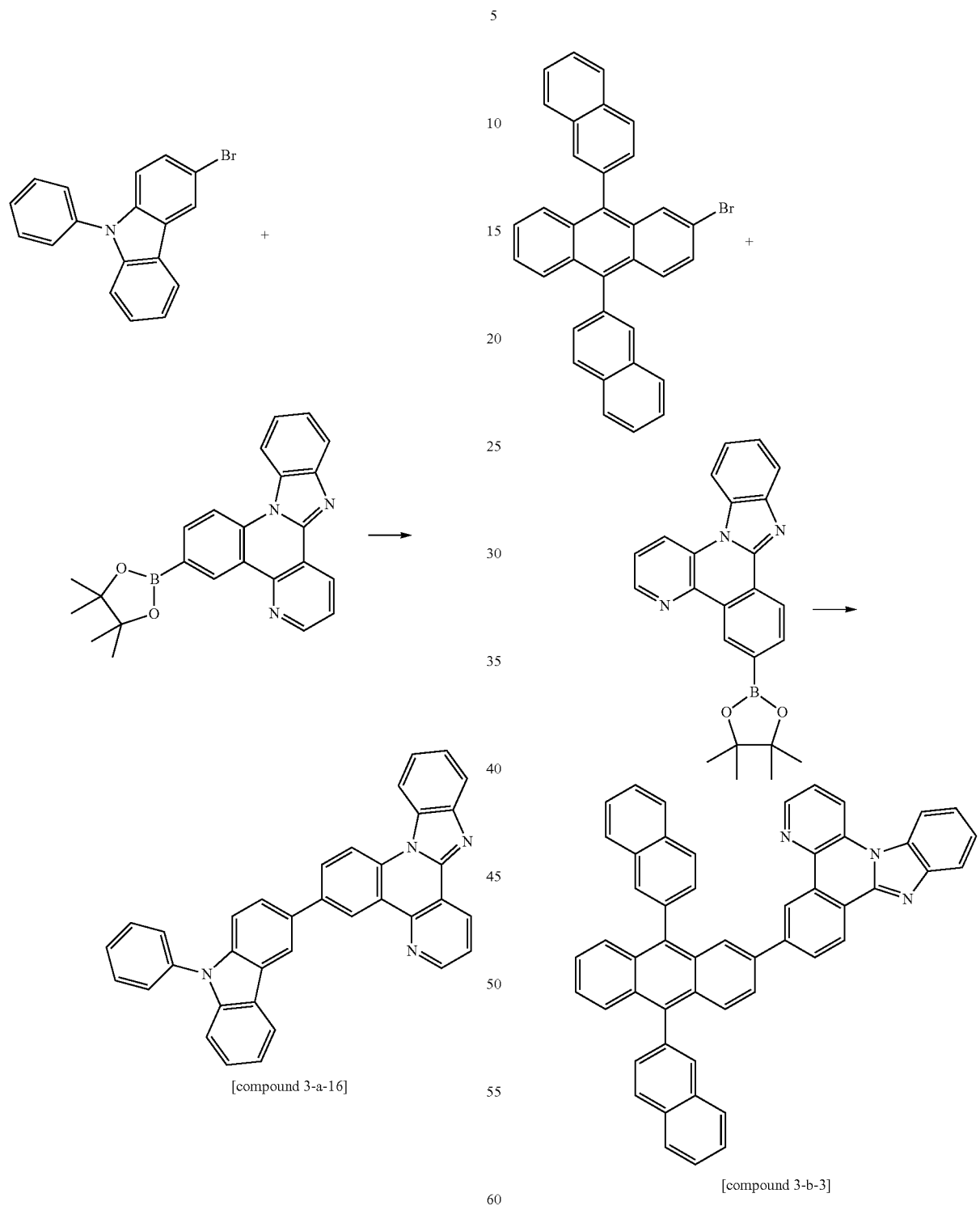

Example 47

Preparation of the Compound of Formula 3-b-3

The compound 3-a-16 (3.82 g, 75%) was prepared by using the same method as Example 1, except that 3-bromo-N-phenyl-carbazole (3.22 g, 10.0 mmol) was used instead of the compound B-1 and the compound A-34 (3.95 g, 10.0 mmol) was used instead of the compound A-4 in Example 1. MS: $[M+H]^+$=511

The compound 3-b-3 (4.95 g, 71%) was prepared by using the same method as Example 1, except that the compound B-12 (5.09 g, 10.0 mmol) was used instead of the compound B-1 and the compound A-30 (3.95 g, 10.0 mmol) was used instead of the compound A-4 in Example 1. MS: $[M+H]^+$= 698

Example 48

Preparation of the Compound of Formula 3-b-13

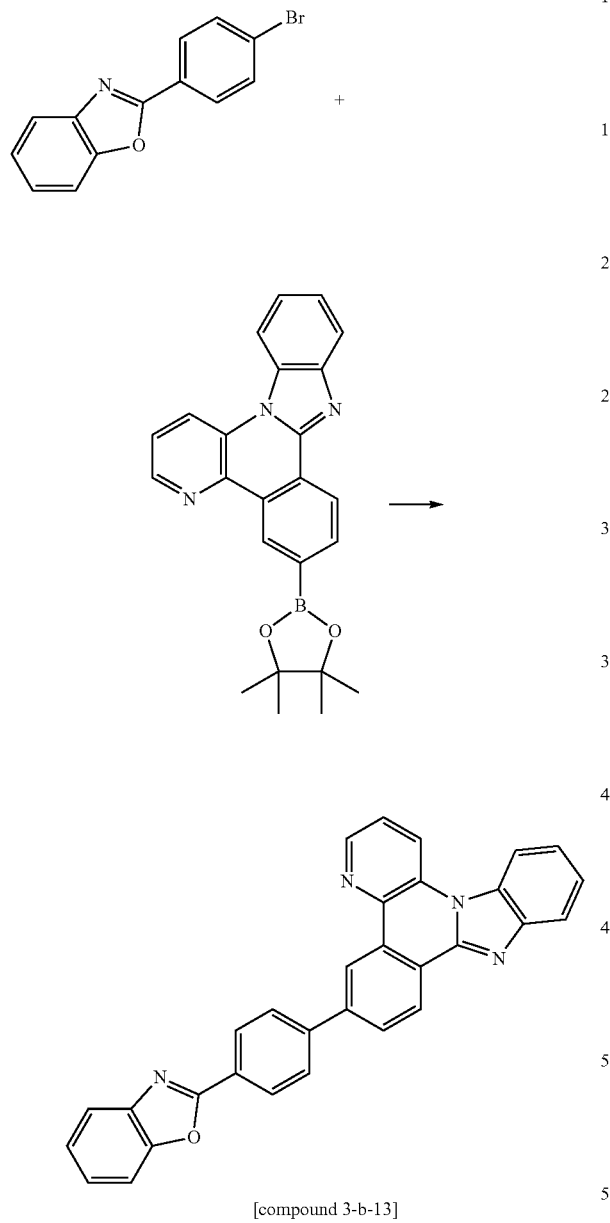

[compound 3-b-13]

The compound 3-b-13 (3.10 g, 67%) was prepared by using the same method as Example 1, except that 2-(4-bromophenyl)benzo[d]oxazole (2.74 g, 10.0 mmol) was used instead of the compound B-1 and the compound A-30 (3.95 g, 10.0 mmol) was used instead of the compound A-4 in Example 1. MS: [M+H]$^+$=463

Example 49

Preparation of the Compound of Formula 3-c-10

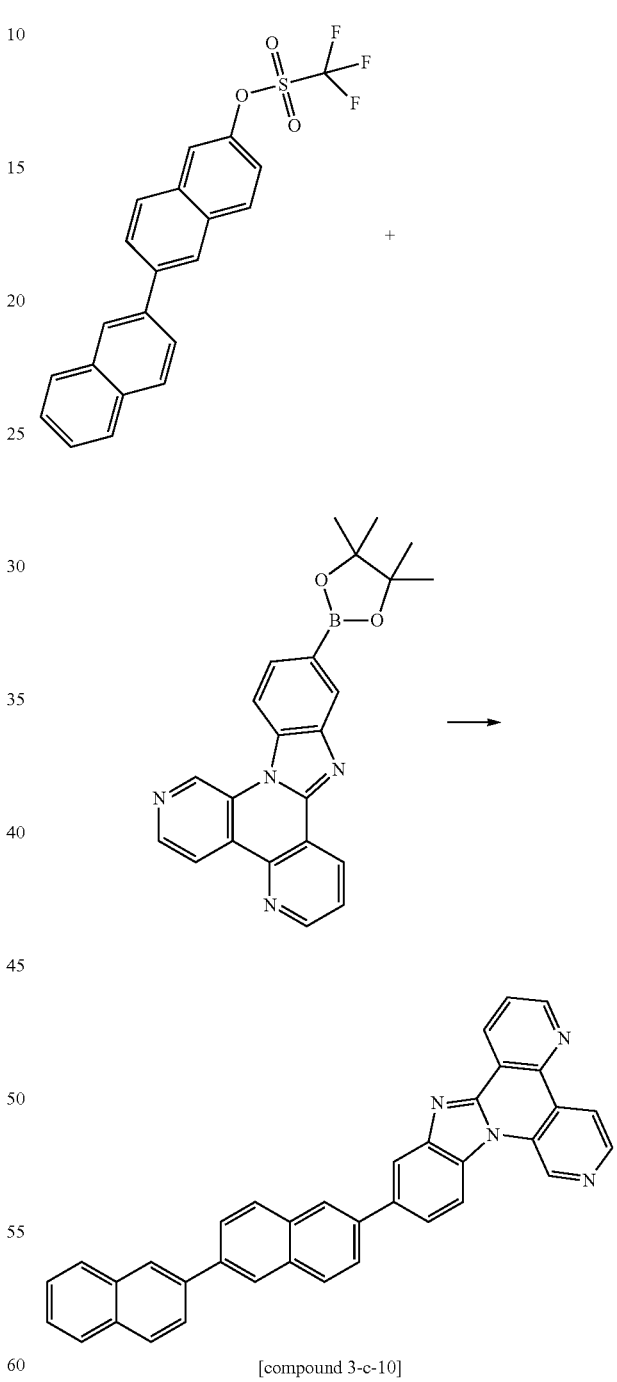

[compound 3-c-10]

The compound 3-c-10 (3.50 g, 67%) was prepared by using the same method as Example 1, except that the compound B-8 (4.02 g, 10.0 mmol) was used instead of the compound B-1 and the compound A-42 (3.96 g, 10.0 mmol) was used instead of the compound A-4 in Example 1. MS: [M+H]$^+$=523

Example 50

Preparation of the Compound of Formula 3-c-11

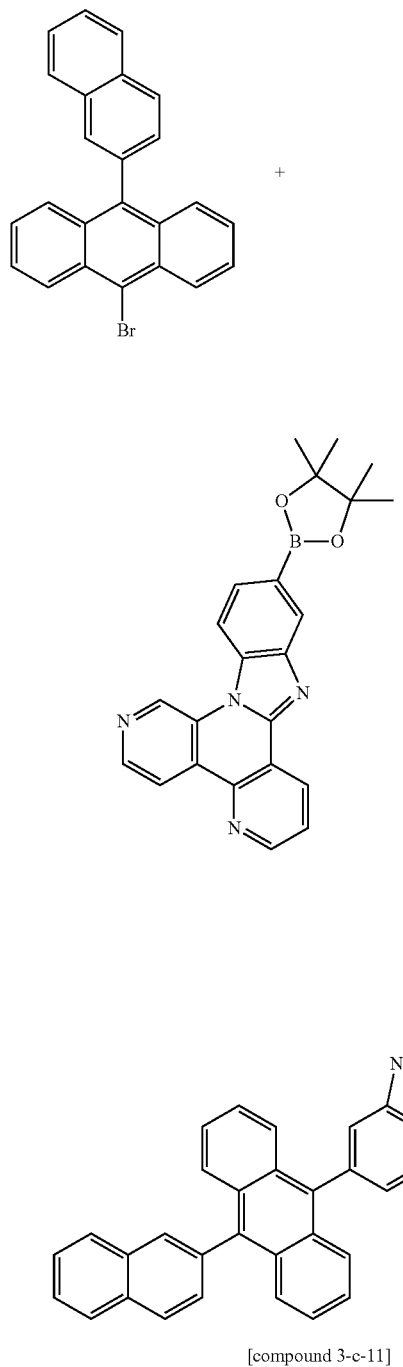

[compound 3-c-11]

The compound 3-c-11 (3.83 g, 67%) was prepared by using the same method as Example 1, except that the compound A-42 (3.96 g, 10.0 mmol) was used instead of the compound A-4 in Example 1. MS: [M+H]$^+$=573

Example 51

Preparation of the Compound of Formula 3-c-12

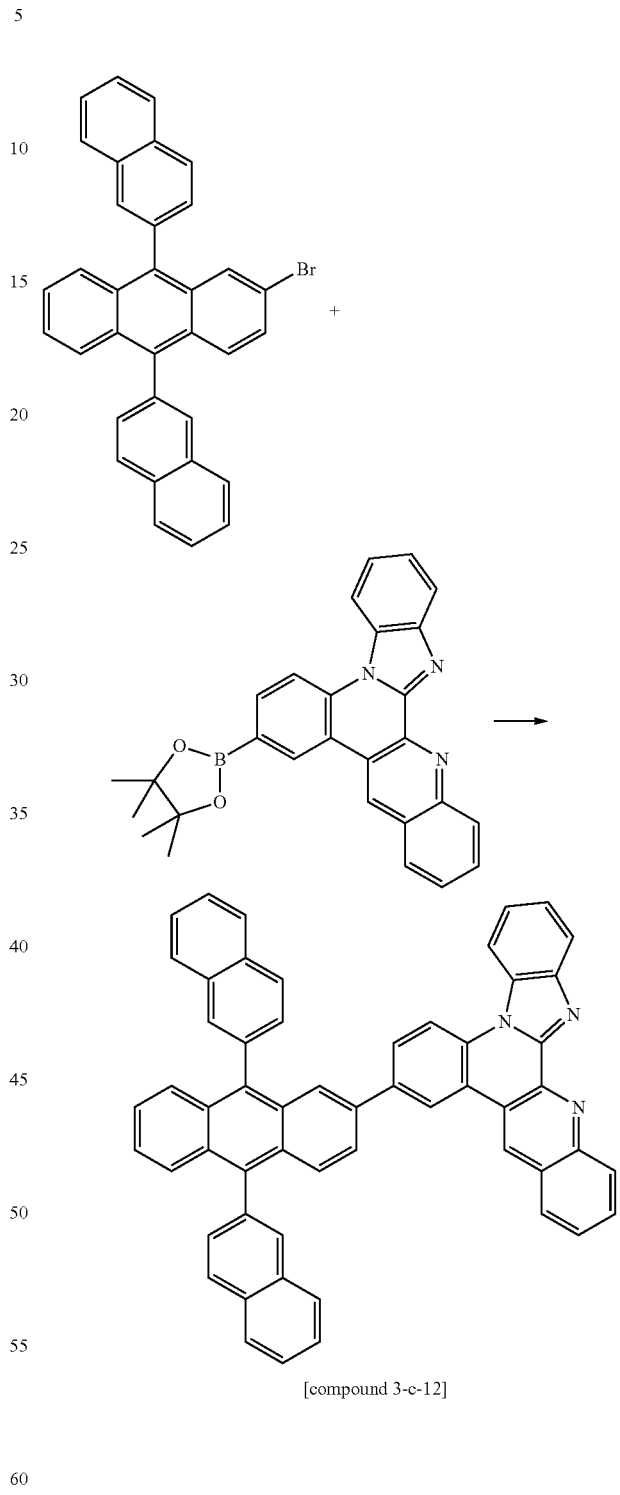

[compound 3-c-12]

The compound 3-c-12 (5.01 g, 67%) was prepared by using the same method as Example 1, except that the compound B-12 (5.09 g, 10.0 mmol) was used instead of the compound B-1 and the compound A-38 (4.45 g, 10.0 mmol) was used instead of the compound A-4 in Example 1. MS: [M+H]$^+$= 748

Example 52

Preparation of the Compound of Formula 3-c-13

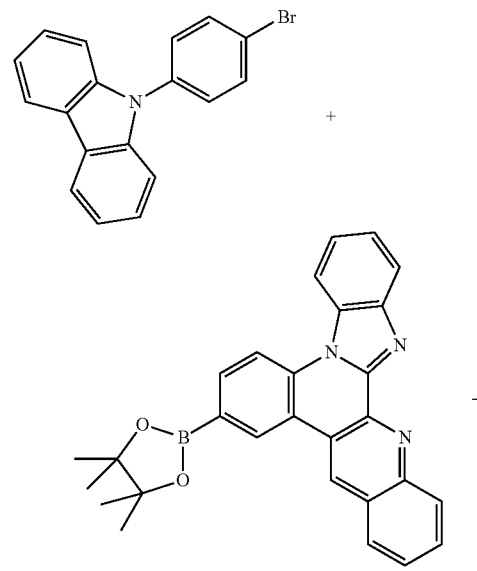

[compound 3-c-13]

The compound 3-c-13 (3.36 g, 60%) was prepared by using the same method as Example 1, except that the compound B-15 (3.21 g, 10.0 mmol) was used instead of the compound B-1 and the compound A-38 (4.45 g, 10.0 mmol) was used instead of the compound A-4 in Example 1. MS: [M+H]$^+$= 561

Example 53

Preparation of the Compound of Formula 3-c-21

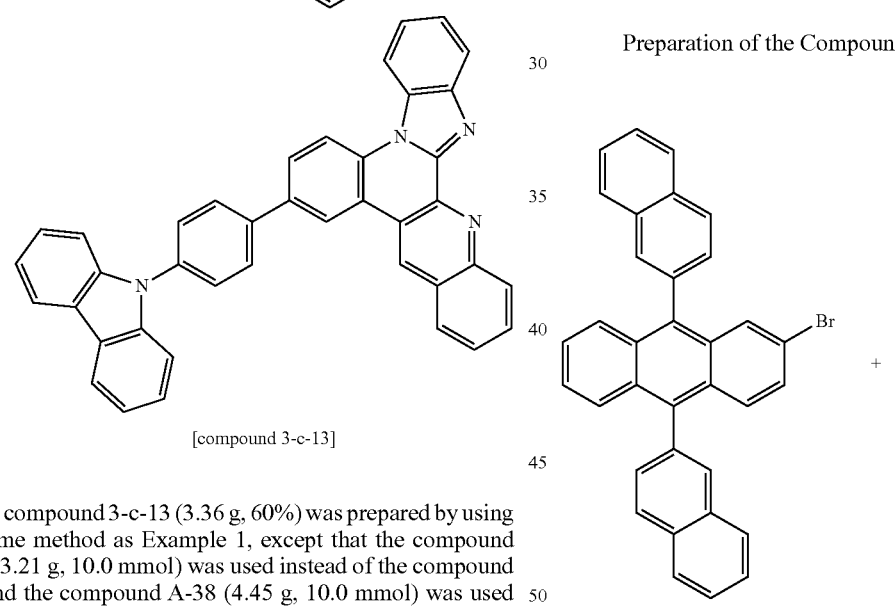

[compound 3-c-21]

The compound 3-c-21 (2.03 g, 43%) was prepared by using the same method as Example 1, except that the compound B-20 (2.83 g, 10.0 mmol) was used instead of the compound B-1 and the compound A-38 (4.45 g, 10.0 mmol) was used instead of the compound A-4 in Example 1. MS: [M+H]$^+$= 473

Example 53

Preparation of the Compound of Formula 4-a-7

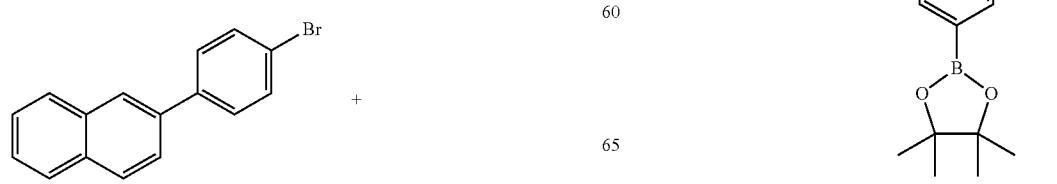

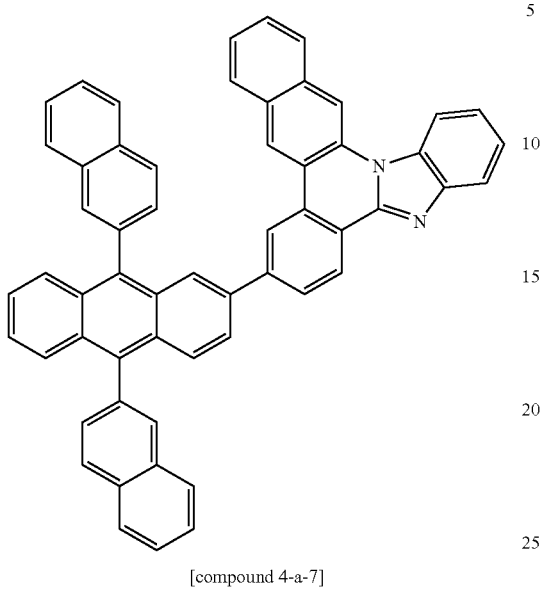

[compound 4-a-7]

The compound 4-a-7 (4.11 g, 55%) was prepared by using the same method as Example 1, except that the compound B-12 (5.09 g, 10.0 mmol) was used instead of the compound B-1 and the compound A-46 (4.44 g, 10.0 mmol) was used instead of the compound A-4 in Example 1. MS: [M+H]$^+$=747

Example 54

Preparation of the Compound of Formula 4-a-8

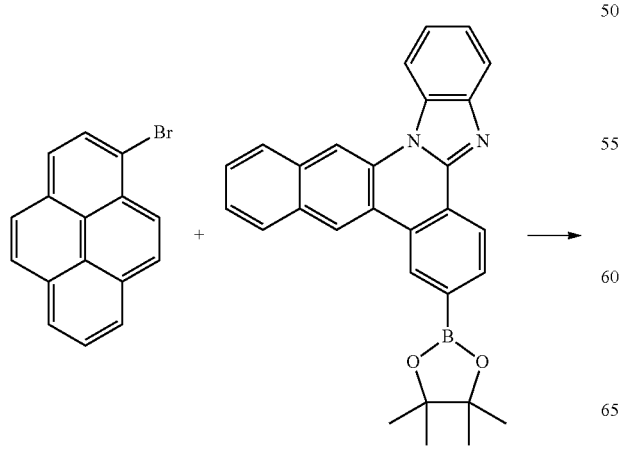

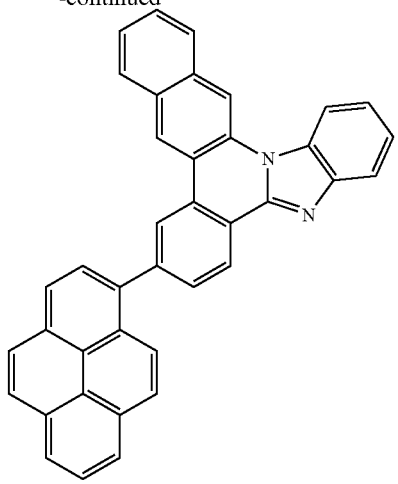

[compound 4-a-8]

The compound 4-a-8 (2.85 g, 55%) was prepared by using the same method as Example 1, except that 1-bromopyrene (2.81 g, 10.0 mmol) was used instead of the compound B-1 and the compound A-46 (4.44 g, 10.0 mmol) was used instead of the compound A-4 in Example 1. MS: [M+H]$^+$=519

Example 55

Preparation of the Compound of Formula 5-a-1

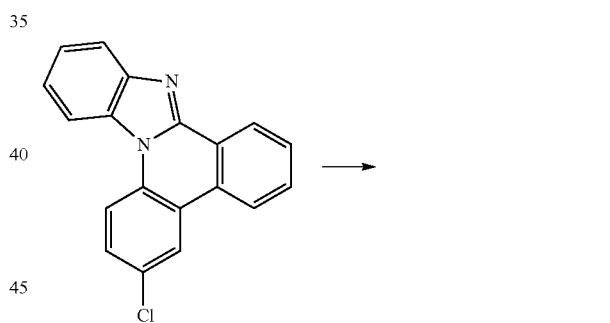

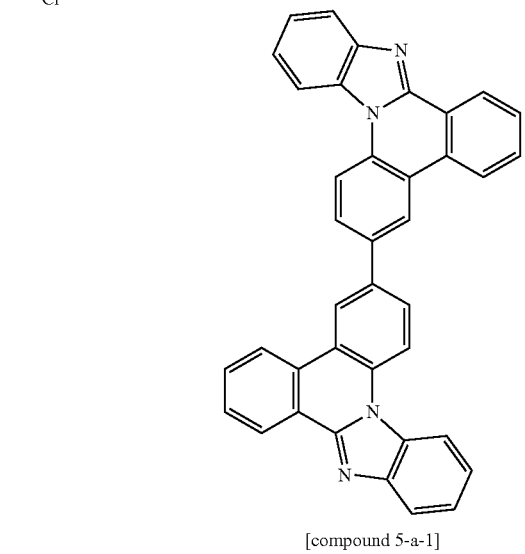

[compound 5-a-1]

After the compound A-3 (3.02 g, 10.0 mmol) was dispersed in 1,4-dioxane (50 mL), bis(pinacolato)diborone (1.27 g, 5.0 mmol), $K_3PO_4 \cdot H_2O$ (6.36 g, 30 mmol), and $Pd[P(t-Bu_3)]_2$ (102 mg, 2 mol%) were added thereto, and they were agitated and refluxed for 7 hours. After the reaction was finished, the temperature was lowered to normal temperature, an excessive amount of water was poured, and the generated solid was filtered. The filtered solid was dissolved in chloroform, dried with anhydrous magnesium sulfate, concentrated under the reduced pressure, and recrystallized with tetrahydrofuran and ethanol to prepare the compound 5-a-1 (3.63 g, 68%). MS: $[M+H]^+ = 535$

Example 56

Preparation of the Compound of Formula 5-a-2

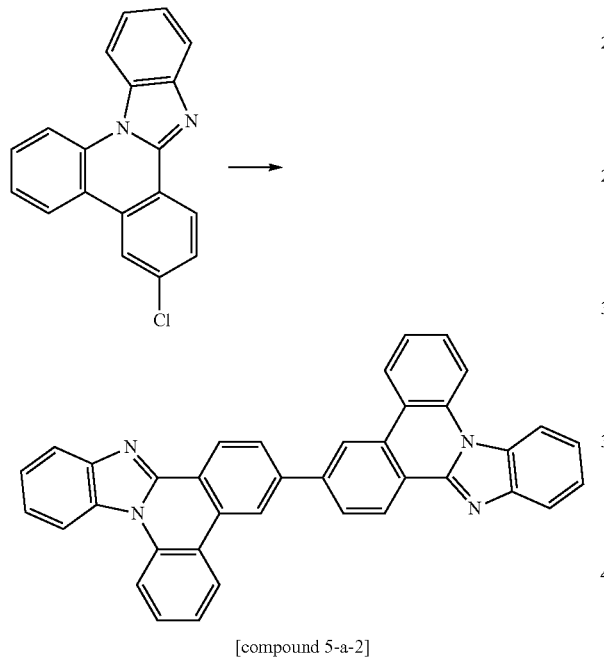

[compound 5-a-2]

The compound 5-a-2 (2.94 g, 55%) was prepared by using the same method as Example 55, except that the compound A-13 (3.02 g, 10.0 mmol) was used instead of the compound A-3 in Example 55. MS: $[M+H]^+ = 535$

Example 57

Preparation of the Compound of Formula 5-a-13

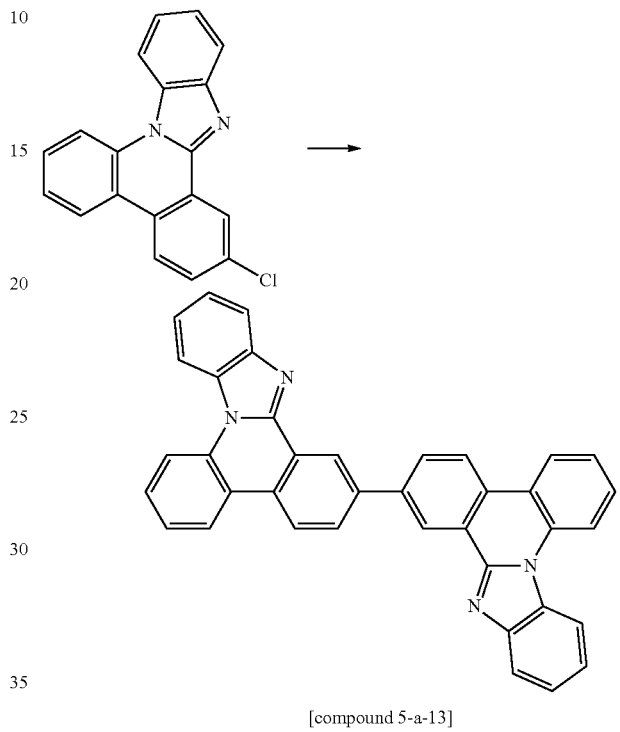

[compound 5-a-13]

The compound 5-a-13 (3.21 g, 60%) was prepared by using the same method as Example 55, except that the compound A-53 (3.02 g, 10.0 mmol) was used instead of the compound A-3 in Example 55. MS: $[M+H]^+ = 535$

Example 58

Preparation of the Compound of Formula 5-a-23

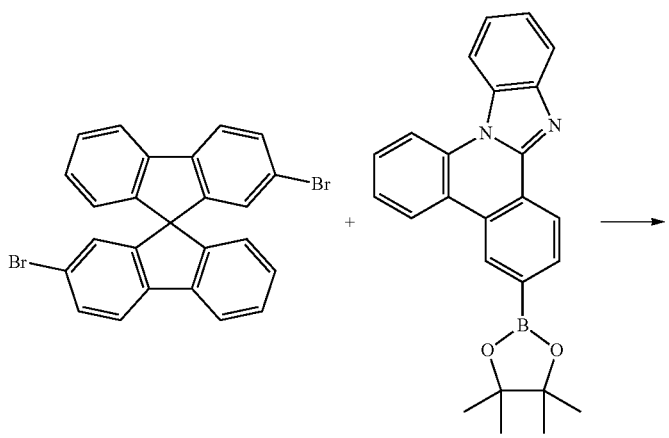

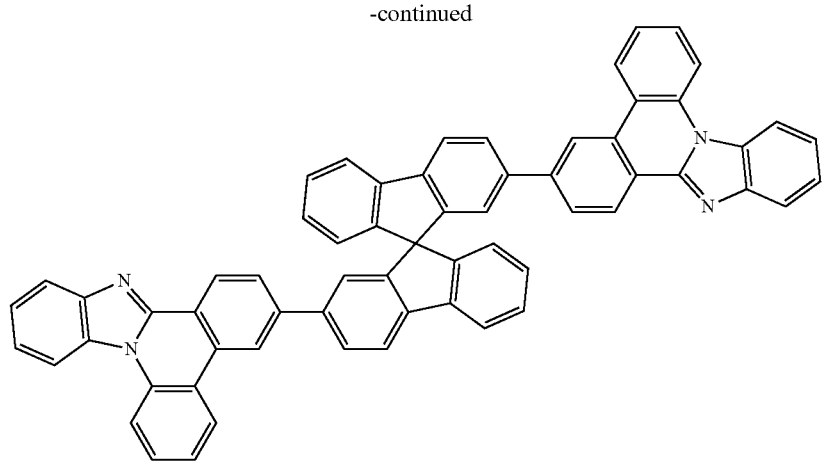

[compound 5-a-23]

The compound 5-a-23 (2.76 g, 65%) was prepared by using the same method as Example 1, except that 2,2'-dibromo-9,9'-spirofluorene (2.37 g, 5.0 mmol) was used instead of the compound B-1 and the compound A-14 (3.94 g, 10.0 mmol) was used instead of the compound A-4 in Example 1. MS: $[M+H]^+ = 849$

Example 59

Preparation of the Compound of Formula 5-a-32

A-49 (3.02 g, 10.0 mmol) was used instead of the compound A-3 in Example 55. MS: $[M+H]^+ = 535$

Example 60

Preparation of the Compound of Formula 5-a-33

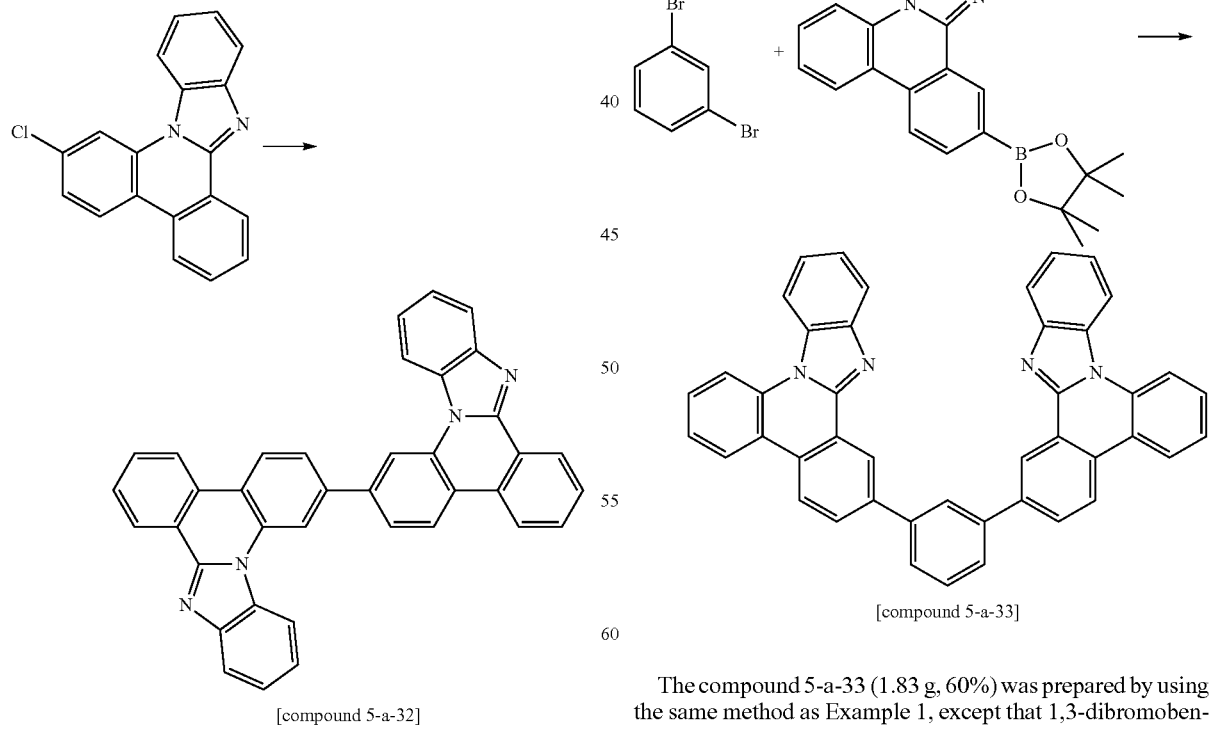

[compound 5-a-32]

[compound 5-a-33]

The compound 5-a-32 (3.21 g, 60%) was prepared by using the same method as Example 55, except that the compound The compound 5-a-33 (1.83 g, 60%) was prepared by using the same method as Example 1, except that 1,3-dibromobenzene (1.18 g, 5.0 mmol) was used instead of the compound B-1 and the compound A-54 (3.94 g, 10.0 mmol) was used instead of the compound A-4 in Example 1. MS: $[M+H]^+ = 611$

Example 61
Preparation of the Compound of Formula 5-a-34
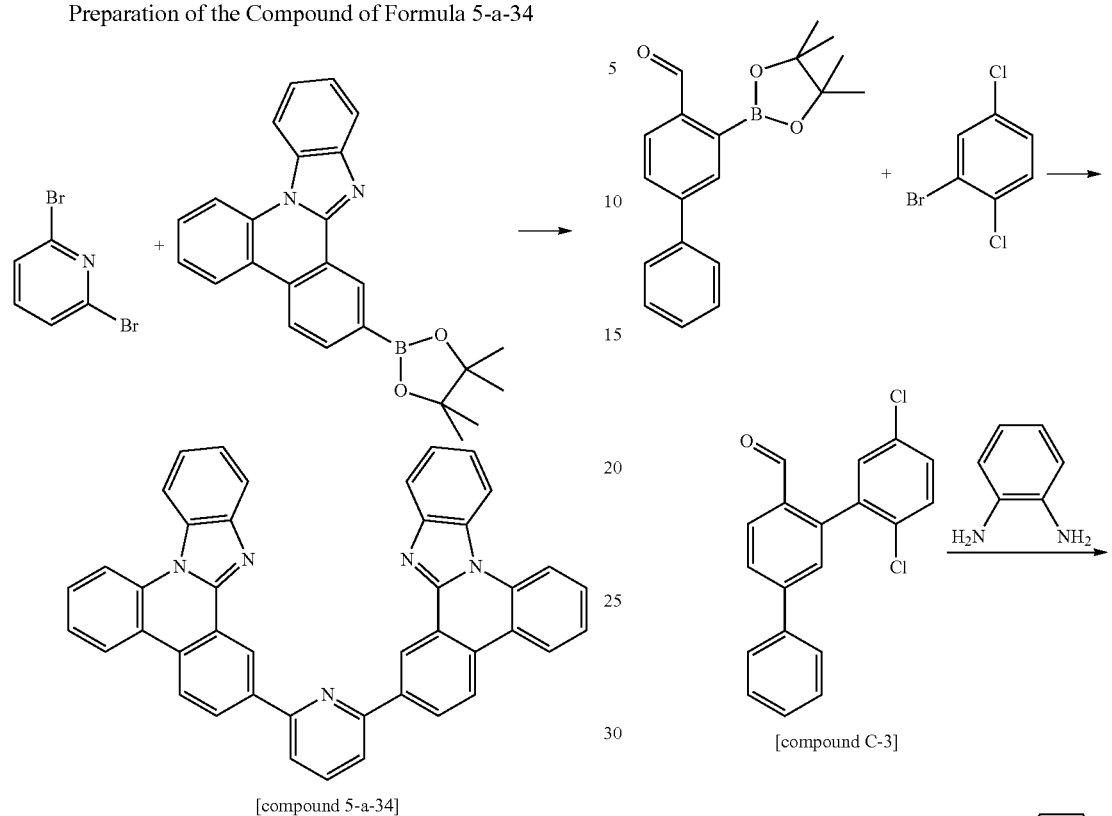
[compound 5-a-34]
The compound 5-a-34 (1.68 g, 55%) was prepared by using the same method as Example 1, except that 2,6-dibromopyridine (1.19 g, 5.0 mmol) was used instead of the compound B-1 and the compound A-54 (3.94 g, 10.0 mmol) was used instead of the compound A-4 in Example 1. MS: $[M+H]^+= 612$
Example 62
Preparation of the Compound of Formula 6-a-1
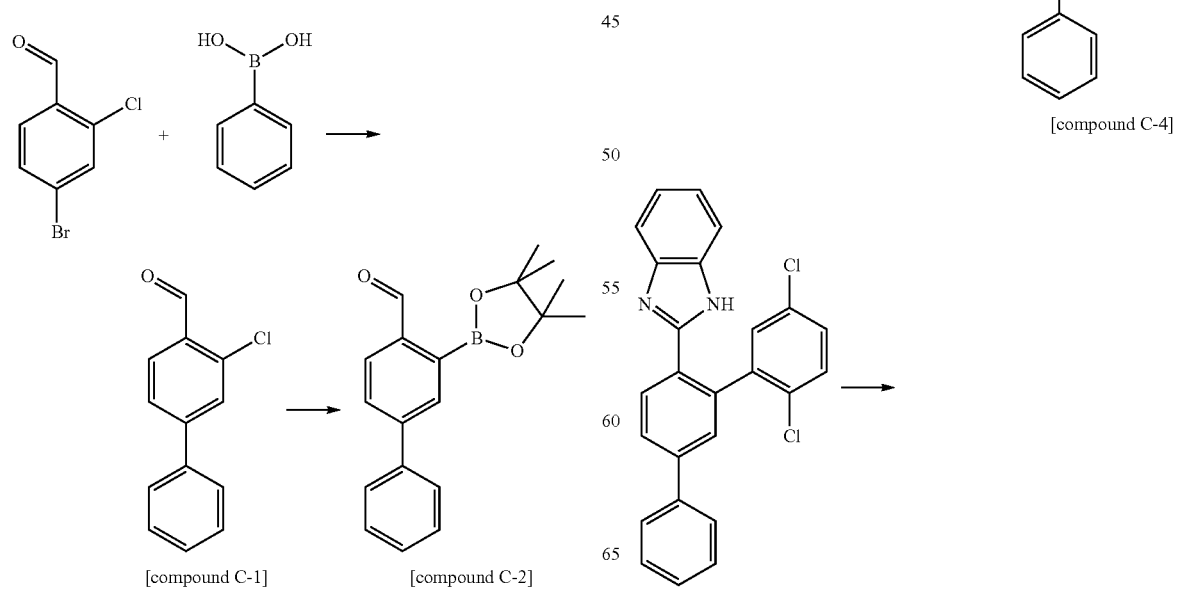

-continued

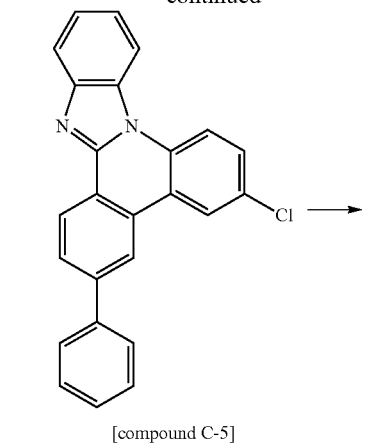

[compound C-5]

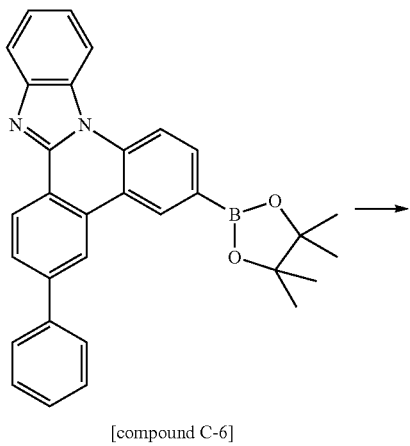

[compound C-6]

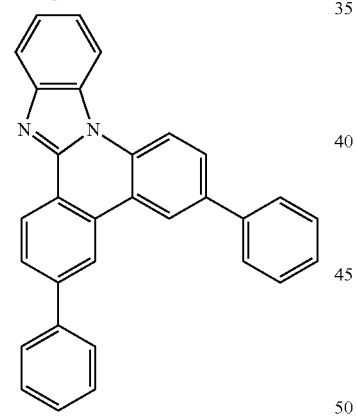

[compound 6-a-1]

(1) Preparation of the Compound C-1

After 4-bromo-2-chlorobenzaldehyde (2.19 g, 10.0 mmol) and phenylboronic acid (1.22 g, 10.0 mmol) were completely dissolved in tetrahydrofuran (50 mL), 2M potassium carbonate aqueous solution (30 mL) was added thereto, and tetrakistriphenylphosphino palladium (Pd(PPh$_3$)$_4$ (231 mg, 2 mol %) was put thereinto, agitated and refluxed for 5 hours. After the reaction was finished, the temperature was cooled to normal temperature, and the produced solid was filtered. The filtered solid was dissolved in chloroform, dried with anhydrous magnesium sulfate, concentrated under the reduced pressure, and recrystallized with chloroform and hexane to prepare the compound C-1 (1.94 g, 90%). MS: [M]$^+$=216

(2) Preparation of the Compound C-2

The compound C-2 (4.14 g, 80%) was prepared by using the same method as Preparation Example 4, except that the compound C-1 (3.63 g, 16.8 mmol) was used instead of the compound A-3 in Preparation Example 4. MS: [M]$^+$=308

(3) Preparation of the Compound C-3

The compound C-3 (18.0 g, 80%) was prepared by using the same method as Preparation Example 1, except that the compound C-2 (23.4 g, 76 mmol) was used instead of the compound 2-formylphenylboronic acid in Preparation Example 1. MS: [M]$^+$=326

(4) Preparation of the Compound C-4

The compound C-4 (14.3 g, 50%) was prepared by using the same method as Preparation Example 2, except that the compound C-3 (22.5 g, 69.1 mmol) was used instead of the compound A-1 in Preparation Example 2. MS: [M]$^+$=414

(5) Preparation of the Compound C-5

The compound C-5 (0.964 g, 50%) was prepared by using the same method as Preparation Example 3, except that the compound C-4 (2.1 g, 5.1 mmol) was used instead of the compound A-2 in Preparation Example 3. MS: [M]$^+$=378

(6) Preparation of the Compound C-6

The compound C-6 (6.32 g, 80%) was prepared by using the same method as Preparation Example 4, except that the compound C-5 (6.35 g, 16.8 mmol) was used instead of the compound A-3 in Preparation Example 4. MS: [M]$^+$=470

(7) Preparation of the Compound 6-a-1

The compound 6-a-1 (3.36 g, 80%) was prepared by using the same method as Example 1, except that bromobenzene (1.57 g, 10.0 mmol) was used instead of the compound B-1 and the compound C-6 (4.70 g, 10.0 mmol) was used instead of the compound A-4 in Example 1. MS: [M+H]$^+$=421

Example 63

Preparation of the Compound of Formula 6-a-2

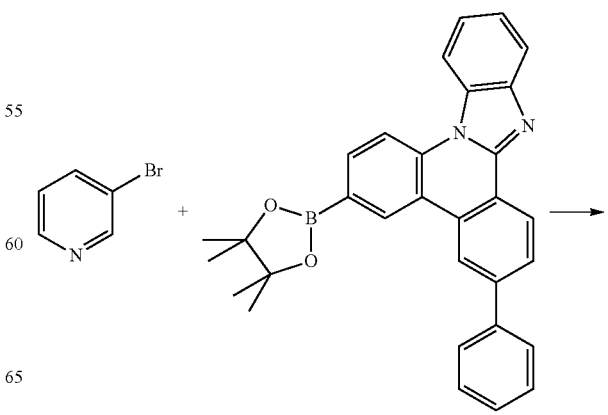

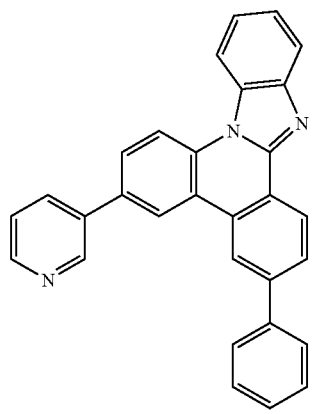
[compound 6-a-2]
The compound 6-a-2 (2.95 g, 70%) was prepared by using the same method as Example 1, except that 3-bromopyridine (1.58 g, 10.0 mmol) was used instead of the compound B-1 and the compound C-6 (4.70 g, 10.0 mmol) was used instead of the compound A-4 in Example 1. MS: [M+H]$^+$=422
Example 64
Preparation of the Compound of Formula 6-a-3
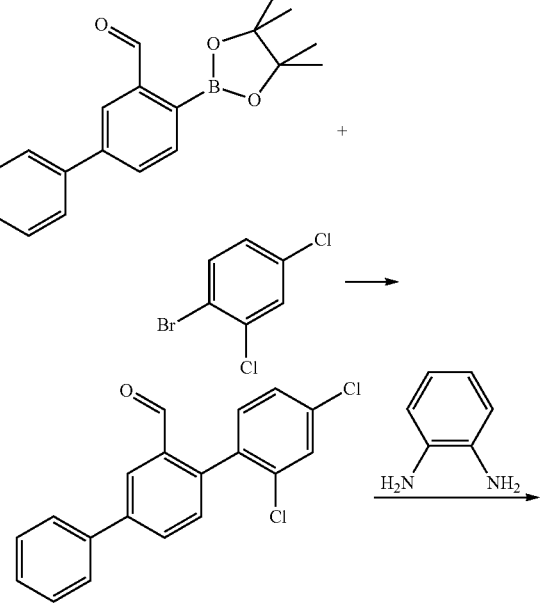
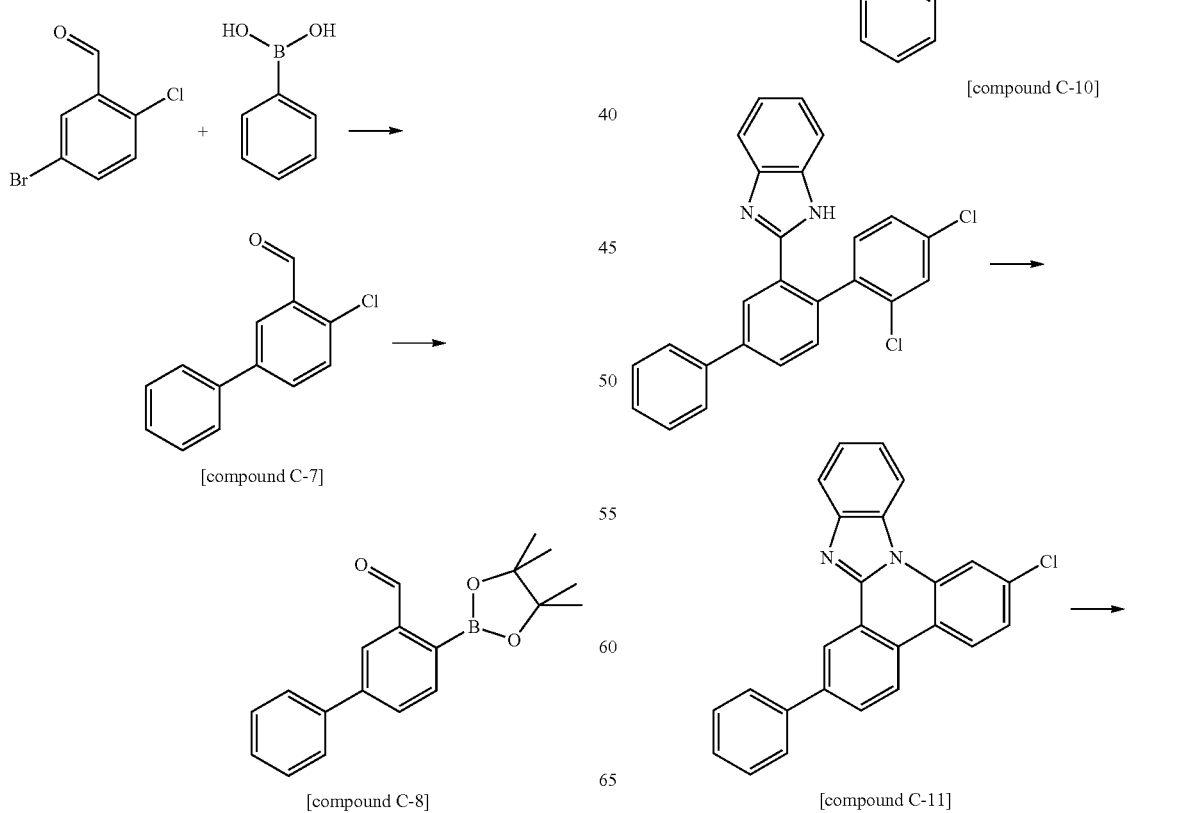

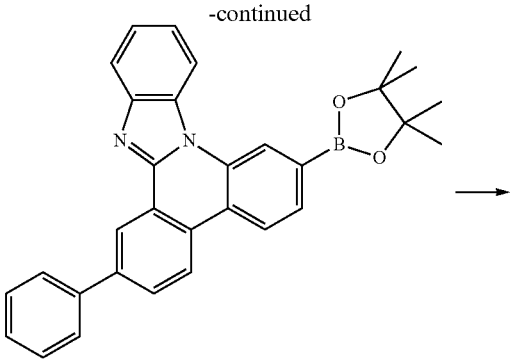

[compound C-12]

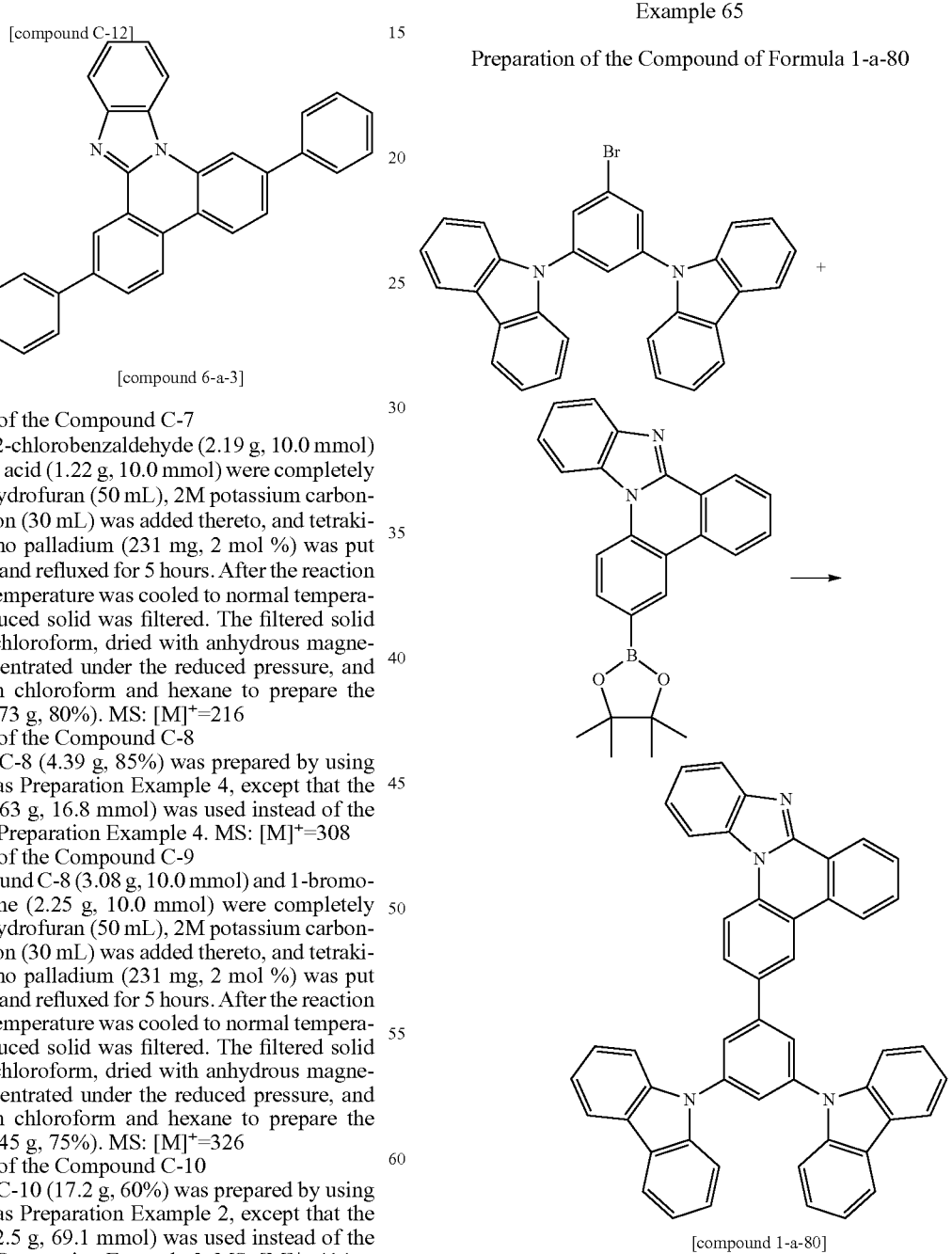

[compound 6-a-3]

(1) Preparation of the Compound C-7

After 5-bromo-2-chlorobenzaldehyde (2.19 g, 10.0 mmol) and phenylboronic acid (1.22 g, 10.0 mmol) were completely dissolved in tetrahydrofuran (50 mL), 2M potassium carbonate aqueous solution (30 mL) was added thereto, and tetrakistriphenylphosphino palladium (231 mg, 2 mol %) was put thereinto, agitated and refluxed for 5 hours. After the reaction was finished, the temperature was cooled to normal temperature, and the produced solid was filtered. The filtered solid was dissolved in chloroform, dried with anhydrous magnesium sulfate, concentrated under the reduced pressure, and recrystallized with chloroform and hexane to prepare the compound C-7 (1.73 g, 80%). MS: $[M]^+=216$ (2) Preparation of the Compound C-8

The compound C-8 (4.39 g, 85%) was prepared by using the same method as Preparation Example 4, except that the compound C-7 (3.63 g, 16.8 mmol) was used instead of the compound A-3 in Preparation Example 4. MS: $[M]^+=308$ (3) Preparation of the Compound C-9

After the compound C-8 (3.08 g, 10.0 mmol) and 1-bromo-2,4-dichlorobenzene (2.25 g, 10.0 mmol) were completely dissolved in tetrahydrofuran (50 mL), 2M potassium carbonate aqueous solution (30 mL) was added thereto, and tetrakistriphenylphosphino palladium (231 mg, 2 mol %) was put thereinto, agitated and refluxed for 5 hours. After the reaction was finished, the temperature was cooled to normal temperature, and the produced solid was filtered. The filtered solid was dissolved in chloroform, dried with anhydrous magnesium sulfate, concentrated under the reduced pressure, and recrystallized with chloroform and hexane to prepare the compound C-9 (2.45 g, 75%). MS: $[M]^+=326$ (4) Preparation of the Compound C-10

The compound C-10 (17.2 g, 60%) was prepared by using the same method as Preparation Example 2, except that the compound C-9 (22.5 g, 69.1 mmol) was used instead of the compound A-1 in Preparation Example 2. MS: $[M]^+=414$ (5) Preparation of the Compound C-11

The compound C-11 (0.868 g, 45%) was prepared by using the same method as Preparation Example 3, except that the compound C-10 (2.11 g, 5.1 mmol) was used instead of the compound A-2 in Preparation Example 3. MS: $[M]^+=378$ (6) Preparation of the Compound C-12

The compound C-12 (6.32 g, 80%) was prepared by using the same method as Preparation Example 4, except that the compound C-11 (6.35 g, 16.8 mmol) was used instead of the compound A-3 in Preparation Example 4. MS: $[M]^+=470$ (7) Preparation of the Compound 6-a-3

The compound 6-a-3 (3.57 g, 85%) was prepared by using the same method as Example 1, except that bromobenzene (1.57 g, 10.0 mmol) was used instead of the compound B-1 and the compound C-12 (4.70 g, 10.0 mmol) was used instead of the compound A-4 in Example 1. MS: $[M+H]^+=421$ Example 65

Preparation of the Compound of Formula 1-a-80

[compound 1-a-80]

The compound 1-a-80 (5.05 g, 75%) was prepared by using the same method as Example 1, except that the compound B-24 (4.87 g, 10.0 mmol) was used instead of the compound B-1 in Example 1. MS: [M+H]⁺=675

Example 66

Preparation of the Compound of Formula 1-b-146

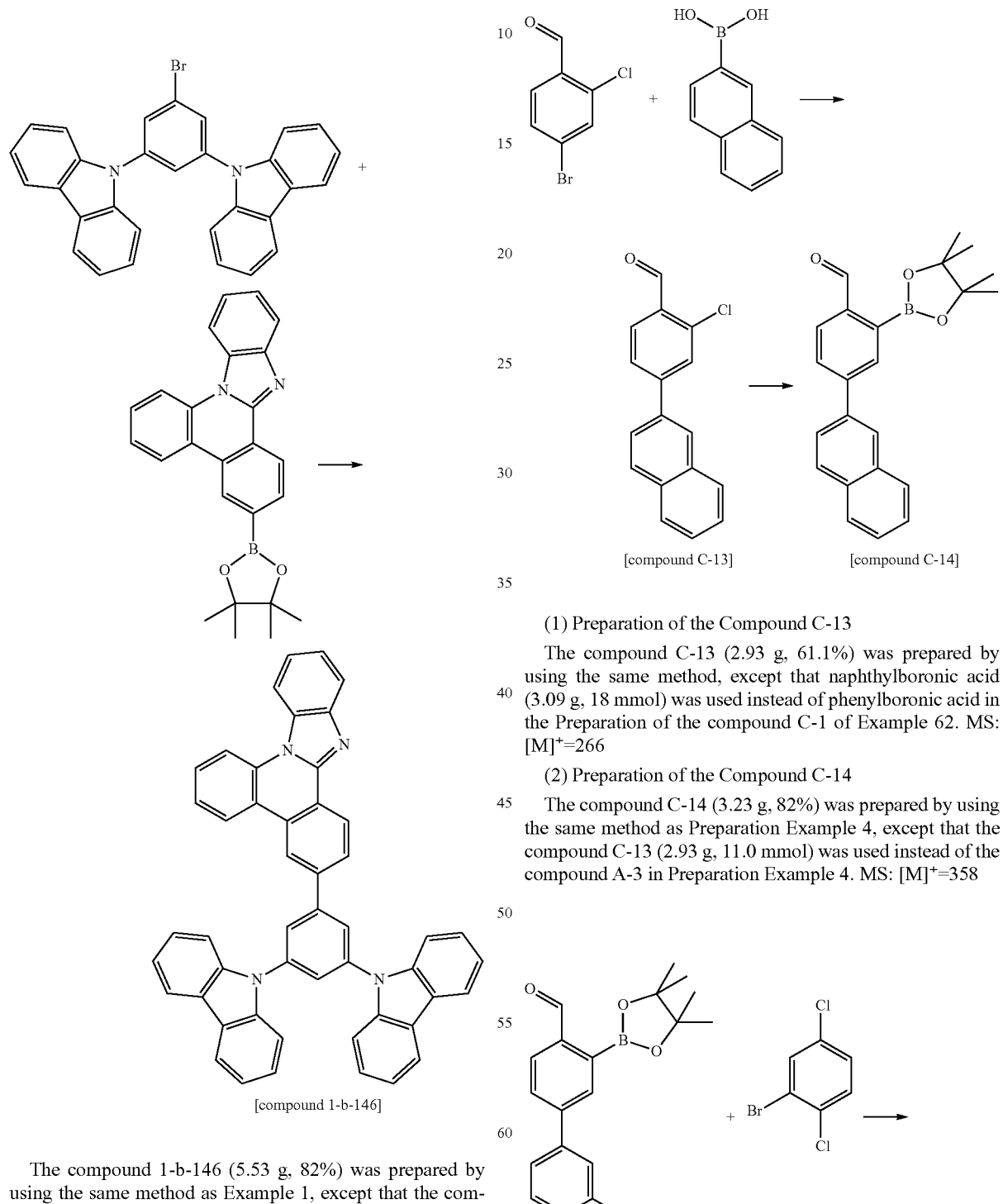

[compound 1-b-146]

The compound 1-b-146 (5.53 g, 82%) was prepared by using the same method as Example 1, except that the compound B-24 (4.87 g, 10.0 mmol) was used instead of the compound B-1 and the compound A-14 (3.94 g, 10.0 mmol) was used instead of the compound A-4 in Example 1. MS: [M+H]⁺=675

Example 67

Preparation of the Compound of Formula 6-a-21

[compound C-13]    [compound C-14]

(1) Preparation of the Compound C-13

The compound C-13 (2.93 g, 61.1%) was prepared by using the same method, except that naphthylboronic acid (3.09 g, 18 mmol) was used instead of phenylboronic acid in the Preparation of the compound C-1 of Example 62. MS: [M]⁺=266

(2) Preparation of the Compound C-14

The compound C-14 (3.23 g, 82%) was prepared by using the same method as Preparation Example 4, except that the compound C-13 (2.93 g, 11.0 mmol) was used instead of the compound A-3 in Preparation Example 4. MS: [M]⁺=358

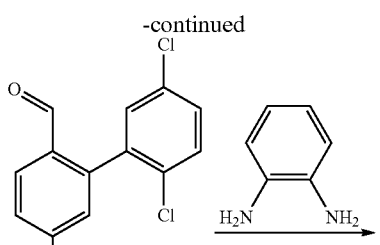

[compound C-15]

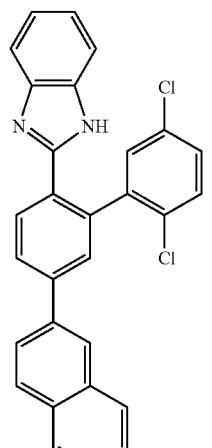

[compound C-16]

(3) Preparation of the Compound C-15

The compound C-15 (7.4 g, 91%) was prepared by using the same method as Preparation Example 1, except that the compound C-14 (7.7 g, 21.5 mmol) was used instead of the compound 2-formylphenylboronic acid in Preparation Example 1. MS: [M]$^+$=376

(4) Preparation of the Compound C-16

The compound C-16 (4.2 g, 46%) was prepared by using the same method as Preparation Example 2, except that the compound C-15 (7.4 g, 19.6 mmol) was used instead of the compound A-1 in Preparation Example 2. MS: [M]$^+$=464

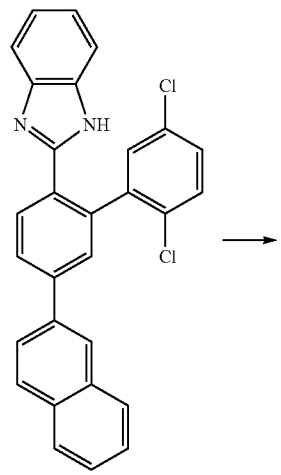

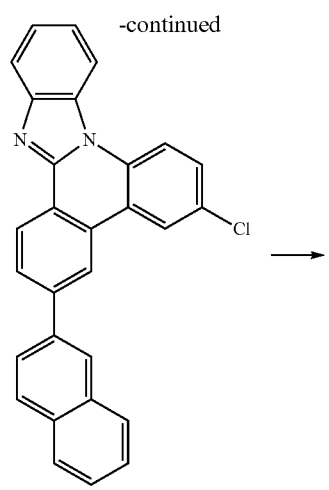

[compound C-17]

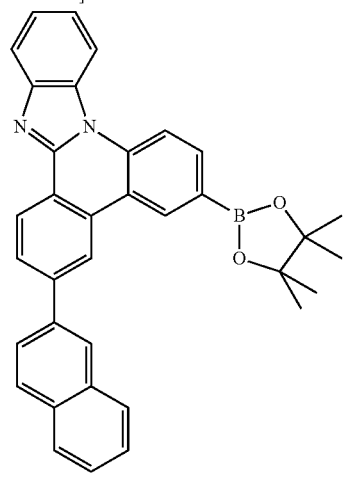

[compound C-18]

(5) Preparation of the Compound C-17

The compound C-17 (2.86 g, 61%) was prepared by using the same method as Preparation Example 3, except that the compound C-16 (4.2 g, 9.0 mmol) was used instead of the compound A-2 in Preparation Example 3. MS: [M]$^+$=428

(6) Preparation of the Compound C-18

The compound C-18 (3.24 g, 93%) was prepared by using the same method as Preparation Example 4, except that the compound C-17 (2.86 g, 6.7 mmol) was used instead of the compound A-3 in Preparation Example 4. MS: [M]$^+$=470

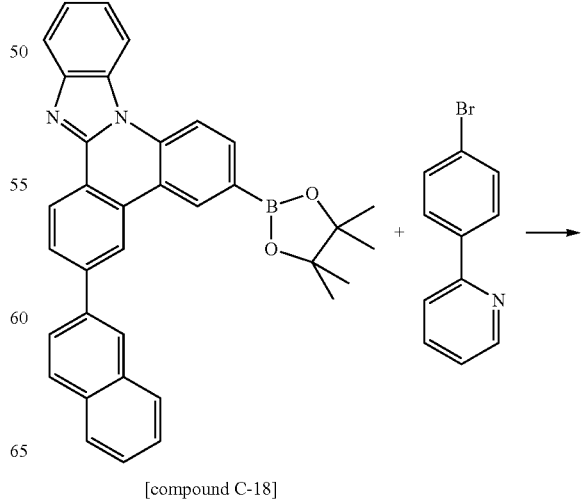

[compound C-18]

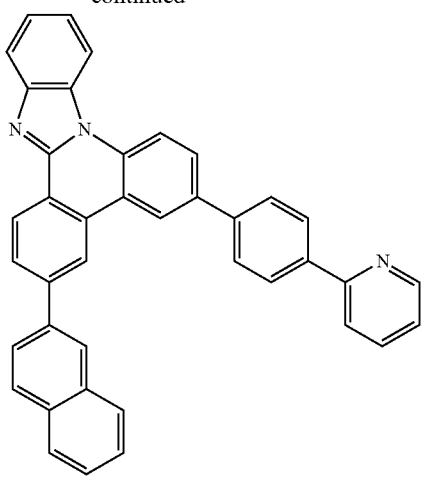

[compound 6-a-21]

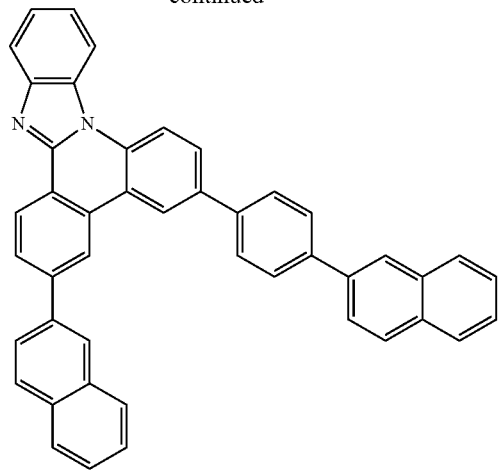

[compound 6-a-22]

(7) Preparation of the Compound 6-a-21

The compound 6-a-21 (3.4 g, 78%) was prepared by using the same method as Example 1, except that 2-(4-bromophenyl)pyridine (2.34 g, 10.0 mmol) was used instead of the compound B-1 and the compound C-18 (4.16 g, 8.0 mmol) was used instead of the compound A-4 in Example 1. MS: $[M+H]^+=548$ Example 68

Preparation of the Compound of Formula 6-a-22

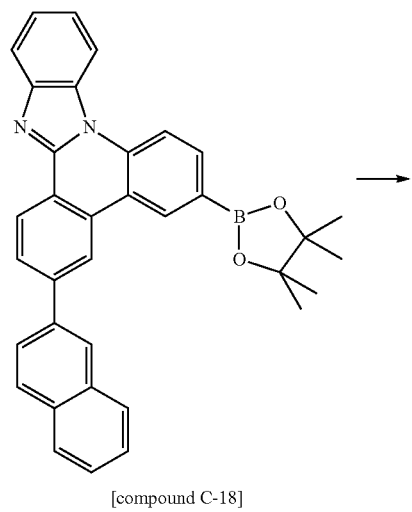

[compound C-18]

The compound 6-a-22 (3.07 g, 88%) was prepared by using the same method as Example 1, except that the compound B-20 (2.83 g, 10.0 mmol) was used instead of the compound B-1 and the compound C-18 (4.58 g, 8.8 mmol) was used instead of the compound A-4 in Example 1. MS: $[M+H]^+=597$ Example 69

Preparation of the Compound of Formula 6-a-23

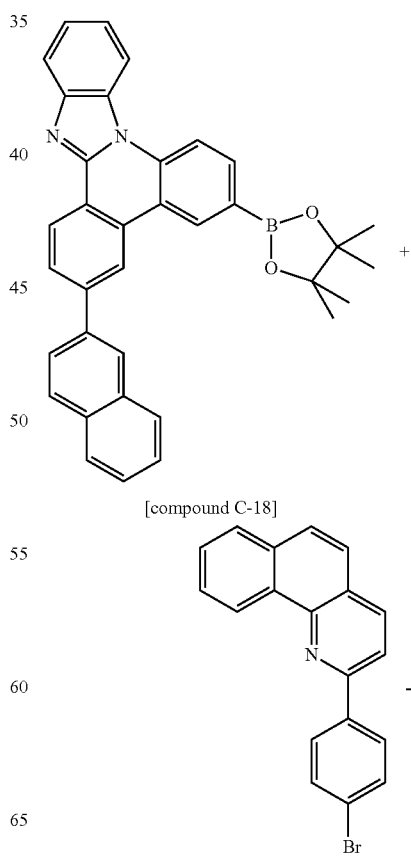

[compound C-18]

-continued

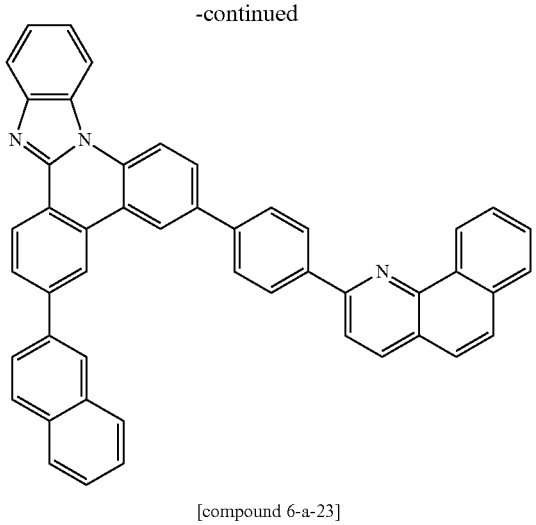

[compound 6-a-23]

The compound 6-a-23 (4.6 g, 82%) was prepared by using the same method as Example 1, except that the compound B-16 (2.9 g, 8.7 mmol) was used instead of the compound B-1 and the compound C-18 (4.58 g, 8.8 mmol) was used instead of the compound A-4 in Example 1. MS: [M+H]$^+$=648

Example 70

Preparation of the Compound of Formula 6-a-33

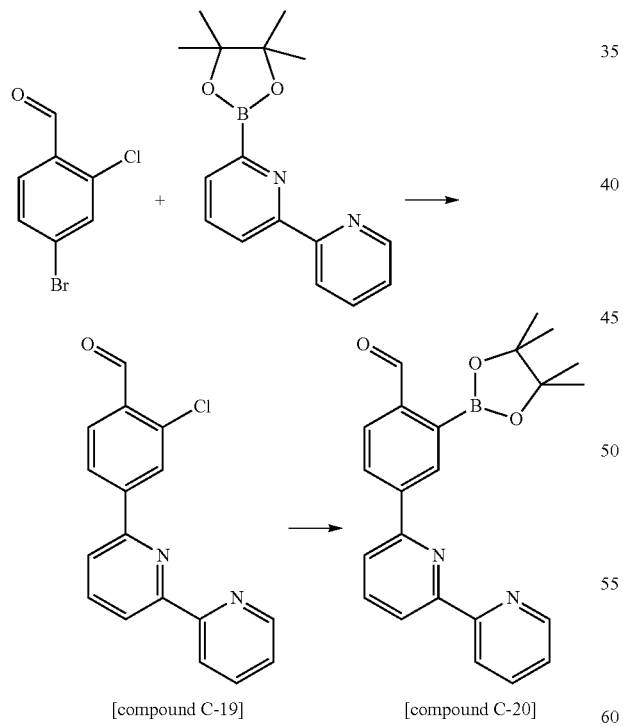

[compound C-19]   [compound C-20]

(1) Preparation of the Compound C-19

The compound C-19 (5.54 g, 94%) was prepared by using the same method, except that 2-(6-(4,4,5,5-tetramethyl-1,3,2-dioxaborolan-2-yl)pyridin-2-yl)pyridine (5.6 g, 20 mmol) was used instead of phenylboronic acid in the Preparation of the compound C-1 of Example 62. MS: [M]$^+$=294

(2) Preparation of the Compound C-20

The compound C-20 (6.47 g, 89%) was prepared by using the same method as Preparation Example 4, except that the compound C-19 (5.54 g, 18.8.0 mmol) was used instead of the compound A-3 in Preparation Example 4. MS: [M]$^+$=386

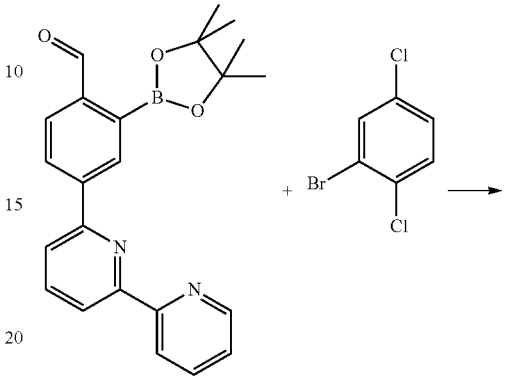

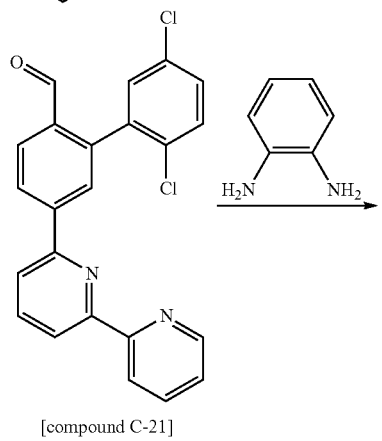

[compound C-21]

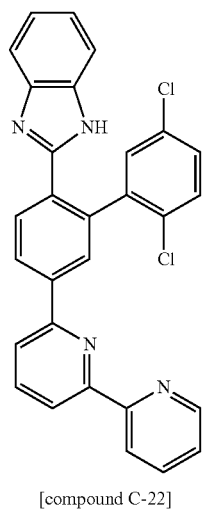

[compound C-22]

(3) Preparation of the Compound C-21

The compound C-21 (5.7 g, 84%) was prepared by using the same method as Preparation Example 1, except that the compound C-20 (6.47 g, 16.8 mmol) was used instead of the compound 2-formylphenylboronic acid in Preparation Example 1. MS: [M]$^+$=404

(4) Preparation of the Compound C-22

The compound C-22 (5.1 g, 73%) was prepared by using the same method as Preparation Example 2, except that the compound C-21 (5.7 g, 14.1 mmol) was used instead of the compound A-1 in Preparation Example 2. MS: [M]$^+$=492

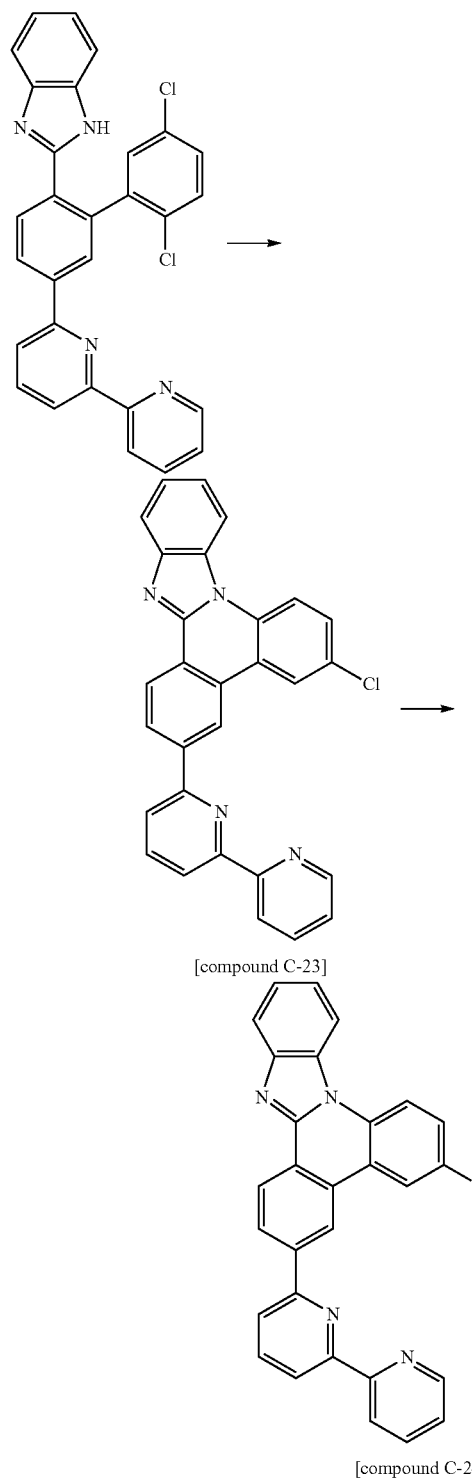

[compound C-23]

[compound C-24]

(5) Preparation of the Compound C-23

The compound C-23 (3.4 g, 72%) was prepared by using the same method as Preparation Example 3, except that the compound C-22 (5.1 g, 10.3 mmol) was used instead of the compound A-2 in Preparation Example 3. MS: [M]$^+$=456

(6) Preparation of the Compound C-24

The compound C-24 (3.4 g, 84%) was prepared by using the same method as Preparation Example 4, except that the compound C-23 (3.4 g, 7.4 mmol) was used instead of the compound A-3 in Preparation Example 4. MS: [M]$^+$=548

(7) Preparation of the Compound 6-a-33

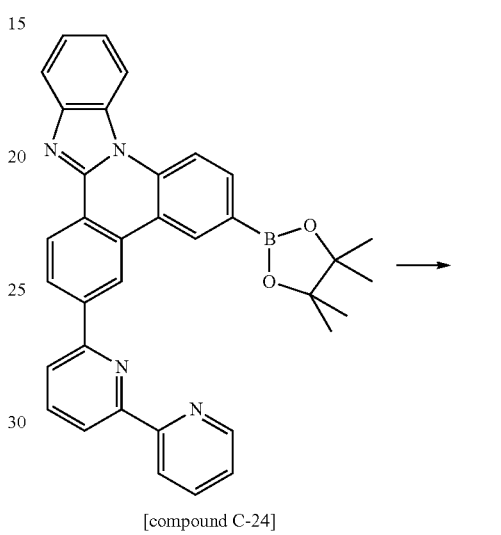

[compound C-24]

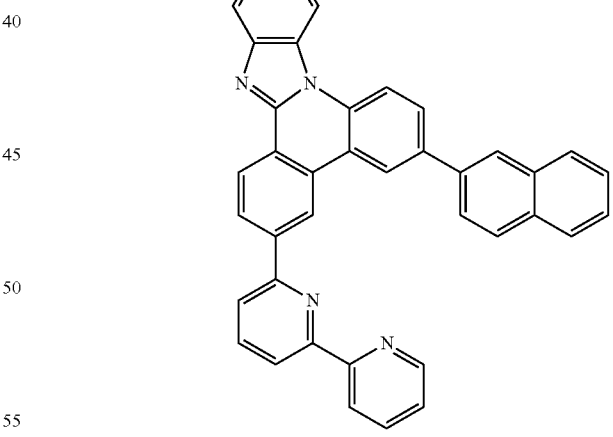

[compound 6-a-33]

The compound 6-a-33 (3.02 g, 89%) was prepared by using the same method as Example 1, except that 2-bromonaphthalene (1.3 g, 6.2 mmol) was used instead of the compound B-1 and the compound C-24 (3.4 g, 6.2 mmol) was used instead of the compound A-4 in Example 1. MS: [M+H]$^+$=549

Example 71

Preparation of the Compound of Formula 6-a-34

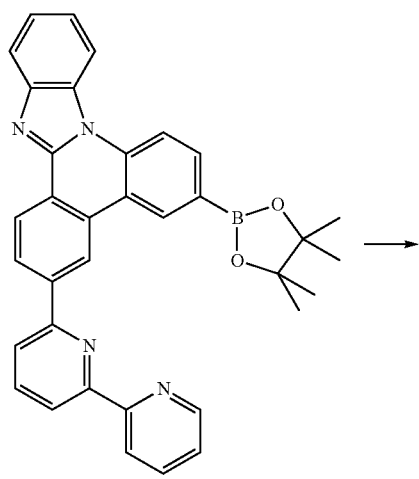

[compound C-24]

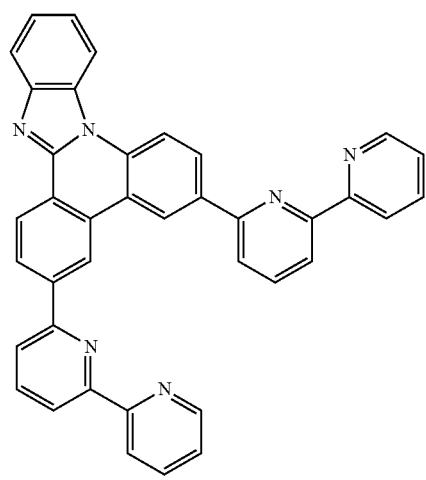

[compound 6-a-34]

The compound 6-a-34 (4.1 g, 72%) was prepared by using the same method as Example 1, except that 2-(6-bromopyridin-2-yl)pyridine (2.3 g, 9.8 mmol) was used instead of the compound B-1 and the compound C-24 (5.4 g, 9.8 mmol) was used instead of the compound A-4 in Example 1. MS: [M+H]$^+$=577

Example 72

Preparation of the Compound of Formula 6-a-35

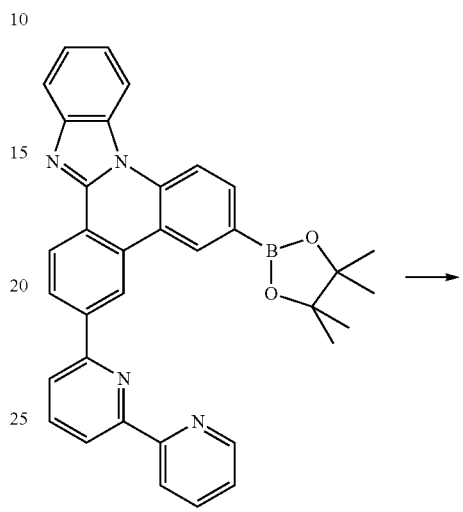

[compound C-24]

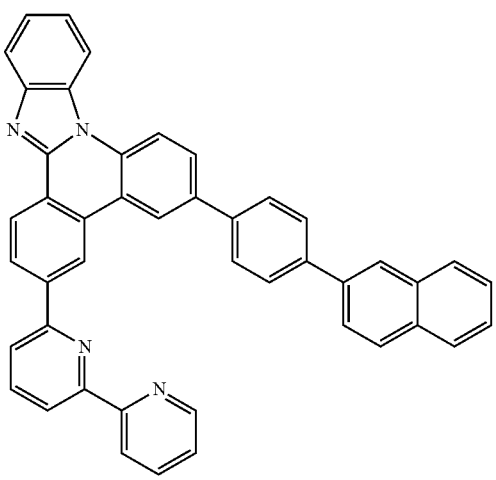

[compound 6-a-35]

The compound 6-a-35 (4.8 g, 77%) was prepared by using the same method as Example 1, except that the compound B-20 (2.8 g, 10.0 mmol) was used instead of the compound B-1 and the compound C-24 (5.5 g, 10.0 mmol) was used instead of the compound A-4 in Example 1. MS: [M+H]$^+$=625

Example 73

Preparation of the Compound of Formula 6-a-36

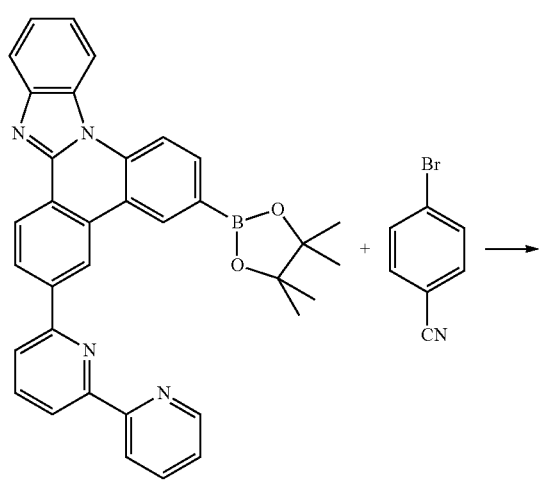

[compound C-24]

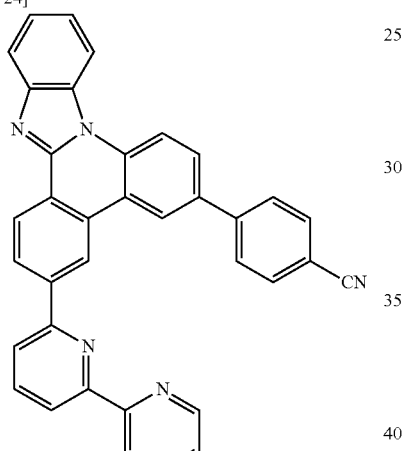

[compound 6-a-36]

The compound 6-a-36 (4.7 g, 90%) was prepared by using the same method as Example 1, except that 4-bromobenzonitrile (1.8 g, 10.0 mmol) was used instead of the compound B-1 and the compound C-24 (5.5 g, 10.0 mmol) was used instead of the compound A-4 in Example 1. MS: [M+H]$^+$=524

Example 74

Preparation of the Compound of Formula 6-a-18

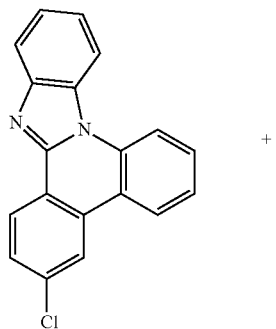

+

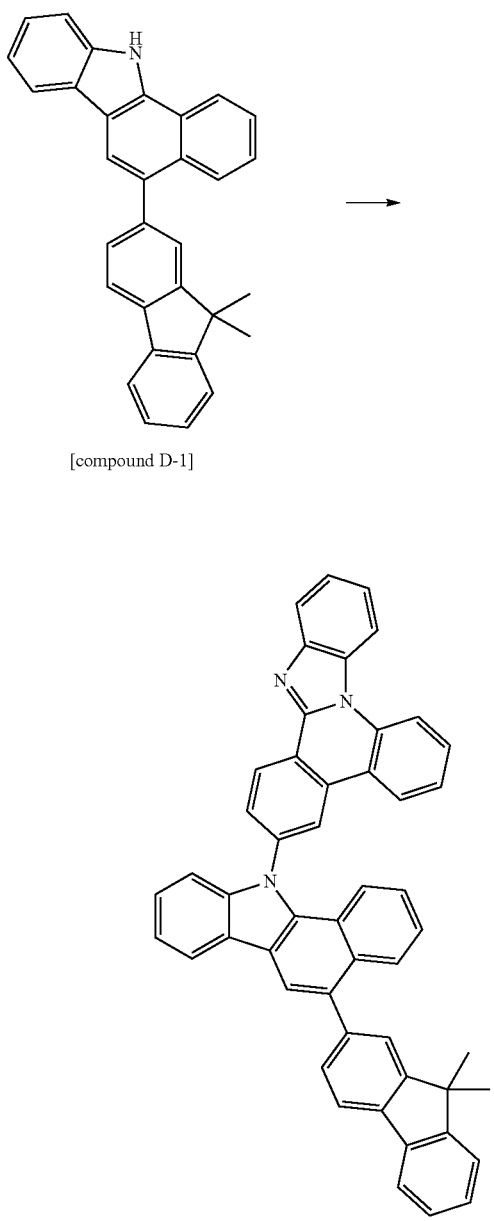

The compound A-13 (6.1 g, 20.2 mmol), and bromobenzene (8.3 g, 20.2 mmol) were dissolved in 100 ml of xylene, 2.9 g of sodium-tertiary-botoxide (30.3 mmol), and Pd[P(t-Bu)$_3$]$_2$ (0.10 g, 0.20 mmol) were added thereto, and refluxed for 5 hours under the nitrogen atmosphere. Distilled water was put into the reaction solution, the termination of the reaction was carried out, and the organic layer was extracted. It was recrystallized in ethylacetate/ethanol to prepare the compound 6-a-18 (5.4 g, 40%). MS: [M+H]$^+$=676

Example 75

Preparation of the Compound of Formula 6-a-39

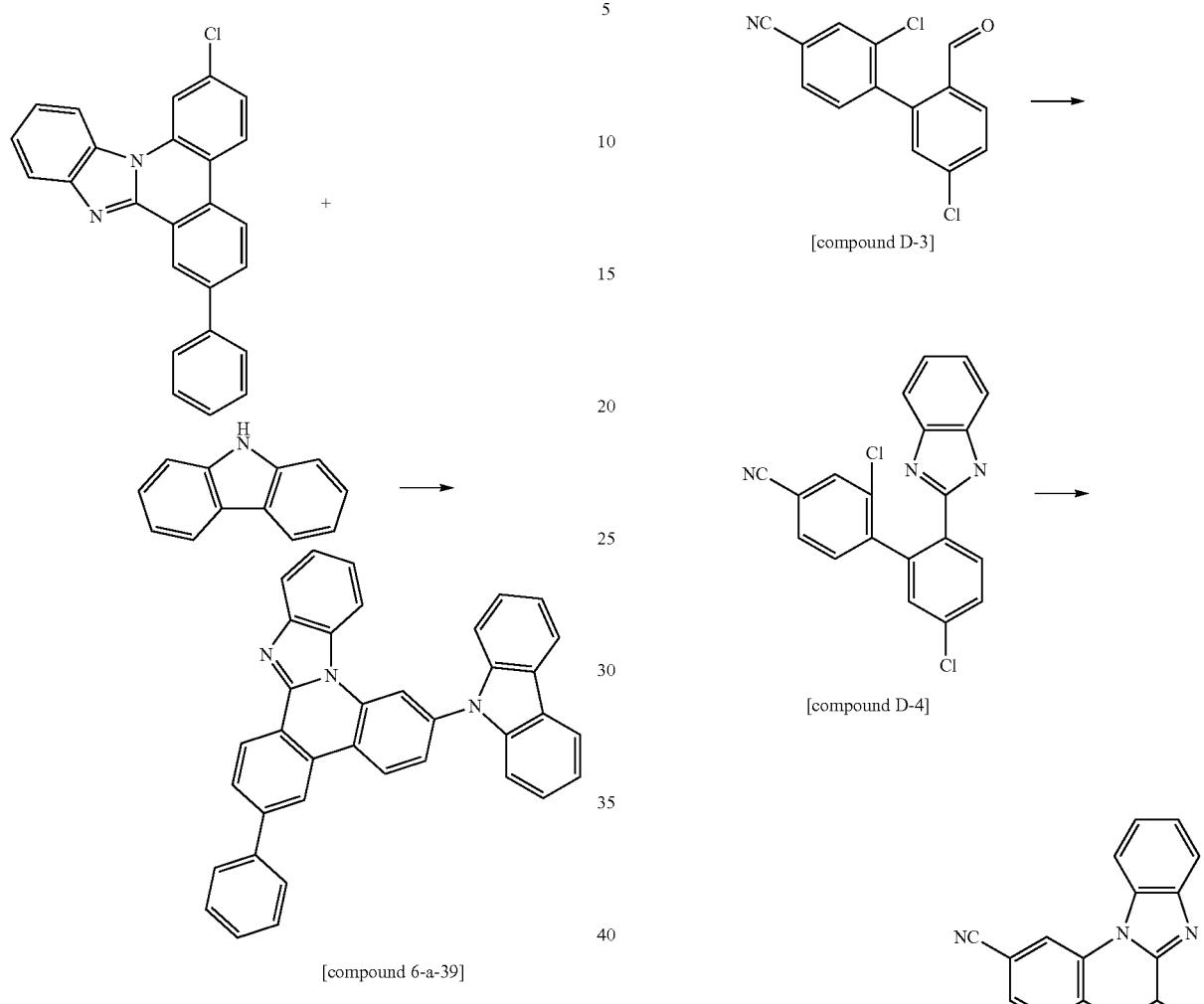

[compound 6-a-39]

The compound 6-a-39 (3.2 g, 62%) was prepared by using the same method as Example 74, except that the compound C-11 (3.8 g, 10.1 mmol) was used instead of the compound A-13 and carbazole (1.8 g, 11.0 mmol) was used instead of the compound D-1 in Example 74. MS: [M+H]$^+$=510

Example 76

Preparation of the Compound of Formula 7-a-1

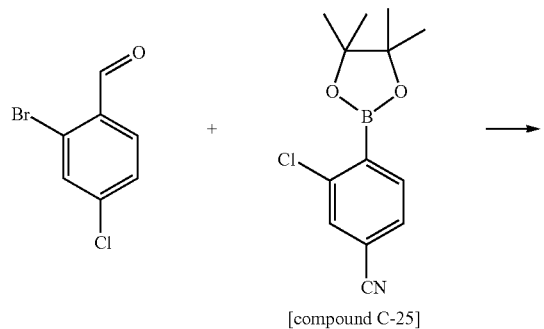

[compound C-25]

(1) Preparation of the Compound D-3

The compound D-3 (3.8 g, 81%) was prepared by using the same method, except that the compound C-25 (4.48 g, 17 mmol) was used instead of phenylboronic acid in the Preparation of the compound C-1 of Example 62. MS: [M]$^+$=275

(2) Preparation of the Compound D-4

The compound D-4 (5.27 g, 77%) was prepared by using the same method as Preparation Example 2, except that the compound D-3 (3.8 g, 18.8.0 mmol) was used instead of the compound A-1 in Preparation Example 2. MS: [M]$^+$=364

(3) Preparation of the Compound D-5

The compound D-5 (4.84 g, 92%) was prepared by using the same method as Preparation Example 3, except that the compound D-4 (5.27 g, 15.3 mmol) was used instead of the compound A-2 in Preparation Example 3. MS: [M]$^+$=343

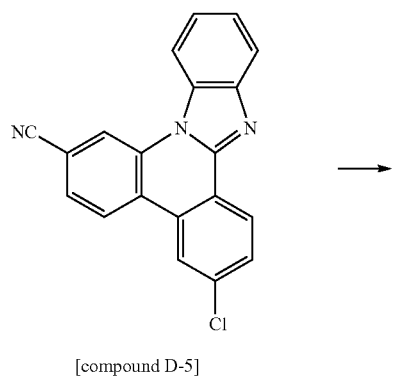

[compound D-5]

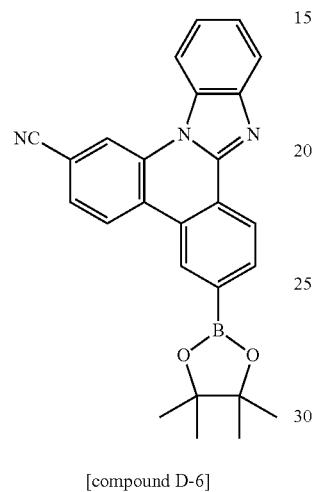

[compound D-6]

(4) Preparation of the Compound D-6

The compound D-6 (5.28 g, 86%) was prepared by using the same method as Preparation Example 4, except that the compound D-5 (4.84 g, 14.1 mmol) was used instead of the compound A-3 in Preparation Example 4. MS: [M]⁺=435

(5) Preparation of the Compound 7-a-1

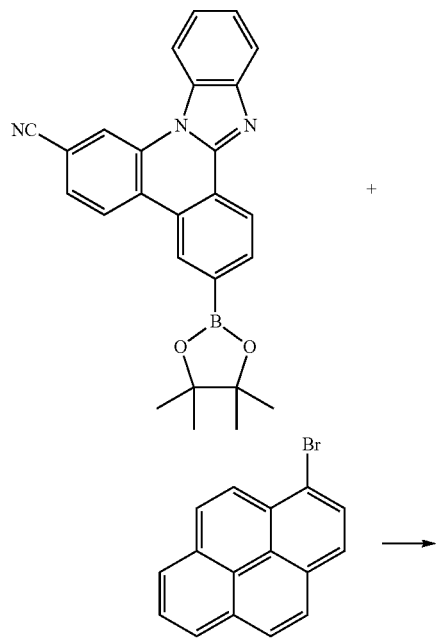

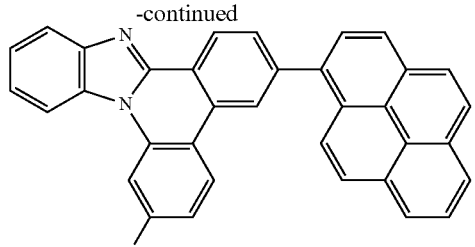

[compound 7-a-1]

The compound 7-a-1 (4.7 g, 93%) was prepared by using the same method as Example 1, except that 1-bromopyrene (2.8 g, 10.0 mmol) was used instead of the compound B-1 and the compound D-6 (4.4 g, 10.0 mmol) was used instead of the compound A-4 in Example 1. MS: [M+H]⁺=510

Example 77

Preparation of the Compound of Formula 7-a-4

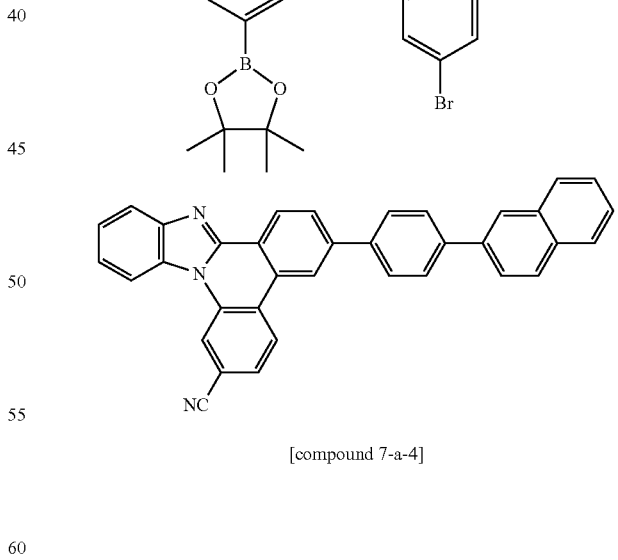

[compound 7-a-4]

The compound 7-a-4 (4.7 g, 61%) was prepared by using the same method as Example 1, except that the compound B-20 (2.8 g, 10.0 mmol) was used instead of the compound B-1 and the compound D-6 (4.4 g, 10.0 mmol) was used instead of the compound A-4 in Example 1. MS: [M+H]⁺= 512

Example 78

Preparation of the Compound of Formula 7-a-6

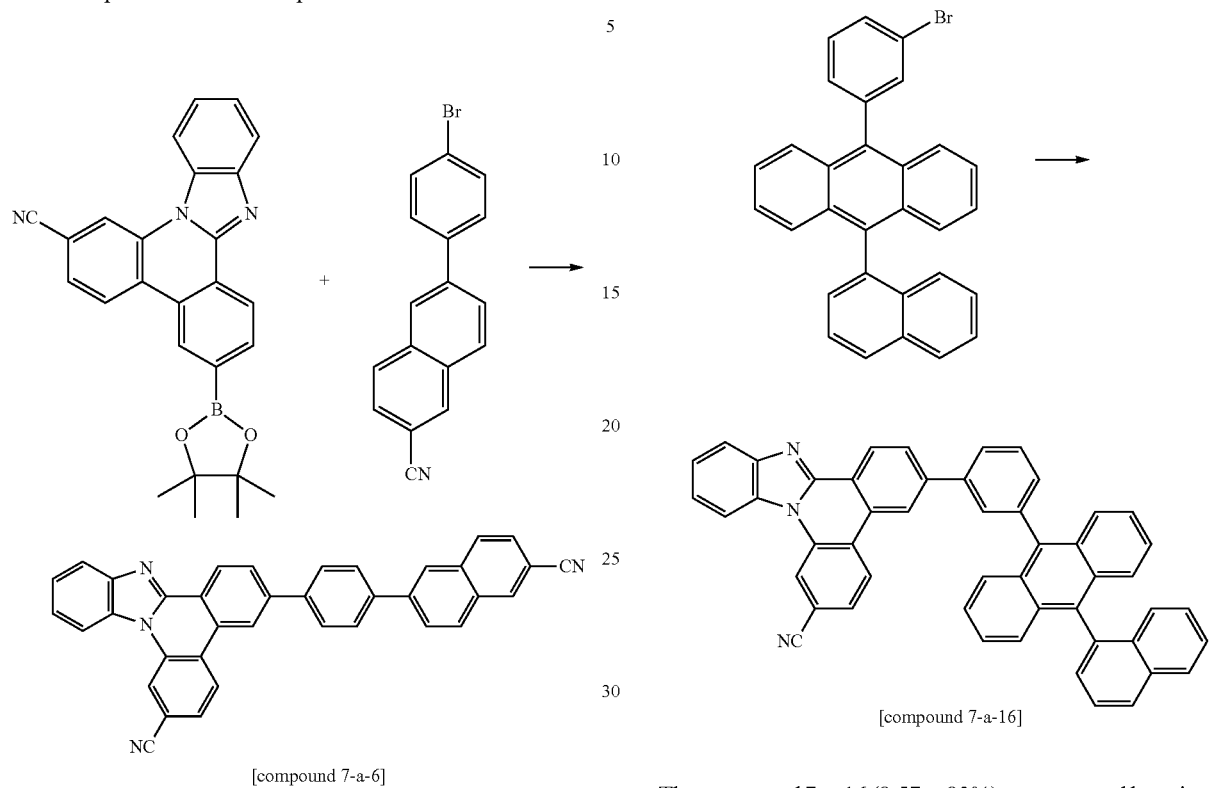

[compound 7-a-6]

The compound 7-a-6 (4.7 g, 87%) was prepared by using the same method as Example 1, except that 6-(4-bromophenyl)naphthalene-2-carbonitrile (3.1 g, 10.0 mmol) was used instead of the compound B-1 and the compound D-6 (4.83 g, 11.1 mmol) was used instead of the compound A-4 in Example 1. MS: [M+H]$^+$=537

Example 79

Preparation of the Compound of Formula 7-a-16

[compound 7-a-16]

The compound 7-a-16 (8.57 g, 82%) was prepared by using the same method as Example 1, except that 10-(3-bromophenyl)-9-(naphthalen-1-yl)anthracene (7.0 g, 15.2 mmol) was used instead of the compound B-1 and the compound D-6 (7.0 g, 16.1 mmol) was used instead of the compound A-4 in Example 1. MS: [M+H]$^+$=688

Example 80

Preparation of the Compound of Formula 7-a-10

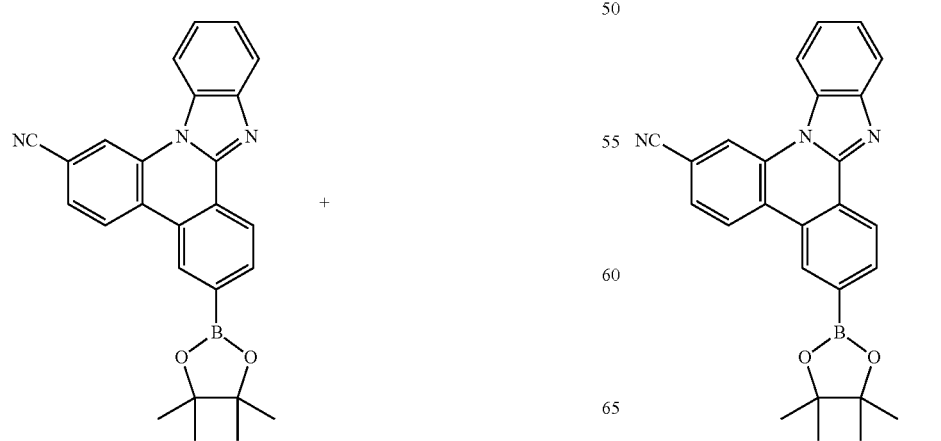

-continued

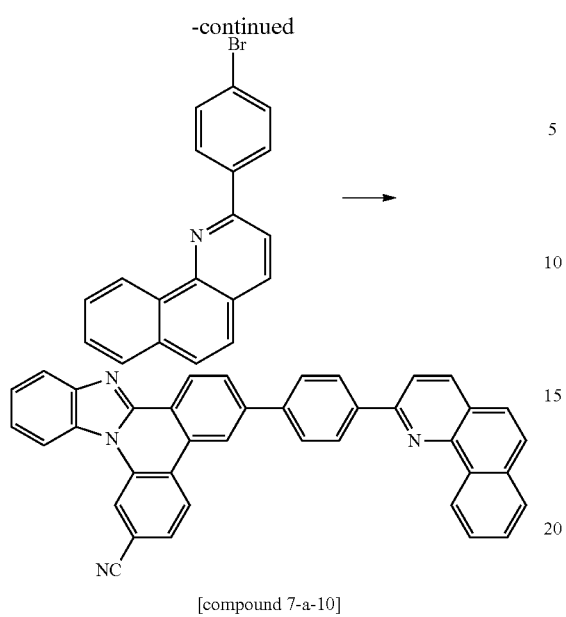

[compound 7-a-10]

The compound 7-a-10 (5.5 g, 93%) was prepared by using the same method as Example 1, except that the compound B-16 (3.7 g, 11.1 mmol) was used instead of the compound B-1 and the compound D-6 (4.83 g, 11.1 mmol) was used instead of the compound A-4 in Example 1. MS: $[M+H]^+=$ 563

Example 81

Preparation of the Compound of Formula 7-a-24

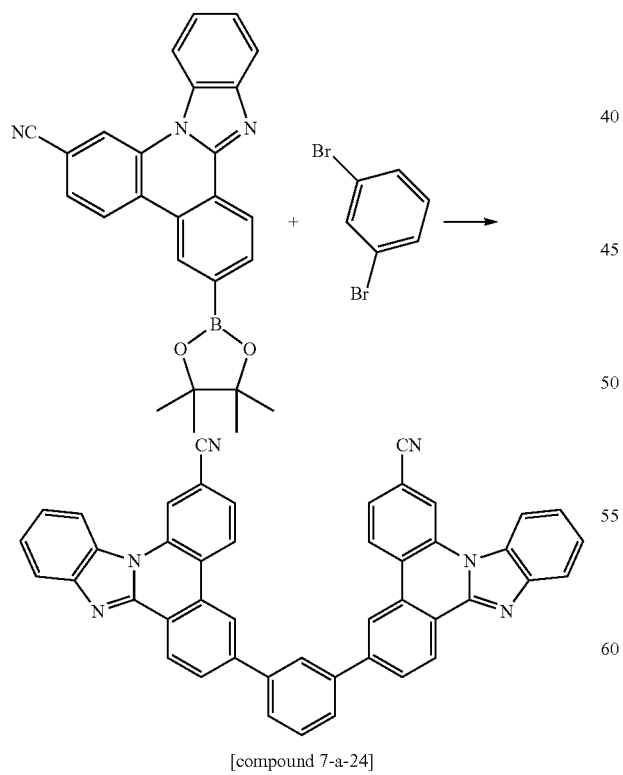

[compound 7-a-24]

The compound 7-a-24 (1.9 g, 67%) was prepared by using the same method as Example 1, except that 1,3-dibromobenzene (2.0 g, 4.2 mmol) was used instead of the compound B-1 and the compound D-6 (4.4 g, 10.0 mmol) was used instead of the compound A-4 in Example 1. MS: $[M+H]^+=677$ Example 82

Preparation of the Compound of Formula 3-c-25

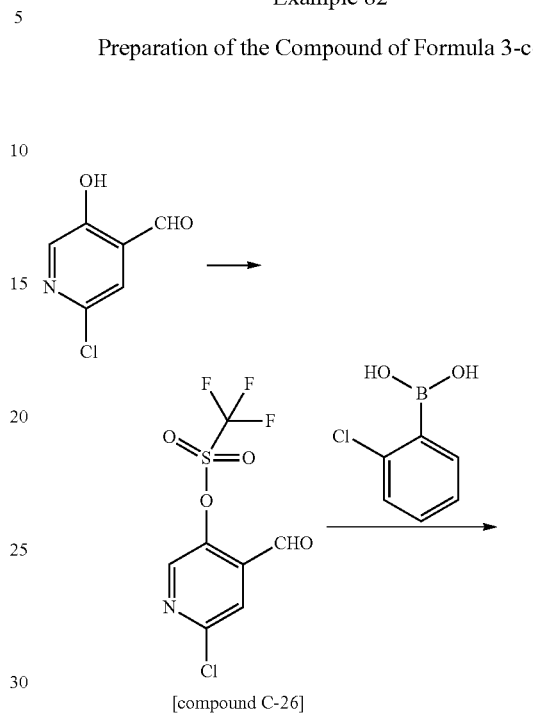

[compound C-26]

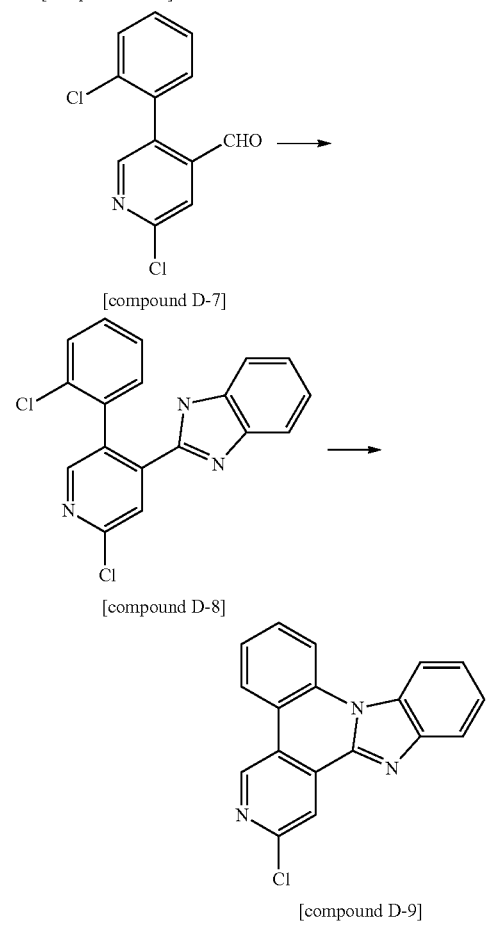

[compound D-7]

[compound D-8]

[compound D-9]

(1) Preparation of the Compound C-26

100 mL of $CH_2Cl_2$ was put into the compound 2-chloro-5-hydroxy-pyridine-4-carbaldehyde (13.7 g, 87 mmol) and agitated, and triethylamine (13.3 g, 130.5 mmol), and trifluoroacetic anhydride (25.8 g, 130.5 mmol) were slowly dropped thereto. The mixture was agitated at normal temperature for 2 hours, water and $CH_2Cl_2$ were added to separate the organic layer, and the organic extract was dried over magnesium sulfate and concentrated under the vacuum. It was purified with $CH_2Cl_2$/EtOH to prepare the compound C-26 (22.7 g, yield 90%). MS $[M+H]^+=289$ (2) Preparation of the Compound D-7

The compound D-7 (12.6 g, 64%) was prepared by using the same method, except that the compound C-26 (22.6 g, 78.0 mmol) was used instead of 2-bromo-3-formyl-pyridine and 2-chloro-phenyl-1-boronic acid (12.2 g, 78.3 mmol) was used instead of 2,5-dichloro-benzeneboronic acid in the Preparation of the compound A-31 of Preparation Example 31. MS: $[M]^+=251$ (3) Preparation of the Compound D-8

The compound D-8 (8.6 g, 68%) was prepared by using the same method as Preparation Example 2, except that the compound D-7 (12.6 g, 37.0 mmol) was used instead of the compound A-1 in Preparation Example 2. MS: $[M]^+=339$ (4) Preparation of the Compound D-9

The compound D-9 (9.7 g, 86%) was prepared by using the same method as Preparation Example 3, except that the compound D-8 (8.6 g, 37.0 mmol) was used instead of the compound A-2 in Preparation Example 3. MS: $[M]^+=303$

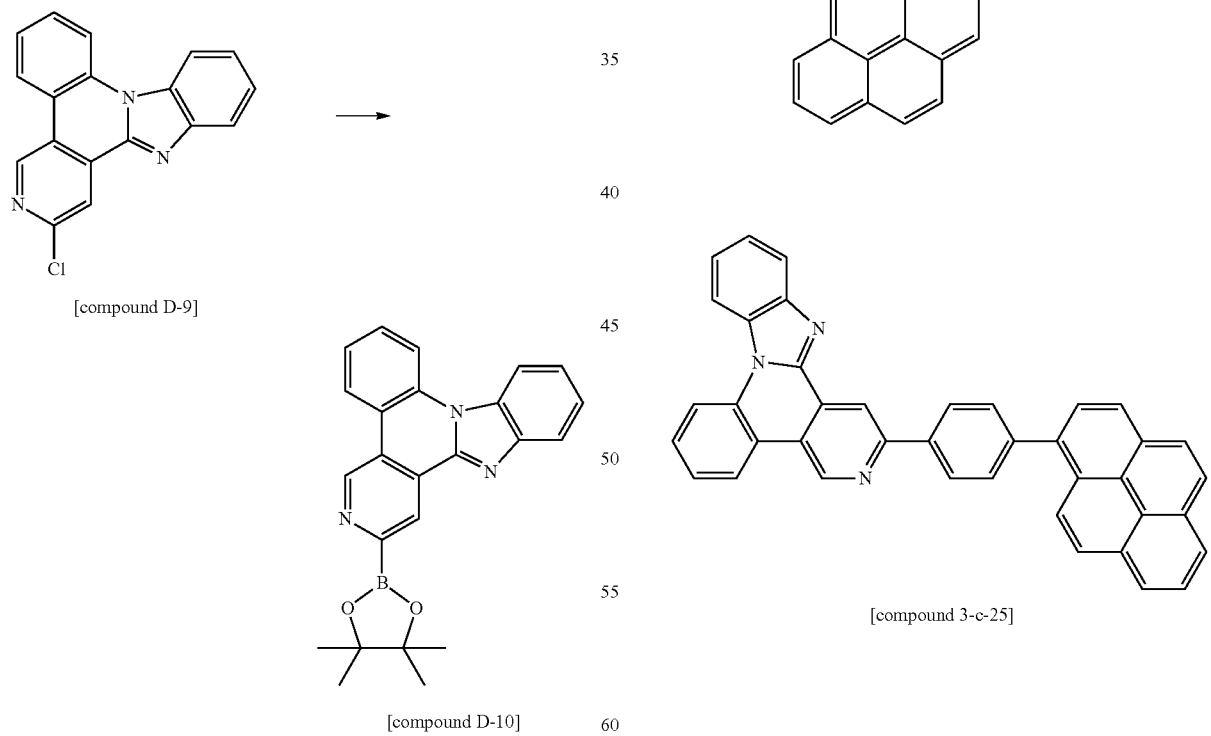

[compound D-9]

[compound D-10]

(5) Preparation of the Compound D-10

The compound D-10 (10.8 g, 86%) was prepared by using the same method as Preparation Example 4, except that the compound D-9 (9.7 g, 31.8 mmol) was used instead of the compound A-3 in Preparation Example 4. MS: $[M]^+=395$ (6) Preparation of the Compound 3-c-25

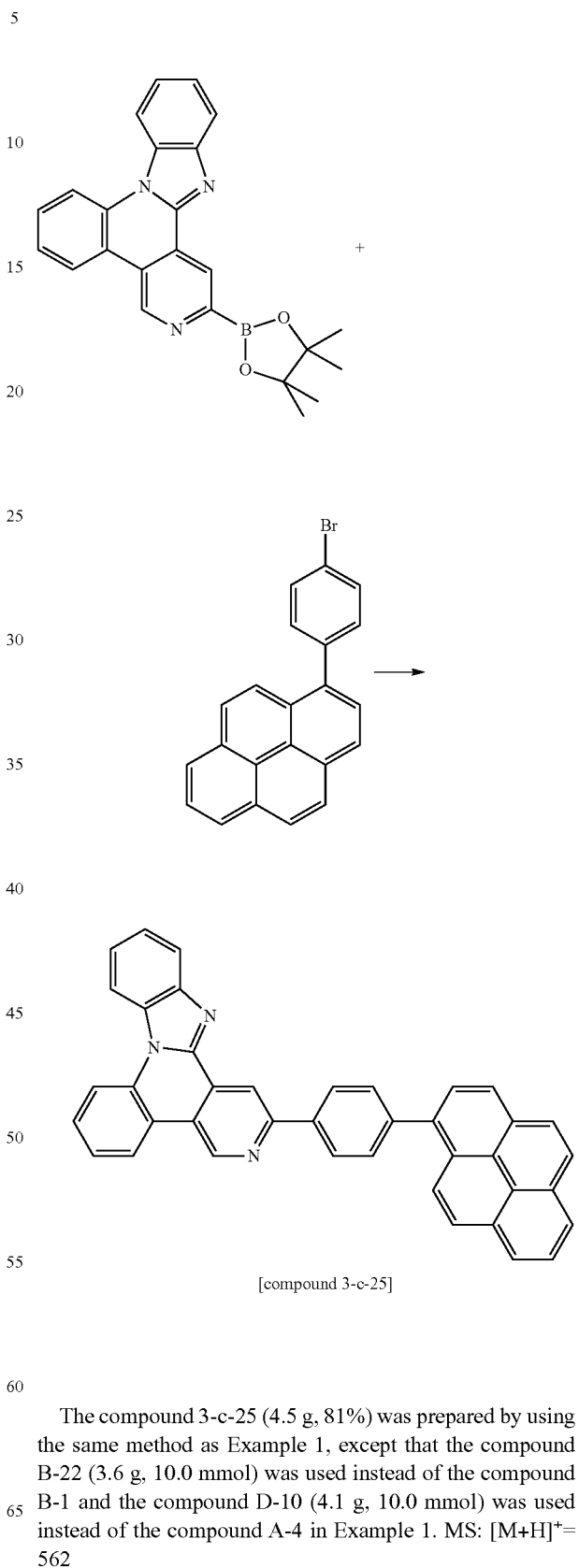

[compound 3-c-25]

The compound 3-c-25 (4.5 g, 81%) was prepared by using the same method as Example 1, except that the compound B-22 (3.6 g, 10.0 mmol) was used instead of the compound B-1 and the compound D-10 (4.1 g, 10.0 mmol) was used instead of the compound A-4 in Example 1. MS: $[M+H]^+=562$

Example 83

Preparation of the Compound of Formula 3-c-30

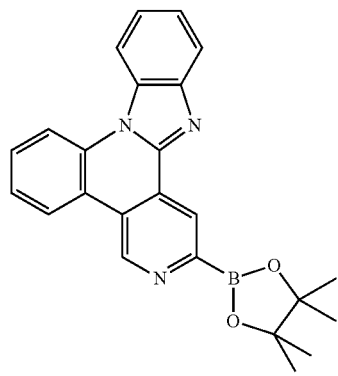

+

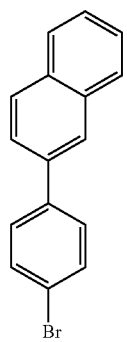

→

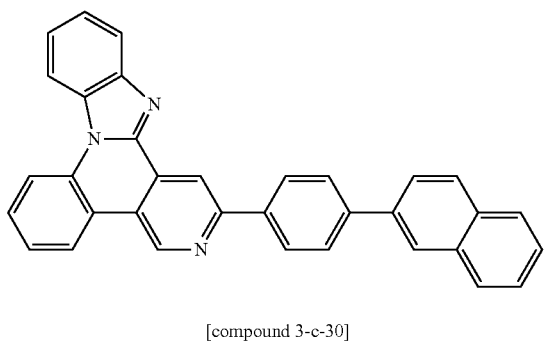

[compound 3-c-30]

The compound 3-c-30 (4.2 g, 79%) was prepared by using the same method as Example 1, except that the compound B-20 (3.4 g, 12.0 mmol) was used instead of the compound B-1 and the compound D-10 (4.5 g, 11.0 mmol) was used instead of the compound A-4 in Example 1. MS: [M+H]$^+$= 488

Example 84

Preparation of the Compound of Formula 5-a-53

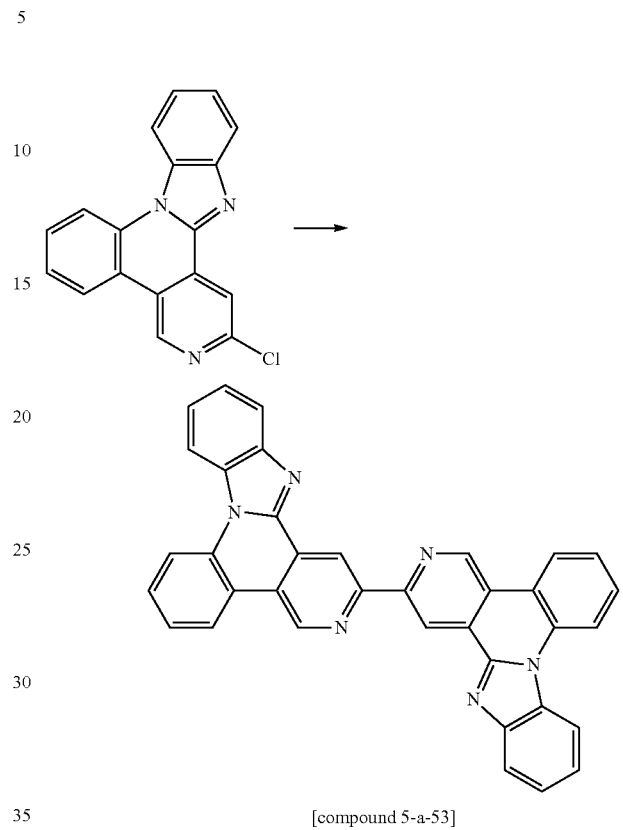

[compound 5-a-53]

The compound 5-a-53 (3.1 g, 54%) was prepared by using the same method as Example 55, except that the compound D-9 (3.2 g, 10.0 mmol) was used instead of the compound A-3 in Example 55. MS: [M+H]$^+$=569

Example 85

Preparation of the Compound of Formula 5-a-55

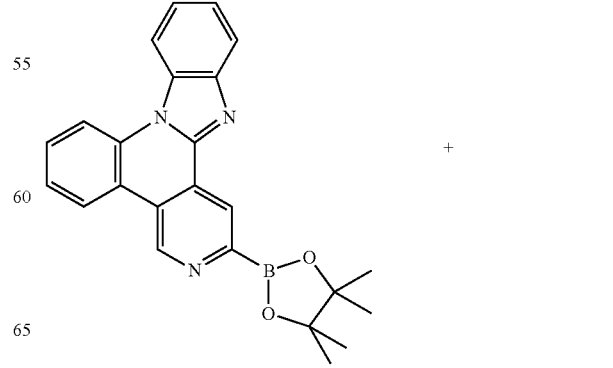

+

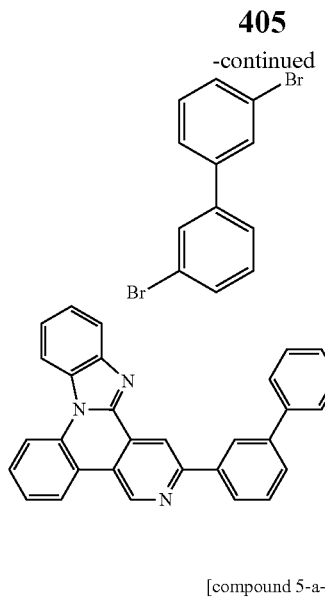

[compound 5-a-55]

The compound 5-a-55 (2.1 g, 58%) was prepared by using the same method as Example 1, except that 3,3'-dibromobiphenyl (1.6 g, 5.0 mmol) was used instead of the compound B-1 and the compound D-6 (4.6 g, 11.2 mmol) was used instead of the compound A-4 in Example 1. MS: $[M+H]^+=$ 721

Example 85

Preparation of the Compound of Formula 3-c-39

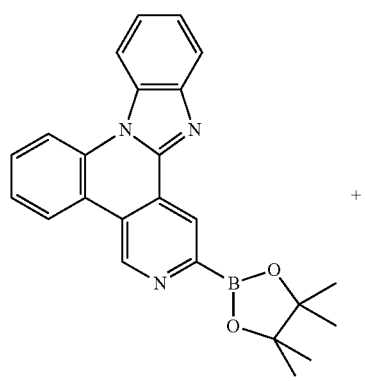

+

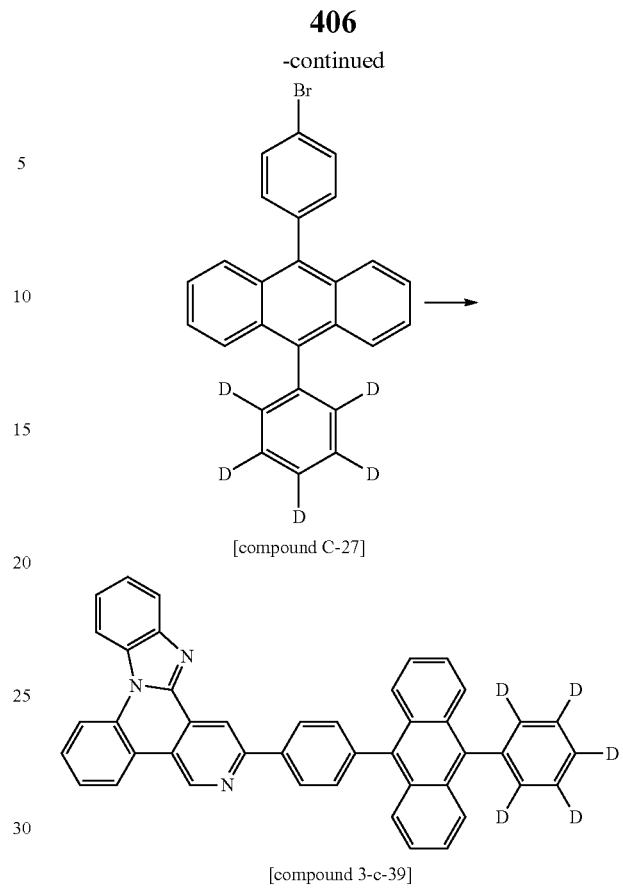

[compound 3-c-39]

The compound 3-c-39 (5.0 g, 72%) was prepared by using the same method as Example 1, except that the compound C-27 (5.2 g, 12.6 mmol) was used instead of the compound B-1 and the compound D-6 (4.6 g, 11.2 mmol) was used instead of the compound A-4 in Example 1. MS: $[M+H]^+=$ 619

Example 86

Preparation of the Compound of Formula 5-a-59

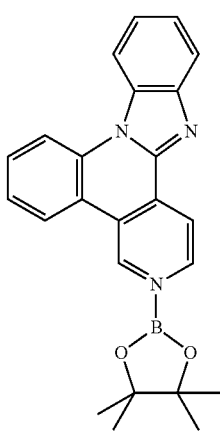

+

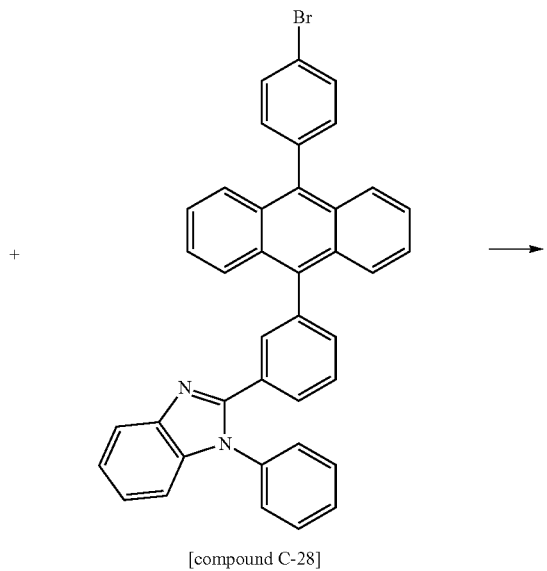

[compound C-28]

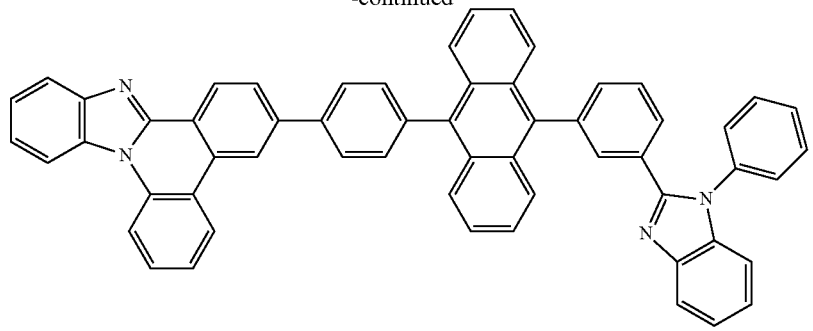
[compound 5-a-59]
The compound 5-a-59 (2.56 g, 65%) was prepared by using the same method as Example 1, except that the compound C-28 (3.0 g, 5.0 mmol) was used instead of the compound B-1 and the compound A-14 (2.0 g, 5.1 mmol) was used instead of the compound A-4 in Example 1. MS: [M+H]$^+$=789
Example 87
Preparation of the Compound of Formula 5-a-62
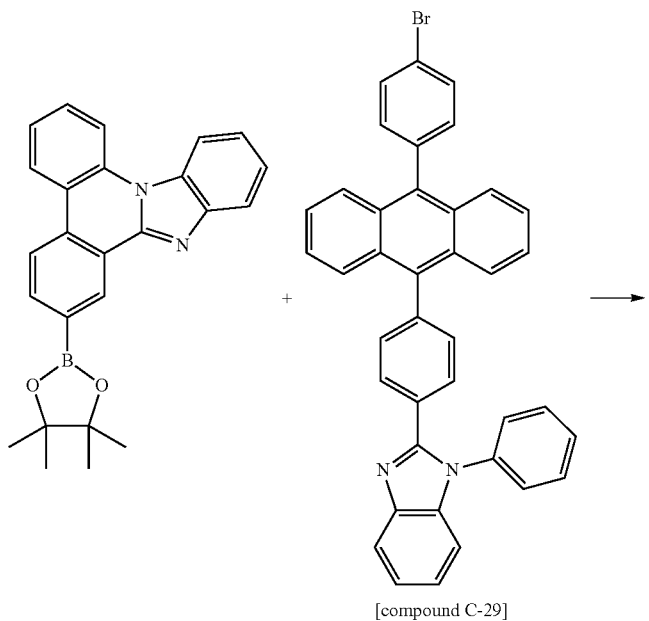
[compound C-29]
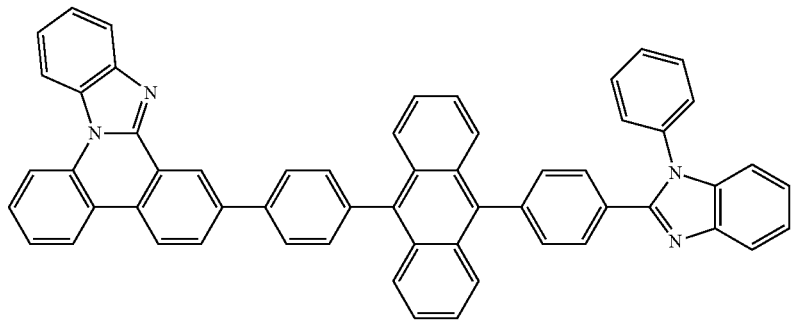
[compound 5-a-62]

The compound 5-a-62 (3.47 g, 71%) was prepared by using the same method as Example 1, except that the compound C-29 (3.2 g, 6.2 mmol) was used instead of the compound B-1 and the compound A-54 (2.68 g, 6.8 mmol) was used instead of the compound A-4 in Example 1. MS: [M+H]$^+$=789

Example 88

Preparation of the Compound of Formula 5-a-64

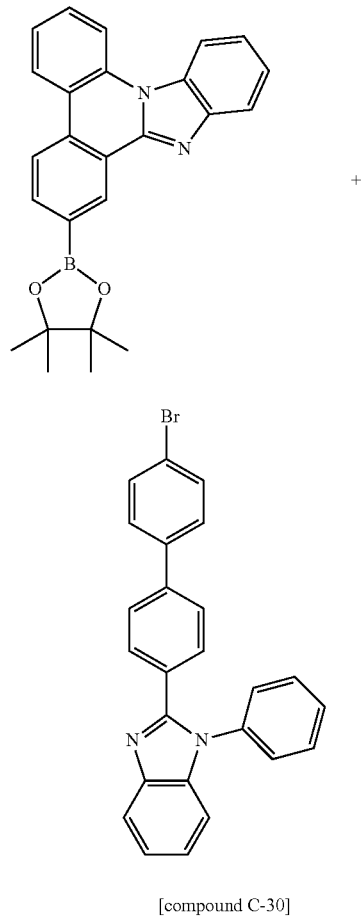

[compound C-30]

[compound 5-a-64]

The compound 5-a-64 (2.25 g, 67%) was prepared by using the same method as Example 1, except that the compound C-30 (2.34 g, 5.5 mmol) was used instead of the compound B-1 and the compound A-54 (2.17 g, 5.5 mmol) was used instead of the compound A-4 in Example 1. MS: [M+H]$^+$=613

Example 89

Preparation of the Compound of Formula 5-a-65

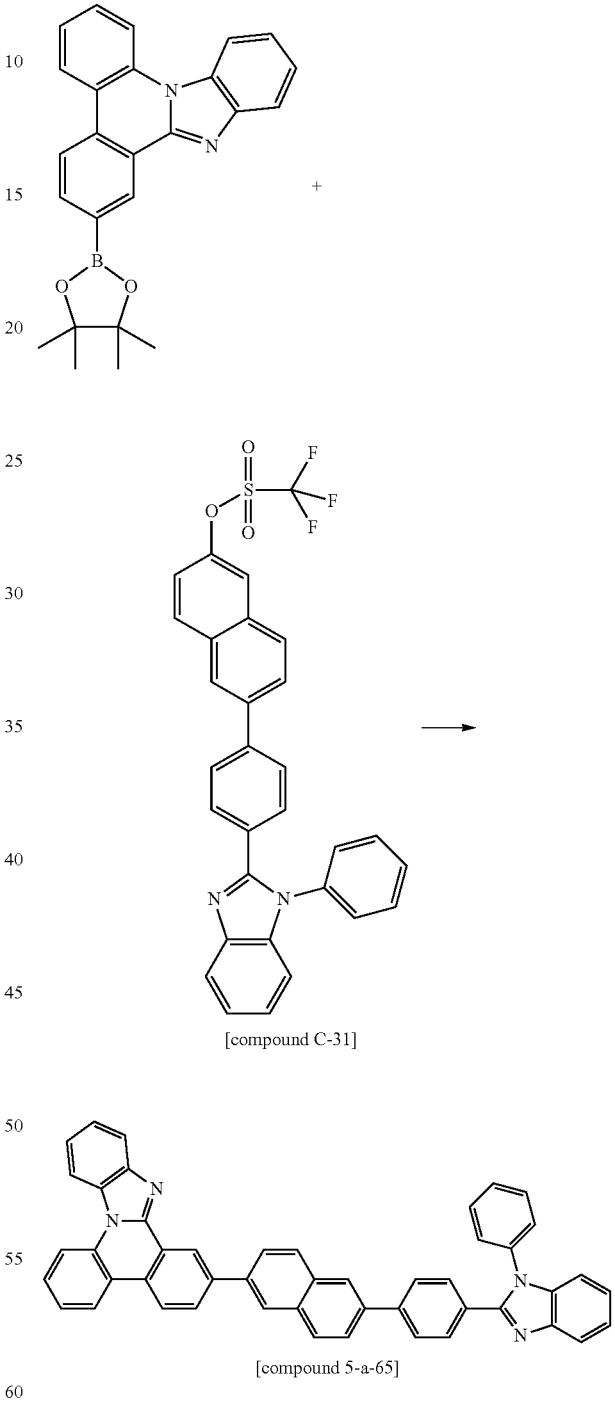

[compound C-31]

[compound 5-a-65]

The compound 5-a-65 (5.04 g, 76%) was prepared by using the same method as Example 1, except that the compound C-31 (5.5 g, 10.1 mmol) was used instead of the compound B-1 and the compound A-54 (3.94 g, 10.0 mmol) was used instead of the compound A-4 in Example 1. MS: [M+H]$^+$=663

Example 90

Preparation of the Compound of Formula 5-a-67

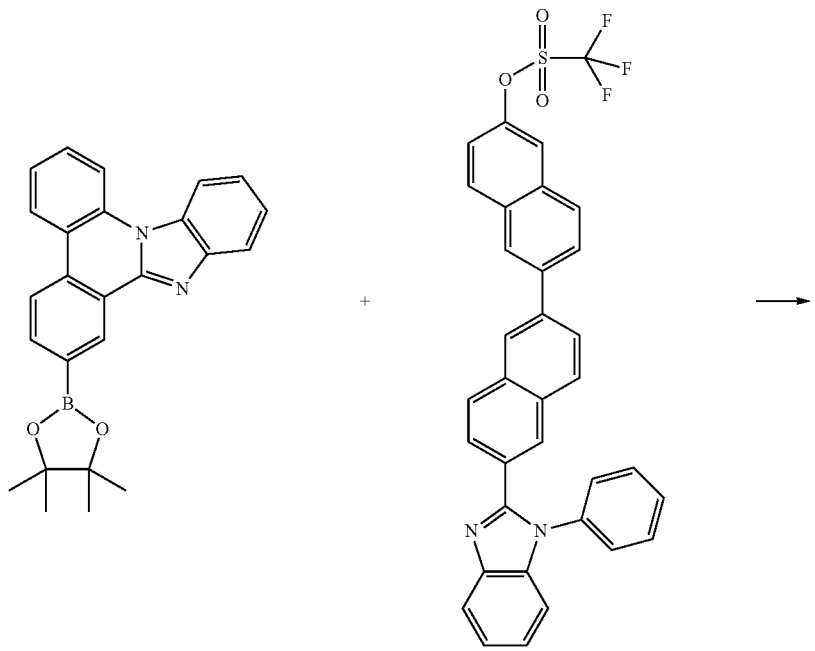

[compound C-32]

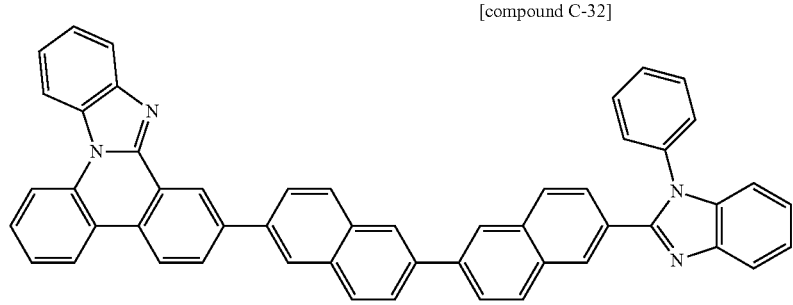

[compound 5-a-67]

The compound 5-a-67 (2.72 g, 83%) was prepared by using the same method as Example 1, except that the compound C-32 (2.73 g, 4.6 mmol) was used instead of the compound B-1 and the compound A-54 (1.81 g, 4.6 mmol) was used instead of the compound A-4 in Example 1. MS: $[M+H]^+$ = 713

EXPERIMENTAL EXAMPLE

Experimental Example 1-1-1

A glass substrate on which a thin film of ITO (indium tin oxide) was coated to a thickness of 1000 Å was immersed in distilled water having a detergent dissolved therein to wash the substrate with ultrasonic waves. At this time, the detergent as used herein was a product commercially available from Fisher Co. and the distilled water was one which had been twice filtered by using a filter commercially available from Millipore Co. ITO was washed for 30 minutes, and then washing with ultrasonic waves was repeated twice for 10 minutes by using distilled water. After the completion of washing with distilled water, washing with ultrasonic waves was subsequently carried out by using solvents such as isopropyl alcohol, acetone and methanol, the resultant product was dried, and transported to the plasma washing machine. In addition, after the substrate was washed for 5 min by using the oxygen plasma, the substrate was transported by using the vacuum deposition device.

On the ITO transparent electrode thus prepared, hexanitrile hexaazatriphenylene (HAT) of the following Formula was coated to thicknesses of 500 Å by thermal vacuum deposition to form a hole injecting layer.

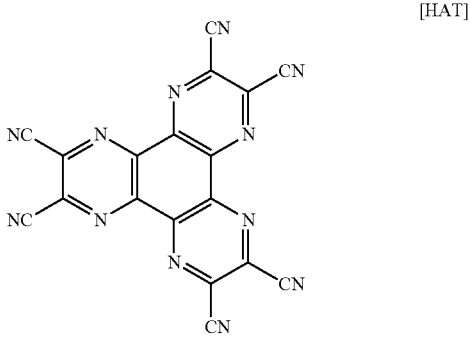 [SMILES: N#Cc1nc2c3nc(C#N)c(C#N)nc3c3nc(C#N)c(C#N)nc3c2nc1C#N]

[HAT]

4,4'-bis[N-(1-naphthyl)-N-phenylamino]biphenyl (NPB) (400 Å) of the following Formula that was the material transporting the holes was deposited under the vacuum on the hole injection layer to form the hole transport layer.

[NPB]

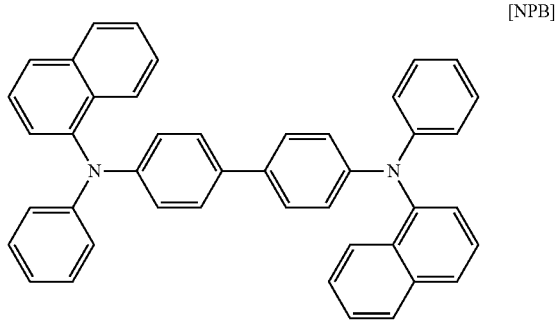 [SMILES: c1ccc(N(c2ccc(-c3ccc(N(c4ccccc4)c4cccc5ccccc45)cc3)cc2)c2cccc3ccccc23)cc1]

Subsequently, GH and GD as shown below were deposited under the vacuum state at the weight ratio of 20:1 in the film thickness of 300 Å on the hole transport layer, thereby forming the light emitting layer.

[GH]

[GD]

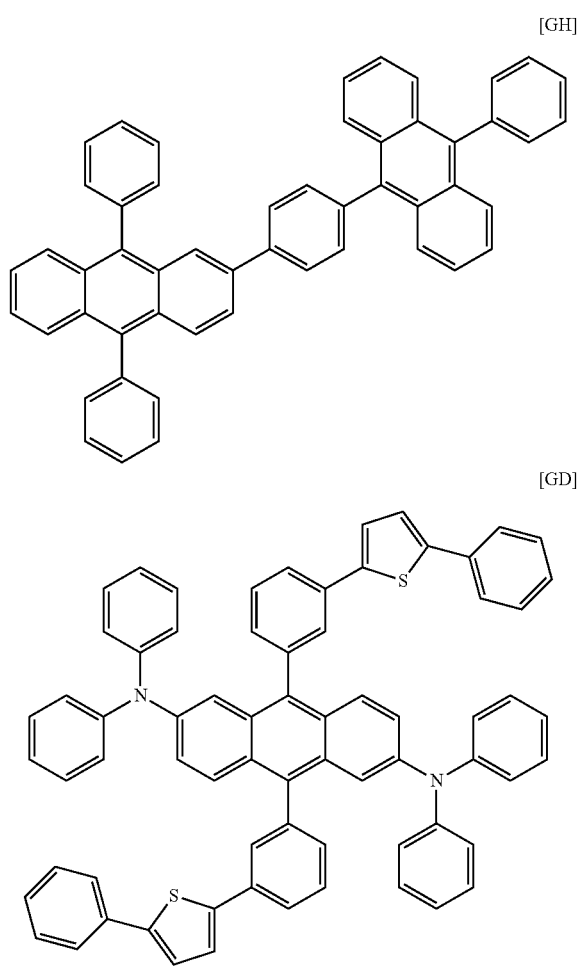

On the light emitting layer, the compound of Formula 1-a-8 that was manufactured in Example 1 was deposited under the vacuum state in the thickness of 200 Å, thereby forming the electron injection and transport layer.

On the electron injection and transport layer, lithium fluoride (LiF) in a thickness of 12 Å and aluminium in a thickness of 2000 Å were subsequently deposited to form a cathode.

In the above process, the deposition speed of the organic material was maintained at 0.4 to 0.7 Å/sec, the deposition speed of the lithium fluoride of the cathode was maintained at 0.3 Å/sec, the deposition speed of aluminium was maintained at 2 Å/sec, and the degree of vacuum in the deposition was maintained at $2\times10^{-7}$ to $5\times10^{-8}$ torr, thereby manufacturing the organic light emitting device.

Comparative Example 1

In Experimental Example 1-1-1, the organic light emitting device was manufactured by using the same method as Experimental Example 1-1-1, except that the compound of the following Formula ET-A1 was used instead of the compound of Formula 1-a-8.

[ET-A1]

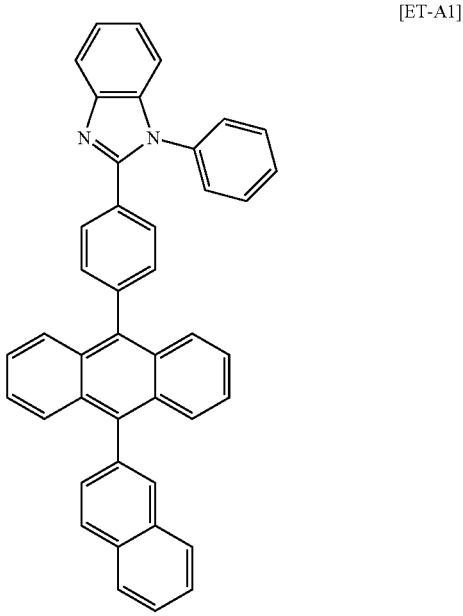 [SMILES: c1ccc(-n2c(-c3ccc(-c4c5ccccc5c(-c5ccc6ccccc6c5)c5ccccc45)cc3)nc3ccccc32)cc1]

Experimental Example 1-1-2 to 1-1-8

In Experimental Example 1-1-1, the organic light emitting device was manufactured by using the same method as Experimental Example 1-1-1, except that the compounds described in Table 4-1 were used instead of the compound of Formula 1-a-8.

When current was applied to the organic light emitting device that was manufactured by Experimental Examples 1-1-1 to 1-1-8 and Comparative Example 1, the results of Table 4-1 were obtained.

TABLE 4-1

| | compound | voltage (V@10 mA/cm$^2$) | efficiency (cd/A @10 mA/cm$^2$) | color coordinate (x, y) |
|---|---|---|---|---|
| Experimental Example 1-1-1 | 1-a-8 | 4.03 | 28.02 | (0.323, 0.645) |
| Experimental Example 1-1-2 | 1-a-10 | 4.52 | 26.47 | (0.326, 0.644) |

TABLE 4-1-continued

| compound | voltage (V@10 mA/cm$^2$) | efficiency (cd/A @10 mA/cm$^2$) | color coordinate (x, y) |
|---|---|---|---|
| Experimental Example 1-1-3 | 1-a-34 | 5.25 | 26.34 | (0.326, 0.645) |
| Experimental Example 1-1-4 | 1-b-8 | 4.33 | 26.06 | (0.323, 0.645) |
| Experimental Example 1-1-5 | 1-b-9 | 4.71 | 20.75 | (0.326, 0.644) |
| Experimental Example 1-1-6 | 1-c-8 | 5.43 | 21.62 | (0.326, 0.644) |
| Experimental Example 1-1-7 | 7-a-16 | 3.81 | 27.16 | (0.326, 0.643) |
| Experimental Example 1-1-8 | 3-c-39 | 3.94 | 25.34 | (0.327, 0.645) |
| Comparative Example 1 | ET-A1 | 4.98 | 23.21 | (0.326, 0.644) |

Comparative Example 2

In Experimental Example 1-1-1, the organic light emitting device was manufactured by using the same method as Experimental Example 1-1-1, except that the compound of the following Formula ET-A2 (Korean Unexamined Patent Application Publication No. 2003-0067773) was used instead of the compound of Formula 1-a-8.

[ET-A2]

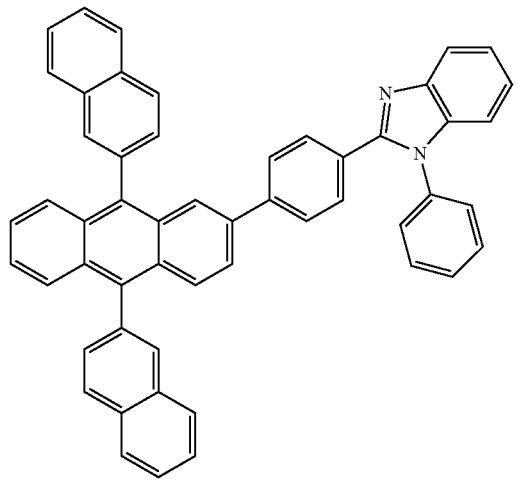

Experimental Example 1-2-1 to 1-2-17

In Experimental Example 1-1-1, the organic light emitting device was manufactured by using the same method as Experimental Example 1-1-1, except that the compounds described in Table 4-2 were used instead of the compound of Formula 1-a-8.

When current was applied to the organic light emitting device that was manufactured by Experimental Examples 1-2-1 to 1-2-17 and Comparative Example 2, the results of Table 4-2 were obtained.

TABLE 4-2

| compound | voltage (V@10 mA/cm$^2$) | efficiency (cd/A @10 mA/cm$^2$) | color coordinate (x, y) |
|---|---|---|---|
| Experimental Example 1-2-1 | 1-a-14 | 3.92 | 29.24 | (0.327, 0.647) |
| Experimental Example 1-2-2 | 1-a-15 | 4.42 | 27.05 | (0.324, 0.651) |
| Experimental Example 1-2-3 | 1-a-35 | 4.87 | 22.73 | (0.323, 0.641) |
| Experimental Example 1-2-4 | 1-a-58 | 4.07 | 30.05 | (0.325, 0.649) |
| Experimental Example 1-2-5 | 1-b-15 | 4.12 | 28.01 | (0.325, 0.650) |
| Experimental Example 1-2-6 | 1-b-37 | 4.98 | 23.69 | (0.323, 0.644) |
| Experimental Example 1-2-7 | 1-b-100 | 5.12 | 19.24 | (0.322, 0.642) |
| Experimental Example 1-2-8 | 1-c-15 | 4.52 | 21.4 | (0.325, 0.645) |
| Experimental Example 1-2-9 | 2-a-6 | 5.57 | 19.29 | (0.325, 0.643) |
| Experimental Example 1-2-10 | 2-a-20 | 4.32 | 28.23 | (0.322, 0.642) |
| Experimental Example 1-2-11 | 2-b-6 | 4.37 | 26.02 | (0.323, 0.644) |
| Experimental Example 1-2-12 | 2-b-19 | 4.45 | 26.08 | (0.326, 0.648) |
| Experimental Example 1-2-13 | 3-a-4 | 4.53 | 25.37 | (0.324, 0.641) |
| Experimental Example 1-2-14 | 3-b-3 | 4.34 | 27.37 | (0.324, 0.641) |
| Experimental Example 1-2-15 | 3-c-12 | 4.21 | 25.09 | (0.327, 0.649) |
| Experimental Example 1-2-16 | 4-a-7 | 4.73 | 24.84 | (0.325, 0.648) |
| Experimental Example 1-2-17 | 4-a-8 | 4.21 | 25.35 | (0.324, 0.643) |
| Comparative Example 2 | ET-A2 | 5.31 | 23.07 | (0.326, 0.644) |

The novel heterocyclic derivative according to the present invention may be used as the material of the organic material layer of the organic electronic device, and the organic electronic device according to the present invention has excellent properties in views of an increase in efficiency, a reduction in driving voltage, a lengthened life span, and an increase in stability.

Comparative Example 3

In Experimental Example 1-1-1, the organic light emitting device was manufactured by using the same method as Experimental Example 1-1-1, except that the compound of the following Formula ET-A3 was used instead of the compound of Formula 1-a-8.

[ET-A3]

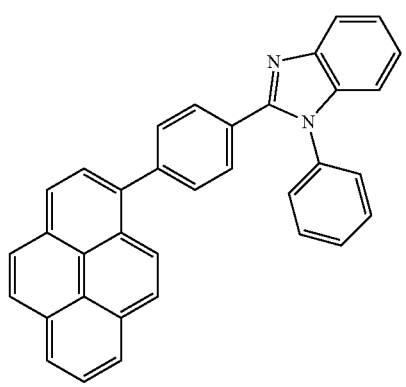

Experimental Example 1-3-1 to 1-3-3

In Experimental Example 1-1-1, the organic light emitting device was manufactured by using the same method as Experimental Example 1-3-1, except that the compounds described in Table 4-3 were used instead of the compound of Formula 1-a-8.

When current was applied to the organic light emitting device that was manufactured by Experimental Examples 1-3-1 to 1-3-3 and Comparative Example 3, the results of Table 4-3 were obtained.

TABLE 4-3

|  | compound | voltage (V@10 mA/cm$^2$) | efficiency (cd/A @10 mA/cm$^2$) | color coordinate (x, y) |
| --- | --- | --- | --- | --- |
| Experimental Example 1-3-1 | 1-a-18 | 5.21 | 27.14 | (0.324, 0.644) |
| Experimental Example 1-3-2 | 1-b-39 | 4.97 | 21.53 | (0.325, 0.646) |
| Experimental Example 1-3-3 | 3-c-25 | 5.12 | 22.25 | (0.325, 0.646) |
| Comparative Example 3 | ET-A3 | 5.91 | 24.76 | (0.323, 0.642) |

Comparative Example 4

In Experimental Example 1-1-1, the organic light emitting device was manufactured by using the same method as Experimental Example 1-1-1, except that the compound of ET-A4 was used instead of the compound of Formula 1-a-8.

[ET-A4]

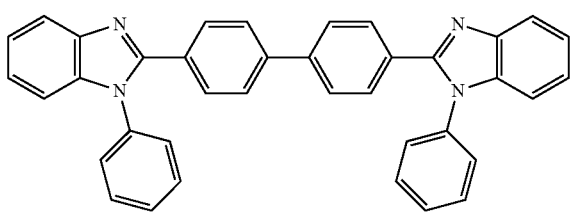

Experimental Example 1-4-1 to 1-4-16

In Experimental Example 1-1-1, the organic light emitting device was manufactured by using the same method as Experimental Example 1-4-1, except that the compounds described in Table 4-4 were used instead of the compound of Formula 1-a-8.

When current was applied to the organic light emitting device that was manufactured by Experimental Examples 1-4-1 to 1-4-16 and Comparative Example 4, the results of Table 4-4 were obtained.

TABLE 4-4

|  | compound | voltage (V@10 mA/cm$^2$) | efficiency (cd/A @10 mA/cm$^2$) | color coordinate (x, y) |
| --- | --- | --- | --- | --- |
| Experimental Example 1-4-1 | 1-a-68 | 5.24 | 26.52 | (0.324, 0.644) |
| Experimental Example 1-4-2 | 1-a-77 | 5.51 | 22.53 | (0.325, 0.646) |
| Experimental Example 1-4-3 | 1-b-139 | 5.07 | 24.15 | (0.327, 0.647) |
| Experimental Example 1-4-4 | 1-b-151 | 5.82 | 22.50 | (0.323, 0.643) |
| Experimental Example 1-4-5 | 2-b-28 | 5.91 | 24.64 | (0.324, 0.644) |
| Experimental Example 1-4-6 | 3-b-13 | 5.13 | 27.37 | (0.325, 0.648) |
| Experimental Example 1-4-7 | 5-a-1 | 4.32 | 26.15 | (0.323, 0.649) |
| Experimental Example 1-4-8 | 5-a-2 | 4.76 | 23.5 | (0.324, 0.651) |
| Experimental Example 1-4-9 | 5-a-13 | 6.78 | 22.24 | (0.327, 0.648) |
| Experimental Example 1-4-10 | 5-a-23 | 5.36 | 18.13 | (0.329, 0.650) |
| Experimental Example 1-4-11 | 5-a-32 | 5.52 | 22.45 | (0.327, 0.649) |
| Experimental Example 1-4-12 | 5-a-33 | 5.03 | 23.87 | (0.330, 0.652) |
| Experimental Example 1-4-13 | 5-a-34 | 6.15 | 20.69 | (0.327, 0.647) |
| Experimental Example 1-4-14 | 7-a-23 | 4.82 | 23.64 | (0.327, 0.644) |
| Experimental Example 1-4-15 | 5-a-53 | 4.95 | 20.83 | (0.326, 0.649) |
| Experimental Example 1-4-16 | 5-a-55 | 5.24 | 22.57 | (0.328, 0.651) |
| Comparative Example 4 | ET-A4 | 7.23 | 19.25 | (0.324, 0.638) |

In Tables 4-1, 4-2, 4-3, and 4-4, the compounds that include the structure of Formula 1 showed characteristics of low voltage and high efficiency as compared to the compounds of Comparative Examples.

Experimental Example 2-1-1 to 2-1-38

In Experimental Example 1-1-1, the organic light emitting device was manufactured by using the same method as Experimental Example 1-1-1, except that the compounds described in the following Table 4-5 were used instead of the compound of Formula 1-a-8.

When current was applied to the organic light emitting device that was manufactured by Experimental Examples 2-1-1 to 2-1-38 and Comparative Example 2, the results of Table 4-5 were obtained.

TABLE 4-5

|  | compound | voltage (V@10 mA/cm$^2$) | efficiency (cd/A @10 mA/cm$^2$) | color coordinate (x, y) |
| --- | --- | --- | --- | --- |
| Experimental Example 2-1-1 | 1-a-29 | 4.23 | 27.12 | (0.324, 0.644) |
| Experimental Example 2-1-2 | 1-a-31 | 4.52 | 21.57 | (0.325, 0.646) |

TABLE 4-5-continued

| | compound | voltage (V@10 mA/cm²) | efficiency (cd/A @10 mA/cm²) | color coordinate (x, y) |
|---|---|---|---|---|
| Experimental Example 2-1-3 | 1-a-37 | 5.06 | 17.93 | (0.327, 0.647) |
| Experimental Example 2-1-4 | 1-a-64 | 4.85 | 21.57 | (0.323, 0.643) |
| Experimental Example 2-1-5 | 1-a-72 | 4.92 | 23.64 | (0.324, 0.644) |
| Experimental Example 2-1-6 | 1-b-31 | 4.18 | 29.39 | (0.325, 0.648) |
| Experimental Example 2-1-7 | 1-b-32 | 4.36 | 27.75 | (0.323, 0.649) |
| Experimental Example 2-1-8 | 1-b-33 | 3.72 | 21.15 | (0.324, 0.651) |
| Experimental Example 2-1-9 | 1-b-80 | 3.91 | 29.07 | (0.327, 0.648) |
| Experimental Example 2-1-10 | 1-b-117 | 4.37 | 25.02 | (0.329, 0.650) |
| Experimental Example 2-1-11 | 1-b-122 | 4.56 | 25.04 | (0.327, 0.649) |
| Experimental Example 2-1-12 | 1-b-130 | 4.07 | 25.02 | (0.330, 0.652) |
| Experimental Example 2-1-13 | 1-b-136 | 5.13 | 23.01 | (0.327, 0.647) |
| Experimental Example 2-1-14 | 1-c-23 | 4.82 | 21.09 | (0.324, 0.644) |
| Experimental Example 2-1-15 | 2-a-29 | 4.53 | 24.28 | (0.325, 0.646) |
| Experimental Example 2-1-16 | 2-a-38 | 4.35 | 25.47 | (0.326, 0.643) |
| Experimental Example 2-1-17 | 2-b-16 | 4.73 | 24.48 | (0.324, 0.645) |
| Experimental Example 2-1-18 | 3-c-10 | 5.16 | 20.72 | (0.323, 0.645) |
| Experimental Example 2-1-19 | 3-c-21 | 4.75 | 24.8 | (0.323, 0.647) |
| Experimental Example 2-1-20 | 6-a-1 | 5.31 | 19.38 | (0.321, 0.642) |
| Experimental Example 2-1-21 | 6-a-2 | 4.51 | 25.35 | (0.322, 0.645) |
| Experimental Example 2-1-22 | 6-a-3 | 4.89 | 23.57 | (0.325, 0.644) |
| Experimental Example 2-1-23 | 6-a-21 | 4.83 | 21.92 | (0.325, 0.644) |
| Experimental Example 2-1-24 | 6-a-22 | 4.71 | 22.76 | (0.322, 0.645) |
| Experimental Example 2-1-25 | 6-a-23 | 4.23 | 23.15 | (0.322, 0.645) |
| Experimental Example 2-1-26 | 6-a-33 | 3.93 | 22.3 | (0.322, 0.642) |
| Experimental Example 2-1-27 | 6-a-34 | 3.74 | 20.45 | (0.322, 0.645) |
| Experimental Example 2-1-28 | 6-a-35 | 4.56 | 25.3 | (0.322, 0.644) |
| Experimental Example 2-1-29 | 7-a-1 | 3.89 | 23.13 | (0.322, 0.644) |
| Experimental Example 2-1-30 | 7-a-4 | 3.95 | 22.72 | (0.322, 0.647) |
| Experimental Example 2-1-31 | 7-a-6 | 4.37 | 27.38 | (0.322, 0.644) |
| Experimental Example 2-1-32 | 7-a-10 | 4.26 | 22.82 | (0.322, 0.645) |
| Experimental Example 2-1-33 | 3-c-30 | 4.56 | 25.24 | (0.322, 0.642) |
| Experimental Example 2-1-34 | 5-a-59 | 4.59 | 22.71 | (0.323, 0.644) |
| Experimental Example 2-1-35 | 5-a-62 | 4.64 | 25.20 | (0.322, 0.644) |
| Experimental Example 2-1-36 | 5-a-64 | 4.52 | 24.71 | (0.321, 0.643) |
| Experimental Example 2-1-37 | 5-a-65 | 3.94 | 25.09 | (0.323, 0.645) |
| Experimental Example 2-1-38 | 5-a-67 | 3.8 | 23.6 | (0.322, 0.644) |
| Comparative Example 2 | ET-A2 | 5.31 | 23.07 | (0.326, 0.644) |

In Table 4-5, since the compounds that have the structure of Formula 1 have excellent electron transport and injection ability, it was confirmed that it was capable of being used to the organic light emitting device.

Experimental Example 3-1-1

A glass substrate (corning 7059 glass) on which a thin film of ITO (indium tin oxide) was coated to a thickness of 1000 Å was immersed in distilled water having a detergent dissolved therein to wash the substrate with ultrasonic waves. The detergent as used herein was a product commercially available from Fisher Co. and the distilled water was one which had been twice filtered by using a filter commercially available from Millipore Co. ITO was washed for 30 minutes, and then washing with ultrasonic waves was repeated twice for 10 minutes by using distilled water. After the completion of washing with distilled water, washing with ultrasonic waves was carried out by using solvents such as isopropyl alcohol, acetone and methanol, and the resultant product was dried.

On the ITO transparent electrode thus prepared, hexanitrile hexaazatriphenylene was coated to thicknesses of 500 Å by thermal vacuum deposition to form a hole injecting layer. 4,4'-bis[N-(1-naphthyl)-N-phenylamino]biphenyl (NPB) (400 Å) of the above Formula that was the material transporting the holes was deposited under the vacuum on the hole injection layer to form the hole transport layer. Subsequently, on the hole transport layer, the compound that is represented by Formula 1-a-29 and prepared in Example 6 and the D3 dopant compound of the following Formula were deposited under the vacuum at the weight ratio of 100:14, thus forming the light emitting layer (300 Å). Next, the ET-A2 compound (300 Å) was deposited under the vacuum as the electron injection and transport layer. On the electron injection and transport layer, lithium fluoride (LiF) in a thickness of 12 Å and aluminum in a thickness of 2,000 Å were deposited to form a cathode, thereby manufacturing the organic light emitting device.

[D3]

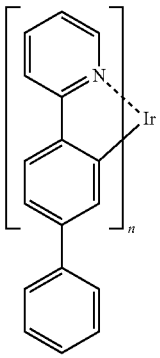

In the above process, the deposition speed of the organic substance was maintained at 0.4 to 0.7 Å/sec, that of lithium fluoride was maintained at 0.2 Å/sec, and that of aluminum was maintained at 3 to 7 Å/sec.

Experimental Example 3-1-2 to 3-1-7

In Experimental Example 3-1-1, the organic light emitting device was manufactured by using the same method as Experimental Example 3-1-1, except that the compounds described in the following Table 4-6 were used instead of the compound of Formula 1-a-29.

Comparative Example 3-1

In Experimental Example 3-1-1, the organic light emitting device was manufactured by using the same method as Experimental Example 3-1-1, except that the compound of PH of the following Formula was used instead of the compound of Formula 1-a-29.

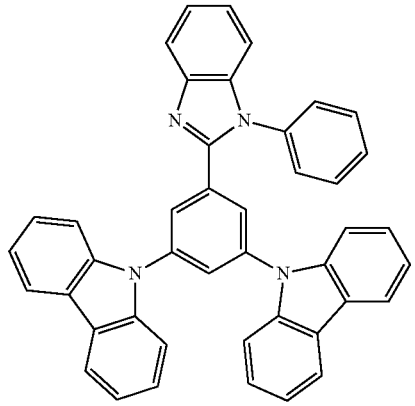
[PH]

When current was applied to the organic light emitting device that was manufactured by Experimental Examples 3-1-1 to 3-1-7 and Comparative Example 3-1, the results of Table 4-6 were obtained.

TABLE 4-6

| | EML (Host: D3) | voltage (V@20 mA/cm²) | Current efficiency (cd/A@ 20 mA/cm²) | Color coordinate (x, y) |
|---|---|---|---|---|
| Comparative Example 3-1 | PH | 6.23 | 15.25 | (0.369, 0.600) |
| Experimental Example 3-1-1 | 1-a-29 | 4.57 | 36.96 | (0.380, 0.589) |
| Experimental Example 3-1-2 | 3-a-16 | 4.57 | 22.57 | (0.354, 0.611) |
| Experimental Example 3-1-3 | 3-c-13 | 5.34 | 28.48 | (0.360, 0.607) |
| Experimental Example 3-1-4 | 1-a-80 | 4.61 | 40.22 | (0.354, 0.609) |
| Experimental Example 3-1-5 | 1-b-146 | 4.31 | 39.07 | (0.362, 0.607) |
| Experimental Example 3-1-6 | 6-a-18 | 4.38 | 29.34 | (0.361, 0.607) |
| Experimental Example 3-1-7 | 6-a-39 | 4.90 | 36.52 | (0.360, 0.608) |

As shown in Table 4-6, the compound derivative that is represented by Formula according to the present invention can function as the light emitting material in the organic light emitting device and the organic electronic device, and the device according to the present invention shows excellent characteristics in views of efficiency, the driving voltage, and stability. In particular, in views of efficiency, the high light emitting characteristics are shown.

Experimental Example 4-1-1 to Experimental Example 4-1-20

On the ITO transparent electrode that was prepared by using the same method as Experimental Example 1-1-1, hexanitrile hexaazatriphenylene (HAT) was coated to thicknesses of 500 Å by thermal vacuum deposition to form a hole injecting layer.

On the hole injection layer, the following compounds HT-1, HT-2, or HT-3 were deposited under the vacuum to form the hole transport layer (400 Å).

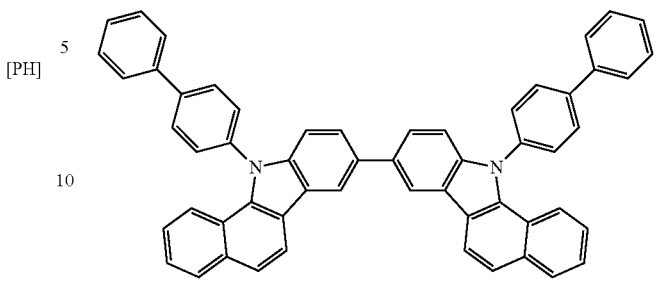
[HT-1]

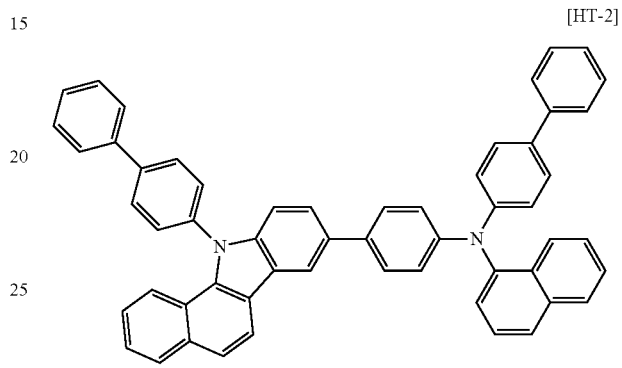
[HT-2]

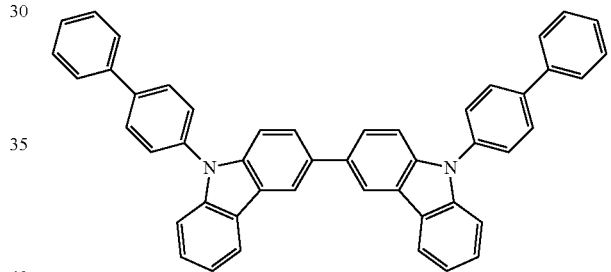
[HT-3]

Subsequently, BH-1 and BD as shown below were deposited under the vacuum state at the weight ratio of 25:1 in the film thickness of 300 Å on the hole transport layer, thereby forming the light emitting layer.

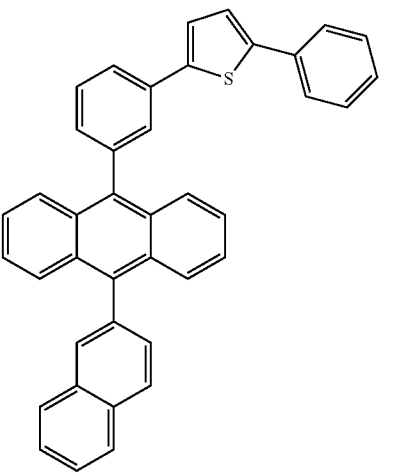
[BH-1]

[BD]

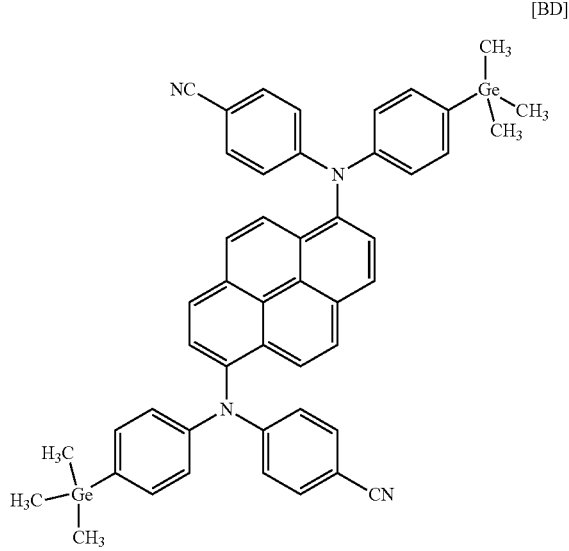

Subsequently, on the light emitting layer, the compound (ETL) shown in Table 4-7 was deposited under the vacuum in the film thickness of 300 Å to form the electron injection and transport layer. On the electron injection and transport layer, lithium fluoride (LiF) in a thickness of 12 Å and aluminum in a thickness of 2000 Å were subsequently deposited to form a cathode.

In the above process, the deposition speed of the organic material was maintained at 0.4 to 0.7 Å/sec, the deposition speed of the lithium fluoride of the cathode was maintained at 0.3 Å/sec, the deposition speed of aluminium was maintained at 2 Å/sec, and the degree of vacuum in the deposition was maintained at $2\times10^{-7}$ to $5\times10^{-8}$ torr, thereby manufacturing the organic light emitting device. When current was applied to the organic light emitting device that was manufactured as described above, the results of Table 4-7 were obtained.

TABLE 4-7

| | compound (HTL) | compound (ETL) | voltage (V@10 mA/cm$^2$) | efficiency (cd/A@ 10 mA/cm$^2$) | color coordinate (x, y) |
|---|---|---|---|---|---|
| Experimental Example 4-1-1 | HT-1 | 1-a-8 | 4.27 | 4.62 | (0.139, 0.158) |
| Experimental Example 4-1-2 | HT-3 | 1-a-8 | 5.01 | 4.51 | (0.138, 0.153) |
| Experimental Example 4-1-3 | HT-1 | 1-a-15 | 3.97 | 4.01 | (0.139, 0.154) |
| Experimental Example 4-1-4 | HT-2 | 1-a-15 | 4.04 | 4.10 | (0.139, 0.154) |
| Experimental Example 4-1-5 | HT-1 | 1-a-58 | 4.10 | 4.67 | (0.139, 0.158) |
| Experimental Example 4-1-6 | HT-3 | 1-a-58 | 5.47 | 4.21 | (0.139, 0.158) |
| Experimental Example 4-1-7 | HT-1 | 1-b-9 | 4.26 | 4.26 | (0.139, 0.156) |
| Experimental Example 4-1-8 | HT-2 | 1-b-9 | 4.21 | 4.07 | (0.139, 0.157) |
| Experimental Example 4-1-9 | HT-1 | 1-b-32 | 4.17 | 4.89 | (0.139, 0.147) |
| Experimental Example 4-1-10 | HT-2 | 1-b-32 | 3.86 | 4.80 | (0.139, 0.149) |
| Experimental Example 4-1-11 | HT-1 | 1-b-33 | 4.04 | 4.69 | (0.139, 0.147) |
| Experimental Example 4-1-12 | HT-2 | 1-b-33 | 4.13 | 4.87 | (0.139, 0.150) |
| Experimental Example 4-1-13 | HT-1 | 1-b-80 | 4.02 | 5.01 | (0.138, 0.147) |
| Experimental Example 4-1-14 | HT-2 | 1-b-80 | 3.85 | 4.96 | (0.138, 0.157) |
| Experimental Example 4-1-15 | HT-2 | 7-a-1 | 4.13 | 4.87 | (0.139, 0.140) |
| Experimental Example 4-1-16 | HT-1 | 7-a-4 | 4.02 | 5.01 | (0.138, 0.157) |
| Experimental Example 4-1-17 | HT-2 | 7-a-6 | 3.85 | 4.96 | (0.138, 0.147) |
| Experimental Example 4-1-18 | HT-1 | 7-a-10 | 4.13 | 4.87 | (0.139, 0.150) |
| Experimental Example 4-1-19 | HT-2 | 7-a-16 | 4.16 | 5.23 | (0.139, 0.151) |
| Experimental Example 4-1-20 | HT-1 | 7-a-23 | 5.12 | 4.38 | (0.139, 0.147) |

As shown in Table 4-7, the compound that is represented by Formula 1 according to the present invention can variously use hole injection and transport materials or the light emitting material in the organic light emitting device and the organic electronic device, and the device according to the present invention shows excellent characteristics in views of efficiency, the driving voltage, and stability.

Experimental Example 5-1-1

Like Experimental Example 1-1-1, on the ITO transparent electrode, hexanitrile hexaazatriphenylene (HAT) of the above Formula was coated to thicknesses of 500 Å by thermal vacuum deposition to form a hole injecting layer.

4,4'-bis[N-(1-naphthyl)-N-phenylamino]biphenyl (NPB) (400 Å) of the above Formula that was the material transporting the holes was deposited under the vacuum on the hole injection layer to form the hole transport layer.

On the hole transport layer, after the light emitting layer was formed at the weight ratio of 25:1 by using the following Formula BH-2 as the host and the above Formula BD as the dopant in the film thickness of 300 Å, the electron injection and transport layers were formed in the thickness of 300 Å by depositing the compound of Formula 1-a-8 prepared in Example 1 and the following Formula LiQ (Lithium Quinolate) under the vacuum at the weight ratio of 1:1. On the electron injection and transport layer, lithium fluoride (LiF) in a thickness of 12 Å and aluminum in a thickness of 2,000 Å were deposited to form a cathode, thereby manufacturing the organic light emitting device.

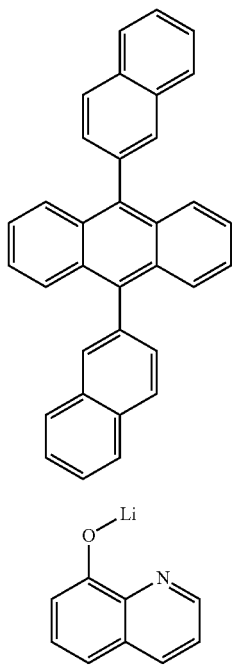

[BH-2]

[LiQ]

Experimental Example 5-1-2 to Experimental Example 5-1-8

In Experimental Example 5-1-1, the organic light emitting device was manufactured by using the same method as Experimental Example 5-1-1, except that the compounds described in the following Table 4-8 were used instead of the compound of Formula 1-a-8.

Comparative Example 5

In Experimental Example 5-1-1, the organic light emitting device was manufactured by using the same method as Experimental Example 5-1-1, except that the compound of the above Formula ET-A1 was used instead of the compound of Formula 1-a-8.

When current was applied to the organic light emitting device that was manufactured by Experimental Examples 5-1-1 to 5-1-8 and Comparative Example 5, the results of Table 4-8 were obtained.

TABLE 4-8

|  | compound | voltage (V@10 mA/cm$^2$) | efficiency (cd/A@ 10 mA/cm$^2$) | color coordinate (x, y) |
| --- | --- | --- | --- | --- |
| Experimental Example 5-1-1 | 1-a-8 | 4.09 | 4.73 | (0.139, 0.147) |
| Experimental Example 5-1-2 | 1-a-14 | 4.13 | 4.86 | (0.138, 0.148) |
| Experimental Example 5-1-3 | 1-a-15 | 3.96 | 4.97 | (0.139, 0.148) |
| Experimental Example 5-1-4 | 1-b-32 | 4.04 | 5.26 | (0.139, 0.147) |
| Experimental Example 5-1-5 | 1-b-33 | 4.28 | 4.67 | (0.138, 0.146) |
| Experimental Example 5-1-6 | 1-b-80 | 3.85 | 5.32 | (0.137, 0.145) |
| Experimental Example 5-1-7 | 5-a-59 | 4.26 | 4.26 | (0.139, 0.146) |
| Experimental Example 5-1-8 | 5-a-67 | 4.21 | 5.21 | (0.140, 0.148) |
| Comparative Example 5 | ET-A1 | 4.73 | 4.12 | (0.138, 0.147) |

As shown in Table 4-8, the compound that is represented by Formula 1 according to the present invention can be mixed with the metal compound such as LiQ to form the electron transport layer, and the device according to the present invention showed excellent characteristics in views of efficiency, the driving voltage, and stability.

The invention claimed is:
1. A nitrogen-containing heterocyclic derivative that is represented by the following Formula 2 or includes two or more structures of the following Formula 2:

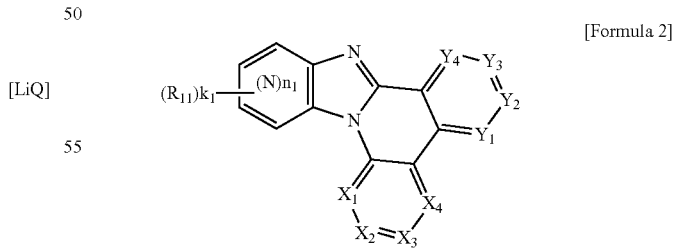

[Formula 2]

wherein
$X_1$ is N or $CR_3$, $X_2$ is N or $CR_4$, $X_3$ is N or $CR_5$, $X_4$ is N or $CR_6$, $Y_1$ is N or $CR_7$, $Y_2$ is N or $CR_8$, $Y_3$ is N or $CR_9$, $Y_4$ is N or $CR_{10}$, $X_1$ to $X_4$ and $Y_1$ to $Y_4$ are not simultaneously N,
$R_3$ to $R_{11}$ are each independently -(L)p-(Y)q, in which p is an integer in the range of 0 to 10, q is an integer in the range of 1 to 10, and two or more adjacent groups of $R_3$ to $R_{11}$ may form a monocyclic or polycyclic ring, for at least one of $R_3$ to $R_{11}$, p is integer in the range of 1 to 10, L is substituted or unsubstituted arylene group; substituted or unsubstituted alkenylene group; substituted or unsubstituted fluorenylene group; substituted or unsubstituted carbazolylene group; or substituted or unsubstituted heteroarylene group that includes one or more of N, O and S atoms, Y is hydrogen; heavy hydrogen; halogen group; nitrile group; nitro group; substituted or unsubstituted alkenyl group; substituted or unsubstituted silyl group; substituted or unsubstituted boron group; substituted or unsubstituted alkylamine group; substituted or unsubstituted aralkylamine group; substituted or unsubstituted arylamine group; substituted or unsubstituted heteroarylamine group; substituted or unsubstituted aryl group; substituted or unsubstituted fluorenyl group; substituted or unsubstituted carbazole group; or substituted or unsubstituted heteroring group that includes one or more of N, O and S atoms;

in the case of when there are two or more L and Y, they are each independently the same as or different from each other, in $(N)n_1$, N means a nitrogen atom, and the nitrogen atom is used instead of a carbon atom in a benzene ring, $n_1$ is an integer in the range of 0 to 2, $k_1$ is an integer in the range of 1 to 4, and in the case of when $k_1$ is an integer of 2 or more, $R_{11}$ may be different from each other.

2. The nitrogen-containing heterocyclic derivative as set forth in claim 1, wherein the nitrogen-containing heterocyclic derivative has a structure in which two structures of Formula 2 are directly connected to each other, or connected through a divalent connection group selected from a substituted or unsubstituted arylene group and a substituted or unsubstituted heterocyclic group.

3. The nitrogen-containing heterocyclic derivative as set forth in claim 1, wherein the nitrogen-containing heterocyclic derivative is represented by one selected from formulas that are described in the following Table 1:

TABLE 1

1-a-1

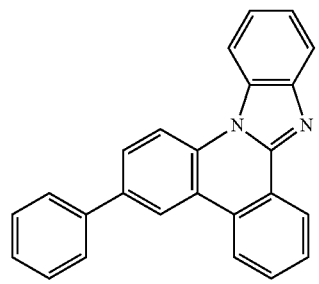 [SMILES: c1ccc(-c2ccc3c(c2)c2ccccc2c2nc4ccccc4n32)cc1]

1-a-2

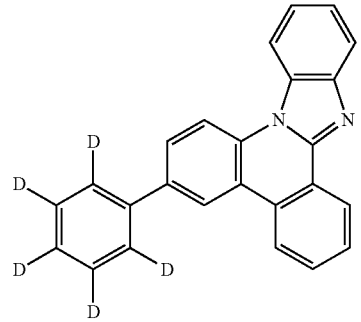 [SMILES: [2H]c1c([2H])c([2H])c(-c2ccc3c(c2)c2ccccc2c2nc4ccccc4n32)c([2H])c1[2H]]

1-a-3

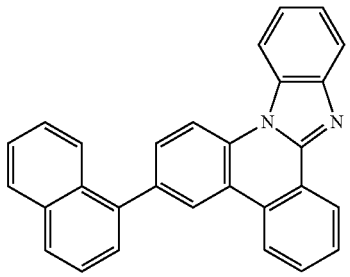 [SMILES: c1ccc2c(-c3ccc4c(c3)c3ccccc3c3nc5ccccc5n43)cccc2c1]

TABLE 1-continued
1-a-4 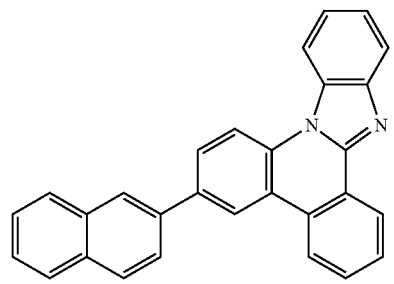 [SMILES: c1ccc2cc(-c3ccc4c(c3)c3ccccc3c3nc5ccccc5n43)ccc2c1]
1-a-5 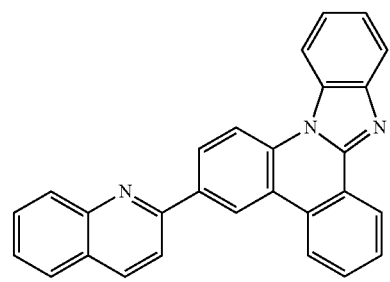 [SMILES: c1ccc2nc(-c3ccc4c(c3)c3ccccc3c3nc5ccccc5n43)ccc2c1]
1-a-6 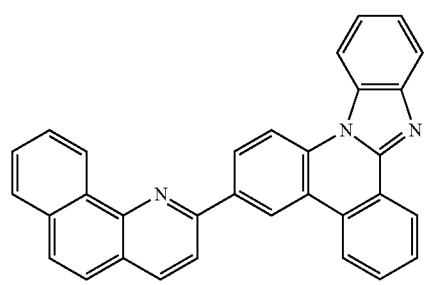 [SMILES: c1ccc2c(c1)ccc1ccc(-c3ccc4c(c3)c3ccccc3c3nc5ccccc5n43)nc12]
1-a-7 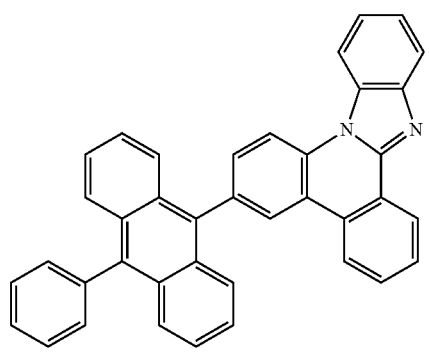 [SMILES: c1ccc(-c2c3ccccc3c(-c3ccc4c(c3)c3ccccc3c3nc5ccccc5n43)c3ccccc23)cc1]
1-a-8 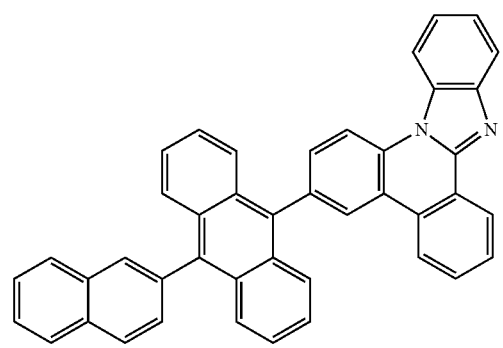 [SMILES: c1ccc2cc(-c3c4ccccc4c(-c4ccc5c(c4)c4ccccc4c4nc6ccccc6n54)c4ccccc34)ccc2c1]

TABLE 1-continued
1-a-9
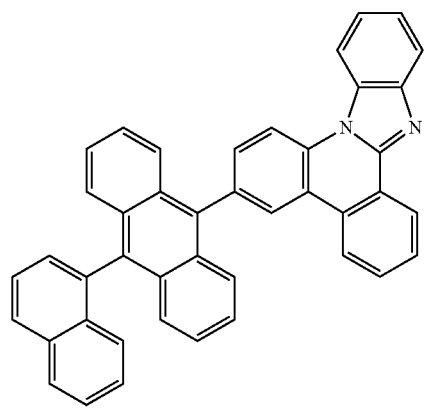 [SMILES: c1ccc2c(-c3c4ccccc4c(-c4ccc5c(c4)c4ccccc4c4nc6ccccc6n54)c4ccccc34)cccc2c1]
1-a-10
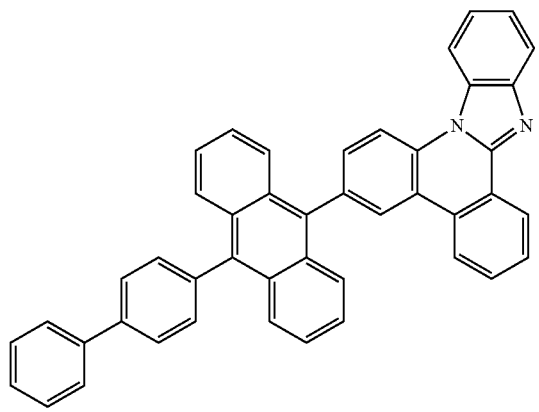 [SMILES: c1ccc(-c2ccc(-c3c4ccccc4c(-c4ccc5c(c4)c4ccccc4c4nc6ccccc6n54)c4ccccc34)cc2)cc1]
1-a-11
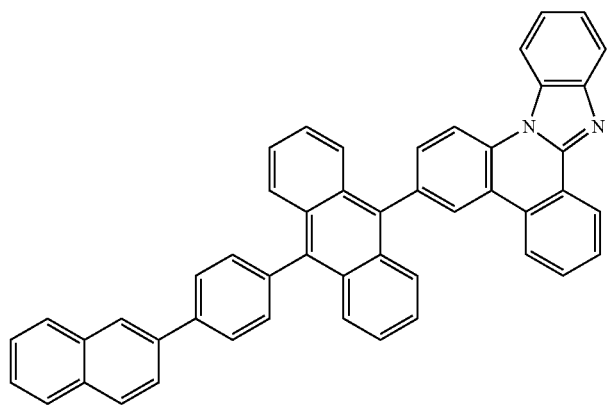 [SMILES: c1ccc2cc(-c3ccc(-c4c5ccccc5c(-c5ccc6c(c5)c5ccccc5c5nc7ccccc7n65)c5ccccc45)cc3)ccc2c1]
1-a-12
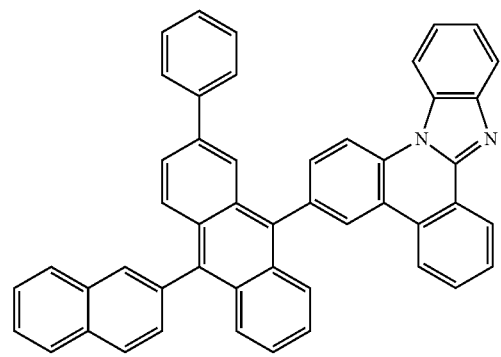 [SMILES: c1ccc(-c2ccc3c(-c4ccc5ccccc5c4)c4ccccc4c(-c4ccc5c(c4)c4ccccc4c4nc6ccccc6n54)c3c2)cc1]

TABLE 1-continued
1-a-13
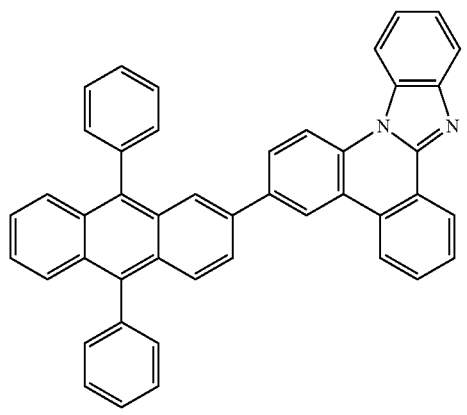 [SMILES: c1ccc(-c2c3ccccc3c(-c3ccccc3)c3cc(-c4ccc5c(c4)c4ccccc4c4nc6ccccc6n54)ccc23)cc1]
1-a-14
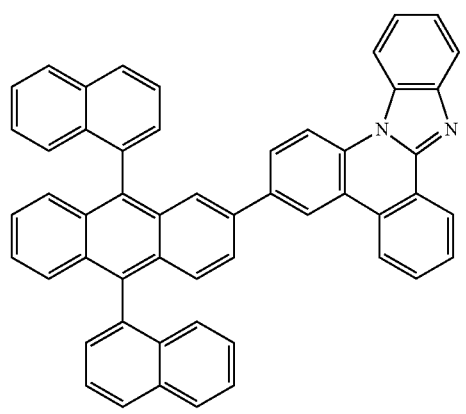 [SMILES: c1ccc2c(-c3c4ccccc4c(-c4cccc5ccccc45)c4cc(-c5ccc6c(c5)c5ccccc5c5nc7ccccc7n65)ccc34)cccc2c1]
1-a-15
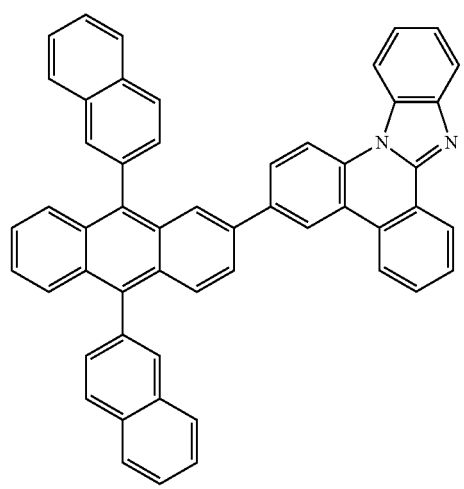 [SMILES: c1ccc2cc(-c3c4ccccc4c(-c4ccc5ccccc5c4)c4cc(-c5ccc6c(c5)c5ccccc5c5nc7ccccc7n65)ccc34)ccc2c1]

TABLE 1-continued
1-a-16
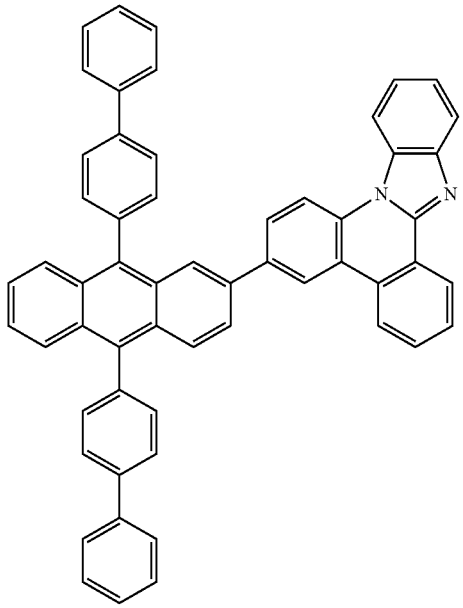 [SMILES: c1ccc(-c2ccc(-c3c4ccccc4c(-c4ccc(-c5ccccc5)cc4)c4cc(-c5ccc6c(c5)c5ccccc5c5nc7ccccc7n65)ccc34)cc2)cc1]
1-a-17
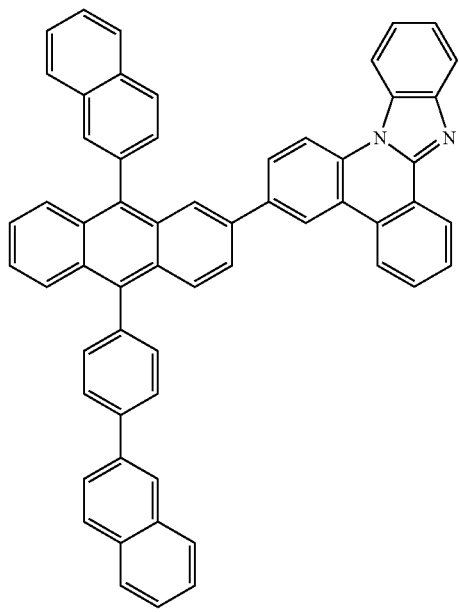 [SMILES: c1ccc2cc(-c3ccc(-c4c5ccccc5c(-c5ccc6ccccc6c5)c5cc(-c6ccc7c(c6)c6ccccc6c6nc8ccccc8n76)ccc45)cc3)ccc2c1]
1-a-18
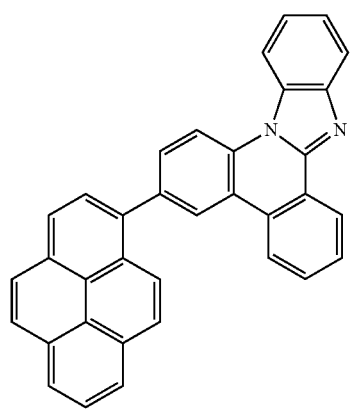 [SMILES: c1cc2ccc3ccc(-c4ccc5c(c4)c4ccccc4c4nc6ccccc6n54)c4ccc(c1)c2c34]

TABLE 1-continued
1-a-19
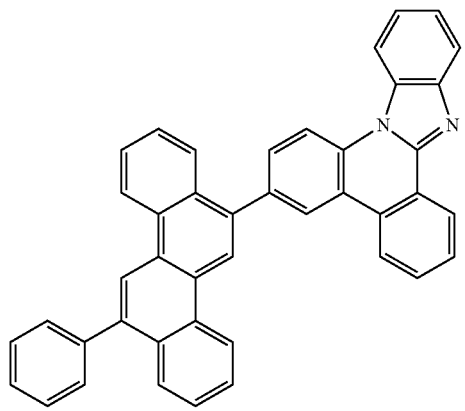 [SMILES: c1ccc(-c2cc3c4ccccc4c(-c4ccc5c(c4)c4ccccc4c4nc6ccccc6n54)cc3c3ccccc23)cc1]
1-a-20
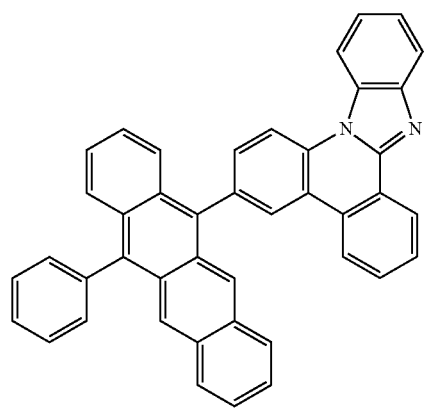 [SMILES: c1ccc(-c2c3ccccc3c(-c3ccc4c(c3)c3ccccc3c3nc5ccccc5n43)c3cc4ccccc4cc23)cc1]
1-a-21
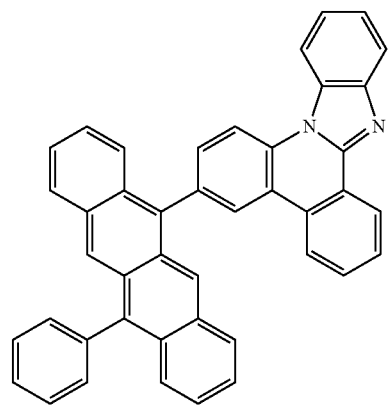 [SMILES: c1ccc(-c2c3ccccc3cc3c(-c4ccc5c(c4)c4ccccc4c4nc6ccccc6n54)c4ccccc4cc23)cc1]
1-a-22
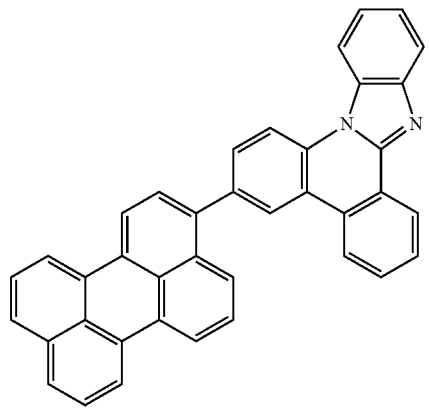 [SMILES: c1ccc2c(c1)nc1c3ccccc3c3cc(-c4ccc5c6cccc7cccc(c8cccc4c85)c76)ccc3n21]

TABLE 1-continued
1-a-23 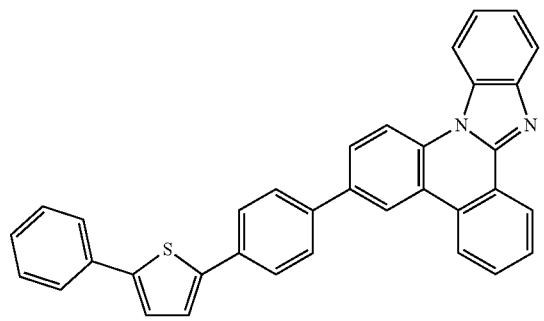 [SMILES: c1ccc(-c2ccc(-c3ccc(-c4ccc5c(c4)c4ccccc4c4nc6ccccc6n54)cc3)s2)cc1]
1-a-24 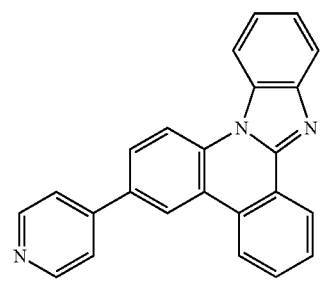 [SMILES: c1ccc2c(c1)nc1c3ccccc3c3cc(-c4ccncc4)ccc3n21]
1-a-25 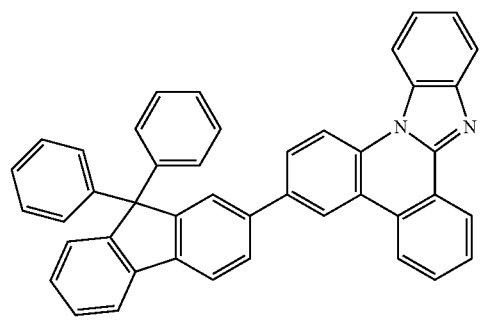 [SMILES: c1ccc(C2(c3ccccc3)c3ccccc3-c3ccc(-c4ccc5c(c4)c4ccccc4c4nc6ccccc6n54)cc32)cc1]
1-a-26 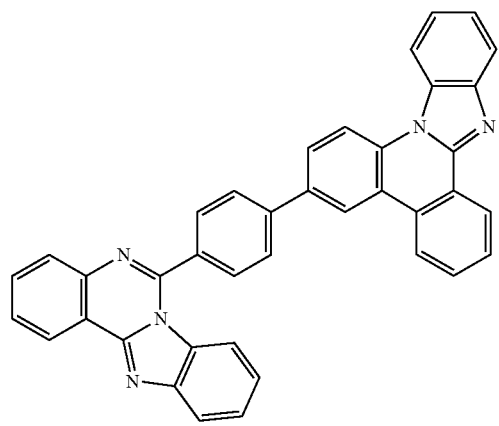 [SMILES: c1ccc2c(c1)nc(-c1ccc(-c3ccc4c(c3)c3ccccc3c3nc5ccccc5n43)cc1)n1c3ccccc3nc21]
1-a-27 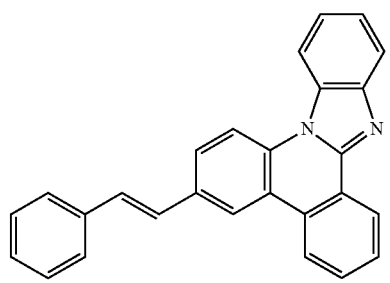 [SMILES: C(=C\c1ccc2c(c1)c1ccccc1c1nc3ccccc3n21)/c1ccccc1]

TABLE 1-continued
1-a-28 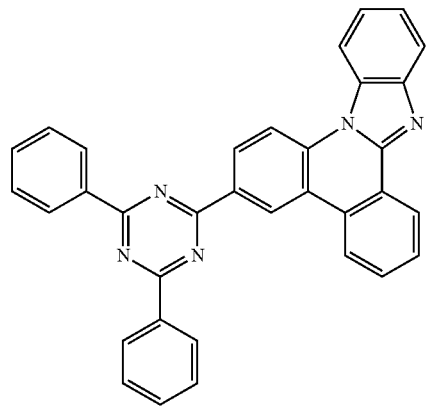 [SMILES: c1ccc(-c2nc(-c3ccccc3)nc(-c3ccc4c(c3)c3ccccc3c3nc5ccccc5n43)n2)cc1]
1-a-29 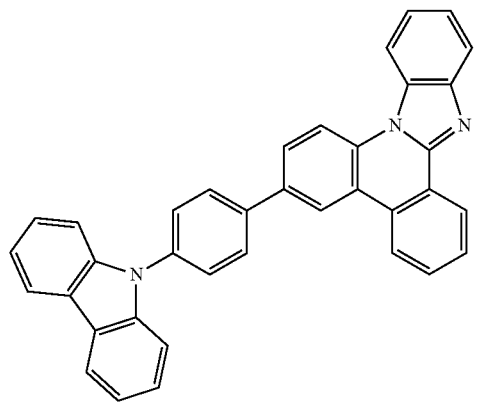 [SMILES: c1ccc2c(c1)nc1c3ccccc3c3cc(-c4ccc(-n5c6ccccc6c6ccccc65)cc4)ccc3n21]
1-a-30 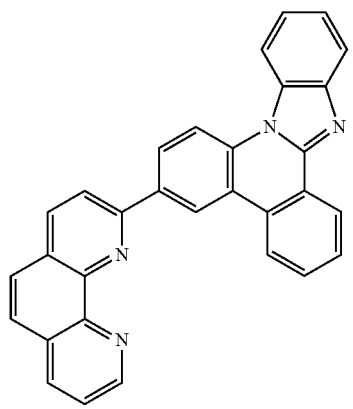 [SMILES: c1cnc2c(c1)ccc1ccc(-c3ccc4c(c3)c3ccccc3c3nc5ccccc5n43)nc12]
1-a-31 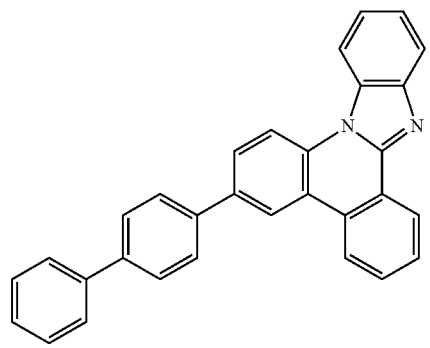 [SMILES: c1ccc(-c2ccc(-c3ccc4c(c3)c3ccccc3c3nc5ccccc5n43)cc2)cc1]

TABLE 1-continued
1-a-32
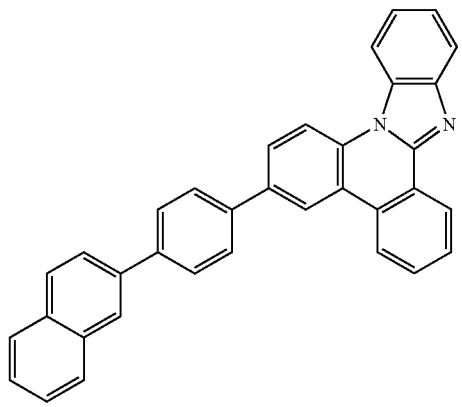 [SMILES: c1ccc2cc(-c3ccc(-c4ccc5c(c4)c4ccccc4c4nc6ccccc6n54)cc3)ccc2c1]
1-a-33
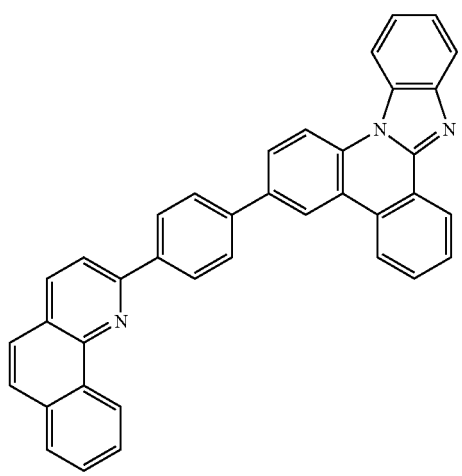 [SMILES: c1ccc2c(c1)ccc1ccc(-c3ccc(-c4ccc5c(c4)c4ccccc4c4nc6ccccc6n54)cc3)nc12]
1-a-34
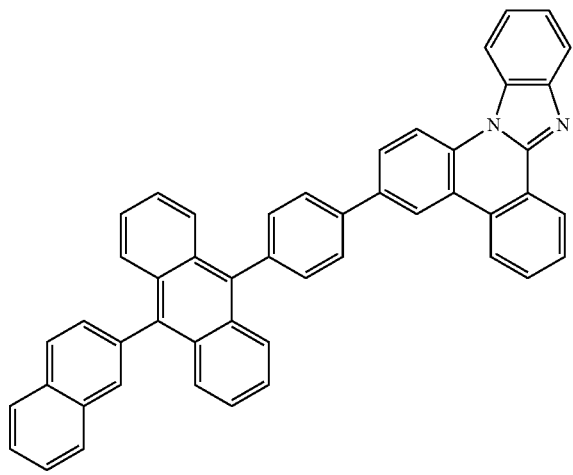 [SMILES: c1ccc2cc(-c3c4ccccc4c(-c4ccc(-c5ccc6c(c5)c5ccccc5c5nc7ccccc7n65)cc4)c4ccccc34)ccc2c1]

TABLE 1-continued
1-a-35
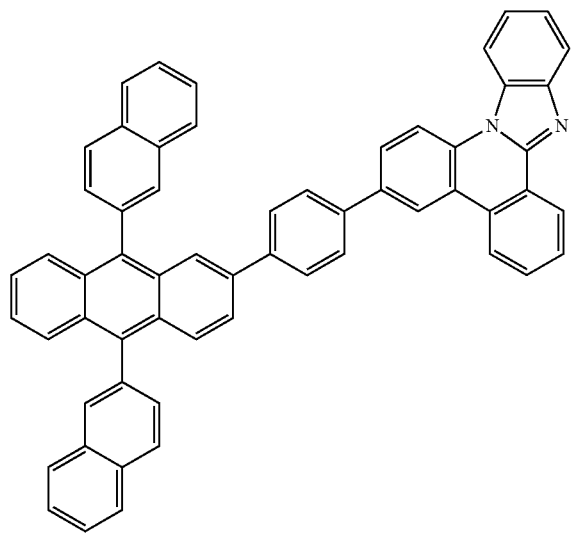 [SMILES: c1ccc2cc(-c3c4ccccc4c(-c4ccc5ccccc5c4)c4cc(-c5ccc(-c6ccc7c(c6)c6ccccc6c6nc8ccccc8n76)cc5)ccc34)ccc2c1]
1-a-36
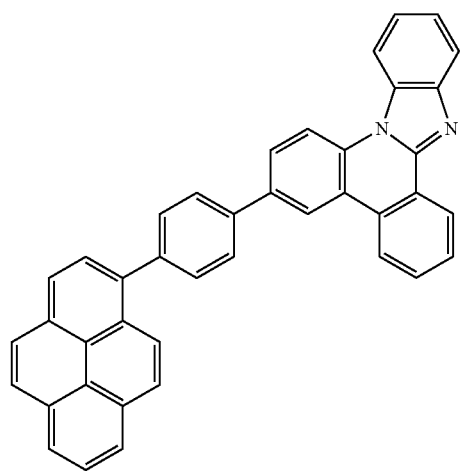 [SMILES: c1cc2ccc3ccc(-c4ccc(-c5ccc6c(c5)c5ccccc5c5nc7ccccc7n65)cc4)c4ccc(c1)c2c34]
1-a-37
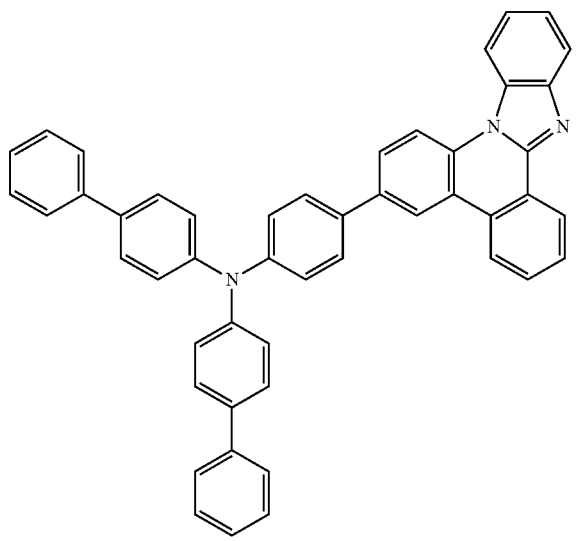 [SMILES: c1ccc(-c2ccc(N(c3ccc(-c4ccccc4)cc3)c3ccc(-c4ccc5c(c4)c4ccccc4c4nc6ccccc6n54)cc3)cc2)cc1]

TABLE 1-continued
1-a-38
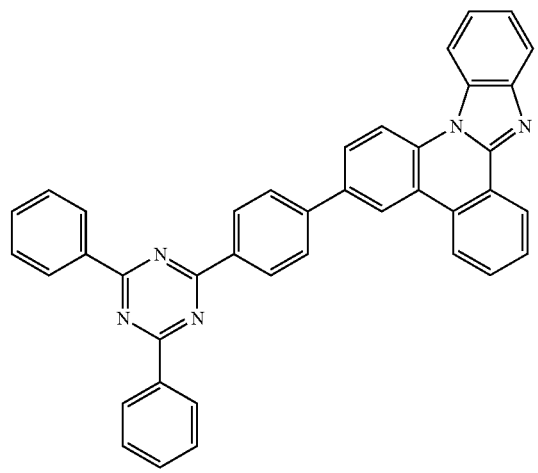 [SMILES: c1ccc(-c2nc(-c3ccccc3)nc(-c3ccc(-c4ccc5c(c4)c4ccccc4c4nc6ccccc6n54)cc3)n2)cc1]
1-a-39
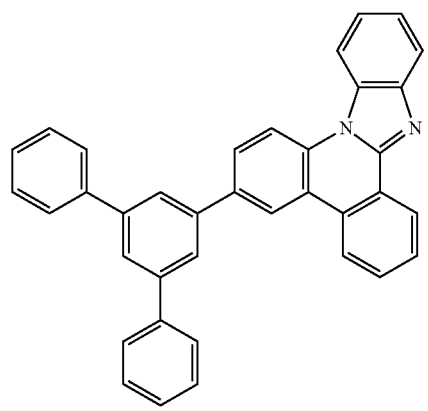 [SMILES: c1ccc(-c2cc(-c3ccccc3)cc(-c3ccc4c(c3)c3ccccc3c3nc5ccccc5n43)c2)cc1]
1-a-40
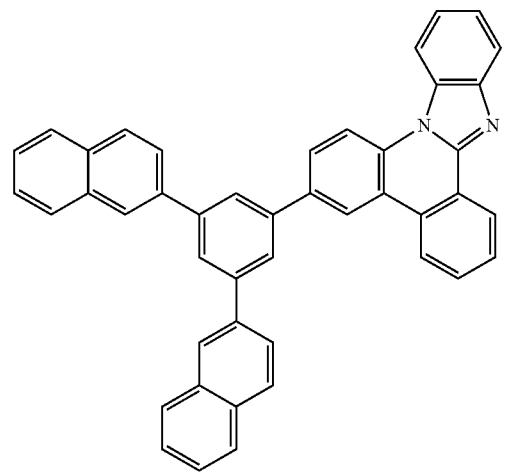 [SMILES: c1ccc2cc(-c3cc(-c4ccc5ccccc5c4)cc(-c4ccc5c(c4)c4ccccc4c4nc6ccccc6n54)c3)ccc2c1]

TABLE 1-continued
1-a-41 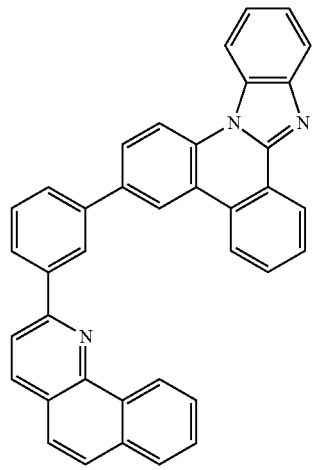 [SMILES: c1cc(-c2ccc3c(c2)c2ccccc2c2nc4ccccc4n32)cc(-c2ccc3ccc4ccccc4c3n2)c1]
1-a-42 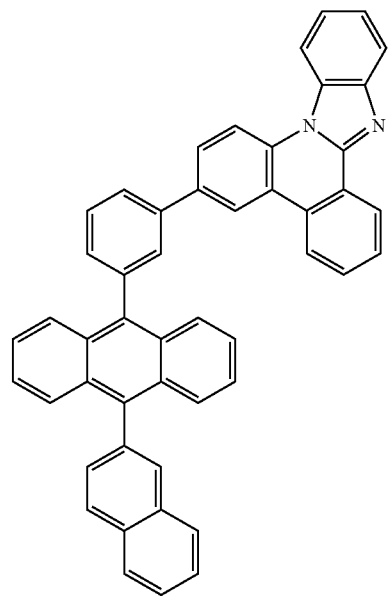 [SMILES: c1cc(-c2ccc3c(c2)c2ccccc2c2nc4ccccc4n32)cc(-c2c3ccccc3c(-c3ccc4ccccc4c3)c3ccccc23)c1]
1-a-43 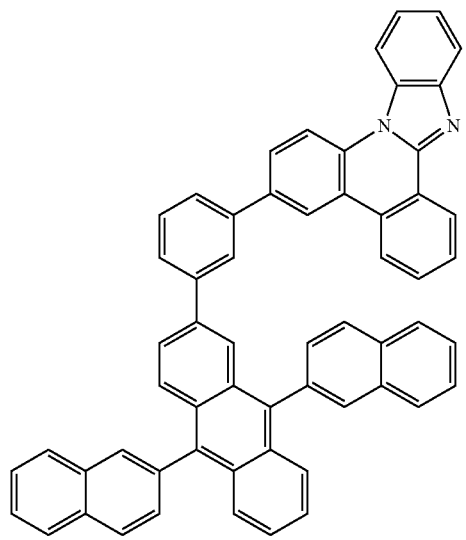 [SMILES: c1cc(-c2ccc3c(-c4ccc5ccccc5c4)c4ccccc4c(-c4ccc5ccccc5c4)c3c2)cc(-c2ccc3c(c2)c2ccccc2c2nc4ccccc4n32)c1]

TABLE 1-continued
1-a-44
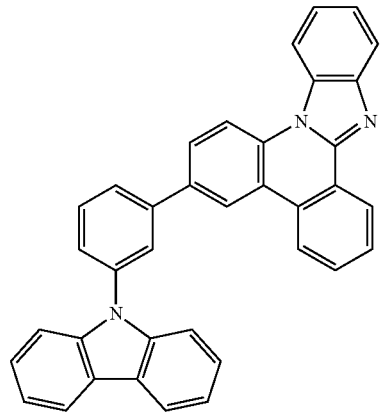 [SMILES: c1cc(-c2ccc3c(c2)c2ccccc2c2nc4ccccc4n32)cc(-n2c3ccccc3c3ccccc32)c1]
1-a-45
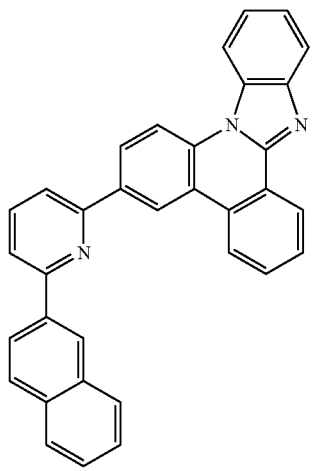 [SMILES: c1cc(-c2ccc3ccccc3c2)nc(-c2ccc3c(c2)c2ccccc2c2nc4ccccc4n32)c1]
1-a-46
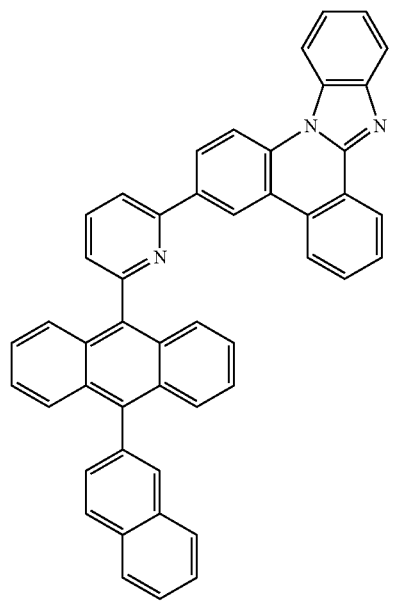 [SMILES: c1cc(-c2ccc3c(c2)c2ccccc2c2nc4ccccc4n32)nc(-c2c3ccccc3c(-c3ccc4ccccc4c3)c3ccccc23)c1]

TABLE 1-continued
1-a-47
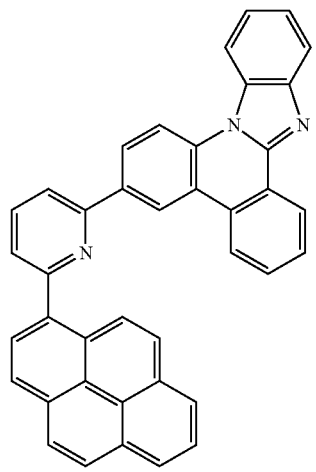 [SMILES: c1cc(-c2ccc3c(c2)c2ccccc2c2nc4ccccc4n32)nc(-c2ccc3ccc4cccc5ccc2c3c45)c1]
1-a-48
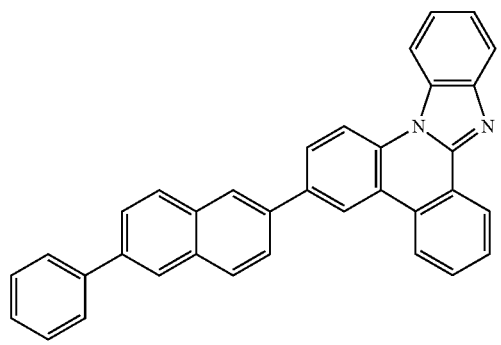 [SMILES: c1ccc(-c2ccc3cc(-c4ccc5c(c4)c4ccccc4c4nc6ccccc6n54)ccc3c2)cc1]
1-a-49
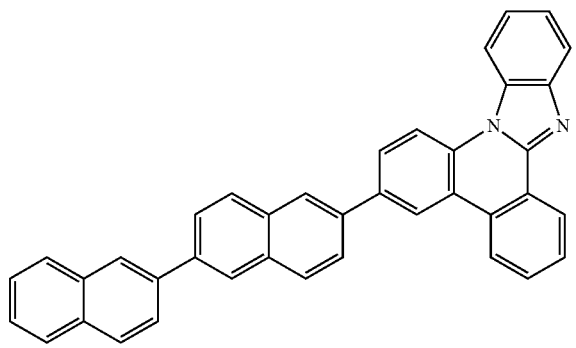 [SMILES: c1ccc2cc(-c3ccc4cc(-c5ccc6c(c5)c5ccccc5c5nc7ccccc7n65)ccc4c3)ccc2c1]
1-a-50
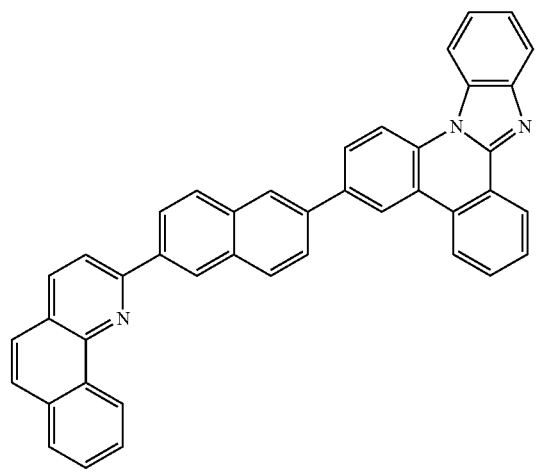 [SMILES: c1ccc2c(c1)ccc1ccc(-c3ccc4cc(-c5ccc6c(c5)c5ccccc5c5nc7ccccc7n65)ccc4c3)nc12]

TABLE 1-continued
1-a-51
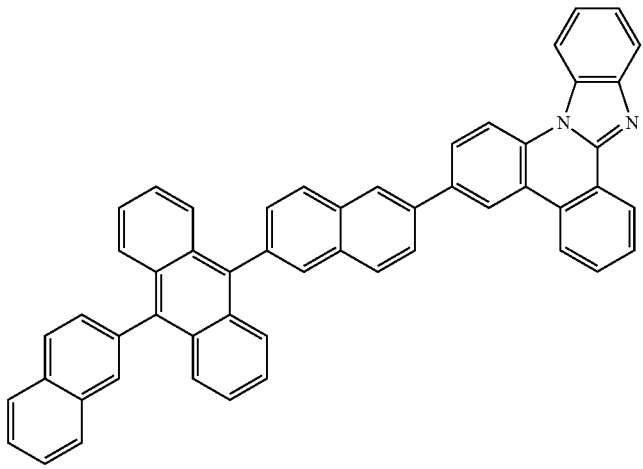 [SMILES: c1ccc2cc(-c3c4ccccc4c(-c4ccc5cc(-c6ccc7c(c6)c6ccccc6c6nc8ccccc8n76)ccc5c4)c4ccccc34)ccc2c1]
1-a-52
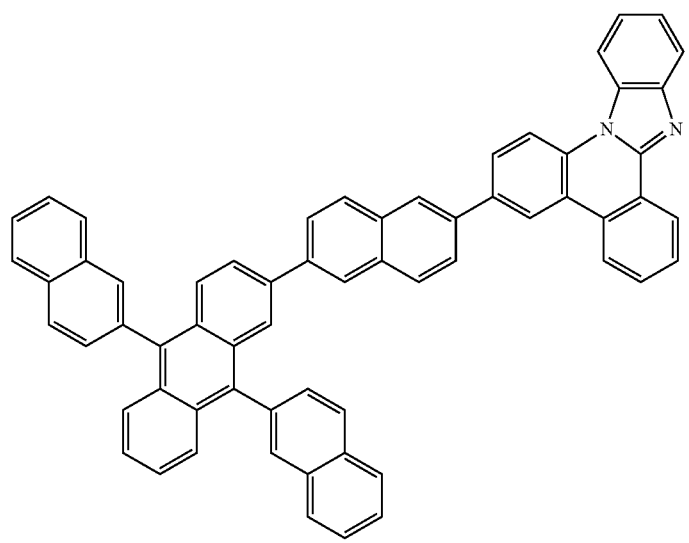 [SMILES: c1ccc2cc(-c3c4ccccc4c(-c4ccc5ccccc5c4)c4cc(-c5ccc6cc(-c7ccc8c(c7)c7ccccc7c7nc9ccccc9n87)ccc6c5)ccc34)ccc2c1]
1-a-53
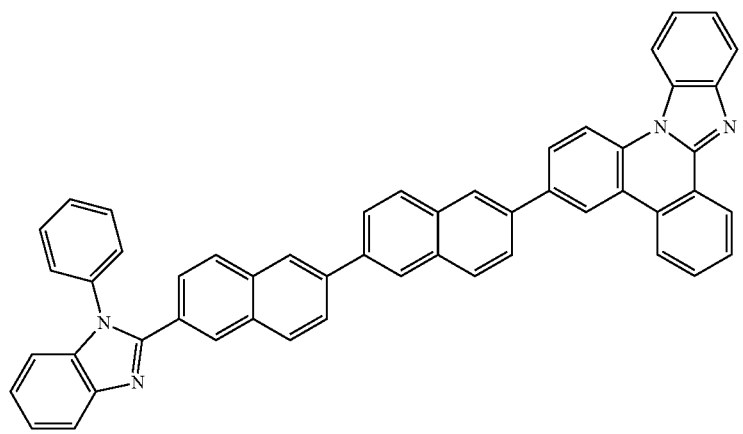 [SMILES: c1ccc(-n2c(-c3ccc4cc(-c5ccc6cc(-c7ccc8c(c7)c7ccccc7c7nc9ccccc9n87)ccc6c5)ccc4c3)nc3ccccc32)cc1]

TABLE 1-continued
1-a-54
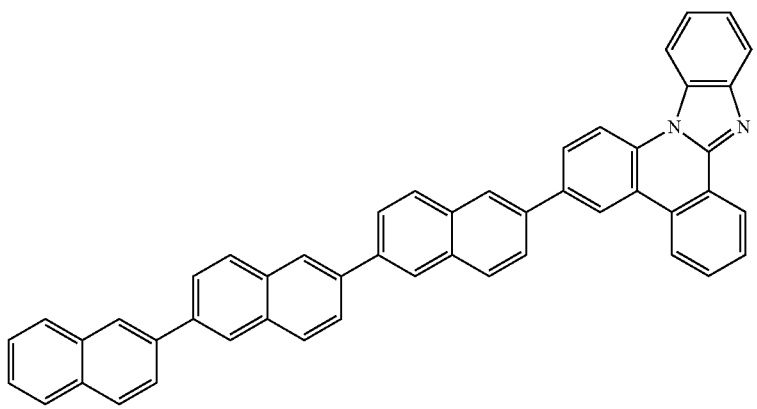 [SMILES: c1ccc2cc(-c3ccc4cc(-c5ccc6cc(-c7ccc8c(c7)c7ccccc7c7nc9ccccc9n87)ccc6c5)ccc4c3)ccc2c1]
1-a-55
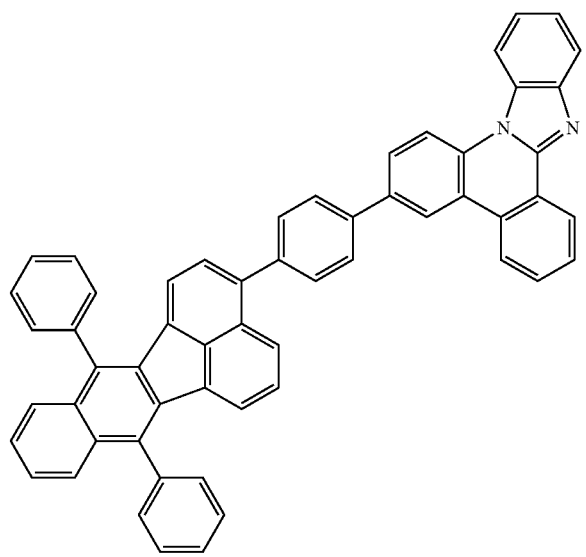 [SMILES: c1ccc(-c2c3c(c(-c4ccccc4)c4ccccc24)-c2ccc(-c4ccc(-c5ccc6c(c5)c5ccccc5c5nc7ccccc7n65)cc4)c4cccc-3c24)cc1]
1-a-56
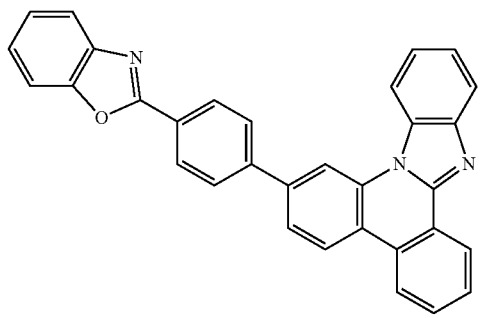 [SMILES: c1ccc2oc(-c3ccc(-c4ccc5c6ccccc6c6nc7ccccc7n6c5c4)cc3)nc2c1]
1-a-57
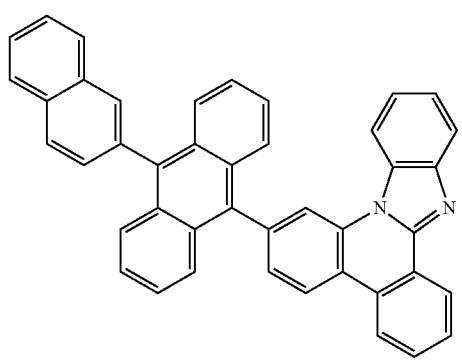 [SMILES: c1ccc2cc(-c3c4ccccc4c(-c4ccc5c6ccccc6c6nc7ccccc7n6c5c4)c4ccccc34)ccc2c1]

TABLE 1-continued
1-a-58 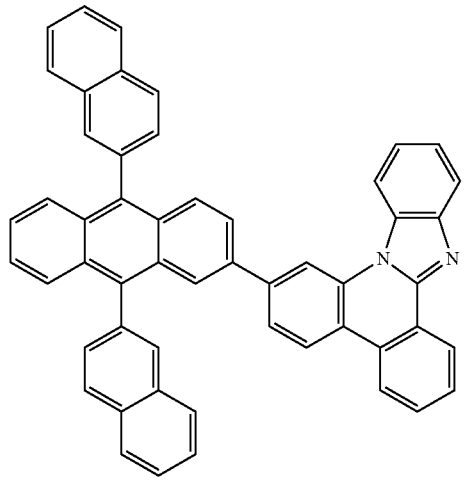 [SMILES: c1ccc2cc(-c3c4ccccc4c(-c4ccc5ccccc5c4)c4cc(-c5ccc6c7ccccc7c7nc8ccccc8n7c6c5)ccc34)ccc2c1]
1-a-59 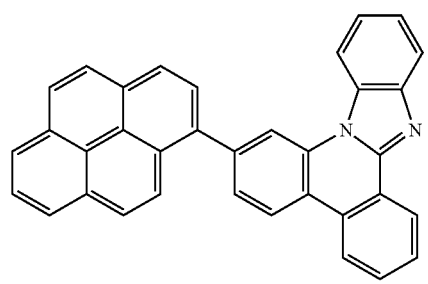 [SMILES: c1cc2ccc3ccc(-c4ccc5c6ccccc6c6nc7ccccc7n6c5c4)c4ccc(c1)c2c34]
1-a-60 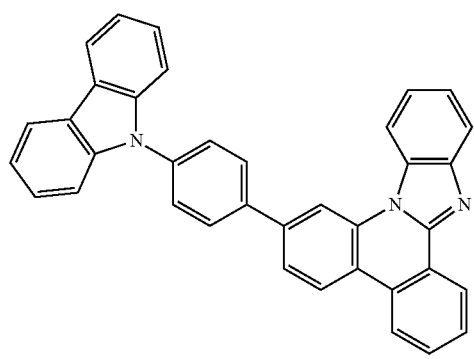 [SMILES: c1ccc2c(c1)nc1c3ccccc3c3ccc(-c4ccc(-n5c6ccccc6c6ccccc65)cc4)cc3n21]
1-a-61 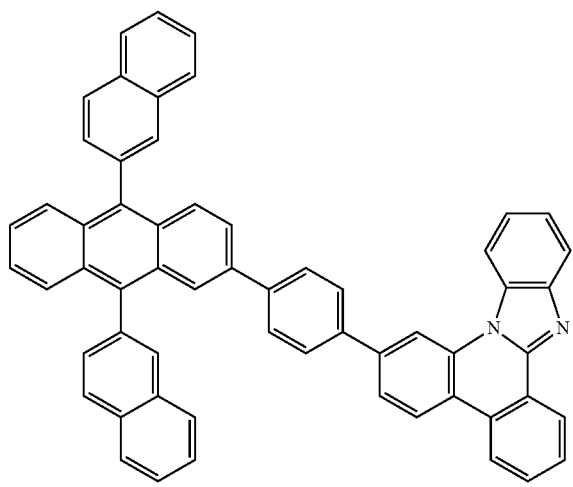 [SMILES: c1ccc2cc(-c3c4ccccc4c(-c4ccc5ccccc5c4)c4cc(-c5ccc(-c6ccc7c8ccccc8c8nc9ccccc9n8c7c6)cc5)ccc34)ccc2c1]

TABLE 1-continued
1-a-62
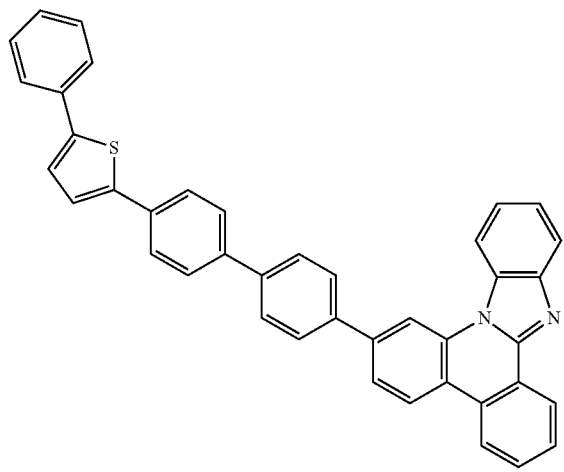 [SMILES: c1ccc(-c2ccc(-c3ccc(-c4ccc(-c5ccc6c7ccccc7c7nc8ccccc8n7c6c5)cc4)cc3)s2)cc1]
1-a-63
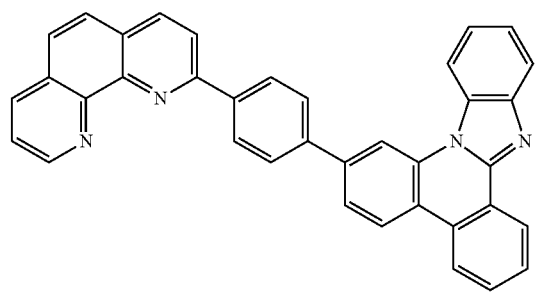 [SMILES: c1cnc2c(c1)ccc1ccc(-c3ccc(-c4ccc5c6ccccc6c6nc7ccccc7n6c5c4)cc3)nc12]
1-a-64
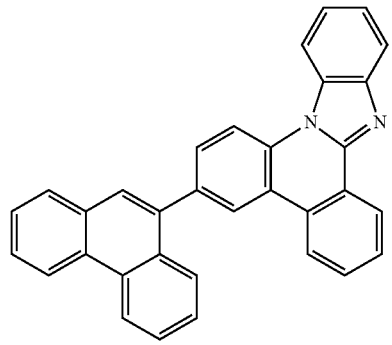 [SMILES: c1ccc2c(c1)cc(-c1ccc3c(c1)c1ccccc1c1nc4ccccc4n31)c1ccccc12]
1-a-65
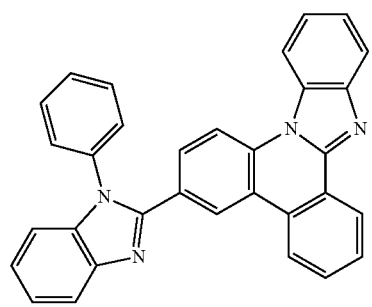 [SMILES: c1ccc(-n2c(-c3ccc4c(c3)c3ccccc3c3nc5ccccc5n43)nc3ccccc32)cc1]

TABLE 1-continued
1-a-66
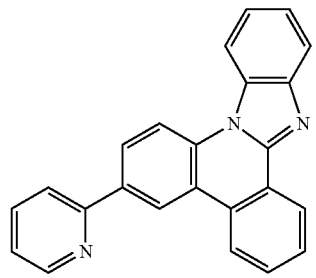 [SMILES: c1ccc(-c2ccc3c(c2)c2ccccc2c2nc4ccccc4n32)nc1]
1-a-67
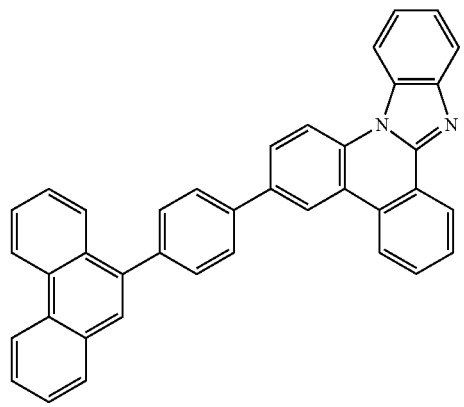 [SMILES: c1ccc2c(c1)cc(-c1ccc(-c3ccc4c(c3)c3ccccc3c3nc5ccccc5n43)cc1)c1ccccc12]
1-a-68
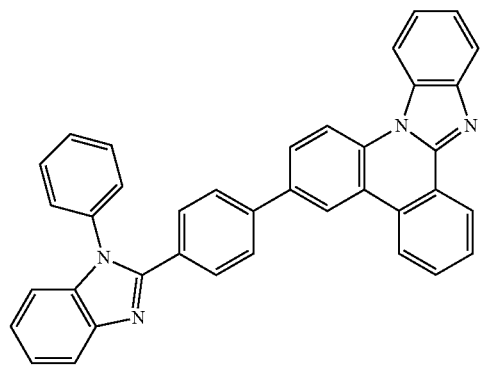 [SMILES: c1ccc(-n2c(-c3ccc(-c4ccc5c(c4)c4ccccc4c4nc6ccccc6n54)cc3)nc3ccccc32)cc1]
1-a-69
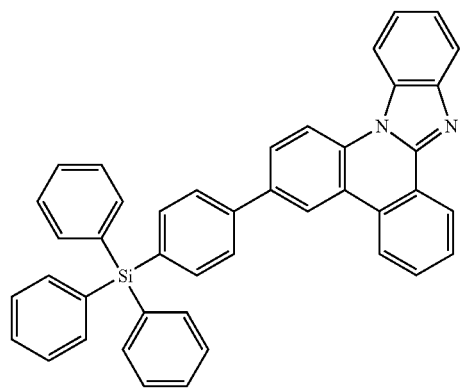 [SMILES: c1ccc([Si](c2ccccc2)(c2ccccc2)c2ccc(-c3ccc4c(c3)c3ccccc3c3nc5ccccc5n43)cc2)cc1]

TABLE 1-continued
1-a-70 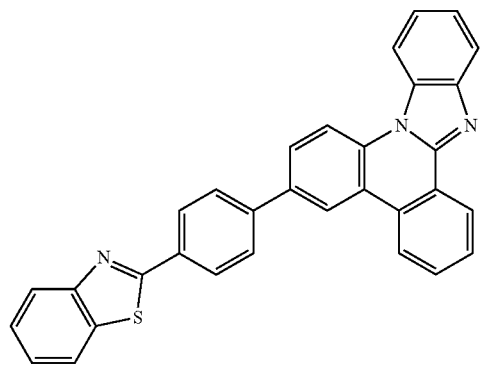 [SMILES: c1ccc2sc(-c3ccc(-c4ccc5c(c4)c4ccccc4c4nc6ccccc6n54)cc3)nc2c1]
1-a-71 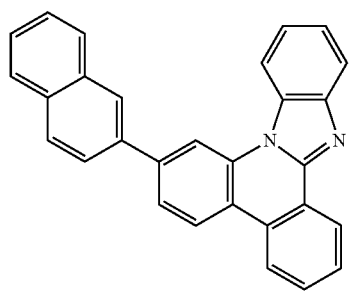 [SMILES: c1ccc2cc(-c3ccc4c5ccccc5c5nc6ccccc6n5c4c3)ccc2c1]
1-a-72 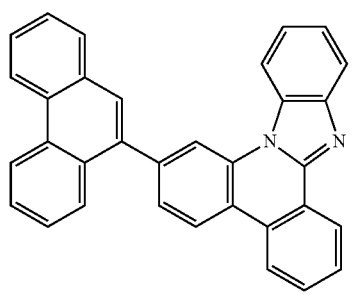 [SMILES: c1ccc2c(c1)cc(-c1ccc3c4ccccc4c4nc5ccccc5n4c3c1)c1ccccc12]
1-a-73 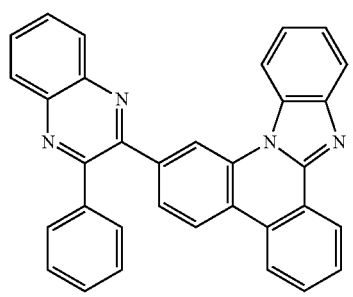 [SMILES: c1ccc(-c2nc3ccccc3nc2-c2ccc3c4ccccc4c4nc5ccccc5n4c3c2)cc1]
1-a-74 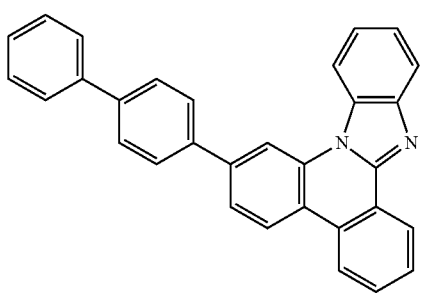 [SMILES: c1ccc(-c2ccc(-c3ccc4c5ccccc5c5nc6ccccc6n5c4c3)cc2)cc1]

TABLE 1-continued
1-a-75
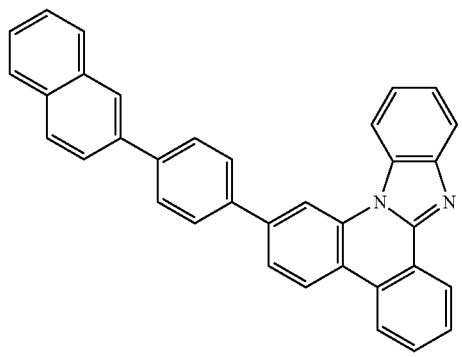 [SMILES: c1ccc2cc(-c3ccc(-c4ccc5c6ccccc6c6nc7ccccc7n6c5c4)cc3)ccc2c1]
1-a-76
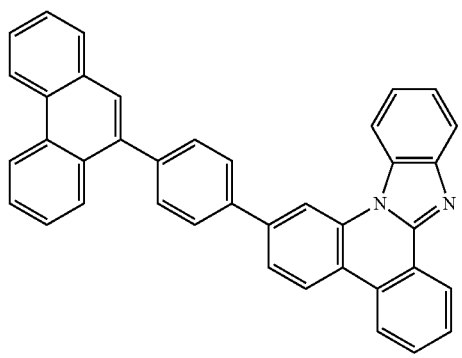 [SMILES: c1ccc2c(c1)cc(-c1ccc(-c3ccc4c5ccccc5c5nc6ccccc6n5c4c3)cc1)c1ccccc12]
1-a-77
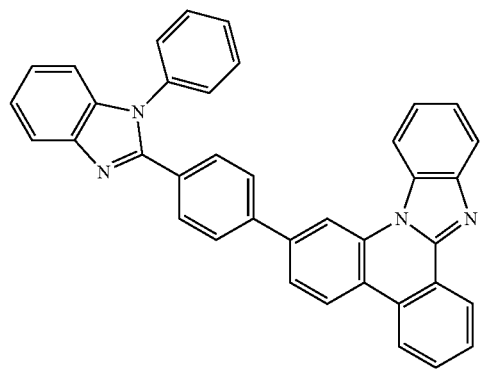 [SMILES: c1ccc(-n2c(-c3ccc(-c4ccc5c6ccccc6c6nc7ccccc7n6c5c4)cc3)nc3ccccc32)cc1]
1-a-78
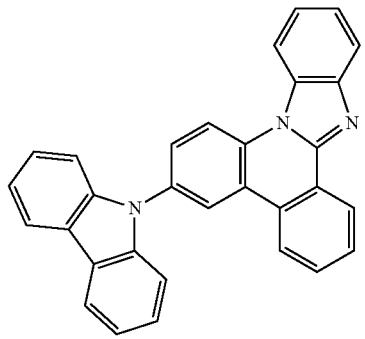 [SMILES: c1ccc2c(c1)nc1c3ccccc3c3cc(-n4c5ccccc5c5ccccc54)ccc3n21]

TABLE 1-continued
1-a-79
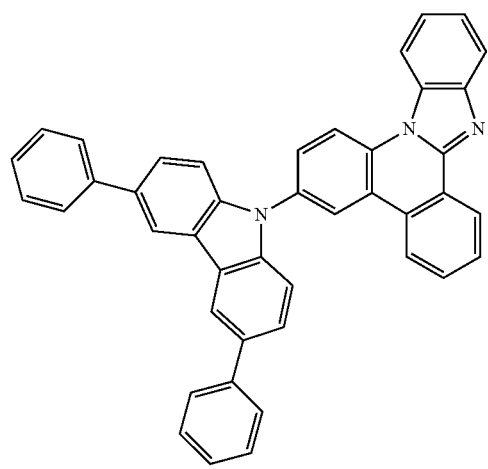 [SMILES: c1ccc(-c2ccc3c(c2)c2cc(-c4ccccc4)ccc2n3-c2ccc3c(c2)c2ccccc2c2nc4ccccc4n32)cc1]
1-a-80
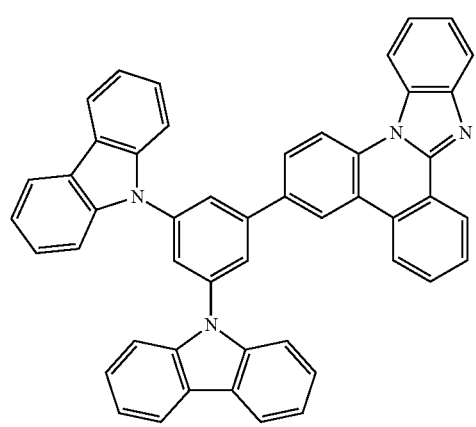 [SMILES: c1ccc2c(c1)nc1c3ccccc3c3cc(-c4cc(-n5c6ccccc6c6ccccc65)cc(-n5c6ccccc6c6ccccc65)c4)ccc3n21]
1-a-81
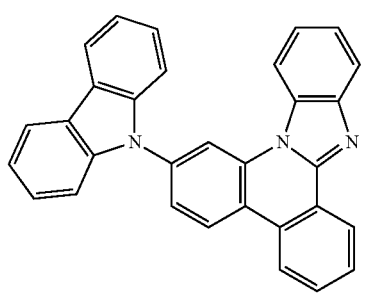 [SMILES: c1ccc2c(c1)nc1c3ccccc3c3ccc(-n4c5ccccc5c5ccccc54)cc3n21]
1-a-82
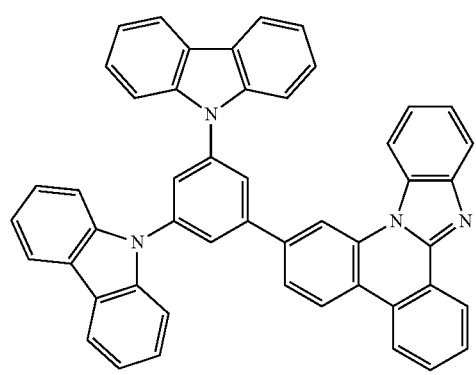 [SMILES: c1ccc2c(c1)nc1c3ccccc3c3ccc(-c4cc(-n5c6ccccc6c6ccccc65)cc(-n5c6ccccc6c6ccccc65)c4)cc3n21]

TABLE 1-continued
1-a-83 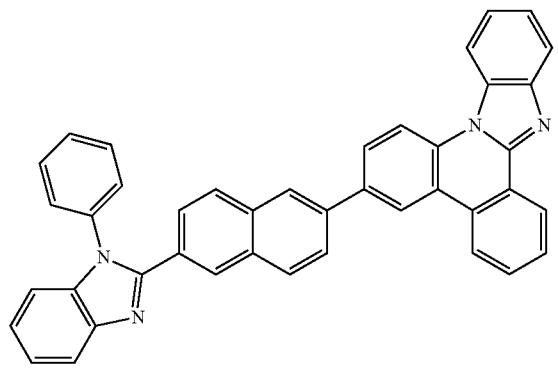 [SMILES: c1ccc(-n2c(-c3ccc4cc(-c5ccc6c(c5)c5ccccc5c5nc7ccccc7n65)ccc4c3)nc3ccccc32)cc1]
1-a-84 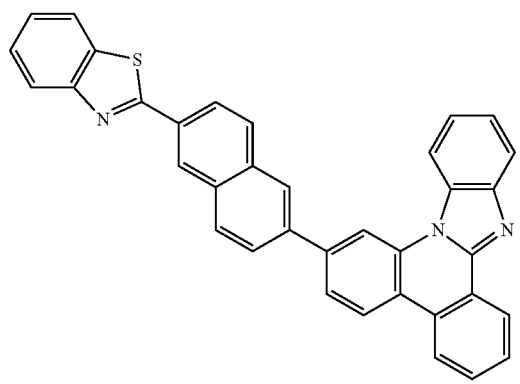 [SMILES: c1ccc2sc(-c3ccc4cc(-c5ccc6c7ccccc7c7nc8ccccc8n7c6c5)ccc4c3)nc2c1]
1-a-85 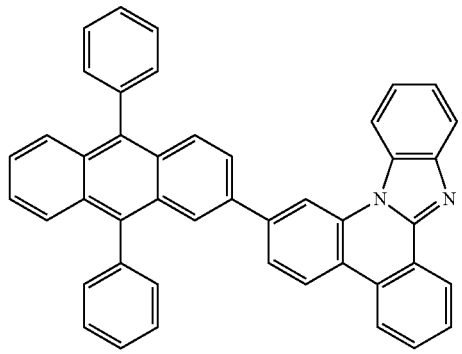 [SMILES: c1ccc(-c2c3ccccc3c(-c3ccccc3)c3cc(-c4ccc5c6ccccc6c6nc7ccccc7n6c5c4)ccc23)cc1]
1-a-86 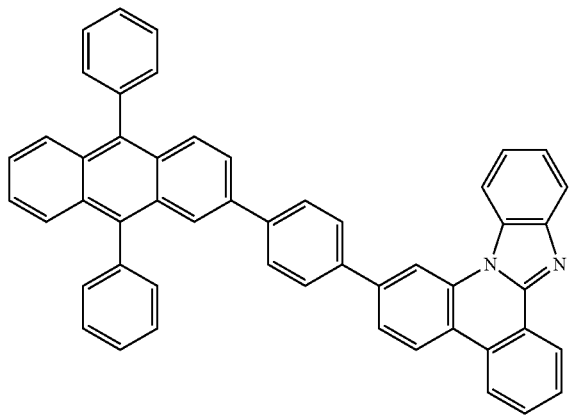 [SMILES: c1ccc(-c2c3ccccc3c(-c3ccccc3)c3cc(-c4ccc(-c5ccc6c7ccccc7c7nc8ccccc8n7c6c5)cc4)ccc23)cc1]

TABLE 1-continued
1-a-87
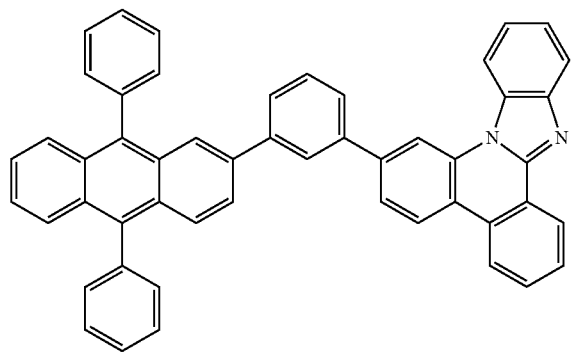 [SMILES: c1ccc(-c2c3ccccc3c(-c3ccccc3)c3cc(-c4cccc(-c5ccc6c7ccccc7c7nc8ccccc8n7c6c5)c4)ccc23)cc1]
1-a-88
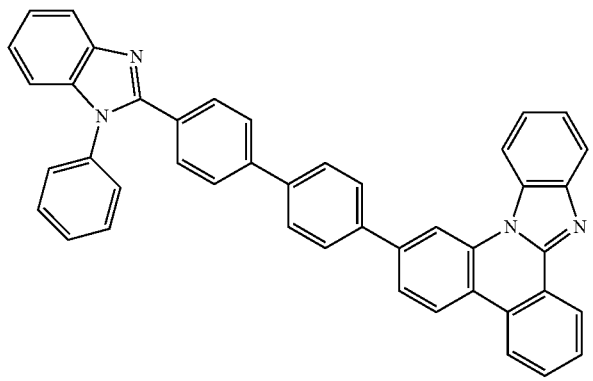 [SMILES: c1ccc(-n2c(-c3ccc(-c4ccc(-c5ccc6c7ccccc7c7nc8ccccc8n7c6c5)cc4)cc3)nc3ccccc32)cc1]
1-a-89
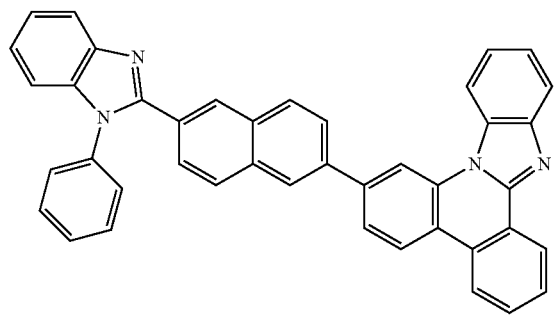 [SMILES: c1ccc(-n2c(-c3ccc4cc(-c5ccc6c7ccccc7c7nc8ccccc8n7c6c5)ccc4c3)nc3ccccc32)cc1]
1-a-90
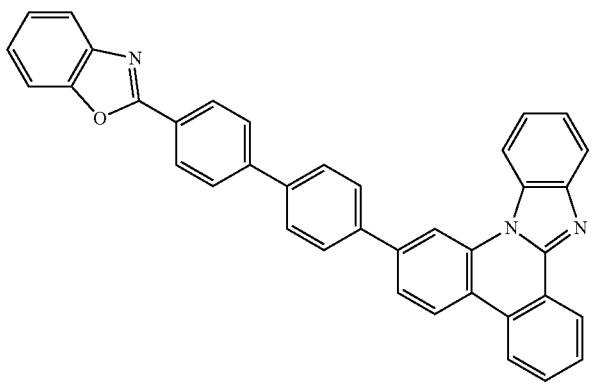 [SMILES: c1ccc2oc(-c3ccc(-c4ccc(-c5ccc6c7ccccc7c7nc8ccccc8n7c6c5)cc4)cc3)nc2c1]

TABLE 1-continued
1-a-91
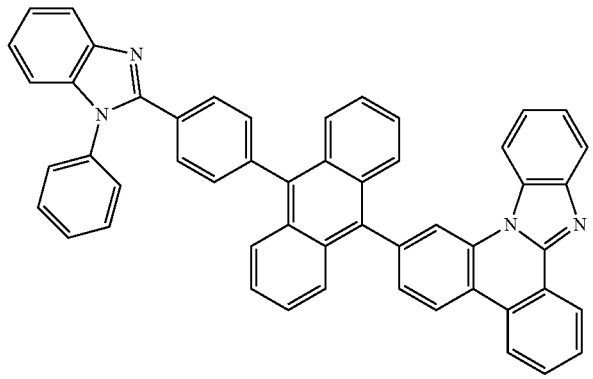 [SMILES: c1ccc(-n2c(-c3ccc(-c4c5ccccc5c(-c5ccc6c7ccccc7c7nc8ccccc8n7c6c5)c5ccccc45)cc3)nc3ccccc32)cc1]
1-a-92
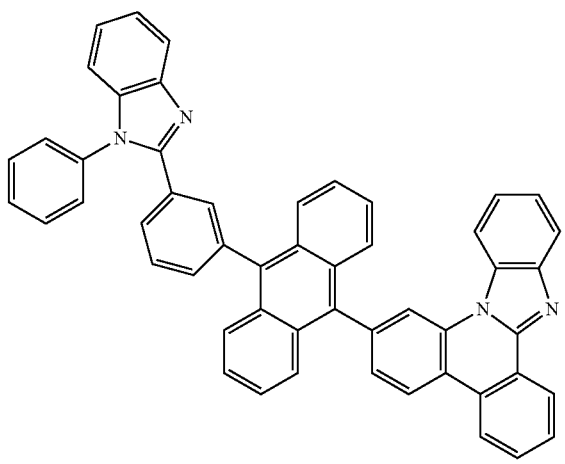 [SMILES: c1ccc(-n2c(-c3cccc(-c4c5ccccc5c(-c5ccc6c7ccccc7c7nc8ccccc8n7c6c5)c5ccccc45)c3)nc3ccccc32)cc1]
1-a-93
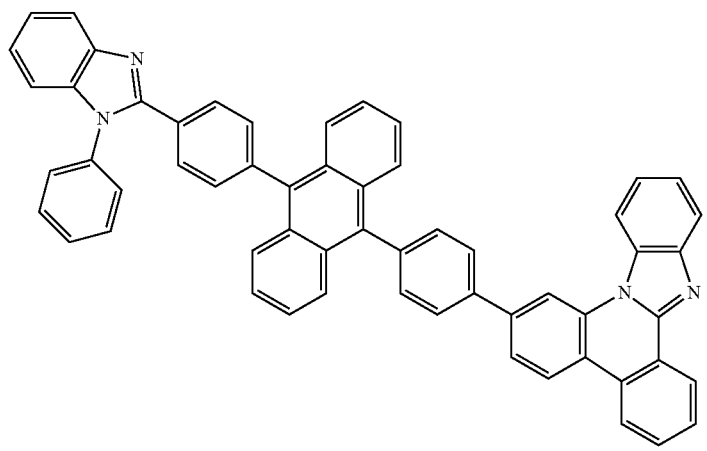 [SMILES: c1ccc(-n2c(-c3ccc(-c4c5ccccc5c(-c5ccc(-c6ccc7c8ccccc8c8nc9ccccc9n8c7c6)cc5)c5ccccc45)cc3)nc3ccccc32)cc1]
1-a-94
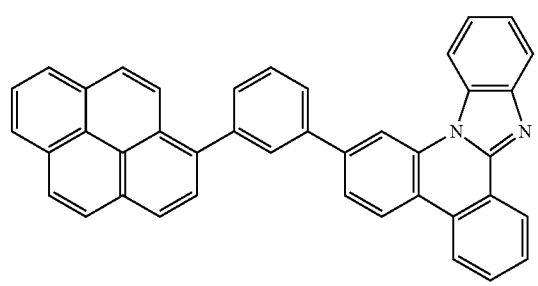 [SMILES: c1cc(-c2ccc3c4ccccc4c4nc5ccccc5n4c3c2)cc(-c2ccc3ccc4cccc5ccc2c3c45)c1]

TABLE 1-continued
1-a-95 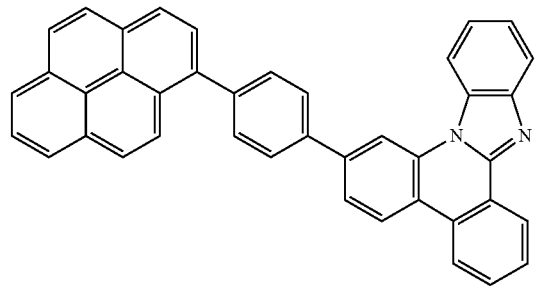 [SMILES: c1cc2ccc3ccc(-c4ccc(-c5ccc6c7ccccc7c7nc8ccccc8n7c6c5)cc4)c4ccc(c1)c2c34]
1-a-96 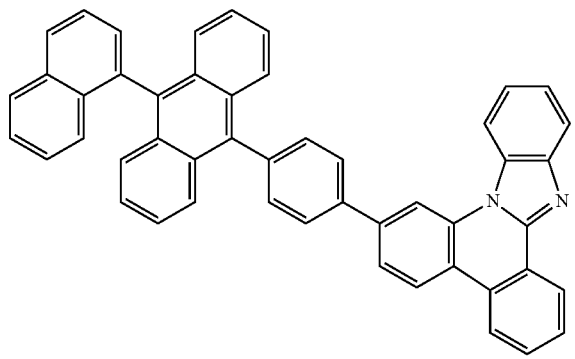 [SMILES: c1ccc2c(-c3c4ccccc4c(-c4ccc(-c5ccc6c7ccccc7c7nc8ccccc8n7c6c5)cc4)c4ccccc34)cccc2c1]
1-a-97 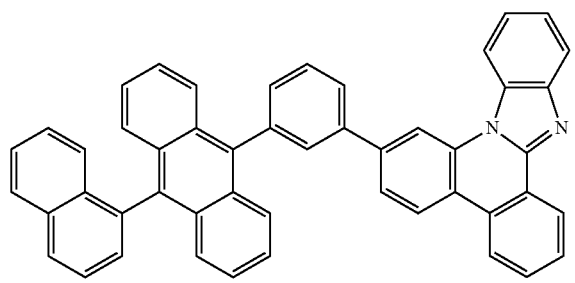 [SMILES: c1cc(-c2ccc3c4ccccc4c4nc5ccccc5n4c3c2)cc(-c2c3ccccc3c(-c3cccc4ccccc34)c3ccccc23)c1]
1-a-98 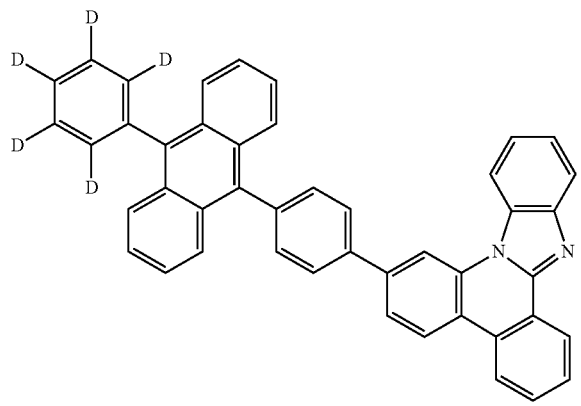 [SMILES: [2H]c1c([2H])c([2H])c(-c2c3ccccc3c(-c3ccc(-c4ccc5c6ccccc6c6nc7ccccc7n6c5c4)cc3)c3ccccc23)c([2H])c1[2H]]

TABLE 1-continued
1-a-99
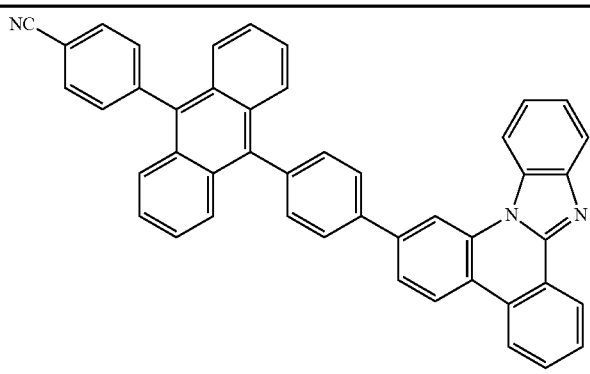
1-a-100
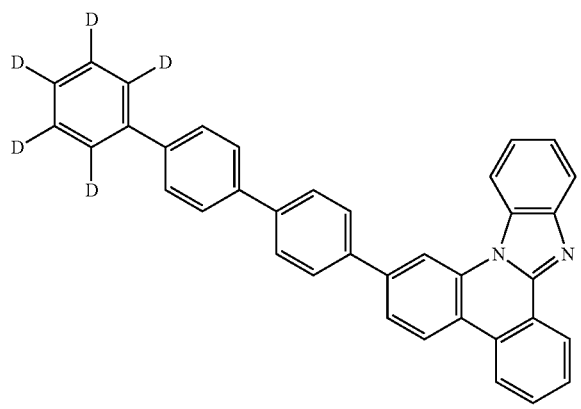 [SMILES: [2H]c1c([2H])c([2H])c(-c2ccc(-c3ccc(-c4ccc5c6ccccc6c6nc7ccccc7n6c5c4)cc3)cc2)c([2H])c1[2H]]
1-a-101
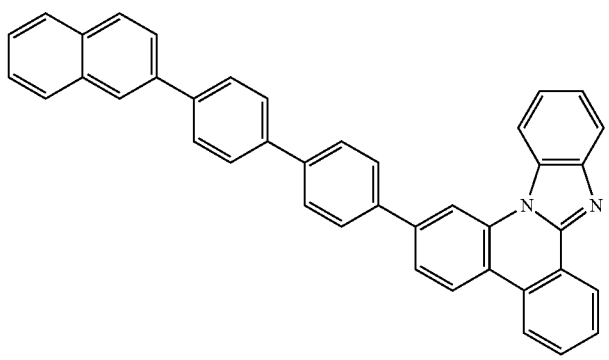 [SMILES: c1ccc2cc(-c3ccc(-c4ccc(-c5ccc6c7ccccc7c7nc8ccccc8n7c6c5)cc4)cc3)ccc2c1]
1-a-102
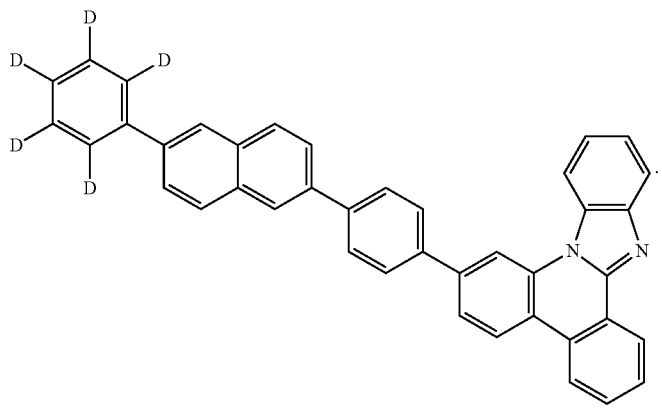 [SMILES: [2H]c1c([2H])c([2H])c(-c2ccc3cc(-c4ccc(-c5ccc6c7ccccc7c7nc8ccccc8n7c6c5)cc4)ccc3c2)c([2H])c1[2H]]
4. The nitrogen-containing heterocyclic derivative as set forth in claim 1, wherein the nitrogen-containing heterocyclic derivative is represented by one selected from formulas that are described in the following Table 2:

TABLE 2
| | |
|---|---|
| 1-b-1 | 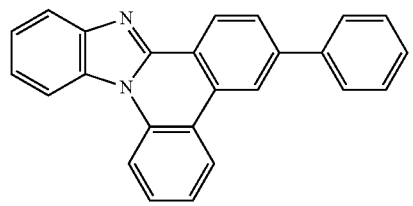 [SMILES: c1ccc(-c2ccc3c(c2)c2ccccc2n2c4ccccc4nc32)cc1] |
| 1-b-2 | 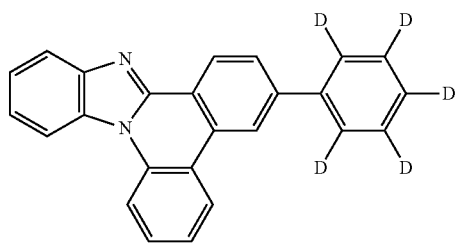 [SMILES: [2H]c1c([2H])c([2H])c(-c2ccc3c(c2)c2ccccc2n2c4ccccc4nc32)c([2H])c1[2H]] |
| 1-b-3 | 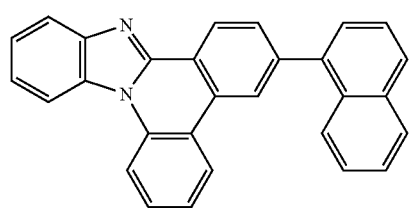 [SMILES: c1ccc2c(-c3ccc4c(c3)c3ccccc3n3c5ccccc5nc43)cccc2c1] |
| 1-b-4 | 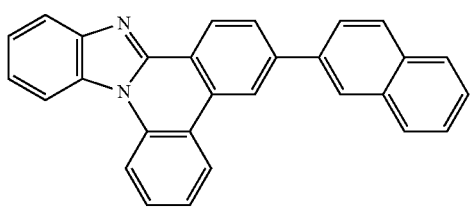 [SMILES: c1ccc2cc(-c3ccc4c(c3)c3ccccc3n3c5ccccc5nc43)ccc2c1] |
| 1-b-5 | 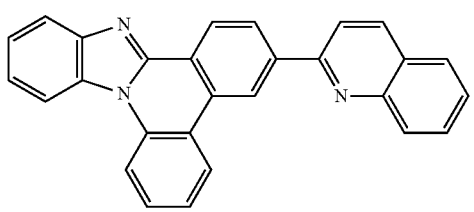 [SMILES: c1ccc2nc(-c3ccc4c(c3)c3ccccc3n3c5ccccc5nc43)ccc2c1] |
| 1-b-6 | 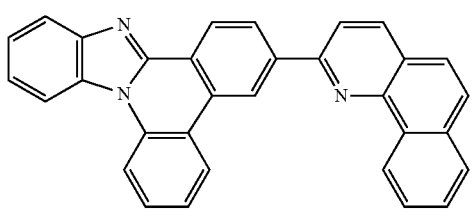 [SMILES: c1ccc2c(c1)ccc1ccc(-c3ccc4c(c3)c3ccccc3n3c5ccccc5nc43)nc12] |
| 1-b-7 | 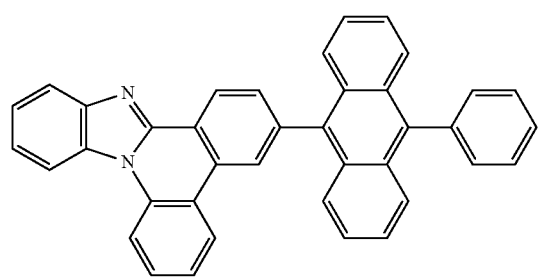 [SMILES: c1ccc(-c2c3ccccc3c(-c3ccc4c(c3)c3ccccc3n3c5ccccc5nc43)c3ccccc23)cc1] |

TABLE 2-continued
1-b-8
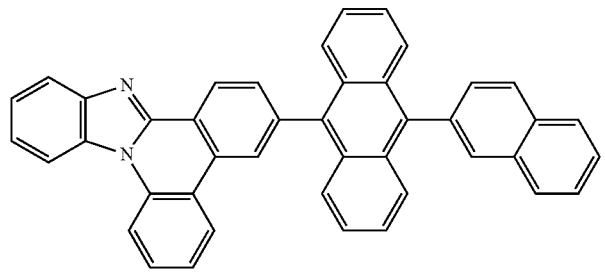 [SMILES: c1ccc2cc(-c3c4ccccc4c(-c4ccc5c(c4)c4ccccc4n4c6ccccc6nc54)c4ccccc34)ccc2c1]
1-b-9
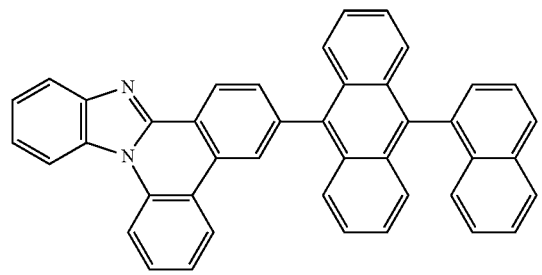 [SMILES: c1ccc2c(-c3c4ccccc4c(-c4ccc5c(c4)c4ccccc4n4c6ccccc6nc54)c4ccccc34)cccc2c1]
1-b-10
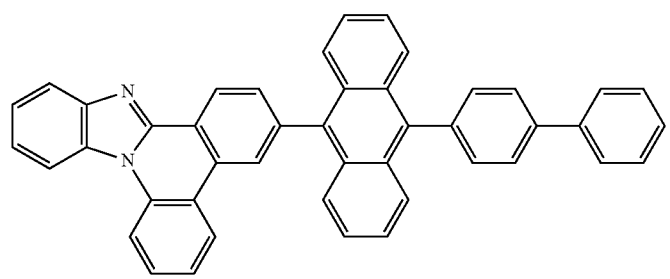 [SMILES: c1ccc(-c2ccc(-c3c4ccccc4c(-c4ccc5c(c4)c4ccccc4n4c6ccccc6nc54)c4ccccc34)cc2)cc1]
1-b-11
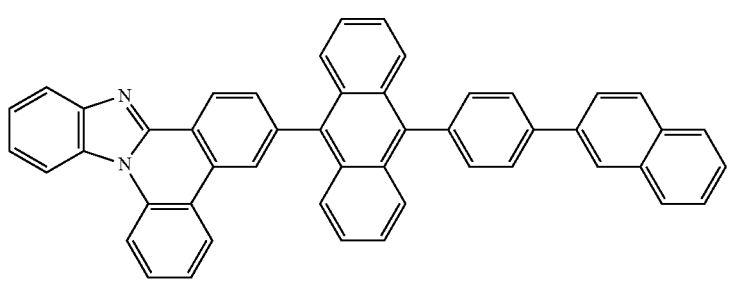 [SMILES: c1ccc2cc(-c3ccc(-c4c5ccccc5c(-c5ccc6c(c5)c5ccccc5n5c7ccccc7nc65)c5ccccc45)cc3)ccc2c1]
1-b-12
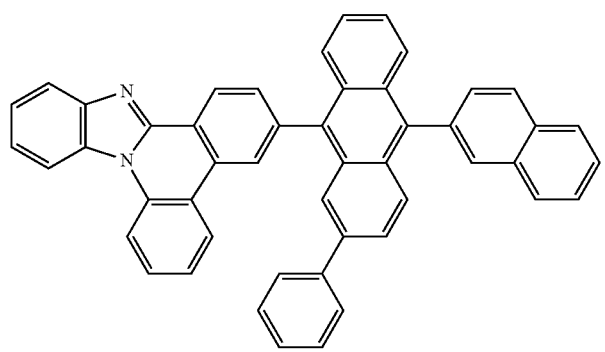 [SMILES: c1ccc(-c2ccc3c(-c4ccc5ccccc5c4)c4ccccc4c(-c4ccc5c(c4)c4ccccc4n4c6ccccc6nc54)c3c2)cc1]

TABLE 2-continued
1-b-13
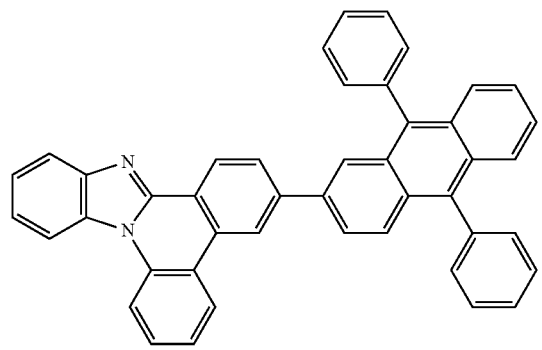 [SMILES: c1ccc(-c2c3ccccc3c(-c3ccccc3)c3cc(-c4ccc5c(c4)c4ccccc4n4c6ccccc6nc54)ccc23)cc1]
1-b-14
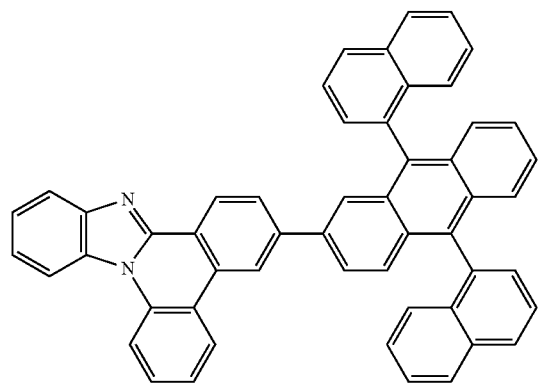 [SMILES: c1ccc2c(-c3c4ccccc4c(-c4cccc5ccccc45)c4cc(-c5ccc6c(c5)c5ccccc5n5c7ccccc7nc65)ccc34)cccc2c1]
1-b-15
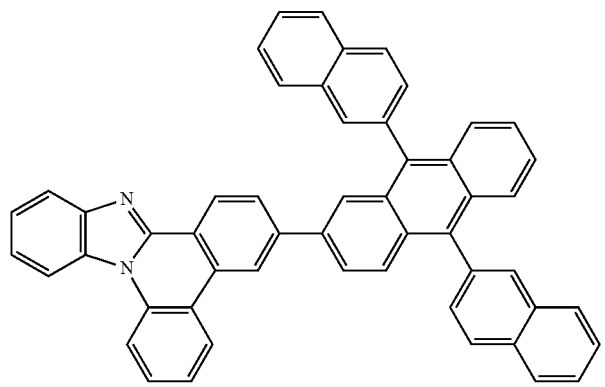 [SMILES: c1ccc2cc(-c3c4ccccc4c(-c4ccc5ccccc5c4)c4cc(-c5ccc6c(c5)c5ccccc5n5c7ccccc7nc65)ccc34)ccc2c1]
1-b-16
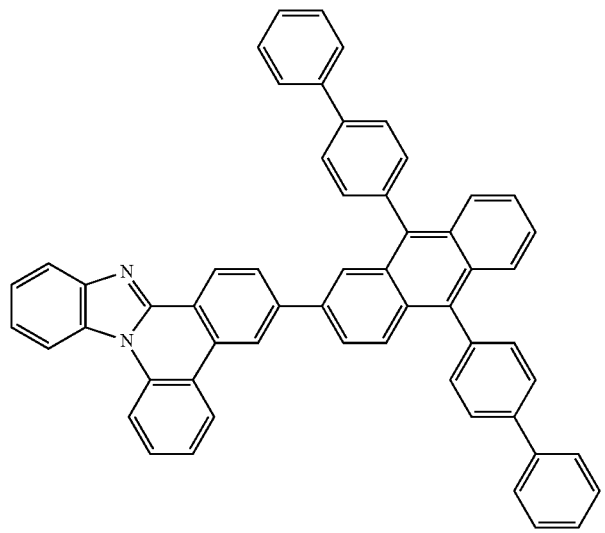 [SMILES: c1ccc(-c2ccc(-c3c4ccccc4c(-c4ccc(-c5ccccc5)cc4)c4cc(-c5ccc6c(c5)c5ccccc5n5c7ccccc7nc65)ccc34)cc2)cc1]

TABLE 2-continued
1-b-17
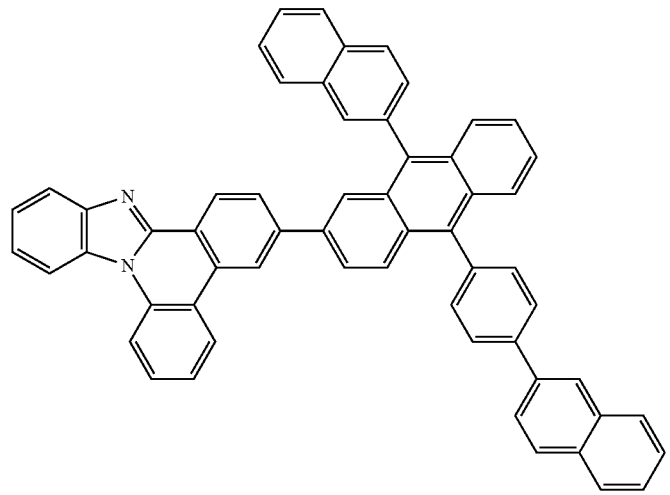 [SMILES: c1ccc2cc(-c3ccc(-c4c5ccccc5c(-c5ccc6ccccc6c5)c5cc(-c6ccc7c(c6)c6ccccc6n6c8ccccc8nc76)ccc45)cc3)ccc2c1]
1-b-18
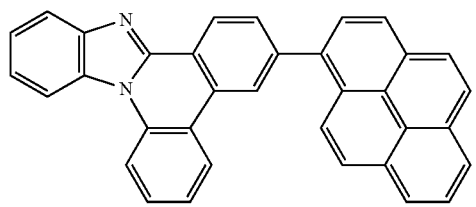 [SMILES: c1cc2ccc3ccc(-c4ccc5c(c4)c4ccccc4n4c6ccccc6nc54)c4ccc(c1)c2c34]
1-b-19
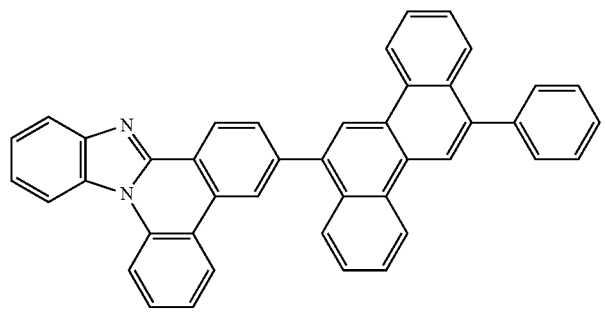 [SMILES: c1ccc(-c2cc3c4ccccc4c(-c4ccc5c(c4)c4ccccc4n4c6ccccc6nc54)cc3c3ccccc23)cc1]
1-b-20
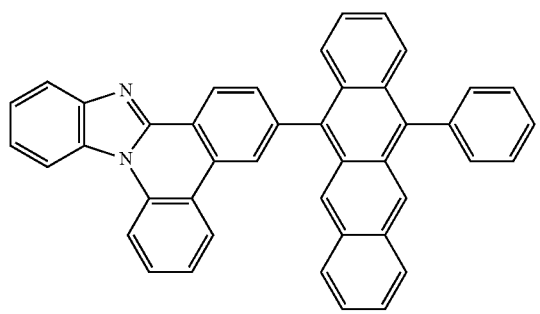 [SMILES: c1ccc(-c2c3ccccc3c(-c3ccc4c(c3)c3ccccc3n3c5ccccc5nc43)c3cc4ccccc4cc23)cc1]
1-b-21
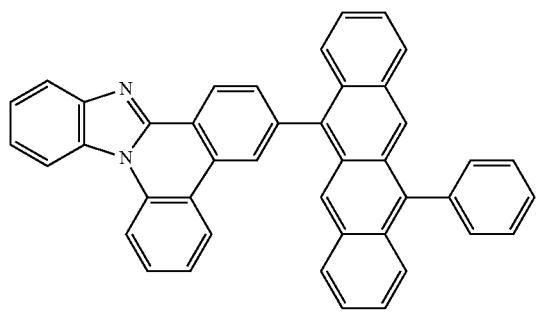 [SMILES: c1ccc(-c2c3ccccc3cc3c(-c4ccc5c(c4)c4ccccc4n4c6ccccc6nc54)c4ccccc4cc23)cc1]

TABLE 2-continued
1-b-22 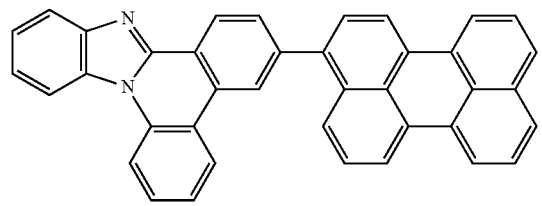 [SMILES: c1ccc2c(c1)nc1c3ccc(-c4ccc5c6cccc7cccc(c8cccc4c85)c76)cc3c3ccccc3n21]
1-b-23 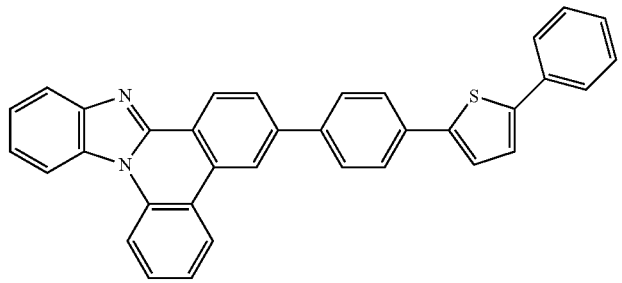 [SMILES: c1ccc(-c2ccc(-c3ccc(-c4ccc5c(c4)c4ccccc4n4c6ccccc6nc54)cc3)s2)cc1]
1-b-24 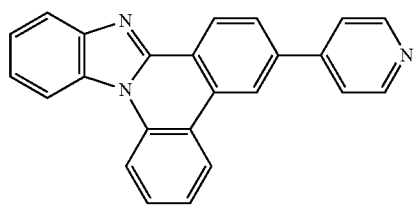 [SMILES: c1ccc2c(c1)nc1c3ccc(-c4ccncc4)cc3c3ccccc3n21]
1-b-25 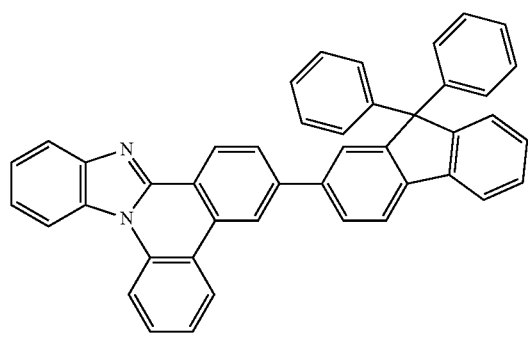 [SMILES: c1ccc(C2(c3ccccc3)c3ccccc3-c3ccc(-c4ccc5c(c4)c4ccccc4n4c6ccccc6nc54)cc32)cc1]
1-b-26 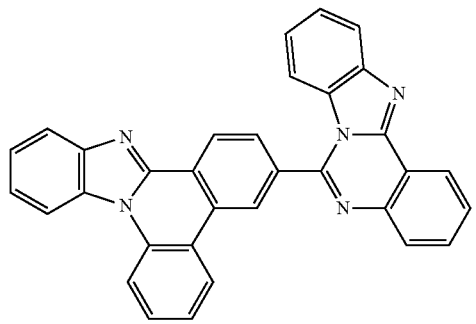 [SMILES: c1ccc2c(c1)nc(-c1ccc3c(c1)c1ccccc1n1c4ccccc4nc31)n1c3ccccc3nc21]
1-b-27 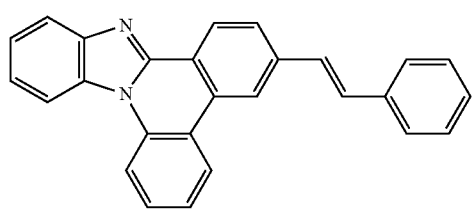 [SMILES: C(=C\c1ccc2c(c1)c1ccccc1n1c3ccccc3nc21)/c1ccccc1]

TABLE 2-continued
1-b-28
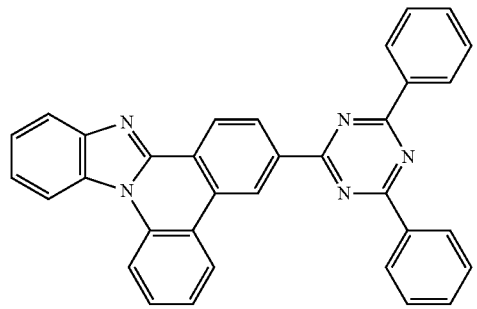 [SMILES: c1ccc(-c2nc(-c3ccccc3)nc(-c3ccc4c(c3)c3ccccc3n3c5ccccc5nc43)n2)cc1]
1-b-29
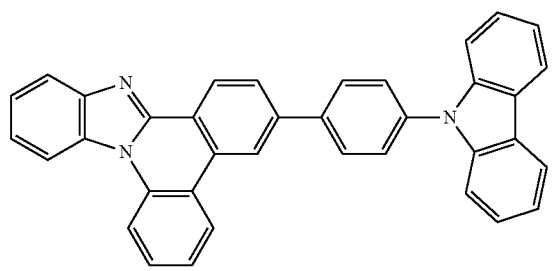 [SMILES: c1ccc2c(c1)nc1c3ccc(-c4ccc(-n5c6ccccc6c6ccccc65)cc4)cc3c3ccccc3n21]
1-b-30
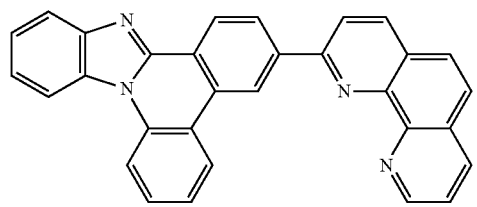 [SMILES: c1cnc2c(c1)ccc1ccc(-c3ccc4c(c3)c3ccccc3n3c5ccccc5nc43)nc12]
1-b-31
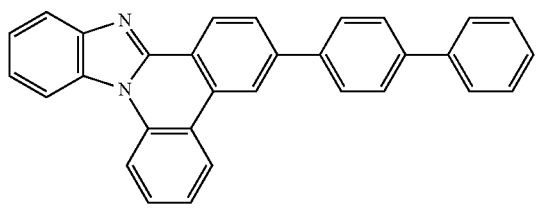 [SMILES: c1ccc(-c2ccc(-c3ccc4c(c3)c3ccccc3n3c5ccccc5nc43)cc2)cc1]
1-b-32
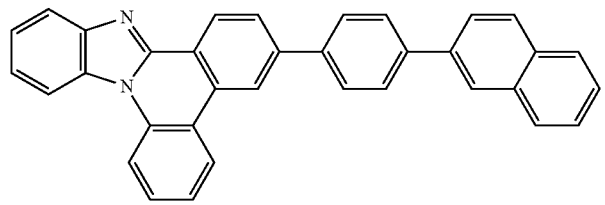 [SMILES: c1ccc2cc(-c3ccc(-c4ccc5c(c4)c4ccccc4n4c6ccccc6nc54)cc3)ccc2c1]
1-b-33
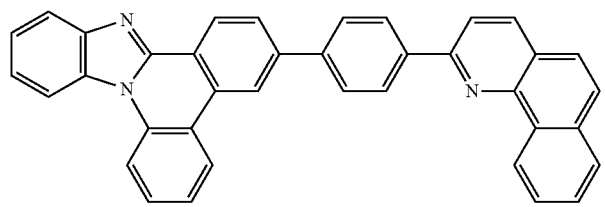 [SMILES: c1ccc2c(c1)ccc1ccc(-c3ccc(-c4ccc5c(c4)c4ccccc4n4c6ccccc6nc54)cc3)nc12]

TABLE 2-continued
1-b-34
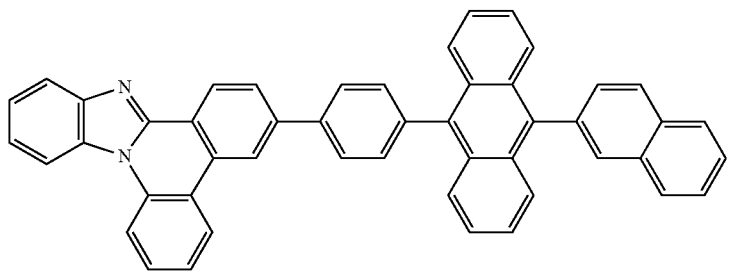 [SMILES: c1ccc2cc(-c3c4ccccc4c(-c4ccc(-c5ccc6c(c5)c5ccccc5n5c7ccccc7nc65)cc4)c4ccccc34)ccc2c1]
1-b-35
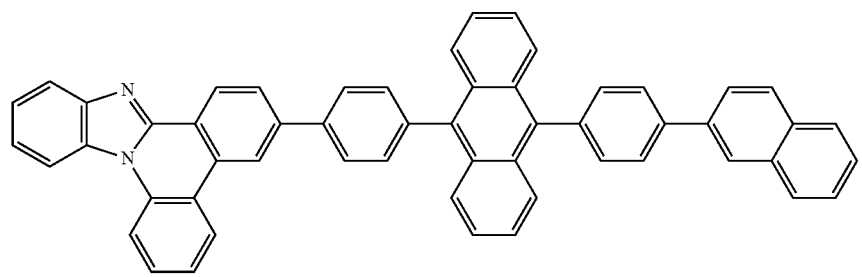 [SMILES: c1ccc2cc(-c3ccc(-c4c5ccccc5c(-c5ccc(-c6ccc7c(c6)c6ccccc6n6c8ccccc8nc76)cc5)c5ccccc45)cc3)ccc2c1]
1-b-36
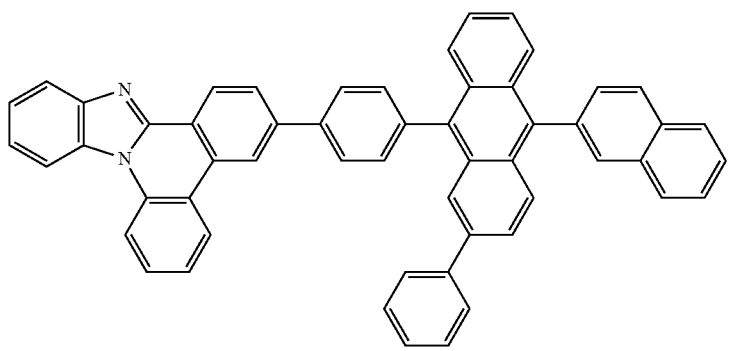 [SMILES: c1ccc(-c2ccc3c(-c4ccc5ccccc5c4)c4ccccc4c(-c4ccc(-c5ccc6c(c5)c5ccccc5n5c7ccccc7nc65)cc4)c3c2)cc1]
1-b-37
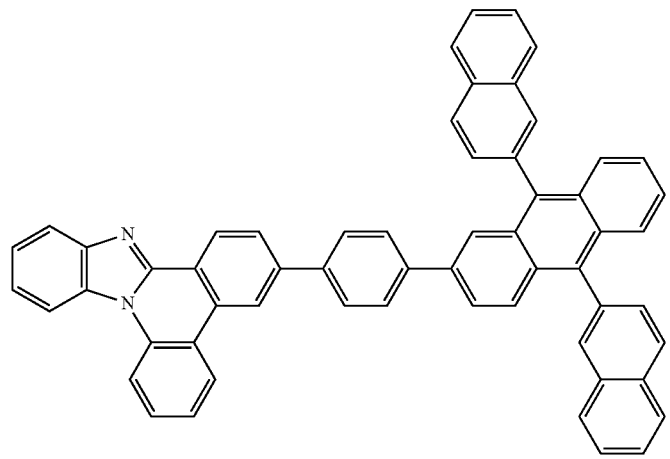 [SMILES: c1ccc2cc(-c3c4ccccc4c(-c4ccc5ccccc5c4)c4cc(-c5ccc(-c6ccc7c(c6)c6ccccc6n6c8ccccc8nc76)cc5)ccc34)ccc2c1]

TABLE 2-continued
1-b-38
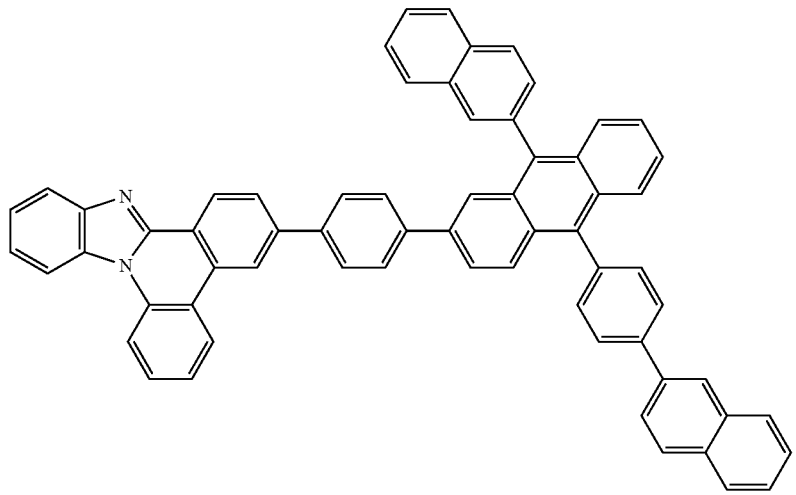 [SMILES: c1ccc2cc(-c3ccc(-c4c5ccccc5c(-c5ccc6ccccc6c5)c5cc(-c6ccc(-c7ccc8c(c7)c7ccccc7n7c9ccccc9nc87)cc6)ccc45)cc3)ccc2c1]
1-b-39
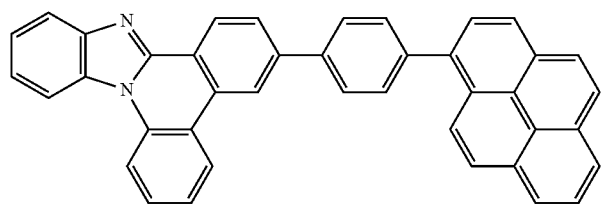 [SMILES: c1cc2ccc3ccc(-c4ccc(-c5ccc6c(c5)c5ccccc5n5c7ccccc7nc65)cc4)c4ccc(c1)c2c34]
1-b-40
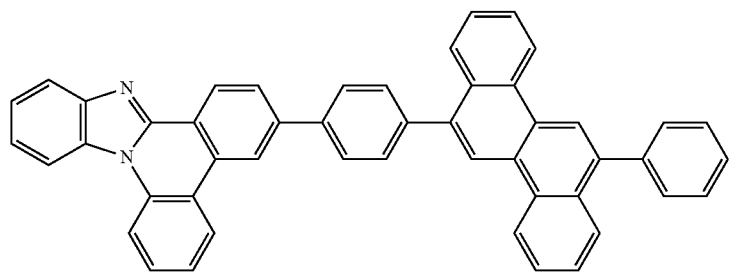 [SMILES: c1ccc(-c2cc3c4ccccc4c(-c4ccc(-c5ccc6c(c5)c5ccccc5n5c7ccccc7nc65)cc4)cc3c3ccccc23)cc1]
1-b-41
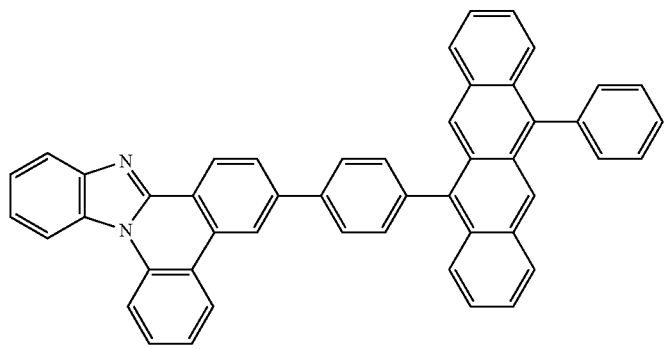 [SMILES: c1ccc(-c2c3ccccc3cc3c(-c4ccc(-c5ccc6c(c5)c5ccccc5n5c7ccccc7nc65)cc4)c4ccccc4cc23)cc1]
1-b-42
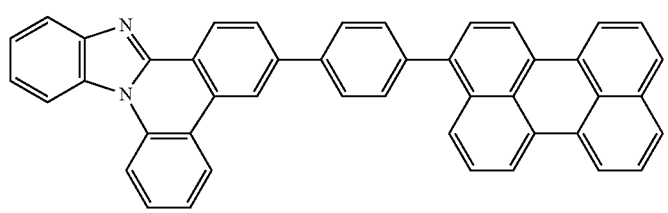 [SMILES: c1ccc2c(c1)nc1c3ccc(-c4ccc(-c5ccc6c7cccc8cccc(c9cccc5c96)c87)cc4)cc3c3ccccc3n21]

TABLE 2-continued
1-b-43
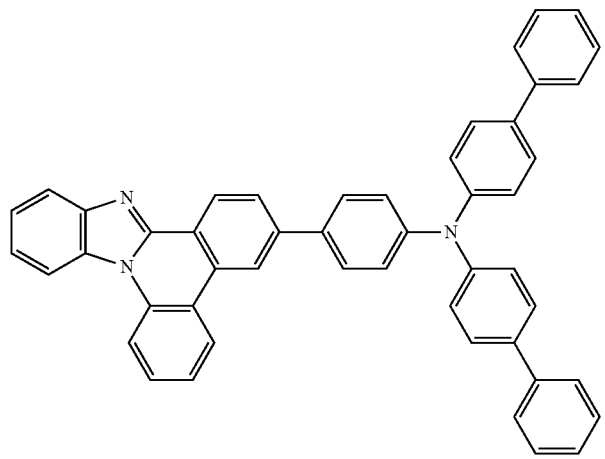 [SMILES: c1ccc(-c2ccc(N(c3ccc(-c4ccccc4)cc3)c3ccc(-c4ccc5c(c4)c4ccccc4n4c6ccccc6nc54)cc3)cc2)cc1]
1-b-44
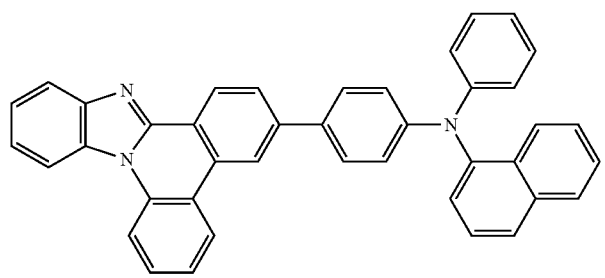 [SMILES: c1ccc(N(c2ccc(-c3ccc4c(c3)c3ccccc3n3c5ccccc5nc43)cc2)c2cccc3ccccc23)cc1]
1-b-45
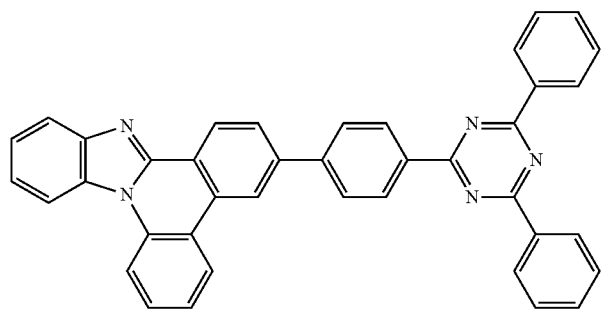 [SMILES: c1ccc(-c2nc(-c3ccccc3)nc(-c3ccc(-c4ccc5c(c4)c4ccccc4n4c6ccccc6nc54)cc3)n2)cc1]
1-b-46
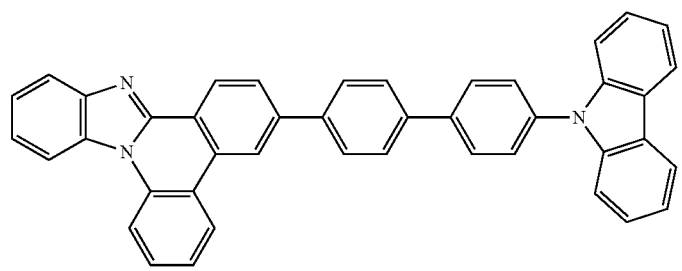 [SMILES: c1ccc2c(c1)nc1c3ccc(-c4ccc(-c5ccc(-n6c7ccccc7c7ccccc76)cc5)cc4)cc3c3ccccc3n21]
1-b-47
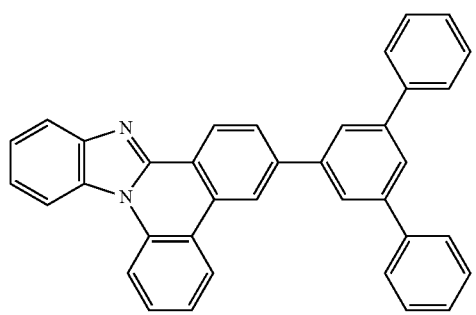 [SMILES: c1ccc(-c2cc(-c3ccccc3)cc(-c3ccc4c(c3)c3ccccc3n3c5ccccc5nc43)c2)cc1]

TABLE 2-continued
1-b-48
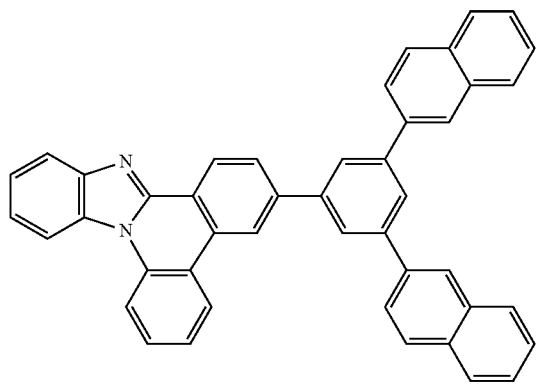 [SMILES: c1ccc2cc(-c3cc(-c4ccc5ccccc5c4)cc(-c4ccc5c(c4)c4ccccc4n4c6ccccc6nc54)c3)ccc2c1]
1-b-49
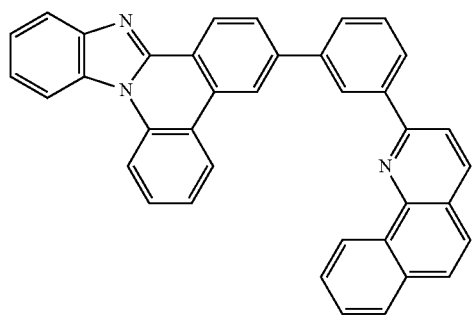 [SMILES: c1cc(-c2ccc3c(c2)c2ccccc2n2c4ccccc4nc32)cc(-c2ccc3ccc4ccccc4c3n2)c1]
1-b-50
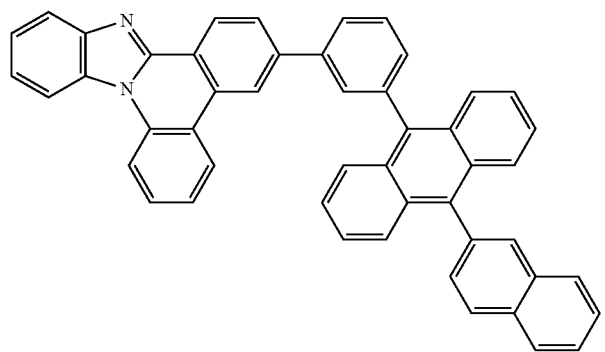 [SMILES: c1cc(-c2ccc3c(c2)c2ccccc2n2c4ccccc4nc32)cc(-c2c3ccccc3c(-c3ccc4ccccc4c3)c3ccccc23)c1]
1-b-51
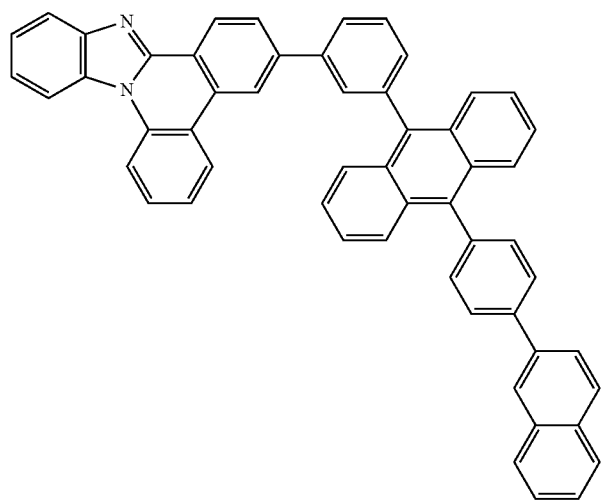 [SMILES: c1cc(-c2ccc3c(c2)c2ccccc2n2c4ccccc4nc32)cc(-c2c3ccccc3c(-c3ccc(-c4ccc5ccccc5c4)cc3)c3ccccc23)c1]

TABLE 2-continued
1-b-52
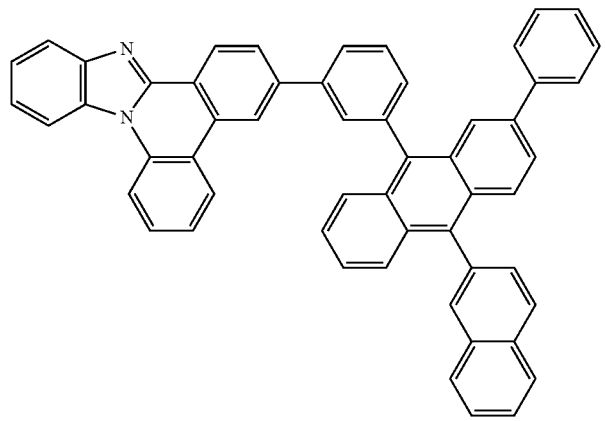 [SMILES: c1ccc(-c2ccc3c(-c4ccc5ccccc5c4)c4ccccc4c(-c4cccc(-c5ccc6c(c5)c5ccccc5n5c7ccccc7nc65)c4)c3c2)cc1]
1-b-53
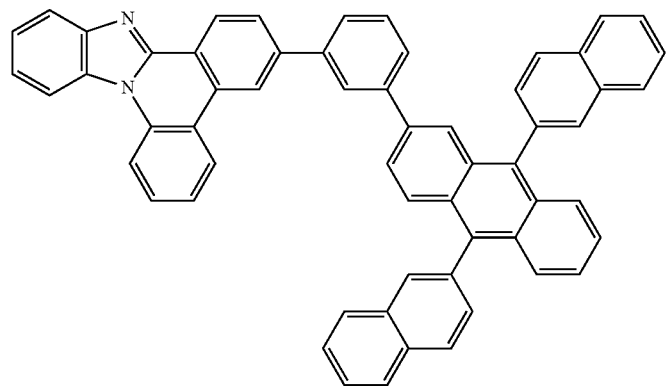 [SMILES: c1cc(-c2ccc3c(-c4ccc5ccccc5c4)c4ccccc4c(-c4ccc5ccccc5c4)c3c2)cc(-c2ccc3c(c2)c2ccccc2n2c4ccccc4nc32)c1]
1-b-54
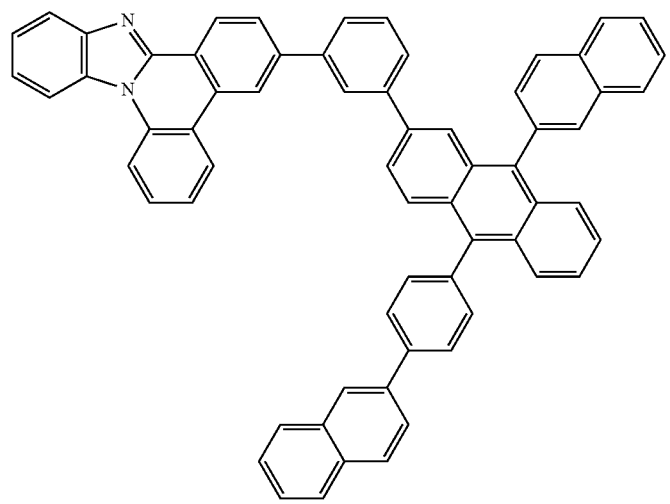
1-b-55
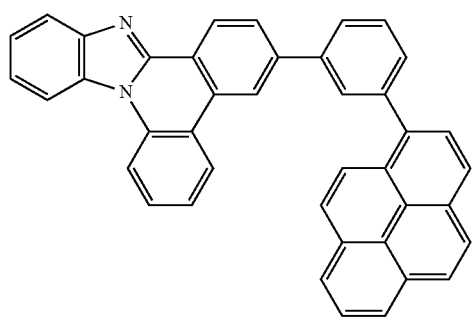

TABLE 2-continued
1-b-56
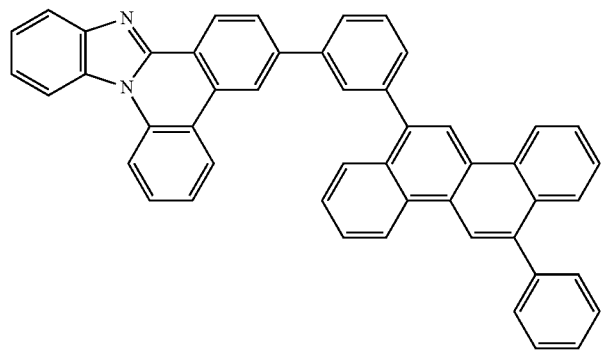 [SMILES: c1ccc(-c2cc3c4ccccc4c(-c4cccc(-c5ccc6c(c5)c5ccccc5n5c7ccccc7nc65)c4)cc3c3ccccc23)cc1]
1-b-57
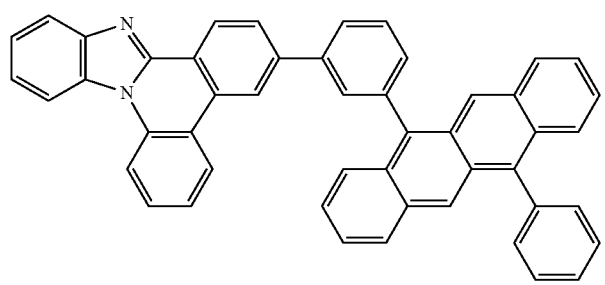 [SMILES: c1ccc(-c2c3ccccc3cc3c(-c4cccc(-c5ccc6c(c5)c5ccccc5n5c7ccccc7nc65)c4)c4ccccc4cc23)cc1]
1-b-58
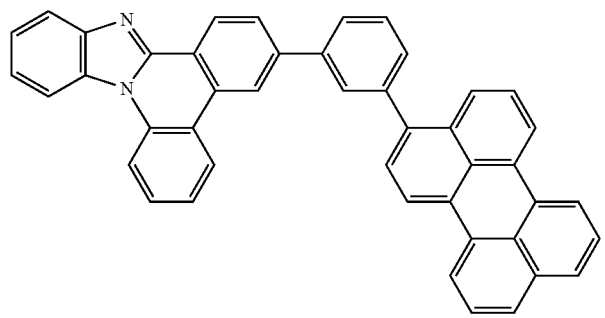
1-b-59
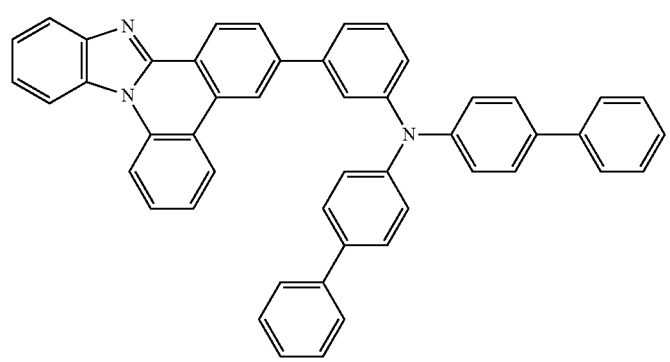 [SMILES: c1ccc(-c2ccc(N(c3ccc(-c4ccccc4)cc3)c3cccc(-c4ccc5c(c4)c4ccccc4n4c6ccccc6nc54)c3)cc2)cc1]
1-b-60
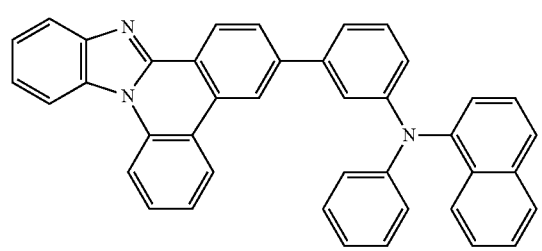

TABLE 2-continued
1-b-61
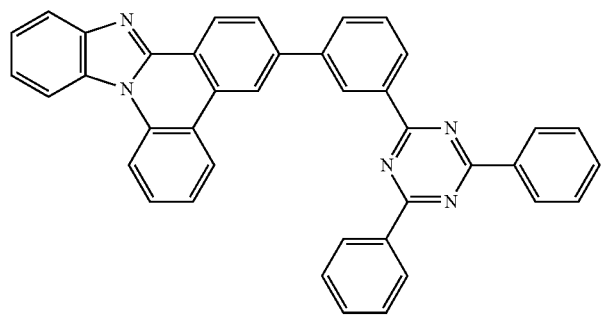
1-b-62
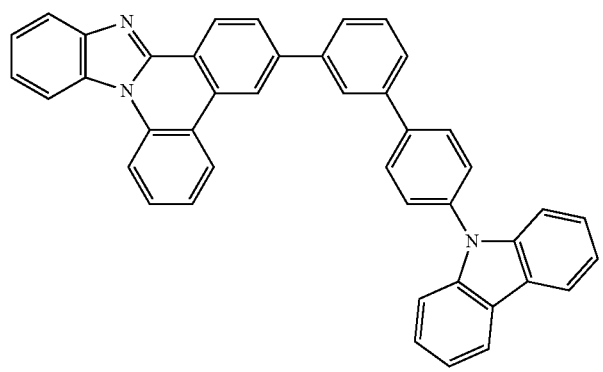 [SMILES: c1cc(-c2ccc(-n3c4ccccc4c4ccccc43)cc2)cc(-c2ccc3c(c2)c2ccccc2n2c4ccccc4nc32)c1]
1-b-63
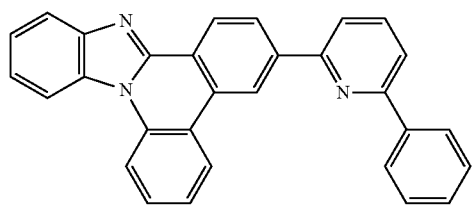 [SMILES: c1ccc(-c2cccc(-c3ccc4c(c3)c3ccccc3n3c5ccccc5nc43)n2)cc1]
1-b-64
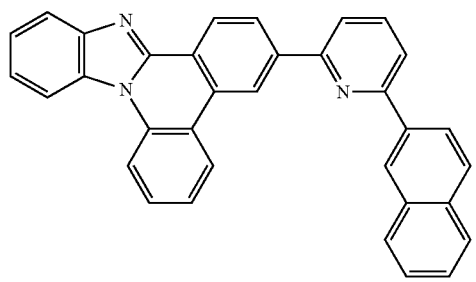 [SMILES: c1cc(-c2ccc3ccccc3c2)nc(-c2ccc3c(c2)c2ccccc2n2c4ccccc4nc32)c1]
1-b-65
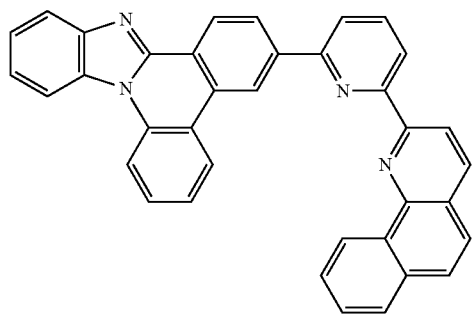 [SMILES: c1cc(-c2ccc3c(c2)c2ccccc2n2c4ccccc4nc32)nc(-c2ccc3ccc4ccccc4c3n2)c1]

TABLE 2-continued
1-b-66 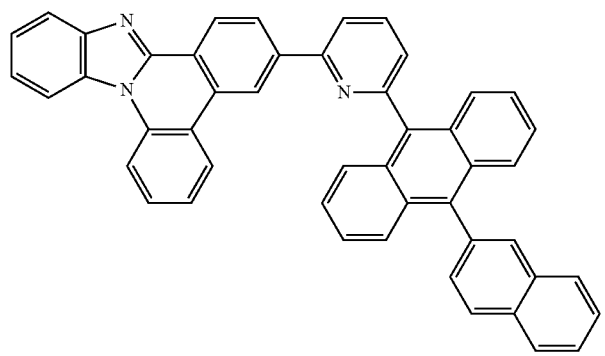
1-b-67 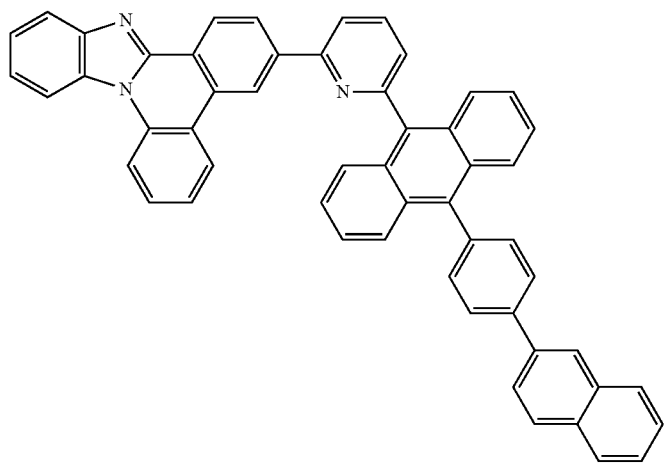 [SMILES: c1cc(-c2ccc3c(c2)c2ccccc2n2c4ccccc4nc32)nc(-c2c3ccccc3c(-c3ccc(-c4ccc5ccccc5c4)cc3)c3ccccc23)c1]
1-b-68 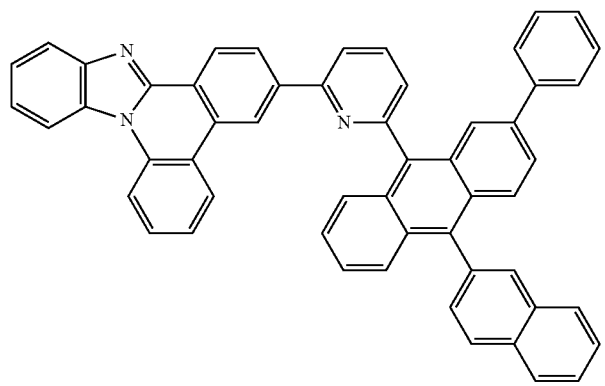 [SMILES: c1ccc(-c2ccc3c(-c4ccc5ccccc5c4)c4ccccc4c(-c4cccc(-c5ccc6c(c5)c5ccccc5n5c7ccccc7nc65)n4)c3c2)cc1]
1-b-69 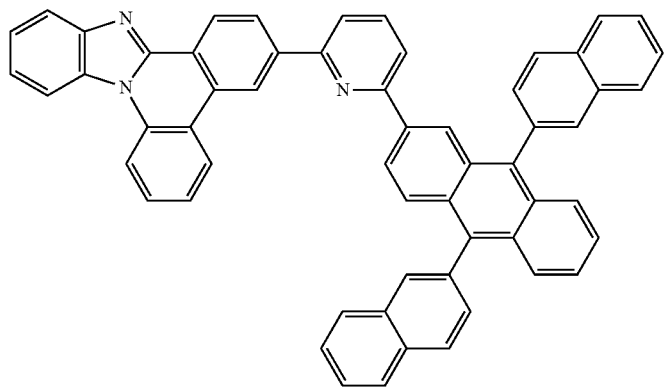

TABLE 2-continued
1-b-70
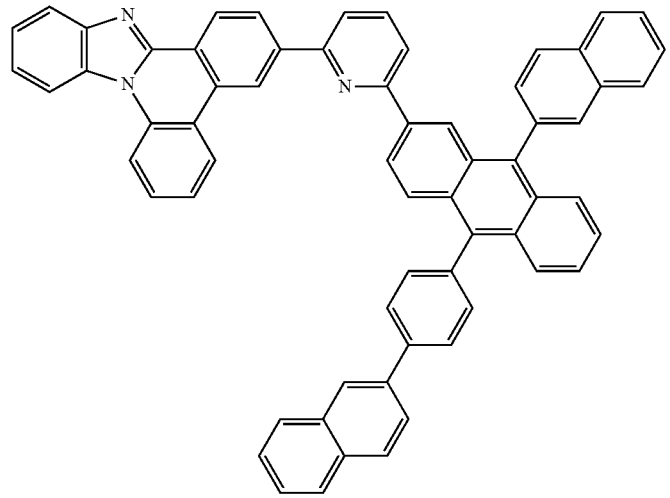
1-b-71
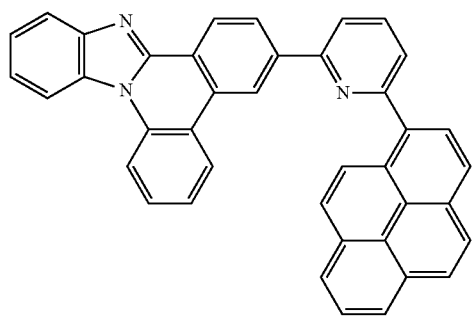 [SMILES: c1cc(-c2ccc3c(c2)c2ccccc2n2c4ccccc4nc32)nc(-c2ccc3ccc4cccc5ccc2c3c45)c1]
1-b-72
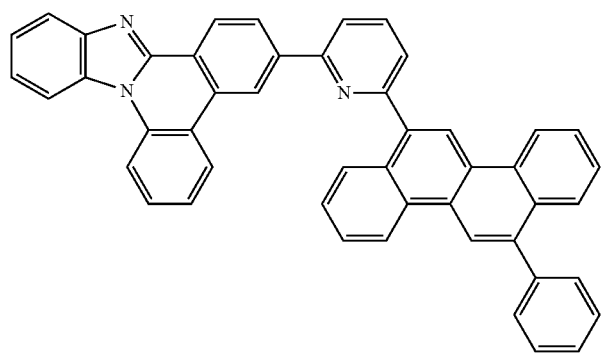
1-b-73
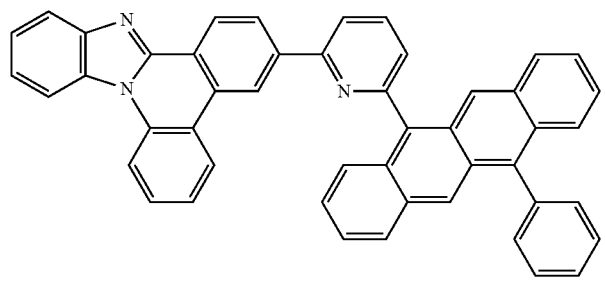

TABLE 2-continued
1-b-74
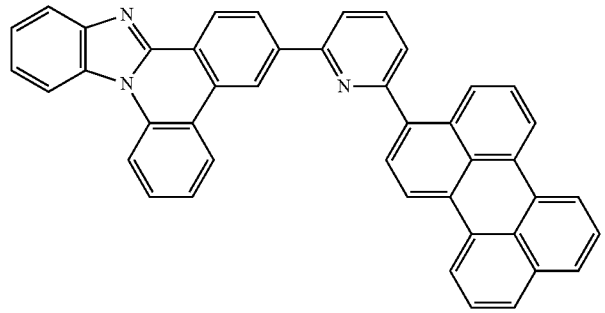 [SMILES: c1cc(-c2ccc3c(c2)c2ccccc2n2c4ccccc4nc32)nc(-c2ccc3c4cccc5cccc(c6cccc2c63)c54)c1]
1-b-75
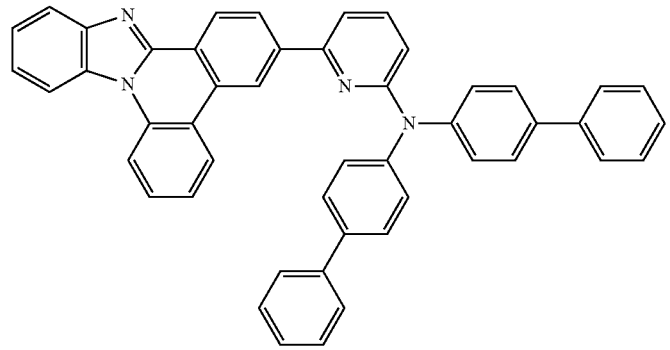
1-b-76
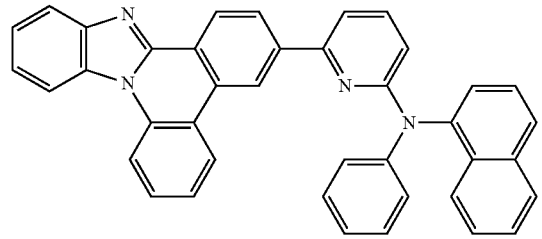 [SMILES: c1ccc(N(c2cccc(-c3ccc4c(c3)c3ccccc3n3c5ccccc5nc43)n2)c2cccc3ccccc23)cc1]
1-b-77
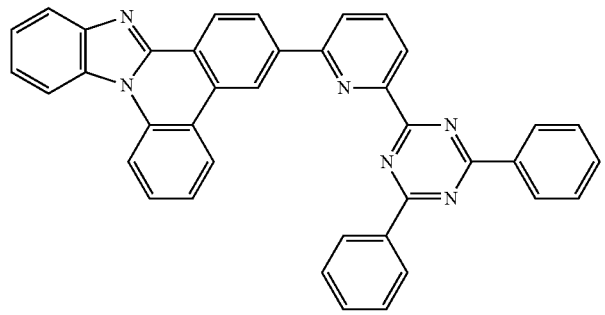 [SMILES: c1ccc(-c2nc(-c3ccccc3)nc(-c3cccc(-c4ccc5c(c4)c4ccccc4n4c6ccccc6nc54)n3)n2)cc1]
1-b-78
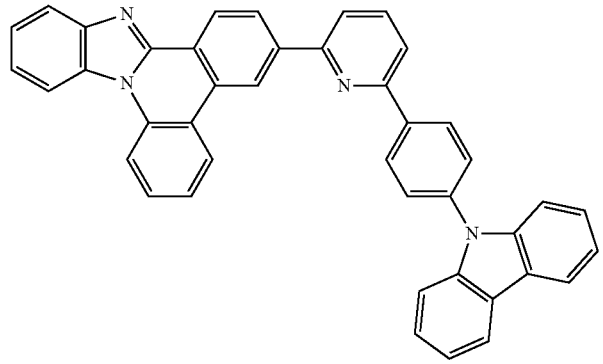 [SMILES: c1cc(-c2ccc(-n3c4ccccc4c4ccccc43)cc2)nc(-c2ccc3c(c2)c2ccccc2n2c4ccccc4nc32)c1]

TABLE 2-continued
1-b-79 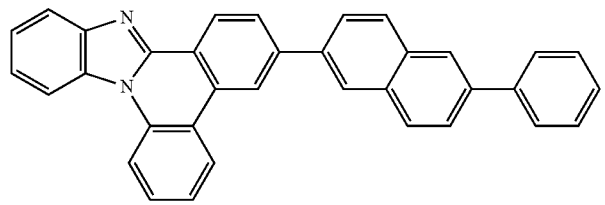 [SMILES: c1ccc(-c2ccc3cc(-c4ccc5c(c4)c4ccccc4n4c6ccccc6nc54)ccc3c2)cc1]
1-b-80 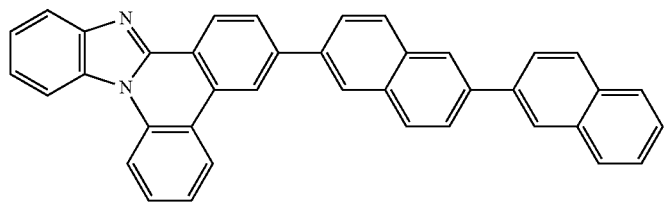 [SMILES: c1ccc2cc(-c3ccc4cc(-c5ccc6c(c5)c5ccccc5n5c7ccccc7nc65)ccc4c3)ccc2c1]
1-b-81 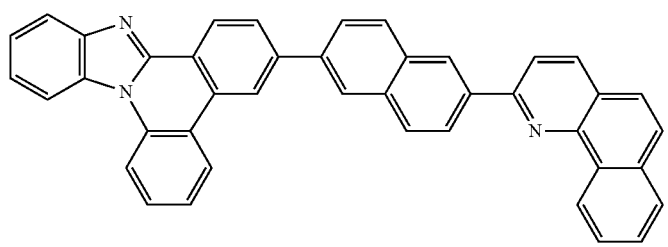 [SMILES: c1ccc2c(c1)ccc1ccc(-c3ccc4cc(-c5ccc6c(c5)c5ccccc5n5c7ccccc7nc65)ccc4c3)nc12]
1-b-82 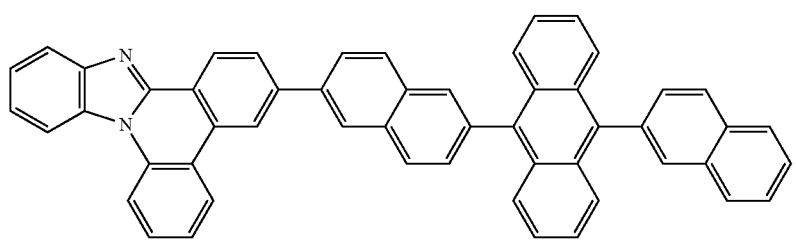 [SMILES: c1ccc2cc(-c3c4ccccc4c(-c4ccc5cc(-c6ccc7c(c6)c6ccccc6n6c8ccccc8nc76)ccc5c4)c4ccccc34)ccc2c1]
1-b-83 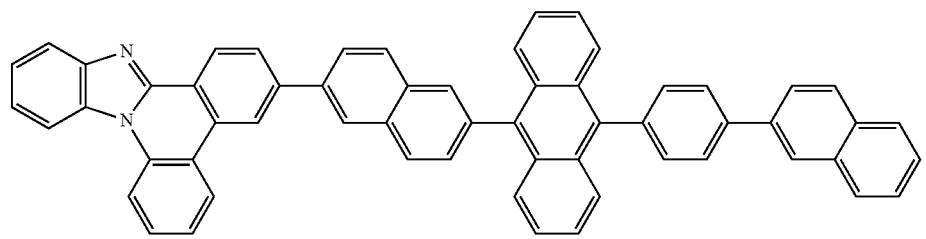 [SMILES: c1ccc2cc(-c3ccc(-c4c5ccccc5c(-c5ccc6cc(-c7ccc8c(c7)c7ccccc7n7c9ccccc9nc87)ccc6c5)c5ccccc45)cc3)ccc2c1]
1-b-84 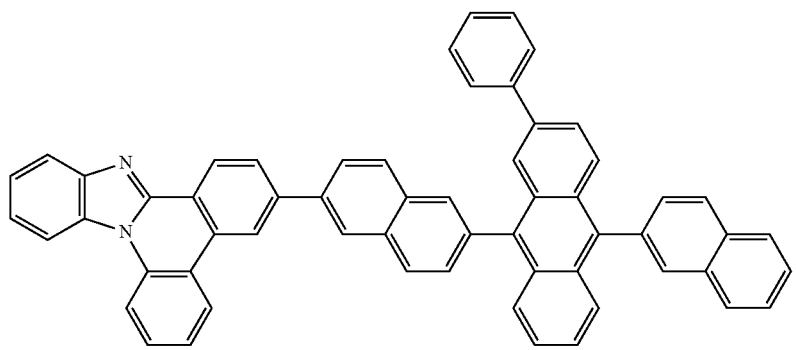 [SMILES: c1ccc(-c2ccc3c(-c4ccc5ccccc5c4)c4ccccc4c(-c4ccc5cc(-c6ccc7c(c6)c6ccccc6n6c8ccccc8nc76)ccc5c4)c3c2)cc1]

TABLE 2-continued
1-b-85
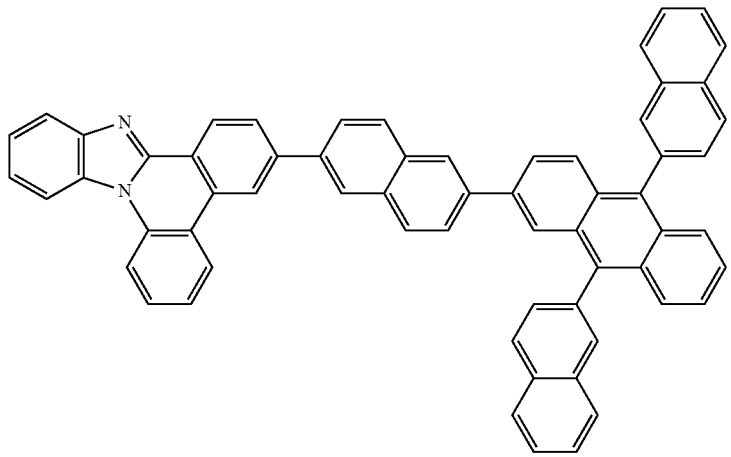 [SMILES: c1ccc2cc(-c3c4ccccc4c(-c4ccc5ccccc5c4)c4cc(-c5ccc6cc(-c7ccc8c(c7)c7ccccc7n7c9ccccc9nc87)ccc6c5)ccc34)ccc2c1]
1-b-86
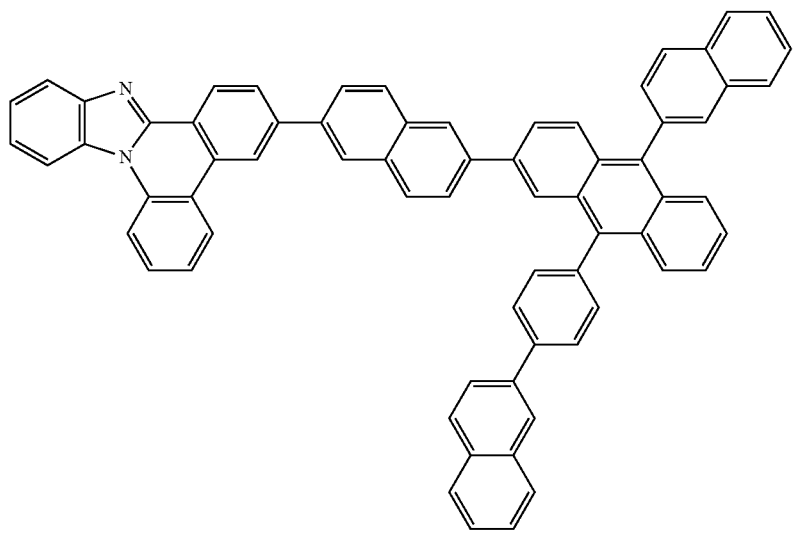 [SMILES: c1ccc2cc(-c3ccc(-c4c5ccccc5c(-c5ccc6ccccc6c5)c5ccc(-c6ccc7cc(-c8ccc9c(c8)c8ccccc8n8c%10ccccc%10nc98)ccc7c6)cc45)cc3)ccc2c1]
1-b-87
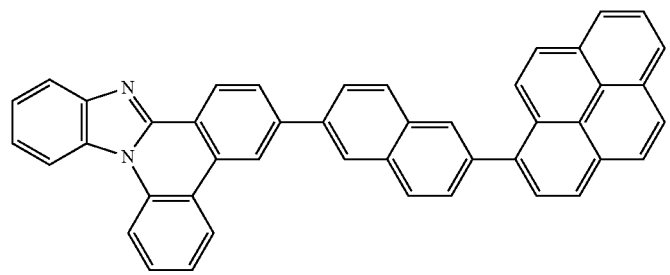 [SMILES: c1cc2ccc3ccc(-c4ccc5cc(-c6ccc7c(c6)c6ccccc6n6c8ccccc8nc76)ccc5c4)c4ccc(c1)c2c34]
1-b-88
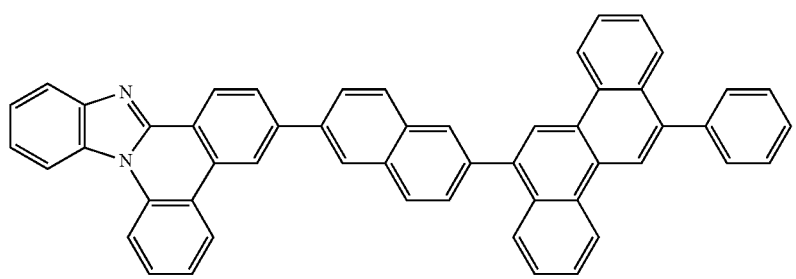 [SMILES: c1ccc(-c2cc3c4ccccc4c(-c4ccc5cc(-c6ccc7c(c6)c6ccccc6n6c8ccccc8nc76)ccc5c4)cc3c3ccccc23)cc1]

TABLE 2-continued
1-b-89
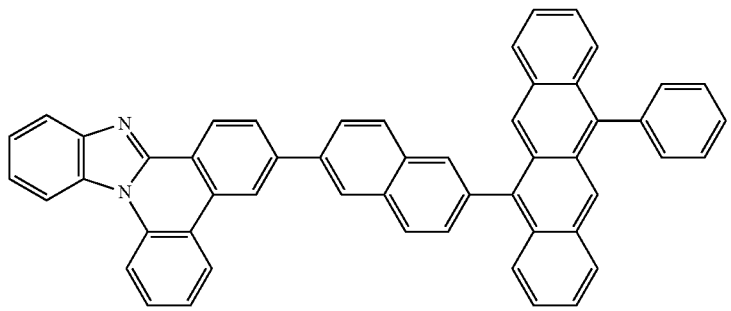 [SMILES: c1ccc(-c2c3ccccc3cc3c(-c4ccc5cc(-c6ccc7c(c6)c6ccccc6n6c8ccccc8nc76)ccc5c4)c4ccccc4cc23)cc1]
1-b-90
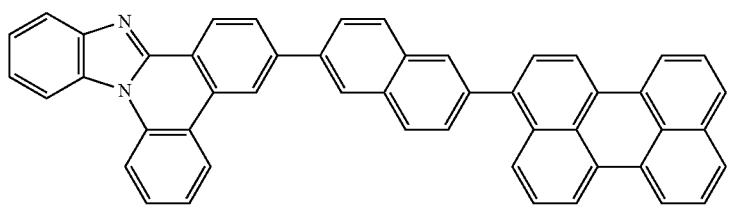 [SMILES: c1ccc2c(c1)nc1c3ccc(-c4ccc5cc(-c6ccc7c8cccc9cccc(c%10cccc6c%107)c98)ccc5c4)cc3c3ccccc3n21]
1-b-91
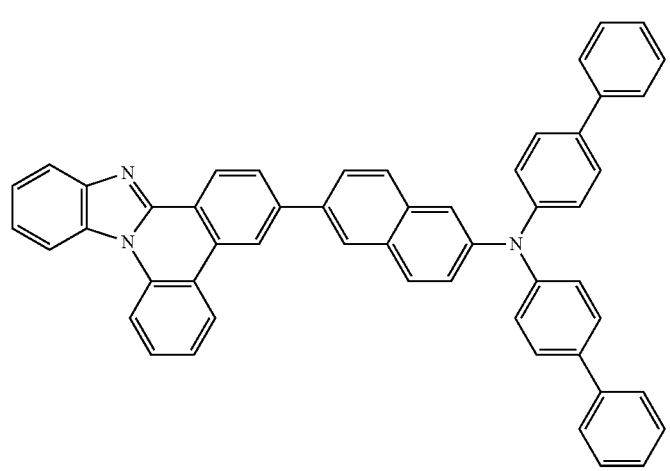 [SMILES: c1ccc(-c2ccc(N(c3ccc(-c4ccccc4)cc3)c3ccc4cc(-c5ccc6c(c5)c5ccccc5n5c7ccccc7nc65)ccc4c3)cc2)cc1]
1-b-92
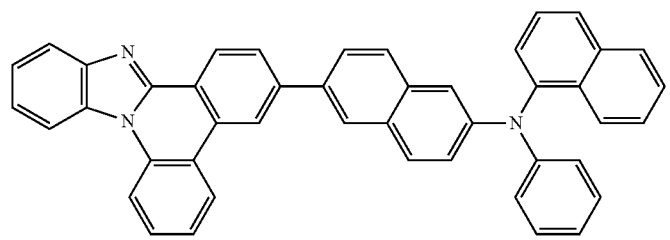 [SMILES: c1ccc(N(c2ccc3cc(-c4ccc5c(c4)c4ccccc4n4c6ccccc6nc54)ccc3c2)c2cccc3ccccc23)cc1]
1-b-93
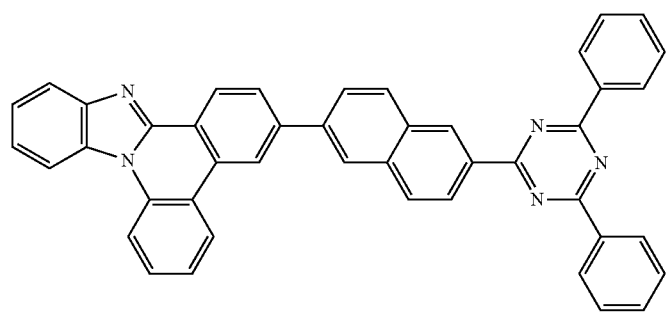 [SMILES: c1ccc(-c2nc(-c3ccccc3)nc(-c3ccc4cc(-c5ccc6c(c5)c5ccccc5n5c7ccccc7nc65)ccc4c3)n2)cc1]

TABLE 2-continued
1-b-94
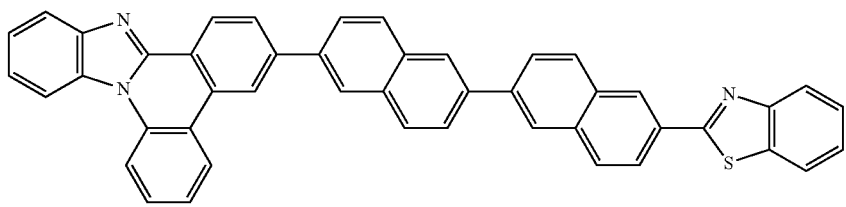 [SMILES: c1ccc2sc(-c3ccc4cc(-c5ccc6cc(-c7ccc8c(c7)c7ccccc7n7c9ccccc9nc87)ccc6c5)ccc4c3)nc2c1]
1-b-95
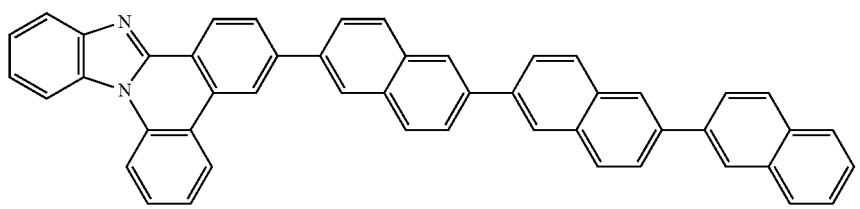 [SMILES: c1ccc2cc(-c3ccc4cc(-c5ccc6cc(-c7ccc8c(c7)c7ccccc7n7c9ccccc9nc87)ccc6c5)ccc4c3)ccc2c1]
1-b-96
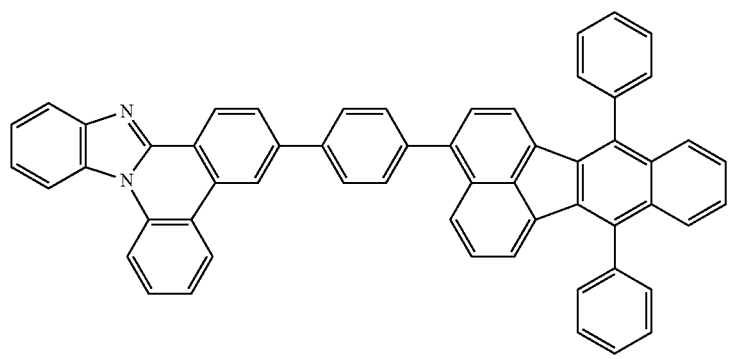 [SMILES: c1ccc(-c2c3c(c(-c4ccccc4)c4ccccc24)-c2ccc(-c4ccc(-c5ccc6c(c5)c5ccccc5n5c7ccccc7nc65)cc4)c4cccc-3c24)cc1]
1-b-97
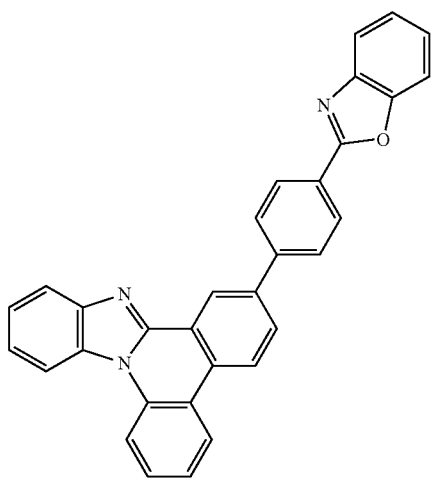 [SMILES: c1ccc2oc(-c3ccc(-c4ccc5c6ccccc6n6c7ccccc7nc6c5c4)cc3)nc2c1]

TABLE 2-continued
1-b-98
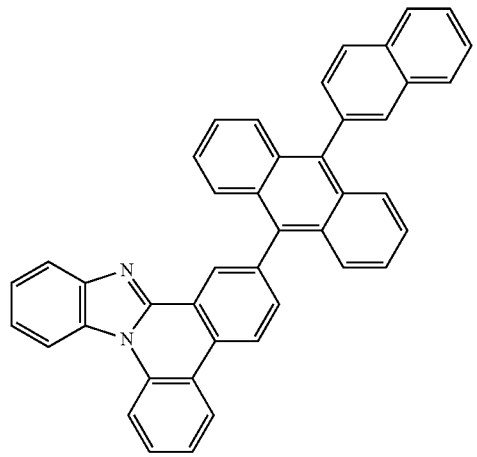 [SMILES: c1ccc2cc(-c3c4ccccc4c(-c4ccc5c6ccccc6n6c7ccccc7nc6c5c4)c4ccccc34)ccc2c1]
1-b-99
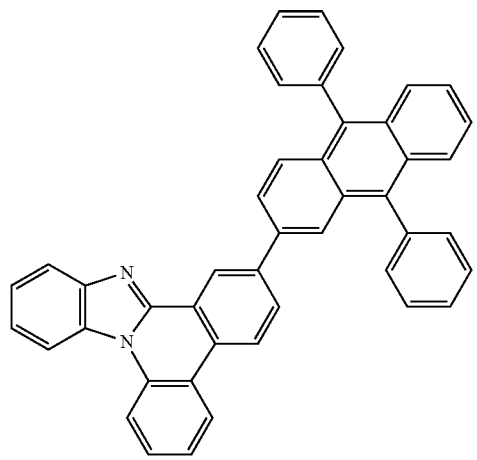 [SMILES: c1ccc(-c2c3ccccc3c(-c3ccccc3)c3cc(-c4ccc5c6ccccc6n6c7ccccc7nc6c5c4)ccc23)cc1]
1-b-100
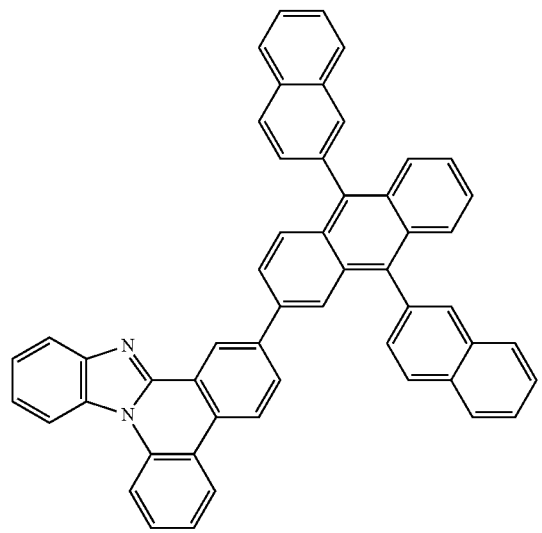 [SMILES: c1ccc2cc(-c3c4ccccc4c(-c4ccc5ccccc5c4)c4cc(-c5ccc6c7ccccc7n7c8ccccc8nc7c6c5)ccc34)ccc2c1]

TABLE 2-continued
1-b-101
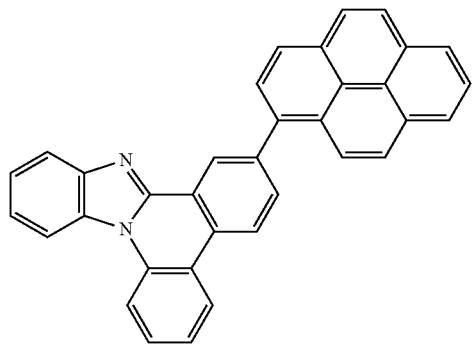 [SMILES: c1cc2ccc3ccc(-c4ccc5c6ccccc6n6c7ccccc7nc6c5c4)c4ccc(c1)c2c34]
1-b-102
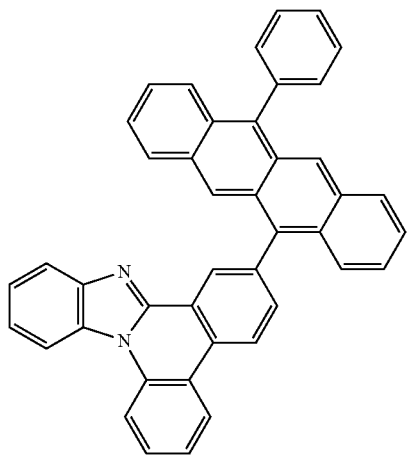 [SMILES: c1ccc(-c2c3ccccc3cc3c(-c4ccc5c6ccccc6n6c7ccccc7nc6c5c4)c4ccccc4cc23)cc1]
1-b-103
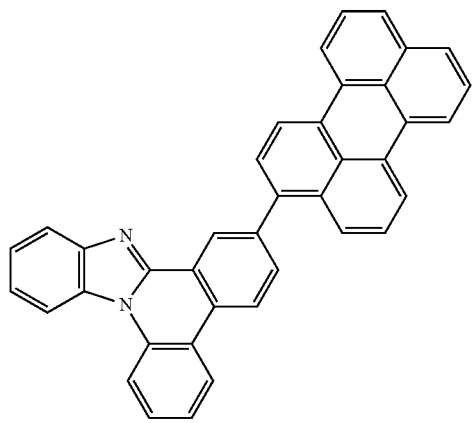 [SMILES: c1ccc2c(c1)nc1c3cc(-c4ccc5c6cccc7cccc(c8cccc4c85)c76)ccc3c3ccccc3n21]

TABLE 2-continued
1-b-104
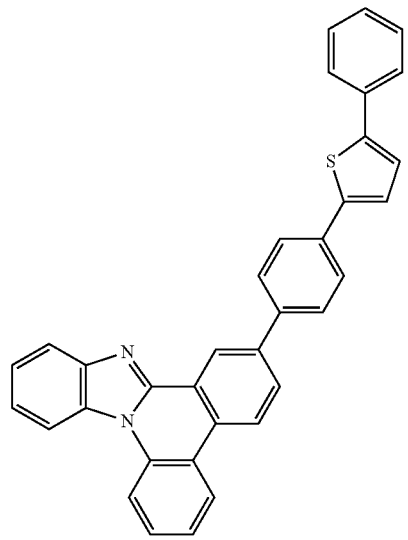 [SMILES: c1ccc(-c2ccc(-c3ccc(-c4ccc5c6ccccc6n6c7ccccc7nc6c5c4)cc3)s2)cc1]
1-b-105
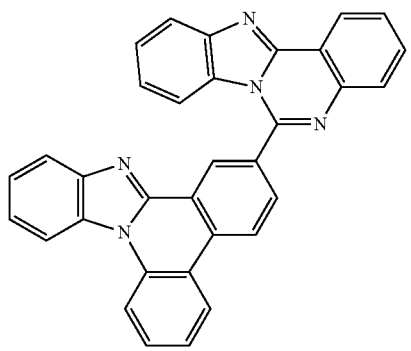 [SMILES: c1ccc2c(c1)nc(-c1ccc3c4ccccc4n4c5ccccc5nc4c3c1)n1c3ccccc3nc21]
1-b-106
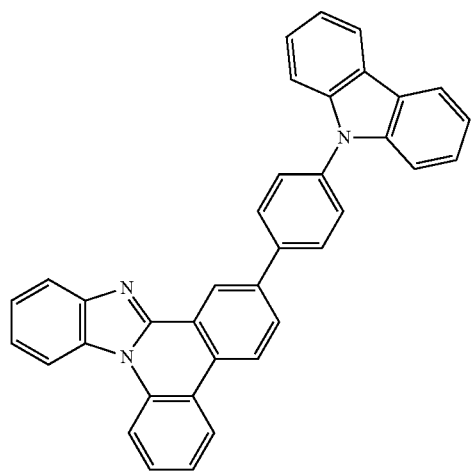 [SMILES: c1ccc2c(c1)nc1c3cc(-c4ccc(-n5c6ccccc6c6ccccc65)cc4)ccc3c3ccccc3n21]

TABLE 2-continued
1-b-107
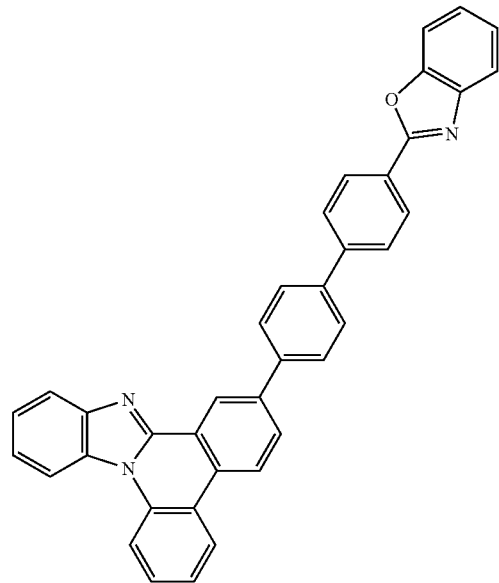 [SMILES: c1ccc2oc(-c3ccc(-c4ccc(-c5ccc6c7ccccc7n7c8ccccc8nc7c6c5)cc4)cc3)nc2c1]
1-b-108
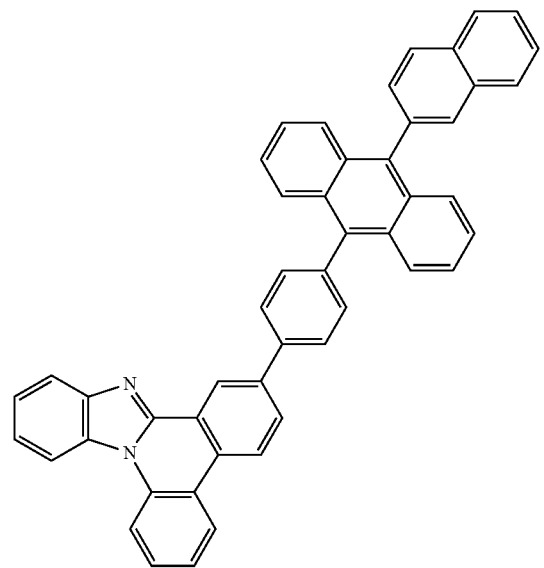 [SMILES: c1ccc2cc(-c3c4ccccc4c(-c4ccc(-c5ccc6c7ccccc7n7c8ccccc8nc7c6c5)cc4)c4ccccc34)ccc2c1]

TABLE 2-continued
1-b-109
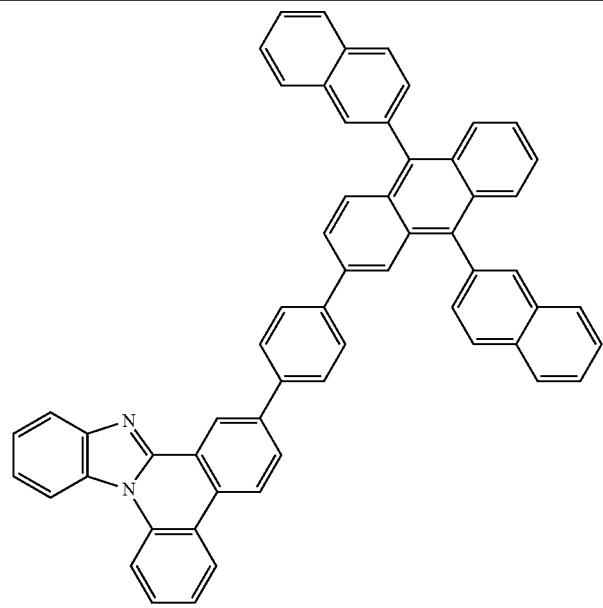
1-b-110
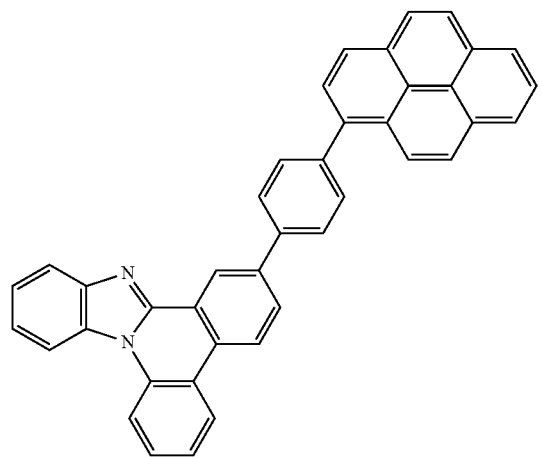 [SMILES: c1cc2ccc3ccc(-c4ccc(-c5ccc6c7ccccc7n7c8ccccc8nc7c6c5)cc4)c4ccc(c1)c2c34]
1-b-111
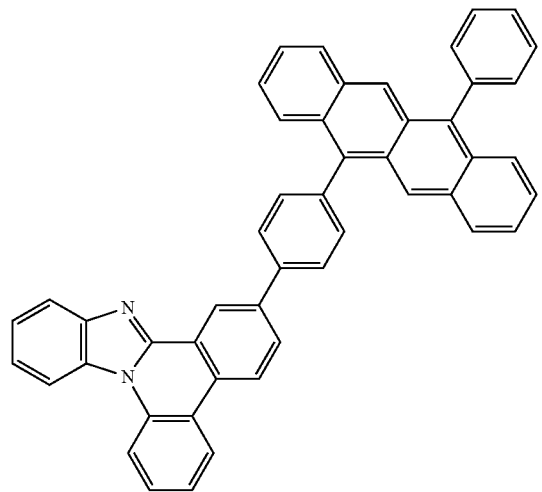 [SMILES: c1ccc(-c2c3ccccc3cc3c(-c4ccc(-c5ccc6c7ccccc7n7c8ccccc8nc7c6c5)cc4)c4ccccc4cc23)cc1]

TABLE 2-continued
1-b-112
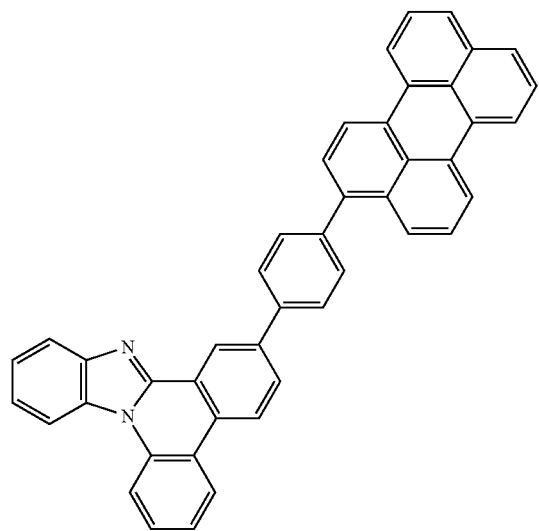 [SMILES: c1ccc2c(c1)nc1c3cc(-c4ccc(-c5ccc6c7cccc8cccc(c9cccc5c96)c87)cc4)ccc3c3ccccc3n21]
1-b-113
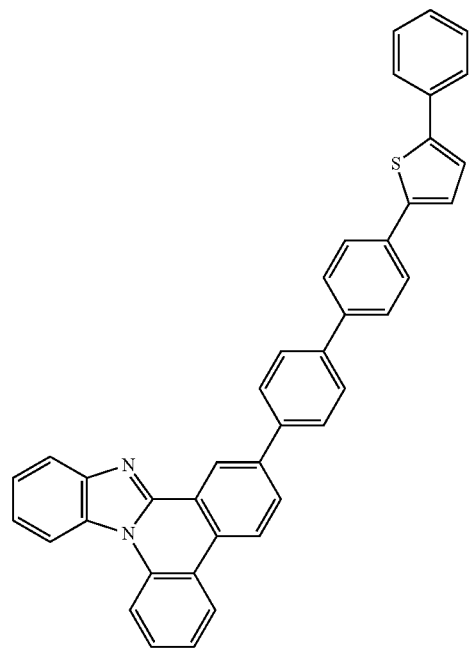 [SMILES: c1ccc(-c2ccc(-c3ccc(-c4ccc(-c5ccc6c7ccccc7n7c8ccccc8nc7c6c5)cc4)cc3)s2)cc1]

TABLE 2-continued
1-b-114
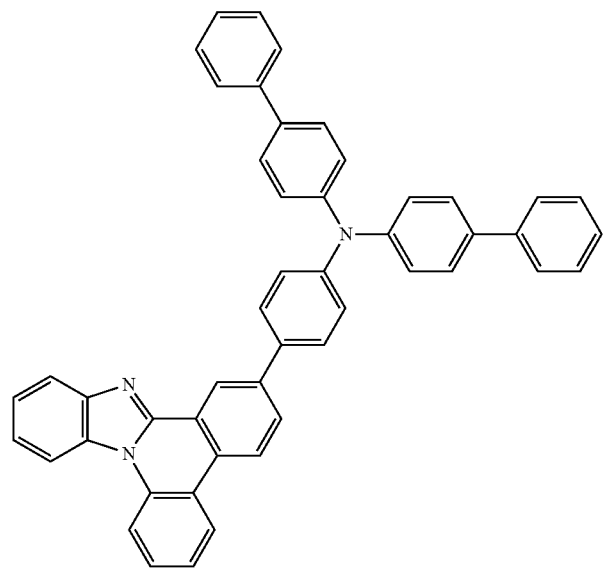 [SMILES: c1ccc(-c2ccc(N(c3ccc(-c4ccccc4)cc3)c3ccc(-c4ccc5c6ccccc6n6c7ccccc7nc6c5c4)cc3)cc2)cc1]
1-b-115
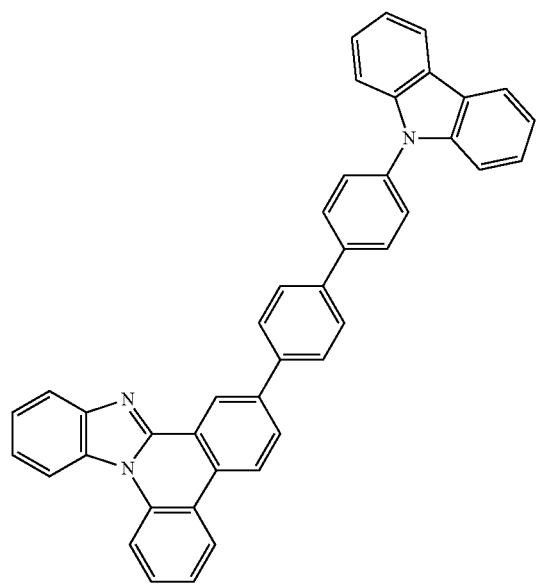 [SMILES: c1ccc2c(c1)nc1c3cc(-c4ccc(-c5ccc(-n6c7ccccc7c7ccccc76)cc5)cc4)ccc3c3ccccc3n21]
1-b-116
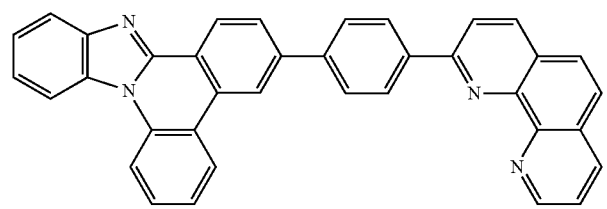 [SMILES: c1cnc2c(c1)ccc1ccc(-c3ccc(-c4ccc5c(c4)c4ccccc4n4c6ccccc6nc54)cc3)nc12]
1-b-117
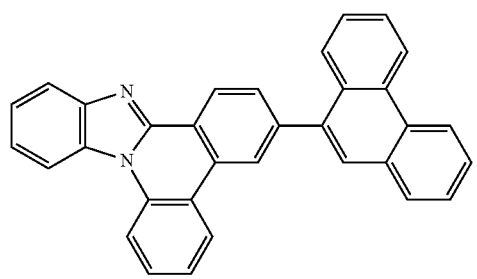 [SMILES: c1ccc2c(c1)cc(-c1ccc3c(c1)c1ccccc1n1c4ccccc4nc31)c1ccccc12]

TABLE 2-continued
1-b-118
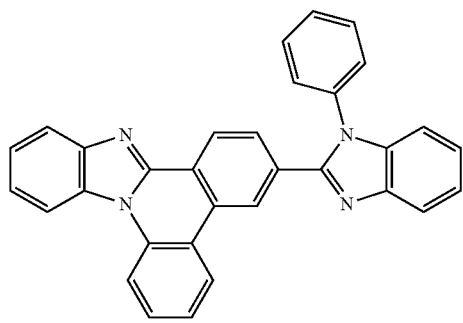 [SMILES: c1ccc(-n2c(-c3ccc4c(c3)c3ccccc3n3c5ccccc5nc43)nc3ccccc32)cc1]
1-b-119
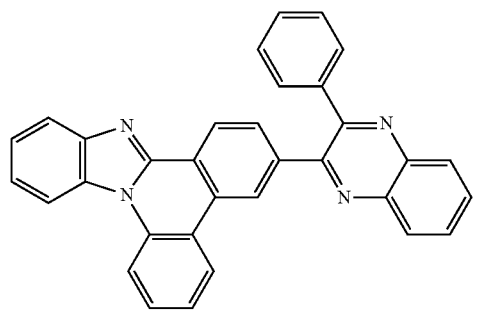 [SMILES: c1ccc(-c2nc3ccccc3nc2-c2ccc3c(c2)c2ccccc2n2c4ccccc4nc32)cc1]
1-b-120
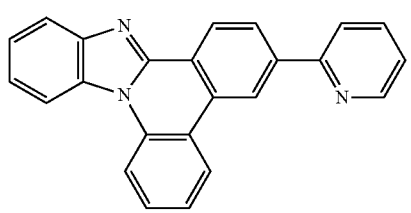
1-b-121
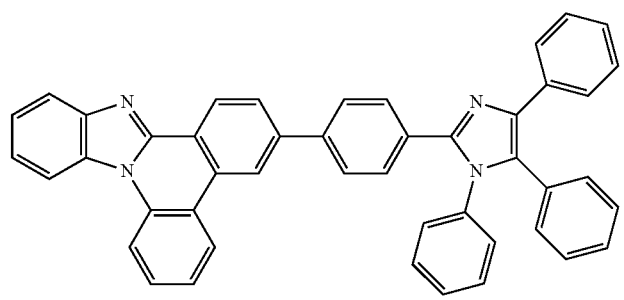 [SMILES: c1ccc(-c2nc(-c3ccc(-c4ccc5c(c4)c4ccccc4n4c6ccccc6nc54)cc3)n(-c3ccccc3)c2-c2ccccc2)cc1]
1-b-122
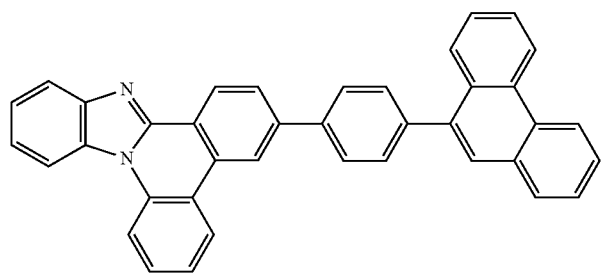 [SMILES: c1ccc2c(c1)cc(-c1ccc(-c3ccc4c(c3)c3ccccc3n3c5ccccc5nc43)cc1)c1ccccc12]
1-b-123
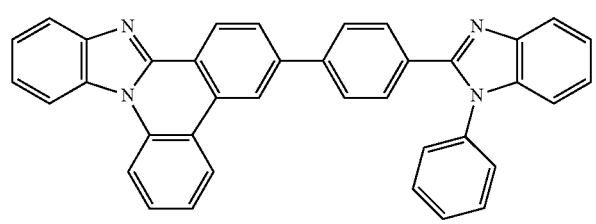 [SMILES: c1ccc(-n2c(-c3ccc(-c4ccc5c(c4)c4ccccc4n4c6ccccc6nc54)cc3)nc3ccccc32)cc1]

TABLE 2-continued
1-b-124
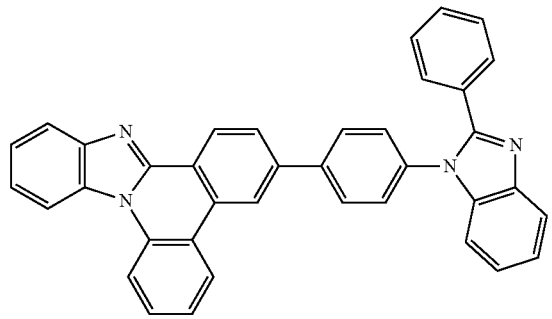 [SMILES: c1ccc(-c2nc3ccccc3n2-c2ccc(-c3ccc4c(c3)c3ccccc3n3c5ccccc5nc43)cc2)cc1]
1-b-125
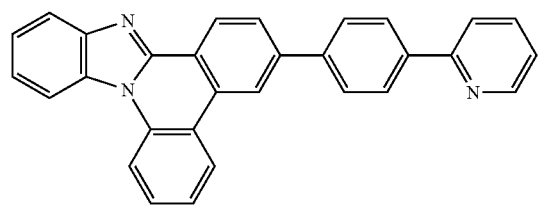
1-b-126
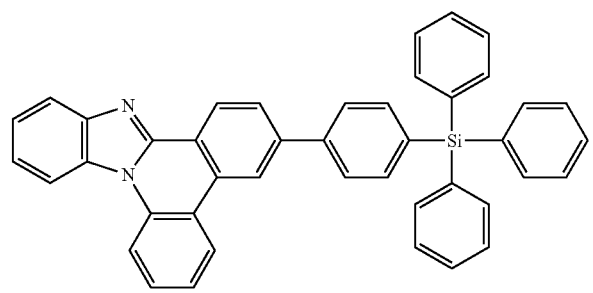 [SMILES: c1ccc([Si](c2ccccc2)(c2ccccc2)c2ccc(-c3ccc4c(c3)c3ccccc3n3c5ccccc5nc43)cc2)cc1]
1-b-127
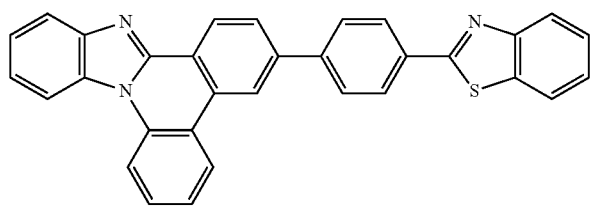 [SMILES: c1ccc2sc(-c3ccc(-c4ccc5c(c4)c4ccccc4n4c6ccccc6nc54)cc3)nc2c1]
1-b-128
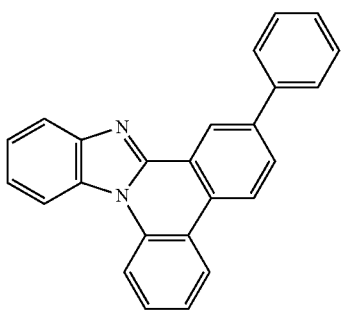 [SMILES: c1ccc(-c2ccc3c4ccccc4n4c5ccccc5nc4c3c2)cc1]

TABLE 2-continued
1-b-129
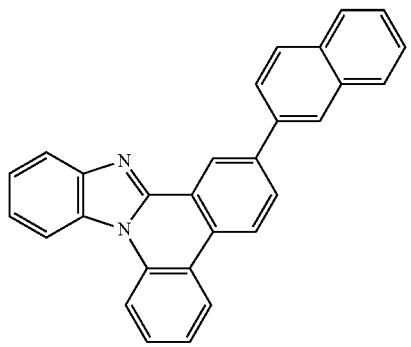 [SMILES: c1ccc2cc(-c3ccc4c5ccccc5n5c6ccccc6nc5c4c3)ccc2c1]
1-b-130
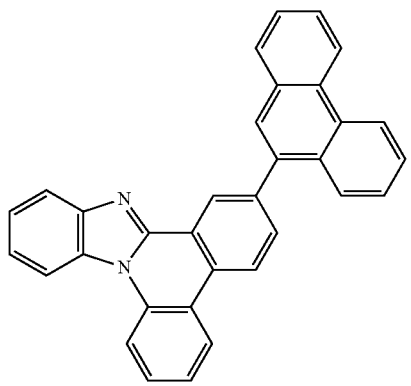 [SMILES: c1ccc2c(c1)cc(-c1ccc3c4ccccc4n4c5ccccc5nc4c3c1)c1ccccc12]
1-b-131
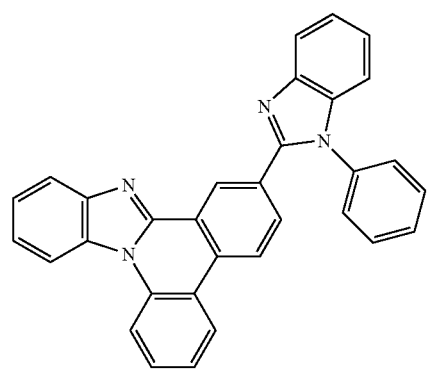 [SMILES: c1ccc(-n2c(-c3ccc4c5ccccc5n5c6ccccc6nc5c4c3)nc3ccccc32)cc1]
1-b-132
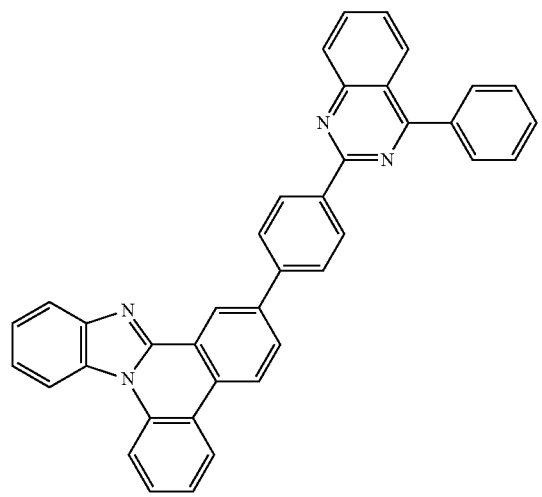 [SMILES: c1ccc(-c2nc(-c3ccc(-c4ccc5c6ccccc6n6c7ccccc7nc6c5c4)cc3)nc3ccccc23)cc1]

TABLE 2-continued
1-b-133
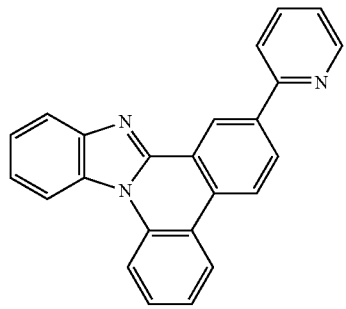
1-b-134
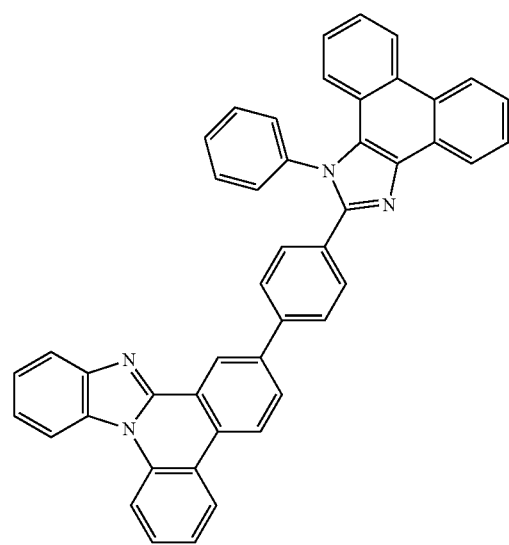 [SMILES: c1ccc(-n2c(-c3ccc(-c4ccc5c6ccccc6n6c7ccccc7nc6c5c4)cc3)nc3c4ccccc4c4ccccc4c32)cc1]
1-b-135
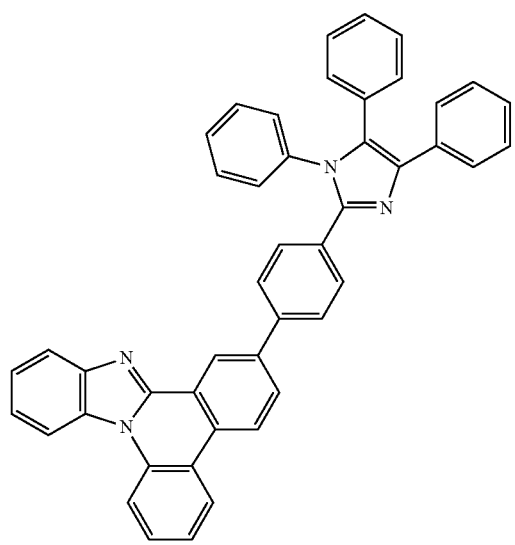 [SMILES: c1ccc(-c2nc(-c3ccc(-c4ccc5c6ccccc6n6c7ccccc7nc6c5c4)cc3)n(-c3ccccc3)c2-c2ccccc2)cc1]

TABLE 2-continued
1-b-136
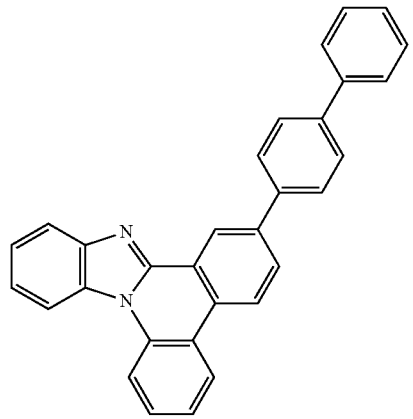 [SMILES: c1ccc(-c2ccc(-c3ccc4c5ccccc5n5c6ccccc6nc5c4c3)cc2)cc1]
1-b-137
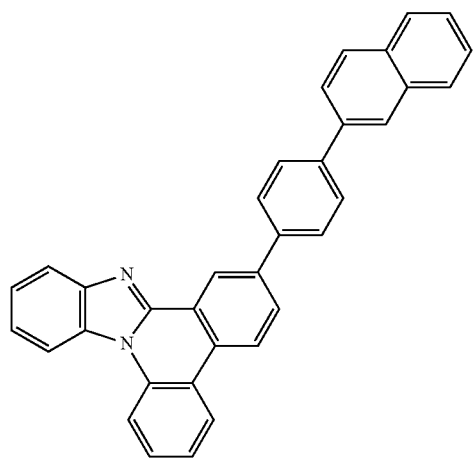 [SMILES: c1ccc2cc(-c3ccc(-c4ccc5c6ccccc6n6c7ccccc7nc6c5c4)cc3)ccc2c1]
1-b-138
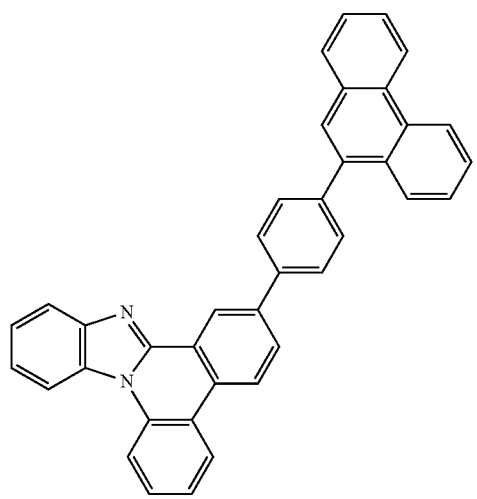 [SMILES: c1ccc2c(c1)cc(-c1ccc(-c3ccc4c5ccccc5n5c6ccccc6nc5c4c3)cc1)c1ccccc12]

TABLE 2-continued
1-b-139
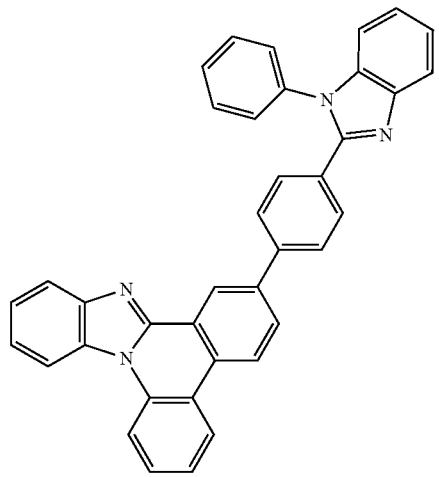 [SMILES: c1ccc(-n2c(-c3ccc(-c4ccc5c6ccccc6n6c7ccccc7nc6c5c4)cc3)nc3ccccc32)cc1]
1-b-140
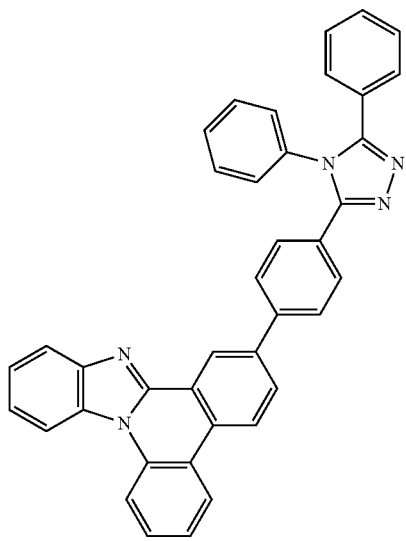 [SMILES: c1ccc(-c2nnc(-c3ccc(-c4ccc5c6ccccc6n6c7ccccc7nc6c5c4)cc3)n2-c2ccccc2)cc1]
1-b-141
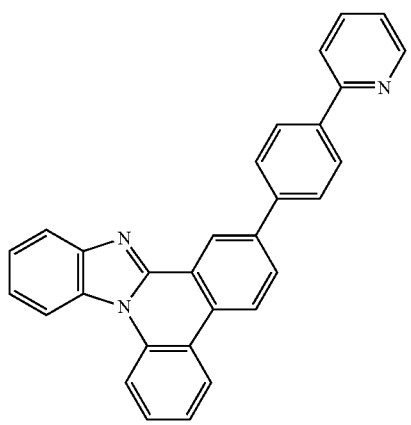 [SMILES: c1ccc(-c2ccc(-c3ccc4c5ccccc5n5c6ccccc6nc5c4c3)cc2)nc1]

TABLE 2-continued
1-b-142
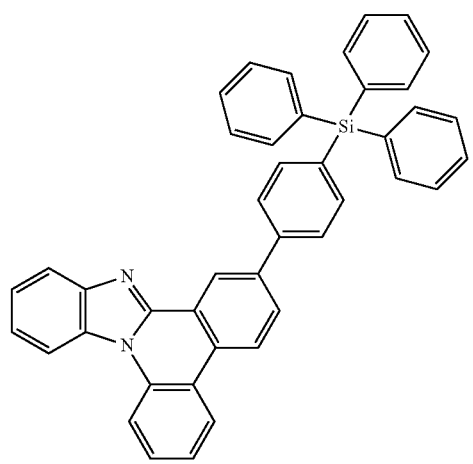 [SMILES: c1ccc([Si](c2ccccc2)(c2ccccc2)c2ccc(-c3ccc4c5ccccc5n5c6ccccc6nc5c4c3)cc2)cc1]
1-b-143
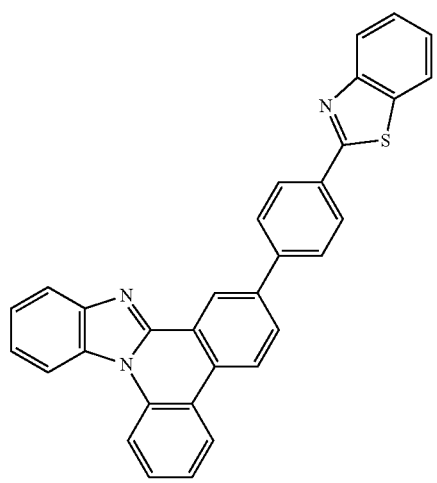
1-b-144
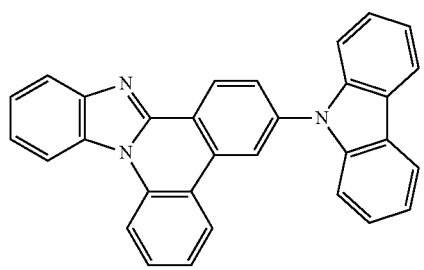 [SMILES: c1ccc2c(c1)nc1c3ccc(-n4c5ccccc5c5ccccc54)cc3c3ccccc3n21]
1-b-145
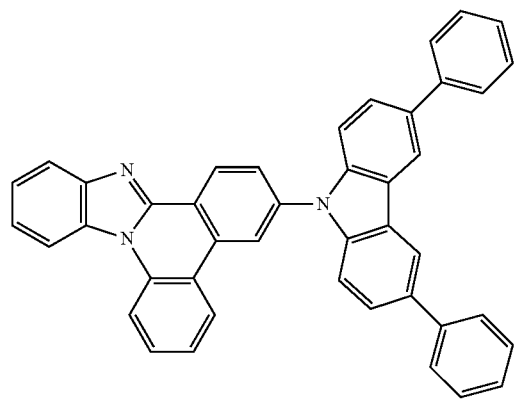 [SMILES: c1ccc(-c2ccc3c(c2)c2cc(-c4ccccc4)ccc2n3-c2ccc3c(c2)c2ccccc2n2c4ccccc4nc32)cc1]

TABLE 2-continued
1-b-146
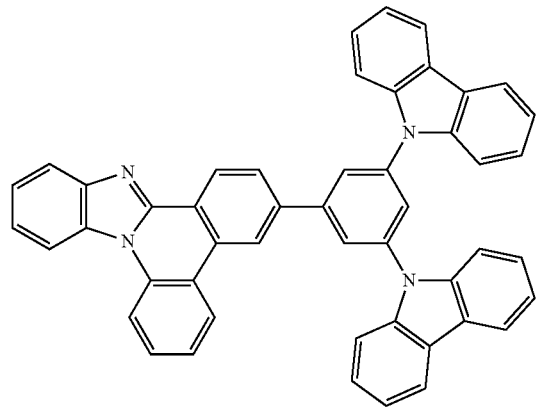 [SMILES: c1ccc2c(c1)nc1c3ccc(-c4cc(-n5c6ccccc6c6ccccc65)cc(-n5c6ccccc6c6ccccc65)c4)cc3c3ccccc3n21]
1-b-147
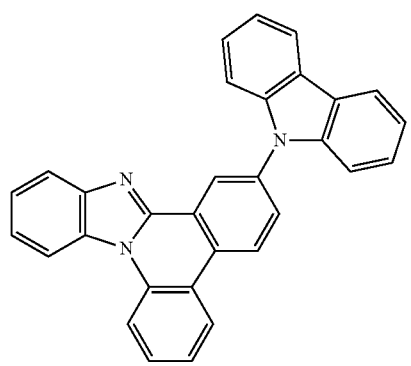 [SMILES: c1ccc2c(c1)nc1c3cc(-n4c5ccccc5c5ccccc54)ccc3c3ccccc3n21]
1-b-148
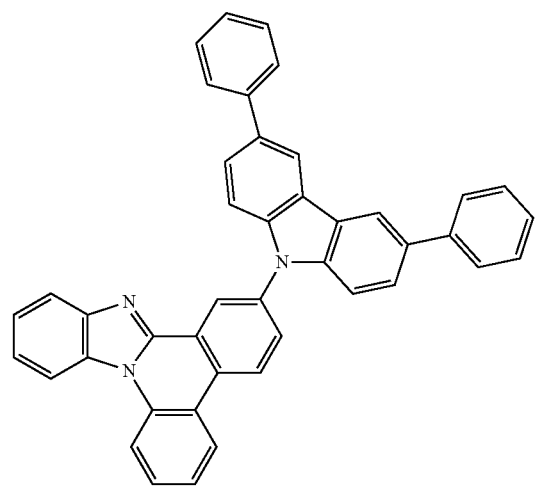 [SMILES: c1ccc(-c2ccc3c(c2)c2cc(-c4ccccc4)ccc2n3-c2ccc3c4ccccc4n4c5ccccc5nc4c3c2)cc1]

TABLE 2-continued
1-b-149
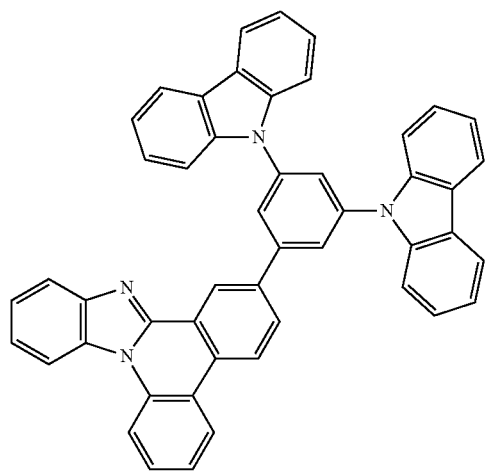 [SMILES: c1ccc2c(c1)nc1c3cc(-c4cc(-n5c6ccccc6c6ccccc65)cc(-n5c6ccccc6c6ccccc65)c4)ccc3c3ccccc3n21]
1-b-150
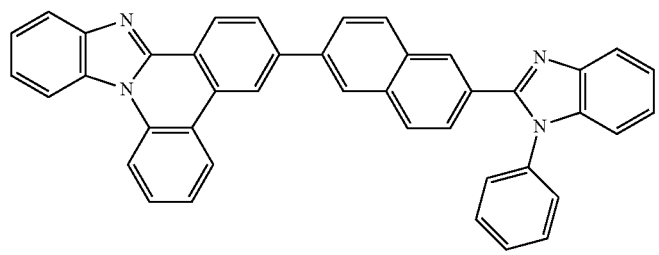 [SMILES: c1ccc(-n2c(-c3ccc4cc(-c5ccc6c(c5)c5ccccc5n5c7ccccc7nc65)ccc4c3)nc3ccccc32)cc1]
1-b-151
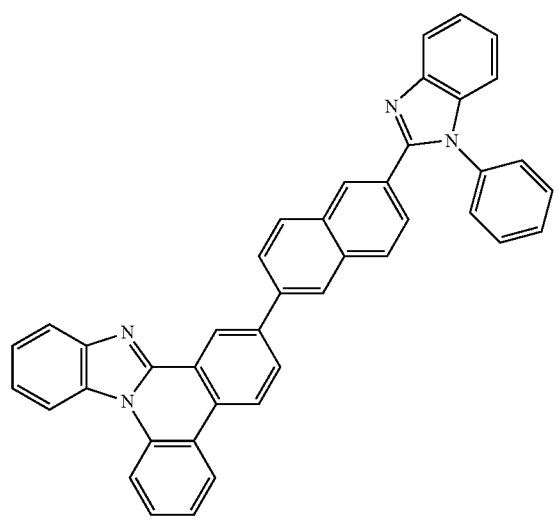 [SMILES: c1ccc(-n2c(-c3ccc4cc(-c5ccc6c7ccccc7n7c8ccccc8nc7c6c5)ccc4c3)nc3ccccc32)cc1]
1-b-152
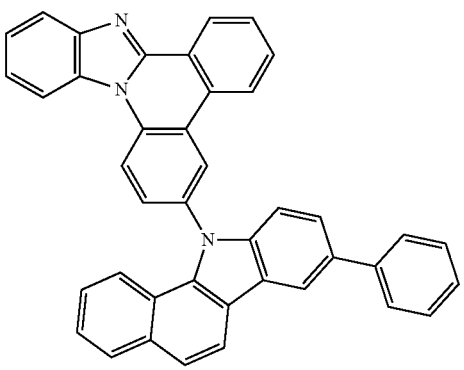 [SMILES: c1ccc(-c2ccc3c(c2)c2ccc4ccccc4c2n3-c2ccc3c(c2)c2ccccc2c2nc4ccccc4n32)cc1]

TABLE 2-continued
1-b-153
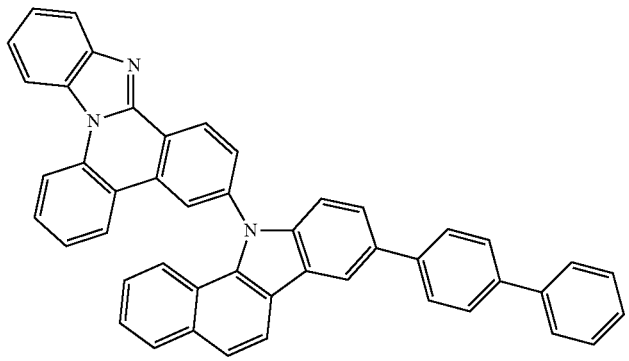 [SMILES: c1ccc(-c2ccc(-c3ccc4c(c3)c3ccc5ccccc5c3n4-c3ccc4c(c3)c3ccccc3n3c5ccccc5nc43)cc2)cc1]
1-b-154
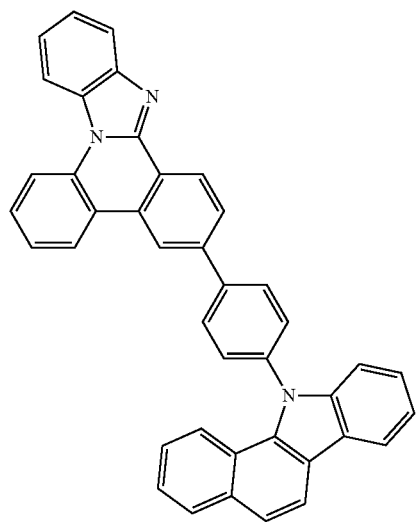 [SMILES: c1ccc2c(c1)ccc1c3ccccc3n(-c3ccc(-c4ccc5c(c4)c4ccccc4n4c6ccccc6nc54)cc3)c21]
1-b-155
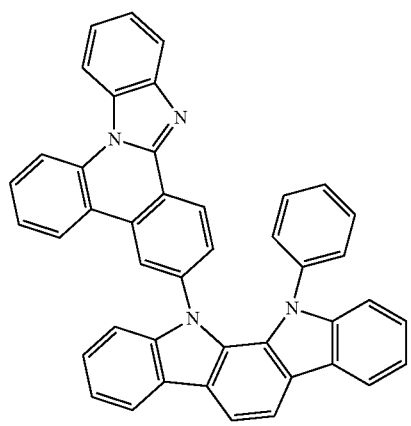 [SMILES: c1ccc(-n2c3ccccc3c3ccc4c5ccccc5n(-c5ccc6c(c5)c5ccccc5n5c7ccccc7nc65)c4c32)cc1]
1-b-156
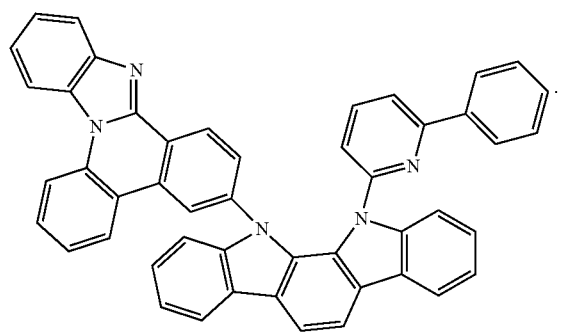 [SMILES: c1ccc(-c2cccc(-n3c4ccccc4c4ccc5c6ccccc6n(-c6ccc7c(c6)c6ccccc6n6c8ccccc8nc76)c5c43)n2)cc1]

5. The nitrogen-containing heterocyclic derivative as set forth in claim 1, wherein the nitrogen-containing heterocyclic derivative is represented by one selected from formulas that are described in the following Table 3:
TABLE 3
1-c-1
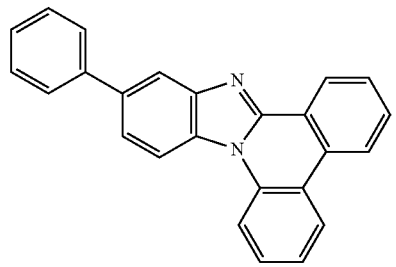 [SMILES: c1ccc(-c2ccc3c(c2)nc2c4ccccc4c4ccccc4n32)cc1]
1-c-2
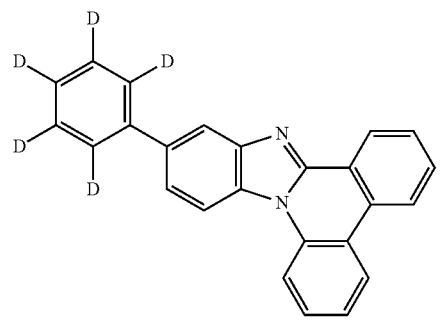 [SMILES: [2H]c1c([2H])c([2H])c(-c2ccc3c(c2)nc2c4ccccc4c4ccccc4n32)c([2H])c1[2H]]
1-c-3
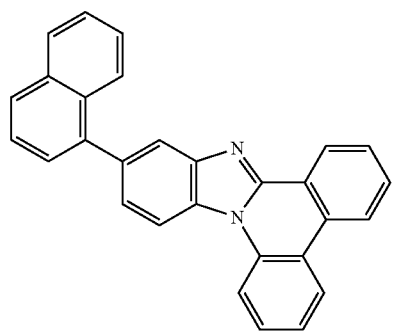 [SMILES: c1ccc2c(-c3ccc4c(c3)nc3c5ccccc5c5ccccc5n43)cccc2c1]
1-c-4
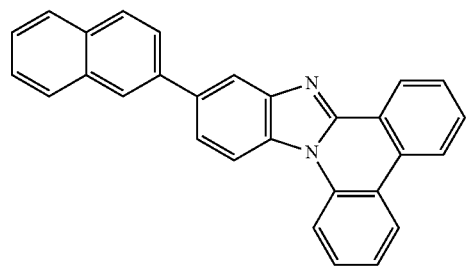 [SMILES: c1ccc2cc(-c3ccc4c(c3)nc3c5ccccc5c5ccccc5n43)ccc2c1]
1-c-5
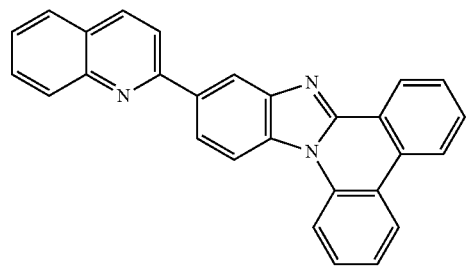 [SMILES: c1ccc2nc(-c3ccc4c(c3)nc3c5ccccc5c5ccccc5n43)ccc2c1]

TABLE 3-continued
1-c-6
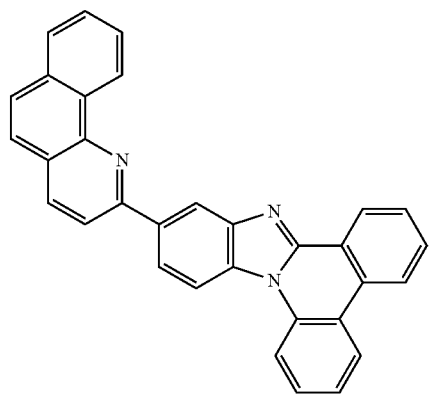 [SMILES: c1ccc2c(c1)ccc1ccc(-c3ccc4c(c3)nc3c5ccccc5c5ccccc5n43)nc12]
1-c-7
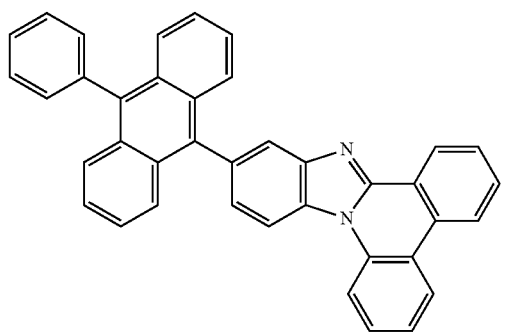 [SMILES: c1ccc(-c2c3ccccc3c(-c3ccc4c(c3)nc3c5ccccc5c5ccccc5n43)c3ccccc23)cc1]
1-c-8
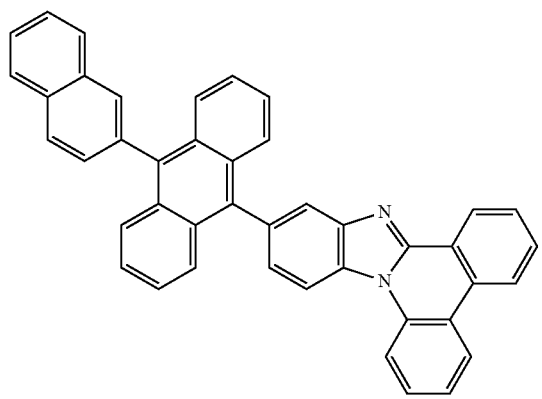 [SMILES: c1ccc2cc(-c3c4ccccc4c(-c4ccc5c(c4)nc4c6ccccc6c6ccccc6n54)c4ccccc34)ccc2c1]
1-c-9
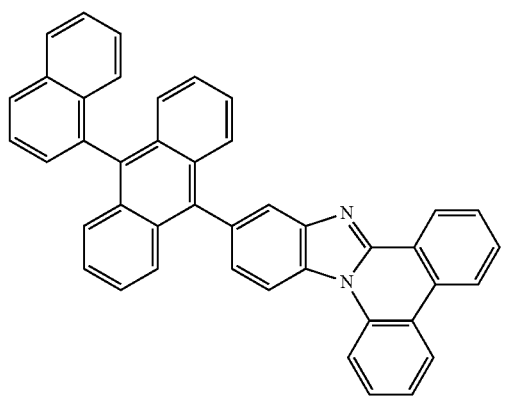 [SMILES: c1ccc2c(-c3c4ccccc4c(-c4ccc5c(c4)nc4c6ccccc6c6ccccc6n54)c4ccccc34)cccc2c1]

TABLE 3-continued
1-c-10
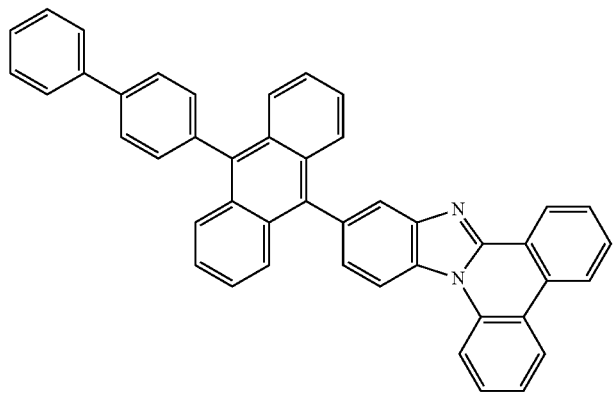 [SMILES: c1ccc(-c2ccc(-c3c4ccccc4c(-c4ccc5c(c4)nc4c6ccccc6c6ccccc6n54)c4ccccc34)cc2)cc1]
1-c-11
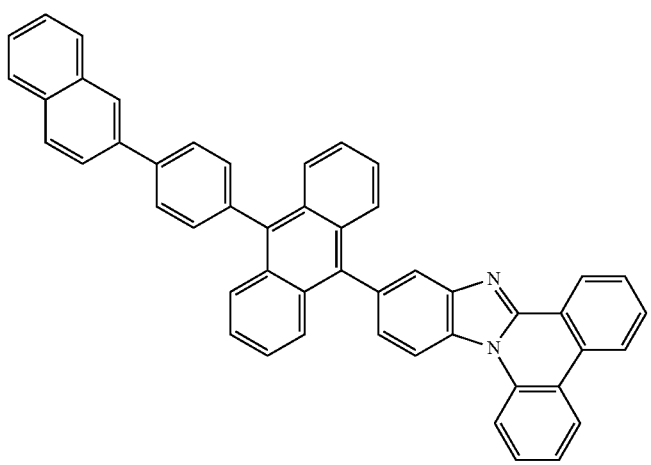 [SMILES: c1ccc2cc(-c3ccc(-c4c5ccccc5c(-c5ccc6c(c5)nc5c7ccccc7c7ccccc7n65)c5ccccc45)cc3)ccc2c1]
1-c-12
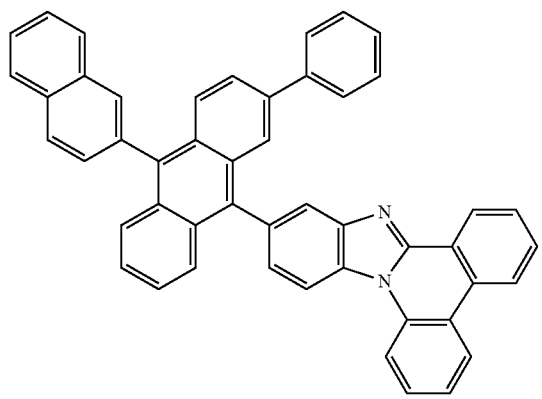 [SMILES: c1ccc(-c2ccc3c(-c4ccc5ccccc5c4)c4ccccc4c(-c4ccc5c(c4)nc4c6ccccc6c6ccccc6n54)c3c2)cc1]
1-c-13
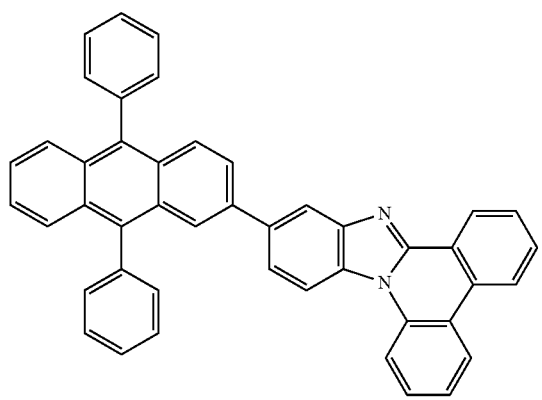 [SMILES: c1ccc(-c2c3ccccc3c(-c3ccccc3)c3cc(-c4ccc5c(c4)nc4c6ccccc6c6ccccc6n54)ccc23)cc1]

TABLE 3-continued
1-c-14
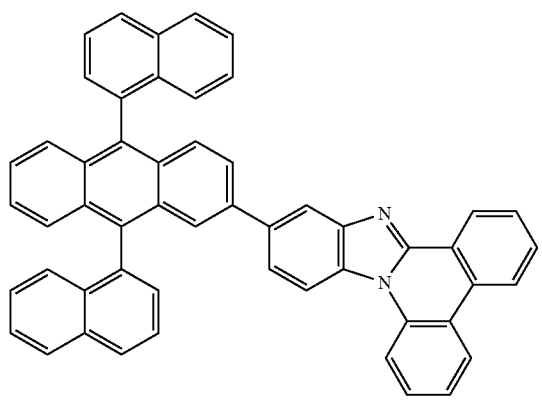 [SMILES: c1ccc2c(-c3c4ccccc4c(-c4cccc5ccccc45)c4cc(-c5ccc6c(c5)nc5c7ccccc7c7ccccc7n65)ccc34)cccc2c1]
1-c-15
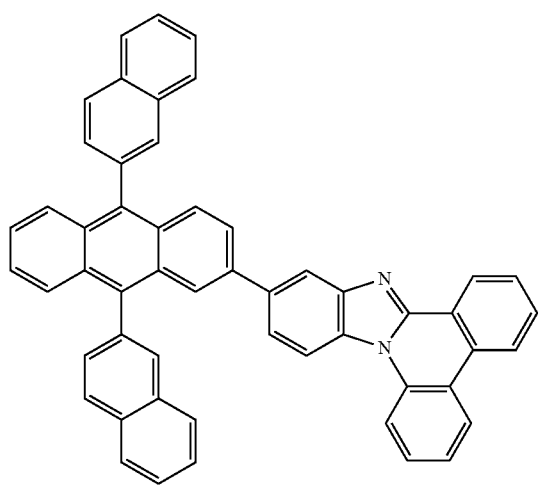 [SMILES: c1ccc2cc(-c3c4ccccc4c(-c4ccc5ccccc5c4)c4cc(-c5ccc6c(c5)nc5c7ccccc7c7ccccc7n65)ccc34)ccc2c1]
1-c-16
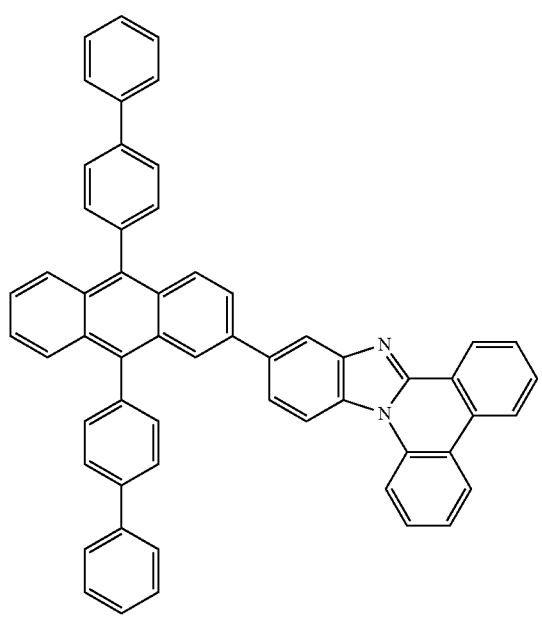 [SMILES: c1ccc(-c2ccc(-c3c4ccccc4c(-c4ccc(-c5ccccc5)cc4)c4cc(-c5ccc6c(c5)nc5c7ccccc7c7ccccc7n65)ccc34)cc2)cc1]

TABLE 3-continued
1-c-17
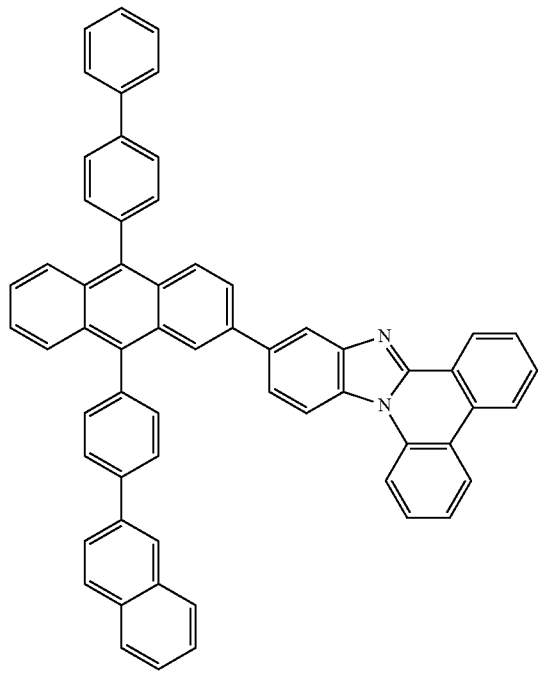 [SMILES: c1ccc(-c2ccc(-c3c4ccccc4c(-c4ccc(-c5ccc6ccccc6c5)cc4)c4cc(-c5ccc6c(c5)nc5c7ccccc7c7ccccc7n65)ccc34)cc2)cc1]
1-c-18
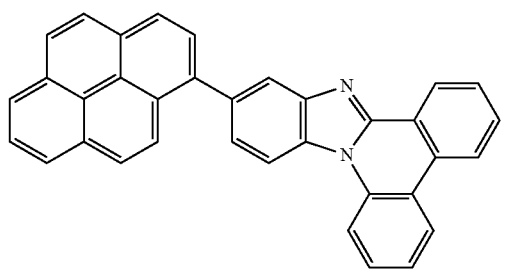 [SMILES: c1cc2ccc3ccc(-c4ccc5c(c4)nc4c6ccccc6c6ccccc6n54)c4ccc(c1)c2c34]
1-c-19
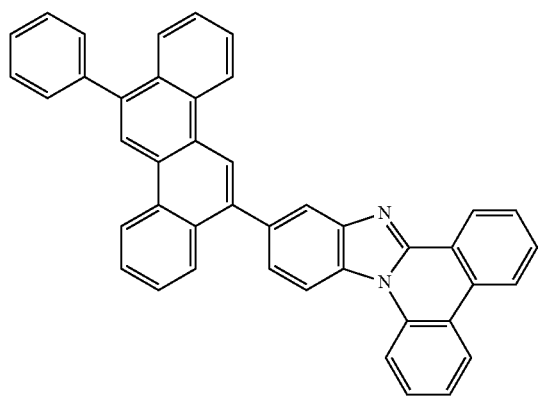 [SMILES: c1ccc(-c2cc3c4ccccc4c(-c4ccc5c(c4)nc4c6ccccc6c6ccccc6n54)cc3c3ccccc23)cc1]

TABLE 3-continued
1-c-20
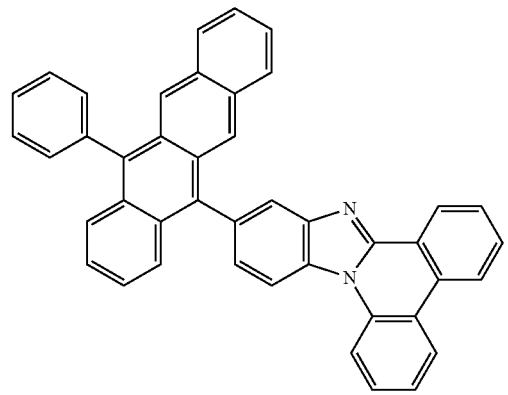 [SMILES: c1ccc(-c2c3ccccc3c(-c3ccc4c(c3)nc3c5ccccc5c5ccccc5n43)c3cc4ccccc4cc23)cc1]
1-c-21
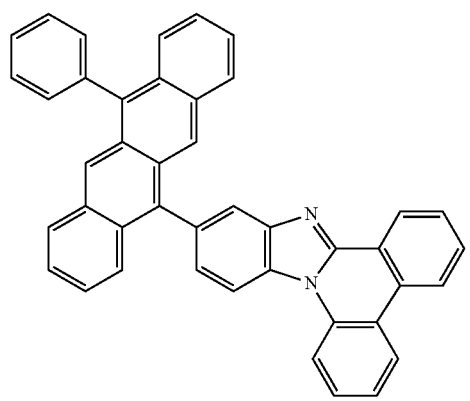 [SMILES: c1ccc(-c2c3ccccc3cc3c(-c4ccc5c(c4)nc4c6ccccc6c6ccccc6n54)c4ccccc4cc23)cc1]
1-c-22
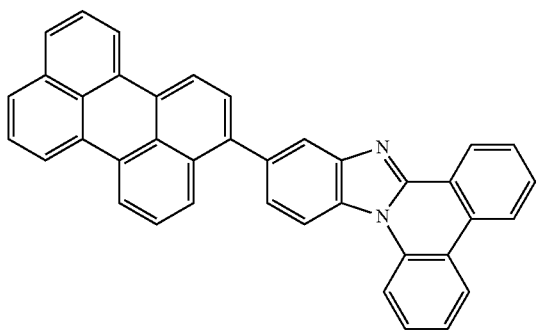 [SMILES: c1ccc2c(c1)c1ccccc1n1c3ccc(-c4ccc5c6cccc7cccc(c8cccc4c85)c76)cc3nc21]
1-c-23
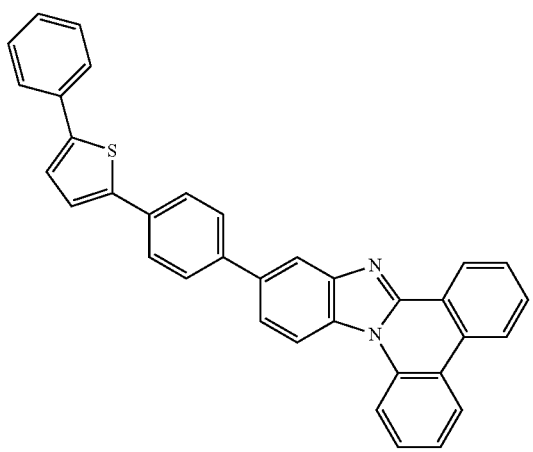 [SMILES: c1ccc(-c2ccc(-c3ccc(-c4ccc5c(c4)nc4c6ccccc6c6ccccc6n54)cc3)s2)cc1]

TABLE 3-continued
1-c-24
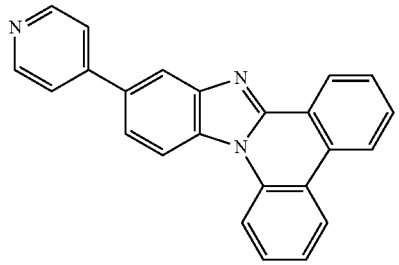 [SMILES: c1ccc2c(c1)c1ccccc1n1c3ccc(-c4ccncc4)cc3nc21]
1-c-25
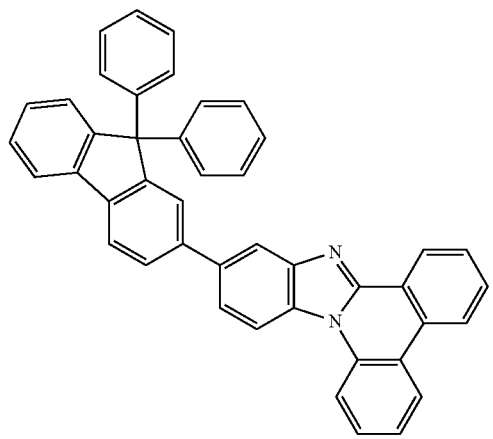 [SMILES: c1ccc(C2(c3ccccc3)c3ccccc3-c3ccc(-c4ccc5c(c4)nc4c6ccccc6c6ccccc6n54)cc32)cc1]
1-c-26
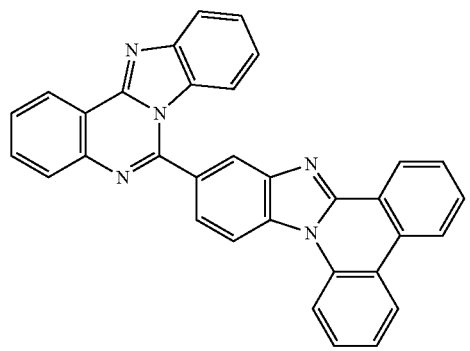 [SMILES: c1ccc2c(c1)nc(-c1ccc3c(c1)nc1c4ccccc4c4ccccc4n31)n1c3ccccc3nc21]
1-c-27
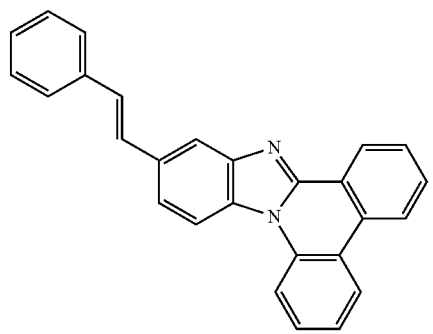 [SMILES: C(=C\c1ccc2c(c1)nc1c3ccccc3c3ccccc3n21)/c1ccccc1]

TABLE 3-continued
1-c-28
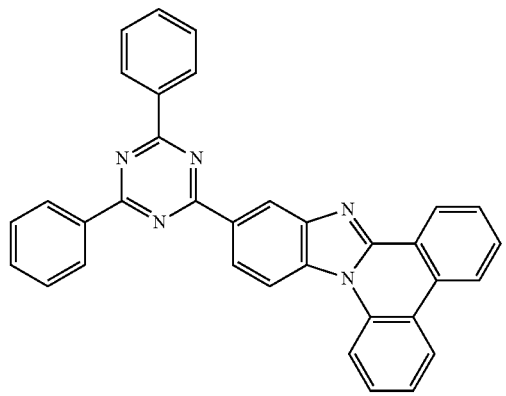 [SMILES: c1ccc(-c2nc(-c3ccccc3)nc(-c3ccc4c(c3)nc3c5ccccc5c5ccccc5n43)n2)cc1]
1-c-29
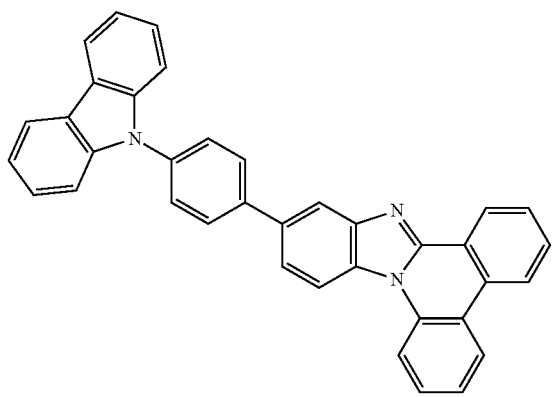 [SMILES: c1ccc2c(c1)c1ccccc1n1c3ccc(-c4ccc(-n5c6ccccc6c6ccccc65)cc4)cc3nc21]
1-c-30
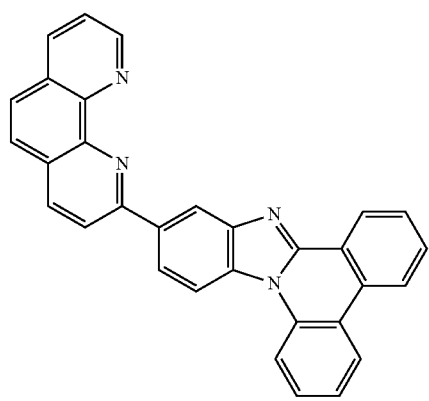 [SMILES: c1cnc2c(c1)ccc1ccc(-c3ccc4c(c3)nc3c5ccccc5c5ccccc5n43)nc12]
1-c-31
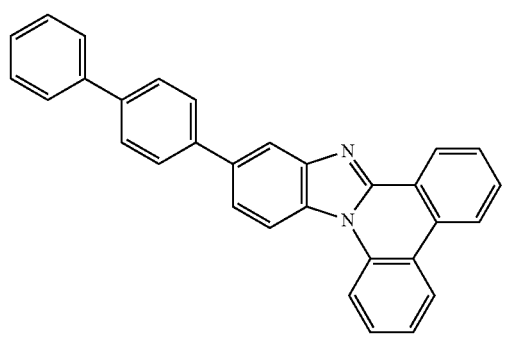 [SMILES: c1ccc(-c2ccc(-c3ccc4c(c3)nc3c5ccccc5c5ccccc5n43)cc2)cc1]

TABLE 3-continued
1-c-32 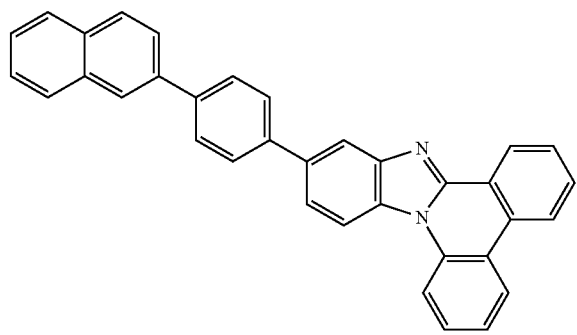 [SMILES: c1ccc2cc(-c3ccc(-c4ccc5c(c4)nc4c6ccccc6c6ccccc6n54)cc3)ccc2c1]
1-c-33 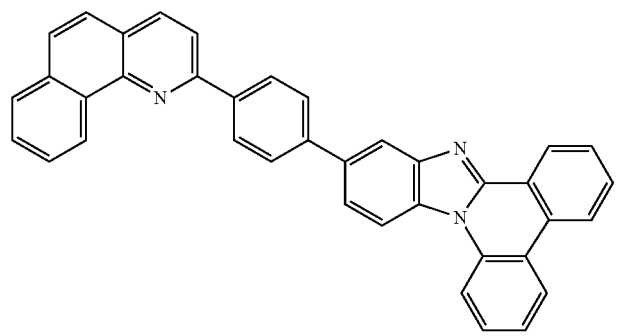 [SMILES: c1ccc2c(c1)ccc1ccc(-c3ccc(-c4ccc5c(c4)nc4c6ccccc6c6ccccc6n54)cc3)nc12]
1-c-34 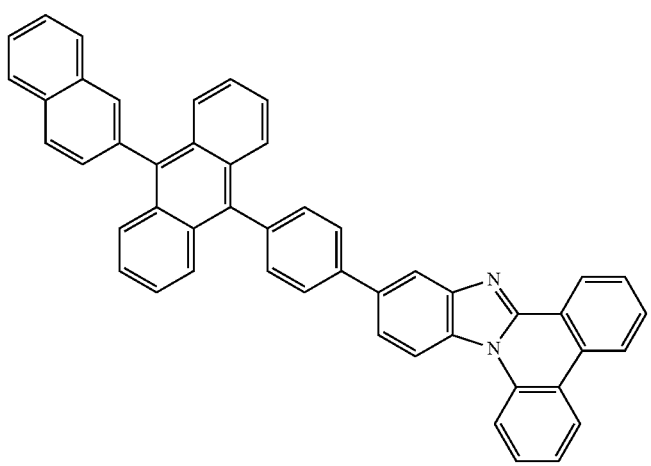 [SMILES: c1ccc2cc(-c3c4ccccc4c(-c4ccc(-c5ccc6c(c5)nc5c7ccccc7c7ccccc7n65)cc4)c4ccccc34)ccc2c1]
1-c-35 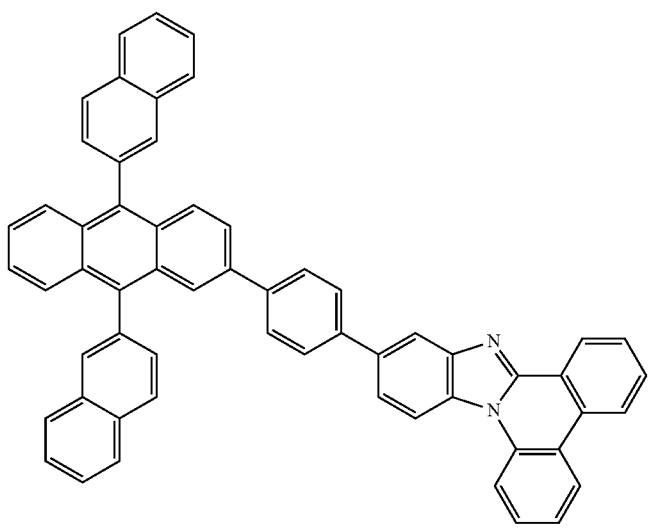 [SMILES: c1ccc2cc(-c3c4ccccc4c(-c4ccc5ccccc5c4)c4cc(-c5ccc(-c6ccc7c(c6)nc6c8ccccc8c8ccccc8n76)cc5)ccc34)ccc2c1]

TABLE 3-continued
1-c-36
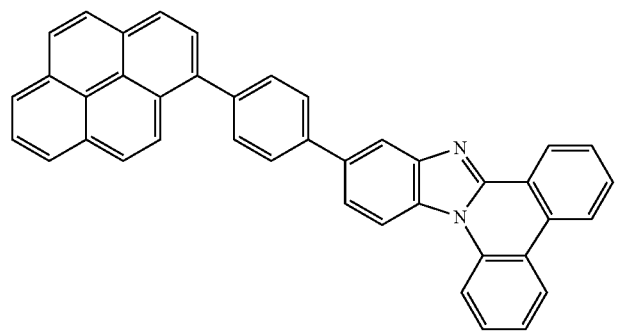 [SMILES: c1cc2ccc3ccc(-c4ccc(-c5ccc6c(c5)nc5c7ccccc7c7ccccc7n65)cc4)c4ccc(c1)c2c34]
1-c-37
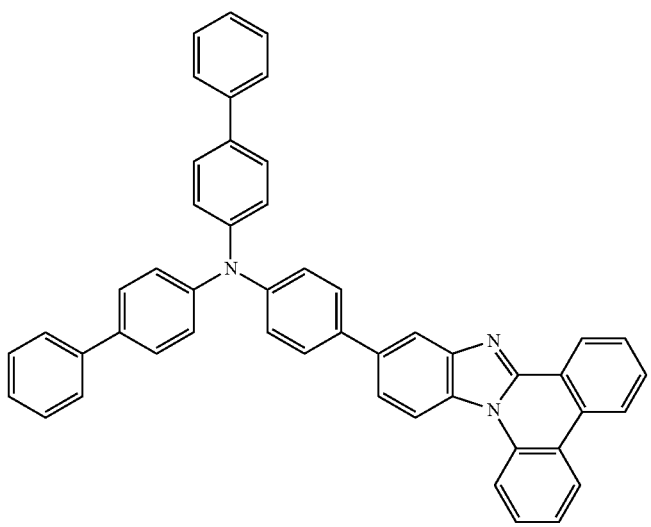 [SMILES: c1ccc(-c2ccc(N(c3ccc(-c4ccccc4)cc3)c3ccc(-c4ccc5c(c4)nc4c6ccccc6c6ccccc6n54)cc3)cc2)cc1]
1-c-38
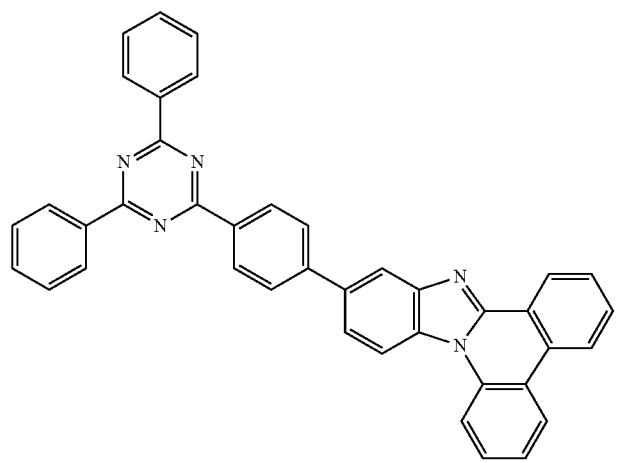 [SMILES: c1ccc(-c2nc(-c3ccccc3)nc(-c3ccc(-c4ccc5c(c4)nc4c6ccccc6c6ccccc6n54)cc3)n2)cc1]

TABLE 3-continued
1-c-39
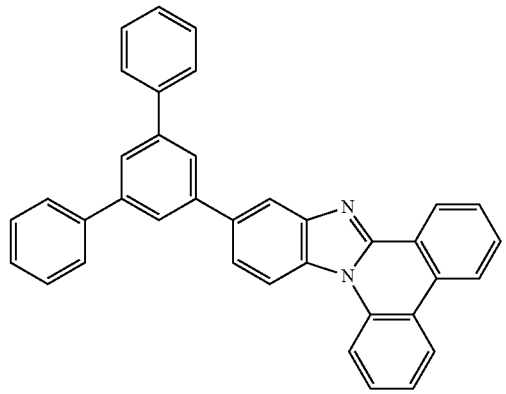 [SMILES: c1ccc(-c2cc(-c3ccccc3)cc(-c3ccc4c(c3)nc3c5ccccc5c5ccccc5n43)c2)cc1]
1-c-40
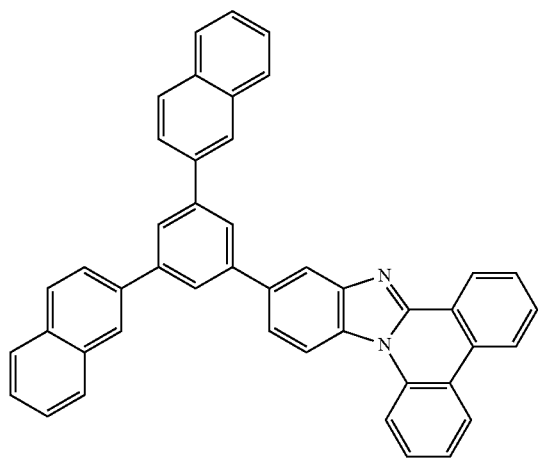 [SMILES: c1ccc2cc(-c3cc(-c4ccc5ccccc5c4)cc(-c4ccc5c(c4)nc4c6ccccc6c6ccccc6n54)c3)ccc2c1]
1-c-41
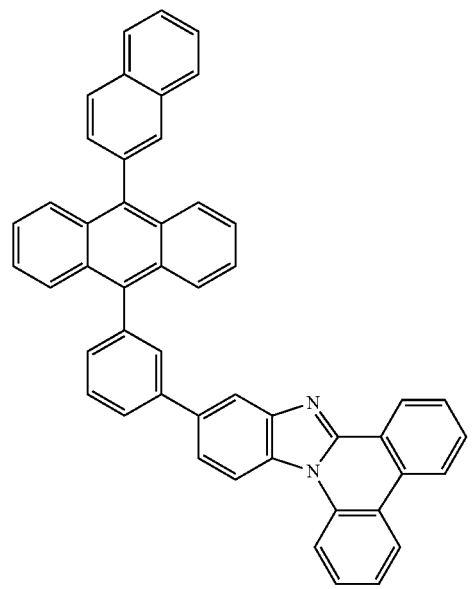 [SMILES: c1cc(-c2ccc3c(c2)nc2c4ccccc4c4ccccc4n32)cc(-c2c3ccccc3c(-c3ccc4ccccc4c3)c3ccccc23)c1]

TABLE 3-continued
1-c-42
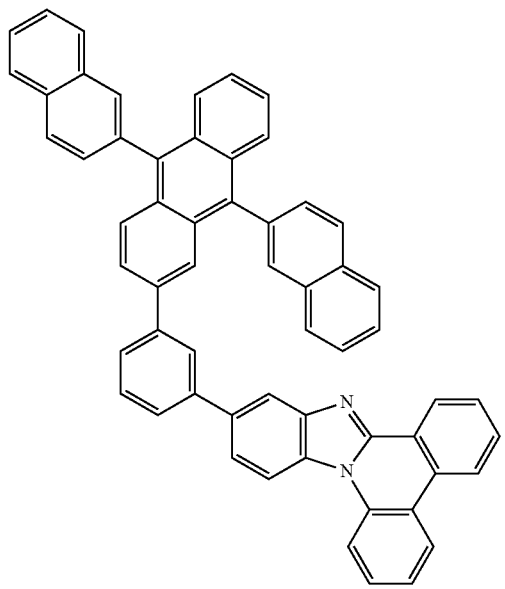 [SMILES: c1cc(-c2ccc3c(c2)nc2c4ccccc4c4ccccc4n32)cc(-c2ccc3c(-c4ccc5ccccc5c4)c4ccccc4c(-c4ccc5ccccc5c4)c3c2)c1]
1-c-43
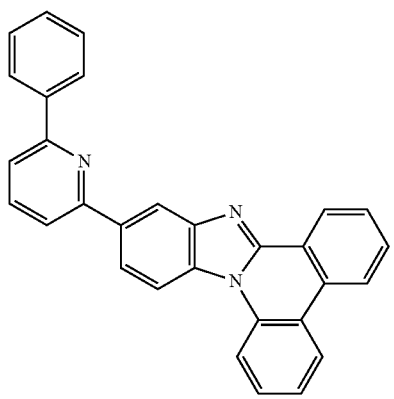 [SMILES: c1ccc(-c2cccc(-c3ccc4c(c3)nc3c5ccccc5c5ccccc5n43)n2)cc1]
1-c-44
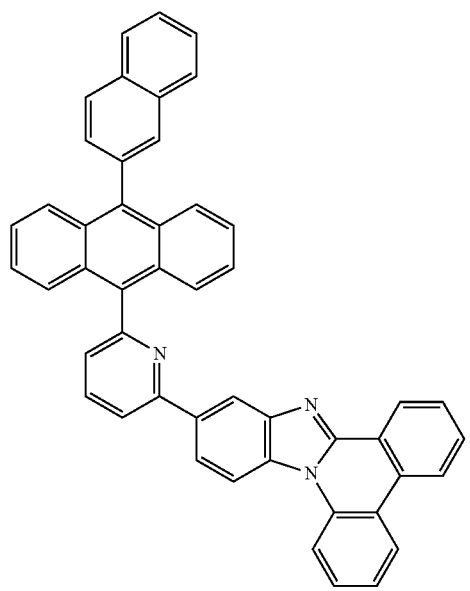 [SMILES: c1cc(-c2ccc3c(c2)nc2c4ccccc4c4ccccc4n32)nc(-c2c3ccccc3c(-c3ccc4ccccc4c3)c3ccccc23)c1]

TABLE 3-continued
1-c-45
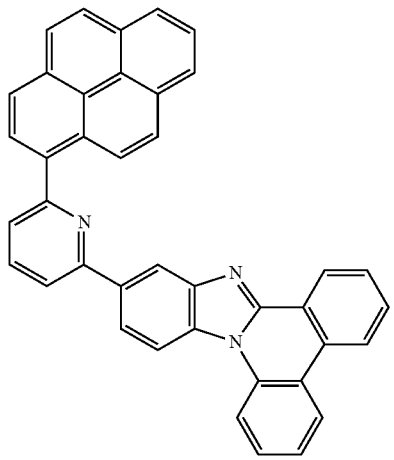 [SMILES: c1cc(-c2ccc3c(c2)nc2c4ccccc4c4ccccc4n32)nc(-c2ccc3ccc4cccc5ccc2c3c45)c1]
1-c-46
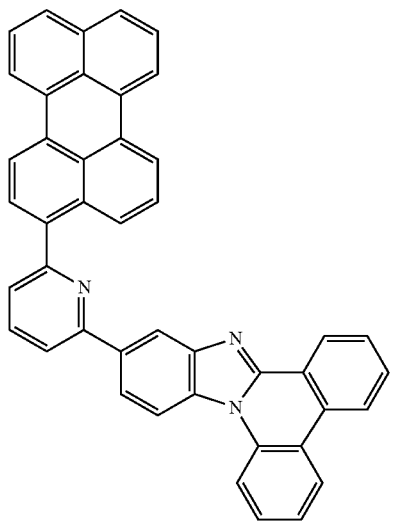 [SMILES: c1cc(-c2ccc3c(c2)nc2c4ccccc4c4ccccc4n32)nc(-c2ccc3c4cccc5cccc(c6cccc2c63)c54)c1]
1-c-47
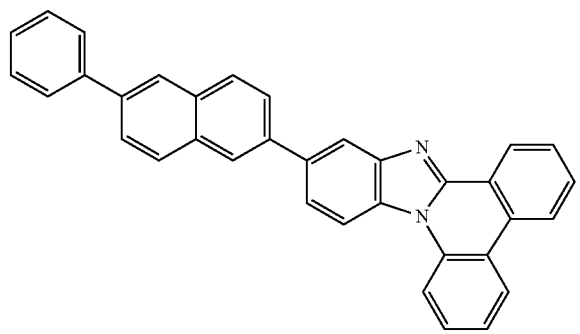 [SMILES: c1ccc(-c2ccc3cc(-c4ccc5c(c4)nc4c6ccccc6c6ccccc6n54)ccc3c2)cc1]

TABLE 3-continued
1-c-48
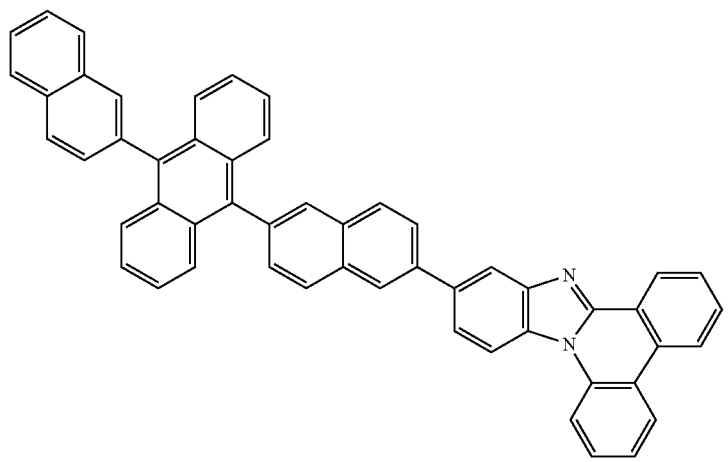 [SMILES: c1ccc2cc(-c3c4ccccc4c(-c4ccc5cc(-c6ccc7c(c6)nc6c8ccccc8c8ccccc8n76)ccc5c4)c4ccccc34)ccc2c1]
1-c-49
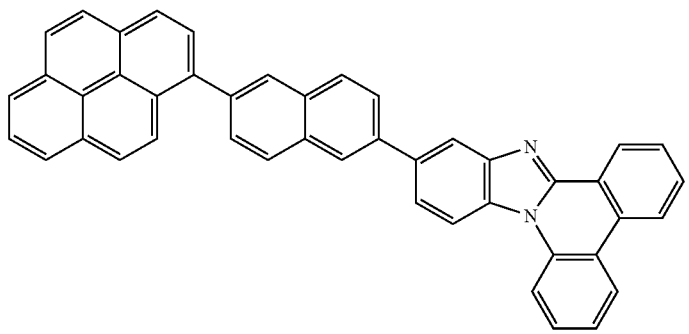 [SMILES: c1cc2ccc3ccc(-c4ccc5cc(-c6ccc7c(c6)nc6c8ccccc8c8ccccc8n76)ccc5c4)c4ccc(c1)c2c34]
1-c-50
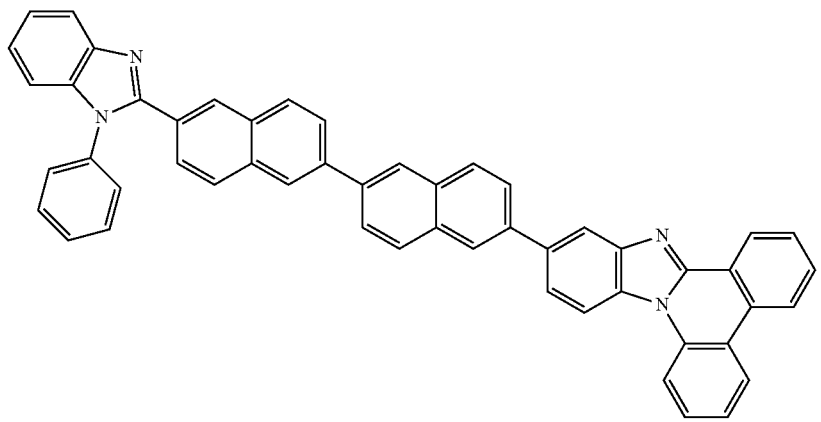 [SMILES: c1ccc(-n2c(-c3ccc4cc(-c5ccc6cc(-c7ccc8c(c7)nc7c9ccccc9c9ccccc9n87)ccc6c5)ccc4c3)nc3ccccc32)cc1]
1-c-51
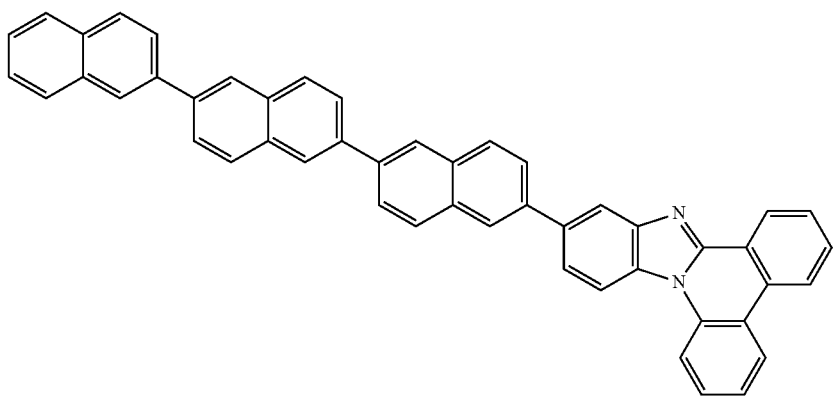 [SMILES: c1ccc2cc(-c3ccc4cc(-c5ccc6cc(-c7ccc8c(c7)nc7c9ccccc9c9ccccc9n87)ccc6c5)ccc4c3)ccc2c1]

TABLE 3-continued
1-c-52
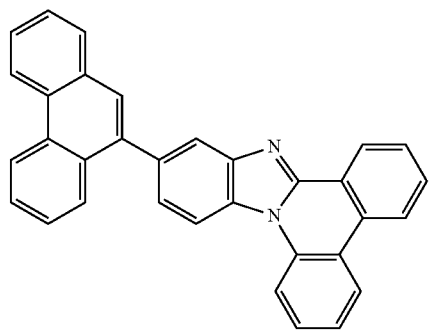 [SMILES: c1ccc2c(c1)cc(-c1ccc3c(c1)nc1c4ccccc4c4ccccc4n31)c1ccccc12]
1-c-53
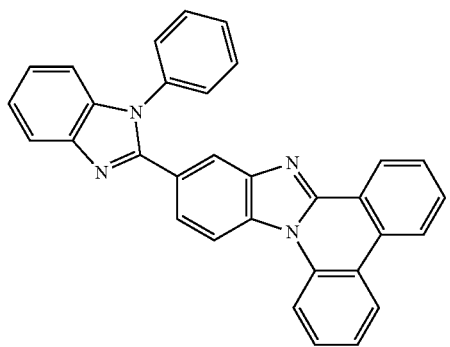 [SMILES: c1ccc(-n2c(-c3ccc4c(c3)nc3c5ccccc5c5ccccc5n43)nc3ccccc32)cc1]
1-c-54
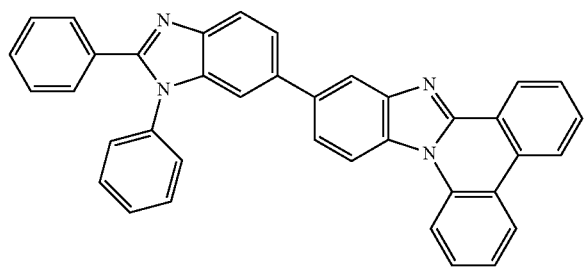 [SMILES: c1ccc(-c2nc3ccc(-c4ccc5c(c4)nc4c6ccccc6c6ccccc6n54)cc3n2-c2ccccc2)cc1]
1-c-55
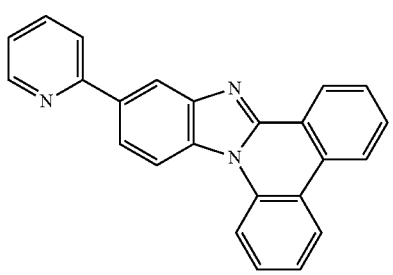 [SMILES: c1ccc(-c2ccc3c(c2)nc2c4ccccc4c4ccccc4n32)nc1]
1-c-56
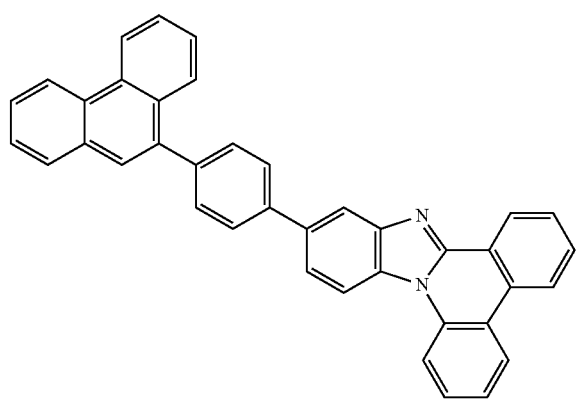 [SMILES: c1ccc2c(c1)cc(-c1ccc(-c3ccc4c(c3)nc3c5ccccc5c5ccccc5n43)cc1)c1ccccc12]

TABLE 3-continued
1-c-57
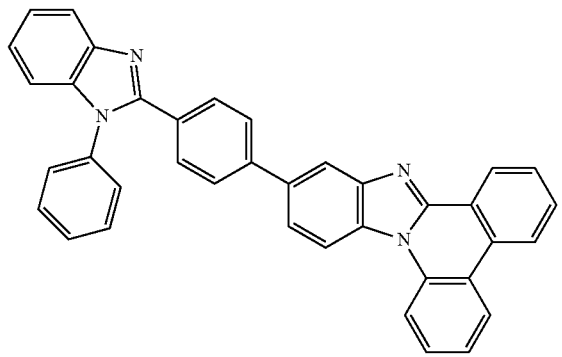 [SMILES: c1ccc(-n2c(-c3ccc(-c4ccc5c(c4)nc4c6ccccc6c6ccccc6n54)cc3)nc3ccccc32)cc1]
1-c-58
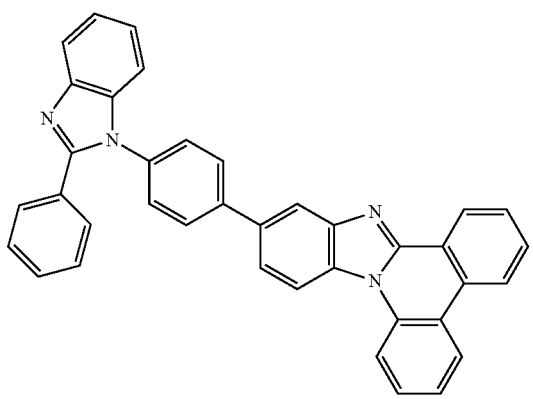 [SMILES: c1ccc(-c2nc3ccccc3n2-c2ccc(-c3ccc4c(c3)nc3c5ccccc5c5ccccc5n43)cc2)cc1]
1-c-59
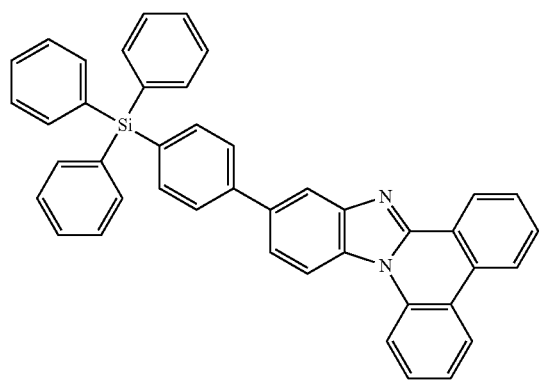 [SMILES: c1ccc([Si](c2ccccc2)(c2ccccc2)c2ccc(-c3ccc4c(c3)nc3c5ccccc5c5ccccc5n43)cc2)cc1]
1-c-60
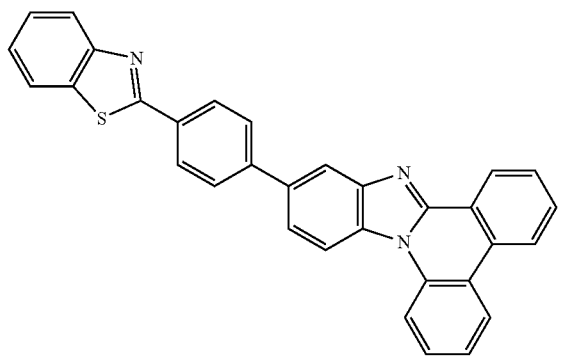 [SMILES: c1ccc2sc(-c3ccc(-c4ccc5c(c4)nc4c6ccccc6c6ccccc6n54)cc3)nc2c1]

TABLE 3-continued
1-c-61
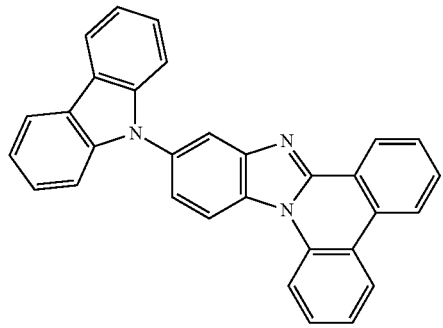 [SMILES: c1ccc2c(c1)c1ccccc1n1c3ccc(-n4c5ccccc5c5ccccc54)cc3nc21]
1-c-62
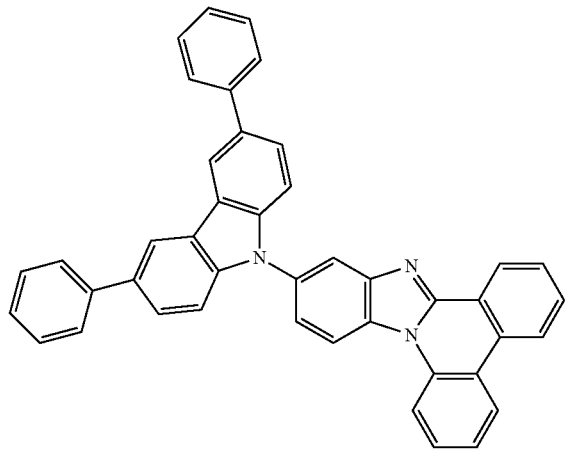 [SMILES: c1ccc(-c2ccc3c(c2)c2cc(-c4ccccc4)ccc2n3-c2ccc3c(c2)nc2c4ccccc4c4ccccc4n32)cc1]
1-c-63
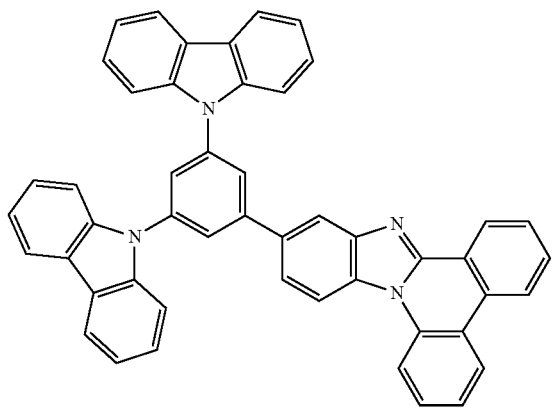 [SMILES: c1ccc2c(c1)c1ccccc1n1c3ccc(-c4cc(-n5c6ccccc6c6ccccc65)cc(-n5c6ccccc6c6ccccc65)c4)cc3nc21]
1-c-64
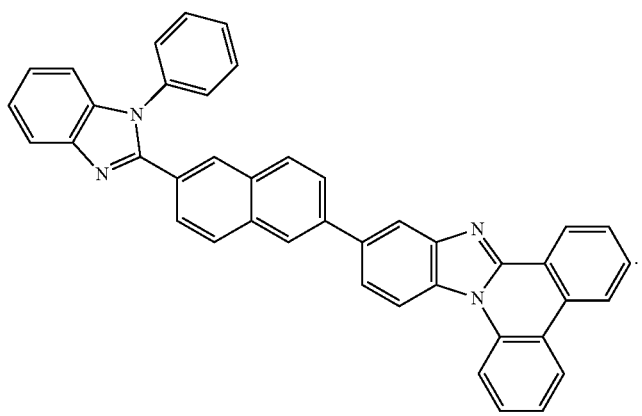 [SMILES: c1ccc(-n2c(-c3ccc4cc(-c5ccc6c(c5)nc5c7ccccc7c7ccccc7n65)ccc4c3)nc3ccccc32)cc1]

6. The nitrogen-containing heterocyclic derivative as set forth in claim 1, wherein the nitrogen-containing heterocyclic derivative is represented by one selected from the following Formulas:
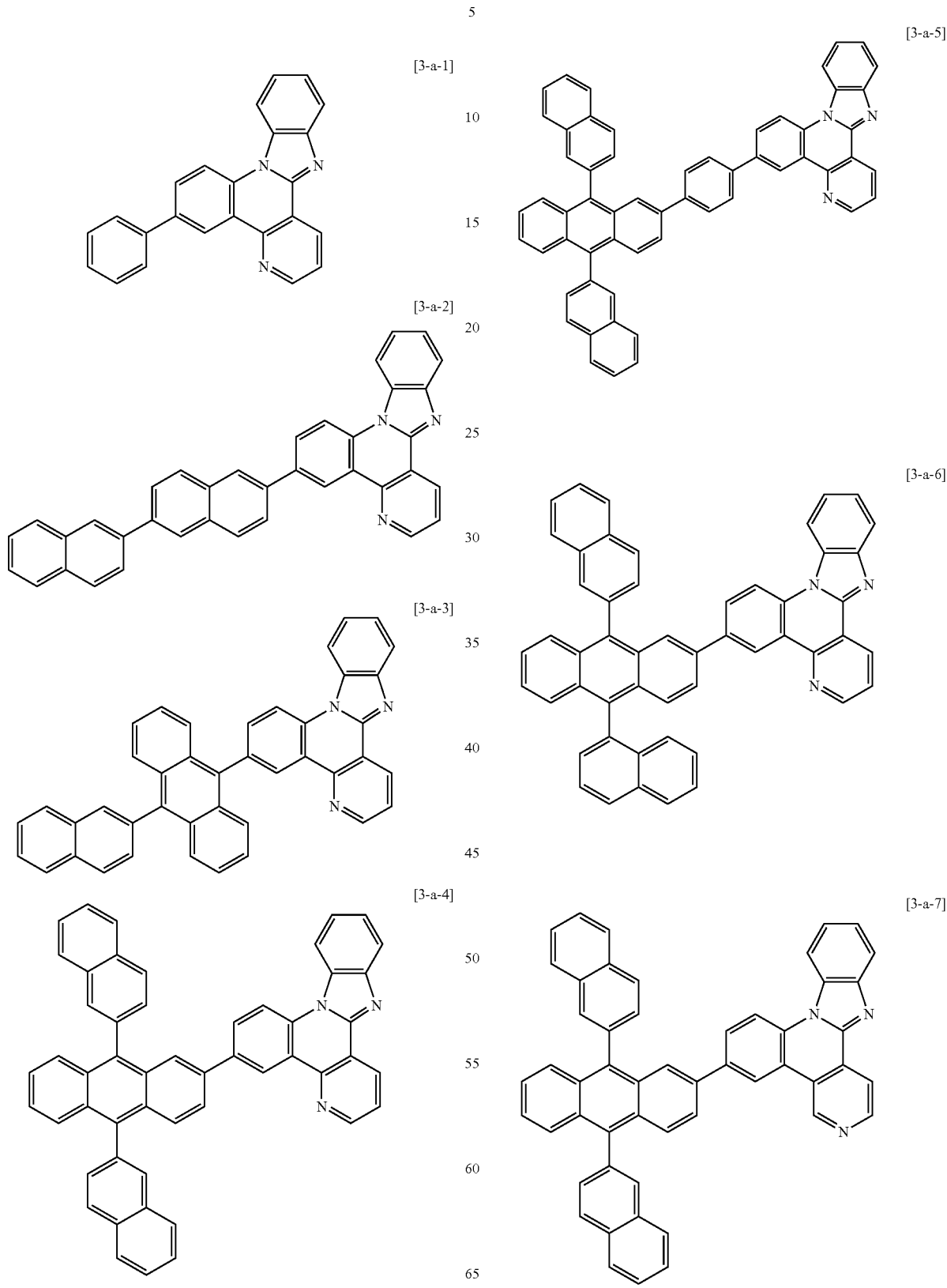

[3-a-8]
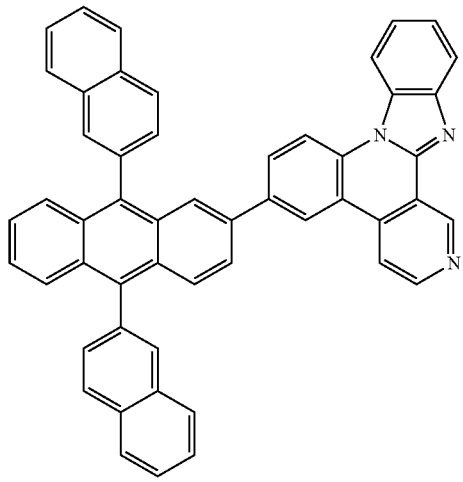
[3-a-9]
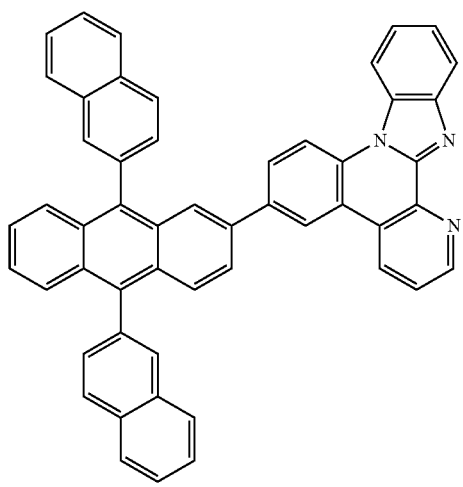
[3-a-10]
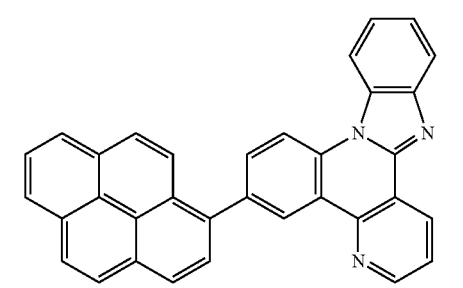
[3-a-11]
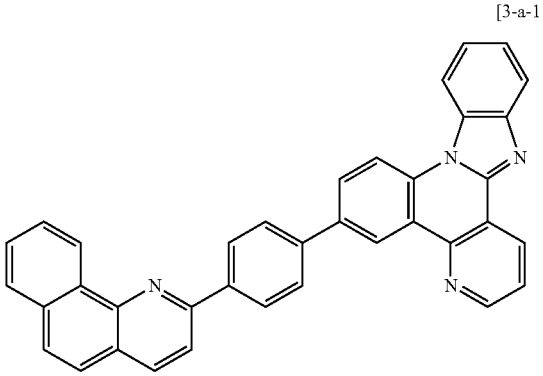
[3-a-12]
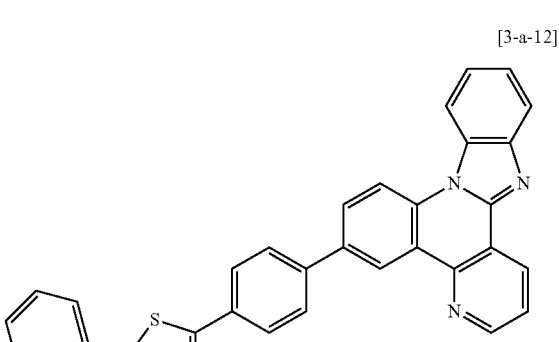
[3-a-13]
[3-a-14]
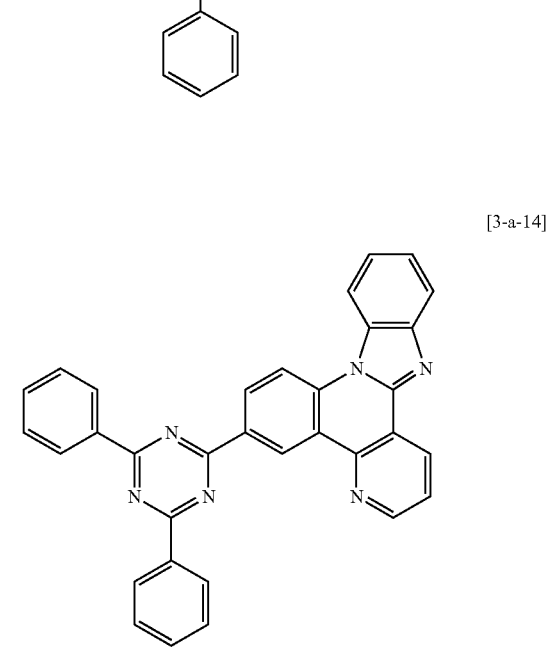

[3-a-15]
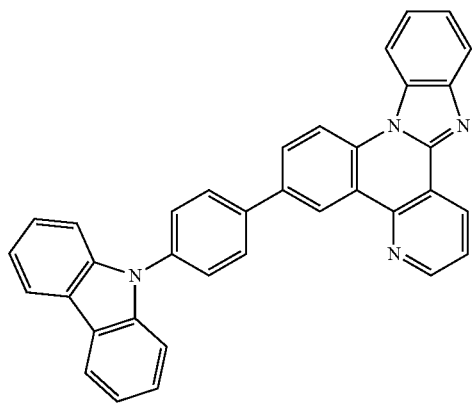
[3-a-16]
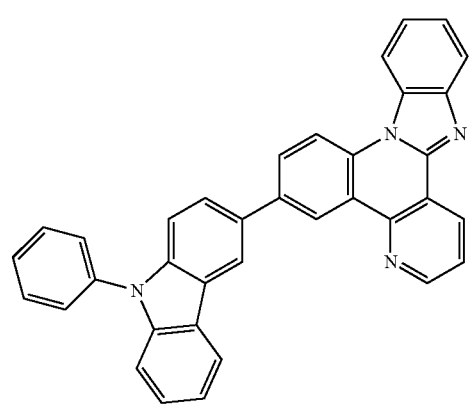
[3-b-1]
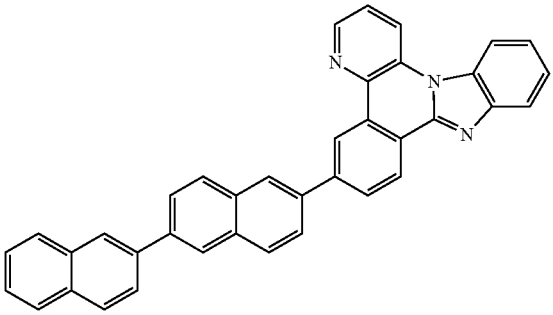
[3-b-2]
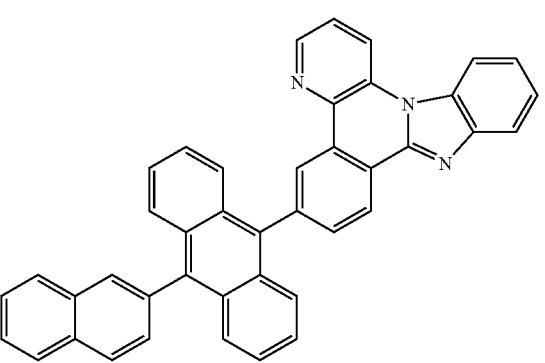
[3-b-3]
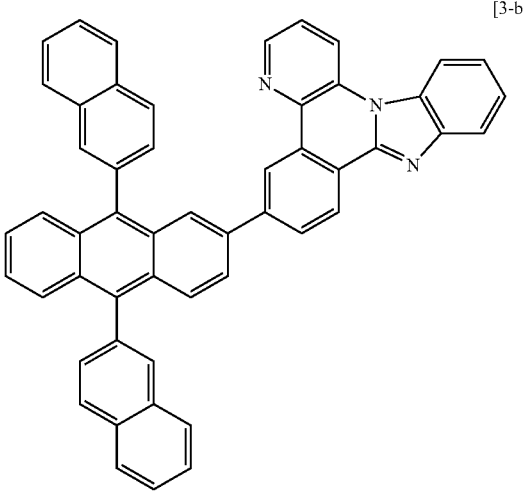
[3-b-4]
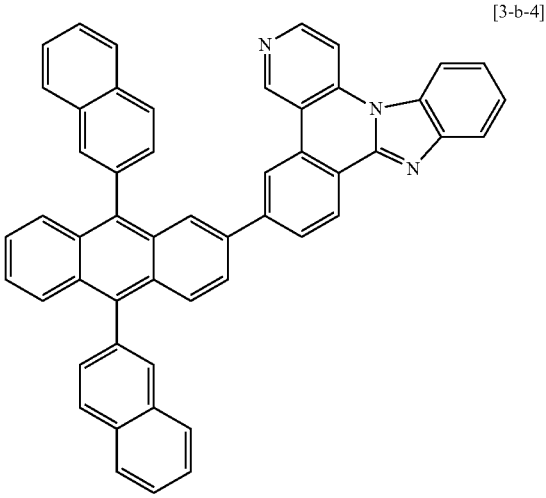
[3-b-5]
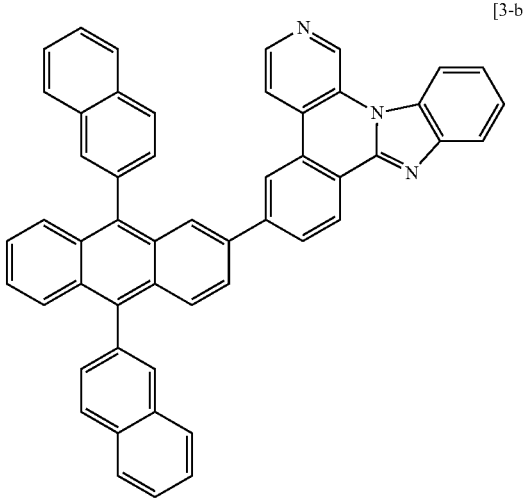

[3-b-6]
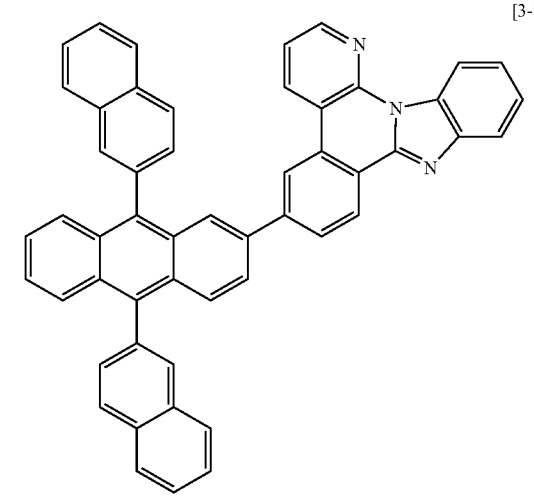
[3-b-9]
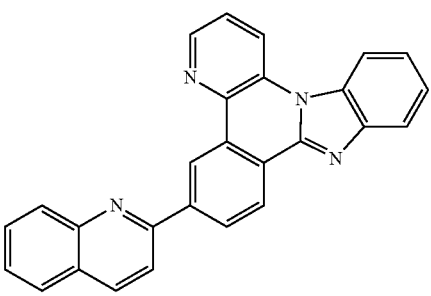
[3-b-10]
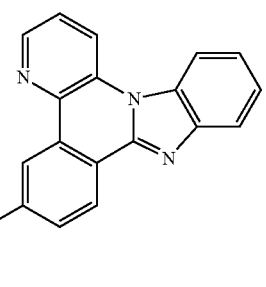
[3-b-7]
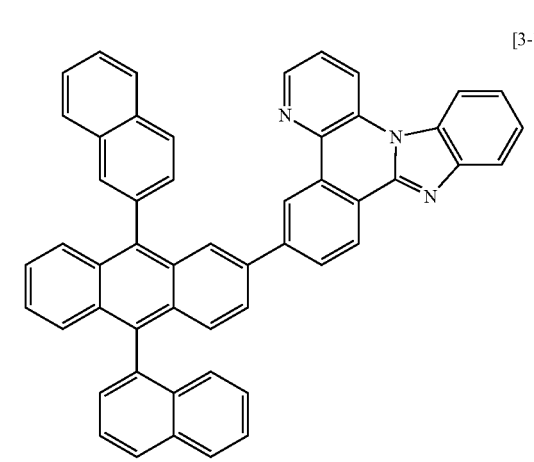
[3-b-11]
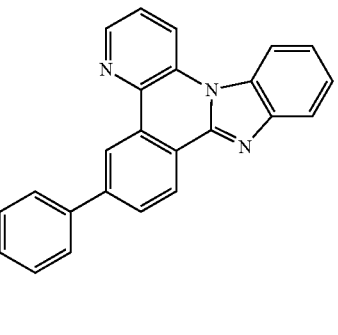
[3-b-8]
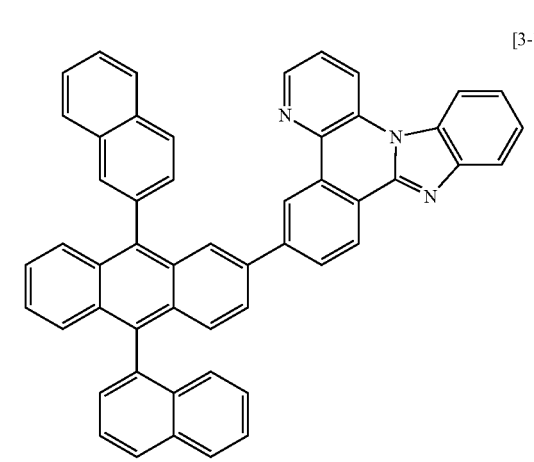
[3-b-12]
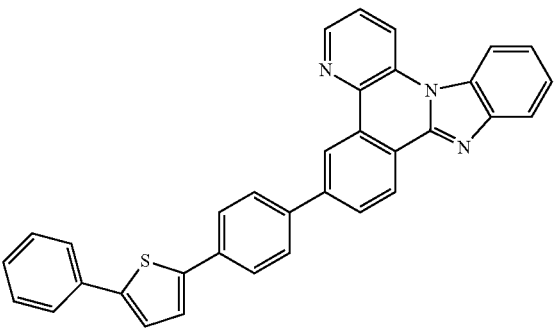

[3-b-13]
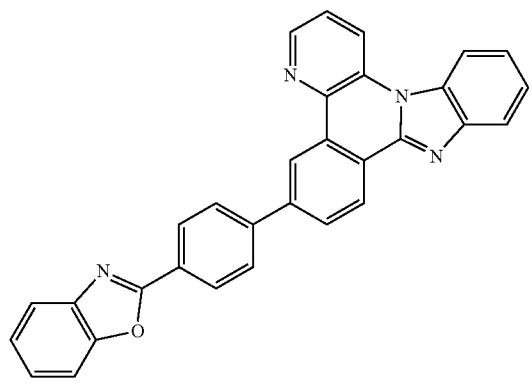
[3-c-1]
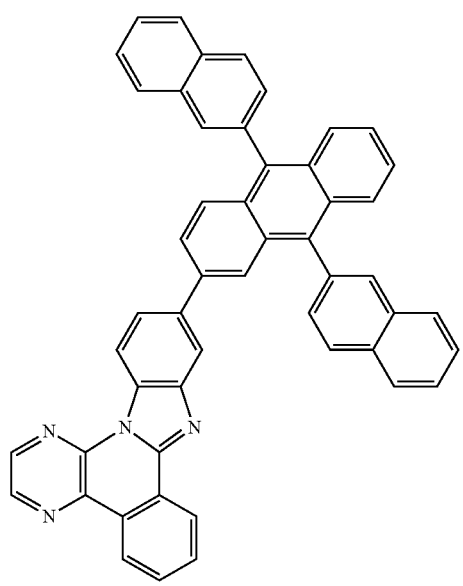
[3-c-2]
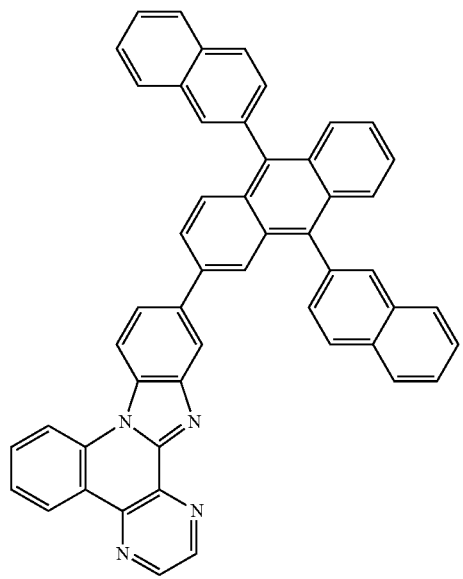
[3-c-3]
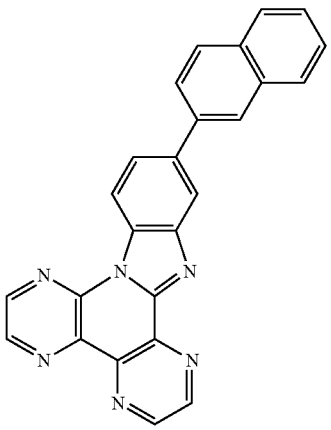
[3-c-4]
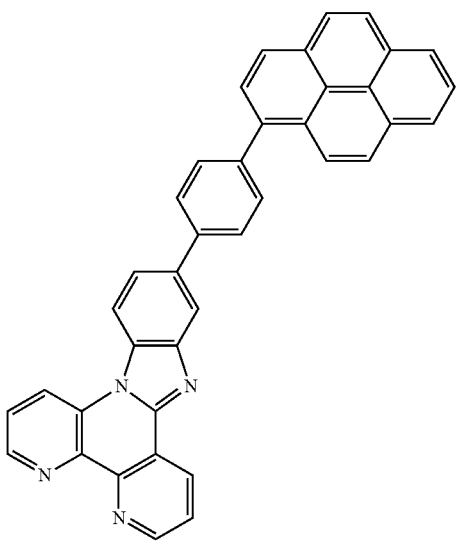
[3-c-5]
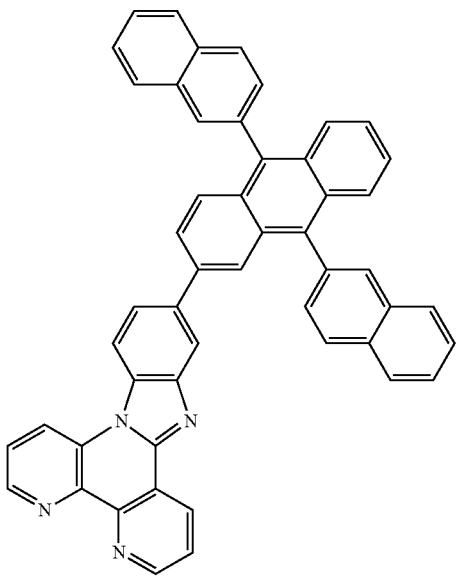

599
-continued
[3-c-6]
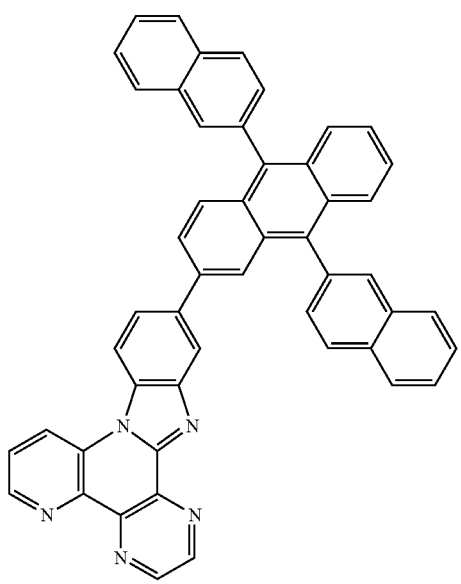
[3-c-7]
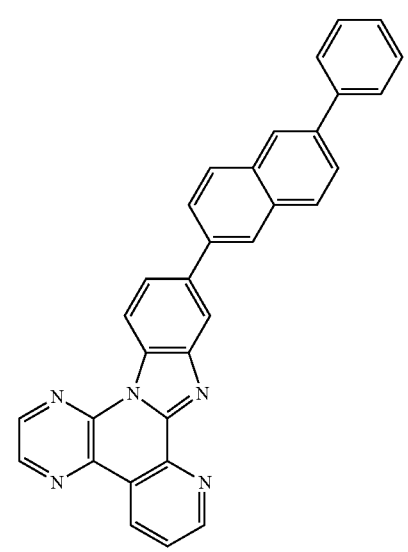
[3-c-8]
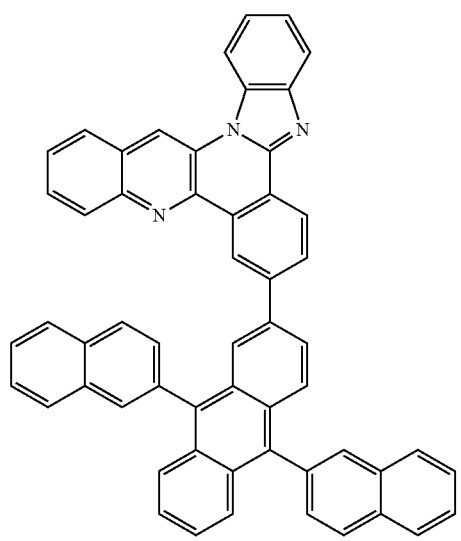
600
-continued
[3-c-9]
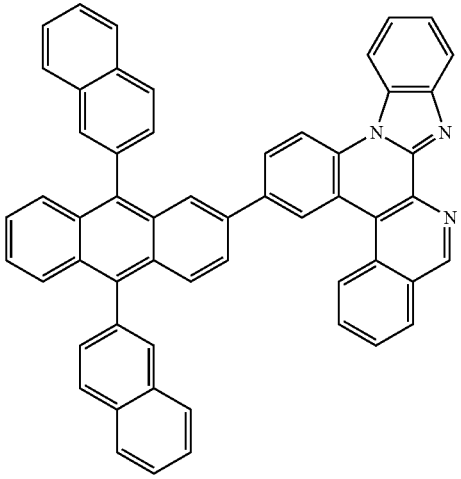
[3-c-10]
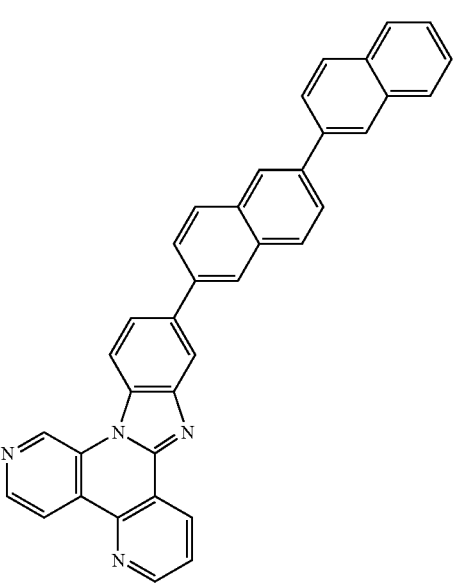
[3-c-11]
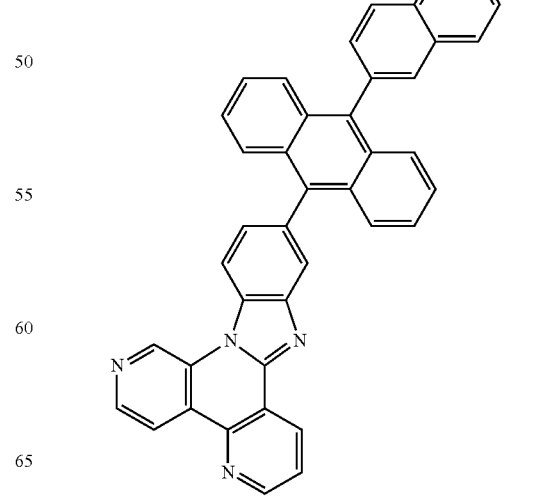

[3-c-12]
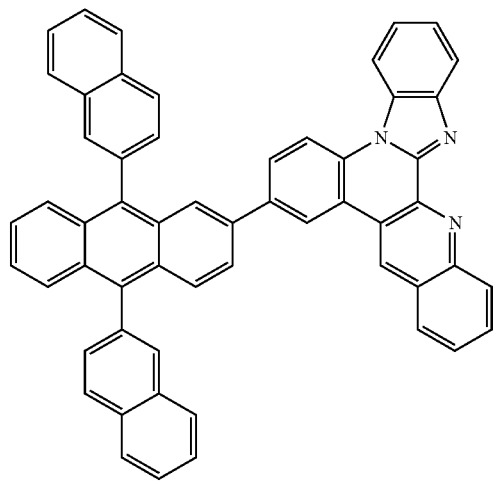
[3-c-13]
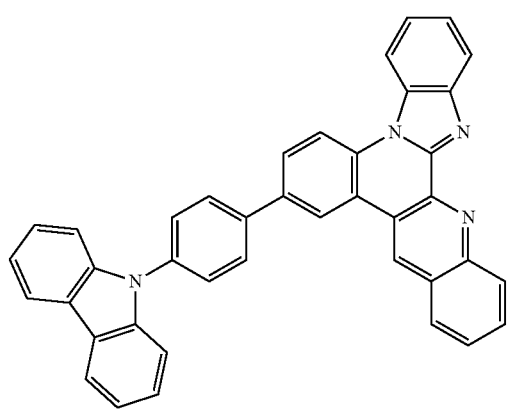
[3-c-14]
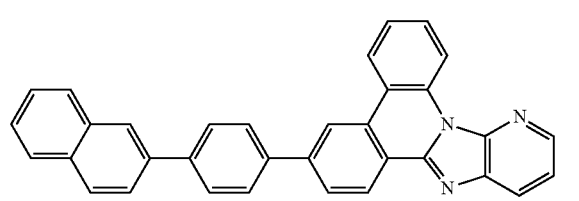
[3-c-15]
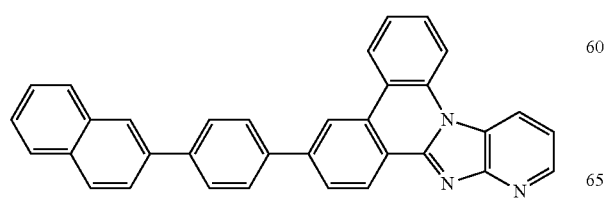
[3-c-16]
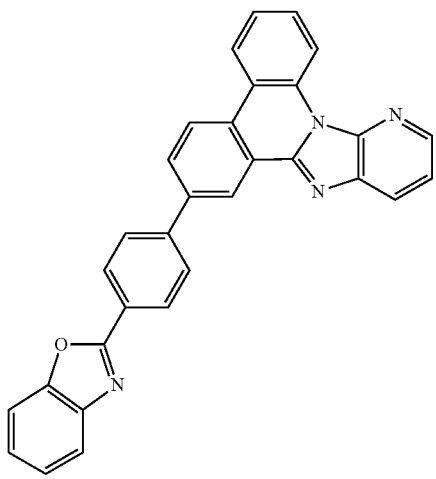
[3-c-17]
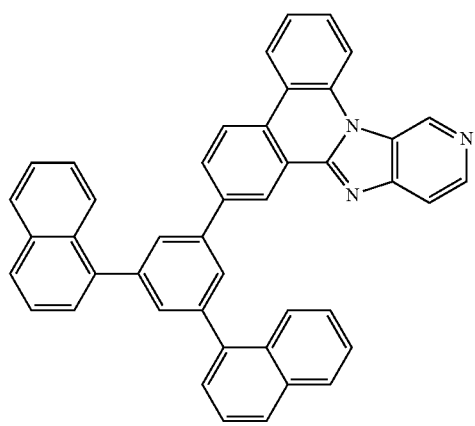
[3-c-18]
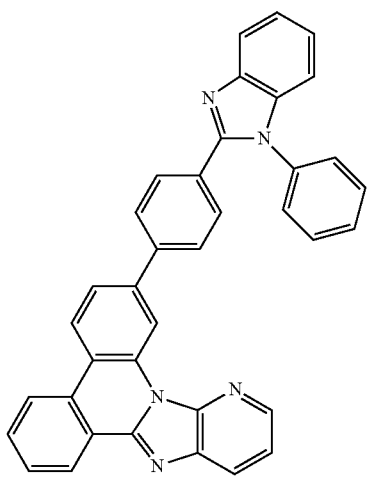

-continued
[3-c-19]
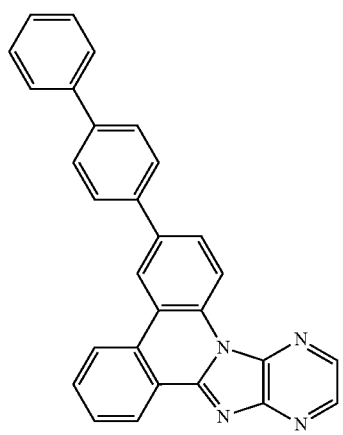
[3-c-20]
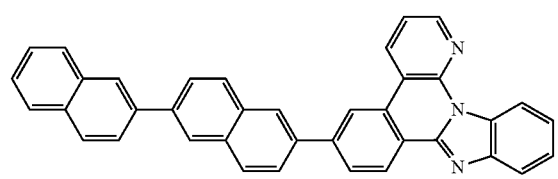
[3-c-21]
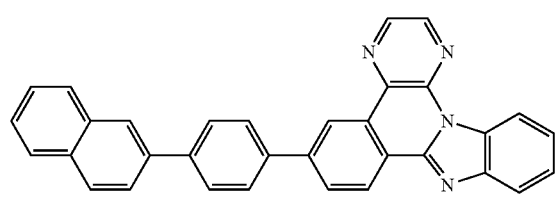
[3-c-22]
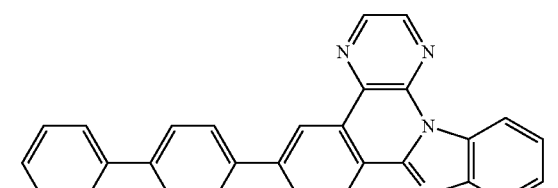
[3-c-23]
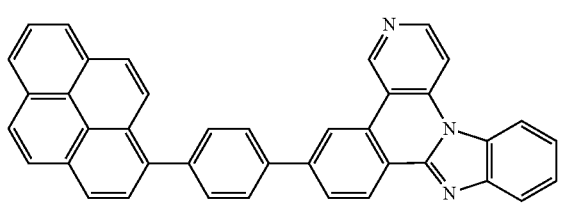
-continued
[3-c-24]
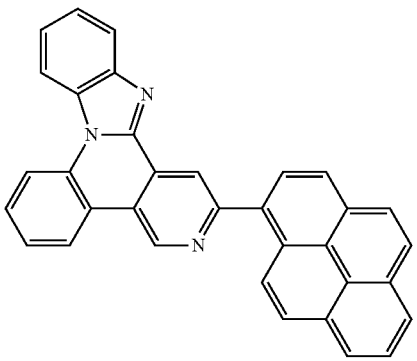
[3-c-25]
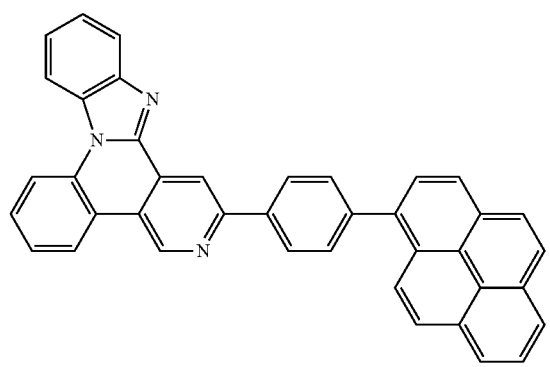
[3-c-26]
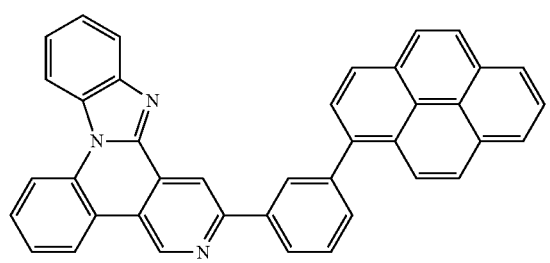
[3-c-27]
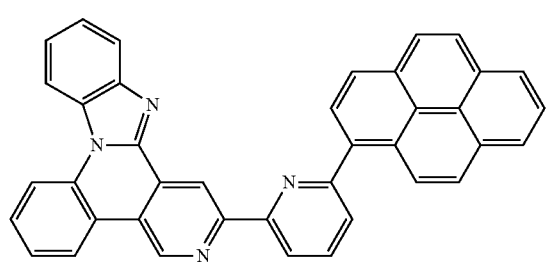
[3-c-28]
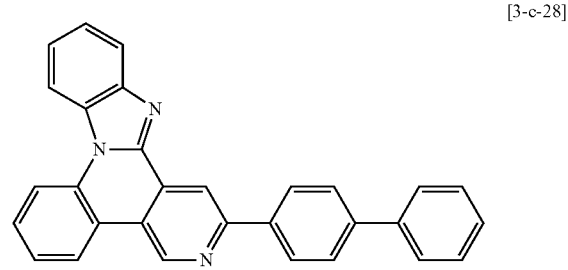

[3-c-29]
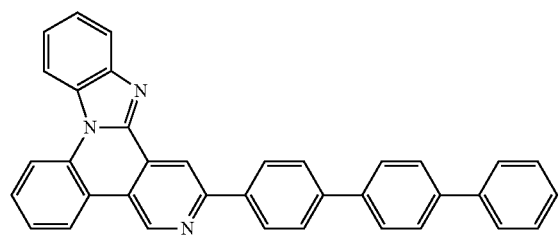
[3-c-30]
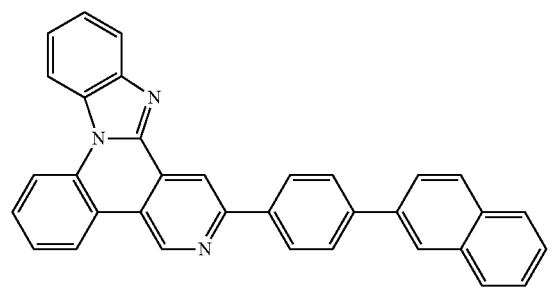
[3-c-31]
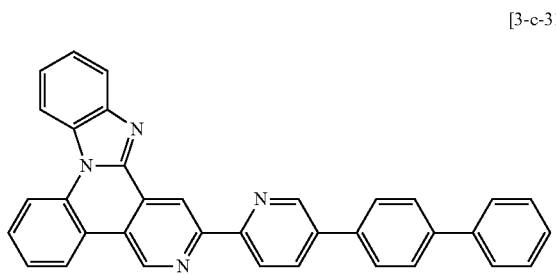
[3-c-32]
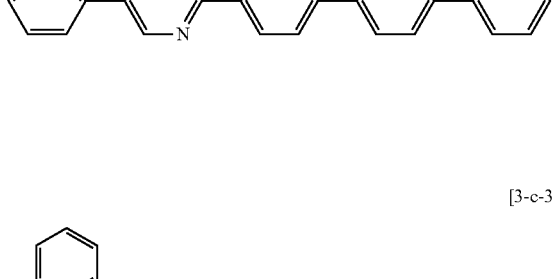
[3-c-33]
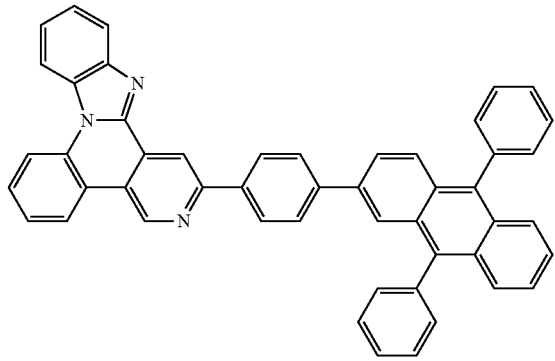
[3-c-34]
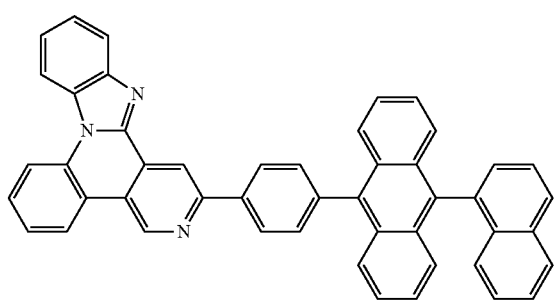
[3-c-35]
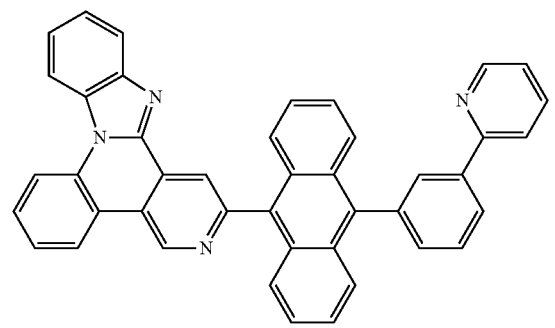
[3-c-36]
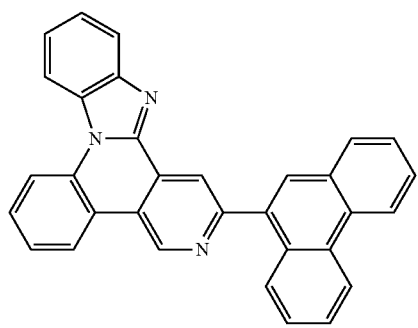

[3-c-37]
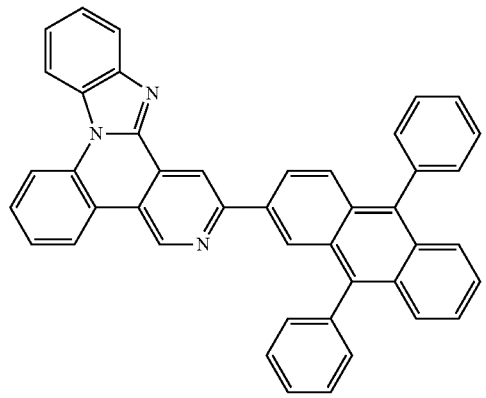
[4-a-1]
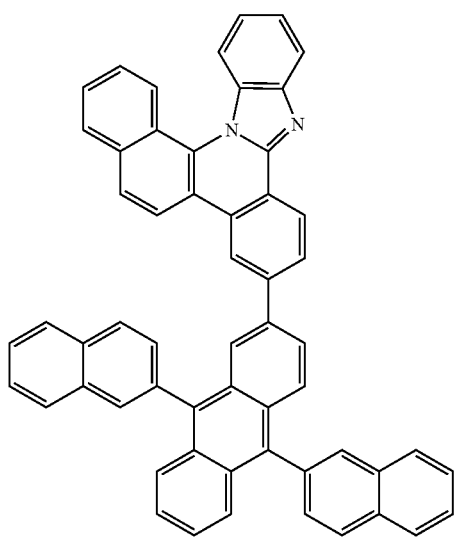
[3-c-38]
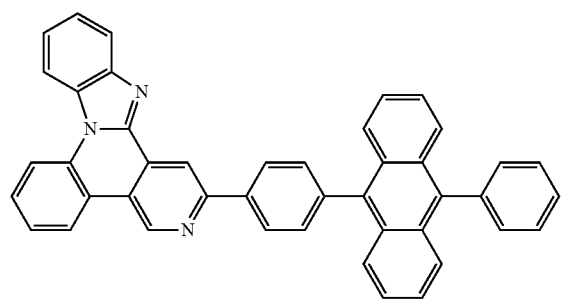
[4-a-2]
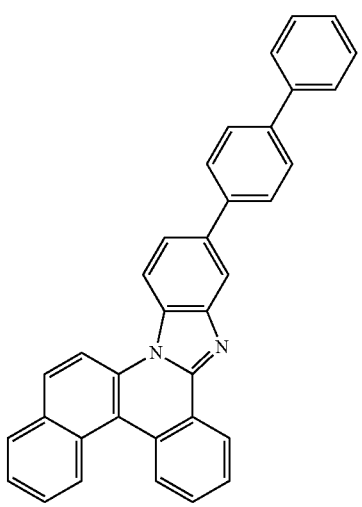
[3-c-39]
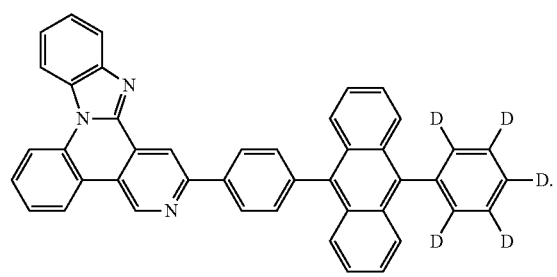
[4-a-3]
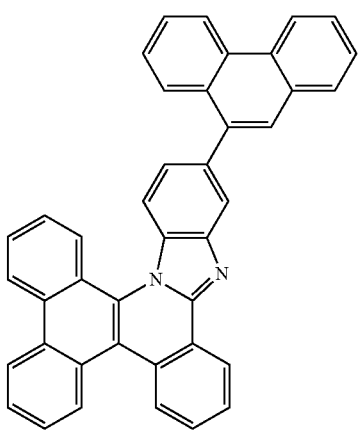
7. The nitrogen-containing heterocyclic derivative as set forth in claim 1, wherein the nitrogen-containing heterocyclic derivative is represented by one selected from the following Formulas:

[4-a-4]
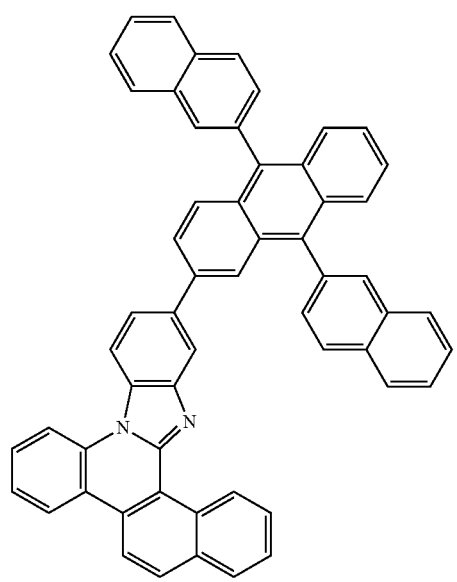
[4-a-7]
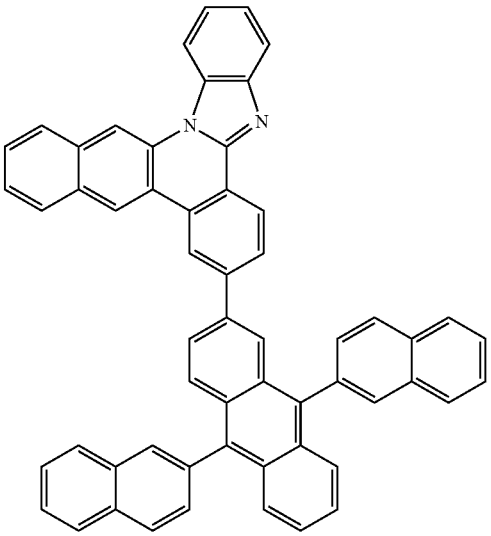
[4-a-5]
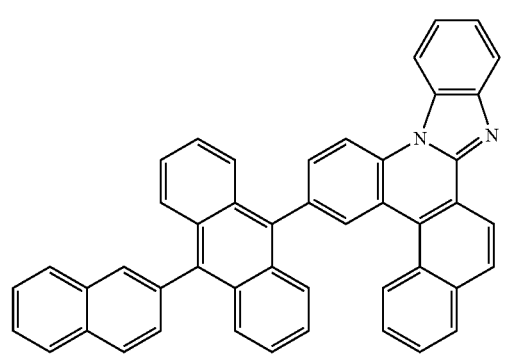
[4-a-8]
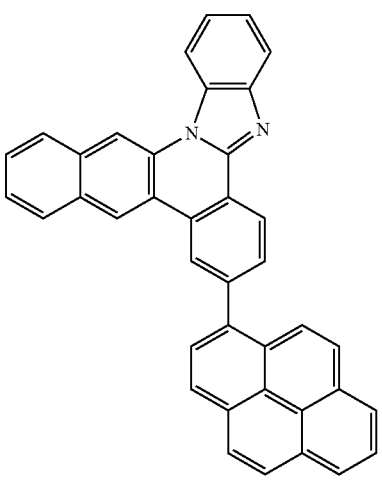
[4-a-6]
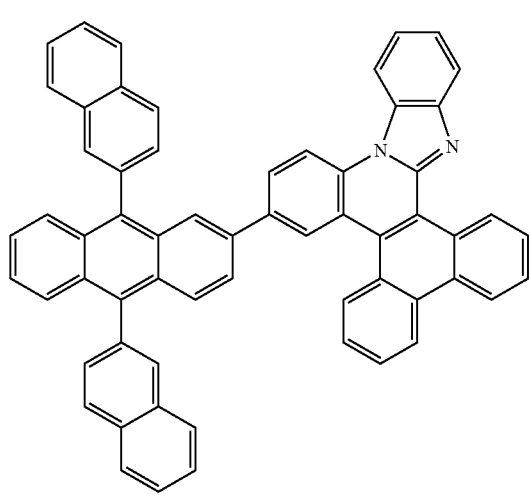
[4-a-9]
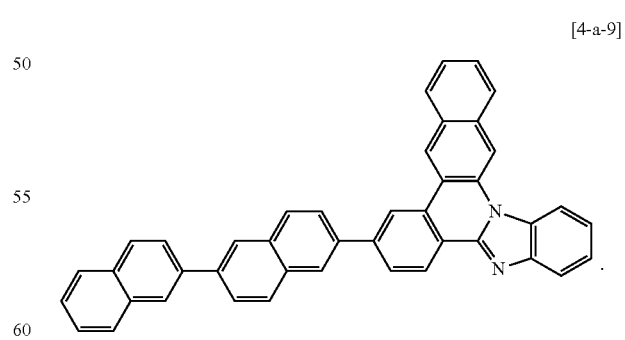
8. The nitrogen-containing heterocyclic derivative as set forth in claim 1, wherein the nitrogen-containing heterocyclic derivative is represented by one selected from the following Formulas:

611 612
[5-a-1]
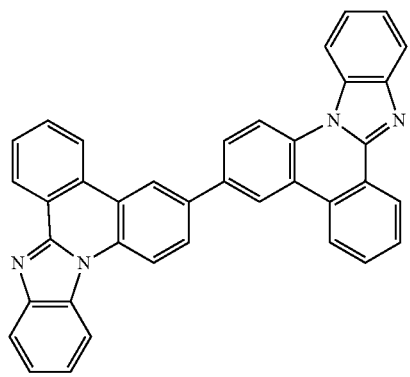
[5-a-2]
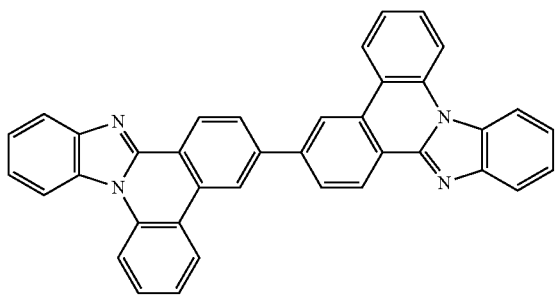
[5-a-3]
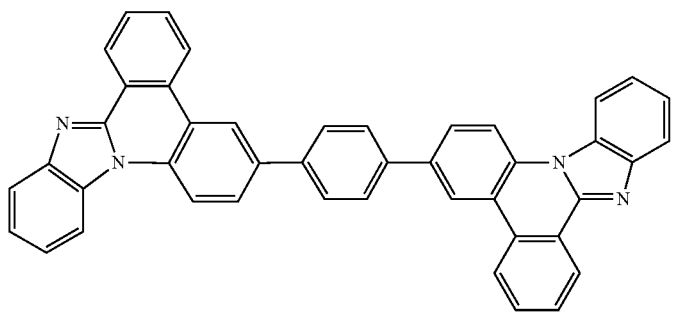
[5-a-4]
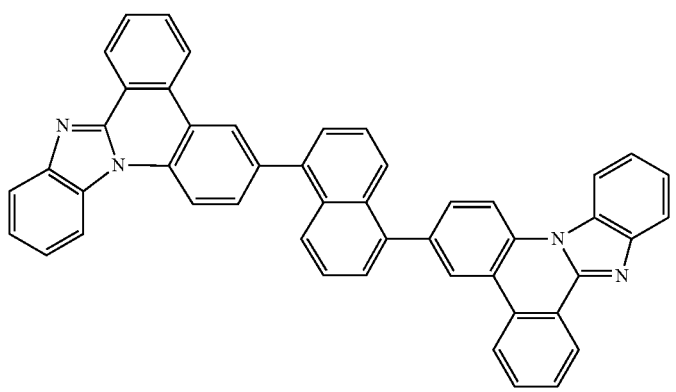
[5-a-5]
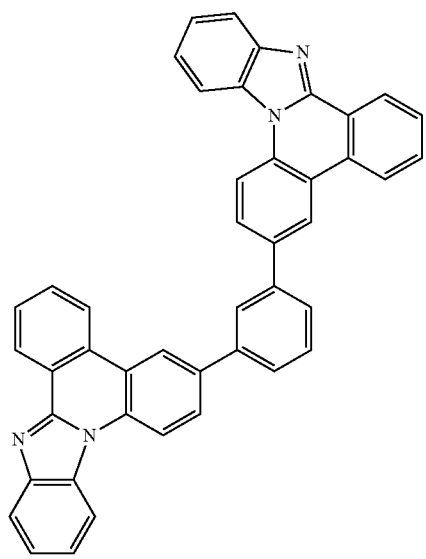
[5-a-6]
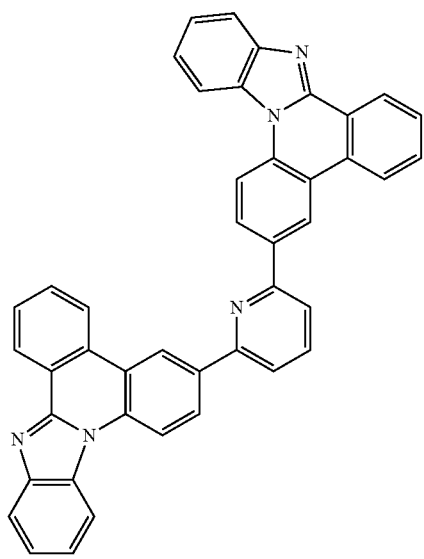

-continued
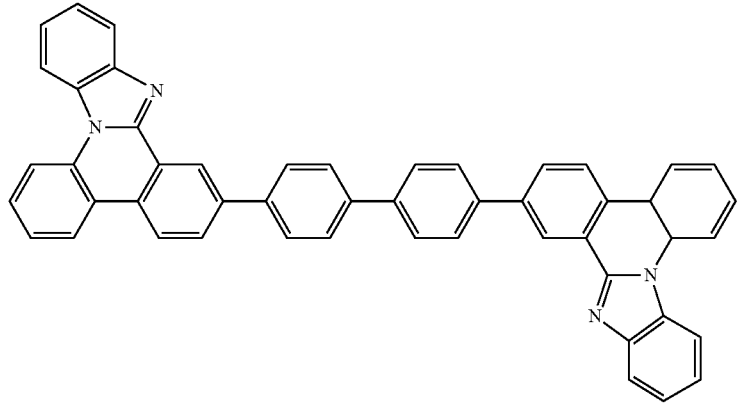
[5-a-7]
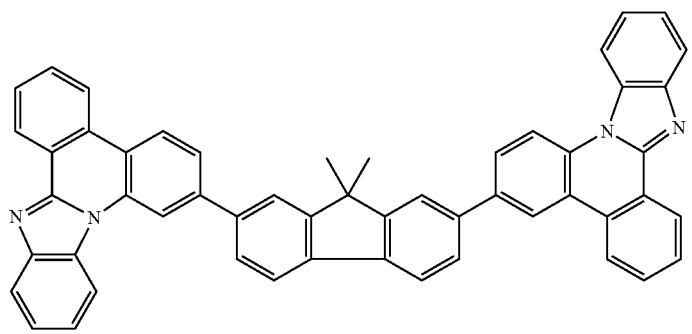
[5-a-8]
[5-a-9]
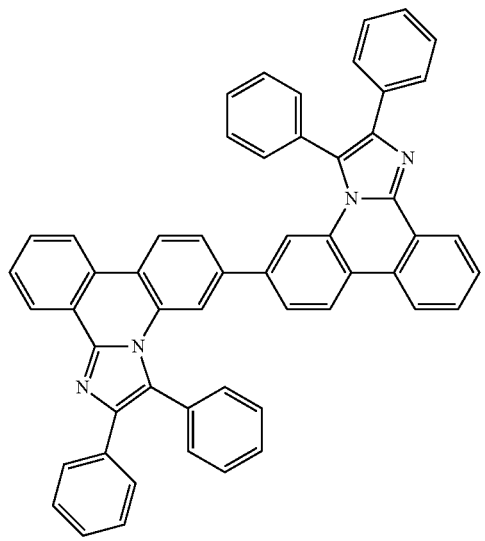
[5-a-10]
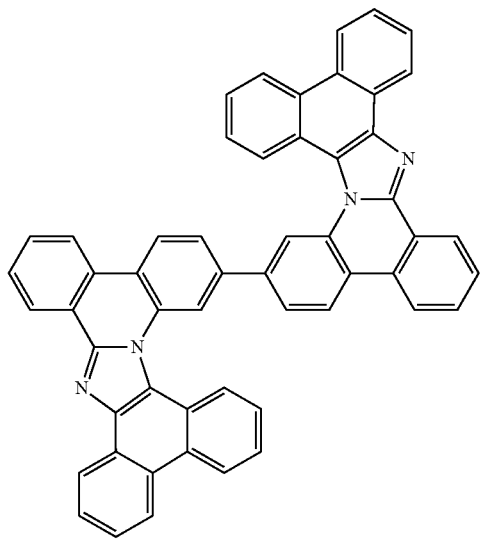

-continued
[5-a-11]
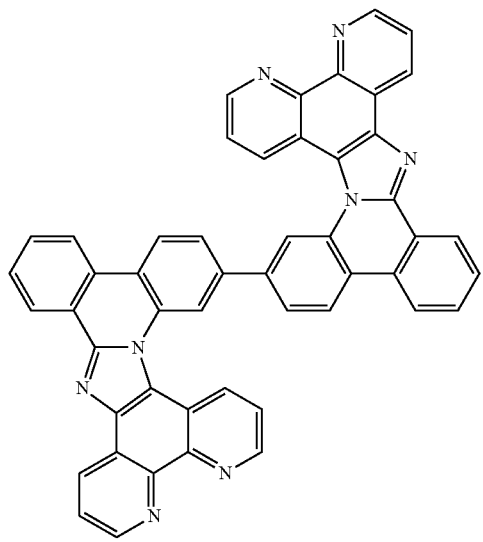
[5-a-12]
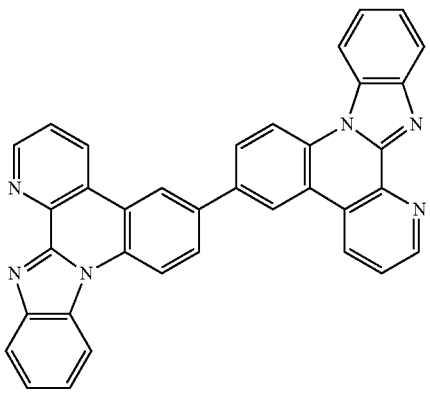
[5-a-13]
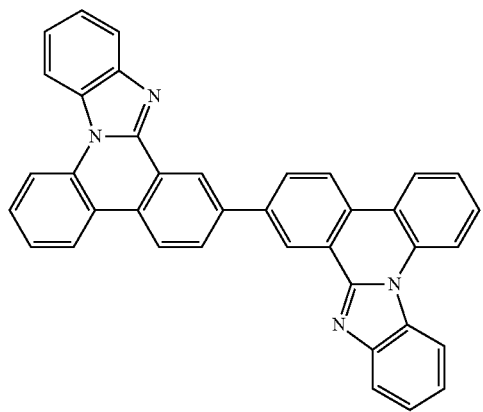
[5-a-14]
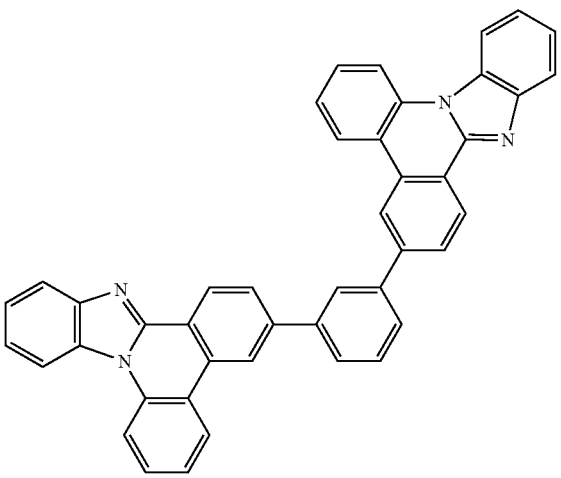
[5-a-15]
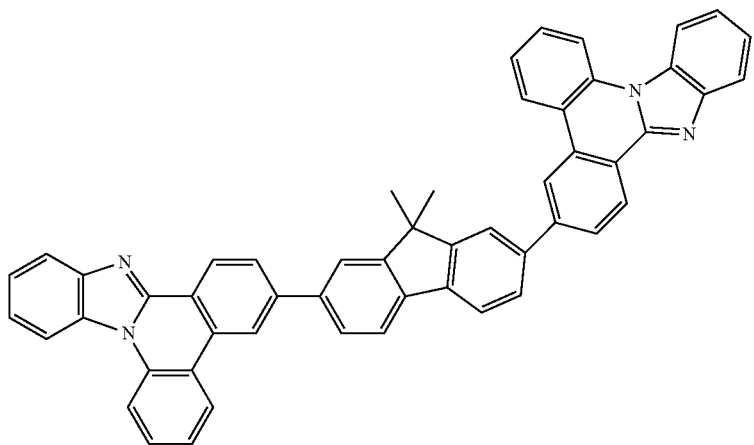

-continued
[5-a-16]
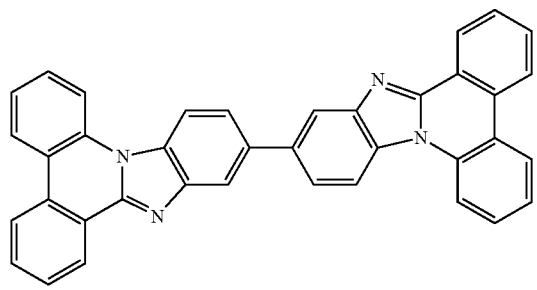
[5-a-17]
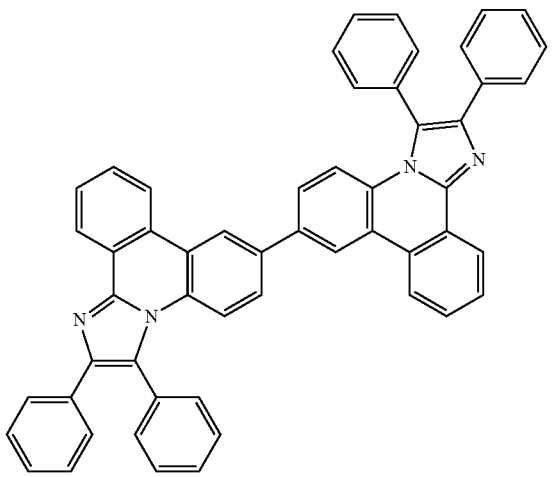
[5-a-18]
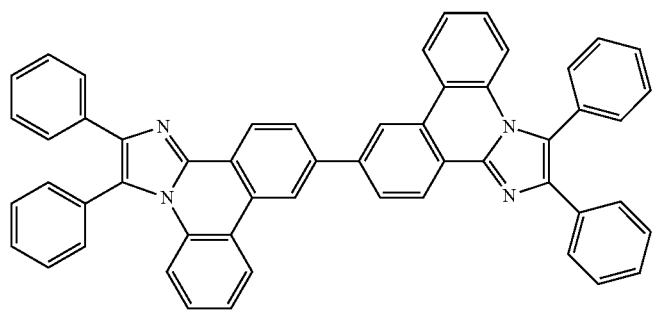
[5-a-19]
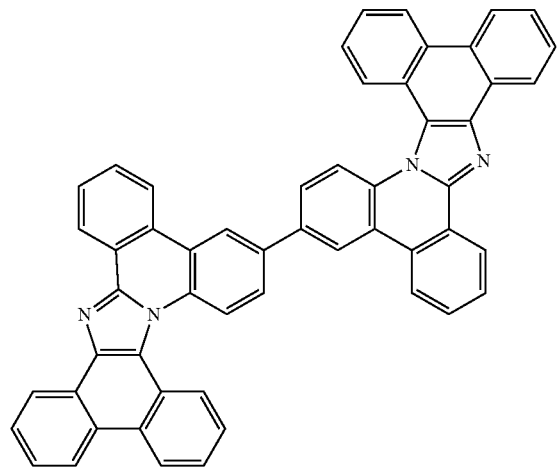
[5-a-20]
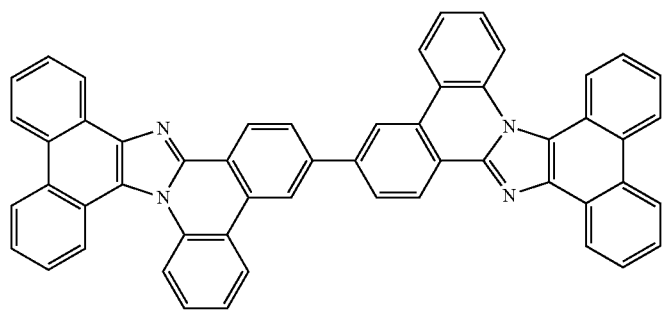

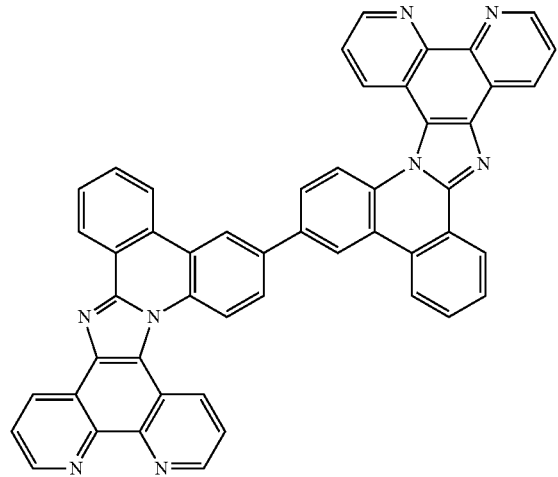
[5-a-21]
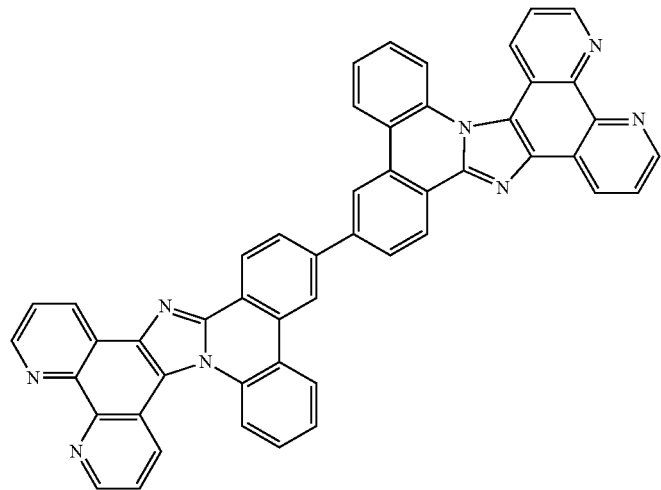
[5-a-22]
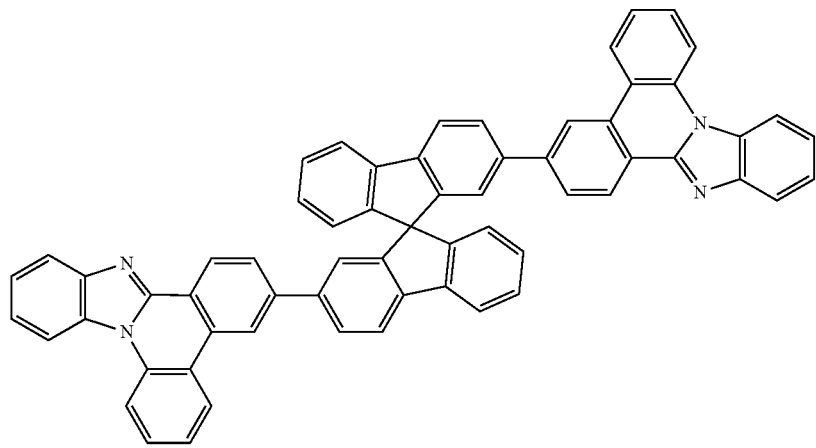
[5-a-23]

[5-a-24]
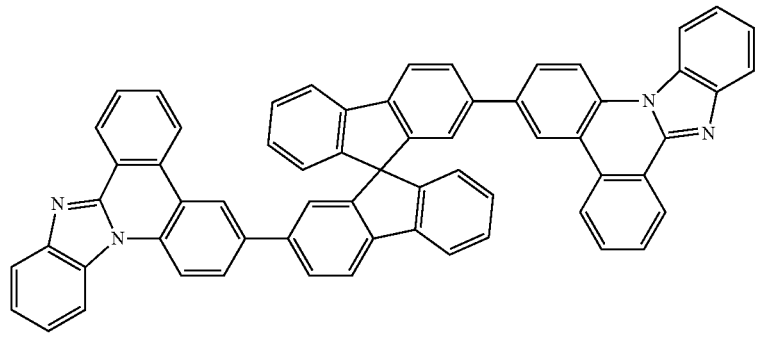
[5-a-25]
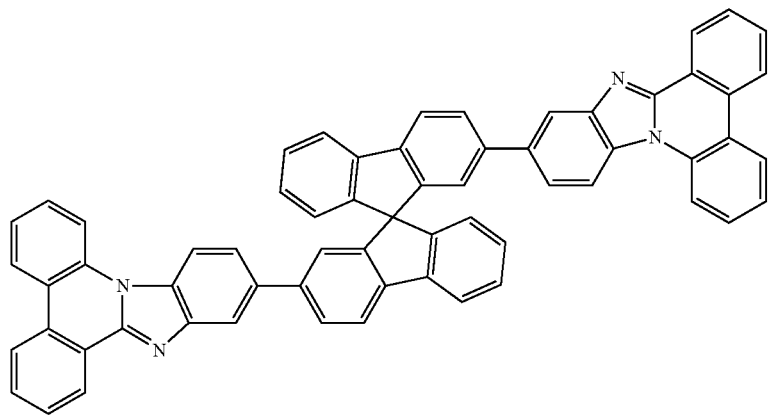
[5-a-26]
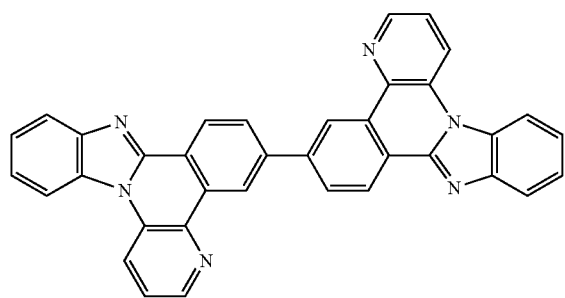
[5-a-27]
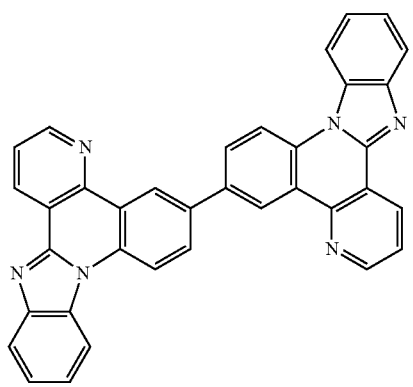
[5-a-28]
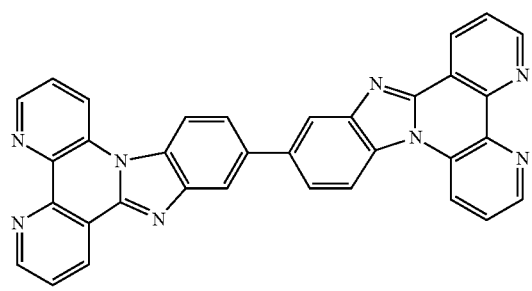
[5-a-29]
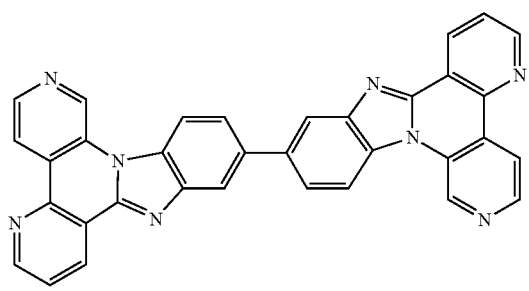

-continued
[5-a-30]
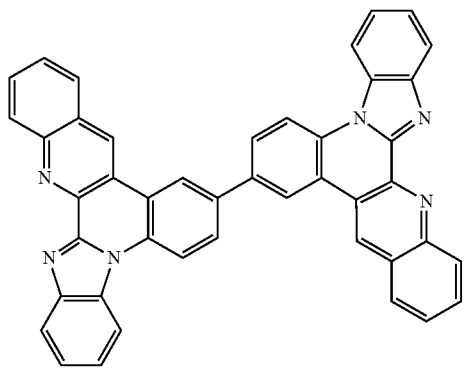
[5-a-31]
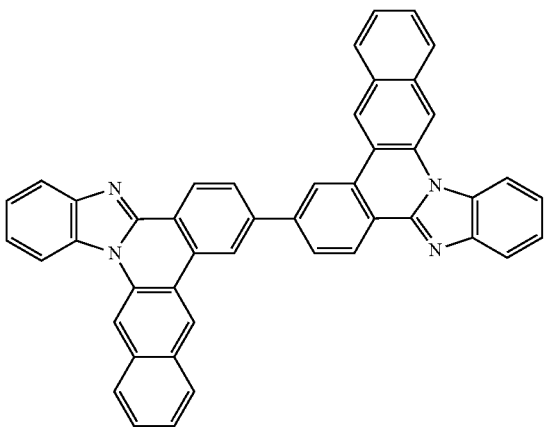
[5-a-32]
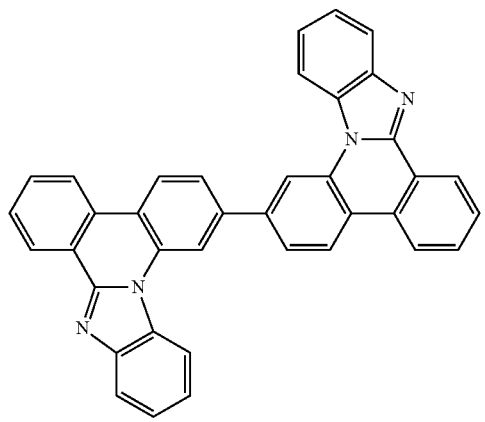
[5-a-33]
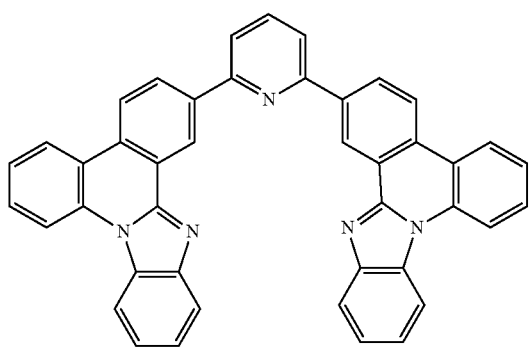
[5-a-34]
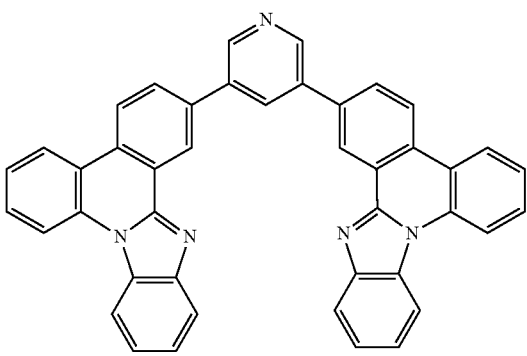
[5-a-35]
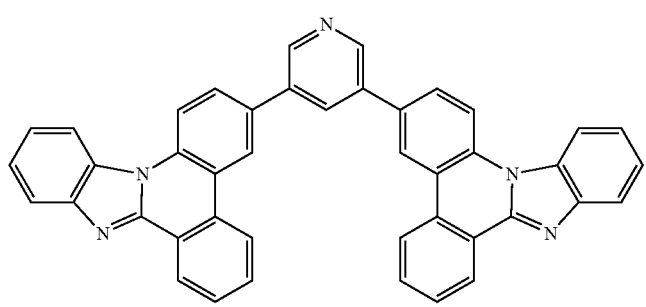
[5-a-36]

[5-a-37]
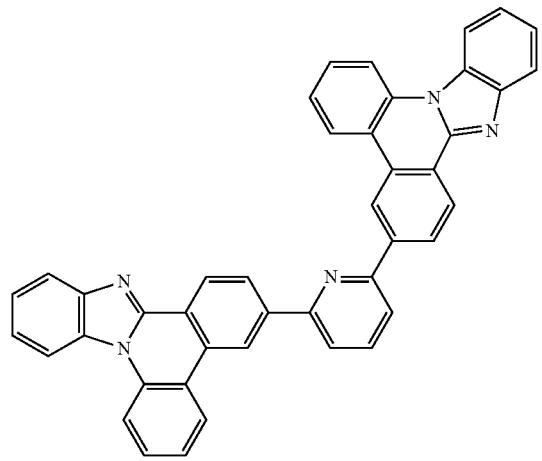
[5-a-38]
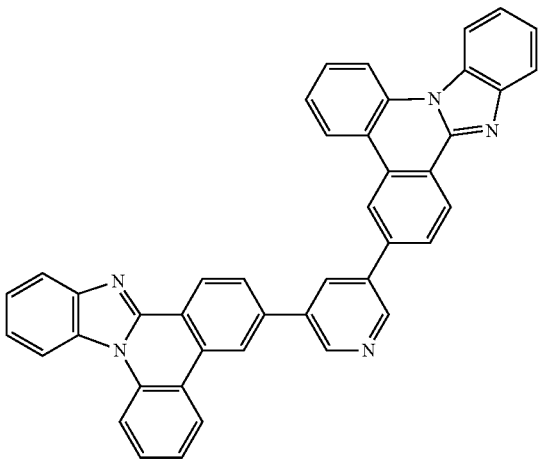
[5-a-39]
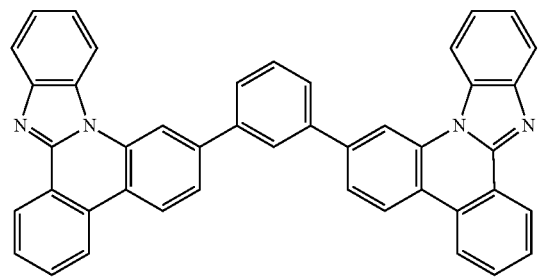
[5-a-40]
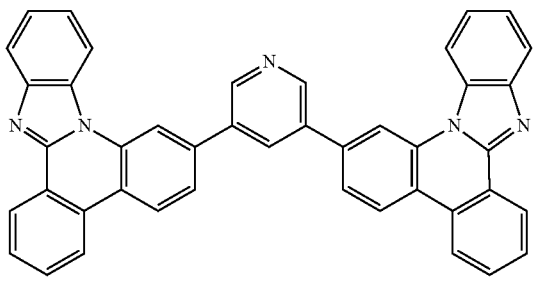
[5-a-41]
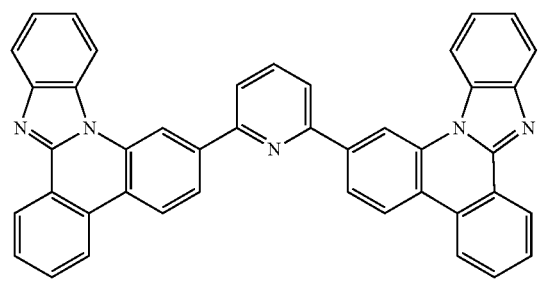
[5-a-42]
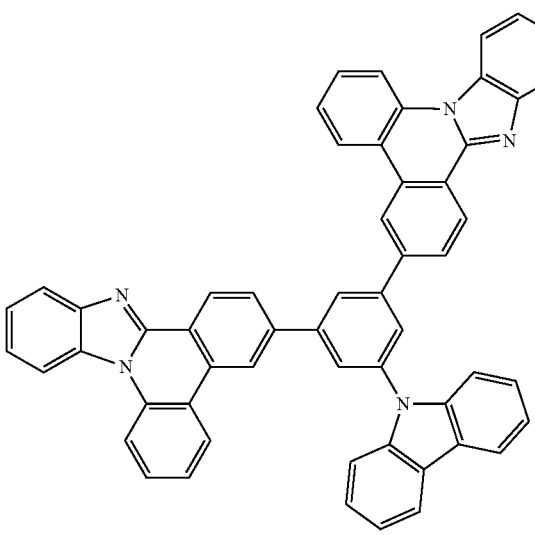

[5-a-43]
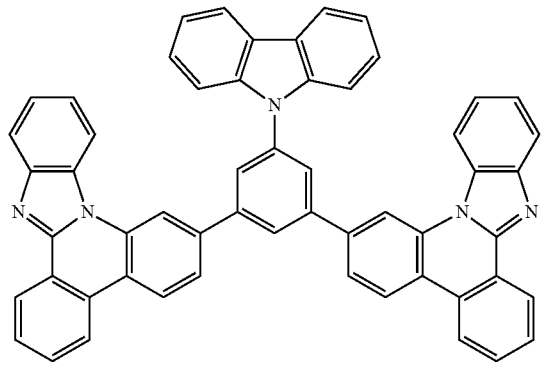
[5-a-44]
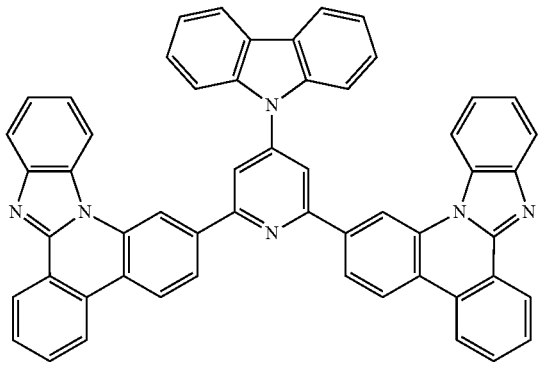
[5-a-45]
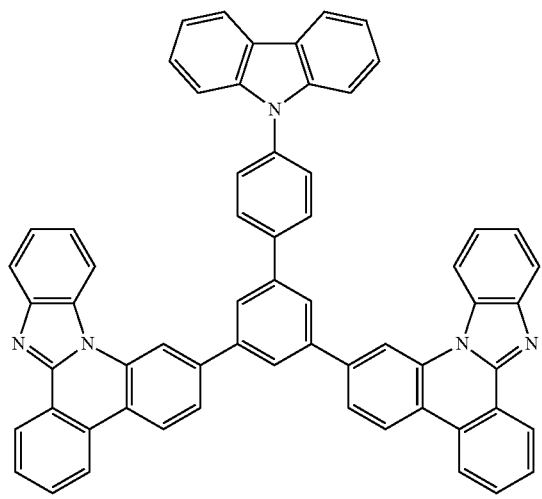
[5-a-46]
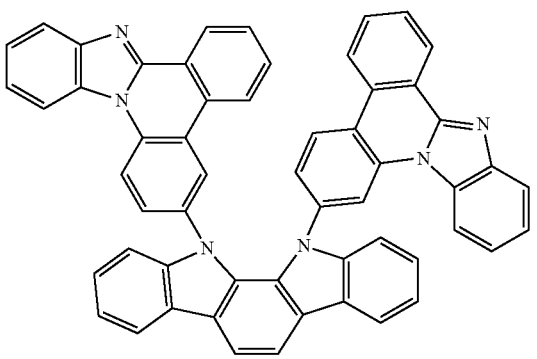
[5-a-47]
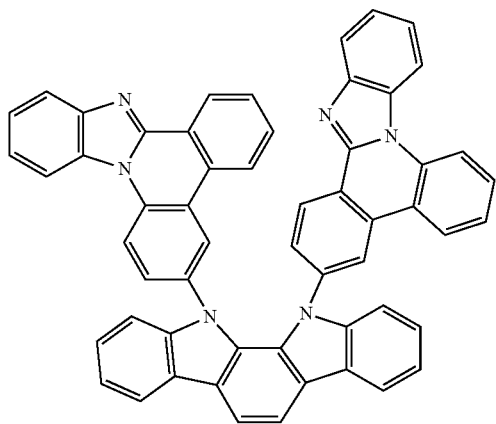
[5-a-48]
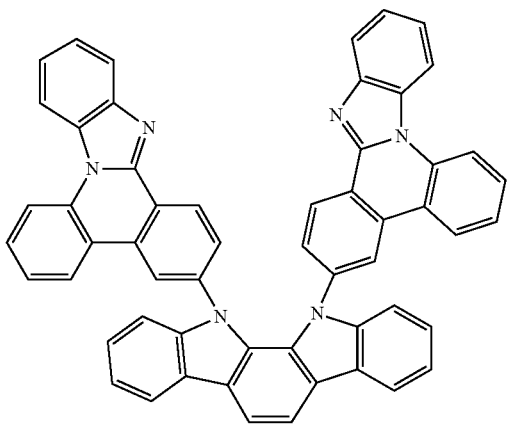

[5-a-49]
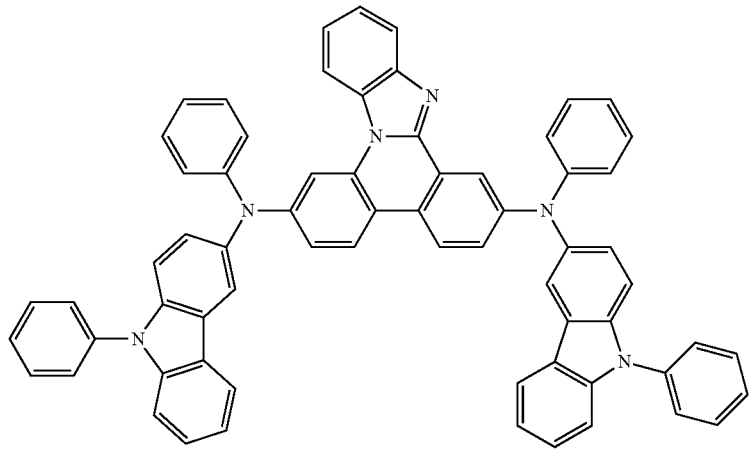
[5-a-50]
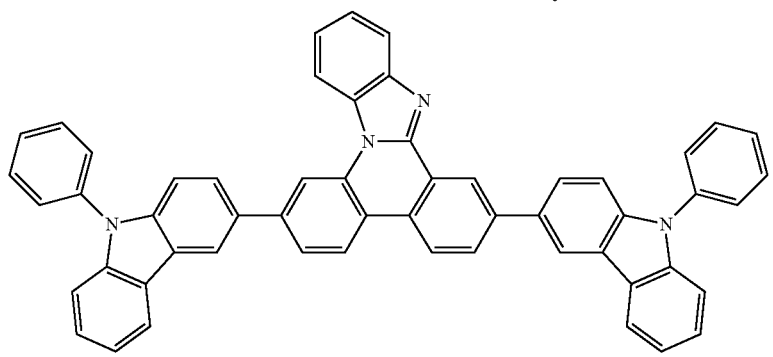
[5-a-51]
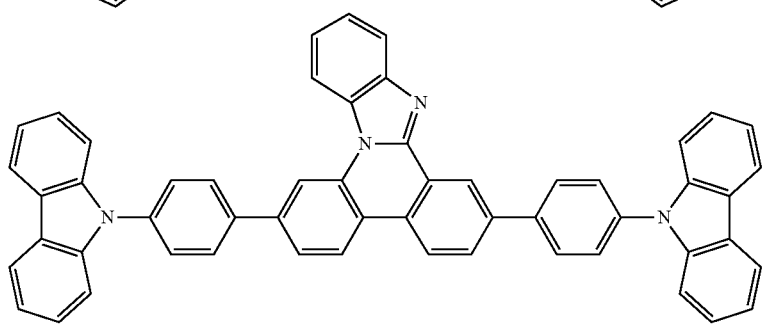
[5-a-52]
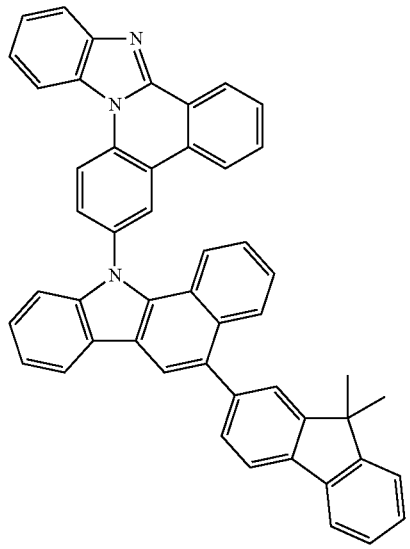
[5-a-53]
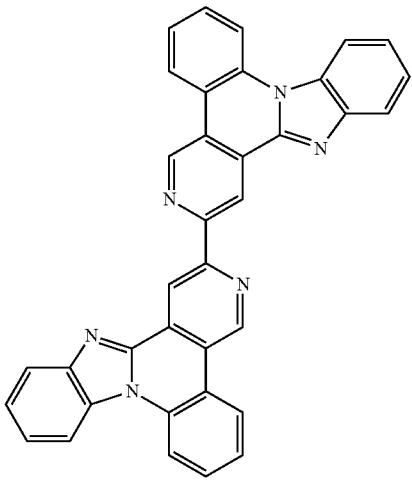

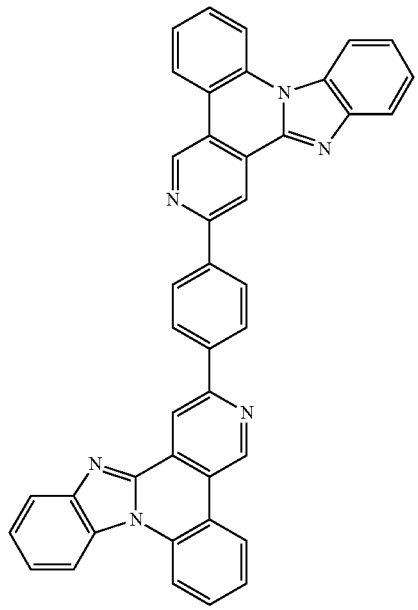
[5-a-54]
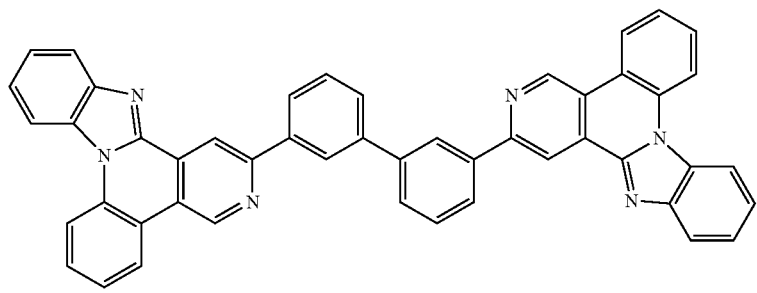
[5-a-55]
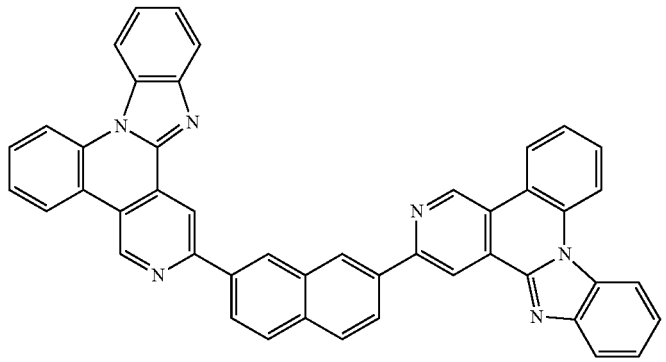
[5-a-56]

[5-a-57]
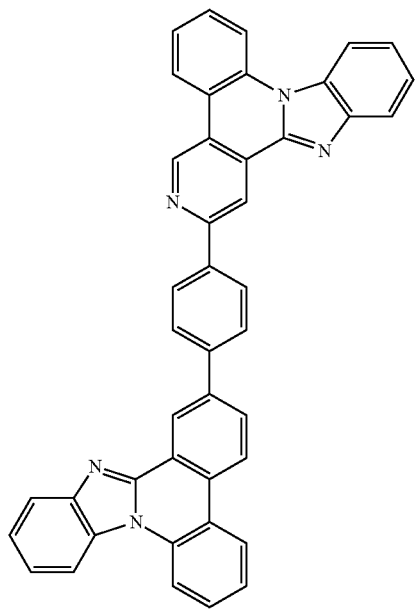
[5-a-58]
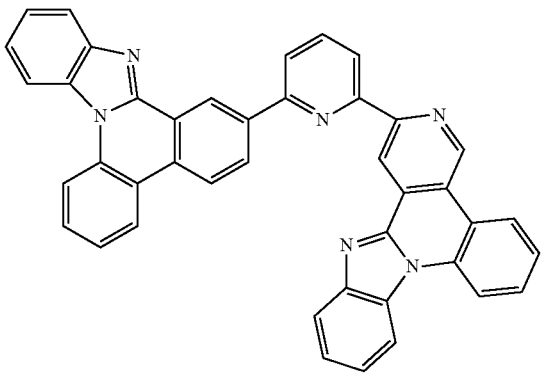
[5-a-59]
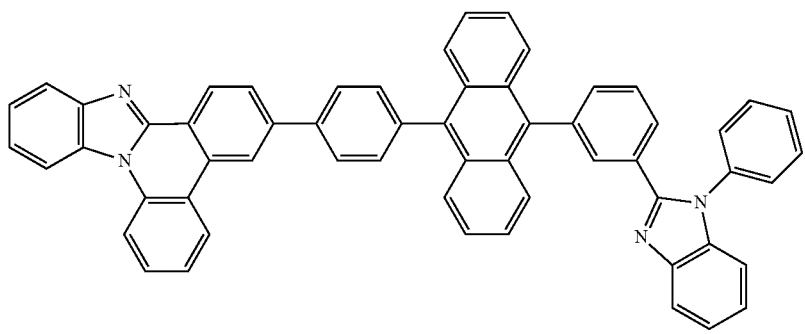
[5-a-60]
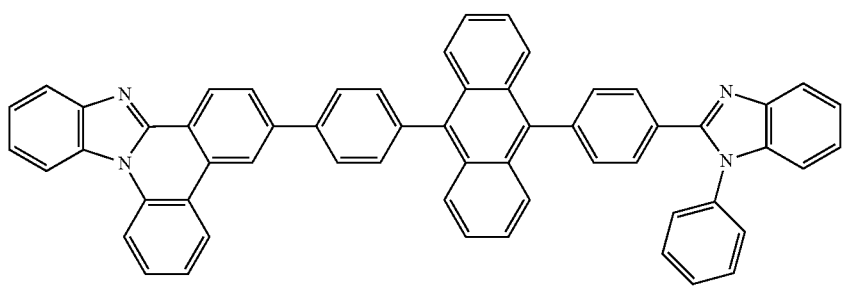

-continued
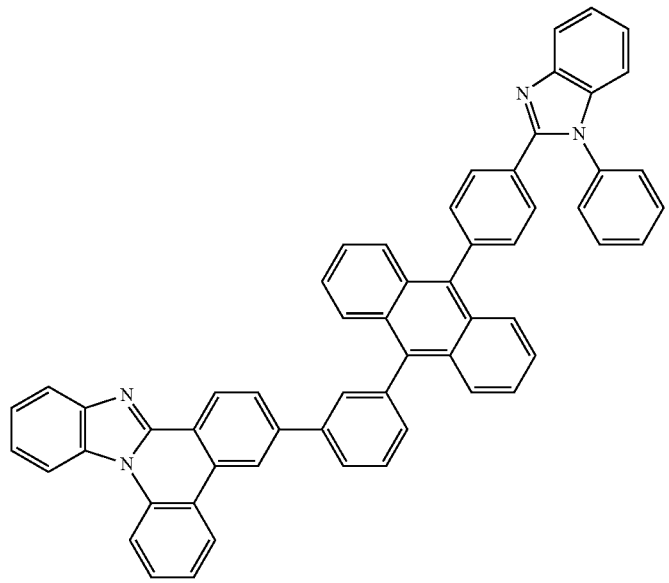
[5-a-61]
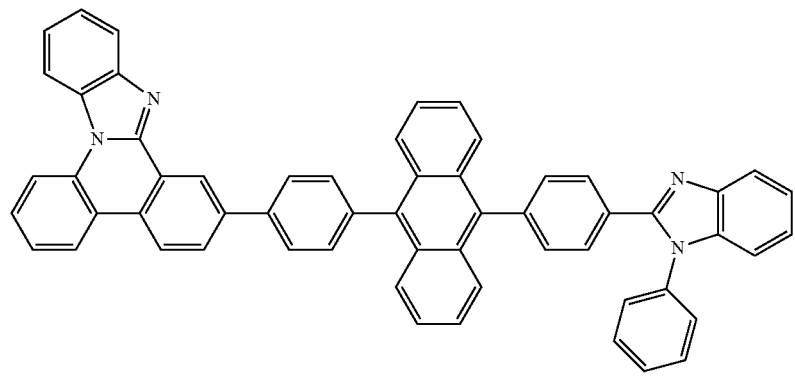
[5-a-62]
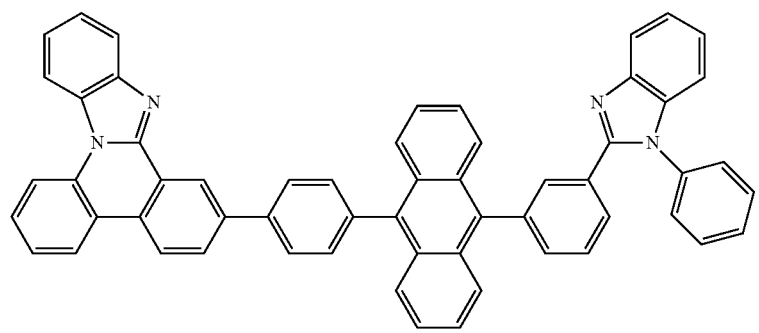
[5-a-63]
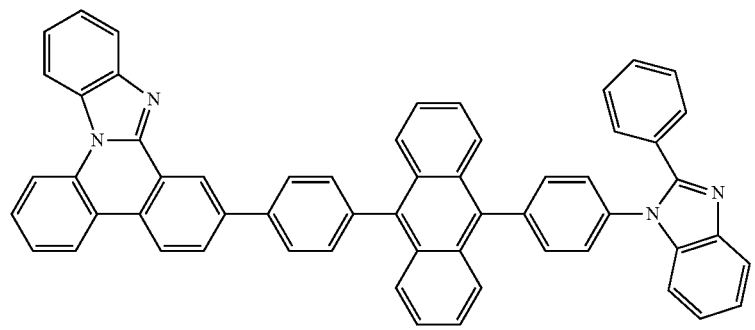
[5-a-62]

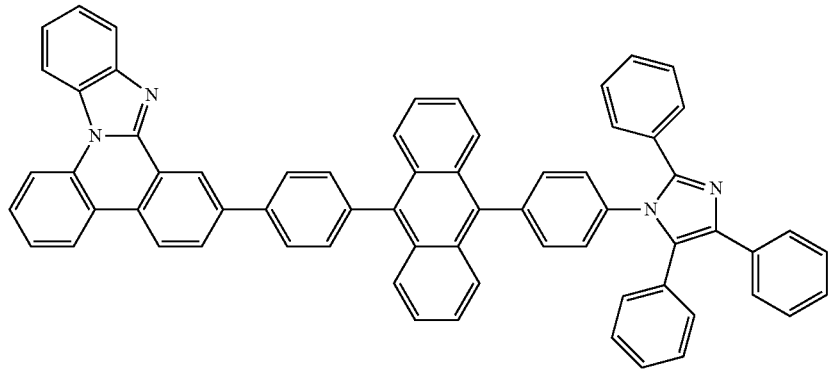
[5-a-63]
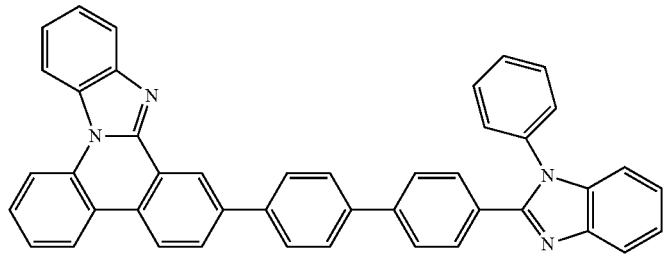
[5-a-64]
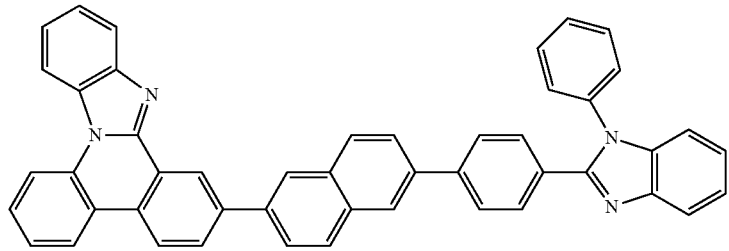
[5-a-65]
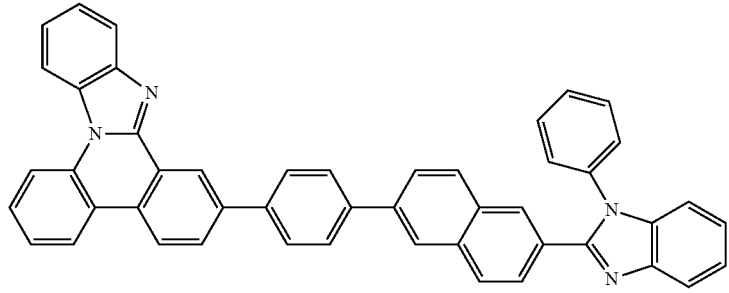
[5-a-66]
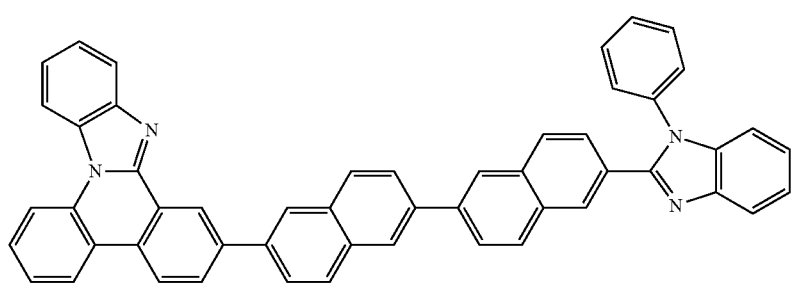
[5-a-67]

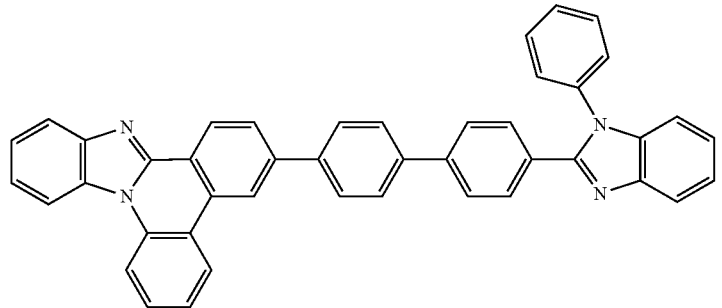
[5-a-68]
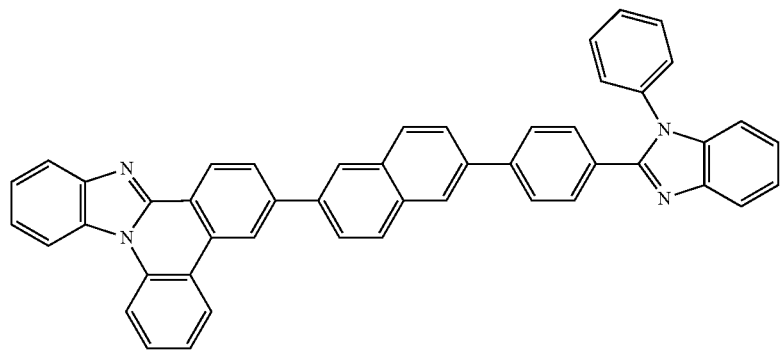
[5-a-69]
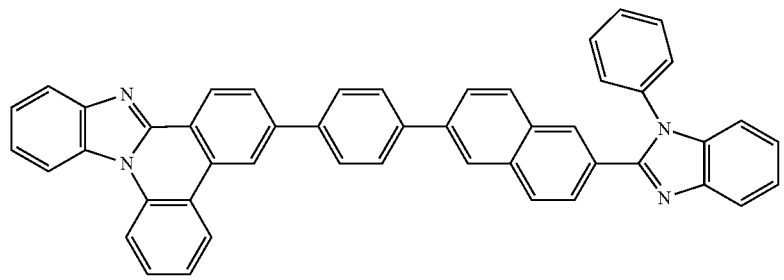
[5-a-70]
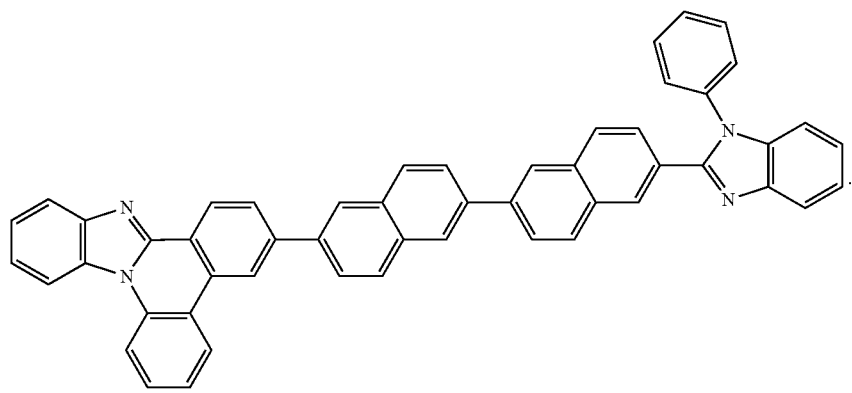
[5-a-71]

9. The nitrogen-containing heterocyclic derivative as set forth in claim 1, wherein the nitrogen-containing heterocyclic derivative is represented by one selected from the following Formulas:
[6-a-1]
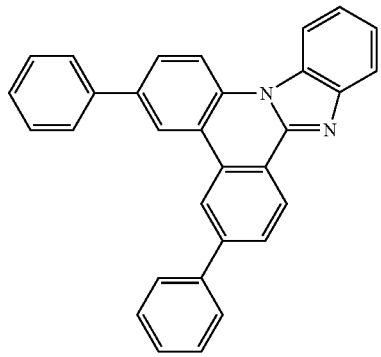
[6-a-2]
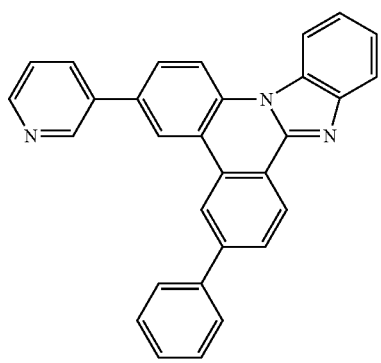
[6-a-3]
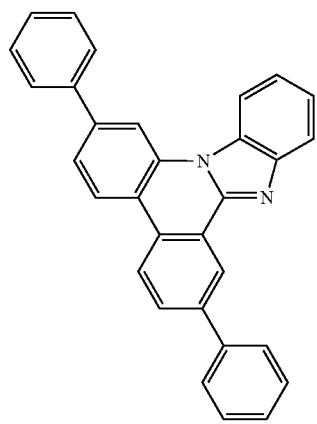
[6-a-4]
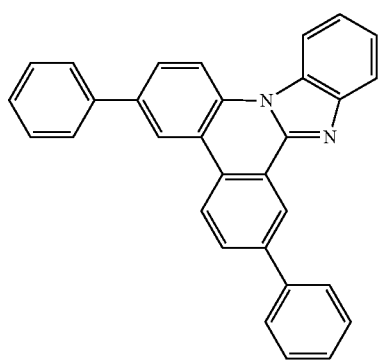
[6-a-5]
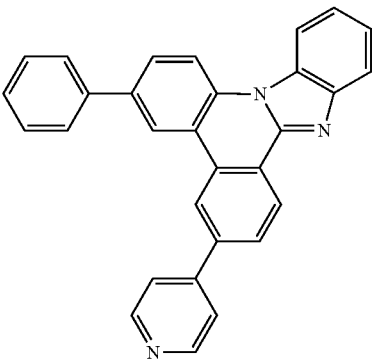
[6-a-6]
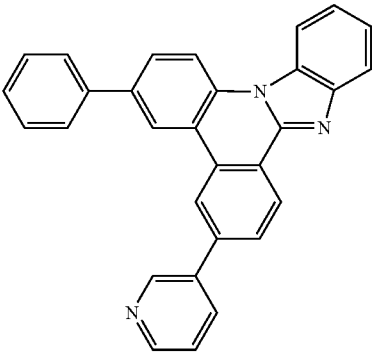
[6-a-7]
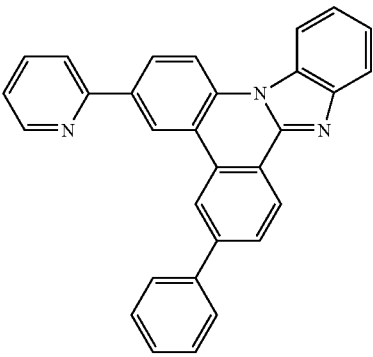
[6-a-8]
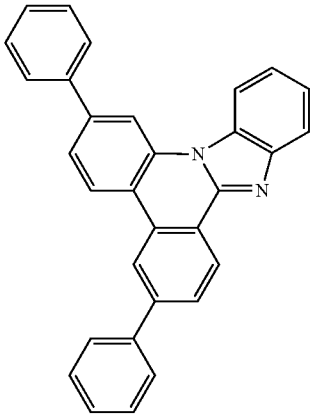

-continued
[6-a-9]
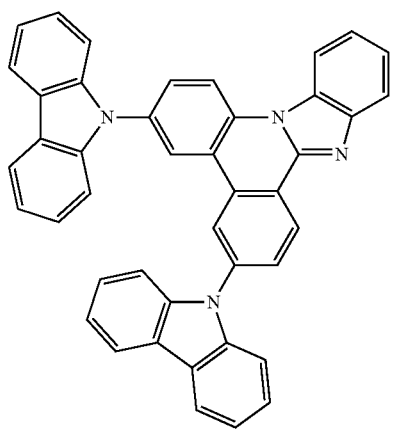
[6-a-10]
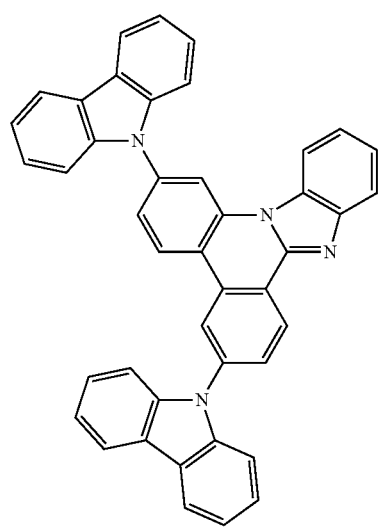
[6-a-11]
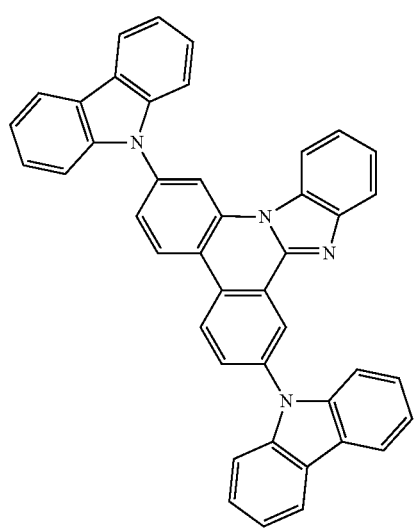
-continued
[6-a-12]
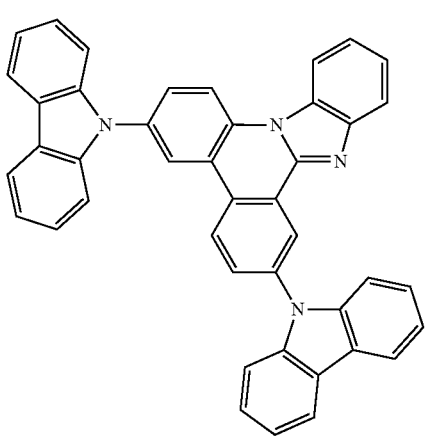
[6-a-13]
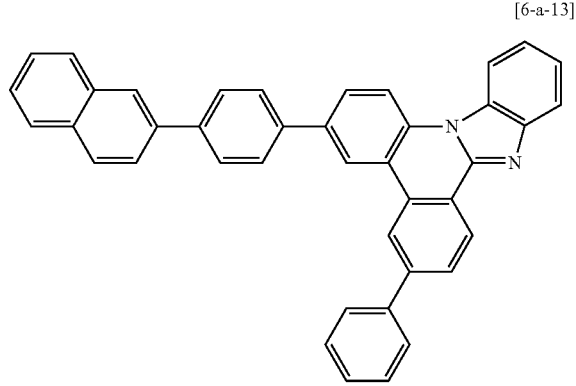
[6-a-14]
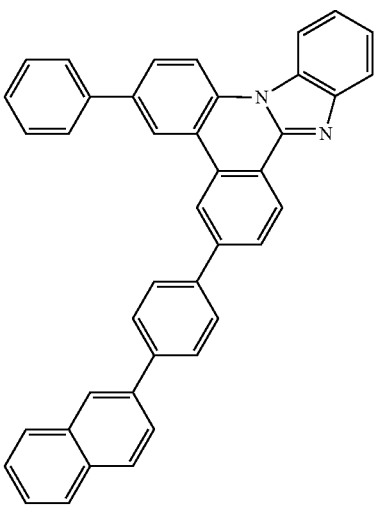

[6-a-15]
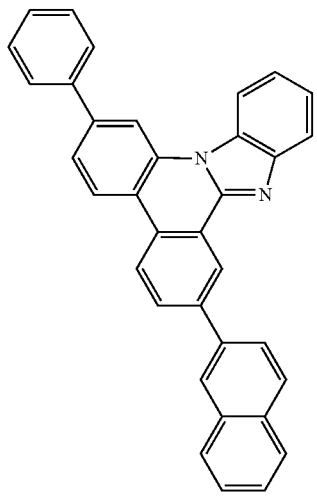
[6-a-16]
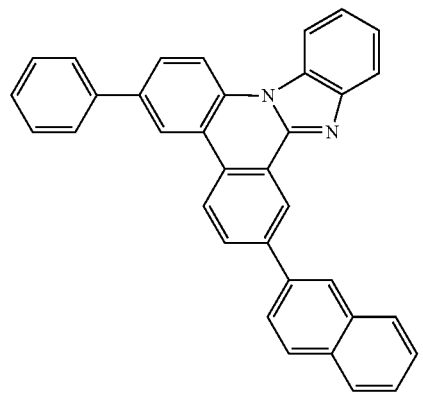
[6-a-17]
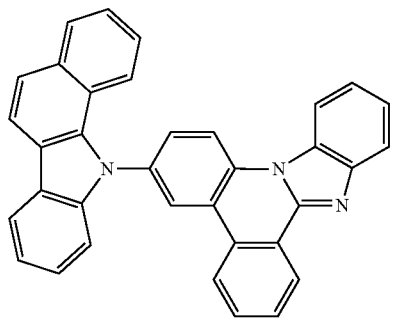
[6-a-18]
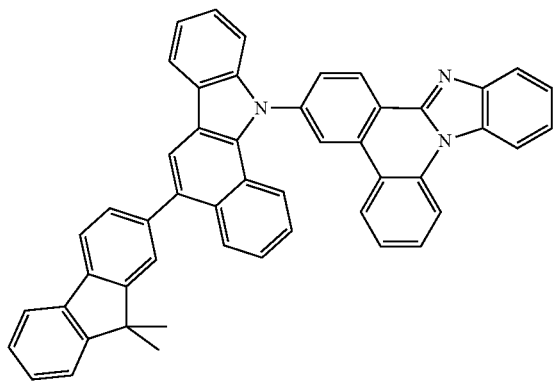
[6-a-19]
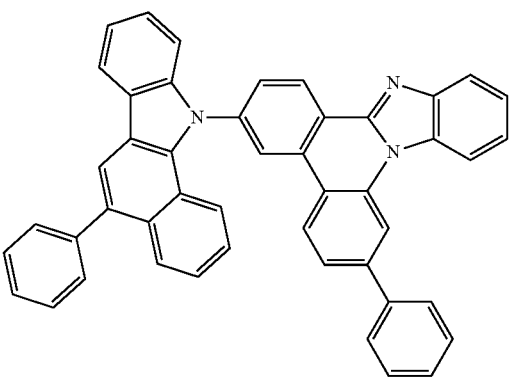
[6-a-20]
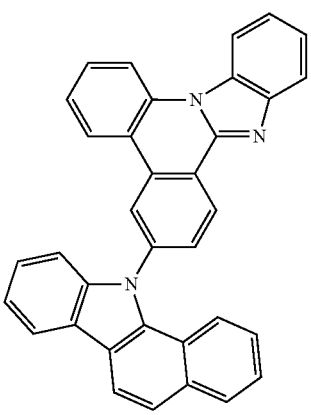
[6-a-21]
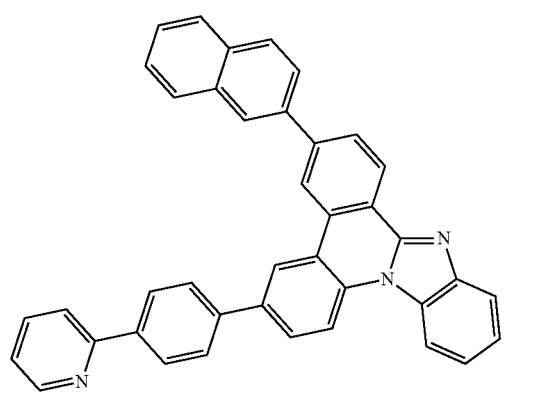

[6-a-22]
[6-a-25]
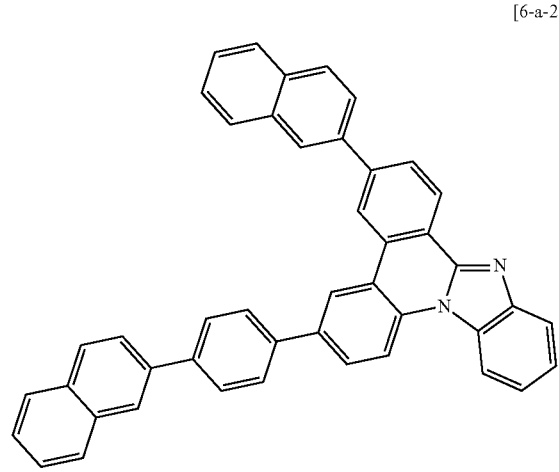
[6-a-23]
[6-a-26]
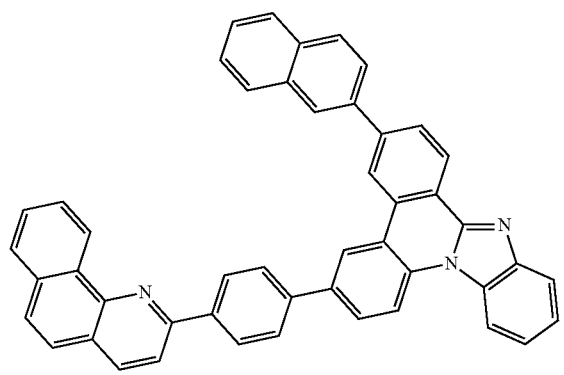
[6-a-24]
[6-a-27]
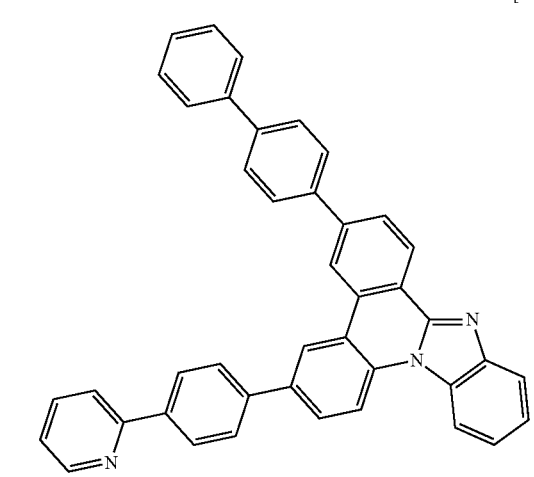
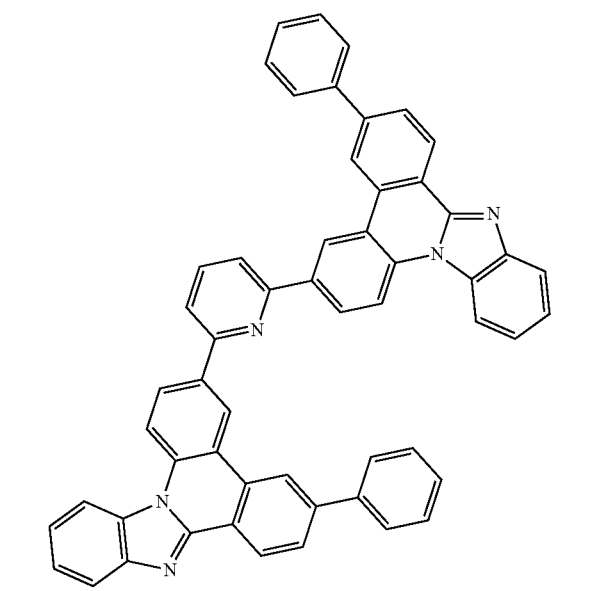

[6-a-28]
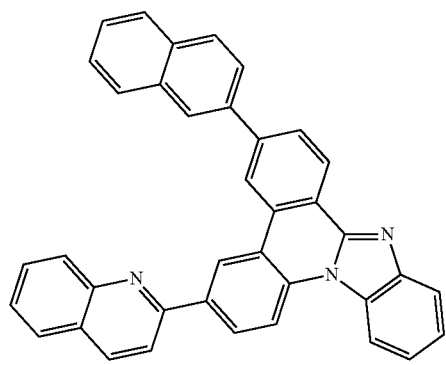
[6-a-29]
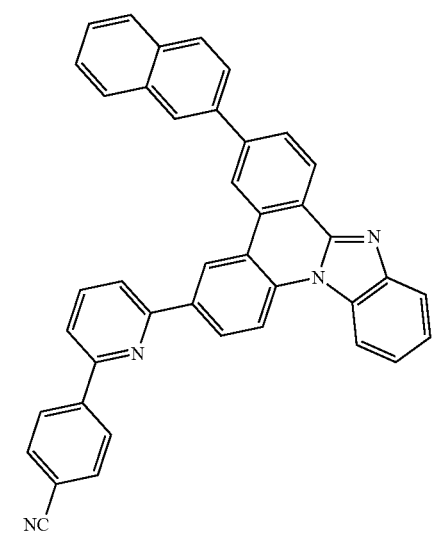
[6-a-30]
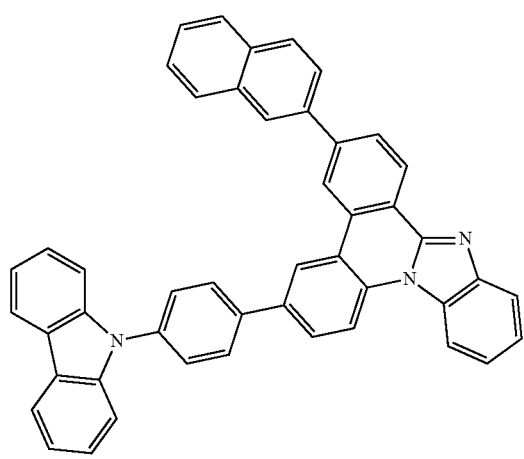
[6-a-31]
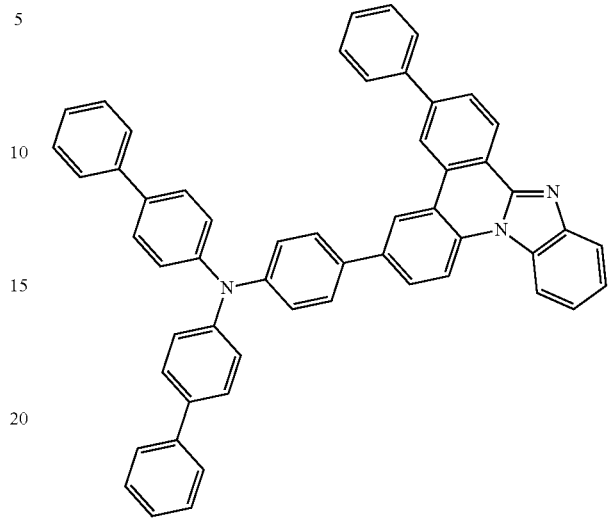
[6-a-32]
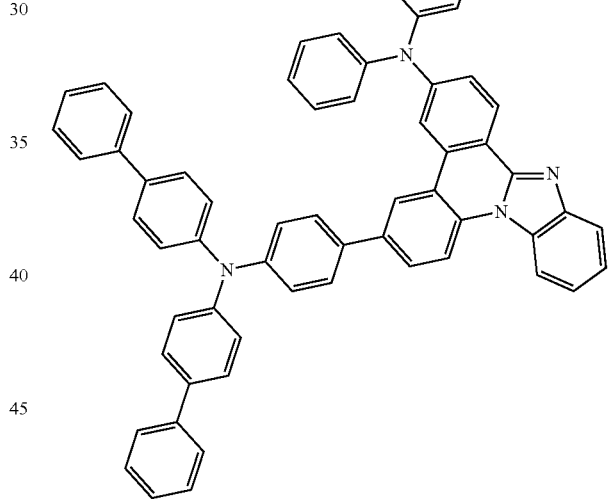
[6-a-33]
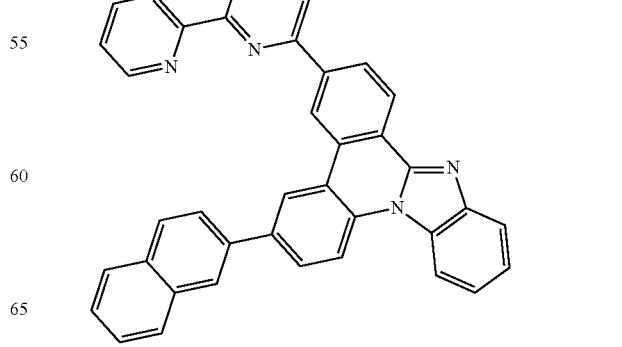

-continued
[6-a-34]
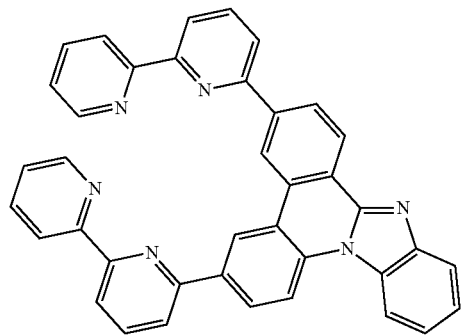
[6-a-35]
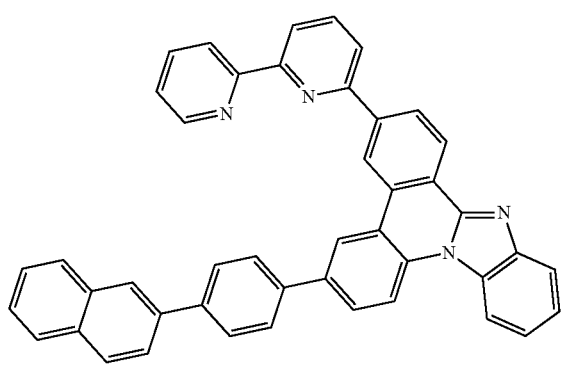
[6-a-36]
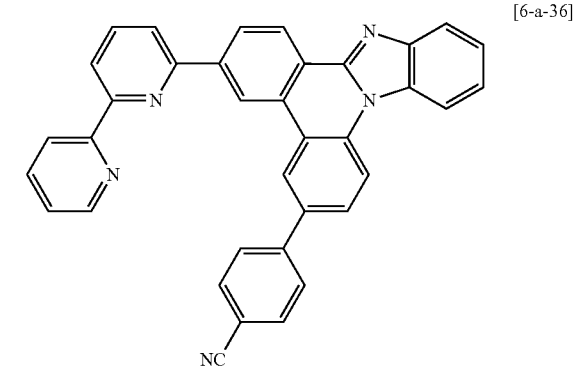
[6-a-37]
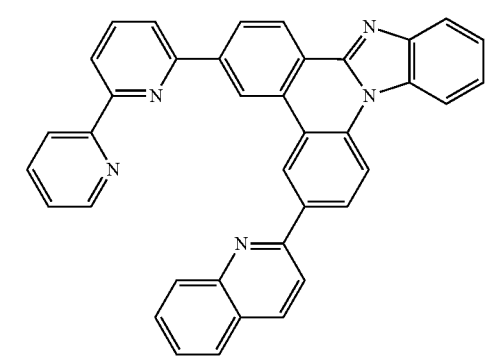
-continued
[6-a-38]
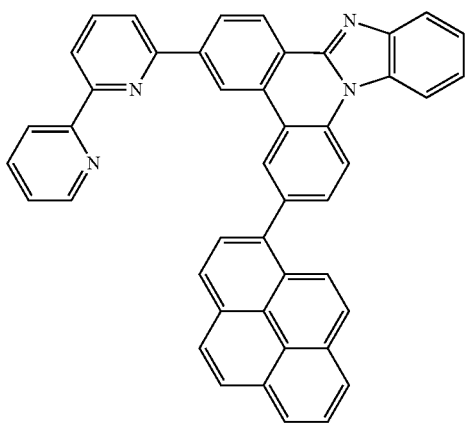
[6-a-39]
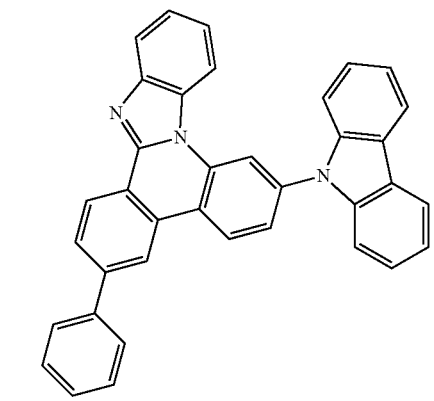
[6-a-40]
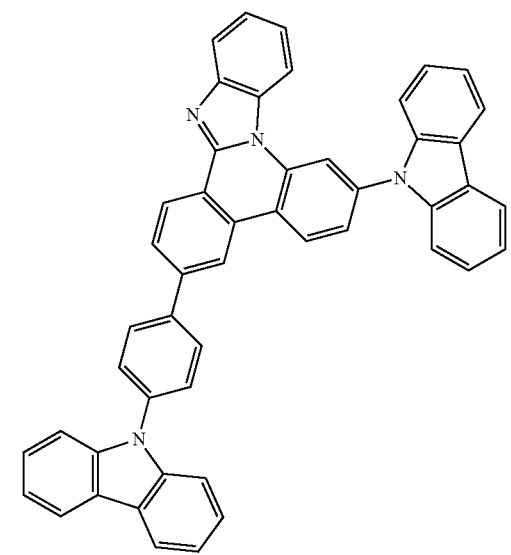

[6-a-41]
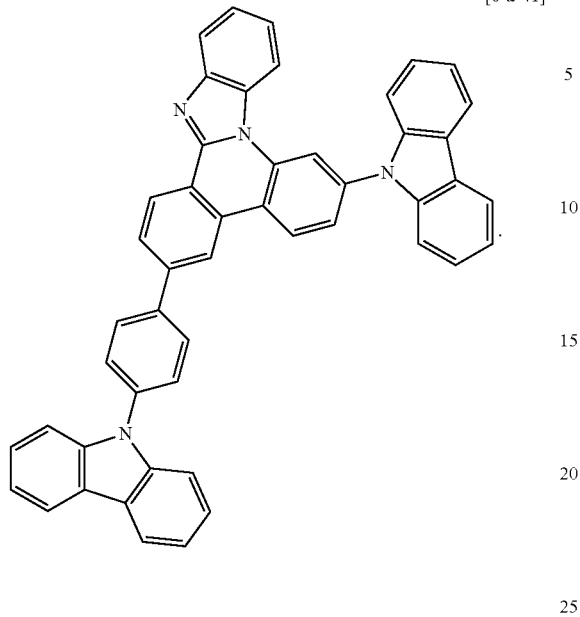
10. The nitrogen-containing heterocyclic derivative as set forth in claim 1, wherein the nitrogen-containing heterocyclic derivative is represented by one selected from the following Formulas:
[7-a-1]
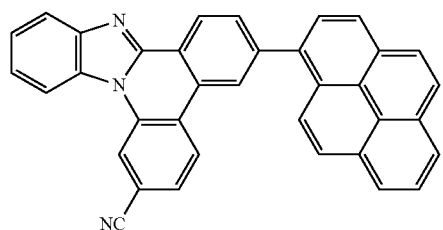
[7-a-2]
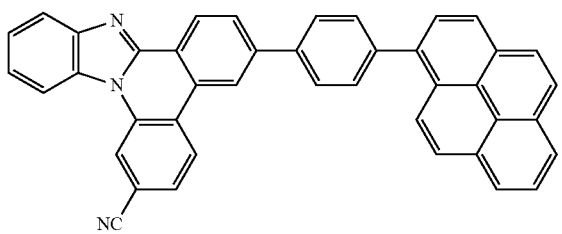
[7-a-3]
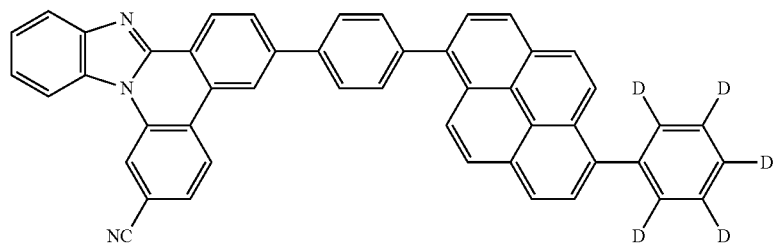
[7-a-4]
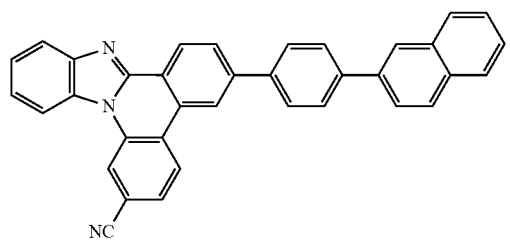
[7-a-5]
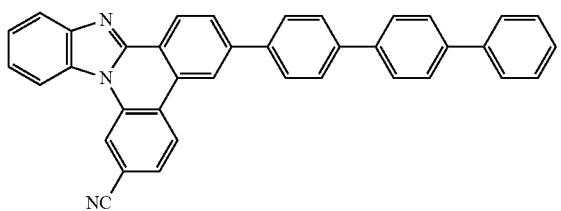

-continued
[7-a-6]
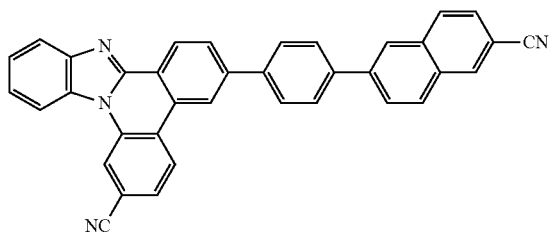
[7-a-7]
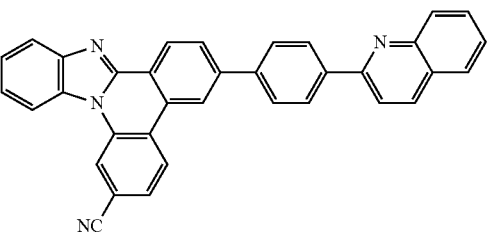
[7-a-8]
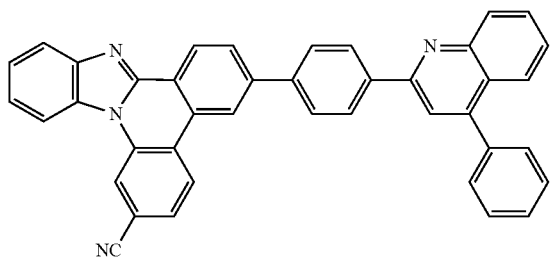
[7-a-9]
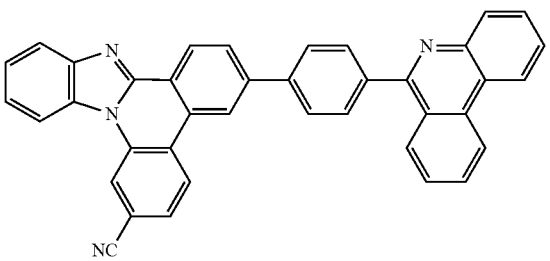
[7-a-10]
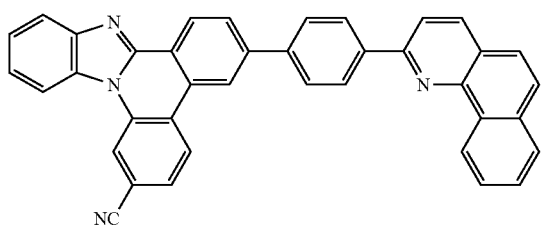
[7-a-11]
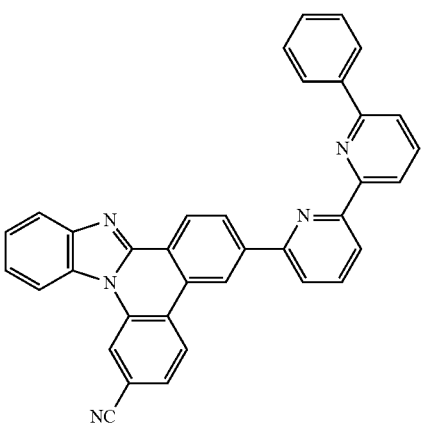
[7-a-12]
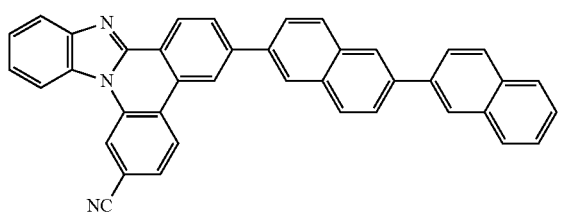
[7-a-13]
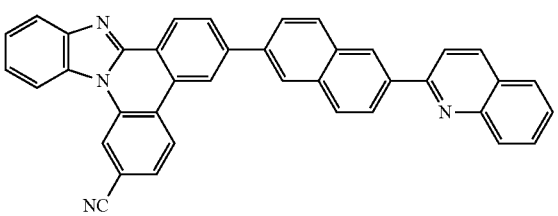
[7-a-14]
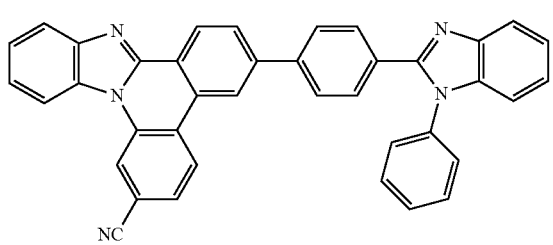
[7-a-15]
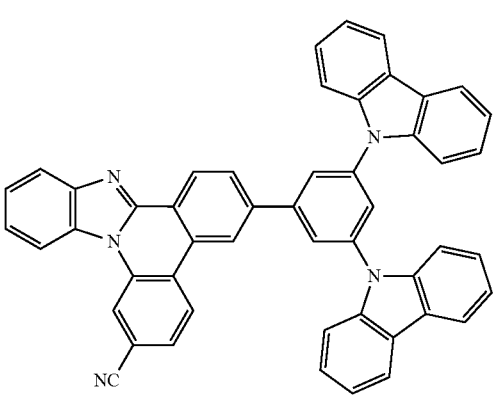

[7-a-16]
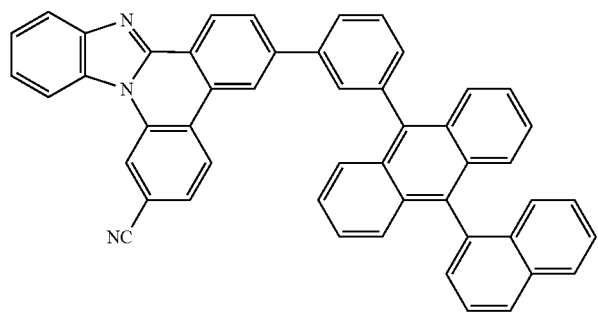
[7-a-17]
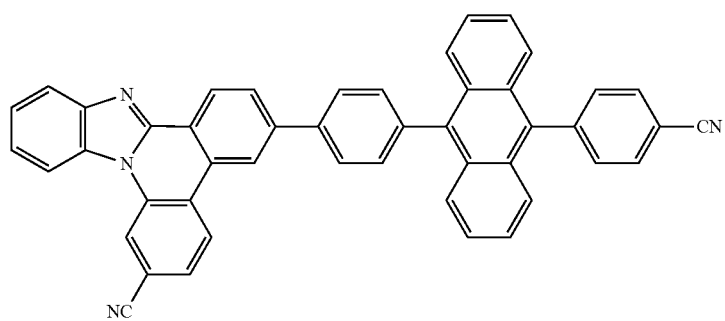
[7-a-18]
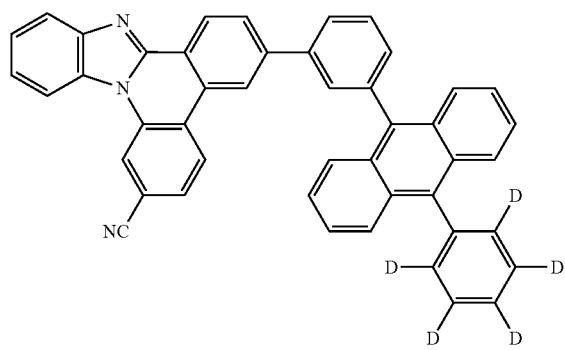
[7-a-19]
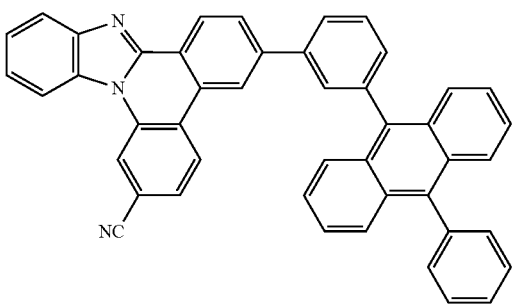
[7-a-20]
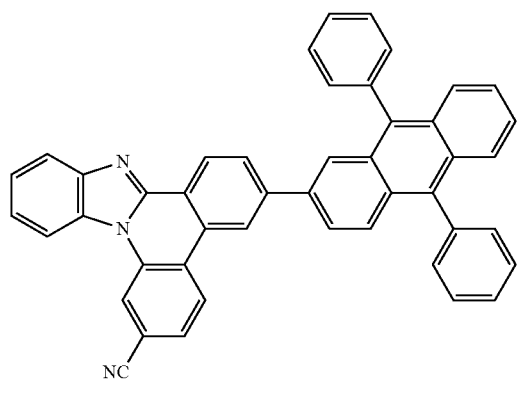
[7-a-21]
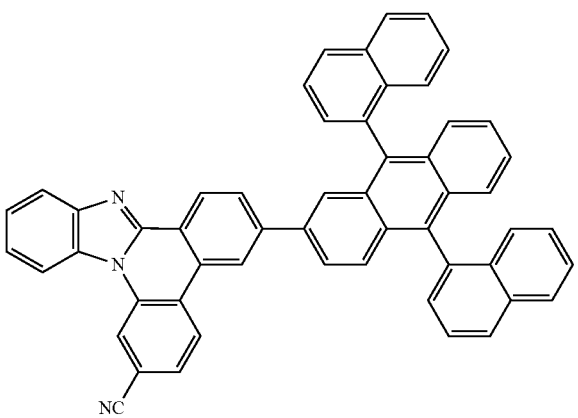

[7-a-21]
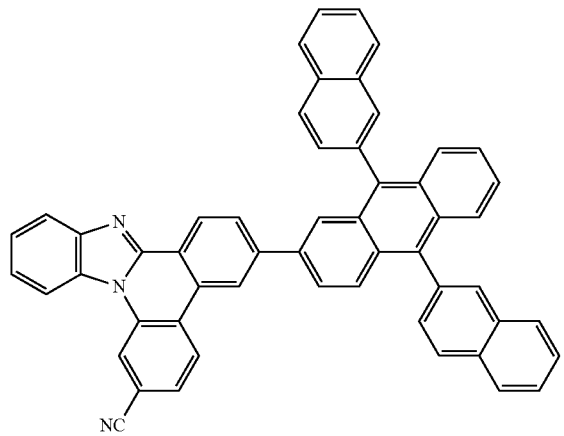
[7-a-22]
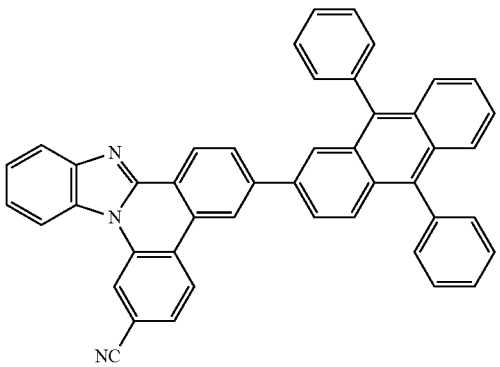
[7-a-23]
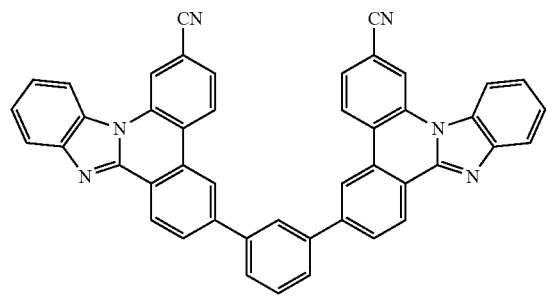
[7-a-24]
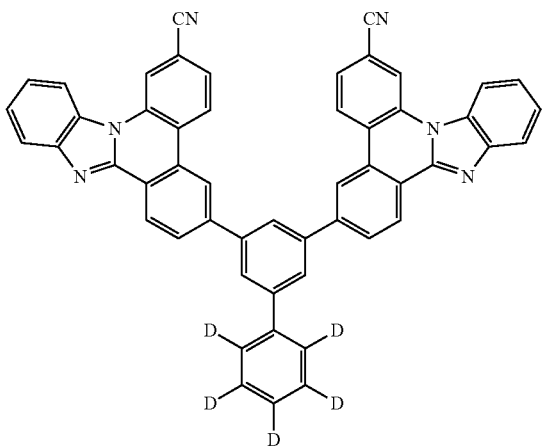
[7-a-25]
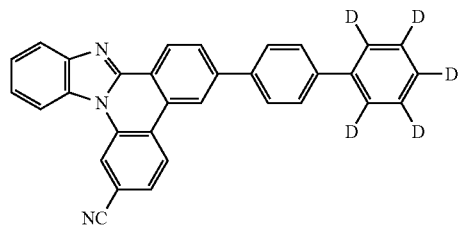
[7-a-26]
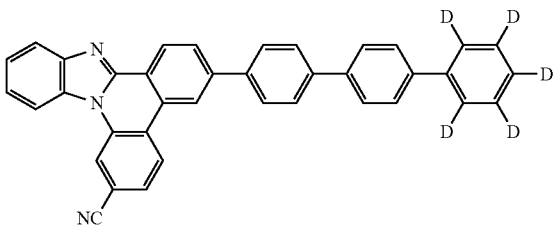
[7-a-27]
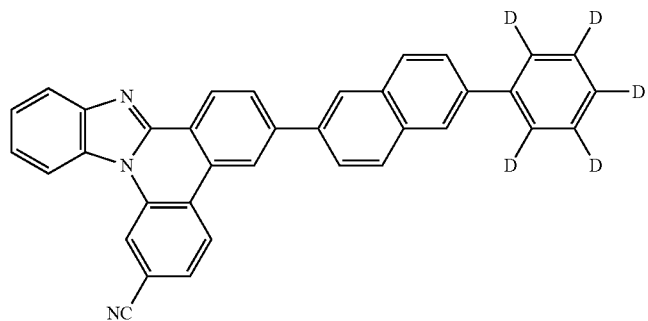

-continued

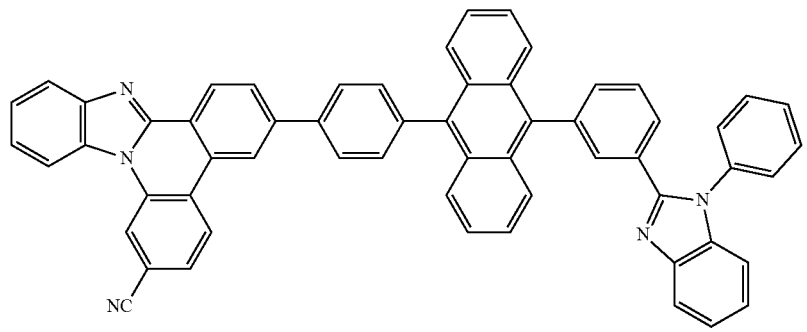

[7-a-28]

11. An organic electronic device which includes a first electrode, a second electrode, and one or more organic material layers that are disposed between the first electrode and the second electrode, wherein one or more layers of the organic material layers include the nitrogen-containing heterocyclic derivative according to claim 1.

12. The organic electronic device as set forth in claim 11, wherein the organic material layer includes a hole injection layer or a hole transport layer, and the hole injection layer or hole transport layer includes the nitrogen-containing heterocyclic derivative.

13. The organic electronic device as set forth in claim 11, wherein the organic material layer includes a light emitting layer, and the light emitting layer includes the nitrogen-containing heterocyclic derivative as a host of the light emitting layer.

14. The organic electronic device as set forth in claim 11, wherein the organic material layer includes an electron transport layer, and the electron transport layer includes the nitrogen-containing heterocyclic derivative.

15. The organic electronic device as set forth in claim 11, wherein the organic material layer includes an organic material layer that includes the nitrogen-containing heterocyclic derivative and a hole injection layer or hole transport layer that includes a compound including arylamino group, carbazole group, or benzcarbazole group.

16. The organic electronic device as set forth in claim 11, wherein the organic material layer that includes the nitrogen-containing heterocyclic derivative includes the nitrogen-containing heterocyclic derivative as a host, and other organic compounds, metal or metal compounds as a dopant.

17. The organic electronic device as set forth in claim 11, wherein the organic electronic device is selected from the group consisting of an organic light emitting device, an organic solar cell, an organic photoconductor (OPC) drum and an organic transistor.

\* \* \* \* \*